(12) United States Patent
Conklin et al.

(10) Patent No.: US 12,065,489 B2
(45) Date of Patent: Aug. 20, 2024

(54) CLAUDIN-6 ANTIBODIES AND DRUG CONJUGATES

(71) Applicant: The Regents of the University of California, Oakland, CA (US)

(72) Inventors: Dylan Conklin, Los Angeles, CA (US); Martina S. McDermott, Los Angeles, CA (US); Neil A. O'Brien, Los Angeles, CA (US); Michael J. Palazzolo, Los Angeles, CA (US); Dennis Slamon, Los Angeles, CA (US); Erika Von Euw, Los Angeles, CA (US); Peter Bowers, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/846,900

(22) Filed: Jun. 22, 2022

(65) Prior Publication Data
US 2023/0049752 A1 Feb. 16, 2023

Related U.S. Application Data

(63) Continuation of application No. 17/441,157, filed as application No. PCT/US2020/023981 on Mar. 20, 2020, now abandoned.

(60) Provisional application No. 62/821,391, filed on Mar. 20, 2019.

(51) Int. Cl.
| | | |
|---|---|---|
| C07K 16/28 | (2006.01) | |
| A61K 39/00 | (2006.01) | |
| A61K 47/65 | (2017.01) | |
| A61K 47/68 | (2017.01) | |
| A61P 35/00 | (2006.01) | |
| G01N 33/574 | (2006.01) | |

(52) U.S. Cl.
CPC ............ *C07K 16/28* (2013.01); *A61K 47/65* (2017.08); *A61K 47/6817* (2017.08); *A61K 47/6849* (2017.08); *A61P 35/00* (2018.01); *G01N 33/5748* (2013.01); *A61K 2039/505* (2013.01); *C07K 2317/24* (2013.01); *C07K 2317/56* (2013.01); *C07K 2317/565* (2013.01); *C07K 2319/00* (2013.01)

(58) Field of Classification Search
None
See application file for complete search history.

(56) References Cited

U.S. PATENT DOCUMENTS

| | | |
|---|---|---|
| 9,718,886 B2 | 8/2017 | Sahin et al. |
| 2010/0111852 A1 | 5/2010 | Yoshida |
| 2017/0015720 A1 | 1/2017 | Sahin et al. |
| 2020/0291111 A1 | 9/2020 | Conklin et al. |
| 2022/0162299 A1 | 5/2022 | Conklin et al. |
| 2022/0177583 A1 | 6/2022 | Conklin et al. |

FOREIGN PATENT DOCUMENTS

| | | | |
|---|---|---|---|
| CA | 2775373 | A1 | 5/2011 |
| CA | 2786940 | A1 | 9/2011 |
| CA | 2928671 | A1 | 5/2015 |
| WO | WO-2009/087978 | A1 | 7/2009 |
| WO | WO-2012/003956 | A1 | 1/2012 |
| WO | WO-2012/156018 | A1 | 11/2012 |
| WO | WO-2014/075697 | A1 | 5/2014 |
| WO | WO-2014/075788 | A1 | 5/2014 |
| WO | WO-2015/014870 | A1 | 2/2015 |
| WO | WO-2015/069794 | A2 | 5/2015 |
| WO | WO-2017/096163 | A1 | 6/2017 |
| WO | WO-2019/056023 | A2 | 3/2019 |
| WO | WO-2020/191342 | A1 | 9/2020 |
| WO | WO-2020/191344 | A1 | 9/2020 |

OTHER PUBLICATIONS

International Preliminary Report on Patentability for International Application No. PCT/US2020/023981 dated Sep. 16, 2021.
International Search Report and Written Opinion for International Application No. PCT/US2020/023981 dated Jun. 15, 2020.
Arabzadeh et al., "Role of the Cldn6 Cytoplasmic Tail Domain in Membrane Targeting and Epidermal Differentiation In Vivo," Molecular and Cellular Biology, 26(15); 5876-5887 (2006).
Extended European Search Report for EP Application No. 18857242.4 dated Jun. 28, 2022.
Extended European Search Report for EP Application No. 20772537.5 dated Oct. 27, 2022.
Extended European Search Report for EP Application No. 20772686.0 dated Oct. 27, 2022.
International Preliminary Report on Patentability for International Application No. PCT/US2020/023986 notification mailed Sep. 30, 2021.
International Search Report and Written Opinion for International Application No. PCT/US2018/051610 mailed Apr. 15, 2019.
International Search Report and Written Opinion for International Application No. PCT/US2020/023986 dated Jun. 15, 2020.
Sukuzi et al., "Therapeutic antitumor efficacy of monoclonal antibody against Claudin-4 for pancreatic and ovarian cancers", Cancer Science 100(9): 1623-1630 (2009).
Winkler et al., "Molecular Determinants of the Interaction between Clostridium perfringens Enterotoxin Fragments and Claudi n-3", Journal of Biological Chemistry 284(28): 18863-18872 (2009).

(Continued)

*Primary Examiner* — Ruixiang Li
(74) *Attorney, Agent, or Firm* — Foley Hoag LLP; Janine S. Ladislaw; Thi K. Dio

(57) ABSTRACT

The present disclosure provides antigen-binding proteins which bind to Claudin-6 (CLDN6). In various aspects, the antigen-binding proteins bind to Extracellular Loop 2 (EL2) of the extracellular domain of CLDN6. Related polypeptides, nucleic acids, vectors, host cells, and conjugates are further provided herein. Kits and pharmaceutical compositions comprising such entities are moreover provided. Also provided are methods of making an antigen-binding protein and methods of treating a subject having cancer.

59 Claims, 68 Drawing Sheets

Specification includes a Sequence Listing.

(56) References Cited

OTHER PUBLICATIONS

Screnci et al., "Antibody specificity against highly conserved membrane protein Claudin 6 driven by single atomic contact point", Iscience 25.12 (2022).
Almagro et al., "Humanization of antibodies", Frontiers in Bioscience 2008; 13: 1619-33.
Li et al., "Clinical pharmacology of vc-MMAE antibody-drug conjugates in cancer patients: learning from eight first-in-human Phase 1 studies",*MAbs*. 12(1). Taylor & Francis, (2020).
McDermott., "Development and characterization of an anti-Claudin-6 (CLDN6) Antibody-Drug Conjugate for the treatment of CLDN6 positive cancer", UCLA, 30 slides, (2022).
Rudikoff et al., Single amino acid substitution altering antigen-binding specificity, PNAS, USA, 1982, 79: 1979-1983.

CLUSTAL O(1.2.1) multiple sequence alignment

```
SP|P56747|CLD6_HUMAN    MASAGMQILGVVLTLLGWVNGLVSCALPMWKVTAFIGNSIVVAQVVWEGLWMSCVVQSTG 60
SP|O15551|CLD3_HUMAN    -MSMGLEITGTALAVLGWLGTIVCCALPMWRVSAFIGSNIITSQNIWEGLWMNCVVQSTG 59
SP|O14493|CLD4_HUMAN    MASMGLQVMGIALAVLGWLAVMLCCALPMWRVTAFIGSNIVTSQTIWEGLWMNCVVQSTG 60
SP|O95484|CLD9_HUMAN    MASTGLELLGMTLAVLGWLGTLVSCALPLWKVTAFIGNSIVVAQVVWEGLWMSCVVQSTG 60
SP|Q9Z262|CLD6_MOUSE    MASTGLQILGIVLTLLGWVNALVSCALPMWKVTAFIGNSIVVAQMVWEGLWMSCVVQSTG 60
                         * *::*.*::***:  :.:****:*:*****.**::** :*****.******

SP|P56747|CLD6_HUMAN    QMQCKVYDSLLALPQDLQAARALCVIALLVALFGLLVYLAGAKCTTCVEEKDSKARLVLT 120
SP|O15551|CLD3_HUMAN    QMQCKVYDSLLALPQDLQAARALIVVAILLAAFGLLVALVGAQCTNCVQDDTAKAKITIV 119
SP|O14493|CLD4_HUMAN    QMQCKVYDSLLALPQDLQAARALVIISIIVAALGVLLSVVGGKCTNCLEDESAKAKTMIV 120
SP|O95484|CLD9_HUMAN    QMQCKVYDSLLALPQDLQAARALCVIALLLALLGLLVAITGAQCTTCVEDEGAKARIVLT 120
SP|Q9Z262|CLD6_MOUSE    QMQCKVYDSLLALPQDLQAARALCVVTLLIVLLGLLVYLAGAKCTTCVEDRNSKSRLVLI 120
                        *********************: ::: :: **:: .**:* :::  :

SP|P56747|CLD6_HUMAN    SGIVFVISGVLTLIPVCWTAHAIIRDFYNPLVAEAQKRELGASLYLGWAASGLLLLGGGL 180
SP|O15551|CLD3_HUMAN    AGVLFLLAALLTLVPVSWSANTIIRDFYNPVVPEAQKREMGAGLYVGWAAAALQLLGGAL 179
SP|O14493|CLD4_HUMAN    AGVVFLLAGLMVIVPVSWTAHNIIQDFYNPLVASGQKREMGASLYVGWAASGLLLLGGGL 180
SP|O95484|CLD9_HUMAN    AGVILLLAGILVLIPVCWTAHAIIQDFYNPLVAEALKRELGASLYLGWAAAALIMLGGGL 180
SP|Q9Z262|CLD6_MOUSE    SGIIFVISGVLTLIPVCWTAHSIIQDFYNPLVADAQKRELGASLYLGWAASGLLLLGGGL 180
                         *: ::.: ::.::**.*:*  **:*****:*:  ***:**.**:*******   :***

SP|P56747|CLD6_HUMAN    LCCTCPSGGSQGPSHYMARYSTSAPA--ISRGPSEYPTKNYV 220
SP|O15551|CLD3_HUMAN    LCCSCPPREKK-YTATKVVYSAPRSTGPASLGTGYDRKDYV 220
SP|O14493|CLD4_HUMAN    LCCNCPPRTDK-PYSAK--YSAARSAAASN----------YV 209
SP|O95484|CLD9_HUMAN    LCCTCPPPQVERPRGPRLGYSIPS-----RSGASGLDKRDYV 217
SP|Q9Z262|CLD6_MOUSE    LCCACSSGGTQGPRHYMACYSTSVPH---SRGPSEYPTKNYV 219
                        *** *       :      **         **
```

ECD Loop 1    SEQ ID NO:177
ECD Loop 2    SEQ ID NO:2

CLD6_HUMAN=SEQ ID NO:1
CLD3_HUMAN=SEQ ID NO:5
CLD4_HUMAN=SEQ ID NO:6
CLD9_HUMAN=SEQ ID NO:7
CLD6_MOUSE=SEQ ID NO:176

FIG. 5

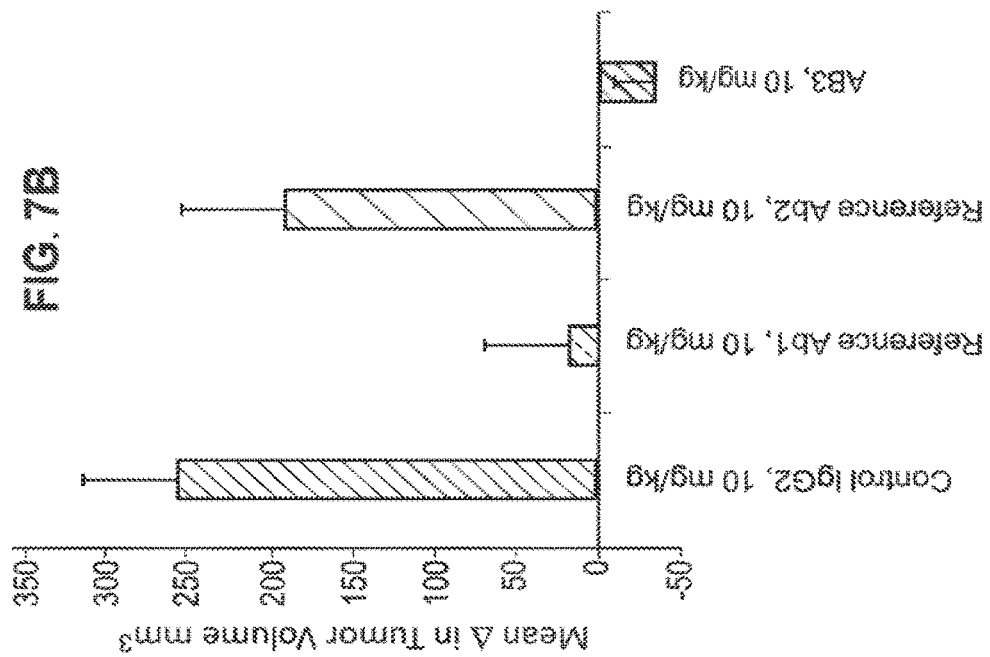
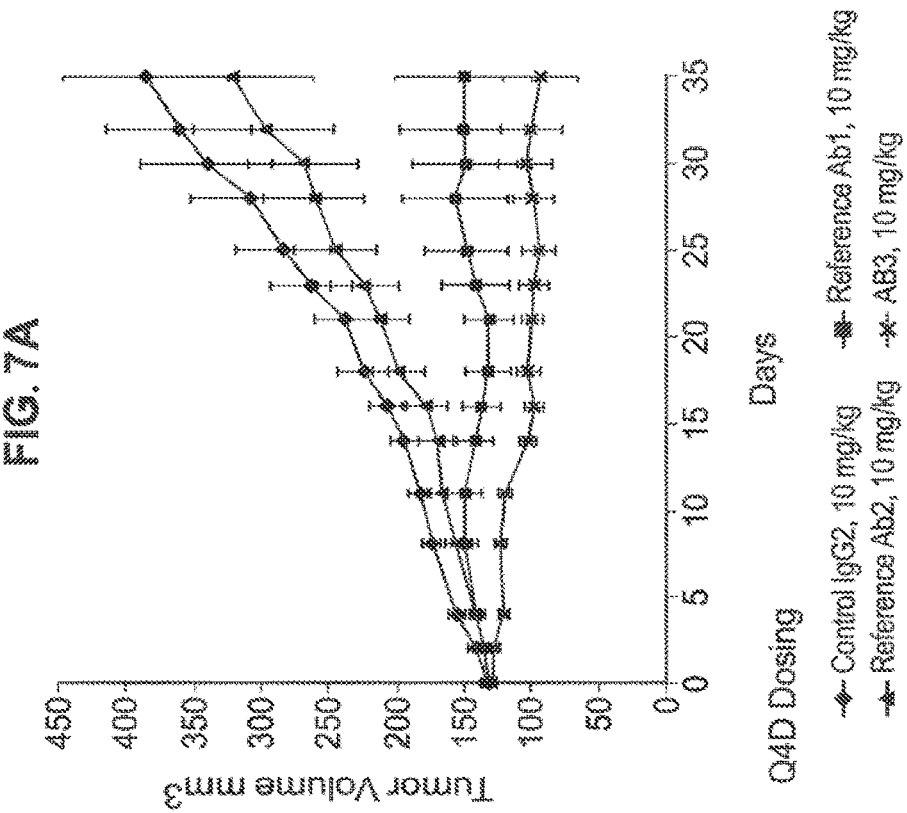

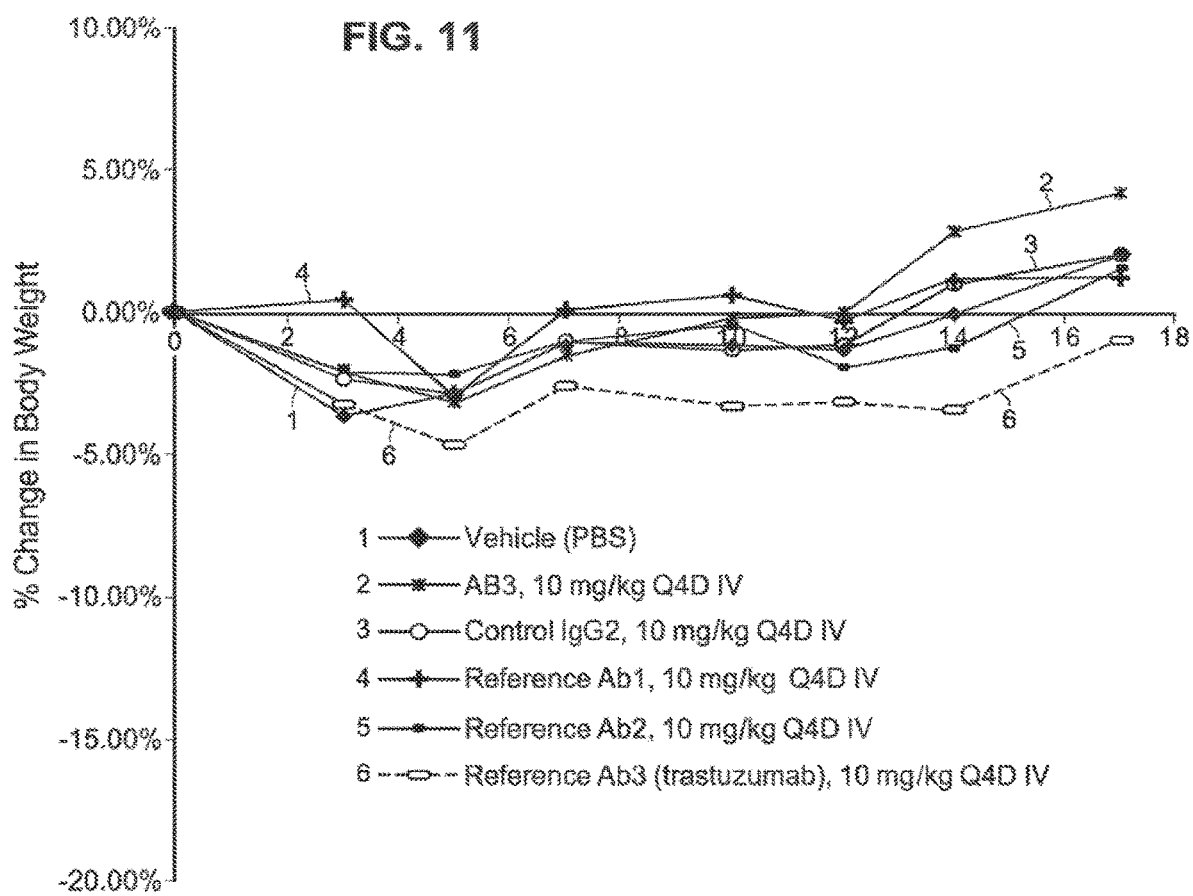

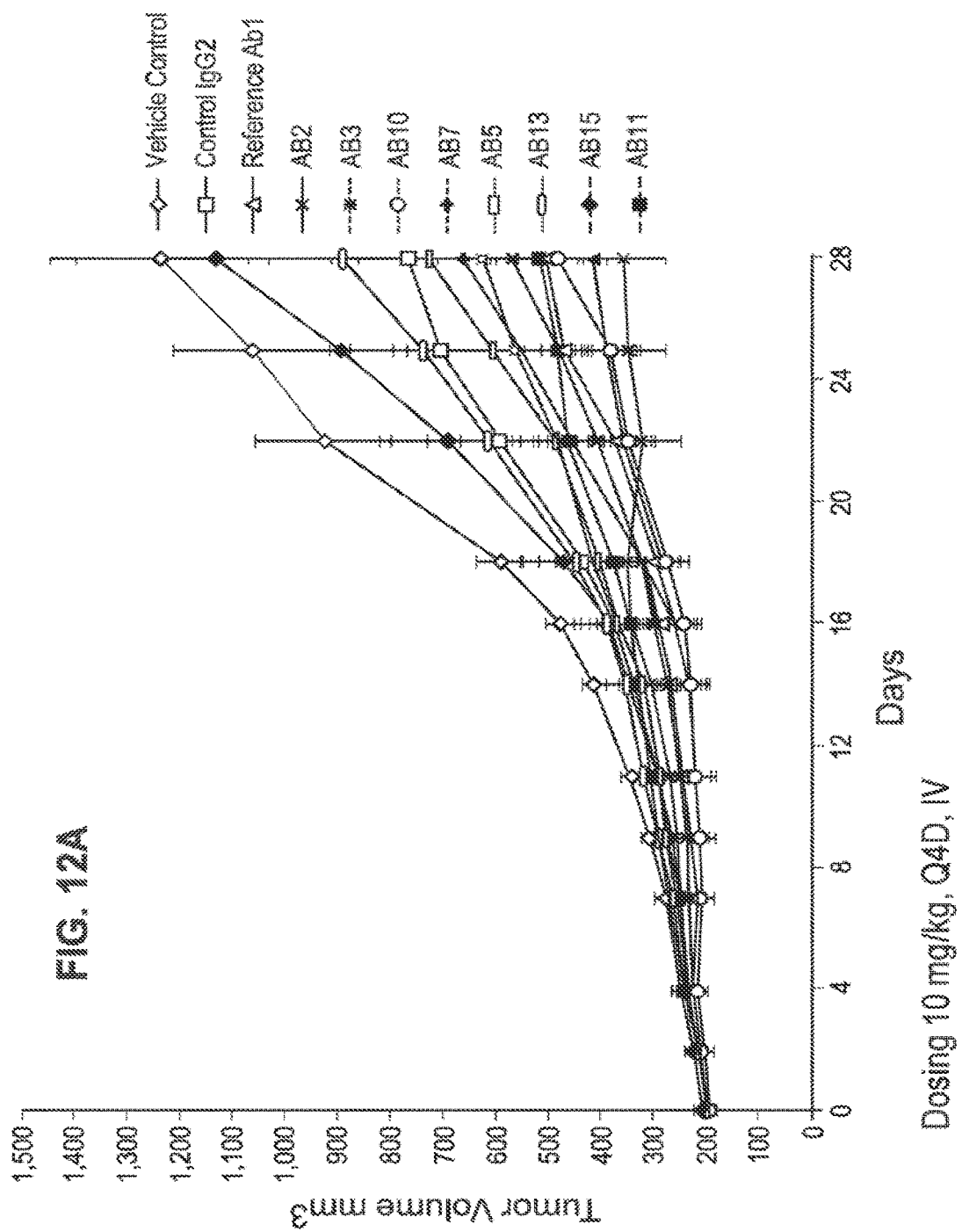

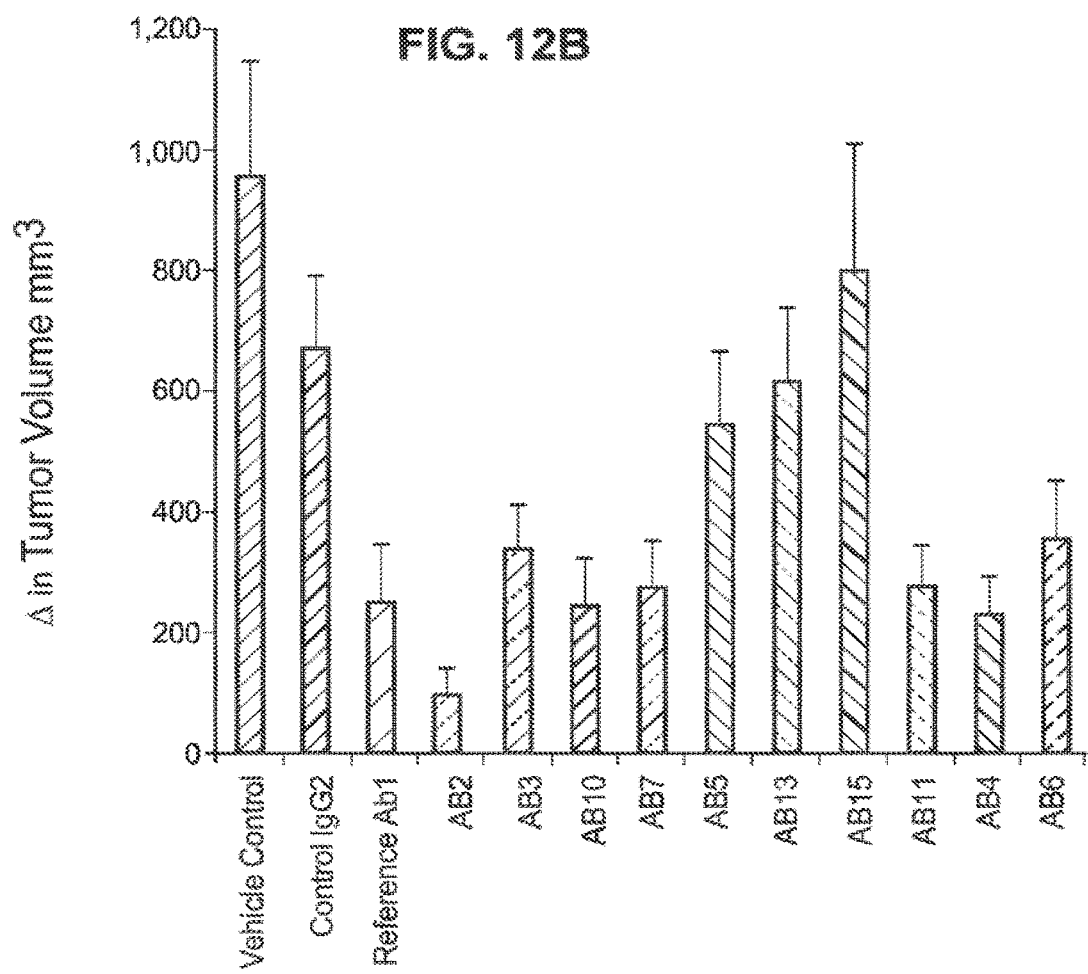

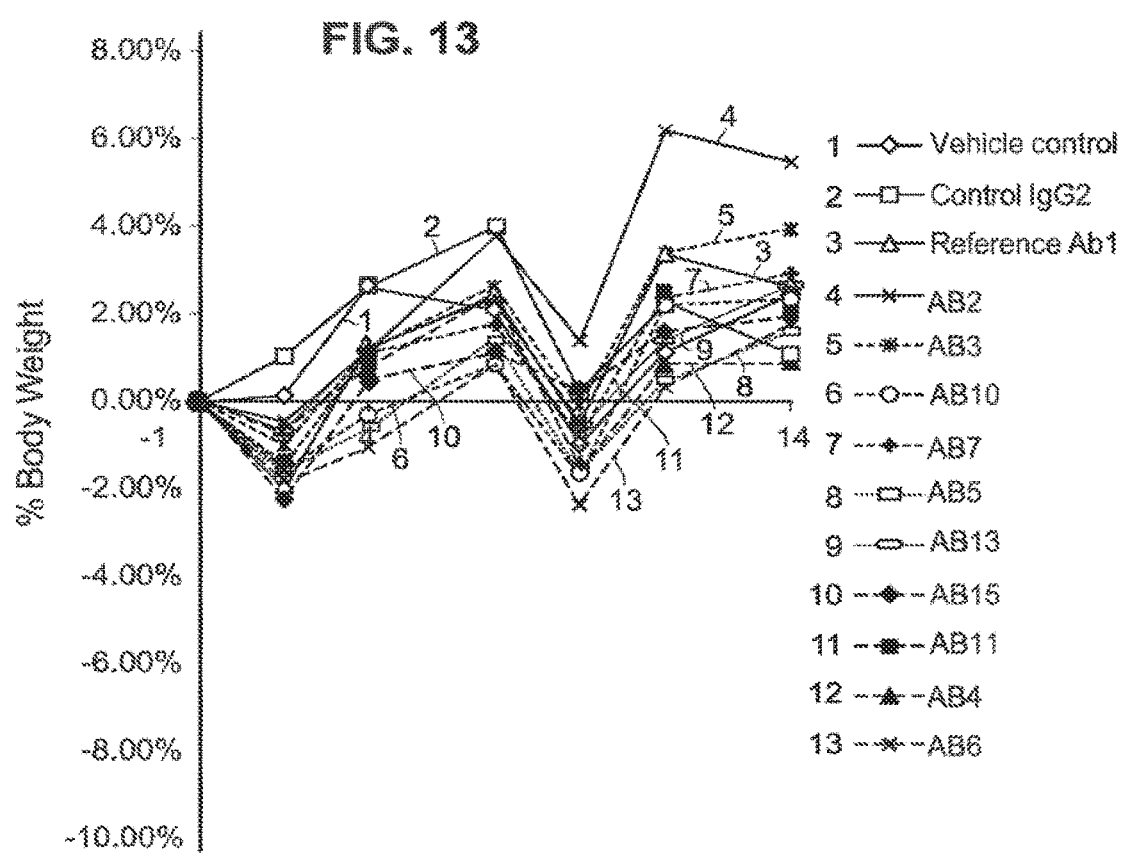

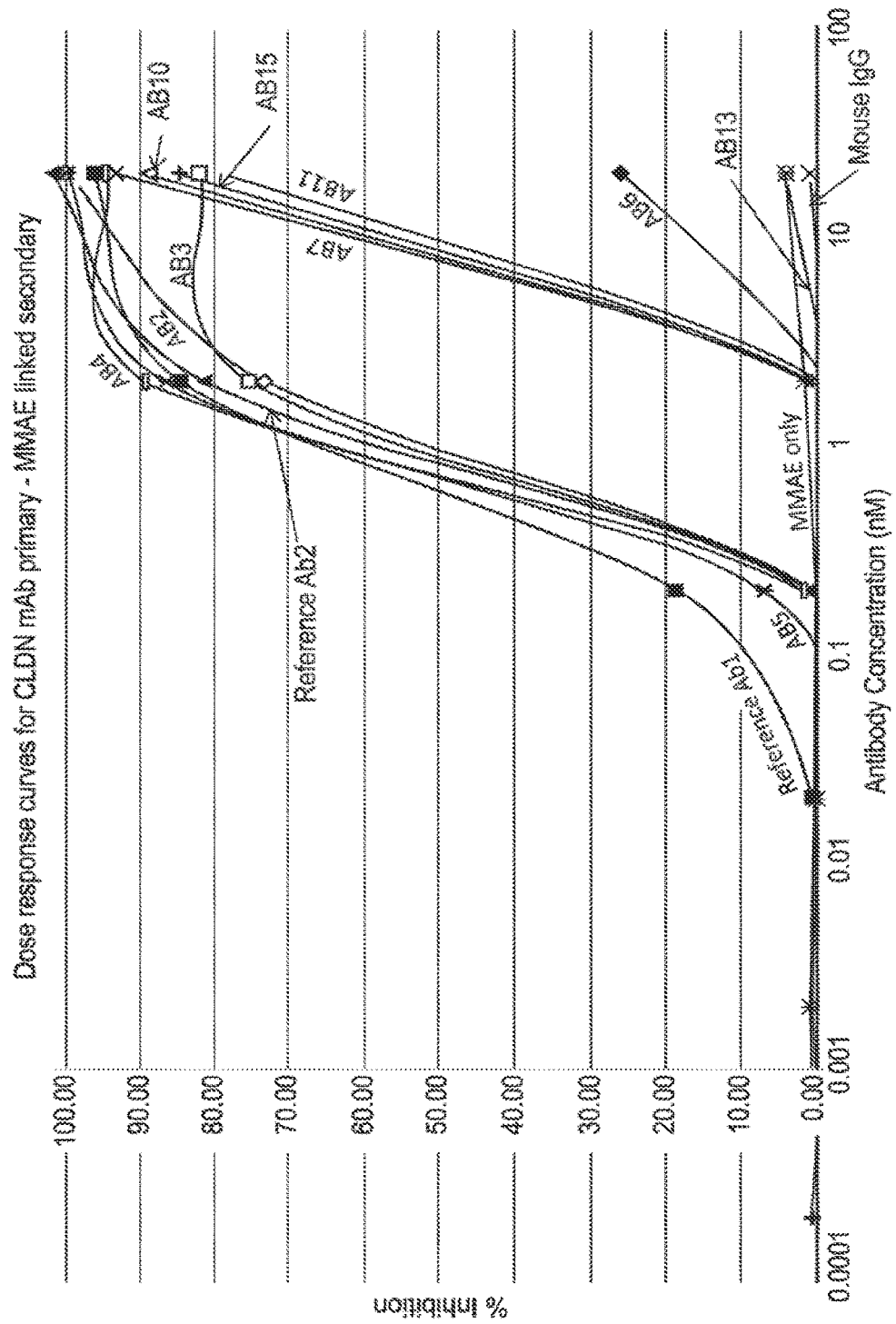

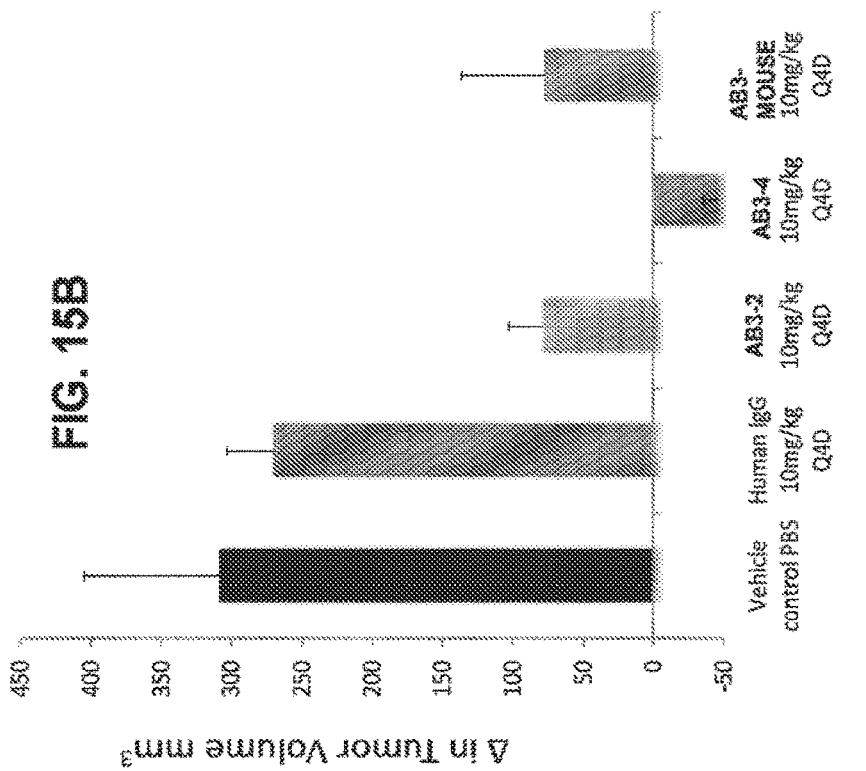
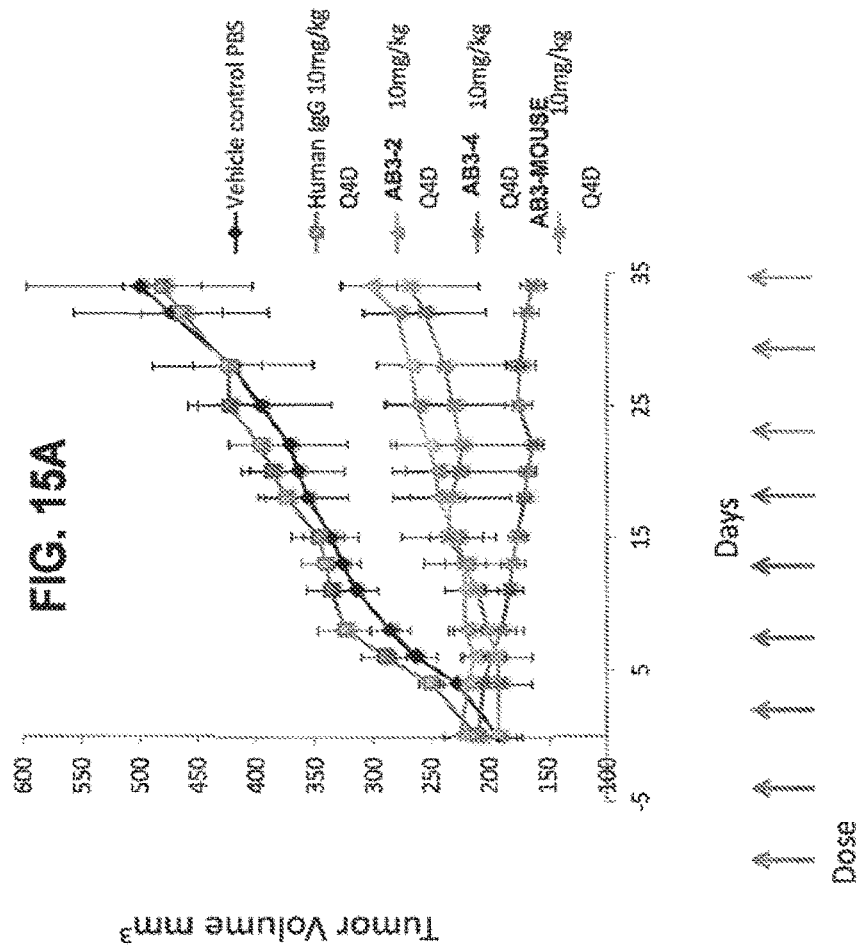

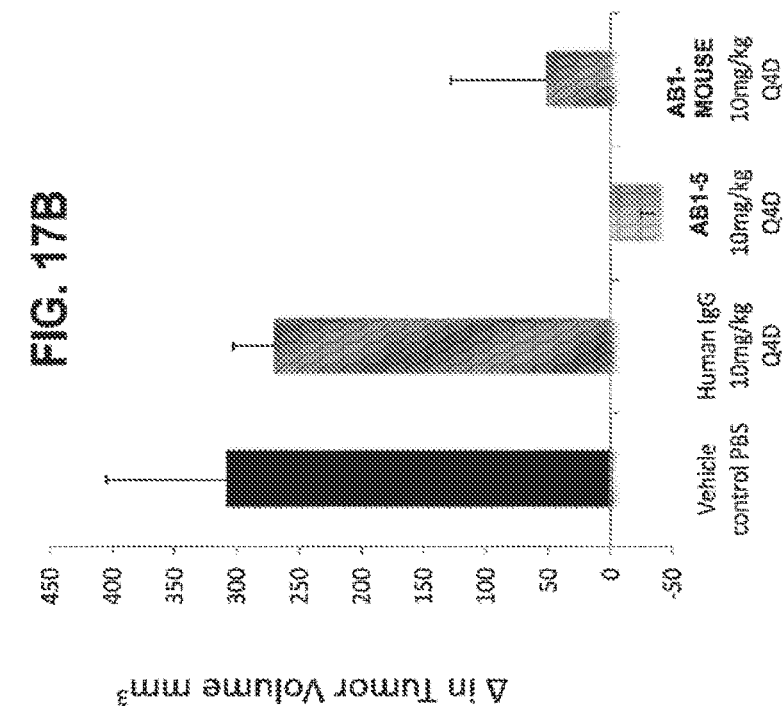
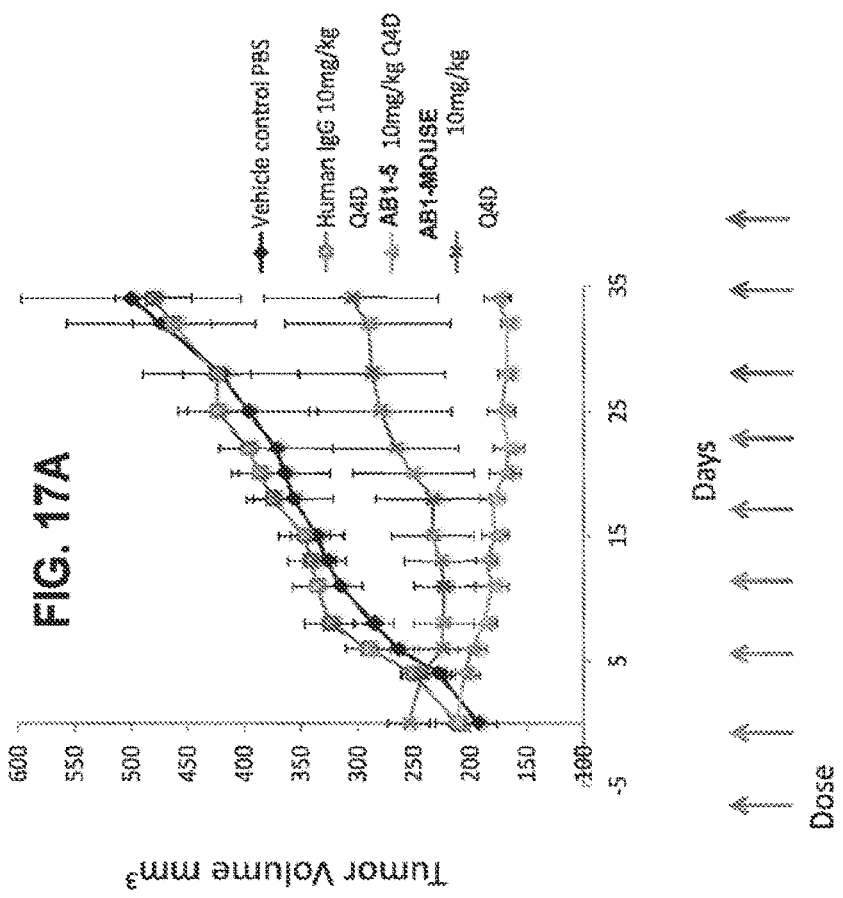

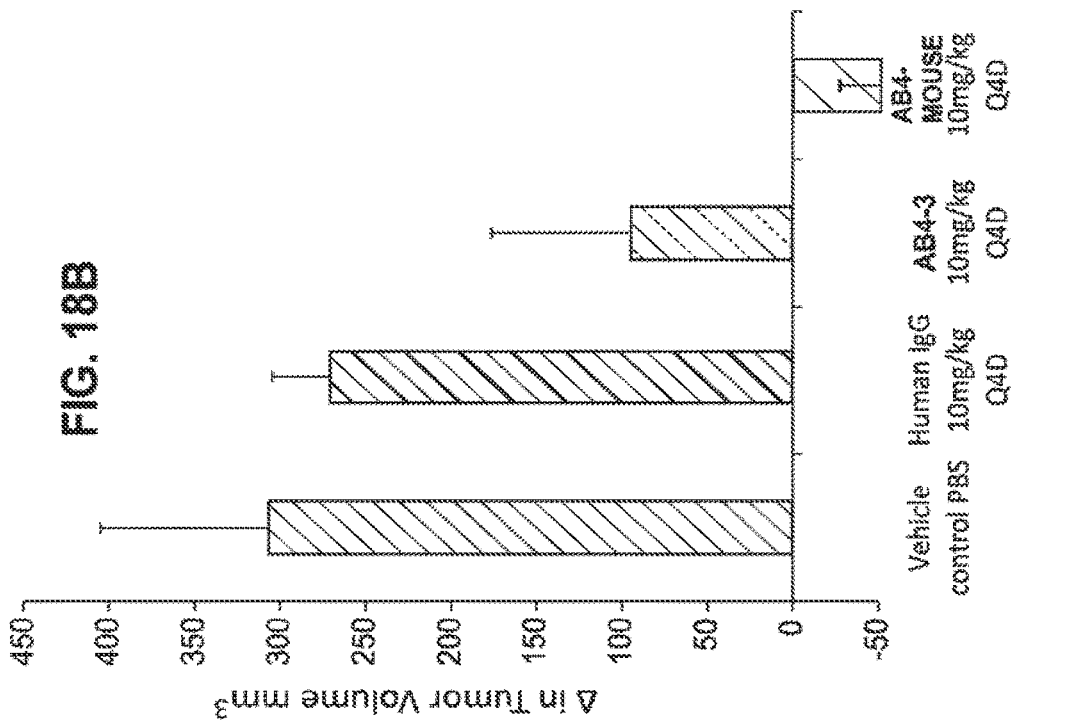
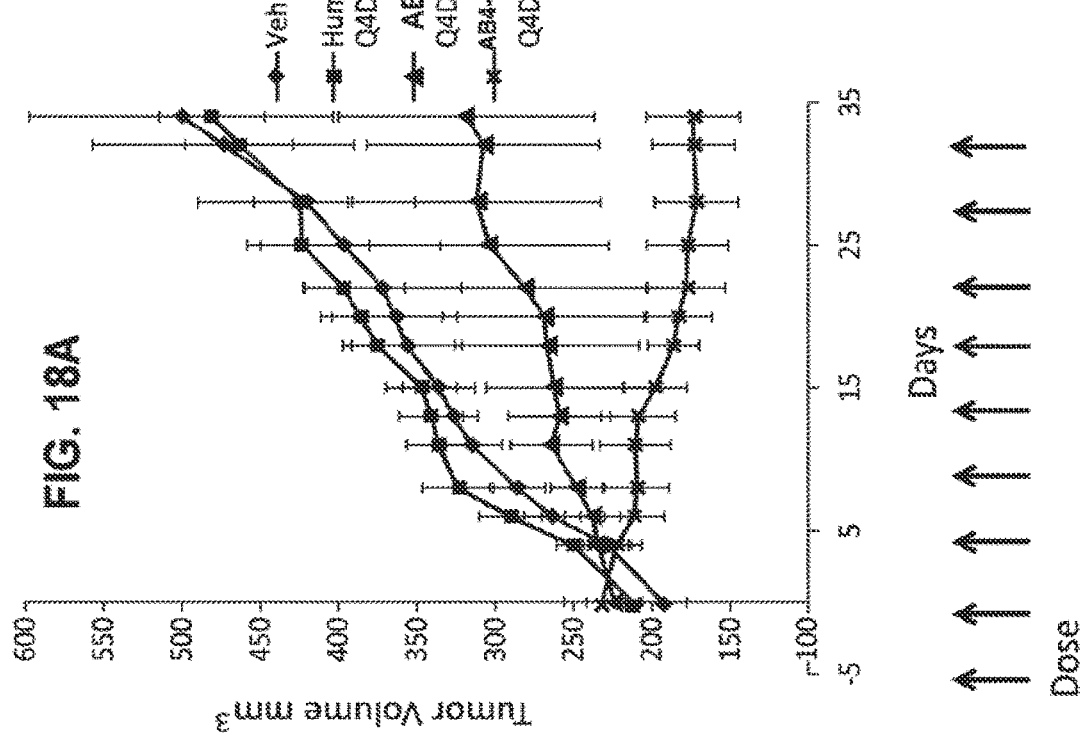

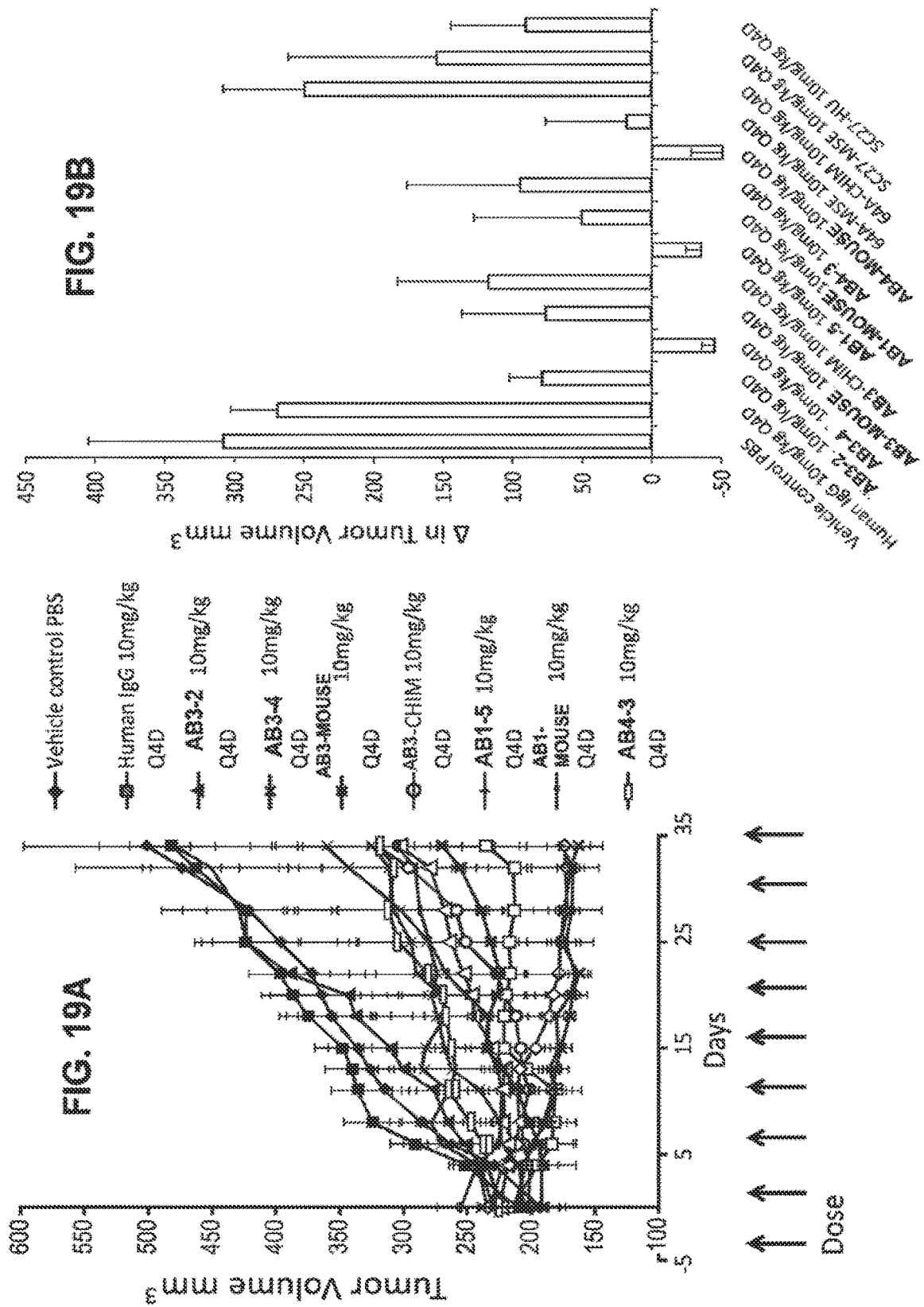

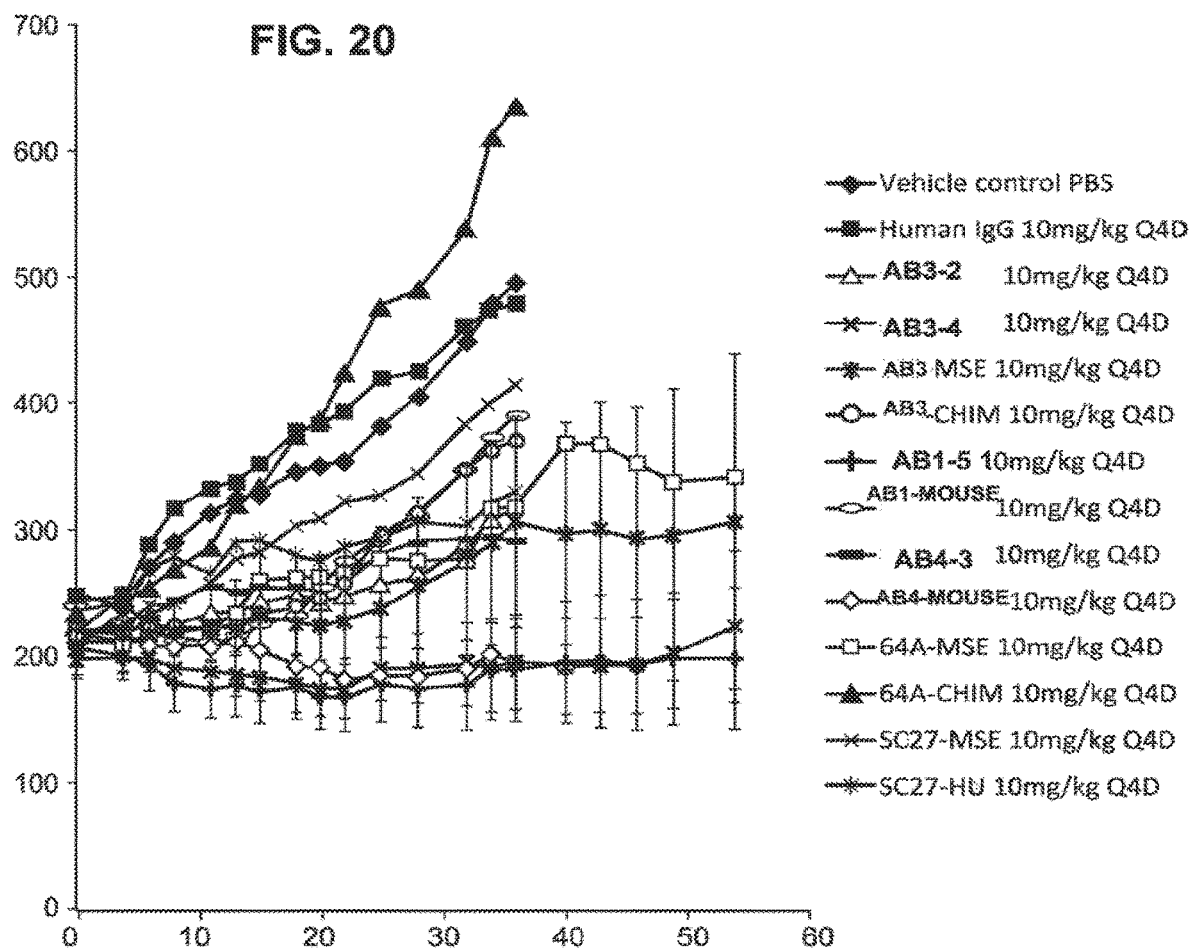

FIG. 22

| | Heavy Chain Variable Region (VH) |
|---|---|
| hAB3 | EVQLLESGGGLVQPGGSMRLSCAASGFTFSNYWMNWVRQAPGKGLEWVAQIRLKSDNYATH YADSVKGRFTISRDDSKNTVYLQMNSLRAEDTGVYYCNDGPPSGSWGQGTLLTVSS |
| S1 | EVQLLESGGGLVQPGGSMRLSCAASGFTFSNYWMNWVRQAPGKGLEWIAQIRLKSDNYATH YTDSVKGRFTISRDDSKRTVYLQMNSLRAEDTGTYYCSDGPPSGSWGQGTLLTVSS |
| S2 | EVQLLESGGGLVQPGGSMRLSCAASGFTFSNYWMNWVRQAPGKGLEWIAQIRLKSDNYATH YADSVKGRFTISRDDSKRTVYLQMNSLRAEDTGTYYCSDGPPSGSWGQGTLLTVSS |
| S3 | EVQLLESGGGLVQPGGSMRLSCAASGFTFSNYWMNWVRQAPGKGLEWIAQIRLKSDNYVTH YTDSVKGRFTISRDDSKRTVYLQMNSLRAEDTGIYYCSDGPPSGSWGQGTLLTVSS |
| S4 | EVQLLESGGGLVQPGGSMRLSCAASGFTFSNYWMNWVRQAPGKGLEWIAQIRLKSDNYATH YTDSVKGRFTISRDDSKSTVYLQMNSLRAEDTGIYYCNDGPPSGSWGQGTLLTVSS |
| S5 | EVQLLESGGGLVQPGGSMRLSCAASGFTFSNYWMNWVRQAPGKGLEWLAQIRLKSDNYATH YTDSVKGRFTISRDDSKRTVYLQMNSLRAEDTGTYYCSDGPPSGSWGQGTLLTVSS |
| S6 | EVQLLESGGGLVQPGGSMRLSCAASGFTFSNYWMNWVRQAPGKGLEWLAQIRLKSDNYVTH YADSVKGRFTISRDDSKRTVYLQMNSLRAEDTGTYYCNDGPPSGSWGQGTLLTVSS |

FIG. 22 (CONT.)

| | Light Chain Variable Region (VL) |
|---|---|
| hAB3 | DIQMTQSPSSLSASVGDRVTITCRISENIYSYLAWYQQKPGKAPKLLVYNAKIL VEGVPSRFSGSGSGTDFTLTISSLQPEDFGTYYCQHHYTVPWTFGQGTKLEIK |
| S1 | DIQMTQSPSSLSASVGDRVTITCRISENIYSYLAWYQQKPGKAPKLLVYNAKIL VEGVPSRFSGSGSGTDFTLTISSLQPEDFGTYYCQHHYTVPWTFGQGTKLEIK |
| S2 | DIQMTQSPSSLSASVGDRVTITCRISENIYSYLAWYQQKPGKAPKLLVYNAKIL VEGVPSRFSGSGSGTDFTLTISSLQPEDFGTYYCQHHYTVPWTFGQGTKLEIK |
| S3 | DIQMTQSPSSLSASVGDRVTITCRISENIYSYLAWYQQKPGKAPKLLVYNAKIL VEGVPSRFSGSGSGTDFTLTISSLQPEDFGTYYCQHHYTVPWTFGQGTKLEIK |
| S4 | DIQMTQSPSSLSASVGDRVTITCRISENIYSYLAWYQQKPGKAPKLLVYNAKIL VEGVPSRFSGSGSGTDFTLTISSLQPEDFGTYYCQHHYTVPWTFGQGTKLEIK |
| S5 | DIQMTQSPSSLSASVGDRVTITCRISENIYSYLAWYQQKPGKAPKLLVYNAKIL VEGVPSRFSGSGSGTDFTLTISSLQPEDFGTYYCQHHYTVPWTFGQGTKLEIK |
| S6 | DIQMTQSPSSLSASVGDRVTITCRISENIYSYLAWYQQKPGKAPKLLVYNAKIL VEGVPSRFSGSGSGTDFTLTISSLQPEDFGTYYCQHHYTVPWTFGQGTKLEIK |

| | |
|---|---|
| hAB1 | QVQLVQSGAEVKKPGASVKMSCKASGYTFTTYTMHWVRQAPGQGLEWIGFINPSSGYTDYA QKFQGRVTLTADKSTSTVYMELSSLRSEDTAVYYCANGDYYVAYWGQGTLVTVSS |
| S7 | QVQLVQSGAEVKKPGASVKMSCKASGYTFTTYTIHWVRQAPGQGLEWIGFINPSSGYTEYA QKFQGRVTLTADKSTSTVYMELSSLRSEDTAVYFCANGDYYVAYWGQGTLVTVSS |
| S8 | QVQLVQSGAEVKKPGASVKMSCKASGYTFTTYTMHWVRQAPGQGLEWIGVINPSSGYTDYA QKFQGRVTLTADKSTSTVYMELSSLRSEDTAVYFCANGDYYVGYWGQGTLVTVSS |
| S9 | QVQLVQSGAEVKKPGASVKMSCKASGYTFTTYTIHWVRQAPGQGLEWIGVINPSSGYTEYA QKFQGRVTLTADKSTSTVYMELSSLRSEDTAVYFCANGDYYVGYWGQGTLVTVSS |
| S10 | QVQLVQSGAEVKKPGASVKMSCKASGYTFTTYTMHWVRQAPGQGLEWIGVINPSSGYTEYA QKFQGRVTLTADKSTSTVYMELSSLRSEDTAVYYCANGDYYVGYWGQGTLVTVSS |
| S11 | QVQLVQSGAEVKKPGASVKMSCKASGYTFTTYTIHWVRQAPGQGLEWIGVINPSSGYTEYA QKFQGRVTLTADKSTSTVYMELSSLRSEDTAVYFCANGDYYVAYWGQGTLVTVSS |
| S12 | QVQLVQSGAEVKKPGASVKMSCKASGYTFTTYTMHWVRQAPGQGLEWIGFINPSSGYTEYA QKFQGRVTLTADKSTSTVYMELSSLRSEDTAVYFCANGDYYVGYWGQGTLVTVSS |

| | Sequence |
|---|---|
| hAB1 | DIQLTQSPSSLSASVGDRVTMTCTASSSVSSTYFHWYQQKPGKAPKLWIYSTSNLASGVPSRFSGSGSGTDYTLTISSMQPEDAATYYCHQYHRSPLTFGQGTKLEIK |
| S7 | DIQLTQSPSSLSASVGDRVTMTCTASSSVSSTYFHWYQQKPGKAPKLWIYSTSNLASGVPSRFSGSGSGTDYTLTISSMQPEDAATYYCHQYHRSPLTFGQGTKLEIK |
| S8 | DIQLTQSPSSLSASVGDRVTMTCTASSSVSSTYFHWYQQKPGKAPKLWIYSTSNLASGVPSRFSGSGSGTDYTLTISSMQPEDAATYYCHQYHRSPLTFGQGTKLEIK |
| S9 | DIQLTQSPSSLSASVGDRVTMTCTASSSVSSTYFHWYQQKPGKAPKLWIYSTSNLASGVPSRFSGSGSGTDYTLTISSMQPEDAATYYCHQYHRSPLTFGQGTKLEIK |
| S10 | DIQLTQSPSSLSASVGDRVTMTCTASSSVSSTYFHWYQQKPGKAPKLWIYSTSNLASGVPSRFSGSGSGTDYTLTISSMQPEDAATYYCHQYHRSPLTFGQGTKLEIK |
| S11 | DIQLTQSPSSLSASVGDRVTMTCTASSSVSSTYFHWYQQKPGKAPKLWIYSTSNLASGVPSRFSGSGSGTDYTLTISSMQPEDAATYYCHQYHRSPLTFGQGTKLEIK |
| S12 | DIQLTQSPSSLSASVGDRVTMTCTASSSVSSTYFHWYQQKPGKAPKLWIYSTSNLASGVPSRFSGSGSGTDYTLTISSMQPEDAATYYCHQYHRSPLTFGQGTKLEIK |

AB3 Heavy Chain: A(H24)SV, G(H26)V, N(H31)D, V(H48)IL, A(H56)V, A(H60)T, S(N76)RK, A(H84)T, I(H89)T, Y(H91)F, A(H93)S, C(H102)W

FIG. 23(CONT.)

AB1 Heavy Chain: S(H31)T, M(H34)IL, Y(H50)FV, T(H57)S, D(H58)E, K(H62)N, D(H72)G, K(H73)R, A(H78)V, S(H82a)N, Y(H98)F, A(H101G)

| | D | E | F | G | H | I | J | K | L | N | O | P | Q |
|---|---|---|---|---|---|---|---|---|---|---|---|---|---|
| | Concentration (mg/ml) | Purity SDS-PAGE (%) | adjusted concentration (mg/ml) | 4.5ug antibody in ul | PBS to make 45ul | HEK293T parental 1.0ug | HEK293T CLDN6 Clone A11 1.0ug | M202- 1.0µg | ARK2- 1.0µg | HEK293T parental 1.0ug GFP | HEK293T CLDN6 Clone A11 1.0ug GFP | M202- 1.0µg GFP | ARK2- 1.0µg GFP |
| 2 | 4.04 | 95 | 3.84 | 1.17 | 43.83 | 790.77 | 159,670.35 | 1,577.77 | 26,871.38 | 1987.72 | 265,609.72 | 3,129.07 | 2,547.29 |
| 3 | 4.86 | 95 | 4.62 | 0.97 | 44.03 | 775.16 | 162,035.50 | 1,031.60 | 38,481.74 | 2,000.32 | 255,311.20 | 3,132.12 | 3,099.45 |
| 4 | 4.19 | 90 | 3.77 | 1.19 | 43.81 | 1,012.63 | 179,399.08 | 1,766.40 | 40,340.11 | 2,035.44 | 268,949.57 | 3,125.73 | 3,264.88 |
| 5 | 4.04 | 90 | 3.64 | 1.24 | 43.76 | 871.63 | 103,300.51 | 1,126.11 | 13,041.68 | 2,099.52 | 256,942.66 | 3,199.44 | 3,037.91 |
| 6 | 4.6 | 90 | 4.14 | 1.09 | 43.91 | 1,182.99 | 172,763.22 | 1,619.41 | 45,508.76 | 2,247.94 | 218,014.63 | 3,097.02 | 3,138.87 |
| 7 | 3.87 | 90 | 3.48 | 1.29 | 43.71 | 1,776.60 | 137,752.47 | 1,911.32 | 30,006.33 | 2,313.18 | 247,752.35 | 3,077.88 | 2,883.57 |
| 8 | 10 | 100 | 10.00 | 0.45 | 44.55 | 588.33 | 107,697.75 | 711.13 | 11,164.56 | 2,342.33 | 231,265.77 | 3,195.62 | 3,260.58 |
| 9 | 7.57 | 95 | 7.19 | 0.63 | 44.37 | 760.56 | 140,464.50 | 859.31 | 30,749.09 | 2,641.52 | 444,449.47 | 2,500.27 | 3,185.14 |
| 10 | 9.03 | 95 | 8.58 | 0.52 | 44.48 | 1,032.63 | 142,324.71 | 4,291.82 | 157,421.48 | 2,865.74 | 454,885.34 | 4,413.56 | 2,906.09 |
| 11 | 3.56 | 95 | 3.38 | 1.33 | 43.67 | 996.33 | 148,768.61 | 1,359.04 | 133,707.53 | 2,806.37 | 468,890.24 | 2,415.04 | 3,467.41 |
| 12 | 9.27 | 90 | 8.34 | 0.54 | 44.46 | 731.67 | 148,025.10 | 1,122.48 | 81,039.93 | 2,882.36 | 466,422.96 | 2,450.33 | 2,685.77 |
| 13 | 3.82 | 95 | 3.63 | 1.24 | 43.76 | 738.75 | 141,975.03 | 813.74 | 109,817.51 | 2,637.38 | 459,943.61 | 2,514.71 | 2,695.76 |
| 14 | 1.58 | 95 | 1.50 | 3.00 | 42.00 | 979.19 | 157,476.89 | 1,208.61 | 110,696.17 | 2,814.89 | 448,763.33 | 2,551.39 | 3,612.99 |
| 15 | 10 | 100 | 10.00 | 0.45 | 44.55 | 1,049.34 | 158,381.25 | 4,056.15 | 161,308.34 | 2,877.20 | 443,566.10 | 4,653.58 | 2,849.07 |

Row 1: AB-S1
Row 2: AB-S2
Row 3: AB-S3
Row 4: AB-S4
Row 5: AB-S5
Row 6: AB-S6
Row 8: humanized AB3-7
Row 9: AB-S7
Row 10: AB-S8
Row 11: AB-S9
Row 12: AB-S10
Row 13: AB-S11
Row 14: AB-S12
Row 15: humanized AB1-11

Column L: cell line artificially overexpressing CLDN6
Column K: cell line with no CLDN6 expression
Column L: cell line with high endogenous expression of CLDN6

| OV90 | | | | | | | | | |
|---|---|---|---|---|---|---|---|---|---|
| nM | AB3-7 | AB-S1 | AB-S2 | AB-S3 | AB-S4 | AB-S5 | AB-S6 | AB1-11 |
| 1000 | 9,389.47 | 100,508.36 | 107,583.14 | 117,619.48 | 41,852.41 | 132,671.44 | 76,606.87 | 72,082.35 |
| 200 | 2,333.88 | 43,482.65 | 53,395.01 | 63,078.33 | 15,902.41 | 73,314.68 | 38,598.51 | 32,455.99 |
| 40 | 1,140.44 | 10,526.93 | 18,070.76 | 19,511.47 | 4,594.96 | 22,485.01 | 12,605.56 | 7,824.04 |
| 8 | 565.19 | 2,354.72 | 3,954.59 | 4,470.79 | 1,359.88 | 5,219.16 | 2,954.23 | 2,146.37 |
| 1.6 | 566.87 | 667.93 | 1,510.81 | 1,044.49 | 514.67 | 1041.22 | 790.82 | 782.7 |
| 0.32 | 393.29 | 474.6 | 536.69 | 482.04 | 431.92 | 557.96 | 466.55 | 451.73 |

| ARK2 | | | | | | | | | |
|---|---|---|---|---|---|---|---|---|---|
| nM | AB3-7 | AB-S1 | AB-S2 | AB-S3 | AB-S4 | AB-S5 | AB-S6 | AB1-11 |
| 1000 | 11,368.22 | 130,296.91 | 133,590.43 | 126,712.81 | 62,464.84 | 140,708.27 | 140,178.29 | 50,496.88 |
| 200 | 3,056.82 | 62,480.67 | 83,339.04 | 83,601.27 | 31,634.82 | 79,817.38 | 54,104.45 | 16,448.77 |
| 40 | 1,636.26 | 25,787.60 | 21,029.91 | 24,569.08 | 6,351.34 | 25,677.71 | 14,613.41 | 3,462.10 |
| 8 | 991.01 | 3,849.71 | 4,842.46 | 4,828.11 | 1,717.35 | 5,558.19 | 3,800.96 | 2,286.95 |
| 1.6 | 538.72 | 1,383.77 | 955.93 | 932.37 | 438.42 | 996.98 | 765.41 | 638.75 |
| 0.32 | 402.37 | 466.3 | 608.48 | 371.86 | 354.47 | 372.11 | 447.6 | 377.07 |

| UMUC4 | | | | | | | | | |
|---|---|---|---|---|---|---|---|---|---|
| nM | AB3-7 | AB-S1 | AB-S2 | AB-S3 | AB-S4 | AB-S5 | AB-S6 | AB1-11 |
| 1000 | 9,837.80 | 41,530.55 | 56,705.72 | 45,256.69 | 35,012.60 | 47,248.78 | 42,258.16 | 117,179.98 |
| 200 | 2,112.03 | 18,694.04 | 20,045.12 | 20,752.72 | 13,455.55 | 19,044.43 | 12,538.34 | 25,700.59 |
| 40 | 1,115.88 | 6,678.95 | 6,965.68 | 7,782.50 | 4,121.95 | 7,079.11 | 4,120.12 | 4,158.48 |
| 8 | 724.24 | 2,333.28 | 2,256.97 | 1,983.08 | 1,298.77 | 2,342.93 | 3,300.30 | 1,605.67 |
| 1.6 | 569.89 | 766.79 | 746.16 | 646.96 | 651.25 | 884.81 | 1,685.97 | 839.48 |
| 0.32 | 604.17 | 639.23 | 506.04 | 532.85 | 518.21 | 491.4 | 1,316.59 | 617.87 |

| AB-S7 | AB-S8 | AB-S9 | AB-S10 | AB-S11 | AB-S12 |
|---|---|---|---|---|---|
| 53,936.25 | 219,778.09 | 227,305.86 | 125,184.17 | 132,526.36 | 83,369.67 |
| 24,011.58 | 165,879.12 | 191,402.29 | 87,858.12 | 85,583.87 | 38,509.78 |
| 9,568.44 | 85,915.42 | 116,775.98 | 50,429.98 | 44,913.69 | 14,607.93 |
| 4,496.10 | 26,639.71 | 48,479.21 | 16,284.85 | 14,736.67 | 4,631.10 |
| 1,912.08 | 6,407.08 | 13,986.99 | 4,685.86 | 4,949.98 | 1,262.03 |
| 586.44 | 834.48 | 2,938.23 | 861.52 | 1,456.35 | 637.98 |

| AB-S7 | AB-S8 | AB-S9 | AB-S10 | AB-S11 | AB-S12 |
|---|---|---|---|---|---|
| 76,677.97 | 249,374.07 | 316,545.05 | 159,908.22 | 145,194.66 | 119,570.21 |
| 46,995.00 | 216,273.29 | 261,296.32 | 124,517.82 | 137,931.27 | 62,341.09 |
| 15,969.78 | 105,970.32 | 136,679.79 | 68,155.49 | 59,411.70 | 22,840.15 |
| 6,294.39 | 42,563.87 | 54,575.38 | 27,535.46 | 20,101.53 | 8,853.51 |
| 2,354.82 | 10,396.67 | 18,443.66 | 7,686.98 | 6,095.07 | 2,082.83 |
| 876.2 | 1,536.34 | 2,993.63 | 2,082.26 | 2,134.09 | 1,313.75 |

| AB-S7 | AB-S8 | AB-S9 | AB-S10 | AB-S11 | AB-S12 |
|---|---|---|---|---|---|
| 37,313.06 | 40,515.64 | 69,054.54 | 35,094.88 | 33,385.97 | 88,517.58 |
| 16,749.15 | 32,938.67 | 35,575.77 | 22,232.27 | 19,859.43 | 37,530.08 |
| 7,974.52 | 16,552.19 | 23,910.57 | 9,941.51 | 12,811.06 | 14,751.85 |
| 3,939.26 | 7,200.07 | 19,833.21 | 6,651.23 | 6,596.29 | 5,035.45 |
| 1,791.21 | 6,216.09 | 11,603.22 | 2,538.59 | 2,765.67 | 1,913.10 |
| 1,441.28 | 719.98 | 1,910.26 | 873.75 | 2,346.83 | 947.24 |

FIG. 34A  Summary table

| Lot# | HIC-DAR | SEC-DAR | D4 (%) | Un-conjugated (%) | Conc. (mg/ml) | Purity (%) | HMWs (%) | Free drug (%) | Endotoxin (EU/mg) | Yield (mg) |
|---|---|---|---|---|---|---|---|---|---|---|
| WBP2227-20191219-23-7-MC-vc-PAB-MMAE-CTRL | 3.92 | - | 33.0 | 6.0 | 5.21 | 97.8 | 2.2 | 1.1 | 0.1 | 65 |
| WBP2227-20200102-23-7-MC-vc-PAB-MMAE-D4 | 4.06 | - | 74.9 | 2.4 | 4.15 | 96.8 | 3.2 | <0.2 | 0.2 | 64 |
| WBP2227-20200109-23-7-MC-GGFG-MMAE-D4 | 3.91 | - | 71.6 | 3.0 | 3.90 | 98.2 | 1.8 | 0.4$^c$ | 0.4$^d$ | 55 |
| WBP2227-20191231-23-7-CL2A-SN38-CTRL$^a$ | - | 4.02 | - | 13.0 | 2.85 | 96.7 | 3.3 | <1$^c$ | 0.1$^d$ | 52 |
| WBP2227-20200113-23-7-CL2A-SN38-D4$^a$ | - | 4.26 | 73.1 | 6.0 | 4.37 | 97.1 | 2.9 | <1$^c$ | 0.1$^d$ | 62 |
| WBP2227-20200010723-23-7-MC-GGFG-Dxd | 3.90 | - | 64.1 | 6.2 | 3.22 | 97.1 | 2.9 | 0.4 | 0.1$^d$ | 65 |
| WBP2227-20200113-23-7-MC-vc-PABDxd$^b$ | 3.90 | - | 61.4 | 10.3 | 4.25 | 97.9 | 2.1 | 1.87 | 0.2 | 66 |

➢ Storage buffer and temperature: 20 mM L-Histidine, pH 5.5; -80°C;
➢ DAR and Unconjugated mAb determined by HIC-HPLC
➢ Concentration determined by Nanodrop One;
➢ Purity and aggregation determined by SEC-HPLC;
➢ Free drug determined by RP-HPLC with C18 column;
➢ Endotoxin level determined by endosafe-PTS 9547.

a. Storage buffer and temperature: 20 mM Succinic Acid, pH 6.0; -80 C;
b. Storage buffer and temperature: 20 mM L-Histidine, pH 6.0; -80°C;
c. Free drug determined by RP-HPLC-Mass Spectrum with C4 column;
d. Endotoxin level determined by kinetic turbidimetric limulus tests.

FIG. 36

| | CLDN6-ADCs | Label in Flow | 0.1μg Ab/Sample | | | | 1μg Ab/Sample | | |
|---|---|---|---|---|---|---|---|---|---|
| | | | Positive Cell Line | Positive Artificial OE Cell Line | Negative Cell Line | | Positive Cell Line | Positive Artificial OE Cell Line | Negative Cell Line |
| | | | UMUC4 | HEK293T CLDN6-mGFP A11 | M202 | | UMUC4 | HEK293T CLDN6-mGFP A11 | M202 |
| 1 | WBP2227-20191219-23-7-MC-vc-PAB-MMAE-CTRL | 23-7-ADC1 | 8,919.55 | 128,043.38 | 927.12 | | 28,670.19 | 306,112.96 | 862.54 |
| 2 | WBP2227-20200102-23-7-MC-vc-PAB-MMAE-D4 | 23-7-ADC2 | 9,446.99 | 126,609.73 | 893.31 | | 26,899.61 | 305,205.73 | 913.31 |
| 3 | WBP2227-20200109-23-7-MC-vc-PAB-MMAE-D4 | 23-7-ADC3 | 8,789.80 | 133,083.24 | 769.02 | | 31,565.36 | 300,903.24 | 726.01 |
| 4 | WBP2227-20191231-23-7-MC-GGFG-MMAE-D4 | 23-7-ADC4 | 9,986.85 | 125,978.13 | 730.25 | | 33,521.28 | 298,078.13 | 934.24 |
| 5 | WBP2227-20200113-23-7-Cl2A-SN38-CTRL | 23-7-ADC5 | 9,153.96 | 134,315.98 | 831.15 | | 34,593.90 | 291,715.98 | 796.68 |
| 6 | WBP2227-20200107-23-7-Cl2A-SN38-D4 | 23-7-ADC6 | 10,469.23 | 120,680.22 | 854.62 | | 32,801.26 | 298,115.76 | 823.43 |
| 7 | WBP2227-20200113-23-7-MC-GGFG-Dxd | 23-7-ADC7 | 10,793.44 | 110,404.22 | 741.90 | | 32,637.46 | 294,403.08 | 939.83 |
| 8 | CLDN6 #23-7 Naked Ab (the Same Batch) | 23-7 | 8,823.06 | 107,260.03 | 744.69 | | 27,278.44 | 295,167.79 | 833.69 |
| 9 | 2nd Ab only | 2nd Ab only | 1,114.73 | 1,242.89 | 778.99 | | 1,114.73 | 1,242.89 | 778.99 |

FIG. 37

| CLDN6 ADCs | KD | | | Expression Level | | Equilibrium Curves | Cells Detached by |
|---|---|---|---|---|---|---|---|
| | KD (nM) | Error% | 95% Confidence Interval (CI) | Expression Level | 95% Confidence Interval (CI) | | |
| WBP2227-20191219-23-7-MC-vc-PAB-MMAE-CTRL | 6.68 | 3.59 | 3.41nM - 34.99nM | 9.843E+05 | 5.714E+05 - 2.220E+06 | 500pM, 10nM | Versene |
| WBP2227-20200102-23-7-MC-vc-PAB-MMAE-D4 | 5.34 | 4.89 | 1.49nM - 17.05nM | 4.324E+05 | 1.112E+05 - 1.447E+06 | 500pM, 10nM | |
| WBP2227-20200109-23-7-MC-GGFG-MMAE-D4 | 1.01 | 2.84 | 0.58nM - 1.66nM | 6.769E+05 | 5.015E+05 - 9.045E+05 | 500pM, 10nM | HEK293T CLDN6-mGFP A11 |
| WBP2227-20191231-23-7-Cl2A-SN38-CTRL | 1.91 | 3.45 | 1.05nM - 3.38nM | 9.892E+05 | 7.024E+05 - 1.456E+06 | 500pM, 10nM | |
| WBP2227-20200113-23-7-Cl2A-SN38-D4 | 2.87 | 4.65 | 1.07nM - 7.74nM | 9.535E+05 | 4.935E+05 - 2.206E+06 | 500pM, 10nM | |
| WBP2227-20200107-23-7-MC-GGFG-Dxd | 3.01 | 3.05 | 1.46nM - 6.47nM | 9.922E+05 | 6.106E+05 - 1.822E+06 | 500pM, 10nM | |
| WBP2227-20200113-23-7-MC-vc-PAB-Dxd | 3.42 | 2.52 | 2.10nM - 5.42nM | 5.176E+05 | 3.440E+05 - 7.643E+05 | 500pM, 10nM | |
| CLDN6 Ab #23-7 (Naked Ab) | 1.13 | 2.57 | 0.53nM - 2.03nM | 4.821E+05 | 3.155E+05 - 6.993E+05 | 500pM, 10nM | |

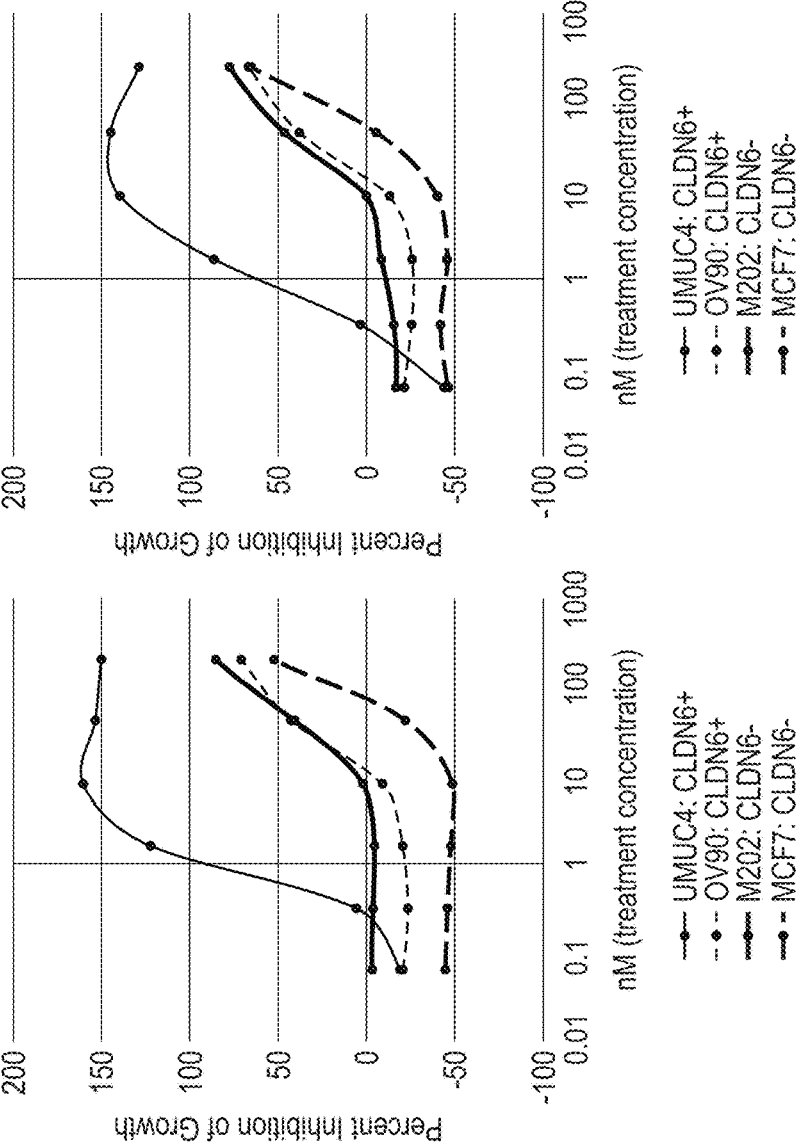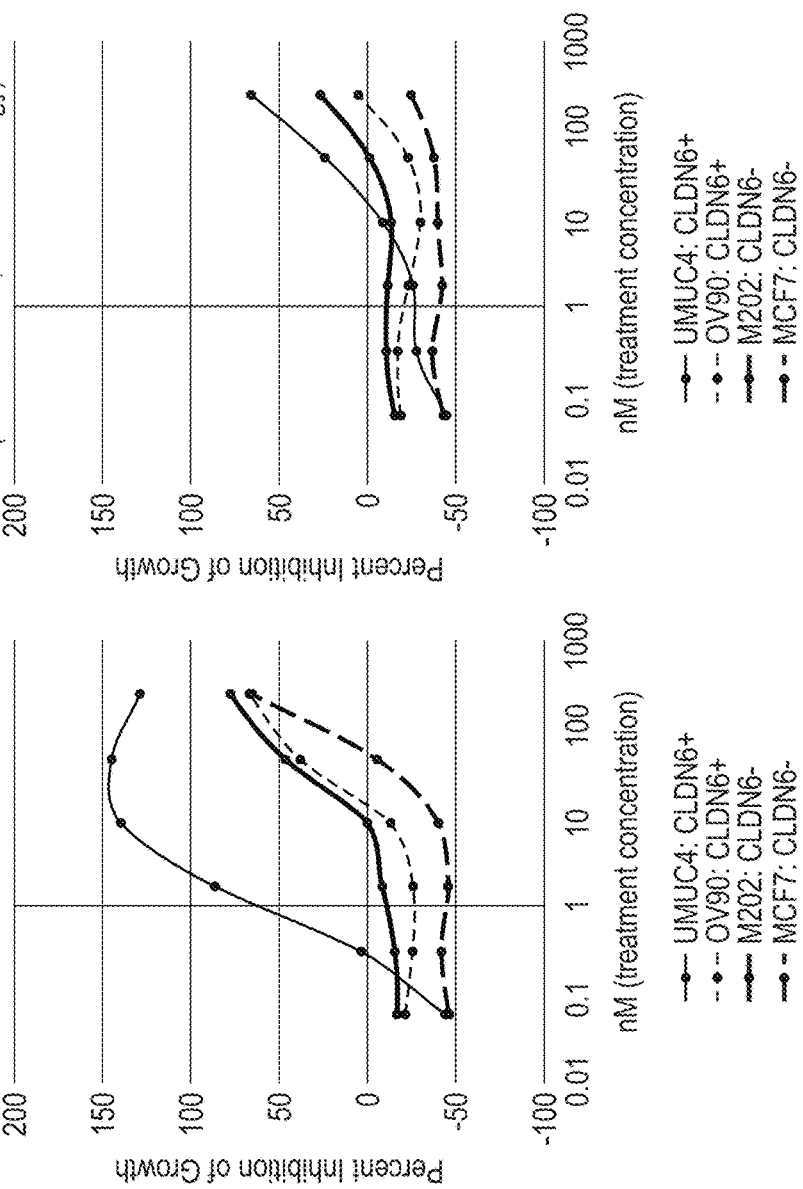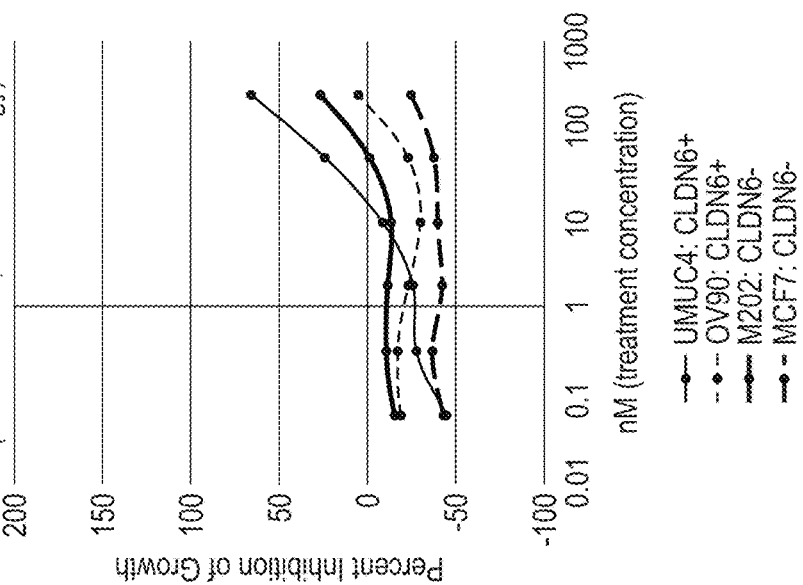

6. MC-GGFG-DXD

7. MC-vc-PAB-DXD

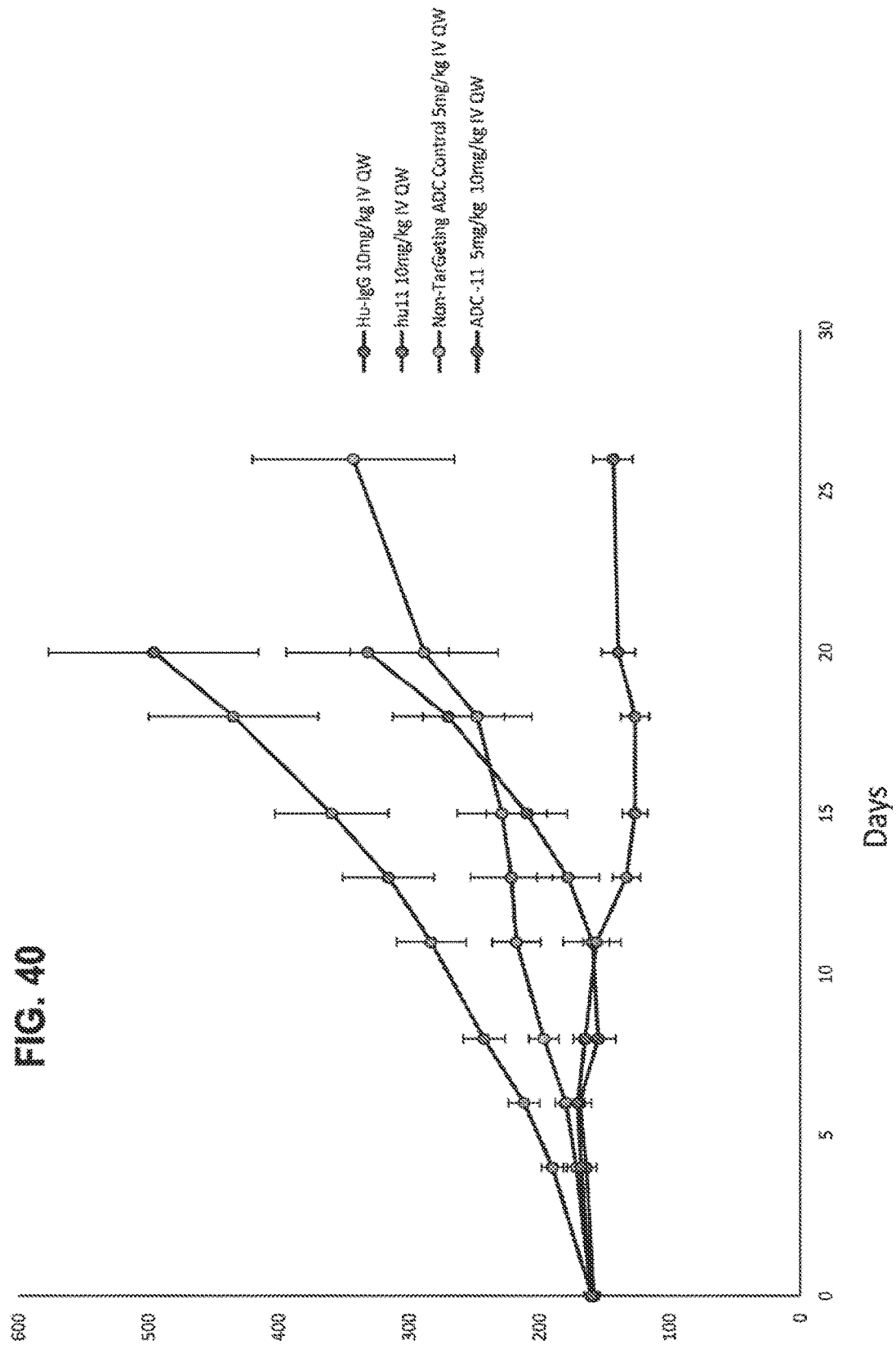

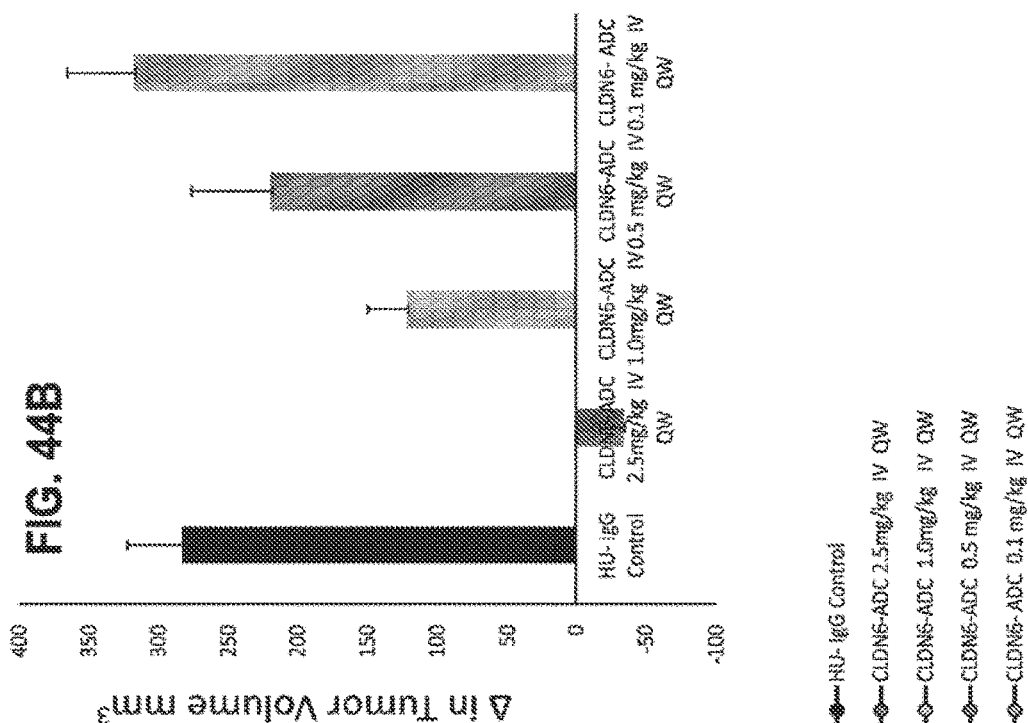
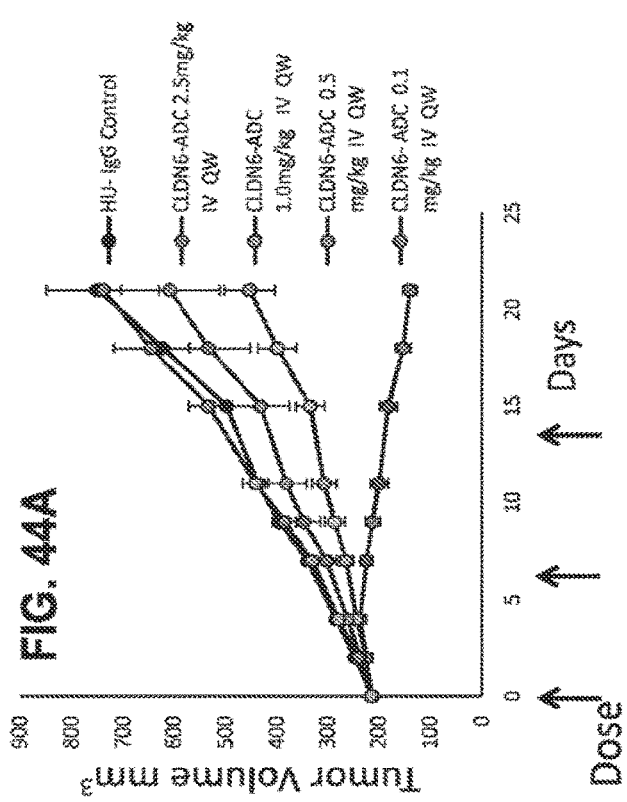
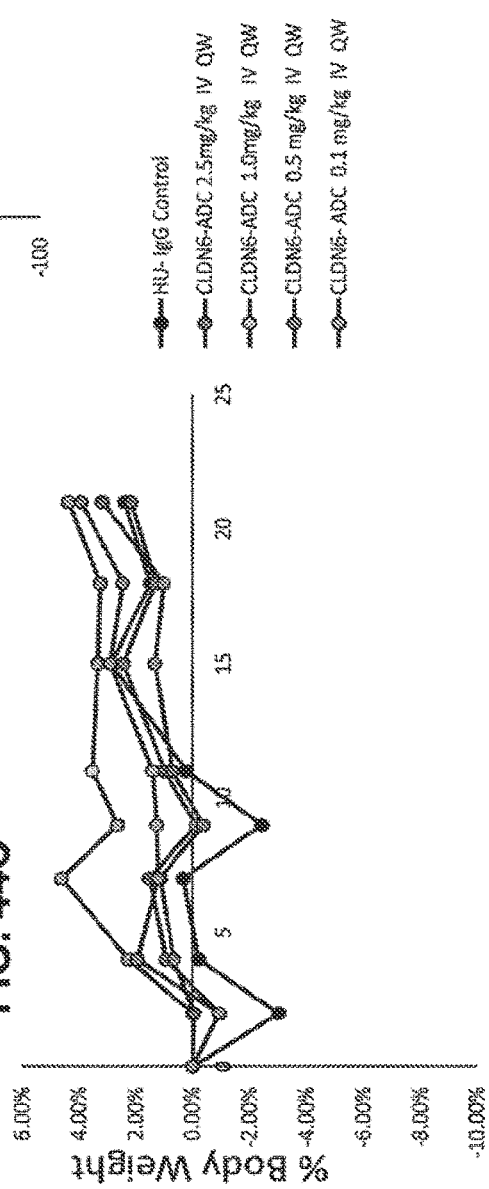

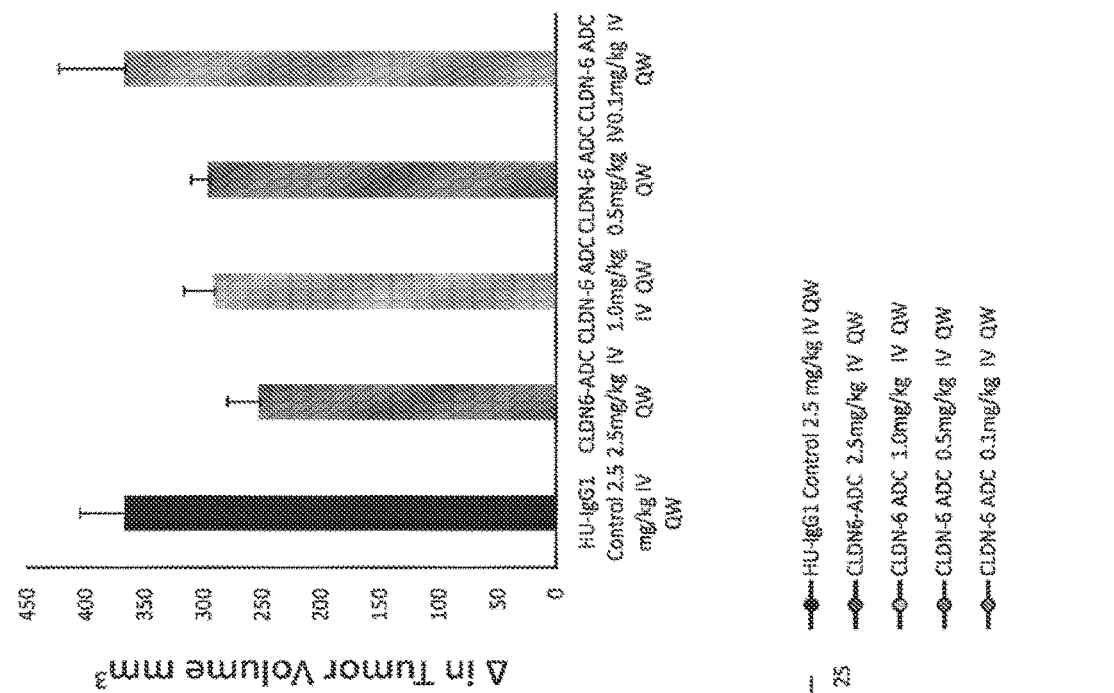
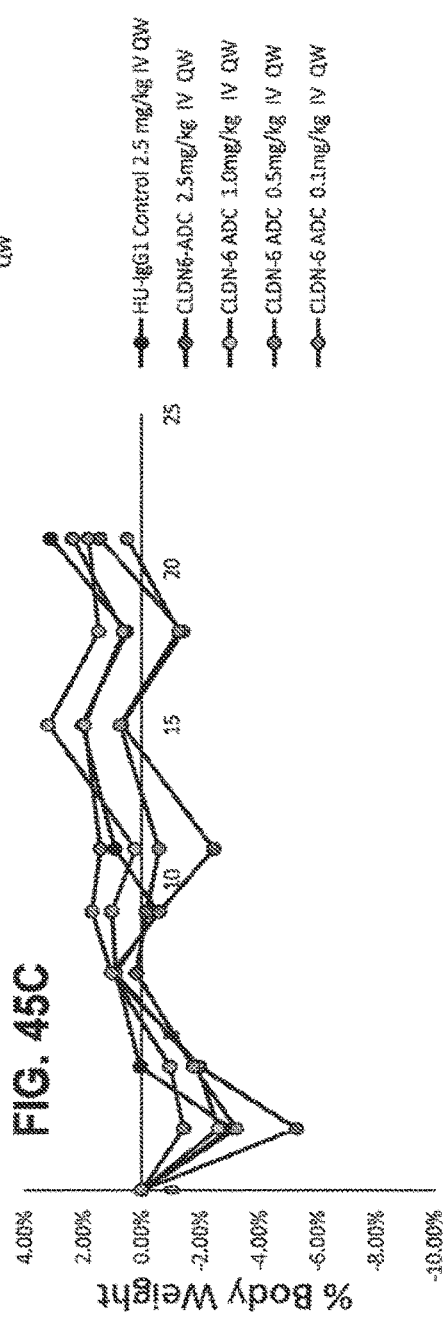
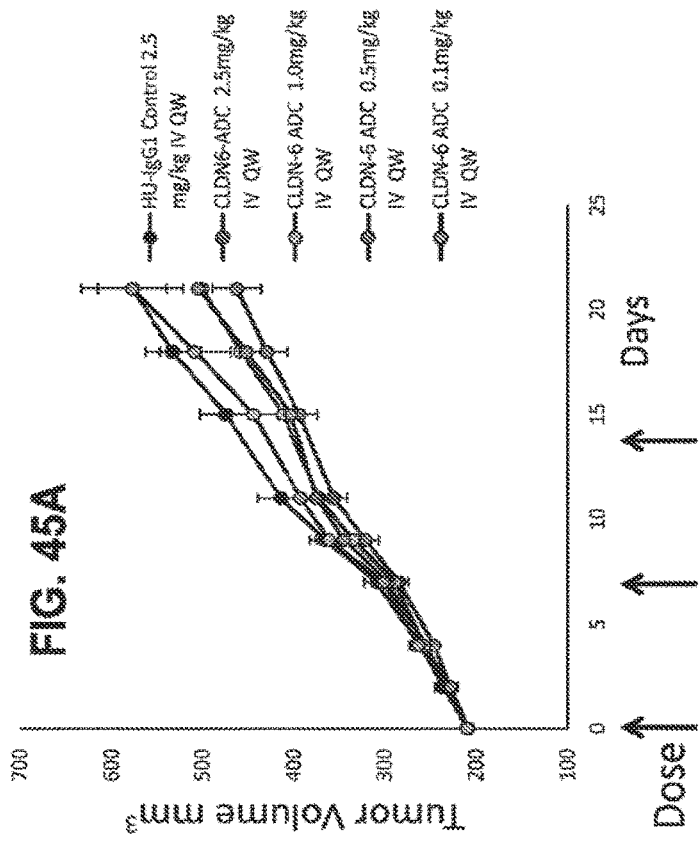

US 12,065,489 B2

CLAUDIN-6 ANTIBODIES AND DRUG CONJUGATES

CROSS-REFERENCE TO RELATED APPLICATIONS

This application is a continuation of U.S. application Ser. No. 17/441,157 filed on Sep. 20, 2021, which is a national-stage filing under 35 U.S.C. § 371 of PCT Application No. PCT/US2020/023981, filed on Mar. 20, 2020, which claims the benefit of priority to U.S. Provisional Application No. 62/821,391, filed on Mar. 20, 2019, the entire contents of each of said applications are incorporated herein in their entirety by this reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: the text file named "UCH_21125_Sequence_Listing.txt", which was created on Mar. 20, 2019 and is 338,715 bytes in size.

BACKGROUND

Antibodies constitute powerful therapeutic agents characterized by limited side effects due to their ability to specifically target a distinct antigen on a cell, bacteria, virus, or toxin. In 1986, the first therapeutic monoclonal antibody, Orthoclone OKT3, was introduced into the market. Since then, this class of biopharmaceutical products has significantly grown. In late 2014, forty-seven monoclonal antibody products had received approval in the U.S. or Europe for the treatment of a variety of diseases, including cancer and inflammatory, cardiovascular, respiratory, and infectious diseases.

More than a dozen monoclonal antibodies are currently approved by the U.S. Food and Drug Administration to treat cancers. Among these agents are alemtuzumab (Campath®), which is indicated for chronic lymphocytic leukemia (CLL), and trastuzumab (Herceptin®), which is used for treating breast cancer. Some antibodies are labeled with chemotherapeutic drugs, including, for example, brentuximab vedotin (Adcetris®) and Ado-trastuzumab emtansine (Kadcyla®). Other antibody products, such as blinatumomab (Blincyto) are designed to recognize and bind to two different antigens. Despite the commercial availability of such antibody products, the current cancer incidence and cancer deaths remain high. It has been reported that cancer incidence is greater than 450 per 100,000 men and women per year, and cancer mortality is just over 170 per 100,000 men and women per year.

SUMMARY

Provided herein are antigen-binding proteins which bind to Claudin-6 (CLDN6). In various aspects, the antigen-binding protein of the present disclosure binds to a human CLDN6 and optionally binds to a mouse CLDN6. In various aspects, the antigen-binding protein binds to the extracellular domain (ECD) of CLDN6. In various instances, the antigen-binding protein binds to Extracellular Loop 2 (EL2) of the ECD of CLDN6. In various aspects, the antigen-binding protein binds to EL2 and does not bind to Extracellular Loop 1 (EL1) of the ECD of CLDN6. In various instances, the antigen binding protein binds to additional members of the human Claudin family, including, for example, Claudin-3 (CLDN3), Claudin-4 (CLDN4), and Claudin-9 (CLDN9). In various instances, the antigen binding protein binds to CLDN6 and at least one of CLDN4 and CLDN9. In various instances, the antigen binding protein binds to CLDN6 and does not bind to any other member of the Claudin family. In various aspects, the antigen binding protein binds to CLDN6 endogenously expressed by human ovarian cancer cells, e.g., OVCA429 cells, and exhibits an IC50 less than about 1200 nM in a FACS affinity assay with OVCA429 cells. In various instances, the antigen-binding proteins of the present disclosure inhibit tumor growth in a subject, e.g., a human, without any other moiety attached to the antigen-binding protein.

In various aspects, an antigen-binding protein comprises (a) a heavy chain CDR1 amino acid sequence of SEQ ID NO: 504 or SEQ ID NO: 507, or a variant sequence thereof which differs by only one or two amino acids or which has at least or about 70% sequence identity; (b) a heavy chain CDR2 amino acid sequence of: SEQ ID NOs: 505 or SEQ ID NO: 508, or a variant sequence thereof which differs by only one or two amino acids or which has at least or about 70% sequence identity; (c) a heavy chain CDR3 amino acid sequence of SEQ ID NO: 506 or SEQ ID NO: 509, or a variant sequence thereof which differs by only one or two amino acids or which has at least or about 70% sequence identity; (d) a light chain CDR1 amino acid sequence of: SEQ ID NO: 449 or SEQ ID NO: 476, or a variant sequence thereof which differs by only one or two amino acids or which has at least or about 70% sequence identity; (e) a light chain CDR2 amino acid sequence of: SEQ ID NO: 450 or SEQ ID NO: 477, or a variant sequence thereof which differs by only one or two amino acids or which has at least or about 70% sequence identity; (f) light chain CDR3 amino acid sequence of: SEQ ID NO: 451 or SEQ ID NO: 454, or a variant sequence thereof which differs by only one or two amino acids or which has at least or about 70% sequence identity; and/or (g) a combination of any two or more of (a)-(f).

In various aspects, an antigen-binding protein comprises (a) a heavy chain variable region amino acid sequence of any one of SEQ ID NOs: 490-503, or a heavy chain variable region amino acid sequence labeled as S1-S12 in FIG. 22, or a variant sequence thereof which differs by only one or two amino acids or which has at least or about 70% sequence identity; or (b) a light chain variable region amino acid sequence of any one of SEQ ID NOs: 380-383, 388-390, 479, and 481, or a light chain variable region amino acid sequence labeled as S1-S12 in FIG. 22, or a variant sequence thereof which differs by only one or two amino acids or which has at least or about 70% sequence identity; or both (a) and (b).

In various aspects, an antigen binding protein comprises a pair of amino acid sequences selected from the group consisting of: (a) SEQ ID NOs: 389 and 490; (b) SEQ ID NOs: 389 and 491; (c) SEQ ID NOs: 389 and 492; (d) SEQ ID NOs: 389 and 493; (e) SEQ ID NOs: 389 and 494; (f) SEQ ID NOs: 389 and 495; (g) SEQ ID NOs: 383 and 496; (h) SEQ ID NOs: 383 and 497; (i) SEQ ID NOs: 383 and 498; (j) SEQ ID NOs: 383 and 499; (k) SEQ ID NOs: 383 and 500; (l) SEQ ID NOs: 383 and 501; (m) SEQ ID NOs: 383 and 503; (n) SEQ ID NOs: 389 and 502; (o) the heavy chain variable region sequence labeled as S1 in FIG. 22 and the light chain variable region sequence labeled as S1 in FIG. 22; (p) the heavy chain variable region sequence labeled as S2 in FIG. 22 and the light chain variable region sequence labeled as S2 in FIG. 22; (q) the heavy chain variable region sequence labeled as S3 in FIG. 22 and the light chain variable region sequence labeled as S3 in FIG. 22; (r) the heavy chain variable region sequence labeled as S4 in FIG. 22 and the light chain variable region sequence labeled as S4 in FIG. 22; (s) the heavy chain variable region sequence labeled as S5 in FIG. 22 and the light chain variable region sequence labeled as S5 in FIG. 22; (t) the heavy chain variable region sequence labeled as S6 in FIG. 22 and the light chain variable region sequence labeled as S6 in FIG. 22; (u) the heavy chain variable region sequence labeled as S7 in FIG. 22 and the light chain variable region sequence labeled as S7 in FIG. 22; (v) the heavy chain variable region sequence labeled as S78 in FIG. 22 and the light chain variable region sequence labeled as S8 in FIG. 22; (w) the heavy chain variable region sequence labeled as S89 in FIG. 22 and the light chain variable region sequence labeled as S9 in FIG. 22; (x) the heavy chain variable region sequence labeled as S910 in FIG. 22 and the light chain variable region sequence labeled as S10 in FIG. 22; (y) the heavy chain variable region sequence labeled as S11 in FIG. 22 and the light chain variable region sequence labeled as S11 in FIG. 22; or (z) the heavy chain variable region sequence labeled as S12 in FIG. 22 and the light chain variable region sequence labeled as S12 in FIG. 22.

In various instances, an antigen-binding protein comprises (a) a heavy chain variable region amino acid sequence set forth as SEQ ID NO: 510 or 513 or in FIG. 23 or FIG. 25, or a variant sequence thereof which differs by only one or two amino acids or which has at least or about 70% sequence identity; or (b) a light chain variable region amino acid sequence set forth as SEQ ID NO: 511 or 512 or in FIG. 24 or FIG. 26, or a variant sequence thereof which differs by only one or two amino acids or which has at least or about 70% sequence identity; or (c) both (a) and (b).

In various instances, an antigen-binding protein comprises a pair of amino acid sequences wherein the pair comprises (a) a heavy chain variable region amino acid sequence set forth as SEQ ID NO: 510 and a light chain variable region amino acid sequence set forth as SEQ ID NO: 511, or a variant sequence thereof which differs by only 1-5 amino acids or which has at least or about 70% sequence identity; optionally, wherein the 1-5 amino acids which differ are as shown in FIG. 23 for the heavy chain or FIG. 24 for the light chain, or (b) a heavy chain variable region amino acid sequence set forth as SEQ ID NO: 513 and a light chain variable region amino acid sequence set forth as SEQ ID NO: 512, or a variant sequence thereof which differs by only 1-5 amino acids or which has at least or about 70% sequence identity; or optionally, wherein the 1-5 amino acids which differ are as shown in FIG. 25 for the heavy chain or FIG. 26 for the light chain.

Further provided herein are antigen-binding proteins conjugated to a heterologous moiety (e.g., conjugated to any chemotherapeutic agent, drug or toxic moiety) inhibit tumor growth in a subject, e.g., a human. In various instances, the conjugated antigen-binding protein is a monoclonal antibody. In various instances, the antibody is conjugated to an agent that alters the microtubule dynamics, e.g., MMAE. In various instances, the conjugate comprises a cleavable linker, e.g., MC-VC-PAB. In various aspects, the conjugate is a homogeneous conjugate or a heterogeneous conjugate. In various aspects, the heterologous moiety is conjugated at a specific site of the antigen-binding protein.

In various aspects, the antigen-binding protein binds to CLDN6 expressed by human cancer cells. In various aspects, the antigen-binding protein inhibits a binding interaction between human CLDN6 and a reference anti-CLDN6 antibody. Without being bound to a particular theory, the inhibiting action of the antigen-binding proteins provided herein allow such entities to be useful in methods of reducing tumor growth and treating a subject with a tumor or cancer. As further discussed herein, in various aspects, the antigen-binding protein is an antibody, antigen-binding antibody fragment thereof, or antibody protein product.

The present disclosure also provides antigen-binding proteins comprising at least 3, 4, 5, or all amino acid sequences of a specified group of amino acid sequences. In various aspects, the antigen-binding proteins comprise at least 3, 4, 5, or 6 complementary determining region (CDR) amino acid sequences of CLDN6 antibodies disclosed herein.

The present disclosure further provides antigen-binding proteins comprising amino acid sequences as detailed herein. In various aspects, the antigen-binding protein comprises an amino acid sequence of any one of SEQ ID NOs: 490-512, or an amino acid sequence as shown in any one of FIG. 22-FIG. 26, or a combination thereof, as further described herein.

Related polypeptides, nucleic acids, vectors, host cells, and conjugates are further provided herein. Kits and pharmaceutical compositions comprising such entities are moreover contemplated.

Also provided are methods of making an antigen-binding protein. In various embodiments, the method comprises culturing a host cell comprising a nucleic acid encoding a antigen-binding protein or a polypeptide as described herein so as to express the antigen-binding protein or polypeptide.

Methods of treating a subject having cancer are additionally provided herein. In various embodiments, the method comprises administering to the subject the pharmaceutical composition of the present disclosure in an amount effective for treating the cancer in the subject.

Also provided are methods of treating a subject with a CLDN6-expressing cancer comprising administering to the subject a pharmaceutical composition described herein. Further contemplated is a method of inhibiting tumor growth in a subject, comprising administering to the subject a pharmaceutical composition described herein.

A method of reducing tumor size in a subject, or preventing the recurrence of cancer in a subject comprising administering to the subject a pharmaceutical composition described herein.

Also provided herein is a method of treating cancer in a subject diagnosed to be a low over-expresser of CLDN6, comprising administering to the subject a pharmaceutical composition described herein.

In various embodiments, the administering induces apoptosis in tumor cells, for example in cells expressing CLDN6. In various embodiments, the administration induces antibody-dependent cell-mediated cytotoxicity (ADCC) or Complement-dependent cytotoxicity (CDC), tumor necrosis and death or depletion of cells, and/or disruption of tumor cell adherence, each of which result tumor regression or slowing of tumor growth.

BRIEF DESCRIPTION OF THE DRAWINGS

FIG. 5 represents a sequence alignment of human CLDN6, human CLDN3, human CLDN4, human CLDN9, and mouse CLDN6. The sequences of the EL1 and EL2 are shown.

FIG. 7A represents a graph of tumor volume ($mm^3$) of tumors in mice bearing bladder tumors as a function of time (days) after treatment with control IgG2 antibody, AB3, Reference Ab1, Reference Ab2, and AB3. FIG. 7B represents a graph of the mean change in tumor volume ($mm^3$) at Day 35 of tumors in mice bearing bladder tumors treated with control IgG2 antibody, AB3, Reference Ab1, Reference Ab2, or AB3.

FIG. 11 represents a graph of the % change in body weight of tumor-bearing mice treated with vehicle control, control antibody, Reference Ab1, Reference Ab2, Reference Ab3, and AB3 as a function of time (days).

FIG. 12A represents a graph of tumor volume ($mm^3$) of tumors in mice bearing ovarian tumors as a function of time (days) after treatment with vehicle control, control IgG2 antibody, AB3, Reference Ab1, or one of the indicated anti-CLDN6 antibodies. FIG. 12B represents a graph of the mean change in tumor volume ($mm^3$) at Day 28 of tumors in mice bearing ovarian tumors treated with vehicle control, control IgG2 antibody, AB3, Reference Ab1, or one of the indicated anti-CLDN6 antibodies.

FIG. 13 represents a graph of the % change in body weight of tumor-bearing mice treated with vehicle control, control antibody, Reference Ab1, and the indicated anti-CLDN6 antibodies as a function of time (days).

FIG. 14 represents a series of dose response curves for several anti-CLDN6 antibodies of the invention and Reference Ab1 and Reference 2. Mouse IgG was used as a control.

FIG. 15A represents a graph of the mean change in tumor volume ($mm^3$) at Day 35 of tumors in mice bearing bladder tumors treated with vehicle control, control IgG antibody, a mouse form of AB3, a first humanized form of AB3, and a second humanized form of AB3. FIG. 15B represents a graph of the changes in tumor volume ($mm^3$) for each of the groups in FIG. 15A.

FIG. 17A represents a graph of the mean change in tumor volume ($mm^3$) at Day 35 of tumors in mice bearing bladder tumors treated with vehicle control, control IgG antibody, a mouse form of AB1, and a humanized form of AB1. FIG. 17B represents a graph of the changes in tumor volume ($mm^3$) for each of the groups in FIG. 17A.

FIG. 18A represents a graph of the mean change in tumor volume ($mm^3$) at Day 35 of tumors in mice bearing bladder tumors treated with vehicle control, control IgG antibody, a mouse form of AB4, and a humanized form of AB4. FIG. 18B represents a graph of the changes in tumor volume ($mm^3$) for each of the groups in FIG. 18A.

FIG. 19A represents a graph of the mean change in tumor volume ($mm^3$) at Day 35 of tumors in mice bearing bladder tumors treated with vehicle control, control IgG antibody, a mouse form of AB3, a chimeric form of AB3, a first humanized form of AB3, a second humanized form of AB3, a mouse form of Ab 1, a humanized form of AB1, a mouse form of AB4, a humanized form of AB4, and four control antibodies (one antibody have either a mouse form or a chimeric form and one antibody having a mouse or human form) are also tested in this experiment. FIG. 19B represents a graph of the changes in tumor volume ($mm^3$) for each of the groups in FIG. 19A.

FIG. 20 represents a graph of the mean change in tumor volume ($mm^3$) at Day 55 of tumors in mice bearing bladder tumors treated as described in FIG. 19A.

FIG. 22 is a listing of sequences of the heavy chain variable region and light chain variable region of 12 CLDN6 antibodies (named S1-S12) made and characterized. S1-S6 were based on a humanized version of AB3 (humanized AB3-7) and S7-S12 were based on a humanized version of AB1 (humanized AB1-11).

FIG. 23 is the illustration of an AB-3-based antibody and NGS-identified SHM in the heavy chain. FIG. 24 is the illustration of an AB-3-based antibody and NGS-identified SHM in the light chain. FIG. 25 is the illustration of an AB-1-based antibody and NGS-identified SHM in the heavy chain. FIG. 26 is the illustration of an AB-1-based antibody and NGS-identified SHM in the light chain. Mutations are listed in Chothia numbering.

FIG. 27 is a table of FACS binding assay results for antibodies S1-S12 based on humanized AB3-7 (AB S1-S6) or humanized AB1-11 (AB S7-S12). Concentrations tested are shown in Column D.

FIG. 28 is a table of FACS binding assay results for antibodies S1-S12 at varied concentrations in different cell lines.

FIG. 34A-FIG. 34H show biochemical characterization of the CLDN6 antibody-drug conjugates (ADC) comprising AB3-7 (also referred to as AB23). FIG. 34A is a table summarizing the biochemical properties of the CLDN6 ADCs. FIG. 34B-FIG. 34H represent chromatograms of HIC-HPLC showing the relative abundance of the antibody conjugated to different numbers of drugs.

FIG. 36 shows the binding activity (flow cytometry) of the CLDN6 antibody-drug conjugate (ADC) comprising AB3-7 to native CLDN6-positive cells or cells artificially overexpressing CLDN6.

FIG. 37 shows the binding affinity of the CLDN6 ADCs comprising AB3-7 to cells expressing CLDN6. The KD (dissociation constant) measurements were made by KinExA 4000 (Sapidyne Instrument, Boise, Idaho) using HEK293T CLDN6-mGFP A11 cells.

FIG. 39A-FIG. 39N show the in vitro anti-cancer activity of CLDN6 ADCs. FIG. 39A-FIG. 39G show the two-dimensional (2D) anti-proliferative effect of different CLDN6 ADCs comprising AB-3-7 on cancer cells: MC-VC-PAB-MMAE (conventional) (FIG. 39A); MC-VC-PAB-MMAE (D4 technology) (FIG. 39B); MC-GGFG-MMAE (D4 technology) (FIG. 39C); CL2A-SN38 (conventional) (FIG. 39D); CL2A-SN38 (D4 technology) (FIG. 39E); MC-GGFG-DXD (FIG. 39F); and MC-VC-PAB-DXD (FIG. 39G). FIG. 39H-FIG. 39N show the 2D anti-proliferative effect of CLDN6 ADC-11 (AB1-11 conjugated to VC-PAB-MMAE) on different cancer cell lines: ARK2 (FIG. 39H); OVCA429 (FIG. 39I); H841 (FIG. 39J); OV90 (FIG. 39K); H1693 (FIG. 39L); M202 (FIG. 39M); and MCF7 (FIG. 39N).

FIG. 40 shows the in vivo anti-cancer efficacy of CLDN6 ADC-11 against CLDN6-positive ovarian cancer cell line (OV90) xenografts.

FIG. 42A shows the anti-cancer activity of CLDN6 ADC-23 against the CLDN6-positive bladder cell line (UMUC4) xenografts. FIG. 42B shows the haemotoxylin and eosin (H&E) staining of the xenograft tissues collected at the indicated time points post-treatment with either control antibody or 5 mg/kg ADC-23.

FIG. 43A shows a panel of ovarian PDX samples that were screened for CLDN6 expression by the Western Blot analysis. FIG. 43B is a schematic diagram showing the injection of the ovarian cancer cells of PDX transfected with a luciferase enzyme into the intraperitoneal space of immunocompromised mice (NSG). FIG. 43C-FIG. 43E show the survival rate of the mice treated with CLDN6 ADC-23 as described herein.

FIG. 44A-FIG. 44C show the dose-dependent anti-cancer efficacy of CLDN6 ADC-23 against CLDN6-positive ovarian cancer cell line (OV90) xenografts. FIG. 44A and FIG. 44B show the regression of the tumor size at the indicated dose and time. FIG. 44C shows the percent change in the body weight of mice dosed with CLDN6 ADC-23.

FIG. 45A-FIG. 45C show that there is no off-target activity of CLDN6 ADC-23 in CLDN6-negative melanoma cancer cell line (M202) xenografts. FIG. 45A and FIG. 45B show a change in tumor volume. The tumor volume shown in FIG. 45B was taken on day 21. FIG. 45C shows the percent change in the body weight of the mice dosed with CLDN6 ADC-23.

DETAILED DESCRIPTION

The Claudin Family

Figure 1:
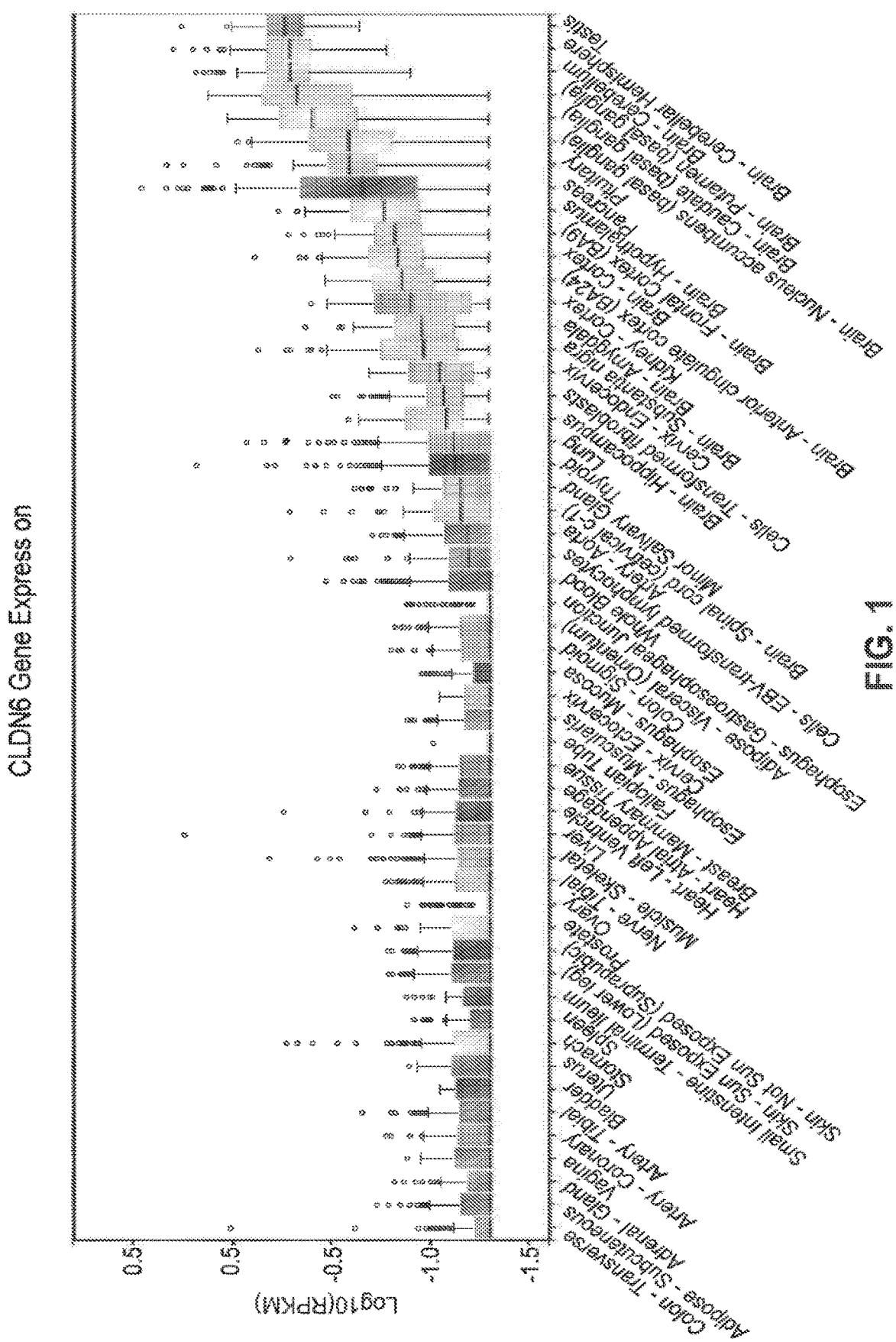
FIG. 1 represents a graph of CLDN6 expression in normal (non-cancerous) tissues.

Tight junctions, also known as occluding junctions or zonulae occludentes, are vertebrate structures located between two adjacent cells that regulate paracellular permeability and maintain cell polarity in epithelial and endothelial cell sheets. The claudin (CLDN) family of genes encodes membrane proteins that are important components of tight junctions. CLDN proteins comprise four transmembrane (TM) helices (TM1, TM2, TM3, and TM4) and two extracellular loops (EL1 and EL2). The extracellular loops of the CLDN proteins of adjacent cells interact with one another to seal the cellular sheet and regulate paracellular transport between the luminal and basolateral spaces.

CLDN proteins play a role in various human diseases and pathologies. For example, mutations in the CLDN1 gene have been shown to result in progressive scaling of the skin along with obstruction of bile ducts. Mutants of the CLDN16 gene cause a magnesium wasting disorder. CLDN19 mutations lead to ocular conditions, such as macular colobomata and myopia, while CLDN14 mutations can lead to nonsyndromic recessive deafness. CLDN3 and CLDN4 are known to be surface receptors for the *Clostridium perfringens* enterotoxin in the gut, and CLDN1, CLDN6, and CLDN9 are co-receptors for hepatitis C virus (HCV) entry. Several CLDN proteins have been shown to be abnormally expressed in cancers. For instance, CLDN1 is downregulated in breast and colon cancer, whereas CLDN3 and CLDN4 are highly upregulated in multiple cancers.

Claudin-6 (CLDN6) is a member of the CLDN family. The gene encoding the human CLDN6 protein is located on the p arm of human chromosome 16 at 16p13.3 and is conserved in chimpanzee, Rhesus monkey, dog, cow, mouse, rat, zebrafish, and frog. CLDN6 is generally expressed in humans as a 220-amino acid precursor protein; the first 21 amino acids of which constitute the signal peptide. The amino acid sequence of the CLDN6 precursor protein is publically available at the National Center for Biotechnology Information (NCBI) website as NCBI Reference Sequence NP 067018.2 and is provided herein as SEQ ID NO: 1. The amino acid at position 143 of SEQ ID NO: 1 is Ile. In some instances, due to a single-nucleotide polymorphism (SNP) in the DNA sequence encoding CLDN6, the amino acid at position 143 is a Val. The amino acid sequence of human CLDN6 having a Val at position 143 is provided herein as SEQ ID NO: 178.

Antigen Binding Proteins

Provided herein are antigen-binding proteins that bind to Claudin-6 (CLDN6). The antigen-binding proteins of the present disclosure can take any one of many forms of antigen-binding proteins known in the art. In various embodiments, the antigen-binding proteins of the present disclosure take the form of an antibody, or antigen-binding antibody fragment, or an antibody protein product.

In various embodiments of the present disclosure, the antigen-binding protein comprises, consists essentially of, or consists of an antibody. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", Immunobiology: The Immune System in Health and Disease, 4th ed. Elsevier Science Ltd./Garland Publishing, (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra).

Antibodies can comprise any constant region known in the art. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the present disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in various embodiments, the antibody is an antibody of isotype IgA, IgD, IgE, IgG, or IgM, including any one of IgG1, IgG2, IgG3 or IgG4. In various aspects, the antibody comprises a constant region comprising one or more amino acid modifications, relative to the naturally-occurring counterpart, in order to improve half-life/stability or to render the antibody more suitable for expression/manufacturability. In various instances, the antibody comprises a constant region wherein the C-terminal Lys residue that is present in the naturally-occurring counterpart is removed or clipped.

The antibody can be a monoclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody can be considered as a mammalian antibody, e.g., a mouse antibody, rabbit antibody, goat antibody, horse antibody, chicken antibody, hamster antibody, human antibody, and the like. In certain aspects, the antigen-binding protein is an antibody, such as a human antibody. In certain aspects, the antigen-binding protein is a chimeric antibody or a humanized antibody. The term "chimeric antibody" refers to an antibody containing domains from two or more different antibodies. A chimeric antibody can, for example, contain the constant domains from one species and the variable domains from a second, or more generally, can contain stretches of amino acid sequence from at least two species. A chimeric antibody also can contain domains of two or more different antibodies within the same species. The term "humanized" when used in relation to antibodies refers to antibodies having at least CDR regions from a non-human source which are engineered to have a structure and immunological function more similar to true human antibodies than the original source antibodies. For example, humanizing can involve grafting a CDR from a non-human antibody, such as a mouse antibody, into a human antibody. Humanizing also can involve select amino acid substitutions to make a non-human sequence more similar to a human sequence. Information, including sequence information for human antibody heavy and light chain constant regions is publicly available through the Uniprot database as well as other databases well-known to those in the field of antibody engineering and production. For example, the IgG2 constant region is available from the Uniprot database as Uniprot number P01859, incorporated herein by reference.

An antibody can be cleaved into fragments by enzymes, such as, e.g., papain and pepsin. Papain cleaves an antibody to produce two Fab fragments and a single Fc fragment. Pepsin cleaves an antibody to produce a F(ab')$_2$ fragment and a pFc' fragment. In various aspects of the present disclosure, the antigen-binding protein of the present disclosure is an antigen-binding fragment of an antibody (a.k.a., antigen-binding antibody fragment, antigen-binding fragment, antigen-binding portion). In various instances, the antigen-binding antibody fragment is a Fab fragment or a F(ab')2 fragment.

The architecture of antibodies has been exploited to create a growing range of alternative antibody formats that spans a molecular-weight range of at least about 12-150 kDa and has a valency (n) range from monomeric (n=1), to dimeric (n=2), to trimeric (n=3), to tetrameric (n=4), and potentially higher; such alternative antibody formats are referred to herein as "antibody protein products". Antibody protein products include those based on the full antibody structure and those that mimic antibody fragments which retain full antigen-binding capacity, e.g., scFvs, Fabs and VHH/VH (discussed below). The smallest antigen-binding fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab fragments can be easily produced in host cells, e.g., prokaryotic host cells. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, bispecific antibody (BsAb) fragments, bispecific fusion proteins, and BsAb conjugates. See, e.g., Spiess et al., Molecular Immunology 67(2) Part A: 97-106 (2015).

In various aspects, the antigen-binding protein of the present disclosure comprises, consists essentially of, or consists of any one of these antibody protein products. In various aspects, the antigen-binding protein of the present disclosure comprises, consists essentially of, or consists of any one of an scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, diabody; a triabody; a tetrabody; a bispecific or trispecific antibody, BsIgG, appended IgG, BsAb fragment, bispecific fusion protein, and BsAb conjugate.

In various instances, the antigen-binding protein of the present disclosure is an antibody protein product in monomeric form, or polymeric, oligomeric, or multimeric form.

In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

In various embodiments, an anti-CLDN6 antibody or antibody variant thereof is selected from the group consisting of a human antibody, a humanized antibody, a chimeric antibody, a monoclonal antibody, a recombinant antibody, an antigen-binding antibody fragment, a single chain antibody, a monomeric antibody, a diabody, a triabody, a tetrabody, a Fab fragment, an IgG1 antibody, an IgG2 antibody, an IgG3 antibody, and an IgG4 antibody.

In various aspects, the antigen-binding protein of the present disclosure is linked to a therapeutic agent. As described below, the therapeutic agent may be any known in the art, including, but not limited to, chemotherapeutic agents, cytokines and growth factors, cytotoxic agents, and the like. See "Conjugates" below.

CLDN6 and Epitopes

The antigen-binding proteins of the present disclosure bind to CLDN6. In various aspects, the CLDN6 is a human CLDN6 having the amino acid sequence of:

```
                                           (SEQ ID NO: 202)
MASAGMQILGVVLTLLGWVNGLVSCALPMWKVTAFIGNSIVVAQVVWEGL

WMSCVVQSTGQMQCKVYDSLLALPQDLQAARALCVIALLVALFGLLVYLA

GAKCTTCVEEKDSKARLVLTSGIVFVISGVLTLIPVCWTAHAXIRDFYNP

LVAEAQKRELGASLYLGWAASGLLLLGGGLLCCTCPSGGSQGPSHYMARY

STSAPAISRGPSEYPTKNYV, wherein X is Ile or Val.
```

In various aspects, the human CLDN6 comprises the amino acid sequence of any one of SEQ ID NOs: 1, 178, and 200-202.

In various aspects, the antigen-binding proteins of the present disclosure bind to an epitope within an amino acid sequence of CLDN6. In various aspects, CLDN6 is a human CLDN6 and the antigen-binding proteins of the present disclosure bind to an epitope within an amino acid sequence of human CLDN6, e.g., SEQ ID NOs: 1, 178, and 200-202. By "epitope" is meant the region of or within CLDN6 which is bound by the antigen-binding protein. In some embodiments, the epitope is a linear epitope. "Linear epitope" refers to the region of or within the CLDN6 which is bound by the antigen-binding protein and which region is composed of contiguous amino acids of the amino acid sequence of the CLDN6. The amino acids of a linear epitope are adjacent to each other in the primary structure of the CLDN6. Accordingly, a linear epitope is a fragment or portion of the amino acid sequence of the antigen, i.e., CLDN6. In other various embodiments, the epitope is a conformational or structural epitope. By "conformational epitope" or "structural epitope" is meant an epitope which is composed of amino acids which are located in close proximity to one another only when the CLDN6 is in its properly folded state. Unlike linear epitopes, the amino acids of a conformational or structural epitope are not adjacent to each other in the primary structure (i.e., amino acid sequence) of the CLDN6. A conformational or structural epitope is not made of contiguous amino acids of the amino acid sequence of the antigen (CLDN6).

In various aspects, the epitope is located within the extracellular domain (ECD) of CLDN6, e.g., human CLDN6. In various aspects, the antigen binding protein binds to Extracellular Loop 2 (EL2) of the ECD of CLDN6 having the amino acid sequence of WTAHAIIRDFYNPL- VAEAQKREL (SEQ ID NO: 2). In various aspects, the epitope to which the antigen-binding protein binds is within SEQ ID NO: 2. In various aspects, the antigen-binding protein of the present disclosure binds to an N-terminal portion of SEQ ID NO: 2, e.g., TAHAIIRDFYNPL (SEQ ID NO: 3). In various aspects, the antigen-binding protein of the present disclosure binds to a C-terminal portion of SEQ ID NO: 2, e.g., LVAEAQKREL (SEQ ID NO: 4). In various instances, the antigen-binding protein of the present disclosure binds to EL2, but not to Extracellular Loop 1 (EL1) of CLDN6. In various aspects, the epitope(s) to which the antigen binding proteins of the present disclosure bind to is different from the epitope bound by an anti-CLDN6 antibody comprising a light chain variable region comprising the sequence of SEQ ID NO: 185 and a heavy chain variable region comprising the sequence of SEQ ID NO: 186. In various aspects, the epitope(s) to which the antigen binding proteins of the present disclosure bind to is different from the epitope bound by an anti-CLDN6 antibody comprising a light chain variable region comprising the sequence of SEQ ID NO: 181 and a heavy chain variable region comprising the sequence of SEQ ID NO: 182.

In various aspects, the antigen-binding proteins bind to human CLDN6 and a non-human CLDN6. In various instances, the non-human CLDN6 is a CLDN6 of chimpanzee, Rhesus monkey, dog, cow, mouse, rat, zebrafish, or frog. In various instances, the antigen-binding proteins bind to human CLDN6 and mouse CLDN6.

Affinity and Avidity

The antigen-binding proteins provided herein bind to CLDN6 in a non-covalent and reversible manner. In various embodiments, the binding strength of the antigen-binding protein to CLDN6 may be described in terms of its affinity, a measure of the strength of interaction between the binding site of the antigen-binding protein and the epitope. In various aspects, the antigen-binding proteins provided herein have high-affinity for CLDN6 and thus will bind a greater amount of CLDN6 in a shorter period of time than low-affinity antigen-binding proteins. In various aspects, the antigen-binding protein has an equilibrium association constant, KA, which is at least $10^5$ mol$^{-1}$, at least $10^6$ mol$^{-1}$, at least $10^7$ mol$^{-1}$, at least $10^8$ mol$^{-1}$, at least $10^9$ mol$^{-1}$, or at least $10^{10}$ mol$^{-1}$ or at least $10^{10}$ mol$^{-1}$ least $10^{10}$ mol$^{-1}$. As understood by the artisan of ordinary skill, KA can be influenced by factors including pH, temperature and buffer composition.

In various embodiments, the binding strength of the antigen-binding protein to CLDN6 may be described in terms of its sensitivity. $K_D$ is the equilibrium dissociation constant, a ratio of $k_{off}/k_{on}$, between the antigen-binding protein and CLDN6. $K_D$ and KA are inversely related. The $K_D$ value relates to the concentration of the antigen-binding protein (the amount of antigen-binding protein needed for a particular experiment) and so the lower the $K_D$ value (lower concentration) the higher the affinity of the antigen-binding protein. In various aspects, the binding strength of the antigen-binding protein to CLDN6 may be described in terms of $K_D$. In various aspects, the $K_D$ of the antigen-binding proteins provided herein is about $10^{-1}$, about $10^{-2}$, about $10^{-3}$, about $10^{-4}$, about $10^{-5}$, about $10^{-6}$, or less. In various aspects, the $K_D$ of the antigen-binding proteins provided herein is micromolar, nanomolar, picomolar or femtomolar. In various aspects, the $K_D$ of the antigen-binding proteins provided herein is within a range of about $10^{-4}$ to $10^{-6}$ or $10^{-7}$ to $10^{-9}$ or $10^{-10}$ to $10^{-12}$ or $10^{-13}$ to $10^{-15}$. In various aspects, the $K_D$ of the antigen-binding proteins provided herein is within a range of about $1.0\times10^{-12}$ M to about $1.0\times10^{-8}$ M. In various aspects, the $K_D$ of the antigen-binding proteins is within a range of about $1.0\times10^{-11}$ M to about $1.0\times10^{-9}$ M.

In various aspects, the affinity of the antigen-binding proteins are measured or ranked using a flow cytometry- or Fluorescence-Activated Cell Sorting (FACS)-based assay. Flow cytometry-based binding assays are known in the art. See, e.g., Cedeno-Arias et al., Sci Pharm 79(3): 569-581 (2011); Rathanaswami et al., Analytical Biochem 373: 52-60 (2008); and Geuijen et al., J Immunol Methods 302(1-2): 68-77 (2005). In various aspects, the affinity of the antigen-binding proteins are measured or ranked using a competition assay as described in Trikha et al., Int J Cancer 110: 326-335 (2004) and Tam et al., Circulation 98(11): 1085-1091 (1998), as well as below. See section titled "*Competition Assays*" below. In Trikh et al., cells that express the antigen were used in a radioassay. The binding of $^{125}$I-labeled antigen-binding protein (e.g., antibody) to the cell surface antigen is measured with the cells in suspension. In various aspects, the relative affinity of a CLDN6 antibody is determined via a FACS-based assay in which different concentrations of a CLDN6 antibody conjugated to a fluorophore are incubated with cells expressing CLDN6 and the fluorescence emitted (which is a direct measure of antibody-antigen binding) is determined. A curve plotting the fluorescence for each dose or concentration is made. The max value is the lowest concentration at which the fluorescence plateaus or reaches a maximum, which is when binding saturation occurs. Half of the max value is considered an EC50 or an IC50 and the antibody with the lowest EC50/IC50 is considered as having the highest affinity relative to other antibodies tested in the same manner. Such an assay is described herein at Example 5.

In various aspects, the IC50 value, as determined in a competitive binding inhibition assay, approximates the $K_D$ of the antigen-binding protein. In various instances, as discussed below, the competition assay is a FACS-based assay carried out with a reference antibody, fluorophore-conjugated secondary antibody, and cells which express CLDN6. In various aspects, the cells are genetically-engineered to overexpress CLDN6. In some aspects, the cells are HEK293T cells transduced with a viral vector to express CLDN6. In alternative aspects, the cells endogenously express CLDN6. Before the FACS-based assay is carried out, in some aspects, the cells which endogenously express CLDN6 are pre-determined as low CLDN6-expressing cells or high CLDN6-expressing cells. In some aspects, the cells are cancer or tumor cells. In various aspects, the cells are cells from a cell line, e.g., an ovarian cell line, endometrial cell line, bladder cell line, lung cell line, gastrointestinal (GI) cell line, liver cell line, lung cell line, and the like. In various aspects, the cells which endogenously express CLDN6 as selected from the group consisting of OVCA429 ovarian cells, ARK2 endometrial cells, OAW28 ovarian cells, UMUC-4 bladder cells, PEO14 ovarian cells, OV177 ovarian cells, H1693 lung cells, MKN7 upper GI cells, OV-90 ovarian cells, HUH-7 liver cells, JHOS-4 ovarian cells, H1435 lung cells, and NUGC3 upper GI cells. In various aspects, the antigen-binding protein inhibits the binding interaction between human CLDN6 expressed by the cells and the reference antibody, which reference antibody is known to bind to CLDN6 but is not an antigen-binding protein of the present disclosure. In various instances, the antigen-binding proteins of the present disclosure compete with the reference antibody for binding to human CLDN6 and thereby reduce the amount of human CLDN6 bound to the reference antibody as determined by an in vitro competitive binding assay. In various aspects, the antigen-binding proteins of the present disclosure inhibit the binding interaction between human CLDN6 and the reference antibody and the inhibition is characterized by an $IC_{50}$. In various aspects, the antigen-binding proteins exhibit an $IC_{50}$ of less than about 2500 nM for inhibiting the binding interaction between human CLDN6 and the reference antibody. In various aspects, the antigen-binding proteins exhibit an $IC_{50}$ of less than about 2000 nM, less than about 1500 nM, less than about 1000 nM, less than about 900 nm, less than about 800 nm, less than about 700 nm, less than about 600 nm, less than about 500 nm, less than about 400 nm, less than about 300 nm, less than about 200 nm, or less than about 100 nm. In various aspects, the antigen-binding proteins exhibit an $IC_{50}$ of less than about 90 nM, less than about 80 nM, less than about 70 nM, less than about 60 nM, less than about 50 nM, less than about 40 nM, less than about 30 nM, less than about 20 nM, or less than about 10 nM. In various instances, the antigen binding proteins of the present disclosure compete against a reference antibody known to bind to CLDN6 (which reference antibody is different from any of the antigen-binding proteins of the present disclosure) for binding to CLDN6. See further description under Competition assays.

Avidity gives a measure of the overall strength of an antibody-antigen complex. It is dependent on three major parameters: affinity of the antigen-binding protein for the epitope, valency of both the antigen-binding protein and CLDN6, and structural arrangement of the parts that interact. The greater an antigen-binding protein's valency (number of antigen binding sites), the greater the amount of antigen (CLDN6) it can bind. In various aspects, the antigen-binding proteins have a strong avidity for CLDN6. In various aspects, the antigen-binding proteins are multivalent. In various aspects, the antigen-binding proteins are bivalent. In various instances, the antigen antigen-binding proteins are monovalent.

Cross-Reactivity

In various embodiments, the antigen-binding proteins of the present disclosure bind to CLDN6 and do not bind to any other member of the CLDN family, e.g., do not cross-react with any other member of the CLDN family. In various instances, the antigen-binding proteins of the present disclosure are CLDN-6 specific. In various embodiments, the antigen-binding proteins of the present disclosure have a selectivity for CLDN6 which is at least 10-fold, 5-fold, 4-fold, 3-fold, 2-fold greater than the selectivity of the antigen-binding protein for CLDN3, CLDN4, CLDN9, or a combination thereof. In various embodiments, the antigen-binding proteins of the present disclosure have a selectivity for CLDN6 which is at least 10-fold, 5-fold, 4-fold, 3-fold, 2-fold greater than the selectivity of the antigen-binding protein for each of CLDN3, CLDN4, and CLDN9. Selectivity may be based on the $K_D$ exhibited by the antigen binding protein for CLDN6, or a CLDN family member, wherein the $K_D$ may be determined by techniques known in the art, e.g., surface plasmon resonance, FACS-based affinity assays.

In various aspects, the antigen-binding proteins of the present disclosure bind to CLDN6 and do not bind to any of Claudin3 (CLDN3), Claudin4 (CLDN4), and Claudin9 (CLDN9). In various aspects, the antigen-binding proteins do not bind to any of CLDN3, CLDN4, and CLDN9 and exhibit an $IC_{50}$ of less than about 1200 nM (e.g., less than about 1000 nM, less than about 750 nM, less than about 500 nM, less than about 250 nM) in a FACS-based assay with OVCA429 cells endogenously expressing CLDN6. In various aspects, the antigen-binding proteins do not bind to any of CLDN3, CLDN4, and CLDN9 and the concentration at which 50% of binding saturation is achieved with OVCA429 cells endogenously expressing CLDN6 is less than about 1200 nM (e.g., less than about 1000 nM, less than about 750 nM, less than about 500 nM, less than about 250 nM). In various aspects, the antigen-binding proteins exhibit at least a 5-fold selectivity for CLDN 6 greater than that for CLDN3, CLDN4, and CLDN9 and the concentration at which 50% of binding saturation is achieved with OVCA429 cells endogenously expressing CLDN6 is less than about 1200 nM (e.g., less than about 1000 nM, less than about 750 nM, less than about 500 nM, less than about 250 nM). In various aspects, the antigen-binding proteins exhibit an IC50 of less than about 1200 nM (e.g., less than about 1000 nM, less than about 750 nM, less than about 500 nM, less than about 250 nM) for CLDN6 artificial and endogenous models and exhibit a greater than about 5-fold ratio separating CLDN6 IC50s from CLDN3, CLDN4 and/or CLDN9. In various instances, the antigen-binding proteins exhibit an IC50 of less than about 1200 nM (e.g., less than about 1000 nM, less than about 750 nM, less than about 500 nM, less than about 250 nM) for CLDN6 and exhibit an IC50 for any one of CLDN3, CLDN4, and CLDN9 at least 5-fold greater than the IC50.

In various embodiments, the antigen-binding proteins of the present disclosure bind to CLDN6 and cross-react with (e.g., bind to) at least one other member of the CLDN family. In various aspects, the antigen-binding proteins of the present disclosure bind to CLDN6 and one or more of CLDN3, CLDN4, and CLDN9. In various aspects, the antigen-binding proteins of the present disclosure bind to CLDN6 and CLDN4 or CLDN9, but do not bind to CLDN3. In various instances, the antigen-binding proteins of the present disclosure bind to CLDN6 and CLDN4 but binds to neither CLDN3 nor CLDN9. In various instances, the antigen-binding proteins of the present disclosure bind to CLDN6 and CLDN9 but do not bind to either CLDN3 or CLDN4.

Competition Assays

In various embodiments, the antigen-binding protein inhibits a binding interaction between human CLDN6 and a reference antibody, which reference antibody is known to bind to CLDN6 but is not an antigen-binding protein of the present disclosure. In various instances, the antigen-binding proteins of the present disclosure compete with the reference antibody for binding to human CLDN6 and thereby reduce the amount of human CLDN6 bound to the reference antibody as determined by an in vitro competitive binding assay. In various embodiments, the reference antibody binds to an epitope within the amino acid sequence of the extracellular domain of human CLDN6, optionally, within EL2 or EL1. In various aspects, the reference antibody comprises a light chain variable sequence encoded by SEQ ID NO: 179, and a heavy chain variable sequence encoded by SEQ ID NO: 180. In various aspects, the reference antibody comprises a light chain variable sequence of SEQ ID NO: 181, and a heavy chain variable sequence of SEQ ID NO: 182. In various aspects, the antigen-binding proteins of the present disclosure inhibit the binding interaction between human CLDN6 and the reference antibody and the inhibition is characterized by an $IC_{50}$. In various aspects, the antigen-binding proteins exhibit an $IC_{50}$ of less than about 2500 nM for inhibiting the binding interaction between human CLDN6 and the reference antibody. In various aspects, the antigen-binding proteins exhibit an $IC_{50}$ of less than about 2000 nM, less than about 1500 nM, less than about 1000 nM, less than about 900 nm, less than about 800 nm, less than about 700 nm, less than about 600 nm, less than about 500 nm, less than about 400 nm, less than about 300 nm, less than about 200 nm, or less than about 100 nm. In various aspects, the antigen-binding proteins exhibit an $IC_{50}$ of less than about 90 nM, less than about 80 nM, less than about 70 nM, less than about 60 nM, less than about 50 nM, less than about 40 nM, less than about 30 nM, less than about 20 nM, or less than about 10 nM.

In various instances, the antigen-binding proteins of the present disclosure compete with the reference antibody for binding to human CLDN6 and thereby reduce the amount of human CLDN6 bound to the reference antibody as determined by an in vitro competitive binding assay. In various aspects, the in vitro competitive binding assay is a FACS-based assay in which the fluorescence of a fluorophore-conjugated secondary antibody which binds to the Fc of the reference antibody is measured in the absence or presence of a particular amount of the antigen-binding protein of the present disclosure. Such a FACS-based assay is described herein in the EXAMPLES. In various aspects, the FACS-based assay is carried out with the reference antibody, fluorphore-conjugated secondary antibody and cells which express CLDN6. In various aspects, the cells are genetically-engineered to overexpress CLDN6. In some aspects, the cells are HEK293T cells transduced with a viral vector to express CLDN6. In alternative aspects, the cells endogenously express CLDN6. Before the FACS-based assay is carried out, in some aspects, the cells which endogenously express CLDN6 are pre-determined as low CLDN6-expressing cells or high CLDN6-expressing cells. In some aspects, the cells are cancer or tumor cells. In various aspects, the cells are cells from a cell line, e.g., an ovarian cell line, endometrial cell line, bladder cell line, lung cell line, gastrointestinal (GI) cell line, liver cell line, lung cell line, and the like. In various aspects, the cells which endogenously express CLDN6 as selected from the group consisting of OVCA429 ovarian cells, ARK2 endometrial cells, OAW28 ovarian cells, UMUC-4 bladder cells, PEO14 ovarian cells, OV177 ovarian cells, H1693 lung cells, MKN7 upper GI cells, OV-90 ovarian cells, HUH-7 liver cells, JHOS-4 ovarian cells, H1435 lung cells, and NUGC3 upper GI cells. In various instances, the antigen binding proteins of the present disclosure bind to CLDN6 endogenously expressed by one or more of ARK2 cells, OVCA429 cells, LS513 cells, or MCF7 cells with high affinity. In various aspects, the antigen binding proteins exhibit an $IC_{50}$ of less than about 3000 nM as determined in a FACS-based competitive binding inhibition assay using one or more of ARK2 cells, OVCA429 cells, LS513 cells, or MCF7 cells. In various aspects, the antigen binding proteins exhibit an $IC_{50}$ of less than about 2500 nM, less than about 2000 nM, less than about 1750 nM, less than about 1500 nM, less than about 1250 nM, less than about 1000 nM, less than about 750 nM, or less than about 500 nM, as determined in a FACS-based competitive binding inhibition assay using one or more of ARK2 cells, OVCA429 cells, LS513 cells, or MCF7 cells. In various aspects, the antigen binding proteins exhibit an $IC_{50}$ of less than about 400 nM, less than about 300 nM, less than about 200 nM, less than about 100 nM, less than about 75 nM, less than about 50 nM, less than about 25 nM, or less than about 10 nM, as determined in a FACS-based competitive binding inhibition assay using one or more of ARK2 cells, OVCA429 cells, LS513 cells, or MCF7 cells.

Other binding assays, e.g., competitive binding assays or competition assays, which test the ability of an antibody to compete with a second antibody for binding to an antigen, or to an epitope thereof, are known in the art. See, e.g., Trikha et al., Int J Cancer 110: 326-335 (2004); Tam et al., Circulation 98(11): 1085-1091 (1998). U.S. Patent Application Publication No. US20140178905, Chand et al., Biologicals 46: 168-171 (2017); Liu et al., Anal Biochem 525: 89-91 (2017); and Goolia et al., J Vet Diagn Invest 29(2): 250-253 (2017). Also, other methods of comparing two antibodies are known in the art, and include, for example, surface plasmon resonance (SPR). SPR can be used to determine the binding constants of the antibody and second antibody and the two binding constants can be compared.

Methods of Antibody Production and Related Methods

Suitable methods of making antigen-binding proteins (e.g., antibodies, antigen-binding antibody fragments, and antibody protein products) are known in the art. For instance, standard hybridoma methods for producing antibodies are described in, e.g., Harlow and Lane (eds.), Antibodies: A Laboratory Manual, CSH Press (1988), and C A. Janeway et al. (eds.), Immunobiology, 5$^{th}$ Ed., Garland Publishing, New York, NY (2001)). An various method of preparing CLDN6 monoclonal antibodies or the present disclosure is provided herein in EXAMPLES.

Depending on the host species, various adjuvants can be used to increase the immunological response leading to greater antibody production by the host. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Other methods of antibody production are summarized in Table 1.

TABLE 1

| Technique | Various references |
| --- | --- |
| EBV-hybridoma methods and Bacteriophage vector expression systems | Haskard and Archer, J. Immunol. Methods, 74(2), 361-67 (1984), Roder et al., Methods Enzymol., 121,140-67 (1986), and Huse et al., Science, 246, 1275-81 (1989)). |
| methods of producing antibodies in non-human animals | U.S. Pat. Nos. 5,545,806, 5,569,825, and 5,714,352, and U.S. Patent Application Publication No. 2002/0197266 |
| inducing in vivo production in the lymphocyte population or by screening recombinant immunoglobulin libraries or panels of highly specific binding reagents | Orlandi et al (Proc Natl Acad Sci 86: 3833-3837; 1989), and Winter G and Milstein C (Nature 349: 293-299, 1991). |
| methods of producing recombinant proteins | Protein production and purification" Nat Methods 5(2): 135-146 (2008). |

TABLE 1-continued

| Technique | Various references |
|---|---|
| Phage display | Janeway et al., supra, Huse et al., supra, and U.S. Pat. No. 6,265,150). Related methods also are described in U.S. Pat. No. 5,403,484; U.S. Pat. No. 5,571,698; U.S. Pat. No. 5,837,500; U.S. Pat. No. 5,702,892. The techniques described in U.S. Pat. No. 5,780,279; U.S. Pat. No. 5,821,047; U.S. Pat. No. 5,824,520; U.S. Pat. No. 5,855,885; U.S. Pat. No. 5,858,657; U.S. Pat. No. 5,871,907; U.S. Pat. No. 5,969,108; U.S. Pat. No. 6,057,098; and U.S. Pat. No. 6,225,447 |
| Antibodies can be produced by transgenic mice | U.S. Pat. Nos. 5,545,806 and 5,569,825, and Janeway et al., supra. |

Methods of testing antibodies for the ability to bind to the epitope of CLDN6 regardless of how the antibodies are produced are known in the art and include any antibody-antigen binding assay, such as, for example, radioimmunoassay (RIA), ELISA, Western blot, immunoprecipitation, SPR, and competitive inhibition assays (see, e.g., Janeway et al., infra, and U.S. Patent Application Publication No. 2002/0197266, and the above section relating to competition assays).

Sequences/Structure

Provided herein are antigen-binding proteins comprising (a) a heavy chain (HC) complementarity-determining region (CDR) 1 amino acid sequence set forth in Table A or a sequence selected from the group consisting of: SEQ ID NOs: 11, 17, 23, 29, 35, 41, 47, 53, 59, 65, 71, 77, 83, 89, 95, 101, 107, 113, 119, 125, and 131, or a variant sequence thereof which differs by only one or two amino acids or which has at least or about 70% (e.g., at least about 80%, at least about 85%, at least about 90%, at least about 95%) sequence identity; (b) an HC CDR2 amino acid sequence set forth in Table A or a sequence selected from the group consisting of: SEQ ID NOs: 12, 18, 24, 30, 36, 42, 48, 54, 60, 66, 72, 78, 84, 90, 86, 102, 108, 114, 120, 126, and 132, or a variant sequence thereof which differs by only one or two amino acids or which has at least or about 70% (e.g., at least about 80%, at least about 85%, at least about 90%, at least about 95%) sequence identity; (c) an HC CDR3 amino acid sequence set forth in Table A or a sequence selected from the group consisting of: SEQ ID NOs: 13, 19, 25, 31, 37, 43, 49, 55, 61, 67, 73, 79, 85, 91, 97, 103, 109, 115, 121, 127, and 133, or a variant sequence thereof which differs by only one or two amino acids or which has at least or about 70% (e.g., at least about 80%, at least about 85%, at least about 90%, at least about 95%) sequence identity; (d) a light chain (LC) CDR1 amino acid sequence set forth in Table A or a sequence selected from the group consisting of: SEQ ID NOs: 8, 14, 20, 32, 38, 44, 50, 56, 62, 68, 74, 80, 86, 92, 98, 104, 110, 116, 122, and 128, or a variant sequence thereof which differs by only one or two amino acids or which has at least or about 70% (e.g., at least about 80%, at least about 85%, at least about 90%, at least about 95%) sequence identity; (e) an LC CDR2 amino acid sequence set forth in Table A or a sequence selected from the group consisting of: SEQ ID NOs: 9, 15, 21, 27, 33, 39, 45, 51, 57, 63, 69, 75, 81, 87, 93, 99, 105, 111, 117, 123, and 129, or a variant sequence thereof which differs by only one or two amino acids or which has at least or about 70% (e.g., at least about 80%, at least about 85%, at least about 90%, at least about 95%) sequence identity; (f) an LC CDR3 amino acid sequence set forth in Table A or a sequence selected from the group consisting of: SEQ ID NOs: 10, 16, 22, 28, 34, 40, 46, 52, 58, 64, 70, 76, 82, 88, 94, 100, 106, 112, 118, 124, and 130, or a variant sequence thereof which differs by only one or two amino acids or which has at least or about 70% (e.g., at least about 80%, at least about 85%, at least about 90%, at least about 95%) sequence identity; or (g) a combination of any two or more of (a)-(f).

TABLE A

| | LC CDR1 | LC CDR2 | LC CDR3 | HC CDR1 | HC CDR2 | HC CDR3 |
|---|---|---|---|---|---|---|
| AB1 | 8 | 9 | 10 | 11 | 12 | 13 |
| AB2 | 14 | 15 | 16 | 17 | 18 | 19 |
| AB3 | 20 | 21 | 22 | 23 | 24 | 25 |
| AB4 | 26 | 27 | 28 | 29 | 30 | 31 |
| AB5 | 32 | 33 | 34 | 35 | 36 | 37 |
| AB6 | 38 | 39 | 40 | 41 | 42 | 43 |
| AB7 | 44 | 45 | 46 | 47 | 48 | 49 |
| AB8 | 50 | 51 | 52 | 53 | 54 | 55 |
| AB9 | 56 | 57 | 58 | 59 | 60 | 61 |
| AB10 | 62 | 63 | 64 | 65 | 66 | 67 |
| AB11 | 68 | 69 | 70 | 71 | 72 | 73 |
| AB12 | 74 | 75 | 76 | 77 | 78 | 79 |
| AB13 | 80 | 81 | 82 | 83 | 84 | 85 |
| AB14 | 86 | 87 | 88 | 89 | 90 | 91 |
| AB15 | 92 | 93 | 94 | 95 | 96 | 97 |
| AB16 | 98 | 99 | 100 | 101 | 102 | 103 |
| AB17 | 104 | 105 | 106 | 107 | 108 | 109 |
| AB18 | 110 | 111 | 112 | 113 | 114 | 115 |
| AB19 | 116 | 117 | 118 | 119 | 120 | 121 |
| AB20 | 122 | 123 | 124 | 125 | 126 | 127 |
| AB21 | 128 | 129 | 130 | 131 | 132 | 133 |

In various aspects, the antigen-binding protein comprises a LC CDR1 amino acid sequence, a LC CDR2 amino acid sequence, and a LC CDR3 amino acid sequence set forth in Table A and at least 1 or 2 of the HC CDR amino acid sequences set forth in Table A. In various aspects, the antigen-binding protein comprises a HC CDR1 amino acid sequence, a HC CDR2 amino acid sequence, and a HC CDR3 amino acid sequence set forth in Table A and at least 1 or 2 of the LC CDR amino acid sequences set forth in Table A.

In various embodiments, the antigen-binding protein comprises at least 3, 4, or 5 of the amino acid sequences designated by the SEQ ID NOs: in a single row of Table A. In various embodiments, the antigen-binding protein comprises each of the LC CDR amino acid sequences designated by the SEQ ID NOs: of a single row of Table A and at least 1 or 2 of the HC CDR amino acid sequences designated by the SEQ ID NOs: in of a single row of Table A. In various embodiments, the antigen-binding protein comprises each of the HC CDR amino acid sequences designated by the SEQ ID NOs: of a single row of Table A and at least 1 or 2 of the LC CDR amino acid sequences designated by the SEQ ID NOs: of a single row of Table A. In various embodiments, the antigen-binding protein comprises all 6 of the CDR amino acid sequences designated by the SEQ ID NOs: of a single row of Table A. In various embodiments, the antigen-binding protein comprises six CDR amino acid sequences selected from the group consisting of: (a) SEQ ID NOs: 74-79; (b) SEQ ID NOs: 50-55; (c) SEQ ID NOs: 122-127; (d) SEQ ID NOs: 26-31; (e) SEQ ID NOs: 128-133; (f) SEQ ID NOs: 38-43; (g) SEQ ID NOs: 62-67; (h) SEQ ID NOs: 80-85; (i) SEQ ID NOs: 44-49; (j) SEQ ID NOs: 86-91; (k) SEQ ID NOs: 104-109; (l) SEQ ID NOs: 56-61; (m) SEQ ID NOs: 32-37; (n) SEQ ID NOs: 110-115; (o) SEQ ID NOs: 98-103; (p) SEQ ID NOs: 92-97; (q) SEQ ID NOs: 116-121; (r) SEQ ID NOs: 8-13; (s) SEQ ID NOs: 68-73; (t) SEQ ID NOs: 14-19; and (u) SEQ ID NOs: 20-25.

In various instances, the amino acid sequences of Table A are separated by at least one or more (e.g., at least 2, 3, 4, 5, 6, 7, 8, 9, 10, or more) intervening amino acid(s). In various instances, there are about 10 to about 20 amino acids between the sequences of the LC CDR1 and the LC CDR2 and about 25 to about 40 amino acids between the sequences of the LC CDR2 and the LC CDR3. In various instances, there are about 14 to about 16 amino acids between the sequences of the LC CDR1 and the LC CDR2 and about 30 to about 35 amino acids between the sequences of LC CDR2 and the LC CDR3. In various instances, there are about 10 to about 20 amino acids between the sequences of the HC CDR1 and HC CDR2 and about 25 to about 40 amino acids between the sequences of the HC CDR2 and the HC CDR3. In various instances, there are about 14 to about 16 amino acids between the sequences of the HC CDR1 and HC CDR2 and about 30 to about 35 amino acids between the sequences of the HC CDR2 and HC CDR3.

In various embodiments, the antigen-binding protein comprises (a) a heavy chain variable region amino acid sequence set forth in in Table B or a sequence selected from the group consisting of: SEQ ID NOs: 135, 137, 139, 141, 143, 145, 147, 149, 151, 153, 155, 157, 159, 161, 163, 165, 167, 169, 171, 173, and 175, or a variant sequence thereof which differs by only one or two amino acids or which has at least or about 70% (e.g., at least about 80%, at least about 85%, at least about 90%, at least about 95%) sequence identity; or (b) a light chain variable region amino acid sequence set forth in Table B or a sequence selected from the group consisting of: SEQ ID NOs: 134, 136, 138, 140, 142, 144, 146, 148, 150, 152, 154, 156, 158, 160, 162, 164, 166, 168, 170, 172, 174, and 176, or a variant sequence thereof which differs by only one or two amino acids or which has at least or about 70% (e.g., at least about 80%, at least about 85%, at least about 90%, at least about 95%) sequence identity; or (c) both (a) and (b).

TABLE B

|  | Light Chain Variable Region | Heavy Chain Variable Region |
| --- | --- | --- |
| AB1 | 134 | 135 |
| AB2 | 136 | 137 |
| AB3 | 138 | 139 |
| AB4 | 140 | 141 |
| AB5 | 142 | 143 |
| AB6 | 144 | 145 |
| AB7 | 146 | 147 |
| AB8 | 148 | 149 |

TABLE B-continued

|  | Light Chain Variable Region | Heavy Chain Variable Region |
| --- | --- | --- |
| AB9 | 150 | 151 |
| AB10 | 152 | 153 |
| AB11 | 154 | 155 |
| AB12 | 156 | 157 |
| AB13 | 158 | 159 |
| AB14 | 160 | 161 |
| AB15 | 162 | 163 |
| AB16 | 164 | 165 |
| AB17 | 166 | 167 |
| AB18 | 168 | 169 |
| AB19 | 170 | 171 |
| AB20 | 172 | 173 |
| AB21 | 174 | 175 |

In various embodiments, the antigen-binding protein comprises a pair of amino acid sequences selected from the group consisting of: (a) SEQ ID NOs: 156 and 157; (b) SEQ ID NOs: 148 and 149; (c) SEQ ID NOs: 172 and 173; (d) SEQ ID NOs: 140 and 141; (e) SEQ ID NOs: 174 and 175; (f) SEQ ID NOs: 144 and 145; (g) SEQ ID NOs: 152 and 153; (h) SEQ ID NOs: 158 and 159; (i) SEQ ID NOs: 146 and 147; (j) SEQ ID NOs: 160 and 161; (k) SEQ ID NOs: 166 and 167; (l) SEQ ID NOs: 150 and 151; (m) SEQ ID NOs: 142 and 143; (n) SEQ ID NOs: 168 and 169; (o) SEQ ID NOs: 164 and 165; (p) SEQ ID NOs: 162 and 163; (q) SEQ ID NOs: 170 and 171; (r) SEQ ID NOs: 134 and 135; (s) SEQ ID NOs: 154 and 155; (t) SEQ ID NOs: 136 and 137; and (u) SEQ ID NOs: 138 and 139.

In various aspects, the antigen-binding protein does not comprise a pair of amino acid sequences encoded by the sequences of SEQ ID NOs: 179 and 180. In various aspects, the antigen-binding protein does not comprise a pair of amino acid sequences of SEQ ID NOs: 181 and 182. In various aspects, the antigen-binding protein does not comprise a pair of amino acid sequences encoded by the sequences of SEQ ID NOs: 183 and 184. In various aspects, the antigen-binding protein does not comprise a pair of amino acid sequences of SEQ ID NOs: 185 and 186.

In various aspects, the antigen-binding protein comprises an amino acid sequence which is similar to an above-referenced amino acid sequence, yet the antigen-binding protein substantially retains its biological function, e.g., its ability to bind to human CLDN6, reduce tumor growth, treat cancer.

In various aspects, the antigen-binding protein comprises an amino acid sequence which differs by only 1, 2, 3, 4, 5, 6, or more amino acids, relative to the above-referenced amino acid sequence(s). In various aspects, the antigen-binding protein comprises a variant sequence of the referenced sequence, which variant sequence differs by only one or two amino acids, relative to the referenced sequence. In various aspects, the antigen-binding protein comprising one or more amino acid substitutions that occur outside of the CDRs, e.g, the one or more amino acid substitutions occur within the framework region(s) of the heavy or light chain. In various aspects, the antigen-binding protein comprising one or more amino acid substitutions yet the antigen-binding protein retains the amino acid sequences of the six CDRs. In various aspects, the antigen-binding protein comprises an amino acid sequence having only 1, 2, 3, 4, 5, 6, or more conservative amino acid substitutions, relative to the above-referenced amino acid sequence(s). As used herein, the term "conservative amino acid substitution" refers to the substitution of one amino acid with another amino acid having similar properties, e.g., size, charge, hydrophobicity, hydrophilicity, and/or aromaticity, and includes exchanges within one of the following five groups:
  I. Small aliphatic, nonpolar or slightly polar residues:
    Ala, Ser, Thr, Pro, Gly;
  II. Polar, negatively charged residues and their amides and esters:
    Asp, Asn, Glu, Gln, cysteic acid and homocysteic acid;
  III. Polar, positively charged residues:
    His, Arg, Lys; Ornithine (Orn)
  IV. Large, aliphatic, nonpolar residues:
    Met, Leu, Ile, Val, Cys, Norleucine (Nle), homocysteine
  V. Large, aromatic residues:
    Phe, Tyr, Trp, acetyl phenylalanine In various aspects, the conservative amino acid substitution is an exchange within one of the following groups of amino acids:
  I. aliphatic amino acids: Gly, Ala, Val, Leu, Ile
  II. non-aromatic amino acids comprising a side chain hydroxyl: Serc Thr
  III. amino acids comprising a sulfur side chain: Cys, Met
  IV: amino acids comprising a side chain aromatic ring: Phe, Tyr, Trp
  V: acidic amino acid: Glu; Asp
  VI: basic amino acid: Arg; Lys
  VII: amino acid comprising a side chain amide: Gln, Asn
  VIII: amino acid comprising a side chain imidazole: His, alpha-dimethyl imidiazole acetic acid (DMIA)
  IX: imino acid: Pro, 4-hydroxy-Pro, 4-amino-Pro In various aspects, the antigen-binding protein comprises an amino acid sequence which has greater than or about 30%, greater than or about 50%, or greater than or about 70% sequence identity to the above-referenced amino acid sequence. In various aspects, the antigen-binding protein comprises an amino acid sequence which has at least 30%, at least 40%, at least 50%, at least 60%, at least 70%, at least 80%, at least 85%, at least 90% or has greater than 90% sequence identity to the above-referenced amino acid sequence. In various aspects, the antigen-binding protein comprises an amino acid sequence that has at least 70%, at least 80%, at least 85%, at least 90% or has greater than 90% sequence identity along the full-length of the above-referenced amino acid sequence. In various aspects, the antigen-binding protein comprises an amino acid sequence having at least 95%, 96%, 97%, 98% or 99% sequence identity along the full-length of the above-referenced amino acid sequence.

In various aspects, the antigen-binding protein comprises a variant sequence of the referenced sequence, which variant sequence has at least or about 70% sequence identity, relative to the above-referenced sequence. In various aspects, the antigen-binding protein comprises a variant sequence of the referenced sequence, which variant sequence has at least or about 80% sequence identity, relative to the above-referenced sequence. In various aspects, the antigen-binding protein comprises a variant sequence of the referenced sequence, which variant sequence has at least or about 90% sequence identity, relative to the above-referenced sequence. In various aspects, the antigen-binding protein comprises a variant sequence of the referenced sequence, which variant sequence has at least or about 95% sequence identity, relative to the above-referenced sequence.

In various embodiments, the antigen-binding protein comprises one, two, three, four, or five sequences of the SEQ ID NOs. in a single row of Table A and at least one variant sequence having at least or about 70% (e.g., at least about 80%, at least about 85%, at least about 90%, at least about 95%) sequence identity to any of SEQ ID NOs: 8-133. In various embodiments, the antigen-binding protein comprises one, two, three, four, or five sequences of a set of sequences selected from: (a) SEQ ID NOs: 74-79; (b) SEQ ID NOs: 50-55; (c) SEQ ID NOs: 122-127; (d) SEQ ID NOs: 26-31; (e) SEQ ID NOs: 128-133; (f) SEQ ID NOs: 38-43; (g) SEQ ID NOs: 62-67; (h) SEQ ID NOs: 80-85; (i) SEQ ID NOs: 44-49; (j) SEQ ID NOs: 86-91; (k) SEQ ID NOs: 104-109; (l) SEQ ID NOs: 56-61; (m) SEQ ID NOs: 32-37; (n) SEQ ID NOs: 110-115; (o) SEQ ID NOs: 98-103; (p) SEQ ID NOs: 92-97; (q) SEQ ID NOs: 116-121; (r) SEQ ID NOs: 8-13; (s) SEQ ID NOs: 68-73; (t) SEQ ID NOs: 14-19; and (u) SEQ ID NOs: 20-25, wherein the antigen-binding protein further comprises at least one variant sequence having at least or about 70% (e.g., at least about 80%, at least about 85%, at least about 90%, at least about 95%) sequence identity to at least one of the sequences of the set. For instance, in various aspects, the antigen-binding protein comprises four sequences of SEQ ID NOs: 74-79, namely, SEQ ID NOs: 74-77, wherein the antigen-binding protein comprises two variant sequences: one variant sequence having at least or about 70% (e.g., at least about 80%, at least about 85%, at least about 90%, at least about 95%) sequence identity to SEQ ID NO: 78 and another variant sequence having at least or about 70% (e.g., at least about 80%, at least about 85%, at least about 90%, at least about 95%) sequence identity to SEQ ID NO: 79.

In various embodiments, the antigen-binding protein comprises a pair of variant sequences having at least or about 70% (e.g., at least about 80%, at least about 85%, at least about 90%, at least about 95%) sequence identity to any of SEQ ID NOs: 134-175. In various instances, the antigen binding protein comprises a pair of variant sequences which have at least or about 70% (e.g., at least about 80%, at least about 85%, at least about 90%, at least about 95%) sequence identity to (a) SEQ ID NOs: 156 and 157; (b) SEQ ID NOs: 148 and 149; (c) SEQ ID NOs: 172 and 173; (d) SEQ ID NOs: 140 and 141; (e) SEQ ID NOs: 174 and 175; (f) SEQ ID NOs: 144 and 145; (g) SEQ ID NOs: 152 and 153; (h) SEQ ID NOs: 158 and 159; (i) SEQ ID NOs: 146 and 147; (j) SEQ ID NOs: 160 and 161; (k) SEQ ID NOs: 166 and 167; (l) SEQ ID NOs: 150 and 151; (m) SEQ ID NOs: 142 and 143; (n) SEQ ID NOs: 168 and 169; (o) SEQ ID NOs: 164 and 165; (p) SEQ ID NOs: 162 and 163; (q) SEQ ID NOs: 170 and 171; (r) SEQ ID NOs: 134 and 135; (s) SEQ ID NOs: 154 and 155; (t) SEQ ID NOs: 136 and 137; and (u) SEQ ID NOs: 138 and 139. In various embodiments, the antigen-binding protein comprises a pair of sequences: one sequence of Table B and another sequence which is a variant sequence having at least or about 70% (e.g., at least about 80%, at least about 85%, at least about 90%, at least about 95%) sequence identity to any of SEQ ID NOs: 134-175. In various embodiments, the antigen-binding protein comprises a pair of sequences: one sequence selected from (a) SEQ ID NOs: 156 and 157; (b) SEQ ID NOs: 148 and 149; (c) SEQ ID NOs: 172 and 173; (d) SEQ ID NOs: 140 and 141; (e) SEQ ID NOs: 174 and 175; (f) SEQ ID NOs: 144 and 145; (g) SEQ ID NOs: 152 and 153; (h) SEQ ID NOs: 158 and 159; (i) SEQ ID NOs: 146 and 147; (j) SEQ ID NOs: 160 and 161; (k) SEQ ID NOs: 166 and 167; (l) SEQ ID NOs: 150 and 151; (m) SEQ ID NOs: 142 and 143; (n) SEQ ID NOs: 168 and 169; (o) SEQ ID NOs: 164 and 165; (p) SEQ ID NOs: 162 and 163; (q) SEQ ID NOs: 170 and 171; (r) SEQ ID NOs: 134 and 135; (s) SEQ ID NOs: 154 and 155; (t) SEQ ID NOs: 136 and 137; and (u) SEQ ID NOs: 138 and 139, and another sequence which is a variant sequence having at least or about 70% (e.g., at least about 80%, at least about 85%, at least about 90%, at least about 95%) sequence identity to a sequence of (a)-(u). For instance, in various aspects, the antigen-binding protein comprises a sequences of SEQ ID NO: 134 and the antigen-binding protein further comprises a variant sequence having at least or about 70% (e.g., at least about 80%, at least about 85%, at least about 90%, at least about 95%) sequence identity to SEQ ID NO 135.

In various instances, the antigen-binding protein comprises an amino acid sequence of an above-referenced amino acid sequence with one or more amino acid substitutions to reduce or eliminate reactive amino acids to decrease or prevent unwanted side chain reactions. For instance, the antigen-binding protein comprises an amino acid sequence of an above-referenced amino acid sequence with one or more (i) Trp residues substituted with His, Tyr, or Phe; (ii) Asn residues substituted with Gln, Ser, Ala, or Asp; (iii) Asp residues occurring immediately before a Pro residue substituted with Ala, Ser, or Glu, (iv) Asn residues substituted with Gln, Ser, or Ala; and/or (v) Cys residues substituted with Tyr, Ser, or Ala. In various aspects, the antigen-binding protein comprises an amino acid sequence of an above-referenced amino acid sequence with an amino acid substitution predicted to have greater binding affinity, greater stability, or other positive attribute, based on SHM events or based on statistical analyses of a multitude of other similar antibody sequences. In some aspects, the antigen-binding protein comprises (a) an HC CDR1 amino acid sequence set forth in Table A1 or a sequence selected from the group consisting of: SEQ ID NOs: 452, 455, 461, 465, 71, and 472, or a variant sequence thereof which differs by only one or two amino acids or which has at least or about 70 (e.g., at least about 80%, at least about 85%, at least about 90%, at least about 95%) sequence identity; (b) an HC CDR2 amino acid sequence set forth in Table A1 or a sequence selected from the group consisting of: SEQ ID NOs: 475, 456, 462, 466, 468, and 473; or a variant sequence thereof which differs by only one or two amino acids or which has at least or about 70% (e.g., at least about 80%, at least about 85%, at least about 90%, at least about 95%) sequence identity; (c) an HC CDR3 amino acid sequence set forth in Table A1 or a sequence selected from the group consisting of: SEQ ID NOs: 453, 457, 463, 467, 469, and 474; or a variant sequence thereof which differs by only one or two amino acids or which has at least or about 70% (e.g., at least about 80%, at least about 85%, at least about 90%, at least about 95%) sequence identity; (d) a LC CDR1 amino acid sequence set forth in Table A1 or a sequence selected from the group consisting of: SEQ ID NOs: 449, 476, 458, 464, 68, and 470; or a variant sequence thereof which differs by only one or two amino acids or which has at least or about 70% (e.g., at least about 80%, at least about 85%, at least about 90%, at least about 95%) sequence identity; (e) an LC CDR2 amino acid sequence set forth in Table A1 or a sequence selected from the group consisting of: SEQ ID NOs: 450, 477, 459, 57, 69, and 471; or a variant sequence thereof which differs by only one or two amino acids or which has at least or about 70% (e.g., at least about 80%, at least about 85%, at least about 90%, at least about 95%) sequence identity; (f) an LC CDR3 amino acid sequence set forth in Table A1 or a sequence selected from the group consisting of: SEQ ID NOs: 451, 454, 460, 58, 70, and 112; or a variant sequence thereof which differs by only one or two amino acids or which has at least or about 85%, at least about 90%, at least about 95%) sequence identity or (g) a combination of any two or more of (a)-(f).

TABLE A1

|  | LC CDR1 | LC CDR2 | LC CDR3 | HC CDR1 | HC CDR2 | HC CDR3 |
| --- | --- | --- | --- | --- | --- | --- |
| AB1* | 449 | 450 | 451 | 452 | 475 | 453 |
| AB3* | 476 | 477 | 454 | 455 | 456 | 457 |
| AB4* | 458 | 459 | 460 | 461 | 462 | 463 |
| AB9* | 464 | 57 | 58 | 465 | 466 | 467 |
| AB11* | 68 | 69 | 70 | 71 | 468 | 469 |
| AB18* | 470 | 471 | 112 | 472 | 473 | 474 |

In some aspects, the HC CDR1 comprises Gly immediately N-terminal of SEQ ID NO: 452 and, optionally, in some aspects, the HC CDR1 comprises MX immediately C-terminal of SEQ 452, wherein X is H, N, or S. In various aspects, the HC CDR3 comprises Ala immediately N-terminal of SEQ ID NO: 453. In various aspects, the LC CDR1 further comprises TAS immediately N-terminal of SEQ ID NO: 449, and, optionally, XH immediately C-terminal of SEQ ID NO: 449, wherein X is H, S, Y, or Q. In some aspects, as described below, the first amino acid of SEQ ID NO: 449 is S or Q. In some aspects, as described below, the first amino acid of SEQ ID NO: 451 is S or Q.

In various aspects, the HC CDR1 comprises Gly immediately N-terminal of SEQ ID NO: 455, and optionally, in various aspects, the HC CDR1 comprises MX immediately C-terminal of SEQ ID NO: 455, wherein X is N, S, or H. In some aspects, HC CDR2 comprises Gln immediately N-terminal of SEQ ID NO: SEQ ID NO: 456, and optionally H immediately C-terminal of SEQ ID NO: 456. In various aspects, the LC CDR1 comprises RIS immediately N-terminal of SEQ ID NO: 476, and optionally, comprises LA immediately C-terminal of SEQ ID NO: 476. In various aspects, the LC CDR2 comprises XLVE immediately C-terminal of SEQ ID NO: 477, wherein X is I or S.

In various aspects, the HC CDR1 comprises MH immediately C-terminal of SEQ ID NO: 461. In various aspects, the HC CDR2 comprises Tyr immediately N-terminal of SEQ ID NO: 462, and optionally, TH immediately C-terminal of SEQ ID NO: 462. In exemplary aspects, the HC CDR3 does not include the first two amino acids of SEQ ID NO: 463. In various aspects, the LC CDR1 comprises RSS immediately N-terminal of SEQ ID NO: 458, and optionally, LN immediately C-terminal of SEQ ID NO: 458. In various aspects, the LC CDR2 comprises XRFS immediately C-terminal of SEQ ID NO: 459, wherein X is Q, S, A, or D.

In various aspects, the HC CDR1 comprises MH immediately C-terminal of SEQ ID NO: 465. In various aspects, the HC CDR2 comprises YI immediately N-terminal of SEQ ID NO: 466, and optionally, Xaa immediately C-terminal of SEQ ID NO: 466, wherein Xaa is N, S, Q, or A. In various aspects, the LC CDR1 comprises LAS immediately N-terminal of SEQ ID NO: 464, and optionally, LA immediately C-terminal of SEQ ID NO: 464. In various aspects, the LC CDR2 comprises SLAD immediately C-terminal of SEQ ID NO: 57.

In various aspects, the HC CDR1 comprises MH immediately C-terminal of SEQ ID NO: 71. In various aspects, the HC CDR2 comprises Tyr immediately N-terminal of SEQ ID NO: 468 and optionally IY immediately C-terminal of SEQ ID NO: 468. In various aspects, the LC CDR1 comprises RAS immediately N-terminal of SEQ ID NO: 68, and optionally SYIH immediately C-terminal to SEQ 68. In various aspects, the LC CDR2 comprises XLES immediately C-terminal to SEQ ID NO: 69, wherein X is N, Q, S, A, or D.

In various aspects, the LC CDR1 comprises KSS immediately N-terminal of SEQ ID NO: 470, and optionally YLA immediately C-terminal to SEQ 470. In various aspects, the LC CDR2 comprises TRES immediately C-terminal of SEQ ID NO: 471. In various aspects, the HC CDR1 comprises MN immediately C-terminal of SEQ ID NO: 472. In various aspects, the HC CDR2 comprises Xaa immediately N-terminal of SEQ 473, wherein Xaa is N, Q, S, or A, and optionally, Thr immediately C-terminal of SEQ 473.

In various aspects, the antigen-binding protein comprises a LC CDR1 amino acid sequence, a LC CDR2 amino acid sequence, and a LC CDR3 amino acid sequence set forth in Table A1 and at least 1 or 2 of the HC CDR amino acid sequences set forth in Table A1. In various aspects, the antigen-binding protein comprises a HC CDR1 amino acid sequence, a HC CDR2 amino acid sequence, and a HC CDR3 amino acid sequence set forth in Table A1 and at least 1 or 2 of the LC CDR amino acid sequences set forth in Table A1.

In various embodiments, the antigen-binding protein comprises at least 3, 4, or 5 of the amino acid sequences designated by the SEQ ID NOs: in a single row of Table A1. In various embodiments, the antigen-binding protein comprises each of the LC CDR amino acid sequences designated by the SEQ ID NOs: of a single row of Table A1 and at least 1 or 2 of the HC CDR amino acid sequences designated by the SEQ ID NOs: in of a single row of Table A1. In various embodiments, the antigen-binding protein comprises each of the HC CDR amino acid sequences designated by the SEQ ID NOs: of a single row of Table A1 and at least 1 or 2 of the LC CDR amino acid sequences designated by the SEQ ID NOs: of a single row of Table A1. In various embodiments, the antigen-binding protein comprises all 6 of the CDR amino acid sequences designated by the SEQ ID NOs: of a single row of Table A1. In various embodiments, the antigen-binding protein comprises six CDR amino acid sequences selected from the group consisting of: (a) SEQ ID NOs: 449-453 and 475; (b) SEQ ID NOs: 476-477, 454-457; (c) SEQ ID NOs: 458-463; (d) SEQ ID NOs: 57, 58, 464-467; (e) SEQ ID NOs: 68-71 and 468-469; and (0 SEQ ID NOs: 112, and 470-474.

In various instances, the amino acid sequences of Table A1 are separated by at least one or more (e.g., at least 2, 3, 4, 5, 6, 7, 8, 9, 10, or more) intervening amino acid(s). In various instances, there are about 10 to about 20 amino acids between the sequences of the LC CDR1 and the LC CDR2 and about 25 to about 40 amino acids between the sequences of the LC CDR2 and the LC CDR3. In various instances, there are about 14 to about 16 amino acids between the sequences of the LC CDR1 and the LC CDR2 and about 30 to about 35 amino acids between the sequences of LC CDR2 and the LC CDR3. In various instances, there are about 10 to about 20 amino acids between the sequences of the HC CDR1 and HC CDR2 and about 25 to about 40 amino acids between the sequences of the HC CDR2 and the HC CDR3. In various instances, there are about 14 to about 16 amino acids between the sequences of the HC CDR1 and HC CDR2 and about 30 to about 35 amino acids between the sequences of the HC CDR2 and HC CDR3.

In various embodiments, the antigen-binding protein comprises (a) a heavy chain variable region amino acid sequence set forth in in Table B1 or a sequence selected from the group consisting of: SEQ ID NO: 478, 480, 482, 484, 486, and 488, or a variant sequence thereof which differs by only one or two amino acids or which has at least or about 70% (e.g., at least about 80%, at least about 85%, at least about 90%, at least about 95%) sequence identity; or (b) a light chain variable region amino acid sequence set forth in Table B1 or a sequence selected from the group consisting of: SEQ ID NO: 479, 481, 483, 485, 487, and 489, or a variant sequence thereof which differs by only one or two amino acids or which has at least or about 70% (e.g., at least about 80%, at least about 85%, at least about 90%, at least about 95%) sequence identity; or (c) both (a) and (b).

TABLE B1

|       | HC variable | LC variable |
|-------|-------------|-------------|
| AB1*  | 478         | 479         |
| AB3*  | 480         | 481         |
| AB4*  | 482         | 483         |
| AB9*  | 488         | 489         |
| AB11* | 486         | 487         |
| AB18* | 484         | 485         |

In various embodiments, the antigen-binding protein comprises a pair of amino acid sequences selected from the group consisting of: (a) SEQ ID NO: 478 and 479; (b) SEQ ID NO: 480 and 481; (c) SEQ ID NO: 482 and 483; (d) SEQ ID NO: 484 and 485; (e) SEQ ID NO: 486 and 487; and (0 SEQ ID NO: 488 and 489. In various aspects, the antigen-binding protein comprises a variant sequence of a sequence having a SEQ ID NO: listed in Table B1 which differs by only one or two amino acids or which has at least or about 70% (e.g., at least about 80%, at least about 85%, at least about 90%, at least about 95%) sequence identity, wherein the different amino acid(s) occur(s) at the positions described below in "Humanized Antibodies".

Humanized Antibodies

In various aspects, the antigen-binding protein is a humanized version of an antigen binding protein described in Table A, Table A1, Table B, or Table B1.

Humanized AB1

In various aspects, the antigen-binding protein is a humanized version of AB1 as set forth in Table B or B1 with one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) amino acid substitutions in the heavy chain variable region at one or more of the following positions: 5, 8, 11, 12, 13, 20, 31, 33, 35, 38, 40, 48, 50, 55, 57, 59, 61, 65, 66, 67, 68, 70, 72, 74, 76, 79, 80, 82, 87, 90, 91, 98, 101, and 116. In various instances, the antigen-binding protein comprises an amino acid sequence of SEQ ID NO: 428. In various aspects, the antigen-binding protein is a humanized version of AB1 as set forth in Table B or B1 with one or more amino acid substitutions in the heavy chain variable region at one or more (e.g., 1, 2, 3, 4, 5, 6, 7, 8, 9, 10, 11, or 12) of the following positions: 20, 31, 35, 48, 50, 59, 67, 70, 74, 79, 98, 101. In various instances, the antigen-binding protein comprises an amino acid sequence of SEQ ID NO: 429. In various aspects, the amino acids at the above-recited positions are selected from the amino acids according to the table below:

| Position | Amino acids | Position | Amino acids | Position | Amino acids |
|----------|-------------|----------|-------------|----------|-------------|
| 5        | Q, V        | 8        | A, G        | 11       | L,V         |
| 12       | A, K        | 13       | R, K        | 20       | M, V        |
| 31       | S, T, V, D  | 33       | Y, T        | 35       | H, N, S     |
| 38       | K, R        | 40       | R, A        | 48       | I, M        |

| Position | Amino acids | Position | Amino acids | Position | Amino acids |
|---|---|---|---|---|---|
| 50 | F, V, T, Y, I | 55 | G, S | 57 | S, Y |
| 59 | D, E, N, S | 61 | N, A | 65 | K, Q |
| 66 | D, G | 67 | R, Q, N,K | 68 | T, V |
| 70 | L, M | 72 | R, A | 74 | K, T |
|  |  | 79 | V, D, S, A | 82 | Q, E |
| 87 | T, R | 91 | S, T | 98 | N, Q, H, D, R |
| 101 | Y | 76 | ST | 116 | A, S |

In various aspects, the antigen-binding protein is a humanized version of AB1 as set forth in Table B or B1 with one or more amino acid substitutions in the light chain variable region at one or more e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41) of the following positions: 1, 3, 4, 9, 10, 11, 15, 17, 21, 24, 27, 29, 32, 34, 35, 43, 44, 48, 51, 52, 53, 54, 55, 56, 61, 67, 71, 72, 73, 79, 80, 81, 84, 90, 92, 93, 94, 95, 96, 101, 107. In various instances, the antigen-binding protein comprises an amino acid sequence of SEQ ID NO: 430. In various aspects, the antigen-binding protein is a humanized version of AB1 as set forth in Table B or B1 with one or more amino acid substitutions in the light chain variable region at one or more (e.g., 1, 2, 3, 4, 5, 6, 7, 8, 9, 10, 11, 12, or 13) of the following positions: 4, 21, 32, 34, 48, 51, 53, 61, 67, 79, 84, 91, and 93. In various instances, the antigen-binding protein comprises an amino acid sequence of SEQ ID NO: 431. In various aspects, the amino acids at the above-recited positions are selected from the amino acids according to the table below:

| Position | Amino acids | Position | Amino acids | Position | Amino acids |
|---|---|---|---|---|---|
| 1 | Q, D | 3 | V, Q | 4 | L, M |
| 9 | A, S | 10 | I, S | 11 | M, L |
| 15 | L, V | 17 | E, D | 21 | M, I |
| 24 | T, R | 27 | S, Q | 32 | T, V, F, D, S |
| 34 | F, L | 35 | H, S, Y, Q, N | 43 | S, K |
| 44 | S, A | 48 | W, L | 51 | S, T, Q, A |
| 52 | T, A | 53 | S, T, D, Q | 54 | N, S |
|  |  | 56 | A, Q | 61 | R, Q, S, D, Y, F |
| 67 | A, S, T, G | 71 | S, D | 72 |  |
| 73 | S, T | 79 | M, L | 80 | E, Q |
| 81 | A, P | 84 | A, F | 90 | H, Q |
| 91 | Q, H, S | 93 | H,Q, S, Y | 94 | R, S |
| 97 | L, P | 101 | A, Q | 107 | L, I |
| 29 | V, I | 92 | Y, S | 95 | S, T |

Humanized AB3

In various aspects, the antigen-binding protein is a humanized version of AB3 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33) of the following positions: 3, 5, 18, 19, 23, 31, 33, 35, 40, 42, 49, 50, 52, 53, 54, 55, 56, 57, 58, 59, 61, 64, 76, 79, 80, 81, 87, 94, 95, 99, 106, 112, 114. In various instances, the antigen-binding protein comprises an amino acid sequence of SEQ ID NO: 432. In various aspects, the antigen-binding protein is a humanized version of AB3 as set forth in Table B or B1 with one or more amino acid substitutions in the heavy chain variable region at one or more (e.g., 1, 2, 3, 4, 5, 6, or 7) of the following positions: 31, 35, 50, 55, 79, 99, 106. In various instances, the antigen-binding protein comprises an amino acid sequence of SEQ ID NO: 433. In various aspects, the amino acids at the above-recited positions are selected from the amino acids according to the table below:

| Position | Amino acids | Position | Amino acids | Position | Amino acids |
|---|---|---|---|---|---|
| 3 | K, Q | 5 | E, L | 18 | M, L |
| 19 | K, R | 23 | V, A | 31 | N, S, R |
| 33 | W, A | 35 | N, S, H | 40 | S, A |
| 42 | E, G | 49 | A, S | 50 | Q, S, N, H, A |
|  |  | 52 | R, S | 53 | L, G |
| 54 | K, S | 55 | S, N,T, A, G | 56 | D, G |
|  |  |  |  | 59 | A, S |
| 61 | H, Y | 64 | E, D | 76 | D, N |
| 79 | R, N, Q, D, S | 80 | S, T | 81 | V, L |
| 87 | N, S | 94 | G, A | 95 | T, V, I |
| 99 | N, D, T, K, A | 106 | C,Y, A, S, T | 112 | T, L |
| 114 | I, T |  |  |  |  |

In various aspects, the antigen-binding protein is a humanized version of AB3 as set forth in Table B or B1 with one or more amino acid substitutions in the light chain variable region at one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29) of the following positions: 9, 17, 18, 25, 27, 28, 30, 34, 40, 43, 45, 48, 50, 52, 53, 55, 56, 70, 72, 74, 76, 84, 85, 90, 91, 93, 94, 97, and 100. In various instances, the antigen-binding protein comprises an amino acid sequence of SEQ ID NO: 434. In various aspects, the antigen-binding protein is a humanized version of AB3 as set forth in Table B or B1 with one or more amino acid substitutions in the light chain variable region at one or more (e.g., 1, 2, 3, 4, 5, 6, 7, 8, or 9) of the following positions: 25, 34, 48, 53, 55, 84, 85, 90, and 93. In various instances, the antigen-binding protein comprises an amino acid sequence of SEQ ID NO: 435. In various aspects, the amino acids at the above-recited positions are selected from the amino acids according to the table below:

| Position | Amino acids | Position | Amino acids | Position | Amino acids |
|---|---|---|---|---|---|
| 9 | A, S | 17 | E, D | 18 | T, R |
| 25 | I, V, L, T, A | 34 | A, S, N | 40 | Q, P |
| 43 | S, A | 45 | Q, K | 48 | V, I |
| 53 | I, V, L, T, S | 55 | V, T, L, A, Q | 70 | Q, D |
| 72 | S, T | 74 | K, T | 76 | N, S |
| 84 | G, A | 85 | N, Q, S, T | 90 | H, Q, S, T |
| 93 | T, S, N, G | 100 | G, Q | 27 | E, Q |
| 28 | N, S | 30 | Y, S | 50 | N, A |
| 52 | K, S | 56 | E, S | 91 | H, S |
| 94 | V, T | 97 | T, P |  |  |

Humanized AB4

In various aspects, the antigen-binding protein is a humanized version of AB4 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, 20, 21, 22, 23, 24, 25, 26, 27, 28, 29, 30, 31, 32, 33, 34, 35, or 36 of the following positions: 5, 11, 12, 13, 20, 29, 31, 33, 37, 38, 40, 45, 48, 50, 55, 56, 57, 59, 61, 62, 65, 66, 67, 68, 70, 72, 74, 76, 79, 82, 84, 87, 91, 97, 101, 117. In various instances, the antigen-binding protein comprises an amino acid sequence of SEQ ID NO: 436. In various aspects, the antigen-binding protein is a humanized version of AB4 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, or 19) of the following positions: 20, 29, 31, 37, 45, 48, 56, 59, 61, 62, 65, 66, 68, 70, 74, 79, 84, 97, and 101. In various instances, the antigen-binding protein comprises an amino acid sequence of SEQ ID NO: 437. In various aspects, the amino acids at the above-recited positions are selected from the amino acids according to the table below:

| Position | Amino acids | Position | Amino acids | Position | Amino acids |
|---|---|---|---|---|---|
| 5 | Q, V | 11 | L, V | 12 | A, K |
| 13 | R, K | 20 | M, V | 33 | T, Y |
| 37 | I, V, F, Y | 38 | K, R | 40 | R, A |
| 45 | Q, L, V, T, N | 48 | I, M | 50 | Y, I |
| 55 | S, G | 56 | T, G, S, V, D | 57 | Y, S |
| 59 | H, K, S, Q, N | 61 | I, A, N, F, Y, V | 62 | K, Q |
| 65 | K, Q | 66 | D, G | 67 | K, R |
| 68 | A, V | 70 | L, M | 72 | A, R |
| 74 | T, K | 76 | S, T | 79 | A, V |
| 82 | Q, E | 84 | R, S, Q, D | 87 | T, R |
| 91 | S, T | 97 | S, A, T, V | 101 | L, V, F |
| 117 | A, S | 29 | F, Y, S, T | 31 | S, T, Y, D |

In various aspects, the antigen-binding protein is a humanized version of AB4 as set forth in Table B or B1 with one or more amino acid substitutions in the light chain variable region at one or more (e.g., 1, 2, 3, 4, 5, 6, 7, 8, 9, 10, 11, 12, 13, 14, 15, 16, 17, 18, 19, 20, 21, 22, 23, or 24) of the following positions: 7, 14, 17, 18, 31, 33, 39, 41, 42, 44, 50, 51, 55, 57, 60, 81, 88, 92, 94, 95, 96, 99, 100, 105. In various instances, the antigen-binding protein comprises an amino acid sequence of SEQ ID NO: 438. In various aspects, the antigen-binding protein is a humanized version of AB4 as set forth in Table B or B1 with one or more amino acid substitutions in the light chain variable region at one or more (e.g., 1, 2, 3, 4, 5, 6, or 7) of the following positions: 33, 39, 55, 57, 81, 95, and 96. In various instances, the antigen-binding protein comprises an amino acid sequence of SEQ ID NO: 439. In various aspects, the amino acids at the above-recited positions are selected from the amino acids according to the table below:

| Position | Amino acids | Position | Amino acids | Position | Amino acids |
|---|---|---|---|---|---|
| 7 | T, S | 14 | S, T | 17 | D, Q |
| 18 | Q, P | 31 | Y, H | 33 | D, N, E, Q |
| 39 | H, N, Q, D | 41 | F, Y | 42 | L, Q |
| 44 | K, R | 50 | K, R | 51 | R, L |
| 55 | K, R, Q | 57 | S, T, V | 60 | D, F |
| 81 | R, S, N, D | 88 | L, V | 92 | F, Y |
| 94 | M, S | 95 | Q, H, T | 96 | S, T, G, D |
| 99 | W, V | 105 | G, Q | | |

Humanized AB18

In various aspects, the antigen-binding protein is a humanized version of AB18 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, 19, 20, 21, 22, 23, 24, or 25) of the following positions: 5, 9, 11, 12, 20, 38, 40, 41, 43, 44, 48, 61, 65, 67, 68, 70, 72, 74, 76, 79, 82, 84, 87, 91, and 116, optionally, one or more (e.g., 1, 2, 3, 4, or 5) of the following positions: 20, 48, 68, 70, 79. In various instances, the antigen-binding protein comprises an amino acid sequence of SEQ ID NO: 440 or 441. In various aspects, the amino acids at the above-recited positions are selected from the amino acids according to the table below:

| Position | Amino acids | Position | Amino acids | Position | Amino acids |
|---|---|---|---|---|---|
| 5 | K, V | 9 | P, A | 11 | L, V |
| 12 | E, K | 20 | I, V | 38 | K, R |
| 40 | S, A | 41 | N, P | 43 | K, Q |
| 44 | S, G | 48 | I, V, M | 61 | N, A |
| 65 | T, Q | 67 | K, R | 68 | A, V |
| 70 | L, M | 72 | V, R | 74 | K, T |
| 76 | S, T | 79 | A, V | 82 | Q, E |
| 84 | K, S | 87 | T, R | 91 | S, T |
| 116 | S, L | | | | |

In various aspects, the antigen-binding protein is a humanized version of AB18 as set forth in Table B or B1 with one or more amino acid substitutions in the light chain variable region at one or more (e.g., 1, 2, 3, 4, 5, 6, 7, 8, 9, 10, 11, 12, 13, 14, 15, or 16) of the following positions: 1, 3, 9, 15, 18, 19, 21, 22, 49, 51, 69, 93, 84, 78, 105, and 111, optionally, one or more (e.g., 1, 2, or 3) of the following positions: 19, 21, or 84. In various instances, the antigen-binding protein comprises an amino acid sequence of SEQ ID NO: 442 or 443. In various aspects, the amino acids at the above-recited positions are selected from the amino acids according to the table below:

| Position | Amino acids | Position | Amino acids | Position | Amino acids |
|---|---|---|---|---|---|
| 1 | N, D | 3 | M, V | 9 | S, D |
| 15 | A, L | 18 | K, R | 19 | V, A |
| 21 | M, I | 22 | S, N | 49 | S, P |
| 51 | R, K | 69 | T, S | 83 | N, S |
| 84 | V, L | 89 | L, V | 105 | A, Q |
| 111 | L, I | | | | |

Humanized AB9

In various aspects, the antigen-binding protein is a humanized version of AB9 as set forth in Table B or B1 with one or more amino acid substitutions in the heavy chain variable region at one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29) of the following positions: 1, 5, 9, 11, 12, 20, 38, 40, 41, 43, 44, 48, 61, 63, 65, 67, 69, 70, 72, 73, 74, 76, 79, 84, 87, 91, 93, 112, and 113. In various instances, the antigen-binding protein comprises an amino acid sequence of SEQ ID NO: 444. In various aspects, the amino acids at the above-recited positions are selected from the amino acids according to the table below:

| Position | Amino acids | Position | Amino acids | Position | Amino acids |
|---|---|---|---|---|---|
| 1 | E, Q | 5 | Q, V | 9 | P, A |
| 11 | L, V | 12 | V, K | 20 | M, V |
| 38 | K R, | 40 | S, A | 41 | H, P |
| 43 | K Q | 44 | S, G | 48 | I, M |
| 61 | N, A | 63 | N, K | 65 | K, Q |
| 67 | K, R | 69 | A, V | 70 | L, M |
| 72 | V, R | 73 | N, D | 74 | K, T |
| 76 | S, T | 79 | A, V | 84 | R, S |
| 87 | T, R | 91 | S, T | 93 | A, V |
| 112 | T, L | 113 | L, V | | |

In various aspects, the antigen-binding protein is a humanized version of AB9 as set forth in Table B or B1 with one or more amino acid substitutions in the light chain variable region at one or more (e.g., 1, 2, 3, 4, 5, 6, 7, 8, 9, 10, 11, 12, 13, 14, or 15) of the following positions: 9, 11, 15, 17, 18, 43, 45, 70, 72, 73, 74, 80, 84, 85, and 100. In various instances, the antigen-binding protein comprises an amino acid sequence of SEQ ID NO: 445. In various aspects, the amino acids at the above-recited positions are selected from the amino acids according to the table below:

| Position | Amino acids | Position | Amino acids | Position | Amino acids |
|---|---|---|---|---|---|
| 9 | A, S | 11 | Q, L | 15 | L, V |
| 17 | E, D | 18 | S, R | 43 | S, A |
| 45 | Q, K | 70 | R, D | 72 | S, T |
| 73 | F, L | 74 | K, R | 80 | A, P |
| 84 | V, A | 85 | S, T | 100 | G, Q |

Humanized AB11

In various aspects, the antigen-binding protein is a humanized version of AB11 as set forth in Table B or B1 with one or more amino acid substitutions in the heavy chain variable region at one or more (e.g., 1, 2, 3, 4, 5, 6, 7, 8, 9, 10, 11, 12, 13, 14, or 15) of the following positions: 1, 15, 18, 19, 42, 49, 63, 75, 76, 78, 80, 84, 88, and 93. In various instances, the antigen-binding protein comprises an amino acid sequence of SEQ ID NO: 446. In various aspects, the amino acids at the above-recited positions are selected from the amino acids according to the table below:

| Position | Amino acids | Position | Amino acids | Position | Amino acids |
|---|---|---|---|---|---|
| 1 | D, E | 15 | R, G | 18 | R, L |
| 19 | K, R | 42 | E, G | 49 | A, S |
| 63 | T, S | 75 | P, A | 76 | T, K |
| 78 | T, S | 80 | F, Y | 84 | T, N |
| 88 | S, A | 93 | M, V | | |

In various aspects, the antigen-binding protein is a humanized version of AB11 as set forth in Table B or B1 with one or more amino acid substitutions in the light chain variable region at one or more (e.g., 1, 2, 3, 4, 5, 6, 7, 8, 9, 10, 11, 12, 13, 14, or 15) of the following positions: 4, 9, 17, 22, 64, 78, 80, 81, 82, 83, 84, 87, 89, 104, and 110, optionally, one or more of the following positions: 4, 82, 110. In various instances, the antigen-binding protein comprises an amino acid sequence of SEQ ID NO: 447 or 448. In various aspects, the amino acids at the above-recited positions are selected from the amino acids according to the table below:

| Position | Amino acids | Position | Amino acids | Position | Amino acids |
|---|---|---|---|---|---|
| 4 | L, M | 9 | A, D | 17 | Q, E |
| 22 | S, N | 64 | A, D | 78 | N, T |
| 80 | H, S | 81 | P, S | 82 | V, L |
| 83 | E, Q | 84 | E, A | 87 | A, V |
| 89 | T, V | 104 | A, Q | 110 | L, I |

In various embodiments, the antigen-binding protein comprises (a) a heavy chain variable region amino acid sequence set forth in in Table C or a sequence selected from the group consisting of: 376-379, 384-387, 391-396, 403-408, 412, 413, 416-419, and 422-427 or a variant sequence thereof which differs by only one or two amino acids or which has at least or about 70%, or about 80%, or about 85%, or about 90%, or about 95% sequence identity; or (b) a light chain variable region amino acid sequence set forth in Table C or a sequence selected from the group consisting of: 380-383, 388-390, 397-402, 409-411, 414, 415, 420, and 421 or a variant sequence thereof which differs by only one or two amino acids or which has at least or about 70%, or about 80%, or about 85%, or about 90%, or about 95% sequence identity; or (c) both (a) and (b).

TABLE C

| | Humanized Light Chain Variable Region | Humanized Heavy Chain Variable Region |
|---|---|---|
| AB1 | 380, 381, 382, 383 | 376, 377, 378, 379 |
| AB3 | 388, 389, 390 | 384, 385, 386, 387, 422 |
| AB4 | 397, 398, 399, 400, 401, 402 | 391, 392, 392, 394, 395, 396, 423, 424, 425, 426, 427 |
| AB9 | 409, 410, 411, | 403, 404, 405, 406, 407, 408 |
| AB11 | 414, 415 | 412, 413 |
| AB18 | 420, 421 | 416, 417, 418, 419 |

In various embodiments, the humanized antigen-binding protein comprises a pair of amino acid sequences as shown in Table D.

TABLE D

| Humanized AB | HC | LC |
|---|---|---|
| 1-1 | 376 | 380 |
| 1-2 | 377 | 380 |
| 1-3 | 377 | 381 |
| 1-4 | 377 | 382 |
| 1-5 | 377 | 383 |
| 1-6 | 378 | 381 |
| 1-7 | 378 | 382 |
| 1-8 | 378 | 383 |
| 1-9 | 379 | 381 |
| 1-10 | 379 | 382 |
| 1-11 | 379 | 383 |
| 3-1 | 384 | 388 |
| 3-2 | 385 | 388 |
| 3-3 | 385 | 389 |
| 3-4 | 386 | 388 |
| 3-5 | 386 | 389 |
| 3-6 | 387 | 388 |
| 3-7 | 387 | 389 |
| 3-9 | 422 | 389 |
| 4-1 | 391 | 397 |
| 4-2 | 392 | 397 |
| 4-3 | 392 | 398 |
| 4-4 | 393 | 398 |
| 4-5 | 394 | 398 |
| 4-6 | 395 | 398 |
| 4-7 | 396 | 398 |
| 4-8 | 423 | 398 |
| 4-9 | 424 | 398 |
| 4-10 | 425 | 398 |
| 4-11 | 426 | 398 |
| 4-12 | 427 | 398 |
| 9-1 | 403 | 409 |
| 9-2 | 404 | 409 |
| 9-3 | 405 | 410 |
| 9-4 | 405 | 411 |
| 9-5 | 406 | 410 |
| 9-6 | 406 | 411 |
| 9-7 | 407 | 410 |
| 9-8 | 407 | 411 |
| 9-9 | 408 | 410 |
| 9-10 | 408 | 411 |
| 11-1 | 412 | 414 |
| 11-2 | 413 | 414 |
| 11-3 | 413 | 415 |
| 18-1 | 416 | 420 |
| 18-2 | 417 | 420 |
| 18-3 | 417 | 420 |
| 18-4 | 417 | 421 |
| 18-5 | 418 | 420 |

TABLE D-continued

| Humanized AB | HC | LC |
|---|---|---|
| 18-6 | 418 | 421 |
| 18-7 | 419 | 420 |
| 18-8 | 419 | 421 |

In various embodiments, the antigen-binding protein comprises a pair of variant sequences, each having at least or about 70% (e.g., at least about 80%, at least about 85%, at least about 90%, at least about 95%) sequence identity to a SEQ ID NO listed in Table C. In various embodiments, the antigen-binding protein comprises a pair of sequences: one sequence selected from a SEQ ID NO: listed in Table C and another sequence which is a variant sequence having at least or about 70% (e.g., at least about 80%, at least about 85%, at least about 90%, at least about 95%) sequence identity to a sequence having a SEQ ID NO: listed in Table D a sequence having a SEQ ID NO: listed in Table C.

In various embodiments, the antigen-binding protein comprises a pair of sequences: one sequence selected from a SEQ ID NO: listed in Table D, and another sequence which is a variant sequence having at least or about 70% (e.g., at least about 80%, at least about 85%, at least about 90%, at least about 95%) sequence identity to a sequence having a SEQ ID NO: listed in Table D. For instance, in various aspects, the antigen-binding protein comprises a sequences of SEQ ID NO: 419 and the antigen-binding protein further comprises a variant sequence having at least or about 70% (e.g., at least about 80%, at least about 85%, at least about 90%, at least about 95%) sequence identity to SEQ ID NO 421.

Figure 23:
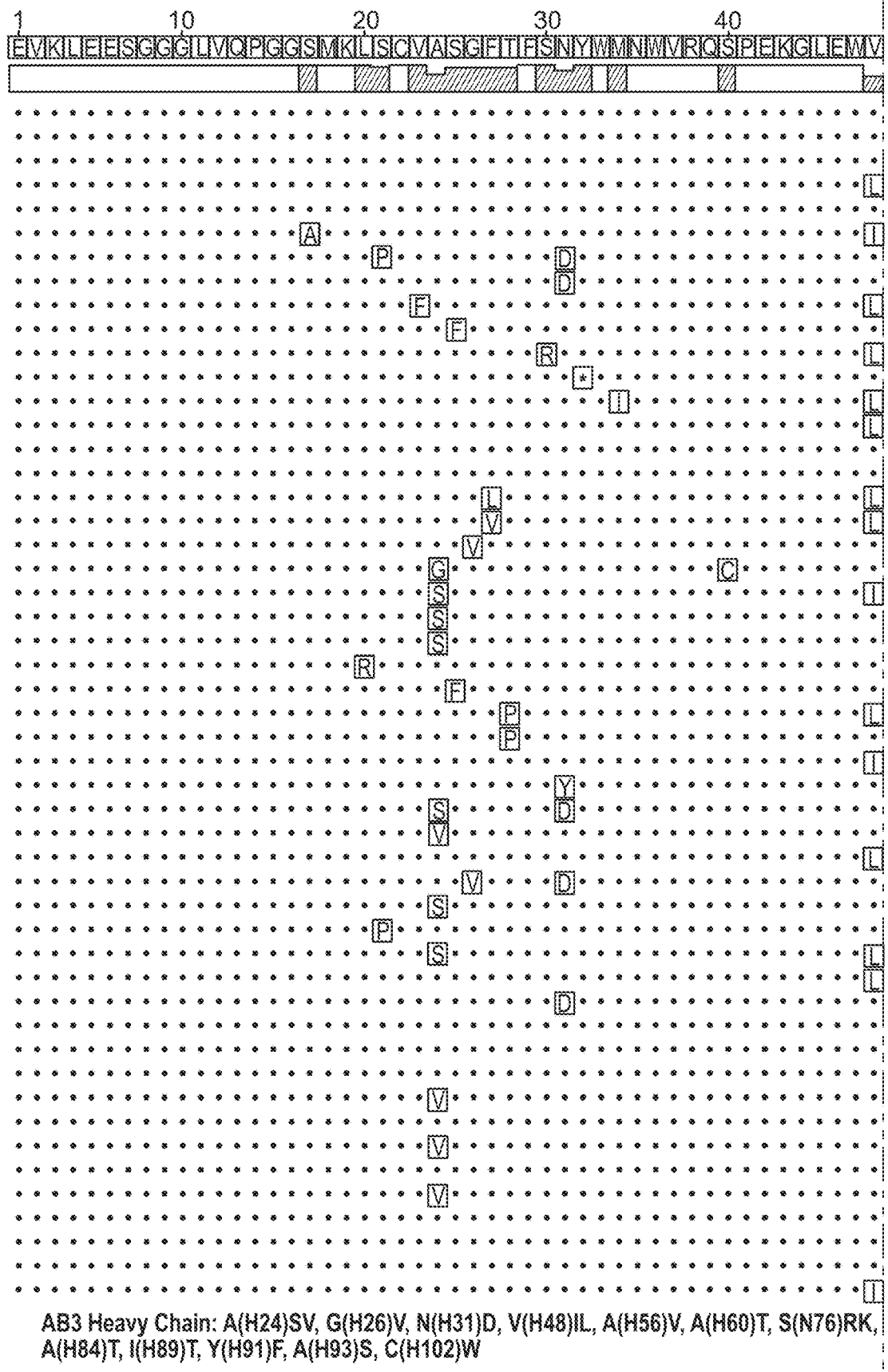
FIG. 23-FIG. 26 are schematic illustrations of exemplary next generation sequencing (NGS)-identified somatic hypermutation (SHM) of CLDN6 antibodies of the present disclosure.
Figure 23:
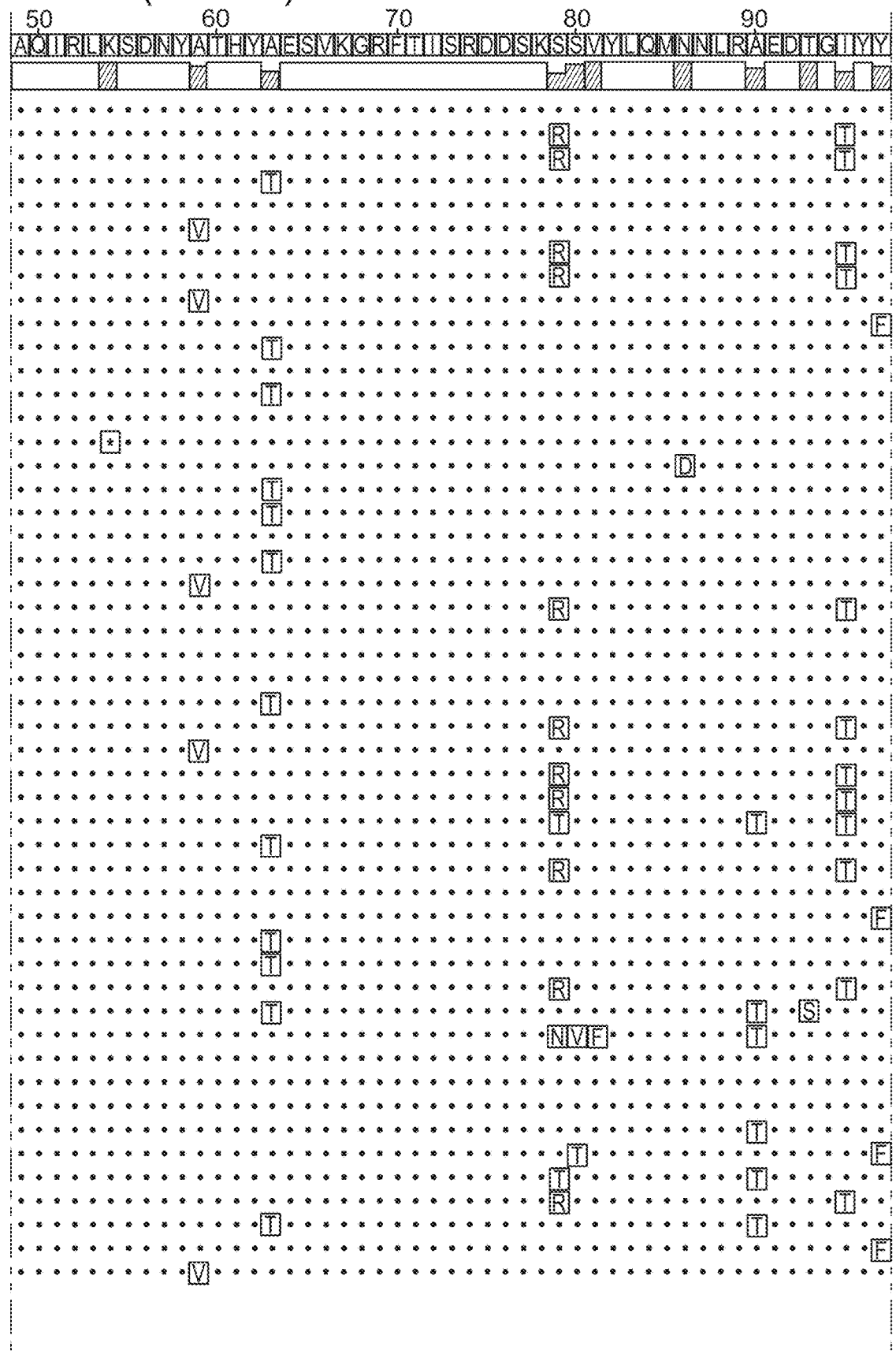
Figure 24:
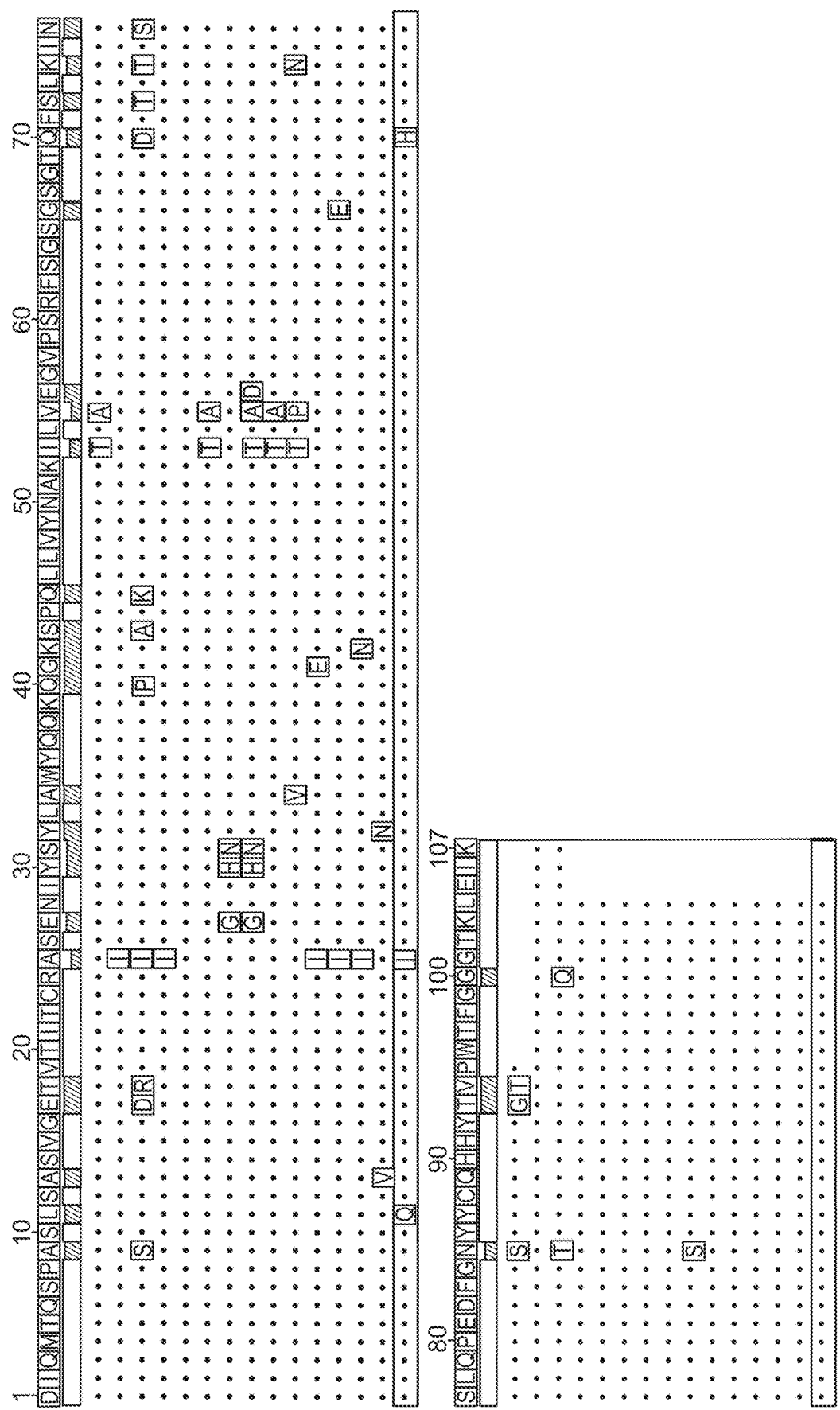
Figure 25:
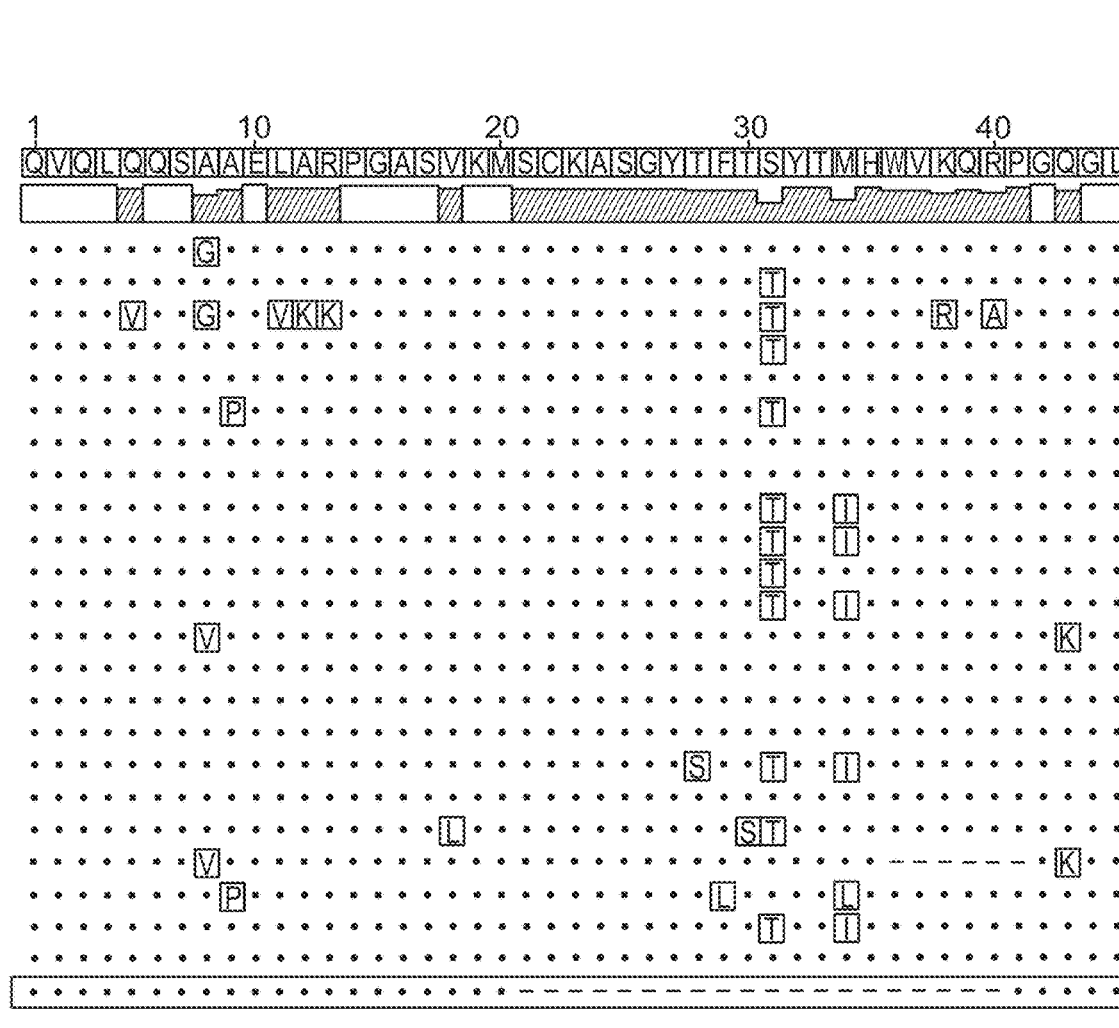
Figure 25:
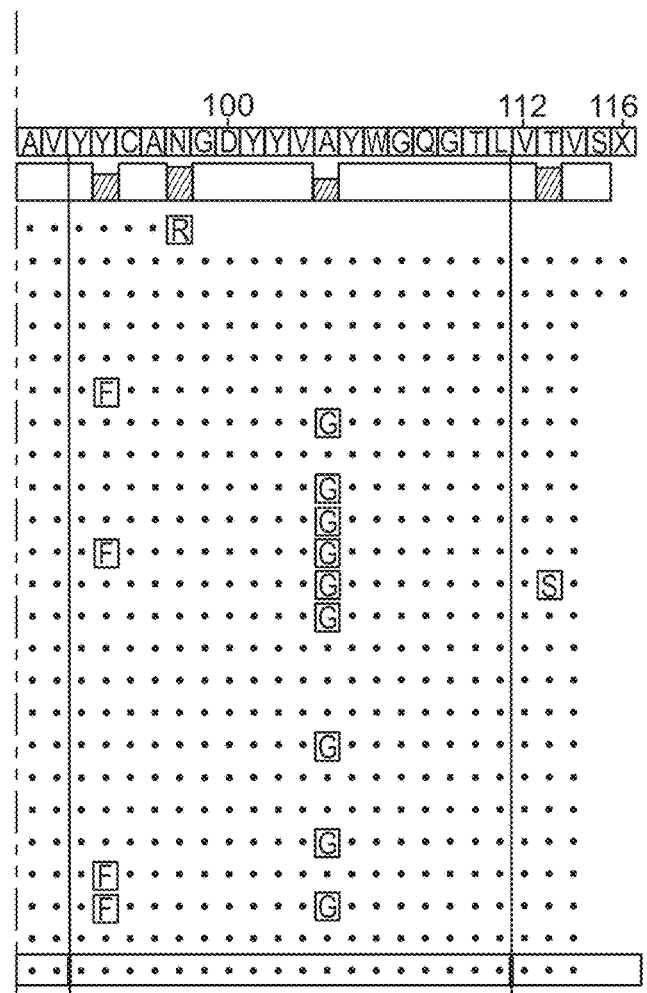
Figure 26:
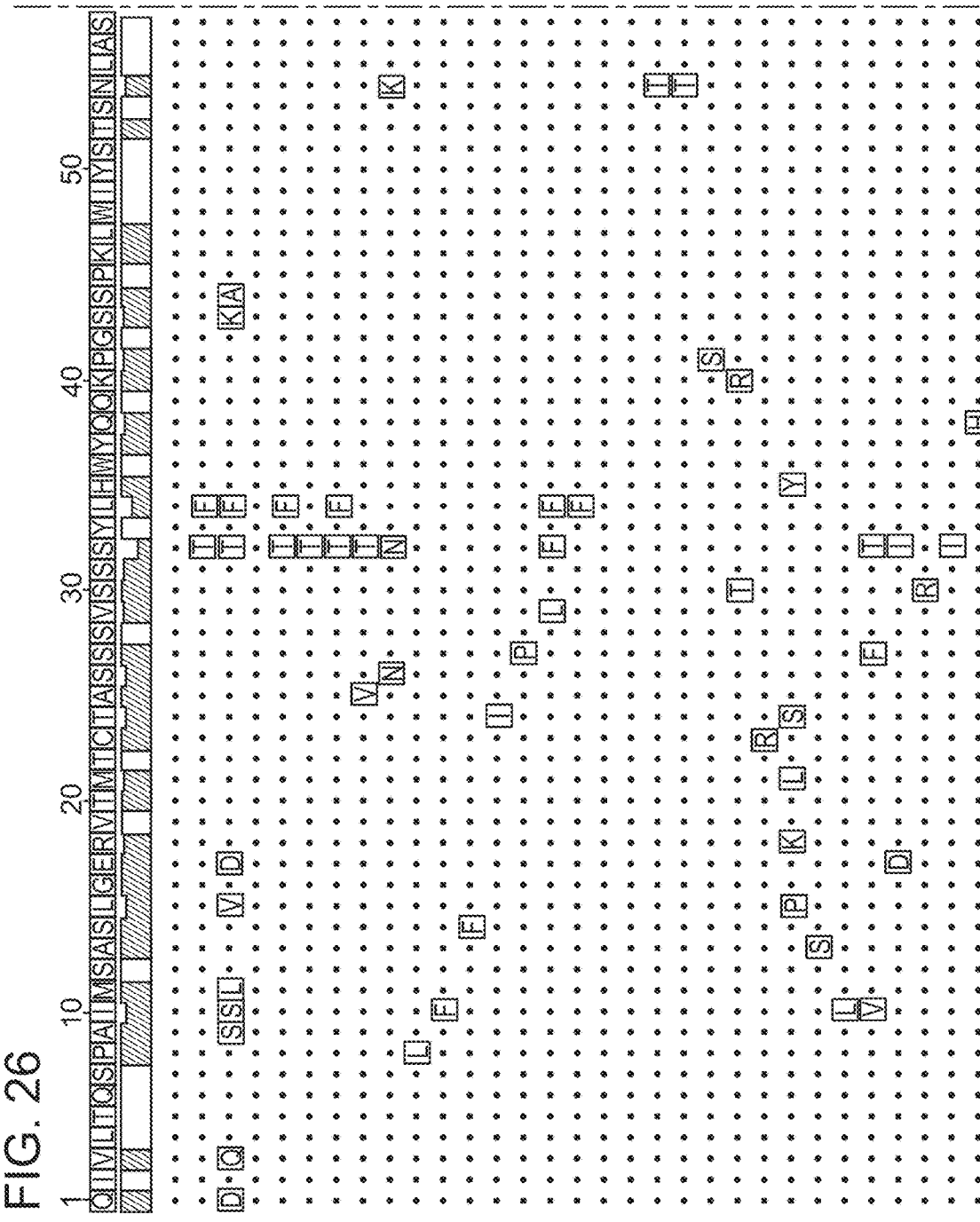
Figure 26:
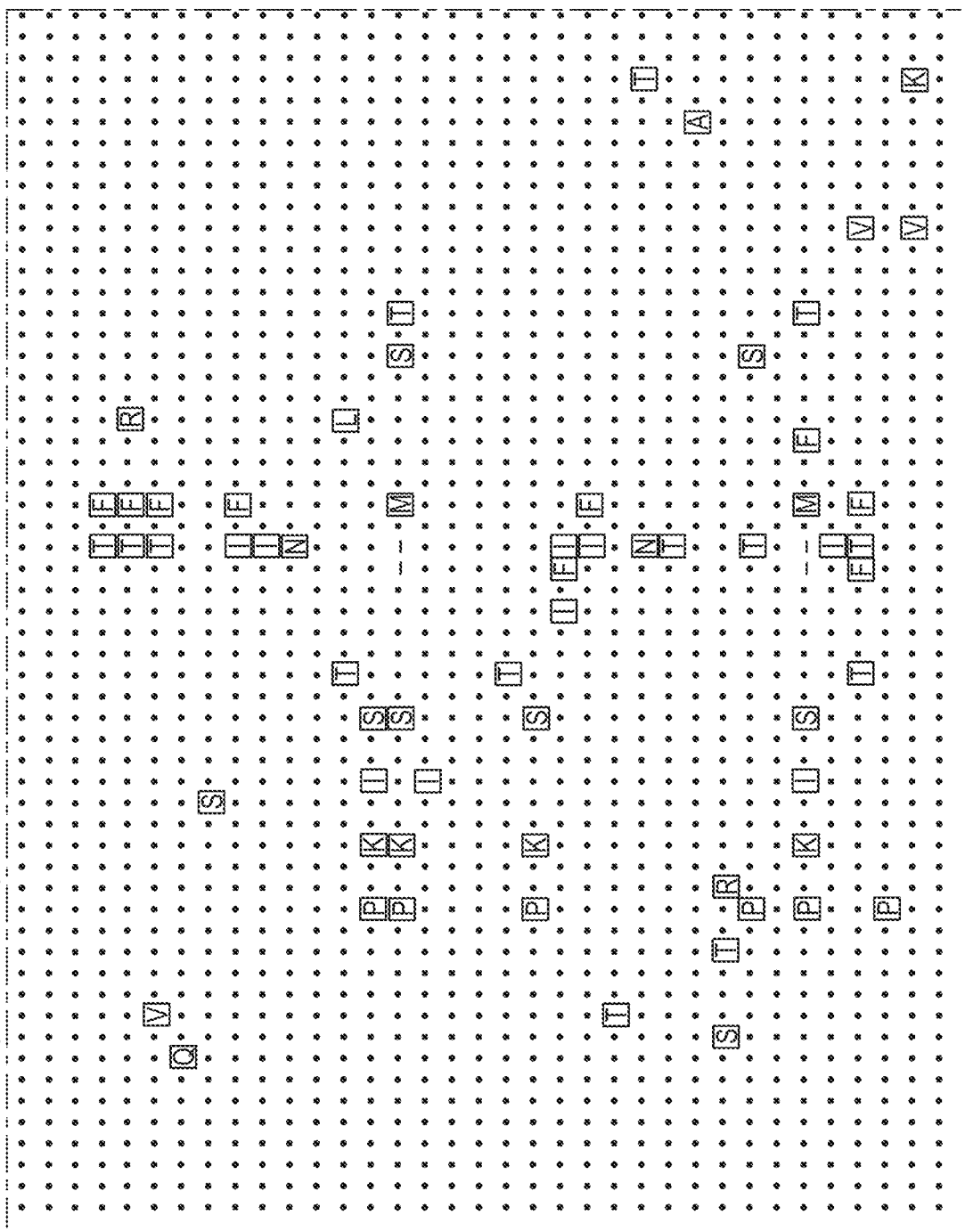
Figure 26:
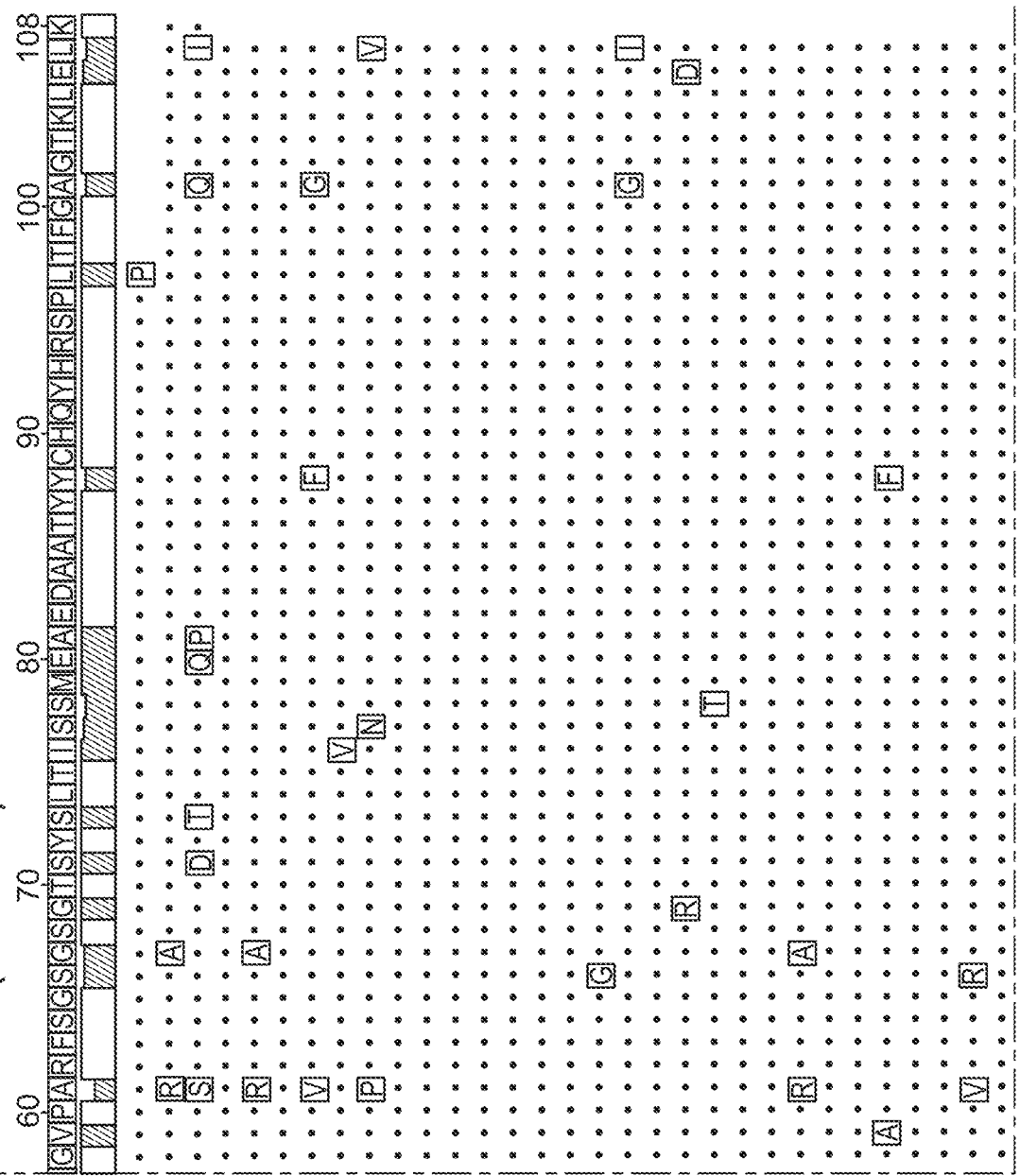
Figure 26:
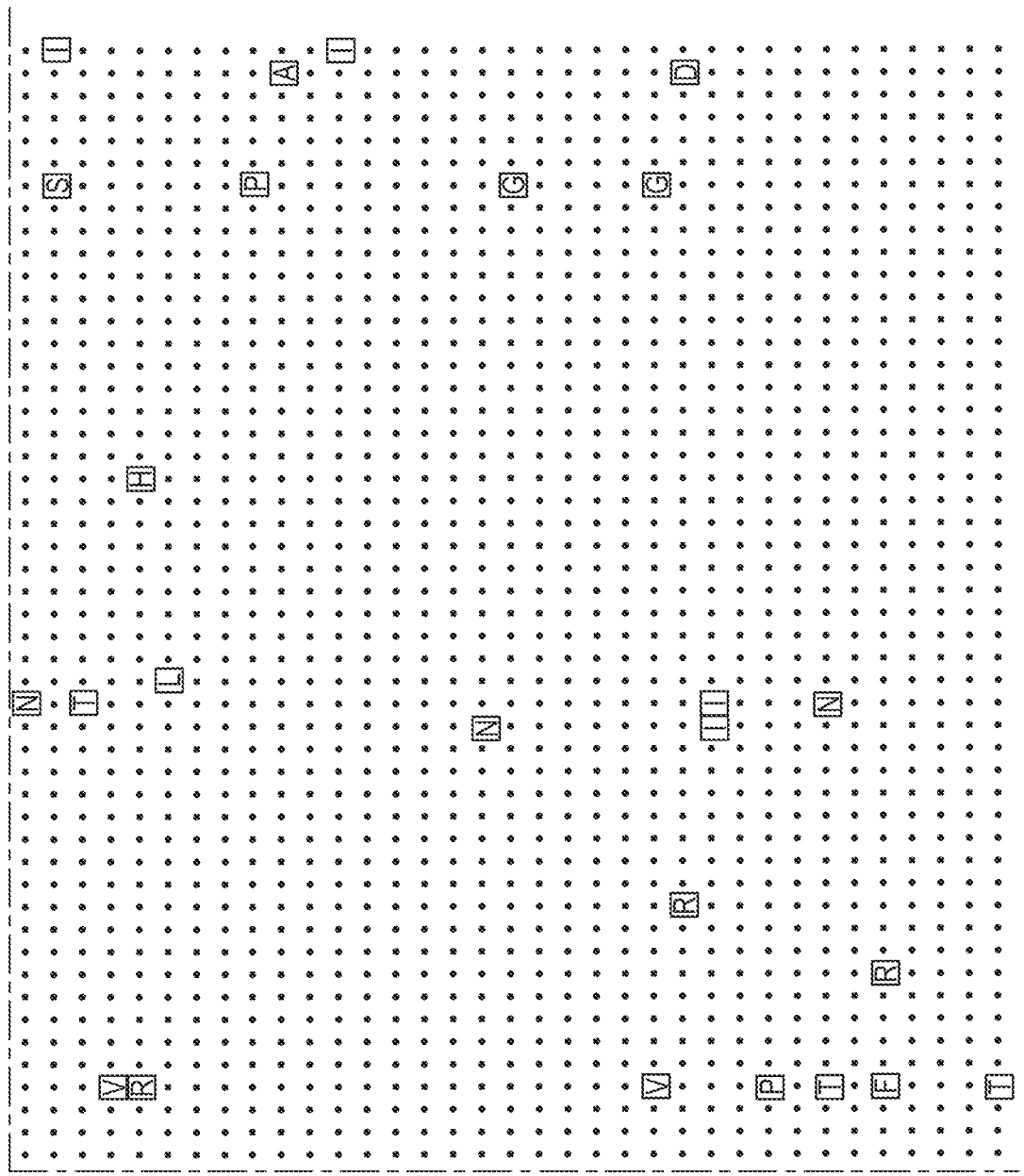

In various instances, the antigen-binding protein is a humanized antigen-binding protein as set forth in Table D with one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) amino acid substitutions in the heavy chain (HC) variable region or in the light chain (LC) variable region, or in both. In exemplary aspects, the antigen-binding protein is a humanized antigen-binding protein of AB1-11 with one or more amino acid substitutions in the HC variable region, the LC variable region, or both. In exemplary aspects, the antigen-binding protein comprises a HC of SEQ ID NO: 379 with 1, 2, 3, 4, or 5 amino acid substitutions. In exemplary aspects, the antigen-binding protein comprises a HC CDR1 of SEQ ID NO: 504, a HC CDR2 of SEQ ID NO: 505, a HC CDR3 of SEQ ID NO: 506, or a combination thereof. In exemplary instances, the antigen-binding protein comprises a HC of SEQ ID NO: 503. In some aspects, the antigen-binding protein comprises a HC of any one of SEQ ID NOs: 496-501. In some aspects, the antigen-binding protein comprises a HC sequence labeled as S7-S12 in FIG. 22. In various instances, the light chain variable region comprises a LC CDR1 of SEQ ID NO: 449, a LC CDR2 of SEQ ID NO: 450, a LC CDR3 of SEQ ID NO: 451, or a combination thereof. In some aspects, the antigen-binding protein comprises a LC of any one of SEQ ID NOs: 380-383, and 479. In exemplary instances, the antigen-binding protein comprises a LC of SEQ ID NO: 383. In some aspects, the antigen-binding protein comprises a LC sequence labeled as S7-S12 in FIG. 22. In exemplary aspects, the antigen-binding protein is a humanized antigen-binding protein of AB3-7 with one or more amino acid substitutions in the HC variable region, the LC variable region, or both. In exemplary aspects, the antigen-binding protein comprises a HC of SEQ ID NO: 387 with 1, 2, 3, 4, 5, or 6 amino acid substitutions. In exemplary aspects, the antigen-binding protein comprises a HC CDR1 of SEQ ID NO: 507, a HC CDR2 of SEQ ID NO: 508, a HC CDR3 of SEQ ID NO: 509, or a combination thereof. In exemplary instances, the antigen-binding protein comprises a HC of SEQ ID NO: 502. In some aspects, the antigen-binding protein comprises a HC of any one of SEQ ID NOs: 490-495. In some aspects, the antigen-binding protein comprises a HC sequence labeled as S1-S6 in FIG. 22. In various instances, the light chain variable region comprises a LC CDR1 of SEQ ID NO: 476, a LC CDR2 of SEQ ID NO: 477, a LC CDR3 of SEQ ID NO: 454, or a combination thereof. In some aspects, the antigen-binding protein comprises a LC of any one of SEQ ID NOs: 388-390, and 481. In exemplary instances, the antigen-binding protein comprises a LC of SEQ ID NO: 389. In some aspects, the antigen-binding protein comprises a LC sequence labeled as S1-S6 in FIG. 22. In exemplary aspects, the antigen-binding protein is a humanized antigen-binding protein of AB3 with one or more amino acid substitutions in the HC variable region, the LC variable region, or both. In exemplary aspects, the antigen-binding protein comprises a HC of SEQ ID NO: 139 with 1, 2, 3, 4, or 5 (or more) amino acid substitutions. In some aspects, the antigen-binding protein comprises a HC of any one of SEQ ID NOs: 510. In some aspects, the antigen-binding protein comprises a HC sequence of SEQ ID NO: 510 with 1, 2, 3, 4, or 5 (or more) amino acid substitutions as shown in FIG. 23. In exemplary aspects, the antigen-binding protein comprises a HC of SEQ ID NO: 138 with 1, 2, 3, 4, or 5 (or more) amino acid substitutions. In some aspects, the antigen-binding protein comprises a HC of any one of SEQ ID NOs: 511. In some aspects, the antigen-binding protein comprises a HC sequence of SEQ ID NO: 511 with 1, 2, 3, 4, or 5 (or more) amino acid substitutions as shown in FIG. 24. In exemplary aspects, the antigen-binding protein is a humanized antigen-binding protein of AB1 with one or more amino acid substitutions in the HC variable region, the LC variable region, or both. In exemplary aspects, the antigen-binding protein comprises a HC of SEQ ID NO: 135 with 1, 2, 3, 4, or 5 (or more) amino acid substitutions. In some aspects, the antigen-binding protein comprises a HC of any one of SEQ ID NOs: 513. In some aspects, the antigen-binding protein comprises a HC sequence of SEQ ID NO: 513 with 1, 2, 3, 4, or 5 (or more) amino acid substitutions as shown in FIG. 25. In exemplary aspects, the antigen-binding protein comprises a HC of SEQ ID NO: 134 with 1, 2, 3, 4, or 5 (or more) amino acid substitutions. In some aspects, the antigen-binding protein comprises a HC of any one of SEQ ID NOs: 512. In some aspects, the antigen-binding protein comprises a HC sequence of SEQ ID NO: 512 with 1, 2, 3, 4, or 5 (or more) amino acid substitutions as shown in FIG. 26.

Afucosylated Antibodies

Many secreted proteins undergo post-translational glycosylation, a process by which sugar moieties (e.g., glycans, saccharides) are covalently attached to specific amino acids of a protein. In eukaryotic cells, two types of glycosylation reactions occur: (1) N-linked glycosylation, in which glycans are attached to the asparagine of the recognition sequence Asn-X-Thr/Ser, where "X" is any amino acid except proline, and (2) O-linked glycosylation in which glycans are attached to serine or threonine. Regardless of the glycosylation type (N-linked or O-linked), microheterogeneity of protein glycoforms exists due to the large range of glycan structures associated with each site (O or N).

All N-glycans have a common core sugar sequence: Manα1-6(Manα1-3)Manβ1-4GlcNAcβ1-4GlcNAcβ1-Asn- X-Ser/Thr (Man$_3$GlcNAc$_2$Asn) and are categorized into one of three types: (A) a high mannose (HM) or oligomannose (OM) type, which consists of two N-acetylglucosamine (GalNAc) moieties and a large number (e.g., 5, 6, 7, 8 or 9) of mannose (Man) residues (B) a complex type, which comprises more than two GlcNAc moieties and any number of other sugar types or (C) a hybrid type, which comprises a Man residue on one side of the branch and GlcNAc at the base of a complex branch. FIG. 1A (taken from Stanley et al., Chapter 8: N-Glycans, Essentials of Glycobiology, 2$^{nd}$ ed., Cold Spring Harbor Laboratory Press; 2009) shows the three types of N-glycans.

Figure 29A:
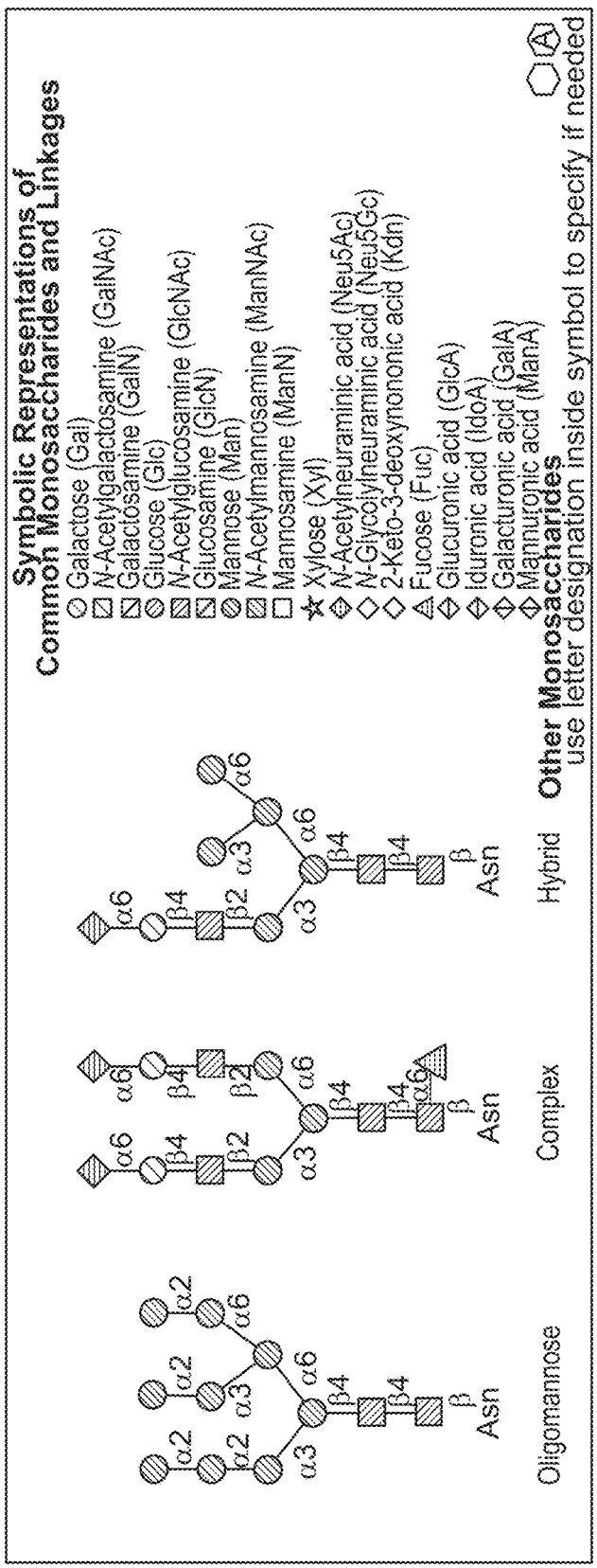
FIG. 29A is an illustration of the three types of N-glycans (oligomannose, complex and hybrid) and commonly used symbols for such saccharides.

N-linked glycans typically comprise one or more monosaccharides of galactose (Gal), N-acetylgalactosamine (GalNAc), galactosamine (GalN), glucose (GLc), N-acetylglucoasamine (ClcNAc), glucoasamine (GlcN), mannose (Man), N-Acetylmannosamine (ManNAc), Mannosamine (ManN), xylose (Xyl), NOAcetylneuraminic acid (Neu5Ac), N-Glycolylneuraminic acid (Neu5Gc), 2-keto-3-doxynononic acid (Kdn), fucose (Fuc), Glucuronic acid (GLcA), Iduronic acid (IdoA), Galacturonic acid (Gal A), mannuronic acid (Man A). The commonly used symbols for such saccharides are shown in FIG. 29A.

N-linked glycosylation begins in the endoplasmic reticulum (ER), where a complex set of reactions result in the attachment of a core glycan structure made essentially of two GlcNAc residues and three Man residues. The glycan complex formed in the ER is modified by action of enzymes in the Golgi apparatus. If the saccharide is relatively inaccessible to the enzymes, it typically stays in the original HM form. If enzymes can access the saccharide, then many of the Man residues are cleaved off and the saccharide is further modified, resulting in the complex type N-glycans structure. For example, mannosidase-1 located in the cis-Golgi, can cleave or hydrolyze a HM glycan, while fucosyltransferase FUT-8, located in the medial-Golgi, fucosylates the glycan (Hanrue Imai-Nishiya (2007), BMC Biotechnology, 7:84).

Accordingly, the sugar composition and the structural configuration of a glycan structure varies, depending on the glycosylation machinery in the ER and the Golgi apparatus, the accessibility of the machinery enzymes to the glycan structure, the order of action of each enzyme and the stage at which the protein is released from the glycosylation machinery, among other factors.

In exemplary embodiments of the present disclosure, the antigen-binding proteins comprise an Fc polypeptide. The term "Fc polypeptide" as used herein includes native and mutein forms of polypeptides derived from the Fc region of an antibody. In exemplary aspects, the Fc polypeptide of the presently disclosed antigen-binding protein comprises a glycan. In various instances, the glycan lacks fucose or is afucosylated. In exemplary aspects, the antigen-binding protein comprises an afucosylated glycan. As used herein, the term "afucosylated glycan" or "afuco glycan" or "afucosylated glycoform" or "Afuc" refers to glycoforms which lack a core fucose, e.g., an α1,6-linked fucose on the GlcNAc residue involved in the amide bond with the Asn of the N-glycosylation site. Afucosylated glycoforms include, but are not limited to, A1G0, A2G0, A2G1a, A2G1b, A2G2, and A1G1M5. Additional afucosylated glycans include, e.g., A1G1a, G0[H3N4], G0[H4N4], G0[H5N4], FO-N[H3N3]. See, e.g., Reusch and Tejada, Glycobiology 25(12): 1325-1334 (2015).

Figure 29B:
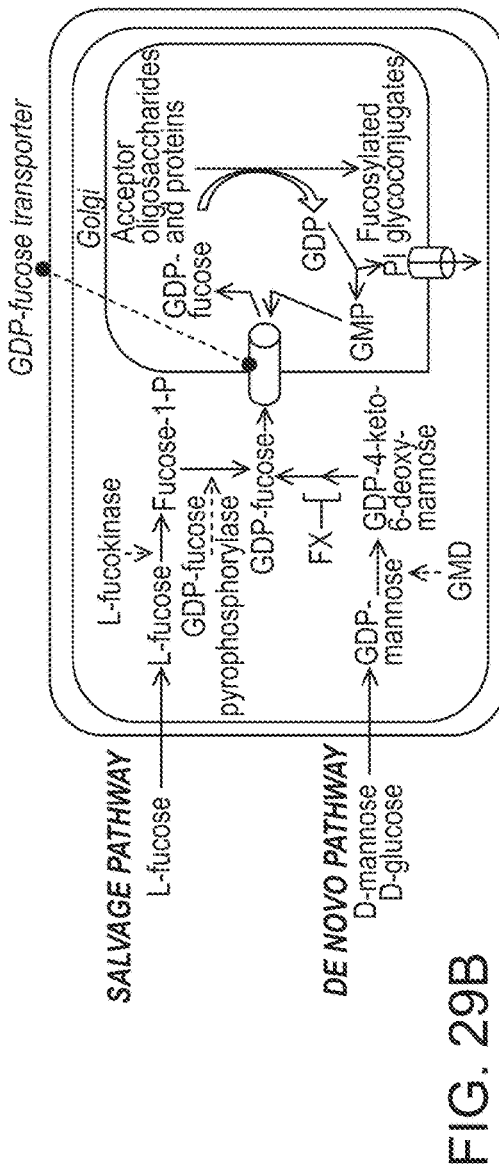
FIG. 29B is a diagram of the salvage pathway and the de novo pathway of fucose metabolism. In the salvage pathway, free L-fucose is converted to GDP-fucose, while in the de novo pathway, GDP-fucose is synthesized via three reactions catalyzed by GMD and FX. GDP-fucose is then transported from the cytosol to the Golgi lumen by GDP-Fuc Transferase and transferred to acceptor oligosaccharides and proteins. The other reaction product, GDP, is converted by a luminal nucleotide diphosphatase to guanosine 5-monophosphate (GMP) and inorganic phosphate (Pi). The former is exported to the cytosol (via an antiport system that is coupled with the transport of GDP-fucose), whereas the latter is postulated to leave the Golgi lumen via the Golgi anion channel, GOLAC. See, e.g., Nordeen et al. 2000; Hirschberg et al. 2001.

The present disclosure also provides a composition, e.g., a pharmaceutical composition, comprising an antigen binding protein comprising an Fc polypeptide comprising an afucosylated glycan. In exemplary aspects, at least or about 25% of the antigen-binding proteins present in the composition are antigen-binding proteins comprising an Fc polypeptide comprising an afucosylated glycan. In exemplary aspects, at least or about 25% of the antigen-binding proteins present in the composition are afucosylated. Optionally, at least 30%, 40%, 50%, 60%, 70%, 80%, or 90% or more of the antigen-binding proteins present in the composition are afucosylated. Methods of producing compositions comprising antigen-binding proteins of a particular glycoprofile are known in the art. In exemplary embodiments, the antigen binding proteins are recombinant produced in cells that are genetically modified to alter the activity of an enzyme of the de novo pathway or the salvage pathway. These two pathways of fucose metabolism are shown in FIG. 29B. In exemplary embodiments, the cells are genetically modified to alter the activity of any one or more of: a fucosyltransferase (FUT, e.g., FUT1, FUT2, FUT3, FUT4, FUT5, FUT6, FUT7, FUT8, FUT9), a fucose kinase, a GDP-fucose pyrophosphorylase, GDP-D-mannose-4,6-dehydratase (GMD), and GDP-keto-6-deoxymannose-3,5-epimerase, 4-reductase (FX). In exemplary embodiments, the cells are genetically modified to knock-out a gene encoding FX. See, e.g., International Patent Publication No. WO2017/079165 A1; Kanda et al., J Biotechnol 130, 2007, 300-310, Yamane-Ohunuki et al., Biotechnol Bioeng 87, 2004, 614-622, Malphettes et al., Biotechnol Bioeng 106, 2010, 774-783.

Nucleic Acids

The present disclosure further provides nucleic acids comprising a nucleotide sequence encoding an antigen-binding protein of the present disclosure. By "nucleic acid" as used herein includes "polynucleotide," "oligonucleotide," and "nucleic acid molecule," and generally means a polymer of DNA or RNA, or modified forms thereof, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. The nucleic acid can comprise any nucleotide sequence which encodes any of the antigen-binding proteins of the present disclosure. In various aspects, the nucleic acid comprises a nucleotide sequence which encodes an antigen-binding protein comprising (a) a heavy chain (HC) complementarity-determining region (CDR) 1 amino acid sequence set forth in Table A or A1 or a sequence selected from the group consisting of: SEQ ID NOs: 11, 17, 23, 29, 35, 41, 47, 53, 59, 65, 71, 77, 83, 89, 95, 101, 107, 113, 119, 125, 131, 452, 455, 461, 465, and 472, or a variant sequence thereof which differs by only one or two amino acids or which has at least or about 70% (e.g., at least or about 80%, at least or about 85%, at least or about 90%, at least or about 95%) sequence identity; (b) an HC CDR2 amino acid sequence set forth in Table A or A1 or a sequence selected from the group consisting of: SEQ ID NOs: 12, 18, 24, 30, 36, 42, 48, 54, 60, 66, 72, 78, 84, 90, 86, 102, 108, 114, 120, 126, 132, 475, 456, 462, 466, 468, and 473; or a variant sequence thereof which differs by only one or two amino acids or which has at least or about 70% (e.g., at least or about 80%, at least or about 85%, at least or about 90%, at least or about 95%) sequence identity; (c) an HC CDR3 amino acid sequence set forth in Table A or A1 or a sequence selected from the group consisting of: SEQ ID NOs: 13, 19, 25, 31, 37, 43, 49, 55, 61, 67, 73, 79, 85, 91, 97, 103, 109, 115, 121, 127, 133, 453, 457, 463, 467, 469, and 474; or a variant sequence thereof which differs by only one or two amino acids or which has at least or about 70% (e.g., at least or about 80%, at least or about 85%, at least or about 90%, at least or about 95%) sequence identity; (d) a light chain (LC) CDR1 amino acid sequence set forth in Table A or A1 or a sequence selected from the group consisting of: SEQ ID NOs: 8, 14, 20, 32, 38, 44, 50, 56, 62, 68, 74, 80, 86, 92, 98, 104, 110, 116, 122, 128, 449, 476, 458, 464, and 470; or a variant sequence thereof which differs by only one or two amino acids or which has at least or about 70% (e.g., at least or about 80%, at least or about 85%, at least or about 90%, at least or about 95%) sequence identity; (e) an LC CDR2 amino acid sequence set forth in Table A or A1 or a sequence selected from the group consisting of: SEQ ID NOs: 9, 15, 21, 27, 33, 39, 45, 51, 57, 63, 69, 75, 81, 87, 93, 99, 105, 111, 117, 123, 129, 450, 477, 459, and 471; or a variant sequence thereof which differs by only one or two amino acids or which has at least or about 70% (e.g., at least or about 80%, at least or about 85%, at least or about 90%, at least or about 95%) sequence identity; (f) an LC CDR3 amino acid sequence set forth in Table A or a sequence selected from the group consisting of: SEQ ID NOs: 10, 16, 22, 28, 34, 40, 46, 52, 58, 64, 70, 76, 82, 88, 94, 100, 106, 112, 118, 124, 130, 451, 454, and 460, or a variant sequence thereof which differs by only one or two amino acids or which has at least or about 70% (e.g., at least or about 80%, at least or about 85%, at least or about 90%, at least or about 95%) sequence identity; or (g) a combination of any two or more of (a)-(f). In various aspects, the nucleic acid comprises a nucleotide sequence encoding an antigen-binding protein comprising a LC CDR1 amino acid sequence, a LC CDR2 amino acid sequence, and a LC CDR3 amino acid sequence set forth in Table A or A1 and at least 1 or 2 of the HC CDR amino acid sequences set forth in Table A or A1. In various aspects, the nucleic acid comprises a nucleotide sequence encoding an antigen-binding protein comprising a HC CDR1 amino acid sequence, a HC CDR2 amino acid sequence, and a HC CDR3 amino acid sequence set forth in Table A or A1 and at least 1 or 2 of the LC CDR amino acid sequences set forth in Table A or A1. In various embodiments, the nucleic acid comprises a nucleotide sequence encoding an antigen-binding protein comprising (a) at least 3, 4, or 5 of the amino acid sequences designated by the SEQ ID NOs: in a single row of Table A or A1, (b) each of the LC CDR amino acid sequences designated by the SEQ ID NOs: of a single row of Table A or A1 and at least 1 or 2 of the HC CDR amino acid sequences designated by the SEQ ID NOs: in of a single row of Table A or A1, (c) each of the HC CDR amino acid sequences designated by the SEQ ID NOs: of a single row of Table A or A1 and at least 1 or 2 of the LC CDR amino acid sequences designated by the SEQ ID NOs: of a single row of Table A or A1, (d) all 6 of the CDR amino acid sequences designated by the SEQ ID NOs: of a single row of Table A, and/or (e) six CDR amino acid sequences selected from the group consisting of: (a) SEQ ID NOs: 74-79; (b) SEQ ID NOs: 50-55; (c) SEQ ID NOs: 122-127; (d) SEQ ID NOs: 26-31; (e) SEQ ID NOs: 128-133; (f) SEQ ID NOs: 38-43; (g) SEQ ID NOs: 62-67; (h) SEQ ID NOs: 80-85; (i) SEQ ID NOs: 44-49; (j) SEQ ID NOs: 86-91; (k) SEQ ID NOs: 104-109; (l) SEQ ID NOs: 56-61; (m) SEQ ID NOs: 32-37; (n) SEQ ID NOs: 110-115; (o) SEQ ID NOs: 98-103; (p) SEQ ID NOs: 92-97; (q) SEQ ID NOs: 116-121; (r) SEQ ID NOs: 8-13; (s) SEQ ID NOs: 68-73; (t) SEQ ID NOs: 14-19; (u) SEQ ID NOs: 20-25, (v) SEQ ID NOs: 449-453 and 475; (w) SEQ ID NOs: 476-477, 454-457; (x) SEQ ID NOs: 458-463; (y) SEQ ID NOs: 57, 58, 464-467; (z) SEQ ID NOs: 68-71 and 468-469; and (aa) SEQ ID NOs: 112, and 470-474. In various embodiments, the nucleic acid comprises a nucleotide sequence encoding an antigen-binding protein comprising (a) a heavy chain variable region amino acid sequence set forth in in Table B or B1 or a sequence selected from the group consisting of: 135, 137, 139, 141, 143, 145, 147, 149, 151, 153, 155, 157, 159, 161, 163, 165, 167, 169, 171, 173, 175, 478, 480, 482, 484, 486 and 488, or a variant sequence thereof which differs by only one or two amino acids or which has at least or about 70% (e.g., at least or about 80%, at least or about 85%, at least or about 90%, at least or about 95%) sequence identity; or (b) a light chain variable region amino acid sequence set forth in Table B or B1 or a sequence selected from the group consisting of: 134, 136, 138, 140, 142, 144, 146, 148, 150, 152, 154, 156, 158, 160, 162, 164, 166, 168, 170, 172, 174, 176, 479, 481, 483, 485, 487, and 489 or a variant sequence thereof which differs by only one or two amino acids or which has at least or about 70% (e.g., at least or about 80%, at least or about 85%, at least or about 90%, at least or about 95%) sequence identity; or (c) both (a) and (b). In various embodiments, the nucleic acid comprises a nucleotide sequence encoding an antigen-binding protein comprising a pair of amino acid sequences selected from the group consisting of: (a) SEQ ID NOs: 156 and 157; (b) SEQ ID NOs: 148 and 149; (c) SEQ ID NOs: 172 and 173; (d) SEQ ID NOs: 140 and 141; (e) SEQ ID NOs: 174 and 175; (f) SEQ ID NOs: 144 and 145; (g) SEQ ID NOs: 152 and 153; (h) SEQ ID NOs: 158 and 159; (i) SEQ ID NOs: 146 and 147; (j) SEQ ID NOs: 160 and 161; (k) SEQ ID NOs: 166 and 167; (l) SEQ ID NOs: 150 and 151; (m) SEQ ID NOs: 142 and 143; (n) SEQ ID NOs: 168 and 169; (o) SEQ ID NOs: 164 and 165; (p) SEQ ID NOs: 162 and 163; (q) SEQ ID NOs: 170 and 171; (r) SEQ ID NOs: 134 and 135; (s) SEQ ID NOs: 154 and 155; (t) SEQ ID NOs: 136 and 137; and (u) SEQ ID NOs: 138 and 139. In various embodiments, the nucleic acid comprises a nucleotide sequence encoding an antigen-binding protein comprising a pair of amino acid sequences selected from the group consisting of the pairs listed in Table D. In various aspects, the nucleic acid comprises a nucleotide sequence comprising a sequence of any one or more of SEQ ID NOs: 208-375. In some embodiments, the nucleic acid does not comprise any insertions, deletions, inversions, and/or substitutions. In other embodiments, the nucleic acid comprises one or more insertions, deletions, inversions, and/or substitutions.

In various aspects, the nucleic acid comprises a nucleotide sequence which encodes the antigen-binding protein which is a humanized antigen-binding protein as set forth in Table D with one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) amino acid substitutions in the heavy chain (HC) variable region or in the light chain (LC) variable region, or in both. In exemplary aspects, the nucleic acid comprises a nucleotide sequence which encodes the antigen-binding protein which is a humanized antigen-binding protein of AB1-11 with one or more amino acid substitutions in the HC variable region, the LC variable region, or both. In exemplary aspects, the nucleic acid comprises a nucleotide sequence which encodes the antigen-binding protein comprising a HC of SEQ ID NO: 379 with 1, 2, 3, 4, or 5 amino acid substitutions. In exemplary aspects, the nucleic acid comprises a nucleotide sequence which encodes the antigen-binding protein comprising a HC CDR1 of SEQ ID NO: 504, a HC CDR2 of SEQ ID NO: 505, a HC CDR3 of SEQ ID NO: 506, or a combination thereof. In exemplary instances, the nucleic acid comprises a nucleotide sequence which encodes the antigen-binding protein comprising a HC of SEQ ID NO: 503. In some aspects, the nucleic acid comprises a nucleotide sequence which encodes the antigen-binding protein comprising a HC of any one of SEQ ID NOs: 496-501. In some aspects, the nucleic acid comprises a nucleotide sequence which encodes the antigen-binding protein comprising a HC sequence labeled as S7-S12 in FIG. 22. In various instances, the nucleic acid comprises a nucleotide sequence which encodes the light chain variable region comprising a LC CDR1 of SEQ ID NO: 449, a LC CDR2 of SEQ ID NO: 450, a LC CDR3 of SEQ ID NO: 451, or a combination thereof. In some aspects, the nucleic acid comprises a nucleotide sequence which encodes the antigen-binding protein comprising a LC of any one of SEQ ID NOs: 380-383, and 479. In exemplary instances, the nucleic acid comprises a nucleotide sequence which encodes the antigen-binding protein comprising a LC of SEQ ID NO: 383. In some aspects, the nucleic acid comprises a nucleotide sequence which encodes the antigen-binding protein comprising a LC sequence labeled as S7-S12 in FIG. 22. In exemplary aspects, the nucleic acid comprises a nucleotide sequence which encodes the antigen-binding protein which is a humanized antigen-binding protein of AB3-7 with one or more amino acid substitutions in the HC variable region, the LC variable region, or both. In exemplary aspects, the nucleic acid comprises a nucleotide sequence which encodes the antigen-binding protein comprising a HC of SEQ ID NO: 387 with 1, 2, 3, 4, 5, or 6 amino acid substitutions. In exemplary aspects, the nucleic acid comprises a nucleotide sequence which encodes the antigen-binding protein comprising a HC CDR1 of SEQ ID NO: 507, a HC CDR2 of SEQ ID NO: 508, a HC CDR3 of SEQ ID NO: 509, or a combination thereof. In exemplary instances, the nucleic acid comprises a nucleotide sequence which encodes the antigen-binding protein comprising a HC of SEQ ID NO: 502. In some aspects, the nucleic acid comprises a nucleotide sequence which encodes the antigen-binding protein comprising a HC of any one of SEQ ID NOs: 490-495. In some aspects, the nucleic acid comprises a nucleotide sequence which encodes the antigen-binding protein comprising a HC sequence labeled as S1-S6 in FIG. 22. In various instances, the nucleic acid comprises a nucleotide sequence which encodes the light chain variable region comprising a LC CDR1 of SEQ ID NO: 476, a LC CDR2 of SEQ ID NO: 477, a LC CDR3 of SEQ ID NO: 454, or a combination thereof. In some aspects, the nucleic acid comprises a nucleotide sequence which encodes the antigen-binding protein comprising a LC of any one of SEQ ID NOs: 388-390, and 481. In exemplary instances, the nucleic acid comprises a nucleotide sequence which encodes the antigen-binding protein comprising a LC of SEQ ID NO: 389. In some aspects, the nucleic acid comprises a nucleotide sequence which encodes the antigen-binding protein comprising a LC sequence labeled as S1-S6 in FIG. 22.

In exemplary aspects, the nucleic acid comprises a nucleotide sequence which encodes the antigen-binding protein which is a humanized antigen-binding protein of AB3 with one or more amino acid substitutions in the HC variable region, the LC variable region, or both. In exemplary aspects, the nucleic acid comprises a nucleotide sequence which encodes the antigen-binding protein comprising a HC of SEQ ID NO: 139 with 1, 2, 3, 4, or 5 (or more) amino acid substitutions. In some aspects, the nucleic acid comprises a nucleotide sequence which encodes the antigen-binding protein comprising a HC of any one of SEQ ID NOs: 510. In some aspects, the nucleic acid comprises a nucleotide sequence which encodes the antigen-binding protein comprising a HC sequence of SEQ ID NO: 510 with 1, 2, 3, 4, or 5 (or more) amino acid substitutions as shown in FIG. 23. In exemplary aspects, the nucleic acid comprises a nucleotide sequence which encodes the antigen-binding protein comprising a HC of SEQ ID NO: 138 with 1, 2, 3, 4, or 5 (or more) amino acid substitutions. In some aspects, the nucleic acid comprises a nucleotide sequence which encodes the antigen-binding protein comprising a HC of any one of SEQ ID NOs: 511. In some aspects, the nucleic acid comprises a nucleotide sequence which encodes the antigen-binding protein comprising a HC sequence of SEQ ID NO: 511 with 1, 2, 3, 4, or 5 (or more) amino acid substitutions as shown in FIG. 24. In exemplary aspects, the nucleic acid comprises a nucleotide sequence which encodes the antigen-binding protein which is a humanized antigen-binding protein of AB1 with one or more amino acid substitutions in the HC variable region, the LC variable region, or both. In exemplary aspects, the nucleic acid comprises a nucleotide sequence which encodes the antigen-binding protein comprising a HC of SEQ ID NO: 135 with 1, 2, 3, 4, or 5 (or more) amino acid substitutions. In some aspects, the nucleic acid comprises a nucleotide sequence which encodes the antigen-binding protein comprising a HC of any one of SEQ ID NOs: 513. In some aspects, the nucleic acid comprises a nucleotide sequence which encodes the antigen-binding protein comprising a HC sequence of SEQ ID NO: 513 with 1, 2, 3, 4, or 5 (or more) amino acid substitutions as shown in FIG. 25. In exemplary aspects, the nucleic acid comprises a nucleotide sequence which encodes the antigen-binding protein comprising a HC of SEQ ID NO: 134 with 1, 2, 3, 4, or 5 (or more) amino acid substitutions. In some aspects, the nucleic acid comprises a nucleotide sequence which encodes the antigen-binding protein comprising a HC of any one of SEQ ID NOs: 512. In some aspects, the nucleic acid comprises a nucleotide sequence which encodes the antigen-binding protein comprising a HC sequence of SEQ ID NO: 512 with 1, 2, 3, 4, or 5 (or more) amino acid substitutions as shown in FIG. 26. In some embodiments, the nucleic acid does not comprise any insertions, deletions, inversions, and/or substitutions. In other embodiments, the nucleic acid comprises one or more insertions, deletions, inversions, and/or substitutions.

In some aspects, the nucleic acids of the present disclosure are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids in some aspects are constructed based on chemical synthesis and/or enzymatic ligation reactions using procedures known in the art. See, for example, Sambrook et al., supra; and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the present disclosure can be purchased from companies, such as Macromolecular Resources (Fort Collins, CO) and Synthegen (Houston, TX).

Vector

The nucleic acids of the present disclosure in some aspects are incorporated into a vector. In this regard, the present disclosure provides vectors comprising any of the presently disclosed nucleic acids. In various aspects, the vector is a recombinant expression vector. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the present disclosure are not naturally-occurring as a whole. However, parts of the vectors can be naturally-occurring. The presently disclosed vectors can comprise any type of nucleotides, including, but not limited to DNA and RNA, which can be single-stranded or double-stranded, synthesized or obtained in part from natural sources, and which can contain natural, non-natural or altered nucleotides. The vectors can comprise naturally-occurring or non-naturally-occurring internucleotide linkages, or both types of linkages. In some aspects, the altered nucleotides or non-naturally occurring internucleotide linkages do not hinder the transcription or replication of the vector.

The vector of the present disclosure can be any suitable vector, and can be used to transduce, transform or transfect any suitable host. Suitable vectors include those designed for propagation and expansion or for expression or both, such as plasmids and viruses. The vector can be a plasmid based expression vector. In various aspects, the vector is selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGTIO, λGT1 1, λZapII (Stratagene), λEMBL4, and λNM1 149, also can be used. Examples of plant expression vectors include pBIOl, pBI101.2, pBI101.3, pBI121 and pBIN19 (Clontech). Examples of animal expression vectors include pEUK-Cl, pMAM and pMAMneo (Clontech). In some aspects, the vector is a viral vector, e.g., a retroviral vector. In various aspects, the vector is an adenovirus vector, an adeno-associated virus (AAV) vector, a Herpes Simplex Virus (HSV) vector, a Vesicular stomatitis virus (VSV) vector, vaccinia virus vector, or lentivirus vector. See, e.g., Howarth et al., Cell Biol. Toxicol. 26(1): 1-20 (2010). In various aspects, the vector is a baculovirus vector which infects arthropods, e.g., insects. In various aspects, the baculovirus vector is an *Autographa californica* multiple nuclear virus (AcMNPV) or a Bombyxmorinuclear polyhedrosis (BmNPV). See, e.g., Khan, Adv Pharm Bull 3(2): 257-263 (2013); Miller, Bioessays 11(4): 91-96 (1989); Atkinson et al., Pestic Sci 28: 215-224 (1990).

The vectors of the present disclosure can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

In some aspects, the vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the presently disclosed expression vectors include, for instance, neomycin/G418 resistance genes, hygromycin resistance genes, histidinol resistance genes, tetracycline resistance genes, and ampicillin resistance genes.

The vector can comprise a native or normative promoter operably linked to the nucleotide sequence encoding the polypeptide (including functional portions and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

Host Cells

Provided herein are host cells comprising a nucleic acid or vector of the present disclosure. As used herein, the term "host cell" refers to any type of cell that can contain the presently disclosed vector and is capable of producing an expression product encoded by the nucleic acid (e.g., mRNA, protein). The host cell in some aspects is an adherent cell or a suspended cell, i.e., a cell that grows in suspension. The host cell in various aspects is a cultured cell or a primary cell, i.e., isolated directly from an organism, e.g., a human. The host cell can be of any cell type, can originate from any type of tissue, and can be of any developmental stage.

In various aspects, the antigen-binding protein is a glycosylated protein and the host cell is a glycosylation-competent cell. In various aspects, the glycosylation-competent cell is an eukaryotic cell, including, but not limited to, a yeast cell, filamentous fungi cell, protozoa cell, algae cell, insect cell, or mammalian cell. Such host cells are described in the art. See, e.g., Frenzel, et al., *Front Immunol* 4: 217 (2013). In various aspects, the eukaryotic cells are mammalian cells. In various aspects, the mammalian cells are non-human mammalian cells. In some aspects, the cells are Chinese Hamster Ovary (CHO) cells and derivatives thereof (e.g., CHO-K1, CHO pro-3), mouse myeloma cells (e.g., NS0, GS-NS0, Sp2/0), cells engineered to be deficient in dihydrofolatereductase (DHFR) activity (e.g., DUKX-X11, DG44), human embryonic kidney 293 (HEK293) cells or derivatives thereof (e.g., HEK293T, HEK293-EBNA), green African monkey kidney cells (e.g., COS cells, VERO cells), human cervical cancer cells (e.g., HeLa), human bone osteosarcoma epithelial cells U2-OS, adenocarcinomic human alveolar basal epithelial cells A549, human fibrosarcoma cells HT1080, mouse brain tumor cells CAD, embryonic carcinoma cells P19, mouse embryo fibroblast cells NIH 3T3, mouse fibroblast cells L929, mouse neuroblastoma cells N2a, human breast cancer cells MCF-7, retinoblastoma cells Y79, human retinoblastoma cells SO-Rb50, human liver cancer cells Hep G2, mouse B myeloma cells J558L, or baby hamster kidney (BHK) cells (Gaillet et al. 2007; Khan, Adv Pharm Bull 3(2): 257-263 (2013)).

For purposes of amplifying or replicating the vector, the host cell is in some aspects is a prokaryotic cell, e.g., a bacterial cell.

Also provided by the present disclosure is a population of cells comprising at least one host cell described herein. The population of cells in some aspects is a heterogeneous population comprising the host cell comprising vectors described, in addition to at least one other cell, which does not comprise any of the vectors. Alternatively, in some aspects, the population of cells is a substantially homogeneous population, in which the population comprises mainly host cells (e.g., consisting essentially of) comprising the vector. The population in some aspects is a clonal population of cells, in which all cells of the population are clones of a single host cell comprising a vector, such that all cells of the population comprise the vector. In various embodiments of the present disclosure, the population of cells is a clonal population comprising host cells comprising a vector as described herein.

Manufacture Methods

Also provided herein are methods of producing an antigen-binding protein which binds to CLDN6. In various embodiments, the method comprises culturing a host cell comprising a nucleic acid comprising a nucleotide sequence encoding the antigen-binding protein as described herein in a cell culture medium and harvesting the antigen-binding protein from the cell culture medium. The host cell can be any of the host cells described herein. In various aspects, the host cell is selected from the group consisting of: CHO cells, NS0 cells, COS cells, VERO cells, and BHK cells. In various aspects, the step of culturing a host cell comprises culturing the host cell in a growth medium to support the growth and expansion of the host cell. In various aspects, the growth medium increases cell density, culture viability and productivity in a timely manner. In various aspects, the growth medium comprises amino acids, vitamins, inorganic salts, glucose, and serum as a source of growth factors, hormones, and attachment factors. In various aspects, the growth medium is a fully chemically defined media consisting of amino acids, vitamins, trace elements, inorganic salts, lipids and insulin or insulin-like growth factors. In addition to nutrients, the growth medium also helps maintain pH and osmolality. Several growth media are commercially available and are described in the art. See, e.g., Arora, "Cell Culture Media: A Review" MATER METHODS 3:175 (2013).

In various aspects, the method comprises culturing the host cell in a feed medium. In various aspects, the method comprises culturing in a feed medium in a fed-batch mode. Methods of recombinant protein production are known in the art. See, e.g., Li et al., "Cell culture processes for monoclonal antibody production" MAbs 2(5): 466-477 (2010).

The method making an antigen-binding protein can comprise one or more steps for purifying the protein from a cell culture or the supernatant thereof and preferably recovering the purified protein. In various aspects, the method comprises one or more chromatography steps, e.g., affinity chromatography (e.g., protein A affinity chromatography), ion exchange chromatography, hydrophobic interaction chromatography. In various aspects, the method comprises purifying the protein using a Protein A affinity chromatography resin.

In various embodiments, the method further comprises steps for formulating the purified protein, etc., thereby obtaining a formulation comprising the purified protein. Such steps are described in Formulation and Process Development Strategies for Manufacturing, eds. Jameel and Hershenson, John Wiley & Sons, Inc. (Hoboken, NJ), 2010.

In various aspects, the antigen-binding protein linked to a polypeptide and the antigen-binding protein is part of a fusion protein. Thus, the present disclosure further provides methods of producing a fusion protein comprising an antigen-binding protein which binds to CLDN6. In various embodiments, the method comprises culturing a host cell comprising a nucleic acid comprising a nucleotide sequence encoding the fusion protein as described herein in a cell culture medium and harvesting the fusion protein from the cell culture medium.

Conjugates

The present disclosure also provides antigen-binding proteins attached, linked or conjugated to a second moiety (e.g., a heterologous moiety, a conjugate moiety). Accordingly, the present disclosure provides a conjugate comprising an antigen-binding protein and a heterologous moiety. As used herein, the term "heterologous moiety" is synonymous with "conjugate moiety" and refers to any molecule (chemical or biochemical, naturally-occurring or non-coded) which is different from the antigen-binding proteins of the present disclosure. Various heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), or a diagnostic agent.

In some embodiments, the heterologous moiety is a polymer. The polymer can be branched or unbranched. The polymer can be of any molecular weight. The polymer in some embodiments has an average molecular weight of between about 2 kDa to about 100 kDa (the term "about" indicating that in preparations of a water soluble polymer, some molecules will weigh more, some less, than the stated molecular weight). The average molecular weight of the polymer is in some aspect between about 5 kDa and about 50 kDa, between about 12 kDa to about 40 kDa or between about 20 kDa to about 35 kDa.

In some embodiments, the polymer is modified to have a single reactive group, such as an active ester for acylation or an aldehyde for alkylation, so that the degree of polymerization can be controlled. The polymer in some embodiments is water soluble so that the protein to which it is attached does not precipitate in an aqueous environment, such as a physiological environment. In some embodiments, when, for example, the composition is used for therapeutic use, the polymer is pharmaceutically acceptable. Additionally, in some aspects, the polymer is a mixture of polymers, e.g., a co-polymer, a block co-polymer.

In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly (methyl methacrylate), poly(ethyl methacrylate), poly (butylmethacrylate), poly(isobutyl methacrylate), poly (hexylmethacrylate), poly(isodecyl methacrylate), poly (lauryl methacrylate), poly(phenyl methacrylate), poly (methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

A particularly preferred water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents.

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

In some embodiments, the heterologous moiety is a therapeutic agent. The therapeutic agent can be any of those known in the art. Examples of therapeutic agents that are contemplated herein include, but are not limited to, natural enzymes, proteins derived from natural sources, recombinant proteins, natural peptides, synthetic peptides, cyclic peptides, antibodies, receptor agonists, cytotoxic agents, immunoglobins, beta-adrenergic blocking agents, calcium channel blockers, coronary vasodilators, cardiac glycosides, antiarrhythmics, cardiac sympathomemetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thizaolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-HT4 partial agonists, antihistamines, cannabinoids, dopamine antagonists, serotonin antagonists, cytoprotectives, histamine H2-receptor antagonists, mucosal protective agent, proton pump inhibitors, H. pylori eradication therapy, erythropoieses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-A2 inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptse inhibitors, protease inhibitors, anemia, Kaposi's sarcoma, aminoglycosides, carbapenems, cephalosporins, glycopoptides, lincosamides, macrolies, oxazolidinones, penicillins, streptogramins, sulfonamides, trimethoprim and derivatives, tetracyclines, anthelmintics, amebicies, biguanides, cinchona alkaloids, folic acid antagonists, quinoline derivatives, Pneumocystis carinii therapy, hydrazides, imidazoles, triazoles, nitroimidzaoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, antracyclines, actinomycinds, camptothecin derivatives, epipodophyllotoxins, taxanes, vinca alkaloids and analogs, antiandrogens, antiestrogens, nonsteroidal aromatase inhibitors, protein kinase inhibitor antineoplastics, azaspirodecanedione derivatives, anxiolytics, stimulants, monoamind reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opioid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, vitamin K analogs and antagonists.

The antigen-binding proteins of the present disclosure can be conjugated to one or more cytokines and growth factors that are effective in inhibiting tumor metastasis, and wherein the cytokine or growth factor has been shown to have an antiproliferative effect on at least one cell population. Such cytokines, lymphokines, growth factors, or other hematopoietic factors include, but are not limited to: M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin. Additional growth factors for use herein include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epithelial-derived neutrophil attractant, glial cell line-derived neutrophic factor receptor α 1, glial cell line-derived neutrophic factor receptor α 2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, pre-B cell growth stimulating factor, stem cell factor, stem cell factor receptor, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, and chimeric proteins and biologically or immunologically active fragments thereof.

In some embodiments, the conjugate comprises a compound as described herein and a cytotoxic agent. The cytotoxic agent is any molecule (chemical or biochemical) which is toxic to a cell. In some aspects, when a cytotoxic agent is conjugated to a compound of the invention, the results obtained are synergistic. That is to say, the effectiveness of the combination therapy of a compound and the cytotoxic agent is synergistic, i.e., the effectiveness is greater than the effectiveness expected from the additive individual effects of each. Therefore, the dosage of the cytotoxic agent can be reduced and thus, the risk of the toxicity problems and other side effects is concomitantly reduced. In some embodiments, the cytotoxic agent is a chemotherapeutic agent. Chemotherapeutic agents are known in the art and include, but not limited to, platinum coordination compounds, topoisomerase inhibitors, antibiotics, antimitotic alkaloids and difluoronucleosides, as described in U.S. Pat. No. 6,630,124.

In some embodiments, the chemotherapeutic agent is a platinum coordination compound. The term "platinum coordination compound" refers to any tumor cell growth inhibiting platinum coordination compound that provides the platinum in the form of an ion. In some embodiments, the platinum coordination compound is cis-diamminediaquoplatinum (II)-ion; chloro(diethylenetriamine)-platinum(II) chloride; dichloro(ethylenediamine)-platinum(II), diammine(1,1-cyclobutanedicarboxylato) platinum(II) (carboplatin); spiroplatin; iproplatin; diammine(2-ethylmalonato)-platinum(II); ethylenediaminemalonatoplatinum (II); aqua(1,2-diaminodyclohexane)-sulfatoplatinum(II); (1,2-diaminocyclohexane)malonatoplatinum(II); (4-carboxyphthalato)(1,2-diaminocyclohexane)platinum(II); (1,2-diaminocyclohexane)-(isocitrato)platinum(II); (1,2-diaminocyclohexane)cis(pyruvato)platinum(II); (1,2-diaminocyclohexane)oxalatoplatinum(II); ormaplatin; and tetraplatin.

In some embodiments, cisplatin is the platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by conventional techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

In some embodiments, the chemotherapeutic agent is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type I and type II. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian, cancer, esophageal cancer or non-small cell lung carcinoma.

In some aspects, the topoisomerase inhibitor is camptothecin or a camptothecin analog. Camptothecin is a water-insoluble, cytotoxic alkaloid produced by *Camptotheca accuminata* trees indigenous to China and *Nothapodytes foetida* trees indigenous to India. Camptothecin exhibits tumor cell growth inhibiting activity against a number of tumor cells. Compounds of the camptothecin analog class are typically specific inhibitors of DNA topoisomerase I. By the term "inhibitor of topoisomerase" is meant any tumor cell growth inhibiting compound that is structurally related to camptothecin. Compounds of the camptothecin analog class include, but are not limited to; topotecan, irinotecan and 9-amino-camptothecin.

In additional embodiments, the cytotoxic agent is any tumor cell growth inhibiting camptothecin analog claimed or described in: U.S. Pat. No. 5,004,758, issued on Apr. 2, 1991 and European Patent Application Number 88311366.4, published on Jun. 21, 1989 as 20' Publication Number EP 0 321 122; U.S. Pat. No. 4,604,463, issued on Aug. 5, 1986 and European Patent Application Publication Number EP 0 137

145, published on Apr. 17, 1985; U.S. Pat. No. 4,473,692, issued on Sep. 25, 1984 and European Patent Application Publication Number EP 0 074 256, published on Mar. 16, 1983; U.S. Pat. No. 4,545,880, issued on Oct. 8, 1985 and European Patent Application Publication Number EP 0 074 256, published on Mar. 16, 1983; European Patent Application Publication Number EP 0 088 642, published on Sep. 14, 1983; Wani et al., J. Med. Chem., 29, 2358-2363 (1986); Nitta et al., Proc. 14th International Congr. Chemotherapy, Kyoto, 1985, Tokyo Press, Anticancer Section 1, p. 28-30, especially a compound called CPT-11. CPT-11 is a camptothecin analog with a 4-(piperidino)-piperidine side chain joined through a carbamate linkage at C-10 of 10-hydroxy-7-ethyl camptothecin. CPT-11 is currently undergoing human clinical trials and is also referred to as irinotecan; Wani et al, J. Med. Chem., 23, 554 (1980); Wani et. al., J. Med. Chem., 30, 1774 (1987); U.S. Pat. No. 4,342,776, issued on Aug. 3, 1982; U.S. patent application Ser. No. 581,916, filed on Sep. 13, 1990 and European Patent Application Publication Number EP 418 099, published on Mar. 20, 1991; U.S. Pat. No. 4,513,138, issued on Apr. 23, 1985 and European Patent Application Publication Number EP 0 074 770, published on Mar. 23, 1983; U.S. Pat. No. 4,399, 276, issued on Aug. 16, 1983 and European Patent Application Publication Number 0 056 692, published on Jul. 28, 1982; the entire disclosure of each of which is hereby incorporated by reference. All of the above-listed compounds of the camptothecin analog class are available commercially and/or can be prepared by conventional techniques including those described in the above-listed references. The topoisomerase inhibitor may be selected from the group consisting of topotecan, irinotecan and 9-aminocamptothecin.

In some embodiments, the camptothecin analog is an active metabolite of irinotecan (CPT-11). In some such embodiments, the camptothecin analog is 7-ethyl-10-hydroxycamptothecin (SN-38). As a metabolite, SN-38 is formed by hydrolysis of irinotecan by carboxylesterases. In some embodiments, SN-38 has one of the following structures:

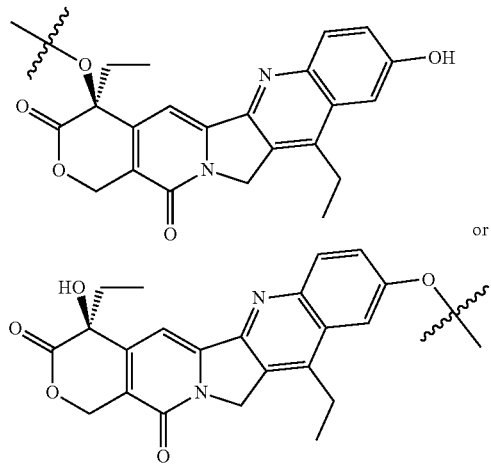

or

SN-38 has been described in U.S. Pat. Nos. 7,999,083; 8,080,250; 8,759,496; 8,999,344; 10,195,288; and 9,808, 537.

In some embodiments, the camptothecin analog is exatecan methanesulfonate. Exatecan methanesulfonate is a water-soluble camptothecin (CPT) that exhibits more potent topoisomerase I inhibitory activity and antitumor activity than other CPT analogs. In addition, exatecan is effective against p-glycoprotein (P-gp)-mediated multi-drug resistant cells.

In some embodiments, the camptothecin analog is deruxtecan (Dxd), a potent derivative of exatecan, which has 10-fold higher topoisomerase I inhibitory potency than SN-38. In some embodiments, Dxd has the following structure:

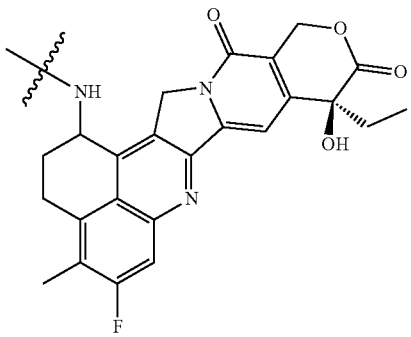 [SMILES: *NC1CCc2c(C)c(F)cc3nc4c(c1c23)Cn1c-4cc2c(c1=O)COC(=O)[C@]2(O)CC]

Dxd has been described in U.S. Pat. Nos. 6,407,115; 10,195, 288; 9,808,537; and 6,407,115.

The preparation of numerous compounds of the camptothecin analog class (including pharmaceutically acceptable salts, hydrates and solvates thereof) as well as the preparation of oral and parenteral pharmaceutical compositions comprising such a compounds of the camptothecin analog class and an inert, pharmaceutically acceptable carrier or diluent, is extensively described in U.S. Pat. No. 5,004,758, issued on Apr. 2, 1991 and European Patent Application Number 88311366.4, published on Jun. 21, 1989 as Publication Number EP 0 321 122, the teachings of which are incorporated herein by reference.

In still yet other embodiments of the invention, the chemotherapeutic agent is an antibiotic compound. Suitable antibiotic include, but are not limited to, doxorubicin, mitomycin, bleomycin, daunorubicin and streptozocin.

In some embodiments, the chemotherapeutic agent is an antimitotic alkaloid. In general, antimitotic alkaloids can be extracted from *Cantharanthus roseus*, and have been shown to be efficacious as anticancer chemotherapy agents. A great number of semi-synthetic derivatives have been studied both chemically and pharmacologically (see, 0. Van Tellingen et al, Anticancer Research, 12, 1699-1716 (1992)). The antimitotic alkaloids of the present invention include, but are not limited to, vinblastine, vincristine, vindesine, Taxol and vinorelbine. The latter two antimitotic alkaloids are commercially available from Eli Lilly and Company, and Pierre Fabre Laboratories, respectively (see, U.S. Pat. No. 5,620, 985). In one embodiment, the antimitotic alkaloid is vinorelbine.

In other embodiments of the invention, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808,614. European Patent Application Publication 184,365 discloses that these same difluoronucleosides have oncolytic activity. In certain aspects, the 2'-deoxy-2',2'-difluoronucleoside used in the compositions and methods of the present invention is 2'-deoxy-2',2'-difluorocytidine hydrochloride, also known as gemcitabine hydrochloride. Gemcitabine is commercially available or can be synthesized in a multi-step process as disclosed and taught in U.S. Pat. Nos. 4,526,988, 4,808,614 and 5,223,608, the teachings of which are incorporated herein by reference.

In various aspects, the chemotherapeutic agent is an anti-mitotic agent which inhibits cell division by blocking tubulin polymerization, destabilizing microtubules, or altering microtubule dynamics, e.g., maytansinoid or a derivative thereof (e.g., DM1 or DM4), auristatin or a derivative thereof. In various instances, the chemotherapeutic agent is an auristatin. For instance, the auristatin is in some aspects, dolastatin, Monomethyl auristatin E (MMAE), Monomethyl auristatin E (MMAE), or PF-06380101. Auristatins are described in the art. See, e.g., Maderna, A.; et al., Mol Pharmaceutics 12(6): 1798-1812 (2015). In various aspects, the conjugate comprises an antibody of the present disclosure in combination with MMAE. Optionally, the conjugate comprises a linker. In some aspects, the linker comprises a cleavable linking moiety. In various instances, the conjugate comprises an antibody of the present disclosure linked to an attachment group which is linked to a cathepsin-cleavable linker, which in turn is linked to a spacer which is linked to MMAE. In aspects, the attachment group is attached to the antibody via a Cys residue of the Fc region of the antibody. In exemplary aspects, the attachment group comprises the structure of Formula I:

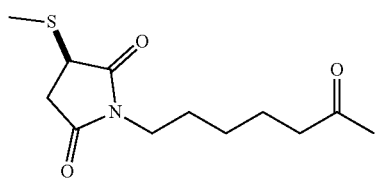

[Formula I]

In exemplary aspects, the cathepsin cleavable linker comprises the structure of Formula II:

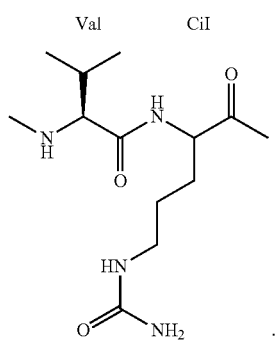

[Formula II]

In exemplary aspects, the spacer comprises the structure of Formula III:

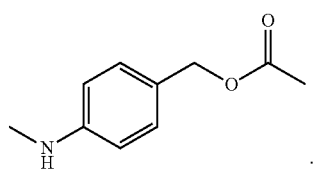

[Formula III]

In some embodiments, MMAE has the following structure:

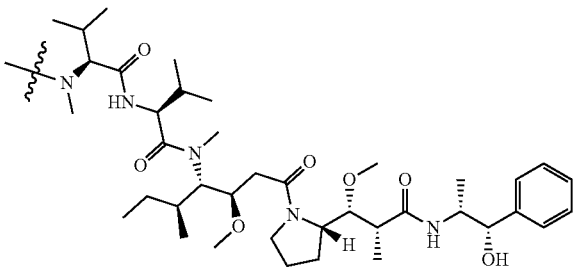 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

The present disclosure also provides conjugates comprising an antigen-binding protein of the present disclosure linked to a polypeptide, such that the conjugate is a fusion protein. Therefore, the present disclosure provides fusion proteins comprising an antigen-binding protein of the present disclosure linked to a polypeptide. In various embodiments, the polypeptide is a diagnostic label, e.g., a fluorescent protein, such as green fluorescent protein, or other tag, e.g., Myc tag. In various aspects, the polypeptide is one of the cytokines, lymphokines, growth factors, or other hematopoietic factors listed above.

Linkers

In some embodiments, the conjugate is directly linked to the heterologous moiety. In alternative embodiments, the conjugate comprises a linker that joins the compound of the present disclosure to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers can be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. In some embodiments, the linker is an amino acid or a peptidyl linker. Such peptidyl linkers can be any length. Various linkers are from about 1 to 50 amino acids in length, 5 to 50, 3 to 5, 5 to 10, 5 to 15, or 10 to 30 amino acids in length.

A variety of suitable linkers are known in the art. The linker can be cleavable (a cleavable linker), e.g., under physiological conditions, e.g., under intracellular conditions, such that cleavage of the linker releases the drug in the intracellular environment. Alternatively, the linker can be cleavable under extracellular conditions, e.g., outside the tumor cells or in the vicinity of the tumor mass, such that cleavage of the linker releases the drug that permeates preferentially inside the tumor cells. In other embodiments, the linker is not cleavable (a non-cleavable linker), and the drug is released, for example, by antibody degradation.

The linker can be bonded to a chemically reactive group on the antibody moiety, e.g., to a free amino, imino, hydroxyl, thiol, or carboxyl group (e.g., to the N- or C-terminus, to the epsilon amino group of one or more lysine residues, to the free carboxylic acid group of one or more glutamic acid or aspartic acid residues, to the sulfhydryl group of one or more cysteinyl residues, or to the hydroxyl group of one or more serine or threonine residues). The site to which the linker is bound can be a natural residue in the amino acid sequence of the antibody moiety, or it can be introduced into the antibody moiety, e.g., by DNA recombinant technology (e.g., by introducing a cysteine or protease cleavage site in the amino acid sequence) or by protein biochemistry (e.g., reduction, pH adjustment, or proteolysis). The site to which the linker is bound can also be a non-natural amino acids. The site to which the linker is bound can also be a glycan on the antibody.

Typically, the linker is substantially inert under conditions for which the two groups it is connecting are linked. The term "bifunctional crosslinking agent," "bifunctional linker" or "crosslinking agent" refers to a modifying agent that possess two reactive groups at each end of the linker, such that one reactive group can be first reacted with the cytotoxic compound to provide a compound bearing the linker moiety and a second reactive group, which can then react with the antibody. Alternatively, one end of the bifunctional crosslinking agent can be first reacted with the antibody to provide an antibody bearing a linker moiety and a second reactive group, which can then react with the cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, protease/peptidase labile bonds, and esterase labile bonds. See, for example, U.S. Pat. Nos. 5,208,020; 5,475,092; 6,441,163; 6,716,821; 6,913,748; 7,276,497; 7,276,499; 7,368,565; 7,388,026 and 7,414,073. In some embodiments, the bonds are disulfide bonds, thioether, and/or protease/peptidase labile bonds. Other linkers that can be used in the present invention include non-cleavable linkers, such as those described in detail in US 20050169933, charged linkers, or hydrophilic linkers, such as those described in US 2009/0274713, US 2010/0129314, and WO 2009/134976, each of which is expressly incorporated herein by reference.

In some embodiments, the linker is a hydrophilic linker that confers hydrophilicity to the conjugate. In some embodiments, the hydrophilic linker comprises polyethylene glycol (PEG). In some embodiments, the hydrophilic linker is CLA2. In some embodiments, the CLA2 linker has the following structure:

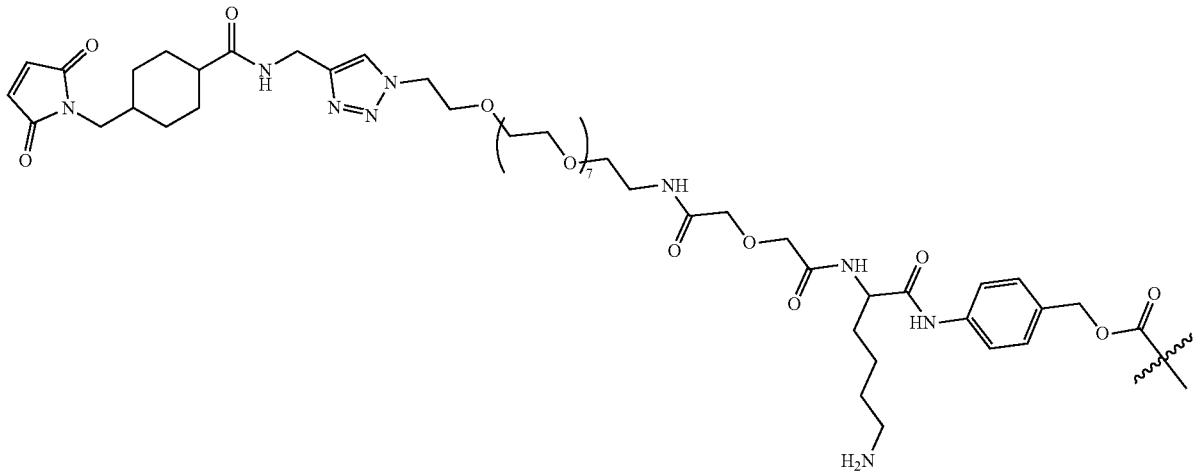

CLA2 has been described in U.S. Pat. Nos. 8,080,250; 8,759,496; and 10,195,288.

In some embodiments, the hydrophilic linker is CL2E. In some embodiments, the CL2E has the following structure:

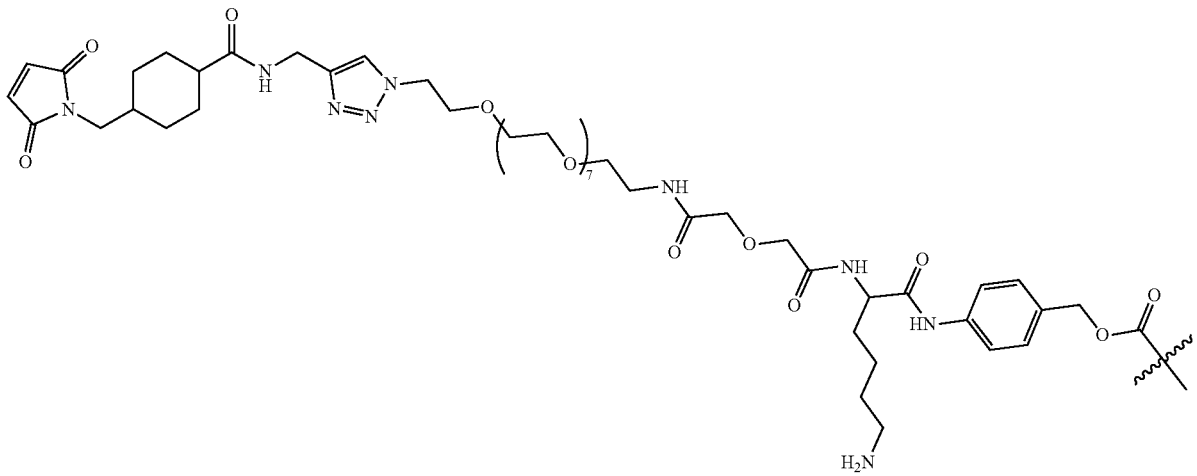

CL2E has been described in U.S. Pat. Nos. 8,080,250; 8,759,496; and 10,195,288.

In some embodiments, the linker is cleavable by a cleaving agent that is present in the intracellular environment (e.g., within a lysosome or endosome or caveolea). The linker can be, e.g., a peptide linker that is cleaved by an intracellular or extracellular peptidase or protease enzyme, including, but not limited to, a lysosomal or endosomal protease. In some embodiments, the peptide linker comprises at least two, at least three, at least four, or at least five amino acids long.

In some embodiments, the peptide linker is MC-VC-PAB, comprising valine and citruline residues. In some embodiments, the MC-VC-PAB linker has the following structure:

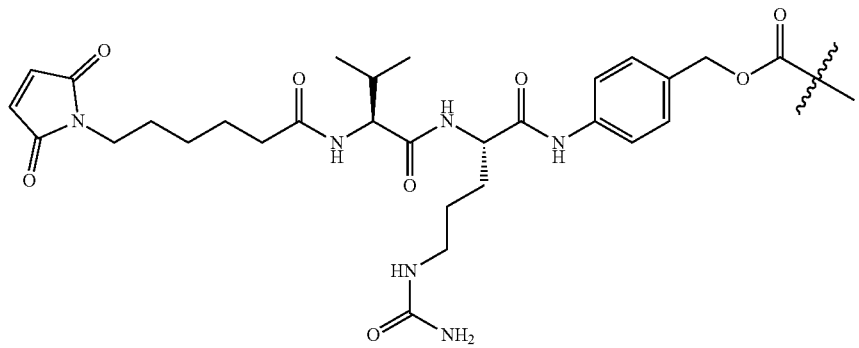 [SMILES: *C(=O)OCc1ccc(NC(=O)[C@H](CCCNC(N)=O)NC(=O)[C@@H](NC(=O)CCCCCN2C(=O)C=CC2=O)C(C)C)cc1]

MC-VC-PAB has been described in U.S. Pat. Nos. 7,659,241; 7,829,531; 6,884,869; 6,214,345; and 6,214,345.

In some embodiments, the peptide linker is maleimidocaproyl glycine-glycine-phenylalanine-glycine (MC-GGFG). In some embodiments, the MC-GGFG linker has the following structure:

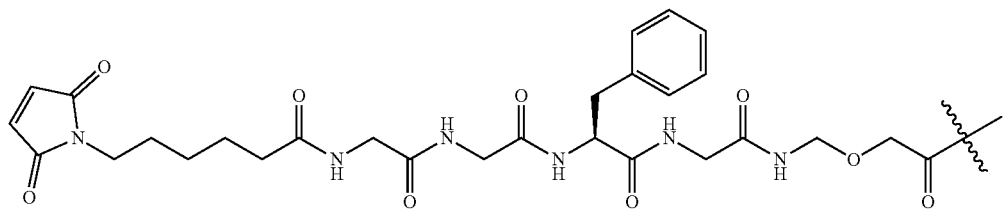 [SMILES: *C(=O)COCNC(=O)CNC(=O)[C@H](Cc1ccccc1)NC(=O)CNC(=O)CNC(=O)CCCCCN1C(=O)C=CC1=O]

MC-GGFG has been described in U.S. Pat. Nos. 9,808,537 and 10,195,288.

In other embodiments, the cleavable linker is pH-sensitive, i.e., sensitive to hydrolysis at certain pH values. In some embodiments, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used (see, e.g., U.S. Pat. Nos. 5,122,368; 5,824,805; 5,622,929; Dubowchik and Walker, 1999, Pharm. Therapeutics 83:67-123; Neville et al, 1989, Biol. Chem. 264: 14653-14661). Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). Bifunctional crosslinking agents that enable the linkage of an antibody with cytotoxic compounds via disulfide bonds include, but are not limited to, N-succinimidyl-4-(4-nitropyridyl-2-dithio)butanoate, N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)-2-sulfo butanoate (sulfo-SPDB). Sulfo-SPDB is described, e.g., in U.S. Pat. No. 8,236,319, incorporated herein by reference. Alternatively, crosslinking agents that introduce thiol groups such as 2-iminothiolane, homocysteine thiolactone, or S-acetylsuccinic anhydride can be used. In other embodiments, the linker may contain a combination of one or more of the peptide, pH-sensitive, or disulfide linkers described previously.

"Heterobifunctional crosslinking agents" are bifunctional crosslinking agents having two different reactive groups. Heterobifunctional crosslinking agents containing both an amine-reactive N-hydroxysuccinimide group (NHS group)

and a carbonyl-reactive hydrazine group can also be used to link cytotoxic compounds with an antibody. Examples of such commercially available heterobifunctional crosslinking agents include succinimidyl 6-hydrazinonicotinamide acetone hydrazone (SANH), succinimidyl 4-hydrazidotere-phthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

The linkers described herein may be used in any combination with the heterologous moiety described herein. All of the above-listed linkers and heterologous moiety described herein are available commercially and/or can be prepared by conventional techniques including those described in the above-listed references.

Conjugation

The heterologous moiety-to-antigen-binding protein ratio (HAR) represents the number of a heterologous moiety linked per antigen-binding molecule. In some embodiments, the HAR ranges from 1 to 15, 1 to 10, 1 to 9, 1 to 8, 1 to 7, 1 to 6, 1 to 5, 1 to 4, 1 to 3, or 1 to 2. In some embodiments, the HAR ranges from 2 to 10, 2 to 9, 2 to 8, 2 to 7, 2 to 6, 2 to 5, 2 to 4 or 2 to 3. In other embodiments, the HAR is about 2, about 2.5, about 3, about 4, about 5, or about 6. In some embodiments, the HAR ranges from about 2 to about 4. The HAR may be characterized by conventional means such as mass spectrometry, UV/Vis spectroscopy, ELISA assay, and/or HPLC.

In some embodiments, the conjugates are heterogeneous conjugates (also referred to as "conventional"), wherein the antigen-binding proteins are conjugated to a different number of the heterologous moiety. In some embodiments, the heterogeneous conjugates follow a Gaussian distribution or quasi-Gaussian distribution of the conjugates, wherein the distribution centers on the average heterologous moiety loading value with some antigen-binding proteins conjugated with higher than average and some antigen-binding proteins conjugated with lower than the average.

In some embodiments, the conjugates are homogeneous conjugates, wherein the substantial percentage of the antigen-binding proteins are conjugated to a defined number of the heterologous moiety. In some embodiments, the homogeneous conjugates comprise the HAR of 1, 2, 3, 4, 5, 6, 7, 8, 9, or 10. In some embodiments, the homogeneous conjugates comprise the HAR of 2, 4, 6, or 8. In preferred embodiments, the homogeneous conjugates comprise the HAR of 4. In other preferred embodiments, the homogeneous conjugates comprise the HAR of 2. In some embodiments, the homogeneous conjugates comprise greater than or equal to 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent conjugates with the defined HAR. In some embodiments, the homogeneous conjugates comprise about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent conjugates with the defined HAR. In some embodiments, the homogeneous conjugates comprise at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent conjugates with the defined HAR. In some embodiments, the homogeneous conjugates comprise the HAR distribution that is not Gaussian or quasi-Gaussian distribution. In some embodiments, the homogeneity of the homogeneous conjugates is determined by a chromatogram, e.g., HPLC or any suitable chromatography. In some embodiments, the chromatogram is a HIC chromatogram. The homogeneous conjugate may be generated by a site-specific conjugation.

In some embodiments, the heterologous moiety is conjugated to the antigen-binding protein (e.g., antibody) in a site-specific manner. Various site-specific conjugation methods are known in the art, e.g., thiomab or TDC or conjugation at an unpaired cysteine residue (Junutula et al. (2008) *Nat. Biotechnol.* 26:925-932; Dimasi et al. (2017) *Mol. Pharm.* 14:1501-1516; Shen et al. (2012) *Nat. Biotechnol.* 30:184-9); thiol bridge linker (Behrens et al. (2015) *Mol. Pharm.* 12:3986-98); conjugation at glutamine using a transglutaminase (Dennler et al. (2013) *Methods Mol. Bio.* 1045: 205-15; Dennler et al. (2014) *Bioconjug Chem.* 25:569-78); conjugation at engineered unnatural amino acid residues (Axup et al. (2012) *Proc Natl Acad Sci U.S.A.* 104-16101-6; Tian et al. (2014) *Proc Natl Acad Sci U.S.A.* 111:1766-71; VanBrunt et al. (2015) *Bioconjug Chem* 26:2249-60; Zimmerman et al. (2014) *Bioconjug Chem* 25:351-61); selenocysteine conjugation (Li et al. (2017) *Cell Chem Biol* 24:433-442); glycan-mediated conjugation (Okeley et al. (2013) *Bioconjug Chem* 24:1650-5); conjugation at galactose or GalNAc analogues (Ramakrishnan and Qasba (2002) *J Biol Chem* 277:20833-9; van Geel et al. (2015) *Bioconjug Chem* 26:2233-42); via glycan engineering (Zhou et al. (2014) *Bioconjug Chem* 25:510-20; Tang et al. (2017) *Nat Protoc* 12:1702-1721); via a short peptide tag, such as engineering a glutamine tag or sortase A-mediated transpeptidation (Strop et al. (2013) *Chem Biol* 20:161-7; Beerli et al. (2015) *PLoS One* 10:e0131177); and via an aldehyde tag (Wu et al. (2009) *Proc Natl Acad Sci U.S.A.* 106:3000-5).

Unpredictability of Conjugate (e.g., ADC)

It is not possible to predict in advance, simply based on an antibody profile, or a drug payload profile, which antibody-drug conjugates will be sufficiently safe and effective for clinical applications. For example, a particular drug payload may function perfectly well when conjugated to an antibody directed to one target, but it may not work nearly as well when conjugated to an antibody directed to a different target, or even to a different antibody directed to the same target. Why different antibody-drug conjugates display different anti-tumor activity in vivo is not sufficiently well understood to allow accurate predictions in the design of new antibody-drug conjugates. It is speculated that an unpredictable interplay of many factors play a role. These factors may include, for example, the binding affinity of an antibody-drug conjugate to a target antigen, the ability of the conjugate to penetrate solid tumors, as well as the half-life in circulation for proper exposure to tumors without causing toxicity.

The complexity and unpredictability is well demonstrated by antibody affinity alone. Antibodies or antibody-drug conjugates with high affinity track with better cellular uptake, which leads to a higher level of the cytotoxic payloads released inside the cells. Higher affinity is also known to enhance the antibody-dependent cellular cytotoxicity (ADCC). All these attributes favor the cell killing property of antibody-drug conjugates. However, it is also known that high affinity of an antibody or antibody-drug conjugate can prevent efficient tumor penetration via an "antigen barrier effect," suggesting that in order to achieve a strong anti-tumor activity in vivo, affinity of the antibody-drug conjugate has to be just right: not too high or not too low. To date, it is not known how to predict what will be the most efficient or effective level of affinity for an antibody-drug conjugate.

In addition, in vivo anti-tumor activity cannot be predicted by the mechanism of linkers and payloads alone. For example, O. Ab et al, *Mol. Cancer Ther.* 14(&):1605-1613 (2015) demonstrated that, when tested in pre-clinical cancer models, the same antibody conjugated to the same anti-tubulin toxin via different linkers exhibited dramatically different anti-tumor activity. This example is particularly surprising because the chemical structures of the two linkers are very similar. Moreover, the linker present in the superior conjugate contained a hydrophilic moiety. Hydrophilic metabolites are generally less membrane-permeable, and are thought to be slower in efflux from the lysosomes (the site of conjugate degradation), leading to a delay in the anti-tubulin activity of the released payload. This finding argues for an "ideal" kinetics of payload delivery, but to date, there is no insight into what constitutes such kinetics. Adding to this complexity is the open question of whether ideal kinetics of payload delivery, even if defined for a particular cell type, would apply to all cell types. Thus, it is not possible to predict the most effective in vivo anti-tumor activity merely from the chemical composition of the linker or payload.

Compositions, Pharmaceutical Compositions and Formulations

Compositions comprising an antigen-binding protein, a nucleic acid, a vector, a host cell, or a conjugate as presently disclosed are provided herein. The compositions in some aspects comprise the antigen-binding proteins in isolated and/or purified form. In some aspects, the composition comprises a single type (e.g., structure) of an antigen-binding protein of the present disclosure or comprises a combination of two or more antigen-binding proteins of the present disclosure, wherein the combination comprises two or more antigen-binding proteins of different types (e.g., structures).

In some aspects, the composition comprises agents which enhance the chemico-physico features of the antigen-binding protein, e.g., via stabilizing the antigen-binding protein at certain temperatures, e.g., room temperature, increasing shelf life, reducing degradation, e.g., oxidation protease mediated degradation, increasing half-life of the antigen-binding protein, etc. In some aspects, the composition comprises any of the agents disclosed herein as a heterologous moiety or conjugate moiety, optionally in admixture with the antigen-binding proteins of the present disclosure or conjugated to the antigen-binding proteins.

In various aspects of the present disclosure, the composition additionally comprises a pharmaceutically acceptable carrier, diluents, or excipient. In some embodiments, the antigen-binding protein, a nucleic acid, a vector, a host cell, or a conjugate as presently disclosed (hereinafter referred to as "active agents") is formulated into a pharmaceutical composition comprising the active agent, along with a pharmaceutically acceptable carrier, diluent, or excipient. In this regard, the present disclosure further provides pharmaceutical compositions comprising an active agent which is intended for administration to a subject, e.g., a mammal.

In some embodiments, the active agent is present in the pharmaceutical composition at a purity level suitable for administration to a patient. In some embodiments, the active agent has a purity level of at least about 90%, about 91%, about 92%, about 93%, about 94%, about 95%, about 96%, about 97%, about 98% or about 99%, and a pharmaceutically acceptable diluent, carrier or excipient. In some embodiments, the compositions contain an active agent at a concentration of about 0.001 to about 30.0 mg/ml.

In various aspects, the pharmaceutical compositions comprise a pharmaceutically acceptable carrier. As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The pharmaceutical composition can comprise any pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety.

In various aspects, the pharmaceutical composition comprises formulation materials that are nontoxic to recipients at the dosages and concentrations employed. In specific embodiments, pharmaceutical compositions comprising an active agent and one or more pharmaceutically acceptable salts; polyols; surfactants; osmotic balancing agents; tonicity agents; anti-oxidants; antibiotics; antimycotics; bulking agents; lyoprotectants; anti-foaming agents; chelating agents; preservatives; colorants; analgesics; or additional pharmaceutical agents. In various aspects, the pharmaceutical composition comprises one or more polyols and/or one or more surfactants, optionally, in addition to one or more excipients, including but not limited to, pharmaceutically acceptable salts; osmotic balancing agents (tonicity agents); anti-oxidants; antibiotics; antimycotics; bulking agents; lyoprotectants; anti-foaming agents; chelating agents; preservatives; colorants; and analgesics.

In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-betacyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapol); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

The pharmaceutical compositions can be formulated to achieve a physiologically compatible pH. In some embodiments, the pH of the pharmaceutical composition can be for example between about 4 or about 5 and about 8.0 or about 4.5 and about 7.5 or about 5.0 to about 7.5. In various embodiments, the pH of the pharmaceutical composition is between 5.5 and 7.5.

The present disclosure provides methods of producing a pharmaceutical composition. In various aspects, the method comprises combining the antigen-binding protein, conjugate, fusion protein, nucleic acid, vector, host cell, or a combination thereof, with a pharmaceutically acceptable carrier, diluent, or excipient.

Routes of Administration

With regard to the present disclosure, the active agent, or pharmaceutical composition comprising the same, can be administered to the subject via any suitable route of administration. For example, the active agent can be administered to a subject via parenteral, nasal, oral, pulmonary, topical, vaginal, or rectal administration. The following discussion on routes of administration is merely provided to illustrate various embodiments and should not be construed as limiting the scope in any way.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The active agent of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations in some embodiments contain from about 0.5% to about 25% by weight of the active agent of the present disclosure in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the present disclosure. The requirements for effective pharmaceutical carriers for injectable compositions are well-known to those of ordinary skill in the art (see, e.g., *Pharmaceutics and Pharmacy Practice*, J. B. Lippincott Company, Philadelphia, PA, Banker and Chalmers, eds., pages 238-250 (1982), and *ASHP Handbook on Injectable Drugs*, Toissel, 4th ed., pages 622-630 (1986)).

Dosages

The active agents of the disclosure are believed to be useful in methods of inhibiting tumor growth, as well as other methods, as further described herein, including methods of treating or preventing cancer. For purposes of the disclosure, the amount or dose of the active agent administered should be sufficient to effect, e.g., a therapeutic or prophylactic response, in the subject or animal over a reasonable time frame. For example, the dose of the active agent of the present disclosure should be sufficient to treat cancer as described herein in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing the extent to which cancer is treated upon administration of a given dose of the active agent of the present disclosure to a mammal among a set of mammals, each set of which is given a different dose of the active agent, could be used to determine a starting dose to be administered to a mammal. The extent to which cancer is treated upon administration of a certain dose can be represented by, for example, the extent of tumor regression achieved with the active agent in a mouse xenograft model. Methods of assaying tumor regression are known in the art and described herein in EXAMPLES.

The dose of the active agent of the present disclosure also will be determined by the existence, nature and extent of any adverse side effects that might accompany the administration of a particular active agent of the present disclosure. Typically, the attending physician will decide the dosage of the active agent of the present disclosure with which to treat each individual patient, taking into consideration a variety of factors, such as age, body weight, general health, diet, sex, active agent of the present disclosure to be administered, route of administration, and the severity of the condition being treated. By way of example and not intending to limit the present disclosure, the dose of the active agent of the present disclosure can be about 0.0001 to about 1 g/kg body weight of the subject being treated/day, from about 0.0001 to about 0.001 g/kg body weight/day, or about 0.01 mg to about 1 g/kg body weight/day.

Controlled Release Formulations

In some embodiments, the active agents described herein can be modified into a depot form, such that the manner in which the active agent of the present disclosure is released into the body to which it is administered is controlled with respect to time and location within the body (see, for example, U.S. Pat. No. 4,450,150). Depot forms of active agents of the present disclosure can be, for example, an implantable composition comprising the active agents and a porous or non-porous material, such as a polymer, wherein the active agent is encapsulated by or diffused throughout the material and/or degradation of the non-porous material. The depot is then implanted into the desired location within the body of the subject and the active agent is released from the implant at a predetermined rate.

The pharmaceutical composition comprising the active agent in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374: 46-52 (2009) and International Patent Application Publication Nos. WO 2008/130158, WO2004/033036; WO2000/032218; and WO 1999/040942.

The instant compositions can further comprise, for example, micelles or liposomes, or some other encapsulated form, or can be administered in an extended release form to provide a prolonged storage and/or delivery effect.

Use

The antigen-binding proteins of the present disclosure are useful for inhibiting tumor growth. Without being bound to a particular theory, the inhibiting action of the antigen-binding proteins provided herein allow such entities to be useful in methods of treating cancer.

Accordingly, provided herein are methods of inhibiting tumor growth in a subject and methods of reducing tumor size in a subject. In various embodiments, the methods comprise administering to the subject the pharmaceutical composition of the present disclosure in an amount effective for inhibiting tumor growth or reducing tumor size in the subject. In various aspects, the growth of an ovarian tumor, melanoma tumor, bladder tumor, or endometrial tumor is inhibited. In various aspects, the size of an ovarian tumor, melanoma tumor, bladder tumor, or endometrial tumor is reduced.

As used herein, the term "inhibit" or "reduce" and words stemming therefrom may not be a 100% or complete inhibition or reduction. Rather, there are varying degrees of inhibition or reduction of which one of ordinary skill in the art recognizes as having a potential benefit or therapeutic effect. In this respect, the antigen-binding proteins of the present disclosure may inhibit tumor growth or reduce tumor size to any amount or level. In various embodiments, the inhibition provided by the methods of the present disclosure is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition). In various embodiments, the reduction provided by the methods of the present disclosure is at least or about a 10% reduction (e.g., at least or about a 20% reduction, at least or about a 30% reduction, at least or about a 40% reduction, at least or about a 50% reduction, at least or about a 60% reduction, at least or about a 70% reduction, at least or about a 80% reduction, at least or about a 90% reduction, at least or about a 95% reduction, at least or about a 98% reduction).

Additionally provided herein are methods of treating a subject with cancer, e.g., CLDN6-expressing cancer. In various embodiments, the method comprises administering to the subject the pharmaceutical composition of the present disclosure in an amount effective for treating the cancer in the subject.

For purposes herein, the cancer of the methods disclosed herein can be any cancer, e.g., any malignant growth or tumor caused by abnormal and uncontrolled cell division that may spread to other parts of the body through the lymphatic system or the blood stream. The cancer in some aspects is one selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma. In various aspects, the cancer is ovarian cancer, melanoma, bladder cancer, lung cancer, liver cancer, endometrial cancer. In various aspects, the cancer is any cancer characterized by moderate to high expression of CLDN6. See, e.g., FIG. 1-FIG. 3. In various aspects, the cancer is acute myeloid leukemia, large B-cell lymphoma, stomach cancer, prostate cancer, melanoma, colon cancer, rectal cancer, bladder cancer, cervical cancer, liver cancer, breast cancer, kidney clear cell carcinoma, head and neck cancer, sarcoma, kidney chromophobe cancer, lower grade glioma, adrenocortical cancer, glioblastoma, kidney papillary cell carcinoma, lung squamous cell carcinoma, thyroid cancer, lung adenocarcinoma, pancreatic cancer, endometroid cancer, uterine carcinsarcoma, or ovarian cancer. In various aspects, the cancer is selected from ovarian cancer, endometrioid cancer, uterine cancer, lung cancer, gastric cancer, breast cancer Head and Neck Squamous Cell Carcinoma (HNSCC) cancer, cervical cancer, and bladder.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating cancer of the present disclosure can provide any amount or any level of treatment. Furthermore, the treatment provided by the method of the present disclosure can include treatment of one or more conditions or symptoms or signs of the cancer being treated. Also, the treatment provided by the methods of the present disclosure can encompass slowing the progression of the cancer. For example, the methods can treat cancer by virtue of enhancing the T cell activity or an immune response against the cancer, reducing tumor or cancer growth, reducing metastasis of tumor cells, increasing cell death of tumor or cancer cells, and the like. In various aspects, the methods treat by way of delaying the onset or recurrence of the cancer by at least 1 day, 2 days, 4 days, 6 days, 8 days, 10 days, 15 days, 30 days, two months, 3 months, 4 months, 6 months, 1 year, 2 years, 3 years, 4 years, or more. In various aspects, the methods treat by way increasing the survival of the subject.

The antigen binding proteins of the present disclosure also may be used to detect CLDN6 in a sample or diagnose a CLDN6-positive cancer. Therefore, the present disclosure provides methods of detecting Claudin6 (CLDN6) in a sample. In various embodiments, the method comprises contacting the sample with an antigen-binding protein, a conjugate, or a fusion protein, as described herein, and assaying for an immunocomplex comprising the antigen-binding protein, conjugate or fusion protein bound to CLDN6. The present disclosure also provides methods of diagnosing a Claudin6 (CLDN6)-positive cancer in a subject. In various embodiments, the method comprises contacting a biological sample comprising cells or tissue obtained from the subject with an antigen-binding protein, a conjugate, or a fusion protein, as described herein, and assaying for an immunocomplex comprising the antigen-binding protein, conjugate or fusion protein bound to CLDN6.

Subjects

In some embodiments of the present disclosure, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human.

Kits

In some embodiments, the antigen-binding proteins of the present disclosure are provided in a kit. In various aspects, the kit comprises the antigen-binding protein(s) as a unit dose. For purposes herein "unit dose" refers to a discrete amount dispersed in a suitable carrier. In various aspects, the unit dose is the amount sufficient to provide a subject with a desired effect, e.g., inhibition of tumor growth, reduction of tumor size, treatment of cancer. Accordingly, provided herein are kits comprising an antigen-binding protein of the present disclosure optionally provided in unit doses. In various aspects, the kit comprises several unit doses, e.g., a week or month supply of unit doses, optionally, each of which is individually packaged or otherwise separated from other unit doses. In some embodiments, the components of the kit/unit dose are packaged with instructions for administration to a patient. In some embodiments, the kit comprises one or more devices for administration to a patient, e.g., a needle and syringe, and the like. In some aspects, the antigen-binding protein of the present disclosure, a pharmaceutically acceptable salt thereof, a conjugate comprising the antigen-binding protein, or a multimer or dimer comprising the antigen-binding protein, is pre-packaged in a ready to use form, e.g., a syringe, an intravenous bag, etc. In some aspects, the kit further comprises other therapeutic or diagnostic agents or pharmaceutically acceptable carriers (e.g., solvents, buffers, diluents, etc.), including any of those described herein. In particular aspects, the kit comprises an antigen-binding protein of the present disclosure, along with an agent, e.g., a therapeutic agent, used in chemotherapy or radiation therapy.

Various Embodiments

In various embodiments of the present disclosure, the antigen-binding protein binds to a human Claudin6 (CLDN6) protein (SEQ ID NO: 200), wherein (a) the antigen-binding protein binds to Extracellular Loop 2 (EL2) of an extracellular domain (ECD) of CLDN6 and does not bind to Extracellular Loop 1 (EL1) of the ECD of CLDN6; or (b) does not bind to any of Claudin3 (CLDN3), Claudin4 (CLDN4), and Claudin9 (CLDN9) and inhibits binding of a reference antibody to CLDN6 endogenously expressed by OVCA429 cells with less than about 1200 nM; or (c) a combination thereof. In various instances, the antigen-binding protein binds to an epitope within the amino acid sequence of WTAHAIIRDFYNPLVAEAQKREL (SEQ ID NO: 2), or binds to the amino acid sequence of TAHAIIRDFYNPL (SEQ ID NO: 3) or LVAEAQKREL (SEQ ID NO: 4) of CLDN 6. In various aspects, the antigen-binding protein does not bind to any one or more of Claudin3 (CLDN3), Claudin4 (CLDN4), and Claudin9 (CLDN9). In various instances, the antigen-binding protein does not bind to CLDN3. In various instances, the antigen-binding protein binds to CLDN6, CLDN4, and CLDN9 but does not bind to CLDN3. In various instances, the antigen-binding protein binds to CLDN6 and CLDN4 but does not bind to CLDN3 or CLDN9. In various aspects, the antigen-binding protein binds to CLDN6 and CLDN9 but does not bind to CLDN3 or CLDN4.

In various instances, the antigen-binding protein of the present disclosure inhibits binding of a reference antibody to CLDN6 endogenously expressed by OVCA429 cells with less than about 1200 nM and the reference antibody comprises a light chain variable sequence of SEQ ID NO: 181 and a heavy chain variable sequence of SEQ ID NO: 182 or a light chain variable sequence of SEQ ID NO: 185 and a heavy chain variable sequence of SEQ ID NO: 186. In various aspects, the antigen-binding protein of the present disclosure inhibits binding of a reference antibody to CLDN6 endogenously expressed by OVCA429 cells with less than about 1000 nM or less than 750 nM (e.g., less than about 500 nM, less than about 250 nM, less than about 100 nM) and the reference antibody comprises a light chain variable sequence of SEQ ID NO: 181 and a heavy chain variable sequence of SEQ ID NO: 182 or a light chain variable sequence of SEQ ID NO: 185 and a heavy chain variable sequence of SEQ ID NO: 186.

In various embodiments, the antigen-binding protein comprises (a) a heavy chain CDR1 amino acid sequence set forth in Table A or A1 or a sequence selected from the group consisting of: SEQ ID NOs: 11, 17, 23, 29, 35, 41, 47, 53, 59, 65, 71, 77, 83, 89, 95, 101, 107, 113, 119, 125, 131, 452, 455, 461, 465, and 472, or a variant sequence thereof which differs by only one or two amino acids or which has at least or about 70% (e.g., at least or about 85%, at least or about 90%) sequence identity; (b) a heavy chain CDR2 amino acid sequence set forth in Table A or A1 or a sequence selected from the group consisting of: SEQ ID NOs: 12, 18, 24, 30, 36, 42, 48, 54, 60, 66, 72, 78, 84, 90, 86, 102, 108, 114, 120, 126, 132, 475, 456, 462, 466, 468, and 473, or a variant sequence thereof which differs by only one or two amino acids or which has at least or about 70% (e.g., at least or about 85%, at least or about 90%) sequence identity; (c) a heavy chain CDR3 amino acid sequence set forth in Table A or A1 or a sequence selected from the group consisting of: SEQ ID NOs: 13, 19, 25, 31, 37, 43, 49, 55, 61, 67, 73, 79, 85, 91, 97, 103, 109, 115, 121, 127, 133, 453, 457, 463, 467, 469, and 474, or a variant sequence thereof which differs by only one or two amino acids or which has at least or about 70% (e.g., at least or about 85%, at least or about 90%) sequence identity; (d) a light chain CDR1 amino acid sequence set forth in Table A or A1 or a sequence selected from the group consisting of: SEQ ID NOs: 8, 14, 20, 32, 38, 44, 50, 56, 62, 68, 74, 80, 86, 92, 98, 104, 110, 116, 122, 128, 449, 476, 458, 464, and 470, or a variant sequence thereof which differs by only one or two amino acids or which has at least or about 70% (e.g., at least or about 85%, at least or about 90%) sequence identity; (e) a light chain CDR2 amino acid sequence set forth in Table A or A1 or a sequence selected from the group consisting of: SEQ ID NOs: 9, 15, 21, 27, 33, 39, 45, 51, 57, 63, 69, 75, 81, 87, 93, 99, 105, 111, 117, 123, 129, 450, 477, 459, and 471, or a variant sequence thereof which differs by only one or two amino acids or which has at least or about 70% (e.g., at least or about 85%, at least or about 90%) sequence identity; (f) a light chain CDR3 amino acid sequence set forth in Table A or A1 or a sequence selected from the group consisting of: SEQ ID NOs: 10, 16, 22, 28, 34, 40, 46, 52, 58, 64, 70, 76, 82, 88, 94, 100, 106, 112, 118, 124, 130, 451, 454, and 460, or a variant sequence thereof which differs by only one or two amino acids or which has at least or about 70% (e.g., at least or about 85%, at least or about 90%) sequence identity; (g) a combination of any two or more of (a)-(f).

In various aspects, the antigen-binding protein comprises a light chain CDR1 amino acid sequence, a light chain CDR2 amino acid sequence, and a light chain CDR3 amino acid sequence set forth in Table A or A1 and 1 or 2 of the heavy chain CDR amino acid sequences set forth in Table A or A1. In some instances, the antigen-binding protein comprises a heavy chain CDR1 amino acid sequence, a heavy chain CDR2 amino acid sequence, and a heavy chain CDR3 amino acid sequence set forth in Table A or A1 and 1 or 2 of the light chain CDR amino acid sequences set forth in Table A or A1. In various aspects, the antigen-binding protein comprises six CDR amino acid sequences selected from the group consisting of: (a) SEQ ID NOs: 74-79; (b) SEQ ID NOs: 50-55; (c) SEQ ID NOs: 122-127; (d) SEQ ID NOs: 26-31; (e) SEQ ID NOs: 128-133; (f) SEQ ID NOs: 38-43; (g) SEQ ID NOs: 62-67; (h) SEQ ID NOs: 80-85; (i) SEQ ID NOs: 44-49; (j) SEQ ID NOs: 86-91; (k) SEQ ID NOs: 104-109; (l) SEQ ID NOs: 56-61; (m) SEQ ID NOs: 32-37; (n) SEQ ID NOs: 110-115; (o) SEQ ID NOs: 98-103; (p) SEQ ID NOs: 92-97; (q) SEQ ID NOs: 116-121; (r) SEQ ID NOs: 8-13; (t) SEQ ID NOs: 68-73; (u) SEQ ID NOs: 14-19; (v) SEQ ID NOs: 20-25, (v) SEQ ID NOs: 449-453 and 475; (w) SEQ ID NOs: 476-477, 454-457, (x) SEQ ID NOs: 458-463; (y) SEQ ID NOs: 57, 58, 464-467; (z) SEQ ID NOs: 68-71 and 468-469; and (aa) SEQ ID NOs: 112, and 470-474. In various aspects, the antigen-binding protein of comprises (a) a heavy chain variable region amino acid sequence set forth in in Table B or a sequence selected from the group consisting of: SEQ ID NOs: 135, 137, 139, 141, 143, 145, 147, 149, 151, 153, 155, 157, 159, 161, 163, 165, 167, 169, 171, 173, and 175, or a variant sequence thereof which differs by only one or two amino acids or which has at least or about 70% (e.g., at least or about 85%, at least or about 90%) sequence identity; or (b) a light chain variable region amino acid sequence set forth in in Table B or a sequence selected from the group consisting of: SEQ ID NOs: 134, 136, 138, 140, 142, 144, 146, 148, 150, 152, 154, 156, 158, 160, 162, 164, 166, 168, 170, 172, 174, and 176, or a variant sequence thereof which differs by only one or two amino acids or which has at least or about 70% (e.g., at least or about 85%, at least or about 90%) sequence identity; or both (a) and (b). In various aspects, the antigen-binding protein comprises a pair of amino acid sequences selected from the group consisting of: (a) SEQ ID NOs: 156 and 157; (b) SEQ ID NOs: 148 and 149; (c) SEQ ID NOs: 172 and 173; (d) SEQ ID NOs: 140 and 141; (e) SEQ ID NOs: 174 and 175; (f) SEQ ID NOs: 144 and 145; (g) SEQ ID NOs: 152 and 153; (h) SEQ ID NOs: 158 and 159; (i) SEQ ID NOs: 146 and 147; (j) SEQ ID NOs: 160 and 161; (k) SEQ ID NOs: 166 and 167; (l) SEQ ID NOs: 150 and 151; (m) SEQ ID NOs: 142 and 143; (n) SEQ ID NOs: 168 and 169; (o) SEQ ID NOs: 164 and 165; (p) SEQ ID NOs: 162 and 163; (q) SEQ ID NOs: 170 and 171; (r) SEQ ID NOs: 134 and 135; (s) SEQ ID NOs: 154 and 155; (t) SEQ ID NOs: 136 and 137; and (u) SEQ ID NOs: 138 and 139.

In various embodiments, the antigen-binding protein comprises (a) a heavy chain variable region amino acid sequence set forth in in Table B1 or C or a sequence selected from the group consisting of: SEQ ID NOs: 376-379, 384-387, 391-396, 403-408, 412, 413, 416-419, 422-427, 478, 480, 482, 484, 486, and 488 or a variant sequence thereof which differs by only one or two amino acids or which has at least or about 70%, or about 80%, or about 90%, or about 95% sequence identity; or (b) a light chain variable region amino acid sequence set forth in Table B1 or C or a sequence selected from the group consisting of: SEQ ID NOs: 380-383, 388-390, 397-402, 409-411, 414, 415, 420, 421, and 479, 481, 483, 485, 487, and 489 or a variant sequence thereof which differs by only one or two amino acids or which has at least or about 70%, or about 80%, or about 90%, or about 95% sequence identity; or (c) both (a) and (b). In various aspects, the antigen-binding protein comprises a pair of amino acid sequences as listed in Table D.

The present disclosure provides an antigen-binding protein comprising: (A) an HC CDR1 comprising the amino acid sequence of YTFTXYT, wherein X is T, V, D, or S (SEQ ID NO: 452), optionally, comprising the amino acid sequence of YTFTTYT (SEQ ID NO: 11); (B) an HC CDR2 comprising the amino acid sequence of IXPSSGYT, wherein X is Q, S, A, or N (SEQ ID NO: 475), optionally, comprising the amino acid sequence of INPSSGYT (SEQ ID NO: 12); (C) an HC CDR3 comprising the amino acid sequence of AXGDYYVAY, wherein X is N, Q, H, or D (SEQ ID NO: 453), optionally, comprising the amino acid sequence of ANGDYYVAY (SEQ ID NO:13); (D) an LC CDR1 comprising the amino acid sequence of SSVSSXY, wherein X is T, V, F, or D (SEQ ID NO: 449), optionally, comprising the amino acid sequence of SSVSSTY (SEQ ID NO: 8); (E) an LC CDR2 comprising the amino acid sequence of XTX, wherein X at position 1 is S, T, Q, or A and X at position 3 is S, T, D, or Q (SEQ ID NO: 450), optionally, comprising the amino acid sequence of STS (SEQ ID NO: 9); and (F) an LC CDR3 comprising the amino acid sequence of HXYXRSPLT, wherein X at position 2 is Q, H, or S and X at position 4 is H, Y, Q, or S (SEQ ID NO: 451), optionally, comprising the amino acid sequence of HQYHRSPLT (SEQ ID NO: 10).

An antigen-binding protein comprising: (A) an HC CDR1 comprising the amino acid sequence of FTFSXYX, wherein X at position 5 is N, S, R, Q, or A and X at position 7 is W, H, Y, F (SEQ ID NO: 455), optionally, comprising the amino acid sequence of FTFSNYW (SEQ ID NO: 23); (B) an HC CDR2 comprising the amino acid sequence of IRLKXDXYAT, wherein X at position 5 is S, N, A, or T and X at position 7 is Q, S, A, N (SEQ ID NO: 456), optionally, comprising the amino acid sequence of IRLKSDNYAT (SEQ ID NO: 24); (C) an HC CDR3 comprising the amino acid sequence of XDGPPSGX, wherein X at position 1 is N, D, or T and X at position 8 is S, T, A, C, or Y (SEQ ID NO: 457), optionally, comprising the amino acid sequence of NDGPPSGC (SEQ ID NO: 25); (D) an LC CDR1 comprising the amino acid sequence of EXIYSY, wherein X is Q, S, A, D, or N (SEQ ID NO: 476), optionally, comprising the amino acid sequence of ENIYSY (SEQ ID NO: 20); (E) an LC CDR2 comprising the amino acid sequence of XAK, wherein X at position 1 is Q, S, A, D, or N (SEQ ID NO: 477), optionally, comprising the amino acid sequence of NAK (SEQ ID NO: 21); and (F) an LC CDR3 comprising the amino acid sequence of QXHYXVPWT, wherein X at position 2 is H, Q, S, or T and X at position 5 is T, S, N, or G (SEQ ID NO: 454), optionally, comprising the amino acid sequence of QHHYTVPWT (SEQ ID NO: 22).

An antigen-binding protein comprising: (A) an HC CDR1 comprising the amino acid sequence of YTXTXYT, wherein X at position 3 is F, Y, S, or T and X at position 5 is S, T, Y, or D (SEQ ID NO: 461), optionally, comprising the amino acid sequence of YTFTSYT (SEQ ID NO: 29); (B) an HC CDR2 comprising the amino acid sequence of IXPSSXYT, wherein X at position 2 is Q, S, A, or N and X at position 6 is T, S, V, D, or G (SEQ ID NO: 462), optionally, comprising the amino acid sequence of INPSSTYT (SEQ ID NO: 30); (C) an HC CDR3 comprising the amino acid sequence of XRGEXGGFAY, wherein X at position 1 is S, A, T, or V and X at position 5 is L, V, or F (SEQ ID NO: 463), optionally, comprising the amino acid sequence of SRGELGGFAY (SEQ ID NO: 31); (D) an LC CDR1 comprising the amino acid sequence of QSLVHSXGXTY, wherein X at position 7 is D, N, E, Q, S, or A and X at position 9 is Q, S, A, D, or N (SEQ ID NO: 458), optionally, comprising the amino acid sequence of QSLVHSDGNTY (SEQ ID NO: 26); (E) an LC CDR2 comprising the amino acid sequence of XVX, wherein X at position 1 is K, Q, or R and X at position 3 is S, T, or V (SEQ ID NO: 459), optionally, comprising the amino acid sequence of KVS (SEQ ID NO: 27); and (F) an LC CDR3 comprising the amino acid sequence of SXXTHVPYT, wherein X at position 2 is Q, H, or T and X at position 3 is S, G, T, or D (SEQ ID NO: 460), optionally, comprising the amino acid sequence of SQSTHVPYT (SEQ ID NO: 28).

In various embodiments, the antigen-binding protein comprises:
  (a) a heavy chain CDR1 amino acid sequence of: SEQ ID NO: 504 or SEQ ID NO: 507, or a variant sequence thereof which differs by only one or two amino acids or which has at least or about 70% sequence identity;
  (b) a heavy chain CDR2 amino acid sequence of: SEQ ID NOs: 505 or SEQ ID NO: 508, or a variant sequence thereof which differs by only one or two amino acids or which has at least or about 70% sequence identity;
  (c) a heavy chain CDR3 amino acid sequence of: SEQ ID NO: 506 or SEQ ID NO: 509, or a variant sequence thereof which differs by only one or two amino acids or which has at least or about 70% sequence identity;
  (d) a light chain CDR1 amino acid sequence of: SEQ ID NO: 449 or SEQ ID NO: 476, or a variant sequence thereof which differs by only one or two amino acids or which has at least or about 70% sequence identity;
  (e) a light chain CDR2 amino acid sequence of: SEQ ID NO: 450 or SEQ ID NO: 477, or a variant sequence thereof which differs by only one or two amino acids or which has at least or about 70% sequence identity;
  (f) a light chain CDR3 amino acid sequence of: SEQ ID NO: 451 or SEQ ID NO: 454, or a variant sequence thereof which differs by only one or two amino acids or which has at least or about 70% sequence identity;
  (g) a combination of any two or more of (a)-(f).

Optionally, the variant sequence has at least about 80%, at least or about 85%, at least or about 90% or at least or about 95% sequence identity.

In exemplary aspects, the antigen-binding protein comprises a light chain CDR1 amino acid sequence of SEQ ID NO: 449, a light chain CDR2 amino acid sequence or SEQ ID NO: 450, and a light chain CDR3 amino acid sequence or SEQ ID NO: 451 and one or two of a heavy chain CDR1 amino acid sequence of SEQ ID NO: 504, a heavy chain CDR2 amino acid sequence or SEQ ID NO: 505, and a heavy chain CDR3 amino acid sequence or SEQ ID NO: 506. In various instances, the antigen-binding protein comprises a light chain CDR1 amino acid sequence of SEQ ID NO: 476, a light chain CDR2 amino acid sequence or SEQ ID NO: 477, and a light chain CDR3 amino acid sequence or SEQ ID NO: 454 and one or two of a heavy chain CDR1 amino acid sequence of SEQ ID NO: 507, a heavy chain CDR2 amino acid sequence or SEQ ID NO: 508, and a heavy chain CDR3 amino acid sequence or SEQ ID NO: 509. Optionally, the antigen-binding protein of comprises six CDR amino acid sequences selected from the group consisting of: SEQ ID NOs: 449-451 and 504-506; and SEQ ID NOs: 476, 477, 454 and 507-509.

In exemplary aspects, the antigen-binding protein comprises: (a) a heavy chain variable region amino acid sequence of any one of SEQ ID NOs: 490-503, or a heavy chain variable region amino acid sequence labeled as S1-S12 in FIG. 22, or a variant sequence thereof which differs by only one or two amino acids or which has at least or about 70% sequence identity; or (b) a light chain variable region amino acid sequence of any one of SEQ ID NOs: 380-383, 388-390, 479, and 481, or a light chain variable region amino acid sequence labeled as S1-S12 in FIG. 22, or a variant sequence thereof which differs by only one or two amino acids or which has at least or about 70% sequence identity; or (c) both (a) and (b). In some aspects, the variant sequence has at least about 80% or at least about 85% sequence identity, or the variant sequence has at least about 90% or at least about 95% sequence identity.

In exemplary instances, the antigen-binding protein comprises a pair of amino acid sequences:

SEQ ID NOs: 389 and 490;
SEQ ID NOs: 389 and 491;
SEQ ID NOs: 389 and 492;
SEQ ID NOs: 389 and 493;
SEQ ID NOs: 389 and 494;
SEQ ID NOs: 389 and 495;
SEQ ID NOs: 383 and 496;
SEQ ID NOs: 383 and 497;
SEQ ID NOs: 383 and 498;
SEQ ID NOs: 383 and 499;
SEQ ID NOs: 383 and 500;
SEQ ID NOs: 383 and 501;
SEQ ID NOs: 383 and 503;
SEQ ID NOs: 389 and 502;

the heavy chain variable region sequence labeled as S1 in FIG. 22 and the light chain variable region sequence labeled as S1 in FIG. 22;
the heavy chain variable region sequence labeled as S2 in FIG. 22 and the light chain variable region sequence labeled as S2 in FIG. 22;
the heavy chain variable region sequence labeled as S3 in FIG. 22 and the light chain variable region sequence labeled as S3 in FIG. 22;
the heavy chain variable region sequence labeled as S4 in FIG. 22 and the light chain variable region sequence labeled as S4 in FIG. 22;
the heavy chain variable region sequence labeled as S5 in FIG. 22 and the light chain variable region sequence labeled as S5 in FIG. 22;
the heavy chain variable region sequence labeled as S6 in FIG. 22 and the light chain variable region sequence labeled as S6 in FIG. 22;
the heavy chain variable region sequence labeled as S7 in FIG. 22 and the light chain variable region sequence labeled as S7 in FIG. 22;
the heavy chain variable region sequence labeled as S78 in FIG. 22 and the light chain variable region sequence labeled as S8 in FIG. 22;
the heavy chain variable region sequence labeled as S89 in FIG. 22 and the light chain variable region sequence labeled as S9 in FIG. 22;
the heavy chain variable region sequence labeled as S910 in FIG. 22 and the light chain variable region sequence labeled as S10 in FIG. 22;
the heavy chain variable region sequence labeled as S11 in FIG. 22 and the light chain variable region sequence labeled as S11 in FIG. 22; or
the heavy chain variable region sequence labeled as S12 in FIG. 22 and the light chain variable region sequence labeled as S12 in FIG. 22.

In some aspects, the antigen-binding protein is an antibody, e.g., monoclonal antibody. In various aspects, antibody is an IgG. Optionally, the antigen-binding protein inhibits at least about 50% colony growth in a soft agar 3D proliferation assays, inhibits tumor growth in xenograft mice injected with human cancer cells, inhibits tumor growth of in xenograft mice injected with ovarian cancer cells, melanoma cancer cells, bladder cancer cells, or endometrial cancer cells, or inhibits at least 50% tumor growth in xenograft mice injected with ovarian cancer cells, bladder cancer cells, or endometrial cancer cells.

Accordingly, the various embodiments, the present disclosure provides an antigen-binding protein comprising
  (a) a heavy chain CDR1 amino acid sequence of: SEQ ID NO: 504 or SEQ ID NO: 507, or a variant sequence thereof which differs by only one or two amino acids or which has at least or about 70% sequence identity;
  (b) a heavy chain CDR2 amino acid sequence of: SEQ ID NOs: 505 or SEQ ID NO: 508, or a variant sequence thereof which differs by only one or two amino acids or which has at least or about 70% sequence identity;
  (c) a heavy chain CDR3 amino acid sequence of: SEQ ID NO: 506 or SEQ ID NO: 509, or a variant sequence thereof which differs by only one or two amino acids or which has at least or about 70% sequence identity;
  (d) a light chain CDR1 amino acid sequence of: SEQ ID NO: 449 or SEQ ID NO: 476, or a variant sequence thereof which differs by only one or two amino acids or which has at least or about 70% sequence identity;
  (e) a light chain CDR2 amino acid sequence of: SEQ ID NO: 450 or SEQ ID NO: 477, or a variant sequence thereof which differs by only one or two amino acids or which has at least or about 70% sequence identity;
  (f) a light chain CDR3 amino acid sequence of: SEQ ID NO: 451 or SEQ ID NO: 454, or a variant sequence thereof which differs by only one or two amino acids or which has at least or about 70% sequence identity; or
  (g) a combination of any two or more of (a)-(f).

Also provided is an antigen-binding protein comprising six CDR amino acid sequences selected from the group consisting of: SEQ ID NOs: 449-451 and 504-506; and SEQ ID NOs: 476, 477, 454 and 507-509.

The present disclosure provides an antigen-binding protein comprising:
  (a) a heavy chain variable region amino acid sequence of any one of SEQ ID NOs: 490-503, or a heavy chain variable region amino acid sequence labeled as S1-S12 in FIG. 22, or a variant sequence thereof which differs by only one or two amino acids or which has at least or about 70% sequence identity; or
  (b) a light chain variable region amino acid sequence of any one of SEQ ID NOs: 380-383, 388-390, 479, and 481, or a light chain variable region amino acid sequence labeled as S1-S12 in FIG. 22, or a variant sequence thereof which differs by only one or two amino acids or which has at least or about 70% sequence identity; or
  (c) both (a) and (b).

In various aspects, the variant sequence has at least about 85% sequence identity or about 90% or about 95% sequence identity.

The present disclosure also provides an antigen-binding protein comprising a pair of amino acid sequences selected from the group consisting of:

SEQ ID NOs: 389 and 490;
SEQ ID NOs: 389 and 491;
SEQ ID NOs: 389 and 492;
SEQ ID NOs: 389 and 493;
SEQ ID NOs: 389 and 494;
SEQ ID NOs: 389 and 495;
SEQ ID NOs: 383 and 496;
SEQ ID NOs: 383 and 497;
SEQ ID NOs: 383 and 498;
SEQ ID NOs: 383 and 499;
SEQ ID NOs: 383 and 500;
SEQ ID NOs: 383 and 501;
SEQ ID NOs: 383 and 503;
SEQ ID NOs: 389 and 502;
the heavy chain variable region sequence labeled as S1 in FIG. 22 and the light chain variable region sequence labeled as S1 in FIG. 22;
the heavy chain variable region sequence labeled as S2 in FIG. 22 and the light chain variable region sequence labeled as S2 in FIG. 22;
the heavy chain variable region sequence labeled as S3 in FIG. 22 and the light chain variable region sequence labeled as S3 in FIG. 22;
the heavy chain variable region sequence labeled as S4 in FIG. 22 and the light chain variable region sequence labeled as S4 in FIG. 22;
the heavy chain variable region sequence labeled as S5 in FIG. 22 and the light chain variable region sequence labeled as S5 in FIG. 22;
the heavy chain variable region sequence labeled as S6 in FIG. 22 and the light chain variable region sequence labeled as S6 in FIG. 22;
the heavy chain variable region sequence labeled as S7 in FIG. 22 and the light chain variable region sequence labeled as S7 in FIG. 22;
the heavy chain variable region sequence labeled as S78 in FIG. 22 and the light chain variable region sequence labeled as S8 in FIG. 22;
the heavy chain variable region sequence labeled as S89 in FIG. 22 and the light chain variable region sequence labeled as S9 in FIG. 22;
the heavy chain variable region sequence labeled as S910 in FIG. 22 and the light chain variable region sequence labeled as S10 in FIG. 22;
the heavy chain variable region sequence labeled as S11 in FIG. 22 and the light chain variable region sequence labeled as S11 in FIG. 22; or
the heavy chain variable region sequence labeled as S12 in FIG. 22 and the light chain variable region sequence labeled as S12 in FIG. 22.

Provided herein is an antigen-binding protein comprising:
(a) a heavy chain variable region amino acid sequence set forth as SEQ ID NO: 510 or 513 or in FIG. 23 or FIG. 25, or a variant sequence thereof which differs by only one or two amino acids or which has at least or about 70% sequence identity; or
(b) a light chain variable region amino acid sequence set forth as SEQ ID NO: 511 or 512 or in FIG. 24 or FIG. 26, or a variant sequence thereof which differs by only one or two amino acids or which has at least or about 70% sequence identity; or
(c) both (a) and (b).

The present disclosure also provides an antigen-binding protein comprising a pair of amino acid sequences wherein the pair comprises
(a) a heavy chain variable region amino acid sequence set forth as SEQ ID NO: 510 and a light chain variable region amino acid sequence set forth as SEQ ID NO: 511, or a variant sequence thereof which differs by only 1-5 amino acids or which has at least or about 70% sequence identity; optionally, wherein the 1-5 amino acids which differ are as shown in FIG. 23 for the heavy chain or FIG. 24 for the light chain, or
(b) a heavy chain variable region amino acid sequence set forth as SEQ ID NO: 513 and a light chain variable region amino acid sequence set forth as SEQ ID NO: 512, or a variant sequence thereof which differs by only 1-5 amino acids or which has at least or about 70% sequence identity; or optionally, wherein the 1-5 amino acids which differ are as shown in FIG. 25 for the heavy chain or FIG. 26 for the light chain.

In various aspects, the presently disclosed antigen-binding protein comprises an Fc polypeptide comprising an afucosylated glycan.

In various aspects, the antigen-binding protein of the present disclosure is an antibody, e.g., a monoclonal antibody. In various instances, the antigen-binding protein is an IgG. In various aspects, the antigen-binding protein inhibits at least about 50% colony growth in a soft agar 3D proliferation assays or inhibits tumor growth in xenograft mice injected with human cancer cells. In various aspects, the antigen-binding protein inhibits tumor growth of in xenograft mice injected with ovarian cancer cells, melanoma cancer cells, bladder cancer cells, or endometrial cancer cells. In various instances, the antigen-binding protein inhibits at least 50% tumor growth in xenograft mice injected with ovarian cancer cells, bladder cancer cells, or endometrial cancer cells.

The present disclosure provides a conjugate comprising an antigen-binding protein described herein and a heterologous moiety. In exemplary aspects, the conjugate comprises a cytotoxic agent or a chemotherapeutic agent, such as, for example, any of those described herein. The chemotherapeutic agent in various aspects is an anti-mitotic agent which inhibits cell division by blocking tubulin polymerization. In some instances, the anti-mitotic agent is an auristatin, optionally, MMAE.

The present disclosure also provides a fusion protein comprising an antigen-binding protein described herein. The present disclosure further provides a nucleic acid comprising a nucleotide sequence encoding an antigen binding protein, a conjugate, or a fusion protein, of the present disclosure. The present disclosure provides a vector comprising the nucleic acid comprising a nucleotide sequence encoding an antigen binding protein, a conjugate, or a fusion protein, of the present disclosure. The present disclosure additionally provides a host cell comprising the nucleic acid or the vector of the present disclosure.

The present disclosure provides a method of producing an antigen-binding protein that binds to a Claudin6 (CLDN6) protein, comprising (i) culturing the host cell of the present disclosure in a cell culture medium, wherein the host cell comprises a nucleic acid comprising a nucleotide sequence encoding an antigen binding protein of any one of the previous claims, and (ii) harvesting the antigen-binding protein from the cell culture medium. Also, provided is a method of producing a fusion protein comprising an antigen-binding protein that binds to a Claudin6 (CLDN6) protein, comprising (i) culturing the host cell of the present disclosure in a cell culture medium, wherein the host cell comprises a nucleic acid comprising a nucleotide sequence encoding a fusion protein of the present disclosure, and (ii) harvesting the fusion protein from the cell culture medium.

The present disclosure furthermore provides a method of producing a pharmaceutical composition comprising combining an antigen-binding protein, a conjugate, a fusion protein, a nucleic acid, a vector, a host cell, of the present disclosure, or a combination thereof, and a pharmaceutically acceptable carrier, diluent or excipient. Also provided are pharmaceutical compositions comprising antigen-binding protein, a conjugate, a fusion protein, a nucleic acid, a vector, a host cell, of the present disclosure, or a combination thereof, and a pharmaceutically acceptable carrier, diluent or excipient.

Provided herein is a method of treating a subject with a CLDN6-expressing cancer comprising administering to the subject a pharmaceutical composition described herein in an amount effective to treat the cancer. Also provided is a method of inhibiting tumor growth in a subject, comprising administering to the subject a pharmaceutical composition described herein in an amount effective to inhibit tumor growth. The present disclosure provides a method of reducing tumor size in a subject, comprising administering to the subject a pharmaceutical composition described herein in an amount effective to reduce tumor size. Further provided is a method of preventing the recurrence of cancer in a subject, comprising administering to the subject a pharmaceutical composition described herein in an amount effective to prevent the recurrence of cancer.

The present disclosure provides a method of detecting Claudin6 (CLDN6) in a sample, comprising contacting the sample with an antigen-binding protein, a conjugate, or a fusion protein, of the present disclosure, and assaying for an immunocomplex comprising the antigen-binding protein, conjugate or fusion protein bound to CLDN6. Also provided herein is a method of diagnosing a Claudin6 (CLDN6)-positive cancer in a subject, comprising contacting a biological sample comprising cells or tissue obtained from the subject with an antigen-binding protein, a conjugate, or a fusion protein, of the present disclosure, and assaying for an immunocomplex comprising the antigen-binding protein, conjugate or fusion protein bound to CLDN6.

The present disclosure also provides a method of treating cancer in a subject diagnosed to be a low over-expresser of CLDN6. In various embodiments, the method comprises administering to the subject a presently disclosed pharmaceutical composition in an amount effective to prevent the recurrence of cancer. In some aspects, the administering induces apoptosis in tumor cells, optionally, the administering induces apoptosis in cells expressing CLDN6. In various aspects, the subject has a tumor and the tumor is semi-quantitatively categorized into one of four groups: high expressers, moderate expressers, low expressers, and non-expressers. In various instances, high expressers are defined as CLDN6 RNA greater than 12 log Fragments Per Kilobase Million (FPKM), wherein the CLDN6 RNA is measured by RNASeq, or CLDN6 protein levels are greater than 3+ as measured by immunohistochemistry (IHC). In various instances, moderate expressers are defined as CLDN6 RNA greater than 10 log FPKM, wherein the CLDN6 RNA is measured by RNASeq, or CLDN6 protein levels are greater than 2+ as measured by IHC. In various instances, low expressers are defined as CLDN6 RNA greater than 6 log FPKM, wherein the CLDN6 RNA is measured by RNASeq, or CLDN6 protein levels are greater than 1+ as measured by IHC. In various instances, non-expressers are defined as CLDN6 RNA less than 6 log FPKM, wherein the CLDN6 RNA is measured by RNASeq, or CLDN6 protein levels are below IHC detection limits. In various aspects, the subject having said tumor is likewise described as a high expresser, moderate expresser, low expresser, or non-expresser of CLDN6.

Exemplary Embodiments: Set 1

1. An antigen-binding protein, wherein the antigen-binding protein:
   a) binds to a human Claudin6 (CLDN6) protein (SEQ ID NO: 200);
   b) binds to Extracellular Loop 2 (EL2) of an extracellular domain (ECD) of CLDN6 and does not bind to Extracellular Loop 1 (EL1) of the ECD of CLDN6;
   c) does not bind to any of Claudin3 (CLDN3), Claudin4 (CLDN4), and Claudin9 (CLDN9) and inhibits binding of a reference antibody to CLDN6 endogenously expressed by OVCA429 cells with less than about 1200 nM; or
   d) a combination thereof.
2. The antigen-binding protein of 1, wherein the antigen-binding protein comprises the heavy chain (HC) CDR amino acid sequences of SEQ ID NOs: 11, 12, and 13, and/or the light chain (LC) CDR amino acid sequences of SEQ ID NOs: 8, 9, and 10; or a variant sequence thereof which differs by only one or two amino acids or which has at least or about 70% sequence identity, optionally wherein the variant sequence has at least about 90% or at least about 95% sequence identity.
3. The antigen-binding protein of 2, wherein the antigen-binding protein comprises HC and LC variable region amino acid sequences of SEQ ID NOs: 379 and/or 383; or a variant sequence thereof which differs by only one or two amino acids or which has at least or about 70% sequence identity, optionally wherein the variant sequence has at least about 90% or at least about 95% sequence identity.
4. The antigen-binding protein of 2, wherein the antigen-binding protein is an antibody, optionally wherein the antibody is an IgG.
5. A pharmaceutical composition comprising (i) an antigen-binding protein of 2; and (ii) a pharmaceutically acceptable carrier, diluent, and/or excipient.
6. A nucleic acid comprising a nucleotide sequence encoding an antigen-binding protein of 2.
7. A vector comprising the nucleic acid of 6.
8. A host cell comprising the nucleic acid of 6.
9. A fusion protein comprising an antigen-binding protein of 2.
10. A conjugate comprising an antigen-binding protein of 2, optionally wherein the conjugate comprises a cytotoxic agent or a chemotherapeutic agent.
11. A method of producing the antigen-binding protein that binds to CLDN6, comprising (i) culturing the host cell of 8 in a cell culture medium, and (ii) harvesting the antigen-binding protein from the cell culture medium.
12. A method of treating a subject with a CLDN6-expressing cancer, comprising administering to the subject the pharmaceutical composition of 5.
13. A method of inhibiting tumor growth or reducing the tumor size in a subject, comprising administering to the subject the pharmaceutical composition of 5.
14. A method of preventing the recurrence of a cancer in a subject, comprising administering to the subject the pharmaceutical composition of 5.

15. A method of treating cancer in a subject diagnosed to be a low over-expresser of CLDN6, comprising administering to the subject the pharmaceutical composition of 5.
16. A method of detecting CLDN6 in a sample, comprising contacting the sample with an antigen-binding protein of 2.
17. A method of diagnosing a CLDN6-positive cancer in a subject, comprising contacting a biological sample comprising cells or tissue obtained from the subject with an antigen-binding protein of 2, and assaying for an immunocomplex comprising the antigen-binding protein bound to CLDN6, optionally further comprising treating the subject who is diagnosed to have a CLDN6-positive cancer.
18. The antigen-binding protein of 1, wherein the antigen-binding protein comprises the HC CDR amino acid sequences of SEQ ID NOs: 17, 18, and 19, and/or the LC CDR amino acid sequences of SEQ ID NOs: 14, 15, and 16; or a variant sequence thereof which differs by only one or two amino acids or which has at least or about 70% sequence identity, optionally wherein the variant sequence has at least about 90% or at least about 95% sequence identity.
19. The antigen-binding protein of 18, wherein the antigen-binding protein comprises HC and LC variable region amino acid sequences of SEQ ID NOs: 137 and/or 136; or a variant sequence thereof which differs by only one or two amino acids or which has at least or about 70% sequence identity, optionally wherein the variant sequence has at least about 90% or at least about 95% sequence identity.
20. The antigen-binding protein of 18, wherein the antigen-binding protein is an antibody, optionally wherein the antibody is an IgG.
21. A pharmaceutical composition comprising (i) an antigen-binding protein of 18; and (ii) a pharmaceutically acceptable carrier, diluent, and/or excipient.
22. A nucleic acid comprising a nucleotide sequence encoding an antigen-binding protein of 18.
23. A vector comprising the nucleic acid of 22.
24. A host cell comprising the nucleic acid of 22.
25. A fusion protein comprising an antigen-binding protein of 18.
26. A conjugate comprising an antigen-binding protein of 18, optionally wherein the conjugate comprises a cytotoxic agent or a chemotherapeutic agent.
27. A method of producing the antigen-binding protein that binds to CLDN6, comprising (i) culturing the host cell of 24 in a cell culture medium, and (ii) harvesting the antigen-binding protein from the cell culture medium.
28. A method of treating a subject with a CLDN6-expressing cancer, comprising administering to the subject the pharmaceutical composition of 21.
29. A method of inhibiting tumor growth or reducing the tumor size in a subject, comprising administering to the subject the pharmaceutical composition of 21.
30. A method of preventing the recurrence of a cancer in a subject, comprising administering to the subject the pharmaceutical composition of 21.
31. A method of treating cancer in a subject diagnosed to be a low over-expresser of CLDN6, comprising administering to the subject the pharmaceutical composition of 21.
32. A method of detecting CLDN6 in a sample, comprising contacting the sample with an antigen-binding protein of 18.
33. A method of diagnosing a CLDN6-positive cancer in a subject, comprising contacting a biological sample comprising cells or tissue obtained from the subject with an antigen-binding protein of 18, and assaying for an immunocomplex comprising the antigen-binding protein bound to CLDN6, optionally further comprising treating the subject who is diagnosed to have a CLDN6-positive cancer.
34. The antigen-binding protein of 1, wherein the antigen-binding protein comprises the HC CDR amino acid sequences of SEQ ID NOs: 23, 24, and 457, wherein the first Xaa is N and the second Xaa is S, and/or the LC CDR amino acid sequences of SEQ ID NOs: 20, 21, and 22; or a variant sequence thereof which differs by only one or two amino acids or which has at least or about 70% sequence identity, optionally wherein the variant sequence has at least about 90% or at least about 95% sequence identity.
35. The antigen-binding protein of 34, wherein the antigen-binding protein comprises HC and LC variable region amino acid sequences of SEQ ID NOs: 387 and/or 389; or a variant sequence thereof which differs by only one or two amino acids or which has at least or about 70% sequence identity, optionally wherein the variant sequence has at least about 90% or at least about 95% sequence identity.
36. The antigen-binding protein of 34, wherein the antigen-binding protein is an antibody, optionally wherein the antibody is an IgG.
37. A pharmaceutical composition comprising (i) an antigen-binding protein of 34; and (ii) a pharmaceutically acceptable carrier, diluent, and/or excipient.
38. A nucleic acid comprising a nucleotide sequence encoding an antigen-binding protein of 34.
39. A vector comprising the nucleic acid of 38.
40. A host cell comprising the nucleic acid of 38.
41. A fusion protein comprising an antigen-binding protein of 34.
42. A conjugate comprising an antigen-binding protein of 34, optionally wherein the conjugate comprises a cytotoxic agent or a chemotherapeutic agent.
43. A method of producing the antigen-binding protein that binds to CLDN6, comprising (i) culturing the host cell of 40 in a cell culture medium, and (ii) harvesting the antigen-binding protein from the cell culture medium.
44. A method of treating a subject with a CLDN6-expressing cancer, comprising administering to the subject the pharmaceutical composition of 37.
45. A method of inhibiting tumor growth or reducing the tumor size in a subject, comprising administering to the subject the pharmaceutical composition of 37.
46. A method of preventing the recurrence of a cancer in a subject, comprising administering to the subject the pharmaceutical composition of 37.
47. A method of treating cancer in a subject diagnosed to be a low over-expresser of CLDN6, comprising administering to the subject the pharmaceutical composition of 37.
48. A method of detecting CLDN6 in a sample, comprising contacting the sample with an antigen-binding protein of 34.
49. A method of diagnosing a CLDN6-positive cancer in a subject, comprising contacting a biological sample comprising cells or tissue obtained from the subject with an antigen-binding protein of 34, and assaying for an immunocomplex comprising the antigen-binding protein bound to CLDN6, optionally further comprising treating the subject who is diagnosed to have a CLDN6-positive cancer.
50. The antigen-binding protein of 1, wherein the antigen-binding protein comprises the HC CDR amino acid sequences of SEQ ID NOs: 29, 30, and 31, and/or the LC CDR amino acid sequences of SEQ ID NOs: 26, 27, and 28; or a variant sequence thereof which differs by only one or two amino acids or which has at least or about 70% sequence identity, optionally wherein the variant sequence has at least about 90% or at least about 95% sequence identity.
51. The antigen-binding protein of 50, wherein the antigen-binding protein comprises HC and LC variable region amino acid sequences of SEQ ID NOs: 141 and/or 140; or a variant sequence thereof which differs by only one or two amino acids or which has at least or about 70% sequence identity, optionally wherein the variant sequence has at least about 90% or at least about 95% sequence identity.
52. The antigen-binding protein of 50, wherein the antigen-binding protein is an antibody, optionally wherein the antibody is an IgG.
53. A pharmaceutical composition comprising (i) an antigen-binding protein of 50; and (ii) a pharmaceutically acceptable carrier, diluent, and/or excipient.
54. A nucleic acid comprising a nucleotide sequence encoding an antigen-binding protein of 50.
55. A vector comprising the nucleic acid of 54.
56. A host cell comprising the nucleic acid of 54.
57. A fusion protein comprising an antigen-binding protein of 50.
58. A conjugate comprising an antigen-binding protein of 50, optionally wherein the conjugate comprises a cytotoxic agent or a chemotherapeutic agent.
59. A method of producing the antigen-binding protein that binds to CLDN6, comprising (i) culturing the host cell of 56 in a cell culture medium, and (ii) harvesting the antigen-binding protein from the cell culture medium.
60. A method of treating a subject with a CLDN6-expressing cancer, comprising administering to the subject the pharmaceutical composition of 53.
61. A method of inhibiting tumor growth or reducing the tumor size in a subject, comprising administering to the subject the pharmaceutical composition of 53.
62. A method of preventing the recurrence of a cancer in a subject, comprising administering to the subject the pharmaceutical composition of 53.
63. A method of treating cancer in a subject diagnosed to be a low over-expresser of CLDN6, comprising administering to the subject the pharmaceutical composition of 53.
64. A method of detecting CLDN6 in a sample, comprising contacting the sample with an antigen-binding protein of 50.
65. A method of diagnosing a CLDN6-positive cancer in a subject, comprising contacting a biological sample comprising cells or tissue obtained from the subject with an antigen-binding protein of 50, and assaying for an immunocomplex comprising the antigen-binding protein bound to CLDN6, optionally further comprising treating the subject who is diagnosed to have a CLDN6-positive cancer.
66. The antigen-binding protein of 1, wherein the antigen-binding protein comprises the HC CDR amino acid sequences of SEQ ID NOs: 35, 36, and 37, and/or the LC CDR amino acid sequences of SEQ ID NOs: 32, 33, and 34; or a variant sequence thereof which differs by only one or two amino acids or which has at least or about 70% sequence identity, optionally wherein the variant sequence has at least about 90% or at least about 95% sequence identity.
67. The antigen-binding protein of 66, wherein the antigen-binding protein comprises HC and LC variable region amino acid sequences of SEQ ID NOs: 143 and/or 142; or a variant sequence thereof which differs by only one or two amino acids or which has at least or about 70% sequence identity, optionally wherein the variant sequence has at least about 90% or at least about 95% sequence identity.
68. The antigen-binding protein of 66, wherein the antigen-binding protein is an antibody, optionally wherein the antibody is an IgG.
69. A pharmaceutical composition comprising (i) an antigen-binding protein of 66; and (ii) a pharmaceutically acceptable carrier, diluent, and/or excipient.
70. A nucleic acid comprising a nucleotide sequence encoding an antigen-binding protein of 66.
71. A vector comprising the nucleic acid of 70.
72. A host cell comprising the nucleic acid of 70.
73. A fusion protein comprising an antigen-binding protein of 66.
74. A conjugate comprising an antigen-binding protein of 66, optionally wherein the conjugate comprises a cytotoxic agent or a chemotherapeutic agent.
75. A method of producing the antigen-binding protein that binds to CLDN6, comprising (i) culturing the host cell of 72 in a cell culture medium, and (ii) harvesting the antigen-binding protein from the cell culture medium.
76. A method of treating a subject with a CLDN6-expressing cancer, comprising administering to the subject the pharmaceutical composition of 69.
77. A method of inhibiting tumor growth or reducing the tumor size in a subject, comprising administering to the subject the pharmaceutical composition of 69.
78. A method of preventing the recurrence of a cancer in a subject, comprising administering to the subject the pharmaceutical composition of 69.
79. A method of treating cancer in a subject diagnosed to be a low over-expresser of CLDN6, comprising administering to the subject the pharmaceutical composition of 69.
80. A method of detecting CLDN6 in a sample, comprising contacting the sample with an antigen-binding protein of 66.
81. A method of diagnosing a CLDN6-positive cancer in a subject, comprising contacting a biological sample comprising cells or tissue obtained from the subject with an antigen-binding protein of 66, and assaying for an immunocomplex comprising the antigen-binding protein bound to CLDN6, optionally further comprising treating the subject who is diagnosed to have a CLDN6-positive cancer.
82. The antigen-binding protein of 1, wherein the antigen-binding protein comprises the HC CDR amino acid sequences of SEQ ID NOs: 41, 42, and 43, and/or the LC CDR amino acid sequences of SEQ ID NOs: 38, 39, and 40; or a variant sequence thereof which differs by only one or two amino acids or which has at least or about 70% sequence identity, optionally wherein the variant sequence has at least about 90% or at least about 95% sequence identity.
83. The antigen-binding protein of 82, wherein the antigen-binding protein comprises HC and LC variable region amino acid sequences of SEQ ID NOs: 145 and/or 144; or a variant sequence thereof which differs by only one or two amino acids or which has at least or about 70% sequence identity, optionally wherein the variant sequence has at least about 90% or at least about 95% sequence identity.
84. The antigen-binding protein of 82, wherein the antigen-binding protein is an antibody, optionally wherein the antibody is an IgG.
85. A pharmaceutical composition comprising (i) an antigen-binding protein of 82; and (ii) a pharmaceutically acceptable carrier, diluent, and/or excipient.
86. A nucleic acid comprising a nucleotide sequence encoding an antigen-binding protein of 82.
87. A vector comprising the nucleic acid of 86.
88. A host cell comprising the nucleic acid of 86.
89. A fusion protein comprising an antigen-binding protein of 82.
90. A conjugate comprising an antigen-binding protein of 82, optionally wherein the conjugate comprises a cytotoxic agent or a chemotherapeutic agent.
91. A method of producing the antigen-binding protein that binds to CLDN6, comprising (i) culturing the host cell of 88 in a cell culture medium, and (ii) harvesting the antigen-binding protein from the cell culture medium.
92. A method of treating a subject with a CLDN6-expressing cancer, comprising administering to the subject the pharmaceutical composition of 85.
93. A method of inhibiting tumor growth or reducing the tumor size in a subject, comprising administering to the subject the pharmaceutical composition of 85.
94. A method of preventing the recurrence of a cancer in a subject, comprising administering to the subject the pharmaceutical composition of 85.
95. A method of treating cancer in a subject diagnosed to be a low over-expresser of CLDN6, comprising administering to the subject the pharmaceutical composition of 85.
96. A method of detecting CLDN6 in a sample, comprising contacting the sample with an antigen-binding protein of 82.
97. A method of diagnosing a CLDN6-positive cancer in a subject, comprising contacting a biological sample comprising cells or tissue obtained from the subject with an antigen-binding protein of 82, and assaying for an immunocomplex comprising the antigen-binding protein bound to CLDN6, optionally further comprising treating the subject who is diagnosed to have a CLDN6-positive cancer.
98. The antigen-binding protein of 1, wherein the antigen-binding protein comprises the HC CDR amino acid sequences of SEQ ID NOs: 47, 48, and 49, and/or the LC CDR amino acid sequences of SEQ ID NOs: 44, 45, and 46; or a variant sequence thereof which differs by only one or two amino acids or which has at least or about 70% sequence identity, optionally wherein the variant sequence has at least about 90% or at least about 95% sequence identity.
99. The antigen-binding protein of 98, wherein the antigen-binding protein comprises HC and LC variable region amino acid sequences of SEQ ID NOs: 147 and/or 146; or a variant sequence thereof which differs by only one or two amino acids or which has at least or about 70% sequence identity, optionally wherein the variant sequence has at least about 90% or at least about 95% sequence identity.
100. The antigen-binding protein of 98, wherein the antigen-binding protein is an antibody, optionally wherein the antibody is an IgG.
101. A pharmaceutical composition comprising (i) an antigen-binding protein of 98; and (ii) a pharmaceutically acceptable carrier, diluent, and/or excipient.
102. A nucleic acid comprising a nucleotide sequence encoding an antigen-binding protein of 98.
103. A vector comprising the nucleic acid of 102.
104. A host cell comprising the nucleic acid of 102.
105. A fusion protein comprising an antigen-binding protein of 98.
106. A conjugate comprising an antigen-binding protein of 98, optionally wherein the conjugate comprises a cytotoxic agent or a chemotherapeutic agent.
107. A method of producing the antigen-binding protein that binds to CLDN6, comprising (i) culturing the host cell of 104 in a cell culture medium, and (ii) harvesting the antigen-binding protein from the cell culture medium.
108. A method of treating a subject with a CLDN6-expressing cancer, comprising administering to the subject the pharmaceutical composition of 101.
109. A method of inhibiting tumor growth or reducing the tumor size in a subject, comprising administering to the subject the pharmaceutical composition of 101.
110. A method of preventing the recurrence of a cancer in a subject, comprising administering to the subject the pharmaceutical composition of 101.
111. A method of treating cancer in a subject diagnosed to be a low over-expresser of CLDN6, comprising administering to the subject the pharmaceutical composition of 101.
112. A method of detecting CLDN6 in a sample, comprising contacting the sample with an antigen-binding protein of 98.
113. A method of diagnosing a CLDN6-positive cancer in a subject, comprising contacting a biological sample comprising cells or tissue obtained from the subject with an antigen-binding protein of 98, and assaying for an immunocomplex comprising the antigen-binding protein bound to CLDN6, optionally further comprising treating the subject who is diagnosed to have a CLDN6-positive cancer.
114. The antigen-binding protein of 1, wherein the antigen-binding protein comprises the HC CDR amino acid sequences of SEQ ID NOs: 53, 54, and 55, and/or the LC CDR amino acid sequences of SEQ ID NOs: 50, 51, and 52; or a variant sequence thereof which differs by only one or two amino acids or which has at least or about 70% sequence identity, optionally wherein the variant sequence has at least about 90% or at least about 95% sequence identity.
115. The antigen-binding protein of 114, wherein the antigen-binding protein comprises HC and LC variable region amino acid sequences of SEQ ID NOs: 149 and/or 148; or a variant sequence thereof which differs by only one or two amino acids or which has at least or about 70% sequence identity, optionally wherein the variant sequence has at least about 90% or at least about 95% sequence identity.

116. The antigen-binding protein of 114, wherein the antigen-binding protein is an antibody, optionally wherein the antibody is an IgG.
117. A pharmaceutical composition comprising (i) an antigen-binding protein of 114; and (ii) a pharmaceutically acceptable carrier, diluent, and/or excipient.
118. A nucleic acid comprising a nucleotide sequence encoding an antigen-binding protein of 114.
119. A vector comprising the nucleic acid of 118.
120. A host cell comprising the nucleic acid of 118.
121. A fusion protein comprising an antigen-binding protein of 114.
122. A conjugate comprising an antigen-binding protein of clai114, optionally wherein the conjugate comprises a cytotoxic agent or a chemotherapeutic agent.
123. A method of producing the antigen-binding protein that binds to CLDN6, comprising (i) culturing the host cell of 114 in a cell culture medium, and (ii) harvesting the antigen-binding protein from the cell culture medium.
124. A method of treating a subject with a CLDN6-expressing cancer, comprising administering to the subject the pharmaceutical composition of 117.
125. A method of inhibiting tumor growth or reducing the tumor size in a subject, comprising administering to the subject the pharmaceutical composition of 117.
126. A method of preventing the recurrence of a cancer in a subject, comprising administering to the subject the pharmaceutical composition of 117.
127. A method of treating cancer in a subject diagnosed to be a low over-expresser of CLDN6, comprising administering to the subject the pharmaceutical composition of 117.
128. A method of detecting CLDN6 in a sample, comprising contacting the sample with an antigen-binding protein of 114.
129. A method of diagnosing a CLDN6-positive cancer in a subject, comprising contacting a biological sample comprising cells or tissue obtained from the subject with an antigen-binding protein of 114, and assaying for an immunocomplex comprising the antigen-binding protein bound to CLDN6, optionally further comprising treating the subject who is diagnosed to have a CLDN6-positive cancer.
130. The antigen-binding protein of 1, wherein the antigen-binding protein comprises the HC CDR amino acid sequences of SEQ ID NOs: 59, 60, and 61, and/or the LC CDR amino acid sequences of SEQ ID NOs: 56, 57, and 58; or a variant sequence thereof which differs by only one or two amino acids or which has at least or about 70% sequence identity, optionally wherein the variant sequence has at least about 90% or at least about 95% sequence identity.
131. The antigen-binding protein of 130, wherein the antigen-binding protein comprises HC and LC variable region amino acid sequences of SEQ ID NOs: 151 and/or 150; or a variant sequence thereof which differs by only one or two amino acids or which has at least or about 70% sequence identity, optionally wherein the variant sequence has at least about 90% or at least about 95% sequence identity.
132. The antigen-binding protein of 130, wherein the antigen-binding protein is an antibody, optionally wherein the antibody is an IgG.
133. A pharmaceutical composition comprising (i) an antigen-binding protein of 130; and (ii) a pharmaceutically acceptable carrier, diluent, and/or excipient.
134. A nucleic acid comprising a nucleotide sequence encoding an antigen-binding protein of 130.
135. A vector comprising the nucleic acid of 134.
136. A host cell comprising the nucleic acid of 134.
137. A fusion protein comprising an antigen-binding protein of 130.
138. A conjugate comprising an antigen-binding protein of 130, optionally wherein the conjugate comprises a cytotoxic agent or a chemotherapeutic agent.
139. A method of producing the antigen-binding protein that binds to CLDN6, comprising (i) culturing the host cell of 136 in a cell culture medium, and (ii) harvesting the antigen-binding protein from the cell culture medium.
140. A method of treating a subject with a CLDN6-expressing cancer, comprising administering to the subject the pharmaceutical composition of 133.
141. A method of inhibiting tumor growth or reducing the tumor size in a subject, comprising administering to the subject the pharmaceutical composition of 133.
142. A method of preventing the recurrence of a cancer in a subject, comprising administering to the subject the pharmaceutical composition of 133.
143. A method of treating cancer in a subject diagnosed to be a low over-expresser of CLDN6, comprising administering to the subject the pharmaceutical composition of 133.
144. A method of detecting CLDN6 in a sample, comprising contacting the sample with an antigen-binding protein of 130.
145. A method of diagnosing a CLDN6-positive cancer in a subject, comprising contacting a biological sample comprising cells or tissue obtained from the subject with an antigen-binding protein of 130, and assaying for an immunocomplex comprising the antigen-binding protein bound to CLDN6, optionally further comprising treating the subject who is diagnosed to have a CLDN6-positive cancer.
146. The antigen-binding protein of 1, wherein the antigen-binding protein comprises the heavy chain (HC) CDR amino acid sequences of SEQ ID NOs: 65, 66, and 67, and/or the LC CDR amino acid sequences of SEQ ID NOs: 62, 63, and 64; or a variant sequence thereof which differs by only one or two amino acids or which has at least or about 70% sequence identity, optionally wherein the variant sequence has at least about 90% or at least about 95% sequence identity.
147. The antigen-binding protein of 146, wherein the antigen-binding protein comprises HC and LC variable region amino acid sequences of SEQ ID NOs: 153 and/or 152; or a variant sequence thereof which differs by only one or two amino acids or which has at least or about 70% sequence identity, optionally wherein the variant sequence has at least about 90% or at least about 95% sequence identity.
148. The antigen-binding protein of 146, wherein the antigen-binding protein is an antibody, optionally wherein the antibody is an IgG.
149. A pharmaceutical composition comprising (i) an antigen-binding protein of 146; and (ii) a pharmaceutically acceptable carrier, diluent, and/or excipient.
150. A nucleic acid comprising a nucleotide sequence encoding an antigen-binding protein of 146.
151. A vector comprising the nucleic acid of 150.
152. A host cell comprising the nucleic acid of 150.
153. A fusion protein comprising an antigen-binding protein of 146.

154. A conjugate comprising an antigen-binding protein of 146, optionally wherein the conjugate comprises a cytotoxic agent or a chemotherapeutic agent.

155. A method of producing the antigen-binding protein that binds to CLDN6, comprising (i) culturing the host cell of 152 in a cell culture medium, and (ii) harvesting the antigen-binding protein from the cell culture medium.

156. A method of treating a subject with a CLDN6-expressing cancer, comprising administering to the subject the pharmaceutical composition of 149.

157. A method of inhibiting tumor growth or reducing the tumor size in a subject, comprising administering to the subject the pharmaceutical composition of 149.

158. A method of preventing the recurrence of a cancer in a subject, comprising administering to the subject the pharmaceutical composition of 149.

159. A method of treating cancer in a subject diagnosed to be a low over-expresser of CLDN6, comprising administering to the subject the pharmaceutical composition of 149.

160. A method of detecting CLDN6 in a sample, comprising contacting the sample with an antigen-binding protein of 146.

161. A method of diagnosing a CLDN6-positive cancer in a subject, comprising contacting a biological sample comprising cells or tissue obtained from the subject with an antigen-binding protein of 146, and assaying for an immunocomplex comprising the antigen-binding protein bound to CLDN6, optionally further comprising treating the subject who is diagnosed to have a CLDN6-positive cancer.

162. The antigen-binding protein of 1, wherein the antigen-binding protein comprises the heavy chain (HC) CDR amino acid sequences of SEQ ID NOs: 71, 72, and 73, and/or the LC CDR amino acid sequences of SEQ ID NOs: 68, 69, and 70; or a variant sequence thereof which differs by only one or two amino acids or which has at least or about 70% sequence identity, optionally wherein the variant sequence has at least about 90% or at least about 95% sequence identity.

163. The antigen-binding protein of 162, wherein the antigen-binding protein comprises HC and LC variable region amino acid sequences of SEQ ID NOs: 155 and/or 154; or a variant sequence thereof which differs by only one or two amino acids or which has at least or about 70% sequence identity, optionally wherein the variant sequence has at least about 90% or at least about 95% sequence identity.

164. The antigen-binding protein of 162, wherein the antigen-binding protein is an antibody, optionally wherein the antibody is an IgG.

165. A pharmaceutical composition comprising (i) an antigen-binding protein of 162; and (ii) a pharmaceutically acceptable carrier, diluent, and/or excipient.

166. A nucleic acid comprising a nucleotide sequence encoding an antigen-binding protein of 162.

167. A vector comprising the nucleic acid of 166.

168. A host cell comprising the nucleic acid of 166.

169. A fusion protein comprising an antigen-binding protein of 162.

170. A conjugate comprising an antigen-binding protein of 162, optionally wherein the conjugate comprises a cytotoxic agent or a chemotherapeutic agent.

171. A method of producing the antigen-binding protein that binds to CLDN6, comprising (i) culturing the host cell of 168 in a cell culture medium, and (ii) harvesting the antigen-binding protein from the cell culture medium.

172. A method of treating a subject with a CLDN6-expressing cancer, comprising administering to the subject the pharmaceutical composition of 165.

173. A method of inhibiting tumor growth or reducing the tumor size in a subject, comprising administering to the subject the pharmaceutical composition of 165.

174. A method of preventing the recurrence of a cancer in a subject, comprising administering to the subject the pharmaceutical composition of 165.

175. A method of treating cancer in a subject diagnosed to be a low over-expresser of CLDN6, comprising administering to the subject the pharmaceutical composition of 165.

176. A method of detecting CLDN6 in a sample, comprising contacting the sample with an antigen-binding protein of 162.

177. A method of diagnosing a CLDN6-positive cancer in a subject, comprising contacting a biological sample comprising cells or tissue obtained from the subject with an antigen-binding protein of 162, and assaying for an immunocomplex comprising the antigen-binding protein bound to CLDN6, optionally further comprising treating the subject who is diagnosed to have a CLDN6-positive cancer.

178. The antigen-binding protein of 1, wherein the antigen-binding protein comprises the heavy chain (HC) CDR amino acid sequences of SEQ ID NOs: 77, 78, and 89, and/or the LC CDR amino acid sequences of SEQ ID NOs: 74, 75, and 76; or a variant sequence thereof which differs by only one or two amino acids or which has at least or about 70% sequence identity, optionally wherein the variant sequence has at least about 90% or at least about 95% sequence identity.

179. The antigen-binding protein of 178, wherein the antigen-binding protein comprises HC and LC variable region amino acid sequences of SEQ ID NOs: 157 and/or 156; or a variant sequence thereof which differs by only one or two amino acids or which has at least or about 70% sequence identity, optionally wherein the variant sequence has at least about 90% or at least about 95% sequence identity.

180. The antigen-binding protein of 178, wherein the antigen-binding protein is an antibody, optionally wherein the antibody is an IgG.

181. A pharmaceutical composition comprising (i) an antigen-binding protein of q78; and (ii) a pharmaceutically acceptable carrier, diluent, and/or excipient.

182. A nucleic acid comprising a nucleotide sequence encoding an antigen-binding protein of 178.

183. A vector comprising the nucleic acid of 182.

184. A host cell comprising the nucleic acid of 182.

185. A fusion protein comprising an antigen-binding protein of 178.

186. A conjugate comprising an antigen-binding protein of 178, optionally wherein the conjugate comprises a cytotoxic agent or a chemotherapeutic agent.

187. A method of producing the antigen-binding protein that binds to CLDN6, comprising (i) culturing the host cell of 184 in a cell culture medium, and (ii) harvesting the antigen-binding protein from the cell culture medium.

188. A method of treating a subject with a CLDN6-expressing cancer, comprising administering to the subject the pharmaceutical composition of 181.

189. A method of inhibiting tumor growth or reducing the tumor size in a subject, comprising administering to the subject the pharmaceutical composition of 181.

190. A method of preventing the recurrence of a cancer in a subject, comprising administering to the subject the pharmaceutical composition of 181.

191. A method of treating cancer in a subject diagnosed to be a low over-expresser of CLDN6, comprising administering to the subject the pharmaceutical composition of 181.

192. A method of detecting CLDN6 in a sample, comprising contacting the sample with an antigen-binding protein of 178.

193. A method of diagnosing a CLDN6-positive cancer in a subject, comprising contacting a biological sample comprising cells or tissue obtained from the subject with an antigen-binding protein of 178, and assaying for an immunocomplex comprising the antigen-binding protein bound to CLDN6, optionally further comprising treating the subject who is diagnosed to have a CLDN6-positive cancer.

194. The antigen-binding protein of 1, wherein the antigen-binding protein comprises the heavy chain (HC) CDR amino acid sequences of SEQ ID NOs: 83, 84, and 85, and/or the LC CDR amino acid sequences of SEQ ID NOs: 80, 81, and 82; or a variant sequence thereof which differs by only one or two amino acids or which has at least or about 70% sequence identity, optionally wherein the variant sequence has at least about 90% or at least about 95% sequence identity.

195. The antigen-binding protein of 194, wherein the antigen-binding protein comprises HC and LC variable region amino acid sequences of SEQ ID NOs: 159 and/or 158; or a variant sequence thereof which differs by only one or two amino acids or which has at least or about 70% sequence identity, optionally wherein the variant sequence has at least about 90% or at least about 95% sequence identity.

196. The antigen-binding protein of 194, wherein the antigen-binding protein is an antibody, optionally wherein the antibody is an IgG.

197. A pharmaceutical composition comprising (i) an antigen-binding protein of 194; and (ii) a pharmaceutically acceptable carrier, diluent, and/or excipient.

198. A nucleic acid comprising a nucleotide sequence encoding an antigen-binding protein of 194.

199. A vector comprising the nucleic acid of 198.

200. A host cell comprising the nucleic acid of 198.

201. A fusion protein comprising an antigen-binding protein of 194.

202. A conjugate comprising an antigen-binding protein of 194, optionally wherein the conjugate comprises a cytotoxic agent or a chemotherapeutic agent.

203. A method of producing the antigen-binding protein that binds to CLDN6, comprising (i) culturing the host cell of 200 in a cell culture medium, and (ii) harvesting the antigen-binding protein from the cell culture medium.

204. A method of treating a subject with a CLDN6-expressing cancer, comprising administering to the subject the pharmaceutical composition of 197.

205. A method of inhibiting tumor growth or reducing the tumor size in a subject, comprising administering to the subject the pharmaceutical composition of 197.

206. A method of preventing the recurrence of a cancer in a subject, comprising administering to the subject the pharmaceutical composition of 197.

207. A method of treating cancer in a subject diagnosed to be a low over-expresser of CLDN6, comprising administering to the subject the pharmaceutical composition of 197.

208. A method of detecting CLDN6 in a sample, comprising contacting the sample with an antigen-binding protein of 194.

209. A method of diagnosing a CLDN6-positive cancer in a subject, comprising contacting a biological sample comprising cells or tissue obtained from the subject with an antigen-binding protein of 194, and assaying for an immunocomplex comprising the antigen-binding protein bound to CLDN6, optionally further comprising treating the subject who is diagnosed to have a CLDN6-positive cancer.

210. The antigen-binding protein of 1, wherein the antigen-binding protein comprises the heavy chain (HC) CDR amino acid sequences of SEQ ID NOs: 89, 90, and 91, and/or the LC CDR amino acid sequences of SEQ ID NOs: 86, 87, and 88; or a variant sequence thereof which differs by only one or two amino acids or which has at least or about 70% sequence identity, optionally wherein the variant sequence has at least about 90% or at least about 95% sequence identity.

211. The antigen-binding protein of 210, wherein the antigen-binding protein comprises HC and LC variable region amino acid sequences of SEQ ID NOs: 161 and/or 160; or a variant sequence thereof which differs by only one or two amino acids or which has at least or about 70% sequence identity, optionally wherein the variant sequence has at least about 90% or at least about 95% sequence identity.

212. The antigen-binding protein of 210, wherein the antigen-binding protein is an antibody, optionally wherein the antibody is an IgG.

213. A pharmaceutical composition comprising (i) an antigen-binding protein of 210; and (ii) a pharmaceutically acceptable carrier, diluent, and/or excipient.

214. A nucleic acid comprising a nucleotide sequence encoding an antigen-binding protein of 210.

215. A vector comprising the nucleic acid of 214.

216. A host cell comprising the nucleic acid of 214.

217. A fusion protein comprising an antigen-binding protein of 210.

218. A conjugate comprising an antigen-binding protein of 210, optionally wherein the conjugate comprises a cytotoxic agent or a chemotherapeutic agent.

219. A method of producing the antigen-binding protein that binds to CLDN6, comprising (i) culturing the host cell of 216 in a cell culture medium, and (ii) harvesting the antigen-binding protein from the cell culture medium.

220. A method of treating a subject with a CLDN6-expressing cancer, comprising administering to the subject the pharmaceutical composition of 213.

221. A method of inhibiting tumor growth or reducing the tumor size in a subject, comprising administering to the subject the pharmaceutical composition of 213.

222. A method of preventing the recurrence of a cancer in a subject, comprising administering to the subject the pharmaceutical composition of 213.

223. A method of treating cancer in a subject diagnosed to be a low over-expresser of CLDN6, comprising administering to the subject the pharmaceutical composition of 213.

224. A method of detecting CLDN6 in a sample, comprising contacting the sample with an antigen-binding protein of 210.

225. A method of diagnosing a CLDN6-positive cancer in a subject, comprising contacting a biological sample comprising cells or tissue obtained from the subject with an antigen-binding protein of 210, and assaying for an immunocomplex comprising the antigen-binding protein bound to CLDN6, optionally further comprising treating the subject who is diagnosed to have a CLDN6-positive cancer.

226. The antigen-binding protein of 1, wherein the antigen-binding protein comprises the heavy chain (HC) CDR amino acid sequences of SEQ ID NOs: 95, 96, and 97, and/or the LC CDR amino acid sequences of SEQ ID NOs: 92, 93, and 94; or a variant sequence thereof which differs by only one or two amino acids or which has at least or about 70% sequence identity, optionally wherein the variant sequence has at least about 90% or at least about 95% sequence identity.

227. The antigen-binding protein of 226, wherein the antigen-binding protein comprises HC and LC variable region amino acid sequences of SEQ ID NOs: 163 and/or 162; or a variant sequence thereof which differs by only one or two amino acids or which has at least or about 70% sequence identity, optionally wherein the variant sequence has at least about 90% or at least about 95% sequence identity.

228. The antigen-binding protein of 226, wherein the antigen-binding protein is an antibody, optionally wherein the antibody is an IgG.

229. A pharmaceutical composition comprising (i) an antigen-binding protein of 226; and (ii) a pharmaceutically acceptable carrier, diluent, and/or excipient.

230. A nucleic acid comprising a nucleotide sequence encoding an antigen-binding protein of 226.

231. A vector comprising the nucleic acid of 230.

232. A host cell comprising the nucleic acid of 230.

233. A fusion protein comprising an antigen-binding protein of 226.

234. A conjugate comprising an antigen-binding protein of 226, optionally wherein the conjugate comprises a cytotoxic agent or a chemotherapeutic agent.

235. A method of producing the antigen-binding protein that binds to CLDN6, comprising (i) culturing the host cell of 232 in a cell culture medium, and (ii) harvesting the antigen-binding protein from the cell culture medium.

236. A method of treating a subject with a CLDN6-expressing cancer, comprising administering to the subject the pharmaceutical composition of 230.

237. A method of inhibiting tumor growth or reducing the tumor size in a subject, comprising administering to the subject the pharmaceutical composition of 229.

238. A method of preventing the recurrence of a cancer in a subject, comprising administering to the subject the pharmaceutical composition of 229.

239. A method of treating cancer in a subject diagnosed to be a low over-expresser of CLDN6, comprising administering to the subject the pharmaceutical composition of 229.

240. A method of detecting CLDN6 in a sample, comprising contacting the sample with an antigen-binding protein of 226.

241. A method of diagnosing a CLDN6-positive cancer in a subject, comprising contacting a biological sample comprising cells or tissue obtained from the subject with an antigen-binding protein of 226, and assaying for an immunocomplex comprising the antigen-binding protein bound to CLDN6, optionally further comprising treating the subject who is diagnosed to have a CLDN6-positive cancer.

242. The antigen-binding protein of 1, wherein the antigen-binding protein comprises the heavy chain (HC) CDR amino acid sequences of SEQ ID NOs: 101, 102, and 103, and/or the LC CDR amino acid sequences of SEQ ID NOs: 98, 99, and 100; or a variant sequence thereof which differs by only one or two amino acids or which has at least or about 70% sequence identity, optionally wherein the variant sequence has at least about 90% or at least about 95% sequence identity.

243. The antigen-binding protein of 242, wherein the antigen-binding protein comprises HC and LC variable region amino acid sequences of SEQ ID NOs: 165 and/or 164; or a variant sequence thereof which differs by only one or two amino acids or which has at least or about 70% sequence identity, optionally wherein the variant sequence has at least about 90% or at least about 95% sequence identity.

244. The antigen-binding protein of 242, wherein the antigen-binding protein is an antibody, optionally wherein the antibody is an IgG.

245. A pharmaceutical composition comprising (i) an antigen-binding protein of 242; and (ii) a pharmaceutically acceptable carrier, diluent, and/or excipient.

246. A nucleic acid comprising a nucleotide sequence encoding an antigen-binding protein of 242.

247. A vector comprising the nucleic acid of 246.

248. A host cell comprising the nucleic acid of 246.

249. A fusion protein comprising an antigen-binding protein of 242.

250. A conjugate comprising an antigen-binding protein of 242, optionally wherein the conjugate comprises a cytotoxic agent or a chemotherapeutic agent.

251. A method of producing the antigen-binding protein that binds to CLDN6, comprising (i) culturing the host cell of 248 in a cell culture medium, and (ii) harvesting the antigen-binding protein from the cell culture medium.

252. A method of treating a subject with a CLDN6-expressing cancer, comprising administering to the subject the pharmaceutical composition of 245.

253. A method of inhibiting tumor growth or reducing the tumor size in a subject, comprising administering to the subject the pharmaceutical composition of 245.

254. A method of preventing the recurrence of a cancer in a subject, comprising administering to the subject the pharmaceutical composition of 245.

255. A method of treating cancer in a subject diagnosed to be a low over-expresser of CLDN6, comprising administering to the subject the pharmaceutical composition of 245.

256. A method of detecting CLDN6 in a sample, comprising contacting the sample with an antigen-binding protein of 242.

257. A method of diagnosing a CLDN6-positive cancer in a subject, comprising contacting a biological sample comprising cells or tissue obtained from the subject with an antigen-binding protein of 242, and assaying for an immunocomplex comprising the antigen-binding protein bound to CLDN6, optionally further comprising treating the subject who is diagnosed to have a CLDN6-positive cancer.

258. The antigen-binding protein of 1, wherein the antigen-binding protein comprises the heavy chain (HC) CDR amino acid sequences of SEQ ID NOs: 107, 108, and 109, and/or the LC CDR amino acid sequences of SEQ ID NOs: 104, 105, and 106; or a variant sequence thereof which differs by only one or two amino acids or which has at least or about 70% sequence identity, optionally wherein the variant sequence has at least about 90% or at least about 95% sequence identity.

259. The antigen-binding protein of 258, wherein the antigen-binding protein comprises HC and LC variable region amino acid sequences of SEQ ID NOs: 167 and/or 166; or a variant sequence thereof which differs by only one or two amino acids or which has at least or about 70% sequence identity, optionally wherein the variant sequence has at least about 90% or at least about 95% sequence identity.

260. The antigen-binding protein of 258, wherein the antigen-binding protein is an antibody, optionally wherein the antibody is an IgG.

261. A pharmaceutical composition comprising (i) an antigen-binding protein of 258; and (ii) a pharmaceutically acceptable carrier, diluent, and/or excipient.

262. A nucleic acid comprising a nucleotide sequence encoding an antigen-binding protein of 258.

263. A vector comprising the nucleic acid of 262.

264. A host cell comprising the nucleic acid of 262.

265. A fusion protein comprising an antigen-binding protein of 258.

266. A conjugate comprising an antigen-binding protein of 258, optionally wherein the conjugate comprises a cytotoxic agent or a chemotherapeutic agent.

267. A method of producing the antigen-binding protein that binds to CLDN6, comprising (i) culturing the host cell of 264 in a cell culture medium, and (ii) harvesting the antigen-binding protein from the cell culture medium.

268. A method of treating a subject with a CLDN6-expressing cancer, comprising administering to the subject the pharmaceutical composition of 261.

269. A method of inhibiting tumor growth or reducing the tumor size in a subject, comprising administering to the subject the pharmaceutical composition of 261.

270. A method of preventing the recurrence of a cancer in a subject, comprising administering to the subject the pharmaceutical composition of 261.

271. A method of treating cancer in a subject diagnosed to be a low over-expresser of CLDN6, comprising administering to the subject the pharmaceutical composition of 261.

272. A method of detecting CLDN6 in a sample, comprising contacting the sample with an antigen-binding protein of 258.

273. A method of diagnosing a CLDN6-positive cancer in a subject, comprising contacting a biological sample comprising cells or tissue obtained from the subject with an antigen-binding protein of 258, and assaying for an immunocomplex comprising the antigen-binding protein bound to CLDN6, optionally further comprising treating the subject who is diagnosed to have a CLDN6-positive cancer.

274. The antigen-binding protein of 1, wherein the antigen-binding protein comprises the heavy chain (HC) CDR amino acid sequences of SEQ ID NOs: 113, 114, and 115, and/or the LC CDR amino acid sequences of SEQ ID NOs: 110, 111, and 112; or a variant sequence thereof which differs by only one or two amino acids or which has at least or about 70% sequence identity, optionally wherein the variant sequence has at least about 90% or at least about 95% sequence identity.

275. The antigen-binding protein of 274, wherein the antigen-binding protein comprises HC and LC variable region amino acid sequences of SEQ ID NOs: 169 and/or 168; or a variant sequence thereof which differs by only one or two amino acids or which has at least or about 70% sequence identity, optionally wherein the variant sequence has at least about 90% or at least about 95% sequence identity.

276. The antigen-binding protein of 274, wherein the antigen-binding protein is an antibody, optionally wherein the antibody is an IgG.

277. A pharmaceutical composition comprising (i) an antigen-binding protein of 274; and (ii) a pharmaceutically acceptable carrier, diluent, and/or excipient.

278. A nucleic acid comprising a nucleotide sequence encoding an antigen-binding protein of 274.

279. A vector comprising the nucleic acid of 278.

280. A host cell comprising the nucleic acid of 278.

281. A fusion protein comprising an antigen-binding protein of 274.

282. A conjugate comprising an antigen-binding protein of 274, optionally wherein the conjugate comprises a cytotoxic agent or a chemotherapeutic agent.

283. A method of producing the antigen-binding protein that binds to CLDN6, comprising (i) culturing the host cell of 280 in a cell culture medium, and (ii) harvesting the antigen-binding protein from the cell culture medium.

284. A method of treating a subject with a CLDN6-expressing cancer, comprising administering to the subject the pharmaceutical composition of 277.

285. A method of inhibiting tumor growth or reducing the tumor size in a subject, comprising administering to the subject the pharmaceutical composition of 277.

286. A method of preventing the recurrence of a cancer in a subject, comprising administering to the subject the pharmaceutical composition of 277.

287. A method of treating cancer in a subject diagnosed to be a low over-expresser of CLDN6, comprising administering to the subject the pharmaceutical composition of 277.

288. A method of detecting CLDN6 in a sample, comprising contacting the sample with an antigen-binding protein of 274.

289. A method of diagnosing a CLDN6-positive cancer in a subject, comprising contacting a biological sample comprising cells or tissue obtained from the subject with an antigen-binding protein of 274, and assaying for an immunocomplex comprising the antigen-binding protein bound to CLDN6, optionally further comprising treating the subject who is diagnosed to have a CLDN6-positive cancer.

290. The antigen-binding protein of 1, wherein the antigen-binding protein comprises the heavy chain (HC) CDR amino acid sequences of SEQ ID NOs: 119, 120, and 121, and/or the LC CDR amino acid sequences of SEQ ID NOs: 116, 117, and 118; or a variant sequence thereof which differs by only one or two amino acids or which has at least or about 70% sequence identity, optionally wherein the variant sequence has at least about 90% or at least about 95% sequence identity.

291. The antigen-binding protein of 290, wherein the antigen-binding protein comprises HC and LC variable region amino acid sequences of SEQ ID NOs: 171 and/or 170; or a variant sequence thereof which differs by only one or two amino acids or which has at least or about 70% sequence identity, optionally wherein the variant sequence has at least about 90% or at least about 95% sequence identity.

292. The antigen-binding protein of 290, wherein the antigen-binding protein is an antibody, optionally wherein the antibody is an IgG.

293. A pharmaceutical composition comprising (i) an antigen-binding protein of 290; and (ii) a pharmaceutically acceptable carrier, diluent, and/or excipient.

294. A nucleic acid comprising a nucleotide sequence encoding an antigen-binding protein of 290.

295. A vector comprising the nucleic acid of 294.

296. A host cell comprising the nucleic acid of 294.

297. A fusion protein comprising an antigen-binding protein of 290.

298. A conjugate comprising an antigen-binding protein of 290, optionally wherein the conjugate comprises a cytotoxic agent or a chemotherapeutic agent.

299. A method of producing the antigen-binding protein that binds to CLDN6, comprising (i) culturing the host cell of 296 in a cell culture medium, and (ii) harvesting the antigen-binding protein from the cell culture medium.

300. A method of treating a subject with a CLDN6-expressing cancer, comprising administering to the subject the pharmaceutical composition of 293.

301. A method of inhibiting tumor growth or reducing the tumor size in a subject, comprising administering to the subject the pharmaceutical composition of 293.

302. A method of preventing the recurrence of a cancer in a subject, comprising administering to the subject the pharmaceutical composition of 293.

303. A method of treating cancer in a subject diagnosed to be a low over-expresser of CLDN6, comprising administering to the subject the pharmaceutical composition of 293.

304. A method of detecting CLDN6 in a sample, comprising contacting the sample with an antigen-binding protein of 290.

305. A method of diagnosing a CLDN6-positive cancer in a subject, comprising contacting a biological sample comprising cells or tissue obtained from the subject with an antigen-binding protein of 290, and assaying for an immunocomplex comprising the antigen-binding protein bound to CLDN6, optionally further comprising treating the subject who is diagnosed to have a CLDN6-positive cancer.

306. The antigen-binding protein of 1, wherein the antigen-binding protein comprises the heavy chain (HC) CDR amino acid sequences of SEQ ID NOs: 125, 126, and 127, and/or the LC CDR amino acid sequences of SEQ ID NOs: 122, 123, and 124; or a variant sequence thereof which differs by only one or two amino acids or which has at least or about 70% sequence identity, optionally wherein the variant sequence has at least about 90% or at least about 95% sequence identity.

307. The antigen-binding protein of 306, wherein the antigen-binding protein comprises HC and LC variable region amino acid sequences of SEQ ID NOs: 173 and/or 172; or a variant sequence thereof which differs by only one or two amino acids or which has at least or about 70% sequence identity, optionally wherein the variant sequence has at least about 90% or at least about 95% sequence identity.

308. The antigen-binding protein of 306, wherein the antigen-binding protein is an antibody, optionally wherein the antibody is an IgG.

309. A pharmaceutical composition comprising (i) an antigen-binding protein of 306; and (ii) a pharmaceutically acceptable carrier, diluent, and/or excipient.

310. A nucleic acid comprising a nucleotide sequence encoding an antigen-binding protein of 306.

311. A vector comprising the nucleic acid of 310.

312. A host cell comprising the nucleic acid of 310.

313. A fusion protein comprising an antigen-binding protein of 306.

314. A conjugate comprising an antigen-binding protein of 306, optionally wherein the conjugate comprises a cytotoxic agent or a chemotherapeutic agent.

315. A method of producing the antigen-binding protein that binds to CLDN6, comprising (i) culturing the host cell of 312 in a cell culture medium, and (ii) harvesting the antigen-binding protein from the cell culture medium.

316. A method of treating a subject with a CLDN6-expressing cancer, comprising administering to the subject the pharmaceutical composition of 309.

317. A method of inhibiting tumor growth or reducing the tumor size in a subject, comprising administering to the subject the pharmaceutical composition of 309.

318. A method of preventing the recurrence of a cancer in a subject, comprising administering to the subject the pharmaceutical composition of 309.

319. A method of treating cancer in a subject diagnosed to be a low over-expresser of CLDN6, comprising administering to the subject the pharmaceutical composition of 309.

320. A method of detecting CLDN6 in a sample, comprising contacting the sample with an antigen-binding protein of 306.

321. A method of diagnosing a CLDN6-positive cancer in a subject, comprising contacting a biological sample comprising cells or tissue obtained from the subject with an antigen-binding protein of 306, and assaying for an immunocomplex comprising the antigen-binding protein bound to CLDN6, optionally further comprising treating the subject who is diagnosed to have a CLDN6-positive cancer.

322. The antigen-binding protein of 1, wherein the antigen-binding protein comprises the heavy chain (HC) CDR amino acid sequences of SEQ ID NOs: 131, 132, and 133, and/or the LC CDR amino acid sequences of SEQ ID NOs: 128, 129, and 130; or a variant sequence thereof which differs by only one or two amino acids or which has at least or about 70% sequence identity, optionally wherein the variant sequence has at least about 90% or at least about 95% sequence identity.

323. The antigen-binding protein of 322, wherein the antigen-binding protein comprises HC and LC variable region amino acid sequences of SEQ ID NOs: 175 and/or 174; or a variant sequence thereof which differs by only one or two amino acids or which has at least or about 70% sequence identity, optionally wherein the variant sequence has at least about 90% or at least about 95% sequence identity.

324. The antigen-binding protein of 322, wherein the antigen-binding protein is an antibody, optionally wherein the antibody is an IgG.

325. A pharmaceutical composition comprising (i) an antigen-binding protein of 322; and (ii) a pharmaceutically acceptable carrier, diluent, and/or excipient.

326. A nucleic acid comprising a nucleotide sequence encoding an antigen-binding protein of 322.

327. A vector comprising the nucleic acid of 326.

328. A host cell comprising the nucleic acid of 326.

329. A fusion protein comprising an antigen-binding protein of 322.

330. A conjugate comprising an antigen-binding protein of 322, optionally wherein the conjugate comprises a cytotoxic agent or a chemotherapeutic agent.

331. A method of producing the antigen-binding protein that binds to CLDN6, comprising (i) culturing the host cell of 328 in a cell culture medium, and (ii) harvesting the antigen-binding protein from the cell culture medium.

332. A method of treating a subject with a CLDN6-expressing cancer, comprising administering to the subject the pharmaceutical composition of 325.

333. A method of inhibiting tumor growth or reducing the tumor size in a subject, comprising administering to the subject the pharmaceutical composition of 325.

334. A method of preventing the recurrence of a cancer in a subject, comprising administering to the subject the pharmaceutical composition of 325.

335. A method of treating cancer in a subject diagnosed to be a low over-expresser of CLDN6, comprising administering to the subject the pharmaceutical composition of 325.

336. A method of detecting CLDN6 in a sample, comprising contacting the sample with an antigen-binding protein of 322.

337. A method of diagnosing a CLDN6-positive cancer in a subject, comprising contacting a biological sample comprising cells or tissue obtained from the subject with an antigen-binding protein of 322, and assaying for an immunocomplex comprising the antigen-binding protein bound to CLDN6, optionally further comprising treating the subject who is diagnosed to have a CLDN6-positive cancer.

Exemplary Embodiments: Set 2

1. An antigen-binding protein, wherein the antigen-binding protein:
   a) binds to a human Claudin6 (CLDN6) protein (SEQ ID NO: 200);
   b) binds to Extracellular Loop 2 (EL2) of an extracellular domain (ECD) of CLDN6 and does not bind to Extracellular Loop 1 (EL1) of the ECD of CLDN6;
   c) does not bind to any of Claudin3 (CLDN3), Claudin4 (CLDN4), and Claudin9 (CLDN9) and inhibits binding of a reference antibody to CLDN6 endogenously expressed by OVCA429 cells with less than about 1200 nM; or
   d) a combination thereof.

2. The antigen-binding protein of 1, wherein the antigen-binding protein comprises:
   (a) an HC CDR1 comprising the amino acid sequence of FTFSXYX (SEQ ID NO: 455), wherein X at position 5 is N, S, R, Q, or A and X at position 7 is W, H, Y, or F;
   (b) an HC CDR2 comprising the amino acid sequence of IRLKXDXYAT (SEQ ID NO: 456), wherein X at position 5 is S, N, A, or T and X at position 7 is Q, S, A, or N;
   (c) an HC CDR3 comprising the amino acid sequence of XDGPPSGX (SEQ ID NO: 457), wherein X at position 1 is N, D, A, or T and X at position 8 is S, T, A, C, or Y;
   (d) an LC CDR1 comprising the amino acid sequence of EXIYSY (SEQ ID NO: 476), wherein X is Q, S, A, D, or N;
   (e) an LC CDR2 comprising the amino acid sequence of XAK (SEQ ID NO: 477), wherein X at position 1 is Q, S, A, D, or N; and
   (f) an LC CDR3 comprising the amino acid sequence of QXHYXVPWT (SEQ ID NO: 454), wherein X at position 2 is H, Q, S, or T and X at position 5 is T, S, N, or G.

3. The antigen-binding protein of 1, wherein the antigen-binding protein comprises the heavy chain (HC) CDR amino acid sequences of SEQ ID NOs: 11, 12, and 13, and/or the light chain (LC) CDR amino acid sequences of SEQ ID NOs: 8, 9, and 10; or a variant sequence thereof which differs by only one or two amino acids or which has at least about 95% sequence identity.

4. The antigen-binding protein of 1, wherein the antigen-binding protein comprises the HC CDR amino acid sequences of SEQ ID NOs: 17, 18, and 19, and/or the LC CDR amino acid sequences of SEQ ID NOs: 14, 15, and 16; or a variant sequence thereof which differs by only one or two amino acids or which has at least about 95% sequence identity.

5. The antigen-binding protein of 1 wherein the antigen-binding protein comprises the HC CDR amino acid sequences of SEQ ID NOs: 23, 24, and 457, wherein the first Xaa is N and the second Xaa is S, and/or the LC CDR amino acid sequences of SEQ ID NOs: 20, 21, and 22; or a variant sequence thereof which differs by only one or two amino acids or which has at least about 95% sequence identity.

6. The antigen-binding protein of 1, wherein the antigen-binding protein comprises the HC CDR amino acid sequences of SEQ ID NOs: 29, 30, and 31, and/or the LC CDR amino acid sequences of SEQ ID NOs: 26, 27, and 28; or a variant sequence thereof which differs by only one or two amino acids or which has at least about 95% sequence identity.

7. The antigen-binding protein of 1, wherein the antigen-binding protein comprises the HC CDR amino acid sequences of SEQ ID NOs: 35, 36, and 37, and/or the LC CDR amino acid sequences of SEQ ID NOs: 32, 33, and 34; or a variant sequence thereof which differs by only one or two amino acids or which has at least about 95% sequence identity.

8. The antigen-binding protein of 1 wherein the antigen-binding protein comprises the HC CDR amino acid sequences of SEQ ID NOs: 41, 42, and 43, and/or the LC CDR amino acid sequences of SEQ ID NOs: 38, 39, and 40; or a variant sequence thereof which differs by only one or two amino acids or which has at least about 95% sequence identity.

9. The antigen-binding protein of 1, wherein the antigen-binding protein comprises the HC CDR amino acid sequences of SEQ ID NOs: 47, 48, and 49, and/or the LC CDR amino acid sequences of SEQ ID NOs: 44, 45, and 46; or a variant sequence thereof which differs by only one or two amino acids or which has at least about 95% sequence identity.

10. The antigen-binding protein of 1, wherein the antigen-binding protein comprises the HC CDR amino acid sequences of SEQ ID NOs: 53, 54, and 55, and/or the LC CDR amino acid sequences of SEQ ID NOs: 50, 51, and 52; or a variant sequence thereof which differs by only one or two amino acids or which has at least about 95% sequence identity.

11. The antigen-binding protein of 1, wherein the antigen-binding protein comprises the HC CDR amino acid sequences of SEQ ID NOs: 59, 60, and 61, and/or the LC CDR amino acid sequences of SEQ ID NOs: 56, 57, and 58; or a variant sequence thereof which differs by only one or two amino acids or which has at least about 95% sequence identity.

12. The antigen-binding protein of 1, wherein the antigen-binding protein comprises the heavy chain (HC) CDR amino acid sequences of SEQ ID NOs: 65, 66, and 67, and/or the LC CDR amino acid sequences of SEQ ID NOs: 62, 63, and 64; or a variant sequence thereof which differs by only one or two amino acids or which has at least about 95% sequence identity.

13. The antigen-binding protein of 1, wherein the antigen-binding protein comprises the heavy chain (HC) CDR amino acid sequences of SEQ ID NOs: 71, 72, and 73, and/or the LC CDR amino acid sequences of SEQ ID NOs: 68, 69, and 70; or a variant sequence thereof which differs by only one or two amino acids or which has at least about 95% sequence identity.

14. The antigen-binding protein of 1, wherein the antigen-binding protein comprises the heavy chain (HC) CDR amino acid sequences of SEQ ID NOs: 77, 78, and 89, and/or the LC CDR amino acid sequences of SEQ ID NOs: 74, 75, and 76; or a variant sequence thereof which differs by only one or two amino acids or which has at least about 95% sequence identity.

15. The antigen-binding protein of 1, wherein the antigen-binding protein comprises the heavy chain (HC) CDR amino acid sequences of SEQ ID NOs: 83, 84, and 85, and/or the LC CDR amino acid sequences of SEQ ID NOs: 80, 81, and 82; or a variant sequence thereof which differs by only one or two amino acids or which has at least about 95% sequence identity.

16. The antigen-binding protein of 1, wherein the antigen-binding protein comprises the heavy chain (HC) CDR amino acid sequences of SEQ ID NOs: 89, 90, and 91, and/or the LC CDR amino acid sequences of SEQ ID NOs: 86, 87, and 88; or a variant sequence thereof which differs by only one or two amino acids or which has at least about 95% sequence identity.

17. The antigen-binding protein of 1, wherein the antigen-binding protein comprises the heavy chain (HC) CDR amino acid sequences of SEQ ID NOs: 95, 96, and 97, and/or the LC CDR amino acid sequences of SEQ ID NOs: 92, 93, and 94; or a variant sequence thereof which differs by only one or two amino acids or which has at least about 95% sequence identity.

18. The antigen-binding protein of 1, wherein the antigen-binding protein comprises the heavy chain (HC) CDR amino acid sequences of SEQ ID NOs: 101, 102, and 103, and/or the LC CDR amino acid sequences of SEQ ID NOs: 98, 99, and 100; or a variant sequence thereof which differs by only one or two amino acids or which has at least about 95% sequence identity.

19. The antigen-binding protein of 1, wherein the antigen-binding protein comprises the heavy chain (HC) CDR amino acid sequences of SEQ ID NOs: 107, 108, and 109, and/or the LC CDR amino acid sequences of SEQ ID NOs: 104, 105, and 106; or a variant sequence thereof which differs by only one or two amino acids or which has at least about 95% sequence identity.

20. The antigen-binding protein of 1, wherein the antigen-binding protein comprises the heavy chain (HC) CDR amino acid sequences of SEQ ID NOs: 113, 114, and 115, and/or the LC CDR amino acid sequences of SEQ ID NOs: 110, 111, and 112; or a variant sequence thereof which differs by only one or two amino acids or which has at least about 95% sequence identity.

21. The antigen-binding protein of 1, wherein the antigen-binding protein comprises the heavy chain (HC) CDR amino acid sequences of SEQ ID NOs: 119, 120, and 121, and/or the LC CDR amino acid sequences of SEQ ID NOs: 116, 117, and 118; or a variant sequence thereof which differs by only one or two amino acids or which has at least about 95% sequence identity.

22. The antigen-binding protein of 1, wherein the antigen-binding protein comprises the heavy chain (HC) CDR amino acid sequences of SEQ ID NOs: 125, 126, and 127, and/or the LC CDR amino acid sequences of SEQ ID NOs: 122, 123, and 124; or a variant sequence thereof which differs by only one or two amino acids or which has at least about 95% sequence identity.

23. The antigen-binding protein of 1, wherein the antigen-binding protein comprises the heavy chain (HC) CDR amino acid sequences of SEQ ID NOs: 131, 132, and 133, and/or the LC CDR amino acid sequences of SEQ ID NOs: 128, 129, and 130; or a variant sequence thereof which differs by only one or two amino acids or which has at least about 95% sequence identity.

24. A pharmaceutical composition comprising (i) the antigen-binding protein of 1; and (ii) a pharmaceutically acceptable carrier, diluent, and/or excipient.

25. A nucleic acid comprising a nucleotide sequence encoding the antigen-binding protein of 1, a vector comprising said nucleic acid, or a host cell comprising said nucleic acid or said vector.

26. The antigen-binding protein of 1, wherein the protein is:
a. an antibody or an antigen-binding antibody fragment;
b. a monoclonal antibody, and/or
c. a human, chimeric, or humanized antibody.

27. A conjugate comprising the antigen-binding protein of 1.

28. A method of treating a subject with a CLDN6-expressing cancer, comprising administering to the subject the pharmaceutical composition of 24.

29. A method of inhibiting tumor growth or reducing the tumor size in a subject, comprising administering to the subject the pharmaceutical composition of 24.

30. A method of diagnosing a CLDN6-positive cancer in a subject, comprising contacting a biological sample comprising cells or tissue obtained from the subject with the antigen-binding protein of 1, and assaying for an immunocomplex comprising the antigen-binding protein bound to CLDN6, optionally further comprising treating the subject who is diagnosed to have a CLDN6-positive cancer.

The following examples are given merely to illustrate the present disclosure and not in any way to limit its scope.

EXAMPLES

Example 1

This example demonstrates an analysis of CLDN6 RNA levels in different cell and tissue sources.

In order to establish a baseline for expression of CLDN6 in different source materials, expression levels of CLDN6 expression in patient samples, normal tissue and cell lines created by the Translational Oncology Research laboratory (TORL) were assayed.

Levels of CLDN6 RNA in patient samples were measured using information contained in The Cancer Genome Atlas (TCGA) database managed by the National Cancer Institute (NCI). CLDN6 levels in normal tissue were measured using information in the Genotype-Tissue Expression (GTEX) database maintained by the Common Fund. The analysis of tissues from the GTEX database showed that CLDN6 is detectable in various sites, including the brain, pituitary, pancreas, kidney, lung, thyroid, and cervix, among other tissues (FIG. 1).

Figure 2:
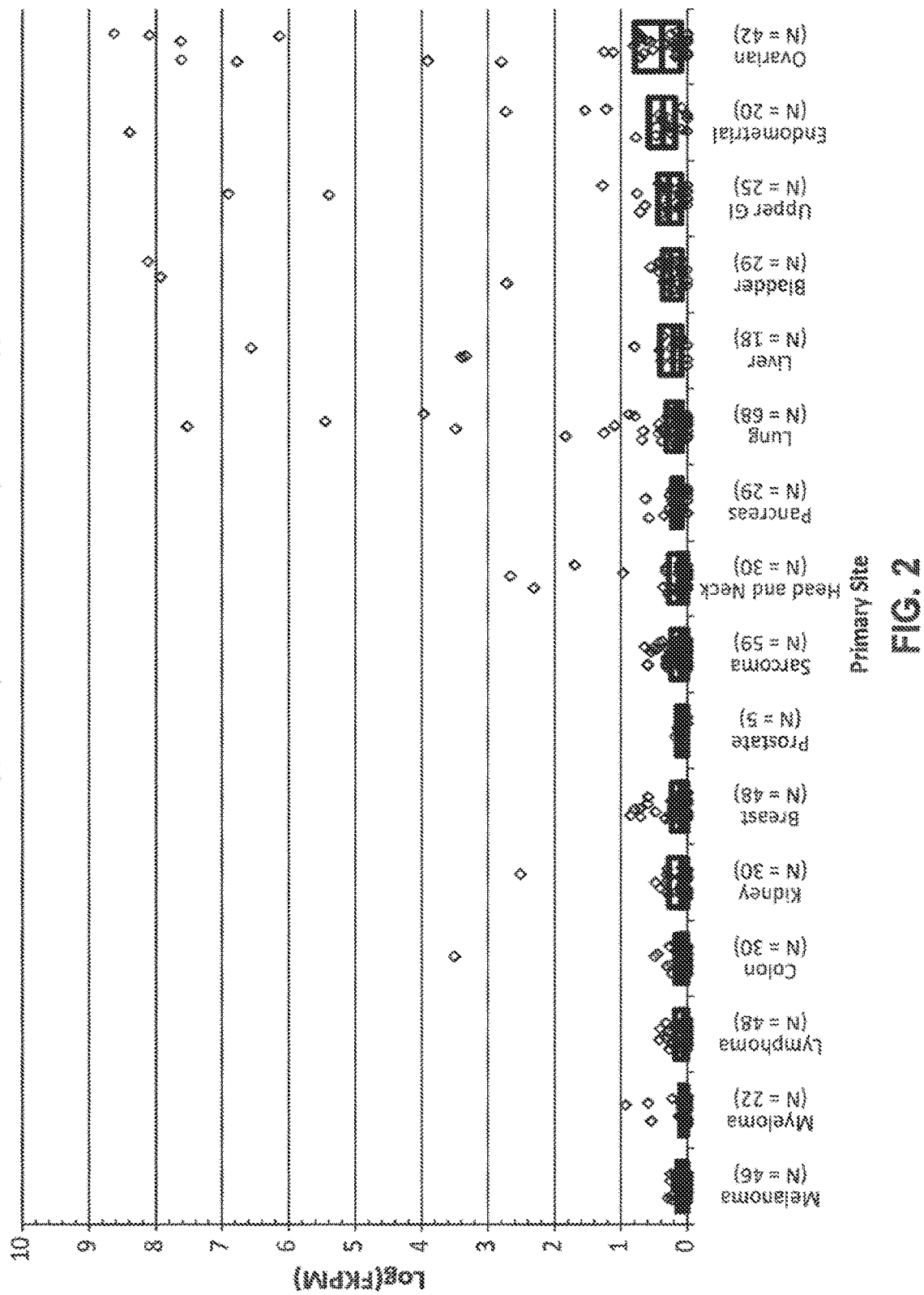
FIG. 2 represents a graph of CLDN6 expression in cancer cell lines as determined by Agilent44K methodology.
Figure 3:
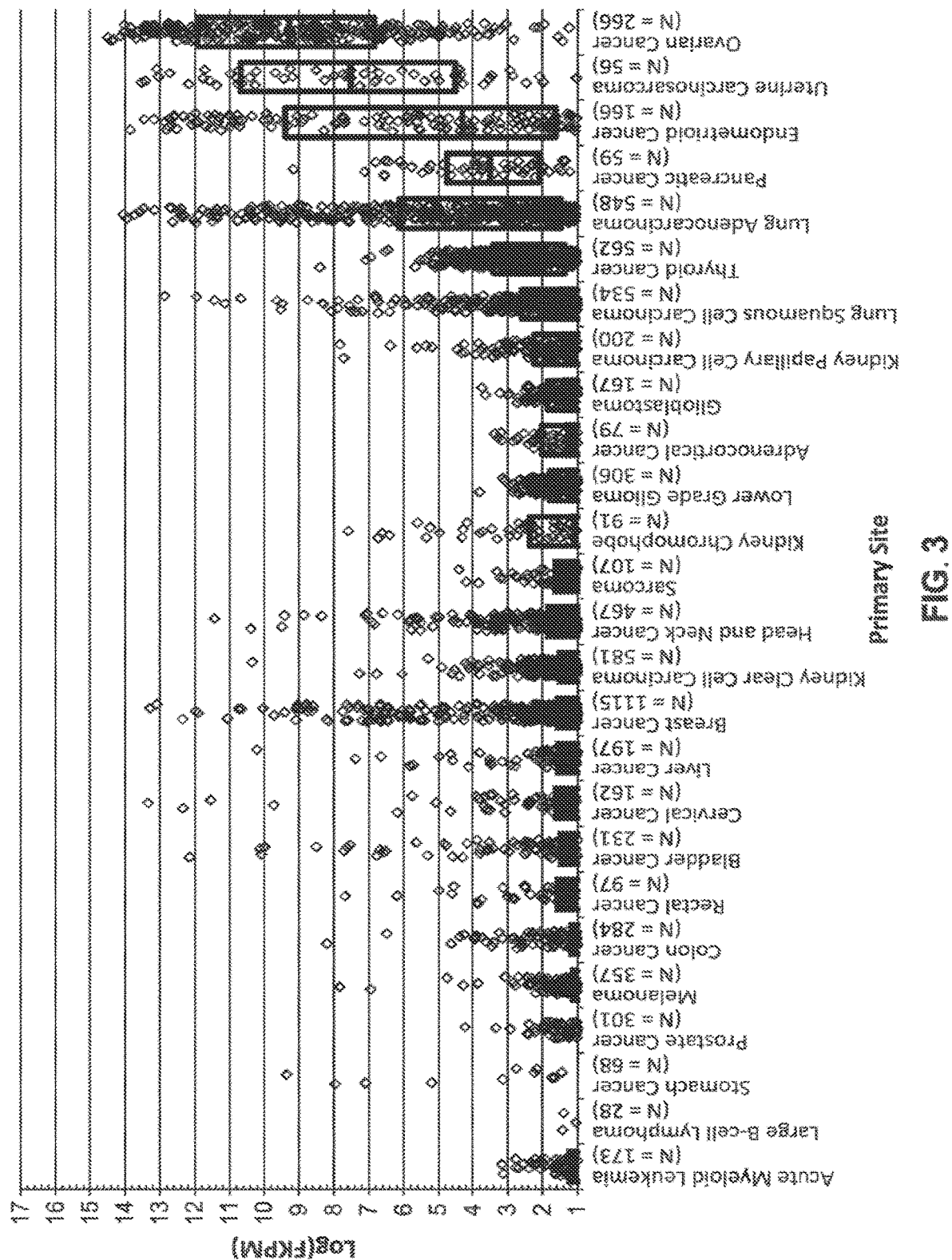
FIG. 3 represents a graph of CLDN6 expression in cancer cell lines as determined by RNASeq.

CLDN6 expression levels were measured in TORL cancer cell lines using Agilent 44K microarrays (4×44K array chip, Agilent Technologies, Santa Clara, CA) and RNA sequencing (RNA-Seq) assays. RNASeq was performed by BGI Americas (Cambridge, MA) using their "RNASeq for quantification" service. As shown in FIG. 2 and FIG. 3, ovarian, head and neck, lung, and bladder cancer cells expressed the highest levels of CLDN6, though CLDN6 expression levels were detectable in breast, kidney, colon, sarcoma and liver cancer cells.

Example 2

This example demonstrates the production of cells engineered to overexpress CLDN6.

Models engineered to overexpress CLDN6 were generated. These models were used to determine the efficacy of CLDN6 antibodies described in Example 5. Briefly, a nucleotide sequence encoding CLDN6 was engineered into a bicistronic vector having a CMV promoter and an attenuated Internal ribosome entry site (IRES) of encephalomyocarditis virus (EMCV). The IRES was located between the Gene of Interest (GOI) cDNA (CLDN6) and puromycin cDNA. A woodchuck posttranscriptional regulatory element (WPRE) was located downstream of the puromycin cDNA. The vector also expressed either a GFP marker sequence or a MycDDK tag. The sequence of the expression vector containing GFP is provided herein as SEQ ID NO: 189.

The expression vector was virally transduced into HEK293T cells (for screening purposes) and NIH3T3 cells (for immunizations). Positively transduced cells were selected based on survival in medium containing puromycin (1 μg/ml). The positive cells were subcloned to obtain a stable, uniform, clonal population of CLDN6 overexpressing cells.

Subclone CLDN6 expression was confirmed by flow cytometry using a reference CLDN6 monoclonal antibody (mAb) on a BD Biosciences Accuri™ flow cytometer (San Jose, CA). Secondary antibody and conjugate: Alexa Fluor® 647 Goat anti-mouse IgG (minimal x-reactivity) antibody (Biolegend, San Diego, CA; Cat #405322) was used to detect binding activity between the reference CLDN6 mAb and the CLDN6 expressed by subclone.

Figure 4:
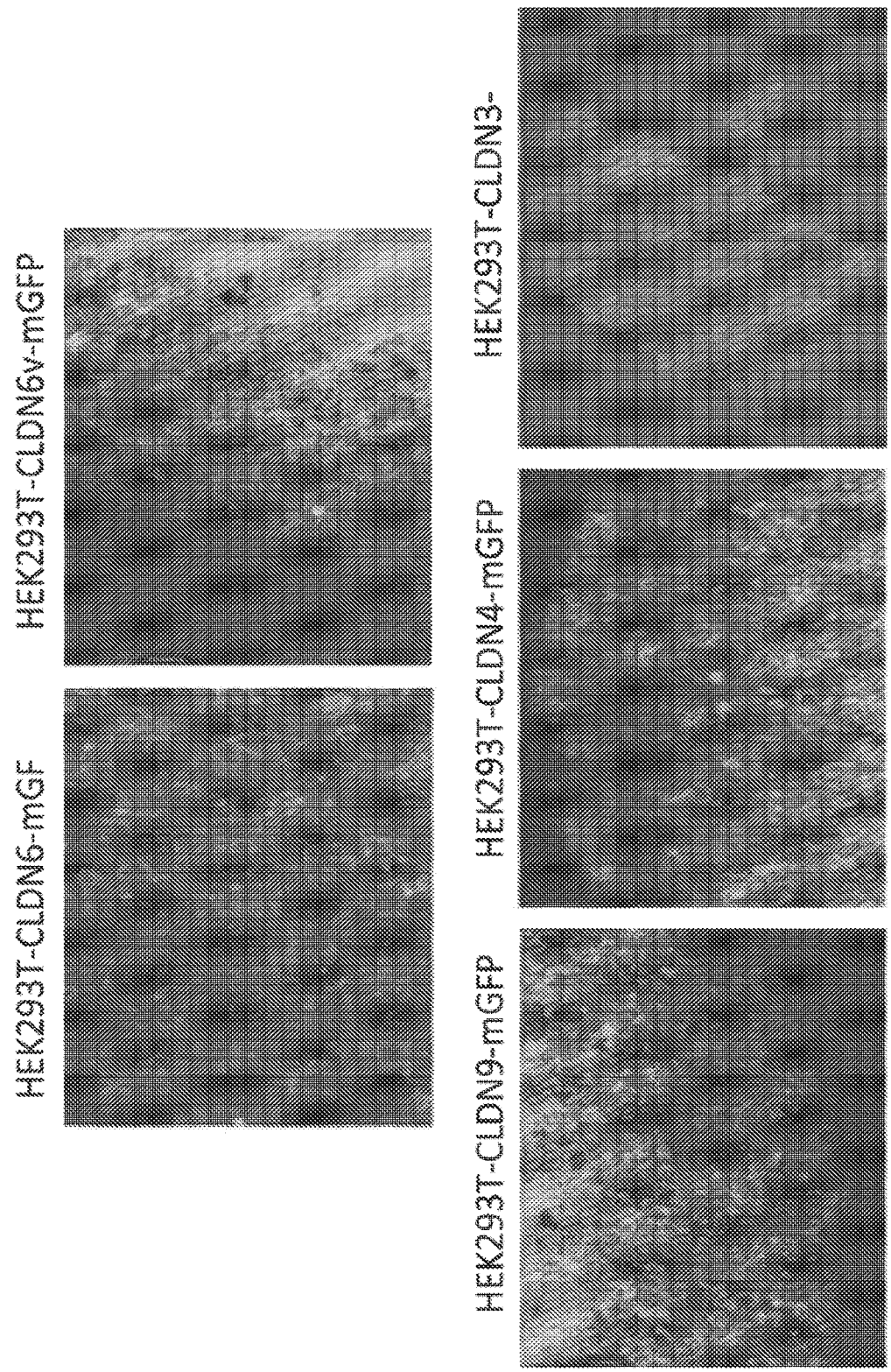
FIG. 4 represents a set of fluorescent images depicting CLDN6-GFP localization in different cell models.
Figure 6B:
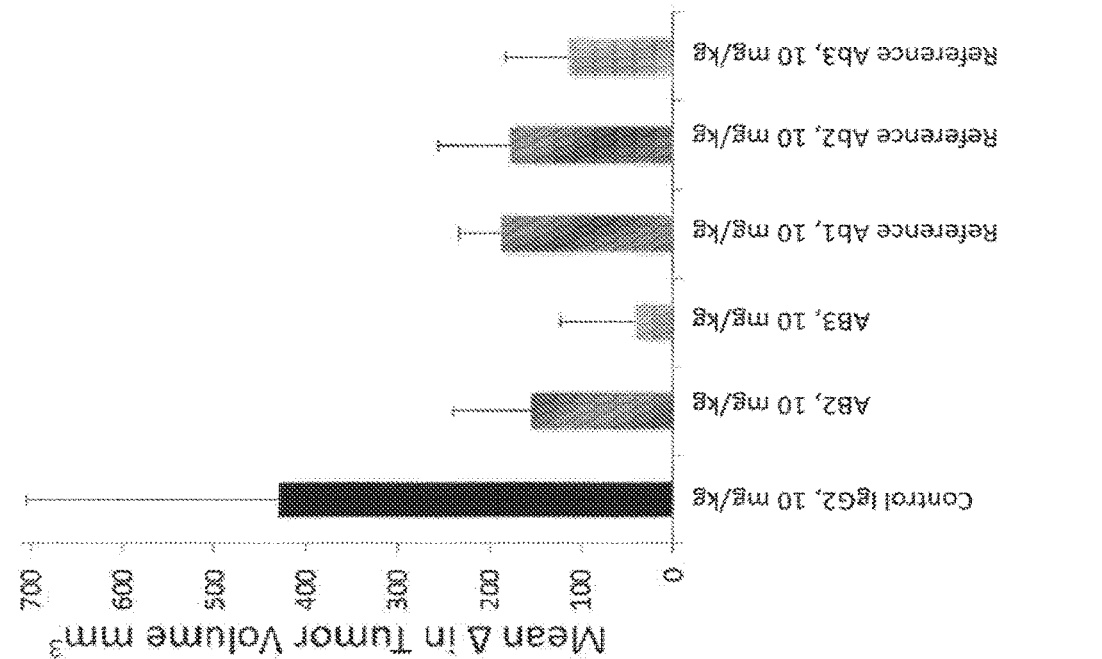
FIG. 6B represents a graph of the mean change in tumor volume ($mm^3$) at Day 14 of tumors in mice bearing endometrial tumors treated with control IgG2 antibody, AB3, Reference Ab1, Reference Ab2, Reference Ab3, AB2, or AB3.
Figure 6A:
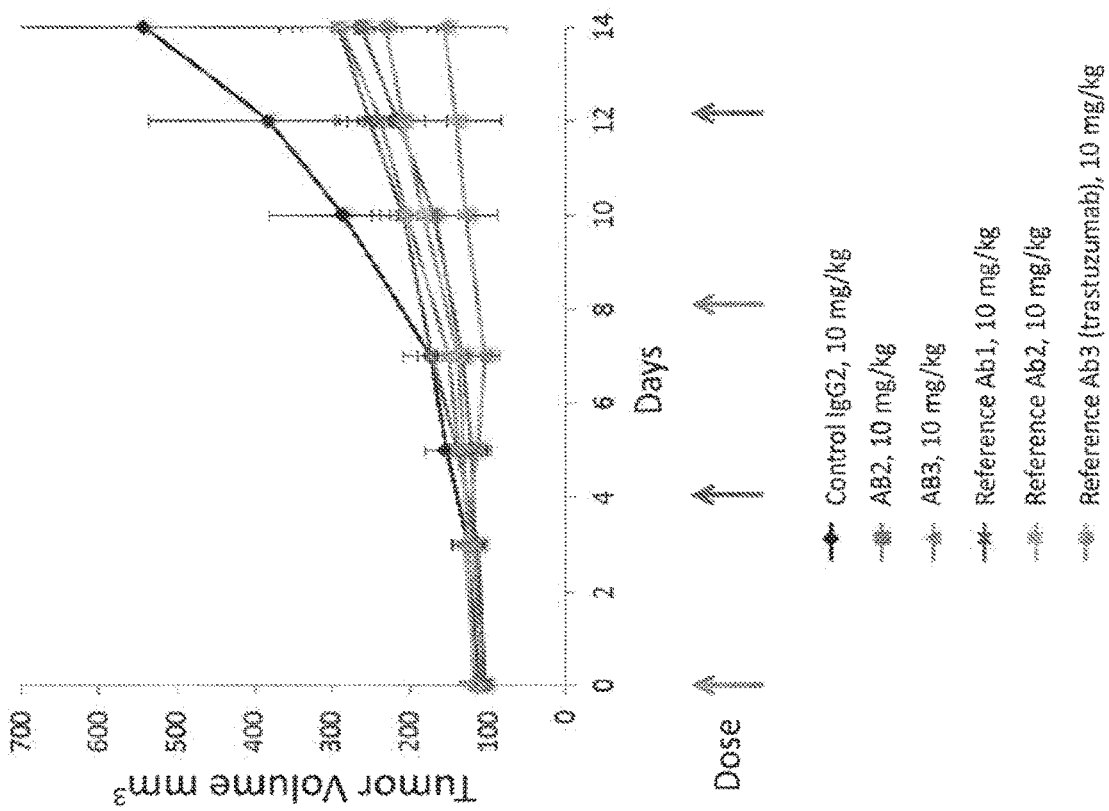
FIG. 6A represents a graph of tumor volume ($mm^3$) of tumors in mice bearing endometrial tumors as a function of time (days) after treatment with control IgG2 antibody, AB3, Reference Ab1, Reference Ab2, Reference Ab3, AB2, and AB3.
Figure 8B:
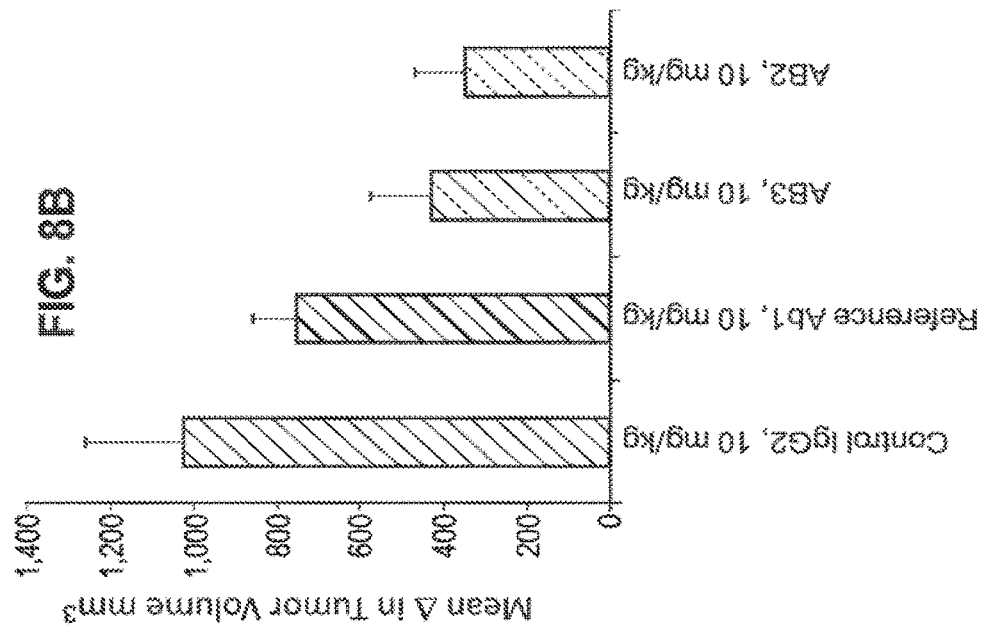
FIG. 8B represents a graph of the mean change in tumor volume ($mm^3$) at Day 20 of tumors in mice bearing ovarian tumors treated with control IgG2 antibody, AB3, Reference Ab1, AB2, or AB3.
Figure 8A:
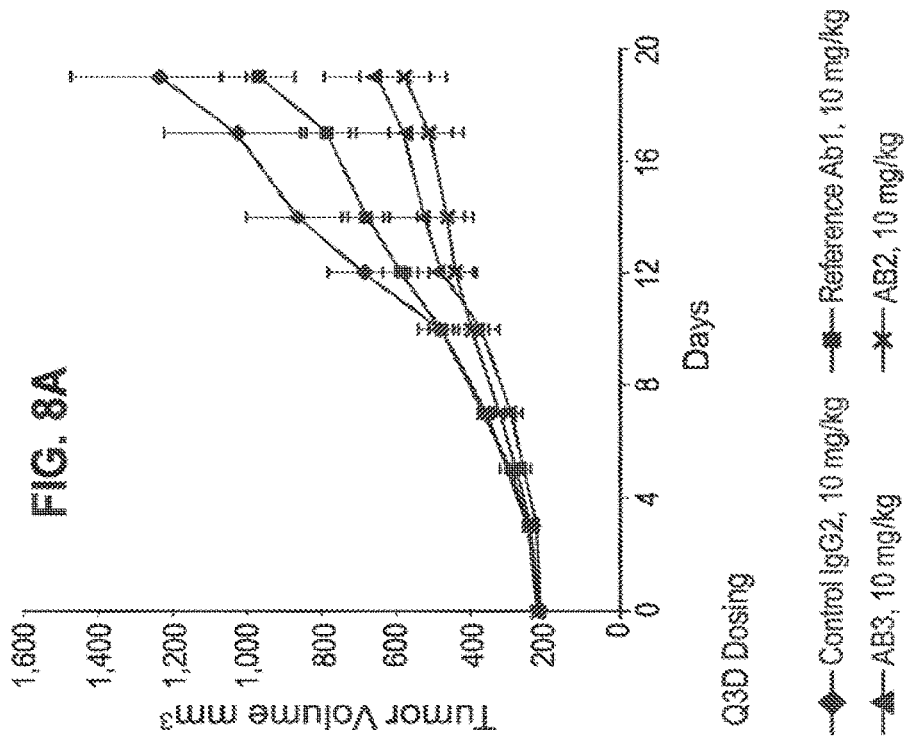
FIG. 8A represents a graph of tumor volume ($mm^3$) of tumors in mice bearing ovarian tumors as a function of time (days) after treatment with control IgG2 antibody, AB3, Reference Ab1, AB2, and AB3.
Figure 9B:
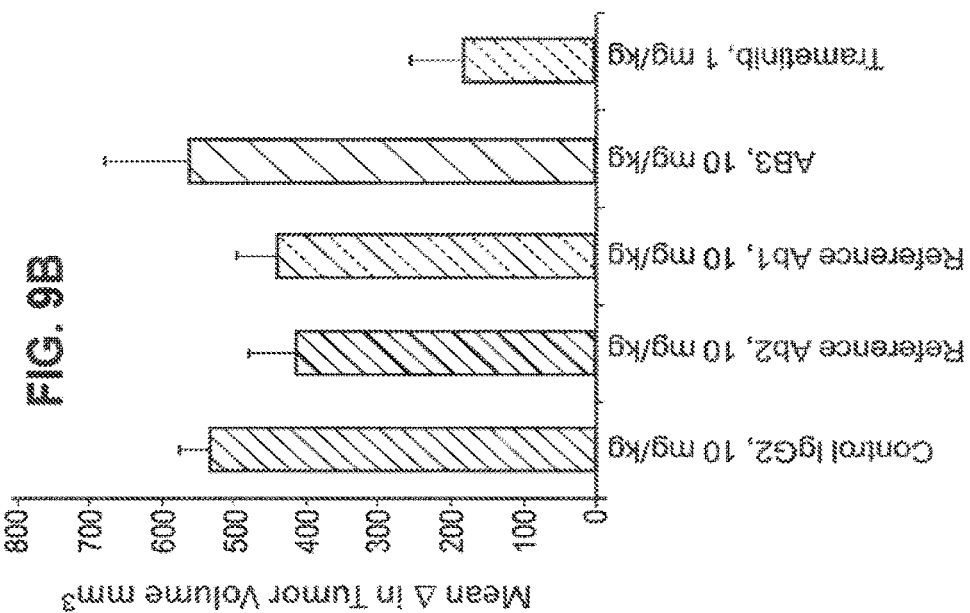
FIG. 9B represents a graph of the mean change in tumor volume ($mm^3$) at Day 21 of tumors in mice bearing melanoma tumors treated with control IgG2 antibody, AB3, Reference Ab1, Reference Ab2, Reference Ab3, or AB3.
Figure 9A:
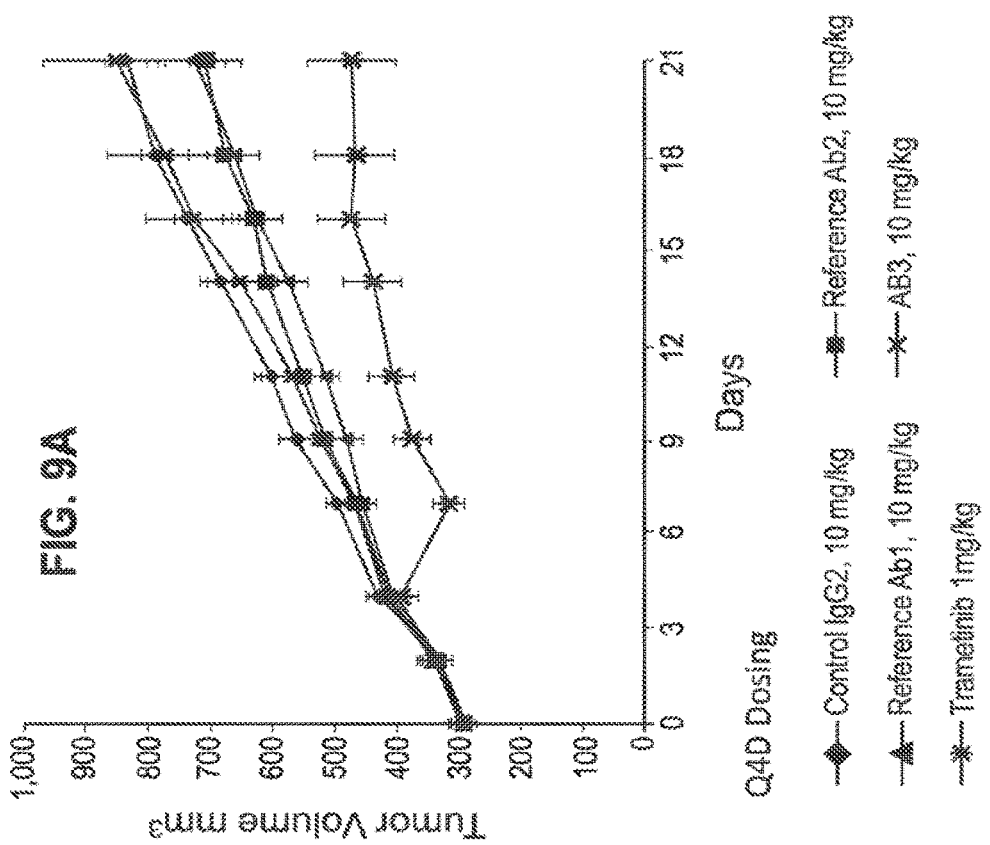
FIG. 9A represents a graph of tumor volume ($mm^3$) of tumors in mice bearing melanoma tumors as a function of time (days) after treatment with control IgG2 antibody, AB3, Reference Ab1, Reference Ab2, Reference Ab3, and AB3.
Figure 10A:
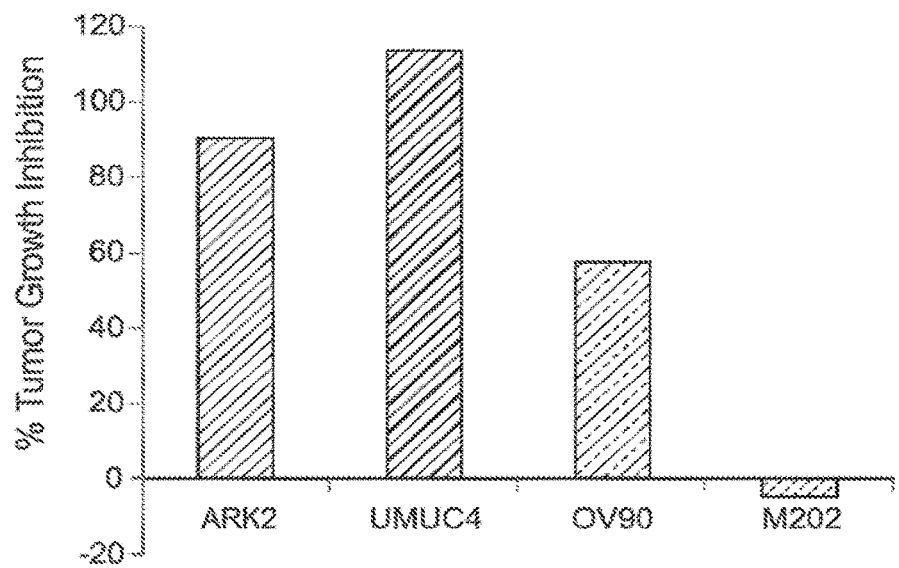
FIG. 10A represents a graph of the % tumor growth inhibition achieved in tumor-bearing mice treated with AB3, relative to mice treated with control antibody.
Figure 10B:
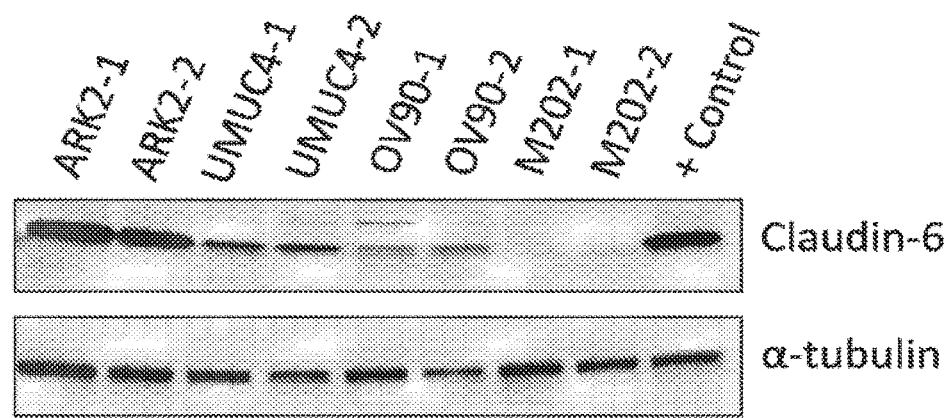
FIG. 10B represents an image of a Western blot demonstrating the different levels of CLDN6 id endometrial cancer cell lines (ARK2), bladder cancer cell lines (UMUC4), ovarian cancer cell lines (OV90) and melanoma cell lines (M202) and control cells. The levels of α-tubulin were approximately the same, demonstrating equal protein loading.

Cellular localization of CLDN6 was determined by fluorescence microscopy using the Cellavista® imaging system (Synentec (Mountain View, CA) with cells expressing a CLDN6-green fluorescence protein (GFP) fusion protein. As shown in FIG. 4, fluorescence of the GFP was detected in the cell membrane, evidencing that CLDN6 localizes to the cell membrane.

Example 3

This example demonstrates the production of reference and control antibodies.

Benchmark (reference) CLDN6-specific antibodies and control antibodies were made by cloning the antibody heavy and light chain variable regions into the ExpiCHO™ expression system (ThermoFisher Scientific, Waltham, MA) to produce recombinant mouse IgG2A chimeric antibodies. These antibodies were tested alongside newly generated CLDN6 specific antibodies described in Example 5.

Briefly, plasmids containing the control and benchmark antibody sequences were transfected using the ExpiCHO™ Expression System (Catalog Number: A29133, ThermoFisher Scientific, USA) according to the manufacturer's protocol. The cells were cultured at 37° C. and 8% $CO_2$ at day 1 and then at 32° C. and 5% $CO_2$ post-transfection in media provided in the kit. Antibodies were purified by clarifying the ExpiCHO™ culture medium by centrifugation at 1,000 g for 10 min followed by 5,000 g for 30 min. The supernatant was then filtered using a 0.45 μm filter followed by a 0.22 μm filter. Subsequently, the supernatant was subjected to affinity purification using protein A/G resins (Life Technologies, Carlsbad, CA; Catalog #20424) according to the manufacturer's protocol. Prior to ELISA purification, antibody titer in the culture medium was roughly determined to ensure the amount of medium loaded occupied less than 80% of the resin binding capacity. After incubation, the resins were washed with PBS and eluted with Elution Buffer (Life Technologies, Catalog #21004). The elution fractions were immediately adjusted to physiologic pH by adding Tris Buffer, pH8.0. The purified antibodies were subsequently subjected to buffer exchange and protein concentration using Amicon Ultra-15 Centrifugal Filter Unit (Life Technologies, Catalog #UFC900324) in PBS buffer. Antibody concentration was determined by BCA Protein Assay. SDS-PAGE and Coomassie-staining were carried out to test the antibody purity. The purified protein was aliquoted and stored at −80° C. for long time storage or kept at 4° C. for immediate use.

The integrity of the antibody was validated by SDS-PAGE followed by Coomassie staining under non-reducing vs reducing conditions; under non-reducing condition, one dominating band around 150 kDa, whereas under reducing conditions, two bands were observed, 50 kDa and 25 kDa.

Antibodies specific for other CLDN family members having sequence similarity (FIG. 5), namely, CLDN3, CLDN4, and CLDN9 were produced in essentially the same manner, except that the antibody sequences contained in the plasmids were antibody sequences specific to CLDN3, CLDN4, or CLDN9.

Example 4

This example demonstrates the characterization of cell lines with high endogenous CLDN6 expression.

A panel of cancer cell lines was analyzed for their endogenous expression of CLDN6 by FACS and Western blot. Briefly, the binding of antibodies to targets were validated by FACS using cells overexpressing CLDN6 (e.g., HEK293T cells overexpressing CLDN6, described in Example 2), and cell lines that endogenously express CLDN6 at high or low levels, as determined in Example 1. The CLDN6-expressing cells were incubated with reference or control antibodies (described in Example 3) for 30 min on ice, and, after washing, incubated with Alexa Fluor® 647 conjugated Goat anti-mouseIgG (minimal x-reactivity) antibody, Biolegend cat #405322 for 30 min on ice. Fluorescence was read by a BD Biosciences Accuri™ flow cytometer (San Jose, CA).

Western blots were carried out on nitrocellulose with reference and control antibodies. Briefly, samples from cell lysates were boiled to denature protein content. SDS-PAGE (SDS-polyacrylamide gel electrophoresis) was used to separate the denatured proteins by the length of the polypeptide. Separated proteins were then transferred from the acrylamide gel to a nitrocellulose membrane. A 2% Bovine Serum Albumin (BSA) solution was used to block the membrane, minimizing non-specific antibody binding. The membrane was incubated with reference or control antibodies. The membrane was stained with a horseradish peroxidase (HRP)-conjugated secondary antibody that recognizes the reference or control antibodies and detection of secondary antibody was via chemiluminescence.

The overexpressed lines were used to validate the control and reference antibodies, and, once validated, the control and reference antibodies were used to characterize the endogenous cell lines. The cells overexpressing CLDN6 were included as positive controls in these assays.

The FACS assays showed that four ovarian cancer cell lines, in addition to an endometrial cancer cell line, bladder cancer cell line, lung cancer cell line, and upper GI cancer cell line, express CLDN6 on the surface at high levels. The high levels of CLDN6 expression was also detected by Western blot. An additional two ovarian cancer cell lines, an additional liver cancer cell line, additional lung cancer cell line, and additional upper GI cancer cell line were shown to express CLDN6 to a moderate level on the surface, as detected by Western blot. Endometrial tumor cells and bladder tumor cells also expressed high levels of CLDN6 as xenografts in vivo. Endogenous expression levels of CLDN6 by the tested cancer cells lines are summarized in Table 2.

TABLE 2

| Cell_Line_Name | Primary Histology | CLDN6 RNASeq | Group | Surface Expression by FACS | Protein Expression by WB (Cell Lines) | Protein Expression by WB (xenograft) | Tumorigenic Sub Q | Tumorigenic IP (Nude) | Tumorigenic IP (SCID) |
|---|---|---|---|---|---|---|---|---|---|
| OVCA429 | Ovarian | 393.99 | Pos Con | ++++ | ++++ | | No | Slow | TBD |
| ARK2 | Endometrial | 335.06 | Pos Con | ++++ | ++++ | +++ | Yes | | |
| OAW28 | Ovarian | 273.78 | Pos Con | ++++ | ++++ | | No | TBD | TBD |
| UMUC-4 | Bladder | 242.93 | Pos Con | ++++ | ++++ | ++ | Yes | Slow | TBD |
| PEO14 | Ovarian | 196.63 | Pos Con | ++++ | +++ | | No | TBD | TBD |
| OV177 | Ovarian | 195.53 | Pos Con | ++++ | + | | No | TBD | TBD |
| H1693 | Lung | 184.12 | Pos Con | ++++ | +++ | | TBD | | |
| MKN7 | Upper GI | 118.6 | Pos Con | +++ | ++ | | TBD | | |
| OV-90 | Ovarian | 108.23 | Pos Con | ++ | ++ | + | Yes | | |
| HUH-7 | Liver | 93.52 | Pos Con | ++ | + | | Yes | | |
| JHOS-4 | Ovarian | 69.3 | Pos Con | ++ | + | | No | TBD | TBD |
| H1435 | Lung | 42.8 | Pos Con | ++ | +/− | | TBD | | |
| NUGC 3 | Upper GI | 41.11 | Pos Con | ++ | ++ | + | Yes | | |
| RMG-1 | Ovarian | 0.63 | Neg Con | − | − | − | Yes | TBD | TBD |
| COLO704 | Ovarian | 0.44 | Neg Con | − | − | − | Yes | TBD | TBD |
| MCF-7 | Breast | 0 | Neg Con | − | − | − | Yes | | |
| LS513 | Colon | 0 | Neg Con | − | − | − | Yes | | |
| M202 | Melanoma | 0 | Neg Con | − | − | − | Yes | | |
| M275 | Melanoma | 0 | Neg Con | − | − | | Yes | | |
| KOC-7C | Ovarian | 0 | Neg Con | − | − | − | Yes | Yes | TBD |

Example 5

This example demonstrates the immunization of mice for the production of CLDN6 specific antibodies.

CLDN6-specific antibodies were produced by immunizing Balb/c and CD1 mice with a mixture of three different peptide immunogens following techniques of the Fred Hutchinson Cancer Research Center. The three peptides spanned the second loop in the CLDN6 extracellular domain (i.e., EL2). The peptides include the full length of EL2, a peptide spanning the first (N-terminal) half of EL2, and a peptide spanning the second (C-terminal) half of EL2. Table 3 provides the sequences of the three peptides.

TABLE 3

| Peptide Immunogen | EL2 | SEQ ID NO: |
|---|---|---|
| Ac-CWTAHAIIRDFYNPL VAEAQKREL-amide | Full length EL2 | 2 |
| Ac-CTAHAIIRDFYNPL-amide | N-terminal half | 3 |
| Ac-LVAEAQKRELGC-amide | C-terminal half | 4 |

Mice also were immunized with 3T3 cells overexpressing full length CLDN6 using a plasmid comprising a human CLDN6-myc-DDK expression vector.

Splenocytes were harvested from the immunized mice and fused with myeloma lines by BTX Electrofusion (BTX, Holliston, MA) to generate hydridomas. 7680 primary hybridoma cultures were generated and cultured in 384-well plates. The ability of the antibodies to bind peptide was assessed by bead array using beads expressing the three different peptides targets. 1920 potential positive antibodies were re-arrayed into 96 well plates further screened by flow cytometry against endogenous and artificial cell line models.

Positive hybridoma supernatants were then counter-screened by flow cytometry against endogenous and artificial models of proteins that have sequence similarity to the target region (e.g., other CLDN proteins). From the secondary screen and counterscreen, ~20 CLDN6-specific antibodies were chosen for additional study. These antibodies were subcloned and the variable heavy and light chain sequences were determined. See Table B and sequence listing.

CLDN6 antibodies were formatted as full-length IgG antibodies using ExpiCHO™ expression. The heavy and light chain variable regions of the antibodies were cloned into an antibody expression vector which was engineered in the lab based on a pcDNATM3.4TOPO® vector (Catalog Number: A14697, ThermoFisher Scientific, USA) and transfected into CHO cells by (According to protocol provided in the kit (ExpiCHO™ Expression System, Catalog Number: A29133, ThermoFisher Scientific, USA)). Antibodies were purified and cell surface binding of the antibodies to CLDN6 and the antibody $IC_{50}$ were determined by FACS in which CLDN6 antibodies were directly conjugated with Alexa Fluor® 647 NHS Ester (Succinimidyl Ester), Cat #A20106 (ThermoFisher Scientific) following the manufacturer's protocol. CLDN6 antibodies were tested from 0.32 nM to 1000 nM (serial dilution 1:5, 6 points) in a 50 μl volume with 150,000 cells system.

CLDN6-expressing cells were used in FACS assays to determine the CLDN6 antibody's ability to bind to CLDN6 on the surface of cells and to cross-react with other CLDN family members. HEK293 T cells engineered to express human CLDN6 fused to GFP, mouse CLDN6 fused to GFP, CLDN9-GFP, CLDN4-GFP, or CLDN3-GFP, or GFP alone (without CLDN6) were used as artificial models of CLDN6 expression. ARK2, OVCA429, LS513 and MCF7 cells were used as endogenous models of CLDN6 expression, as well as models for CLDN3/4 expression.

For each type of cell tested and for each mAb, cells were detached from the surface of the culture flasks by EDTA (instead of trypsin) in order to protect the cell surface proteins. The detached cells were then incubated with Alexa Fluor®-labeled CLDN6 mAbs for 30 min in the dark on ice at a pre-determined concentration. The CLDN6 mAbs were directly labeled with Alexa Fluor® 647 NHS Ester (Succinimidyl Ester). After washing, the cells were read by a BD Accuri™ Flow Cytometer C6 to detect antibody-antigen protein binding in channel FL4H. Each antibody was tested at varied concentrations to establish a dose-fluorescence curve. The EC50/$IC_{50}$ of the antibodies (the concentration of the antibody at which half the max value were calculated based on the values of FL4H (gated in viable singlet cells) using the Very Simple $IC_{50}$ Tool kit available online which allows biological dose-response data to be plotted and fitted to curve types to give the EC50/IC50. The max value was the lowest concentration of the antibody at which fluorescence maxes out. The antibodies were also screened for their ability to cross-react with other CLDN proteins such as CLDN9, CLDN3, and CLDN4. These values were used to determine each antibody's relative affinity among the set of antibodies tested. Cross-reactivity data were obtained using a similar methodology, but with cells having a different expression profile for CLDN6, CLDN3, CLDN4 and CLDN9.

Relative affinity data and cross-reactivity data as determined in this manner are set out in Tables 4 and 5.

TABLE 4

| AB# | Rank | HEK293T-CLDN6-mGFP Artificial CLDN6+ | HEK293T-CLDN6-mGFP Artificial CLDN6+ (mouse) | HEK293T CLDN9-mGFP Artificial CLDN9+ | HEK293T CLDN4-mGFP Artificial CLDN4+ | HEK293T CLDN3-mGFP Artificial CLDN3+ | HEK293T-mGFP Parental |
|---|---|---|---|---|---|---|---|
| 1 | 1 | 109 | 72 | 2765 | 5000 | 5000 | 5000 |
| 2 | 2 | 182 | 5000 | 5000 | 5000 | 5000 | 5000 |
| 3 | 3 | 604 | 2487 | 5000 | 5000 | 5000 | 5000 |
| 4 | 4 | 17 | 5000 | 1860 | 739 | 5000 | 5000 |
| 5 | 5 | 10 | 11 | 25 | 5000 | 5000 | 5000 |
| 6 | 6 | 1427 | 2222 | 2769 | 26 | 5000 | 5000 |
| 7 | 7 | 579 | 1548 | 1938 | 2088 | 5000 | 5000 |
| 8 | 8 | 1918 | 5000 | 2769 | 5000 | 5000 | 5000 |
| 9 | 9 | 2671 | 5000 | 5000 | 5000 | 5000 | 5000 |
| 10 | 10 | 2757 | 5000 | 246 | 5000 | 5000 | 5000 |
| 11 | 11 | 1696.29 | 2375 | 5000 | 2238 | 5000 | 5000 |
| 12 | Neg | 5000 | 5000 | 2468 | 2087 | 5000 | 5000 |
| 13 | Neg | 5000 | 5000 | 5000 | 5000 | 5000 | 5000 |
| 14 | Neg | 5000 | 5000 | 5000 | 5000 | 5000 | 5000 |
| 16 | Neg | 5000 | 5000 | 5000 | 5000 | 5000 | 5000 |
| 17 | Neg | 2,645.95 | 5000 | 5000 | 5000 | 5000 | 5000 |
| 18 | Neg | 5000 | 5000 | 5000 | 5000 | 5000 | 5000 |
| 15 | Neg | 5000 | 5000 | 5000 | 5000 | 5000 | 5000 |

TABLE 4-continued

| AB# | Rank | HEK293T-CLDN6-mGFP Artificial CLDN6+ | HEK293T-CLDN6-mGFP Artificial CLDN6+ (mouse) | HEK293T CLDN9-mGFP Artificial CLDN9+ | HEK293T CLDN4-mGFP Artificial CLDN4+ | HEK293T CLDN3-mGFP Artificial CLDN3+ | HEK293T-mGFP Parental |
|---|---|---|---|---|---|---|---|
| 19 | Neg | 5000 | 5000 | 5000 | 5000 | 5000 | 5000 |
| Reference Ab2 | 0 | 122 | 46 | 5000 | 5000 | 5000 | 5000 |
| Reference Ab1 | 0 | 57 | 651 | 2943 | 5000 | 5000 | 5000 |

AB# corresponds to AB# listed in Tables A and B.

TABLE 5

| AB# | ARK2 Endogenous CLDN6+ | OVCA429 Endogenous CLDN6+ | LS513 Endogenous CLDN3/4+ | MCF7 Endogenous CLDN3/4+ |
|---|---|---|---|---|
| 1 | 105 | 84 | 5000 | 5000 |
| 2 | 1365 | 912 | 5000 | 5000 |
| 3 | 1653 | 1096 | 5000 | 5000 |
| 4 | 48 | 168 | 730 | 653 |
| 5 | 8 | 5 | 781 | 1485 |
| 6 | 765 | 394 | 133 | 1135 |
| 7 | 353 | 531 | 635 | 979 |
| 8 | 1136 | 1090 | 1126 | 1063 |
| 9 | 1140 | 1165 | 1040 | 5000 |
| 10 | 2143 | 2473 | 1947 | 5000 |
| 11 | 362.81 | 834.65 | 492.567 | 427.031 |
| 12 | 1297 | 2294 | 2266 | 5000 |
| 13 | 1147 | 2287 | 1594 | 5000 |
| 14 | 1304 | 1661 | 1161 | 546 |
| 16 | 5000 | 5000 | 5000 | 5000 |
| 17 | 5000 | 5000 | 5000 | 5000 |
| 18 | 1,354.80 | 2,435.18 | 5000 | 5000 |
| 15 | 5000 | 5000 | 5000 | 5000 |
| 19 | 5000 | 5000 | 5000 | 5000 |
| Reference Ab2 | 1115 | 1283 | 2222 | 5000 |
| Reference Ab1 | 162 | 62 | 5000 | 5000 |

AB# corresponds to AB# listed in Tables A and B.

Example 6

This example demonstrates the characterization of chimeric mouse IgG mAbs.

Soft agar 3D proliferation assays and xenograft binding assays were carried out to further characterize mAbs described in Example 5. Briefly, a 250 µL top layer mixture containing 10,000 cells in 0.6% SeaPlaque agarose in 1×RPMI medium was plated on top of a solidified 250 uL bottom layer of 0.6% SeaPlaque agarose in 1×RPMI medium for each well of a 48-well plate. A 250 uL liquid feeder layer containing 1×RPMI medium was placed above the solidified top layer. All three layers of the soft agar assay were prepared with or without Trastuzumab, Cldn6 mAbs, or mouse IgG2a control starting at 150 ng/mL (1 uM) and ending at 1.5 ng/mL, diluting 1:10. Each test condition was performed in duplicates. Cells were allowed to form colonies for 3 weeks before staining with 0.05% neutral red, and imaged on the EVOS XL inverted light microscope. Cell lines with a ≥20% decrease in colony number in treated versus control were considered sensitive.

As shown in Table 6, many of cell lines exhibited a decrease in colony number when treated with the indicated antibody.

TABLE 6

| | Activity in vitro 3D |
|---|---|
| Reference Ab1** | 70% |
| Reference Ab2** | 50% |
| AB1 | 50% |
| AB2 | 50% |
| AB3 | 50% |
| AB4 | 70% |
| AB5 | 70% |
| AB6 | 70% |
| AB7 | 50% |
| AB8 | 0% |
| AB9 | 0% |
| AB10 | 50% |
| AB11 | 50% |
| AB12 | 0% |
| AB13 | 50% |
| AB14 | 0% |
| AB19 | 50% |
| AB16 | 25% |
| AB17 | 0% |
| AB18 | 0% |
| AB19 | 0% |

In vivo binding studies were carried out in xenograft mice injected with human cancer cell lines. Briefly, xenograft models of human cancer cell lines were established in six-week-old CD-1 athymic nude mice (Charles River Laboratories). The following conditions were followed for subcutaneous injection of each cell line: ARK2 $0.75 \times 10^7$, UMUC4 $1.0 \times 10^7$, OV90 $1.0 \times 10^7$ and M202 $0.5 \times 10^7$ cells all with 50% matrigel (BD Biosciences). Sufficient numbers of mice were injected to achieve 8 mice per treatment arm. When tumors reached an average size of 150 to 300 $mm^3$, mice were randomized into treatment groups. For treatment, each therapeutic antibody (AB3, AB2, Reference Ab1, Reference Ab2, Reference Ab 3 (trastuzumab) and non-targeting IgG2-control were diluted in sterile saline to a working concentration of 1 mg/ml for intravenous tail vein (IV) injection. For the M202 study, trametinib (DMSO-solvate, MedChem Express) was dosed at 1.0 mg/kg (10% Cremaphor, 10% PEG400) by PO on a 5 days on, 2 days off schedule for the first weekly cycle, followed by reduction to 0.5 mg/kg for the remaining two weeks of dosing. Tumor xenografts were measured with calipers thrice a week, and tumor volume in $mm^3$ was determined by multiplying height×width×length. Mice were treated for 2-7 weeks. At the end of study, animals were euthanized and tumor tissue was excised and divided to be stored as snap-frozen or formalin fixed paraffin embedded (FFPE) tissue for biomarker analysis. All animal work was carried out under a protocol approved by IACUC and the University of California at Los Angeles Animal Research Committee. Data was analyzed using StudyLog software from StudyDirector (San Francisco, CA). Results are presented as mean volumes for each group. Error bars represent the standard error (SE) of the mean.

The results of the xenograft assays are shown in FIG. 6-FIG. 10. As shown in FIG. 6A and FIG. 6B, each of AB2 and AB3 caused a substantial mean change in tumor volume at Day 14, relative to control IgG2 antibody, in mice bearing endometrial tumors. As shown in FIG. 7A and FIG. 7B, AB3 caused a substantial mean change in tumor volume at Day 35, relative to control IgG2 antibody, in mice bearing bladder tumors. FIG. 8A and FIG. 8B show that each of AB2 and AB3 caused a substantial mean change in tumor volume at Day 20, relative to control IgG2 antibody, in mice bearing ovarian tumors. FIG. 9A and FIG. 9B demonstrates that AB3 functions in a CLDN-specific manner, since the model used in FIG. 9A and FIG. 9B did not express any of CLDN6, CLDN3, CLDN4, and CLDN9 and was, therefore, used as a negative control. The data of FIG. 9A and FIG. 9B also suggests that AB3 has less off-target activity than Reference Ab1 and Reference Ab2. FIG. 10A summarizes the results of FIG. 6-FIG. 9. As shown in FIG. 10A, AB3 significantly reduced tumor growth in mice bearing endometrial, bladder, and ovarian tumors, each of which express CLDN6, but did not reduce tumor growth in mice bearing melanoma tumors, which did not express CLDN6 (FIG. 10B). As shown in FIG. 11, the mean chain in mouse body weight during treatment did not substantially change, suggesting the safety of the treatment.

A second set of experiments were carried out in xenograft models of a human ovarian cancer cell line, OV90. Mice were injected with one of 10 mAbs described in Example 5 or with a control antibody (mouse IgG2a antibody, reference CLDN6 ab) or with a PBS vehicle control. There were 8 mice per group and each animal was intravenously injected with 10 mg/kg antibody every 4 days. As shown in FIG. 12A and FIG. 12B, several antibodies described in Example 5 reduced tumor volume in mice bearing ovarian tumors. Among the best performers were AB3, AB4, AB7, and AB10, though all antibodies tested reduced tumor volume, relative to vehicle control. As shown in FIG. 13, the body weight of the animals treated with AB3, AB4, AB7, or AB10 did not significantly change, suggesting their safety.

Example 7

This example demonstrates the further characterization of chimeric mouse IgG mAbs.

Internalization quantification assays were carried out. Briefly, the study of CLDN6 protein internalization triggered by Reference Ab1, AB3, or AB4 binding was performed with a positive control, ubiquitously expressed Transferrin Receptor (TfR) which is a known cell surface receptor that is internalized after antibody binding.

TfR and CLDN6 antibodies were labeled with Texas Red™-X, Succinimidyl Ester, mixed isomers, cat #T6134 (ThermoFisher Scientific). Cells were seeded in a μ-Slide 8 Well chamber (Cat #80826, ibidi Cells In Focus Inc.) one day before the antibody treatment to allow cells to attach and grow. Cells were incubated with labeled antibodies for 30 min in dark on ice. Then the chamber containing CLDN6 or TfR labeled cells were read by Echo lab fluorescence microscope to collect images before internalization. The chamber was then incubated at 37° C. for 40 min to allow internalization process and images were collected again by the Echo lab fluorescence microscope. AB3 and AB4 caused a greater degree of CLDN6 internalization, compared to that caused by Reference Ab1 (Data not shown).

Example 8

This example demonstrates the further characterization of chimeric mouse IgG mAbs.

Two-dimensional (2D) proliferation assays were carried out with select antibodies described in Example 5 as follows: Cells were seeded in duplicate at 5,000 to 20,000 cells per well in a 24-well plate. On the following day, cells were treated with six 1-5 dilutions of mAb (starting at 100 nM of either Trastuzumab, Cldn6 mAbs, or mouse IgG2A control) and a fixed concentration of 1 ng/μL Monomethyl auristatin E (MMAE)-conjugated anti-mouse secondary (Moradec, LLC) to generate dose response curves. Untreated wells of cells were quantified on Day 1, the day of antibody treatment, and later on Day 6 to determine the range of cell growth. Wells treated with mAbs were quantified on Day 6 and a growth in each treatment condition was determined as a normalized percent ratio against the growth of untreated cells. Quantification was performed on the Z1 Particle Counter (Beckman Coulter, Inc).

The results are shown in FIG. 14. AB2, AB3, AB4, and AB5 demonstrated the greatest efficacy at inhibiting proliferation. The $IC_{50}$ for each of these antibodies was between 0.1 nM and 1 nM. Each of AB7, AB10, AB11, and AB15 also demonstrated the ability to inhibit proliferation in this assay, though to a lesser extent than AB2, AB3, AB4, and AB5.

Example 9

This example demonstrates the humanization of antibodies of the present disclosures.

A subset of antibodies listed in Table A were selected for humanization analysis. The heavy chain variable (VH) and light chain variable (VL) sequences of AB1, AB3, AB4, AB9, AB11, and AB18 antibodies were compared to a library of known human germline sequences from human VH genes and human VLkappa genes (IMGT® the international ImMunoGeneTics information System® www.imgt.org; founder and director: Marie-Paule Lefranc, Montpellier, France).; the databases used were IMGT human VH genes (F+ORF, 273 germline sequences) and IMGT human VLkappa genes (F+ORF, 74 germline sequences). The acceptor human germline was chosen from those closest in sequence to the parental antibody.

Table 7 provides, for each VH and VL of each antibody, information on the human germline sequences chosen as the acceptor sequence and the human heavy chain joining region (J gene) chosen. The joining region (J gene) was chosen from human joining region sequences compiled at IMGT® the international ImMunoGeneTics information System® www.imgt.org (founder and director: Marie-Paule Lefranc, Montpellier, France)

TABLE 7

| | Human HC germline | Human HC joining region (J gene) | Human LC germline | Human LC joining region (J gene) |
|---|---|---|---|---|
| AB1 | IGHV1-46(allele 1) | IGHJ4(allele 1) | IGLV1-39(allele 1) | IGKJ2(allele 1) |
| AB3 | IGHV3-23(allele 1) | IGHJ4(allele 1) | IGLV1-39(allele 1) | IGKJ2(allele 1) |

TABLE 7-continued

| | Human HC germline | Human HC joining region (J gene) | Human LC germline | Human LC joining region (J gene) |
|---|---|---|---|---|
| AB4 | IGHV1-46(allele 1) | IGHJ4(allele 1) | IGLV2-30(allele 1) | IGKJ2(allele 1) |
| AB9 | IGHV1-46(allele 1) | IGHJ4(allele 1) | IGLV1-39(allele 1) | IGKJ2(allele 1) |
| AB11 | IGHV3-48(allele 1) | IGHJ4(allele 1) | IGLV4-1(allele 1) | IGKJ2(allele 1) |
| AB18 | IGHV1-46(allele 1) | IGHJ4(allele 1) | IGLV4-1(allele 1) | IGKJ2(allele 1) |

CDRs were defined according to the AbM definition (see the website of Dr. Andrew C. R. Martin www.bioinf.org.uk/abs/ for a table comparing CDR definitions).

Alteration of human germline framework (i.e., non-CDR residues in VH and VL) positions to corresponding parental murine sequence might be required to optimize binding of the humanized antibody. The sequences for versions of humanized antibodies are provided as SEQ ID NOs: 376-421.

For AB1, each of Asn52 (sequential numbering) of CDR2 of the HC and Asn54 of CDR2 in the LC was determined to have a low potential for deamidation based on sequence and conformation.

For AB3, each of Asn31 (sequential numbering) of CDR1 of the HC, Asn57 of CDR2 of the HC, Asn 28 of CDR1 of LC, and Asn50 of CDR2 of the LC was determined to have a low potential for deamidation based on sequence and conformation. Trp33 of CDR1 of the HC was determined as likely solvent-exposed and to have potential for oxidation, especially under stress conditions. In CDR3 of the HC it was determined that there is a free Cys106 within the CDR that could be problematic when manufacturing the antibody, as it is likely solvent-exposed. This Cys residue was recommended for alteration to Tyr, Ser or Ala. The maintenance of binding of these altered antibodies are tested. Ile53 of CDR2 of the LC was determined to be solvent-exposed and could lead to non-specific binding. It was suggested that this Ile residue be altered to Ser. The maintenance of binding of this altered antibody is tested.

For AB4, each of Asn52 (sequential numbering) of the CDR2 of HC and Asn58 of CDR2 of the LC was determined to have a low potential for deamidation based on sequence and conformation. The sequence DGNT in the CDR1 of the LC was determined as problematic, as it was determined to have a high potential for isoaspartate formation (at the sequence DG) as well as a potential for deamidation (at the sequence NT). This sequence was recommended for alteration.

For AB9, Asn33 (sequential numbering) in CDR1 of HC, and Asn52 and Asn59 in CDR2 of HC were determined to have a low potential for deamidation based on sequence and conformation. Asn54 was determined to have a medium potential for deamidation based on sequence and conformation. The NGG sequence in CDR2 of the HC was determined to have a high/medium potential for deamidation followed by isoaspartate formation. Thus, it was recommended that this amino acid sequence is altered. A free Cys106 in CDR3 of the HC may be problematic when manufacturing the antibody, as it is determined as likely solvent-exposed. This Cys residue is suggested for alteration to Tyr, Ser or Ala. The maintenance of binding of these altered antibodies is tested. Arg28 in CDR1 of HC is not often found in human antibodies. This residue is altered to Thr and the maintenance of binding tested. For AB 9, Trp32 (sequential numbering) in CDR1 of the LC was determined as likely solvent-exposed and could undergo oxidation, especially under stress conditions. Leu24 of the same CDR is not often found in human antibodies. This residue is altered to Arg and maintenance of binding is tested.

For AB11, Asp54-Ser55 (sequential numbering) in CDR2 of the HC was determined as having a low potential for isoaspartate formation. Asn57 in CDR2 of the LC was determined as having a low potential for deamidation based on sequence and conformation.

For AB18, Asn33 and CDR-H2 Asn50 (sequential numbering) in CDR1 of the HC was determined as having a low potential for deamidation based on sequence and conformation. In CDR2 of the HC, the Asp-Pro (DP) sequence was determined as having a potential for undergoing fragmentation under acidic conditions. In the VL domain, Asn34 and Asn37 in the CDR1 of the LC was determined as having a low potential for deamidation based on sequence and conformation. In CDR3 of the LC, Trp56 was determined as likely solvent-exposed and could undergo oxidation, especially under stress conditions.

Table 8 shows a scheme for combining the humanized VH and VL. If none of the humanized versions is equivalent to the chimeric mAb. Preferred pairs are shown in bold underlined text.

TABLE 8

| Parental | Humanized Ab # | VH (SEQ ID NO:) | VL (SEQ ID NO:) |
|---|---|---|---|
| AB1 | AB1-1 | 376 | 380 |
| | AB1-2 | 377 | 380 |
| | AB1-3 | 377 | 381 |
| | AB1-4 | 377 | 382 |
| | AB1-5 | 377 | 383 |
| | AB1-6 | 378 | 381 |
| AB3 | AB3-1 | 384 | h21G5-L1 (optional) |
| | AB3-2 | 385 | 388 |
| | AB3-3 | 385 | 389 |
| | AB3-4 | 386 | 388 |
| | AB3-5 | 386 | 389 |
| | AB3-6 | 387 | 388 |
| | AB3-7 (also referred to as AB23) | 387 | 389 |
| AB4 | AB4-1 | 391 | 397 |
| | AB4-2 | 392 | 397 |
| | AB4-3 | 392 | 398 |
| | AB4-4 | 393 | 398 |
| | AB4-5 | 394 | 398 |
| | AB4-6 | 395 | 398 |
| | AB4-7 | 396 | 398 |
| AB9 | AB9-1 | 403 | 409 |
| | AB9-2 | 404 | 409 |
| | AB9-3 | 405 | 410 |
| | AB9-4 | 405 | 411 |
| | AB9-5 | 406 | 410 |
| | AB9-6 | 406 | 411 |
| | AB9-7 | 407 | 410 |
| | AB9-8 | 407 | 411 |
| | AB9-9 | 408 | 410 |
| | AB9-10 | 408 | 411 |
| AB11 | AB11-1 | 412 | 414 |
| | AB11-2 | 413 | 414 |
| | AB11-3 | 413 | 415 |
| AB18 | AB18-1 | 416 | 420 |
| | AB18-2 | 417 | 420 |
| | AB18-3 | 417 | 420 |
| | AB18-4 | 417 | 421 |
| | AB18-5 | 418 | 420 |
| | AB18-6 | 418 | 421 |
| | AB18-7 | 419 | 420 |

Humanized antibodies described in Table 8 were constructed and expressed as essentially described in Example 5. FACS assays were carried out as essentially described in Example 5 to determine relative antigen binding strengths of the humanized antibodies. Two doses (1.5 µg or 0.3 µg) of the humanized antibodies were tested for binding to either human CLDN6 or murine CLDN6 which proteins were expressed by engineered 293T clones. The results of the assays are provided in Table 9.

TABLE 9

| Humanized Ab Designation | Human CLDN6 (1.5 µg Ab) | Human CLDN6 (0.3 µg Ab) | Mouse CLDN6 |
|---|---|---|---|
| 2nd Ab only | 768.07 | 768.07 | 1061.72 |
| 64A-chim | 224297.77 | 124463.44 | 170906.13 |
| h64A | 233932.53 | 93415.06 | 188577.77 |
| SC27-108-chim | 320381.33 | 150854.98 | 284326.77 |
| AB1-Chim | 364416.49 | 311923.02 | 513665.18 |
| AB1-3 | 142182.2 | 141773.57 | 89292.21 |
| AB1-4 | 197142.08 | 101763.71 | 75860.6 |
| AB1-5 | 213233.57 | 137828.05 | 128498.45 |
| AB1-6 | 227152.34 | 119699.97 | 77561.34 |
| AB1-7 | 207009.91 | 79207.94 | 99740.72 |
| AB1-8 | 209971.67 | 98785.97 | 121717.49 |
| AB1-11 | 112923.25 | 64892.04 | 101386.62 |
| AB3-chim | 459373.03 | 267327.83 | 67927.47 |
| AB3-2 | 395813.97 | 309318.89 | 31741.02 |
| AB3-3 | 339510.79 | 250519.45 | 23038.44 |
| AB3-4 | 55845.14 | 11641.7 | 1521.79 |
| AB3-5 | 48550.83 | 13335.93 | 783.28 |
| AB3-7 | 169209.42 | 105881.93 | 56071.82 |
| AB3-8 | 151519.51 | 108419.64 | 21509.63 |
| AB4-chim | 326603.58 | 176289.63 | 3639.29 |
| AB4-3 | 47760.08 | 14309.78 | 671.08 |
| AB4-4 | 48975.26 | 14081.47 | 741.03 |
| AB4-5 | 43385.34 | 16765.44 | 2003.95 |
| AB4-6 | 29243.78 | 10841.68 | 14205.6 |
| AB4-7 | 33342.17 | 19215.28 | 6635.91 |
| AB4-8 | 77642.77 | 49310.15 | 4703.98 |
| AB4-9 | 56854.11 | 37231.13 | 1778.41 |
| AB4-10 | 77159.9 | 50809.2 | 2647.29 |
| AB4-11 | 61204.92 | 37798.69 | 1227.86 |
| AB4-12 | 86189.87 | 71121.12 | 1133.16 |
| AB18-chim | 135142.76 | 73775.39 | 57373.94 |
| AB18-3 | 58948.59 | 30357.27 | 2512.77 |
| AB18-4 | 54378.24 | 32424.7 | 4294.94 |
| AB18-5 | 51871.17 | 29448.66 | 8191.13 |
| AB18-6 | 58464.54 | 26883.47 | 3680.42 |
| AB9-chim | 72036.29 | 46694.71 | 6745.58 |
| AB9-3 | 24649.43 | 9504.6 | 3175.17 |
| AB9-4 | 34309.83 | 15331.51 | 1709.25 |
| AB11-chim | 3491.4 | 1671.35 | 5490.52 |
| AB11-2 | 2557.3 | 1289.17 | 7160.15 |
| AB11-3 | 2364.44 | 1009.7 | 5521.52 |

FACS assays were also carried out to determine relative antigen binding strengths of the humanized antibodies (at either 1.5 µg or 0.3 µg) for binding to CLDN6 as expressed by the indicated cancer cell lines. The results of the assays are provided in Table 10. 2nd Ab only was used as a negative control. 64A-chim, h64A, and SC27-108-chim were used as reference antibodies Corresponding Parental antibodies (antibodies prior to humanization) were used as controls and designated with "chim".

TABLE 10

| Humanized Ab Designation | OVCA429 1.5 µg | ARK2 1.5 µg | ARK2 0.3 µg | M202 1.5 µg | M202 0.3 µg |
|---|---|---|---|---|---|
| 2nd Ab only | 885.77 | 1351.21 | 1351.21 | 638.83 | 638.83 |
| 64A-chim | 140378.55 | 80449.93 | 66518.52 | 1456.2 | 628.72 |
| h64A | 161168.87 | 69118.48 | 90346.66 | 3093.69 | 2467.63 |
| SC27-108-chim | 54987.78 | 25522.86 | 62410.85 | 2293.1 | 742.74 |
| AB1-Chim | 176836.16 | 51913.52 | 58762.01 | 23377.33 | 9426.64 |
| AB1-3 | 27535.69 | 10776.6 | 2829.25 | 1225.78 | 694.08 |
| AB1-4 | 34551.99 | 10039.46 | 3641.11 | 970.7 | 697.98 |
| AB1-5 | 54331.07 | 22353.67 | 7494.86 | 869.06 | 684.3 |
| AB1-6 | 29949.91 | 7743.19 | 2816.15 | 880.4 | 1423.53 |
| AB1-7 | 44711.89 | 11224.28 | 4443.54 | 876.24 | 611.15 |
| AB1-8 | 65974.83 | 17642.9 | 5805.35 | 583.54 | 1886.84 |
| AB1-11 | untested | 97659.62 | 53926.71 | 5079.26 | 978.76 |
| AB3-chim | 138190.1 | 29114.68 | 17055.33 | 1120.39 | 843.5 |
| AB3-2 | 85941.69 | 33618.84 | 14656.49 | 1483.17 | 727.98 |
| AB3-3 | 88679.61 | 54901.39 | 1156.25 | 801.56 | 749.95 |
| AB3-4 | 2955.8 | 1459.46 | 1315.36 | 839.75 | 563.41 |
| AB3-5 | 2951.18 | 2909.74 | 1275.51 | 713.46 | 611.66 |
| AB3-7 | untested | 90420.04 | 35995.73 | 7841 | 1742.34 |
| AB3-8 | untested | 23259.52 | 11856.48 | 1903.05 | 952.71 |
| AB4-chim | 64796.15 | 38447.83 | 19142.38 | 1343.31 | 1007.71 |
| AB4-3 | 1155.95 | 1522.98 | 1192.96 | 708.25 | 984.95 |
| AB4-4 | 1203.16 | 1398.82 | 1048.05 | 899.25 | 618.43 |
| AB4-5 | 1351.27 | 1198.66 | 966.62 | 1203.98 | 653.41 |
| AB4-6 | untested | 9842.52 | 3303.34 | 2520.88 | 1281.68 |
| AB4-7 | untested | 7563.59 | 2765.93 | 3322.65 | 1444.19 |
| AB4-8 | untested | 7313.46 | 3118.74 | 1495.74 | 974.83 |
| AB4-9 | untested | 7787.35 | 3058.96 | 1179.5 | 825.33 |
| AB4-10 | untested | 20227.28 | 7212.1 | 1392.45 | 546.63 |
| AB4-11 | untested | 9167.61 | 6392.04 | 895.77 | 549.19 |
| AB4-12 | untested | 24221.65 | 9690.02 | 2015.4 | 1506.93 |
| AB18-chim | 25521.37 | 9149.19 | 3442.7 | 1048.6 | 895.4 |
| AB18-3 | 2703.41 | 1210.4 | 1079.32 | 684.33 | 592.8 |
| AB18-4 | 3220.08 | 1379.11 | 1134.22 | 1231.31 | 762.51 |
| AB18-5 | 4273.83 | 1330.44 | 1313.83 | 1001.99 | 594.43 |
| AB18-6 | 6753.92 | 1936.48 | 1393.53 | 914.2 | 865.43 |
| AB9-chim | 3569.69 | 4487.55 | 3508.75 | 1331.44 | 680.03 |
| AB9-3 | 1257.3 | 1471.97 | 1139.54 | 1659.76 | 1111.31 |
| AB9-4 | 1110.93 | 1553.6 | 1116.78 | 1149.55 | 625.38 |
| AB11-chim | 2440.63 | 1260.97 | 1315.28 | 973.48 | 610.05 |
| AB11-2 | 2694.81 | 1937.51 | 1400.43 | 1766.07 | 872.68 |
| AB11-3 | 2201.32 | 1541.47 | 1320.38 | 1134.3 | 940.92 |

"chim" is pre-humanized form of antibody.

Based on the in vitro antigen binding data, three humanized antibodies were selected for further testing and development. The antibodies were derived from AB1, AB3, and AB4.

In vivo binding studies of the humanized versions of AB1, AB3, and AB4 were carried out in xenograft mice injected with bladder cancer cell lines UMUC4, as essentially described in Example 6. Briefly, xenograft models of UMUC4 were established in six-week-old CD-1 athymic nude mice (Charles River Laboratories). After tumors reached an average size of 150 to 300 mm$^3$, mice were randomized into treatment groups. Humanized antibodies were diluted in sterile saline to a working concentration of 1 mg/ml for intravenous tail vein (IV) injection. Tumor xenografts were measured with calipers thrice a week, and tumor volume in mm$^3$ was determined by multiplying height×width×length. Mice were treated for 2-7 weeks. At the end of study, animals were euthanized and tumor tissue was excised and divided to be stored as snap-frozen or formalin fixed paraffin embedded (FFPE) tissue for biomarker analysis.

Figure 16B:
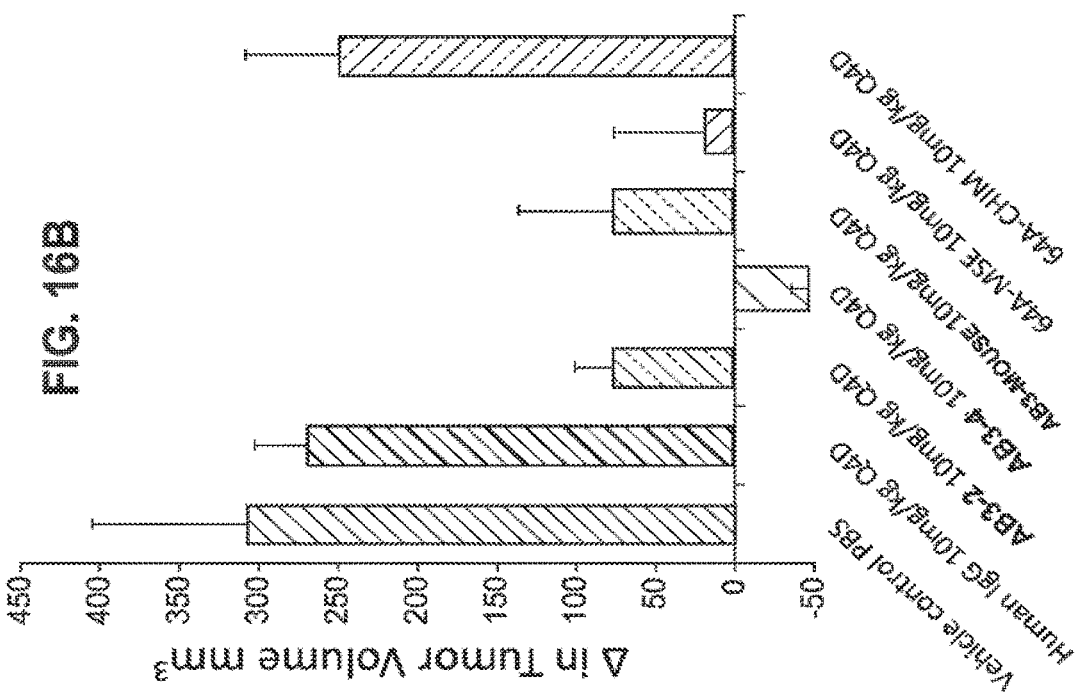
FIG. 16B represents a graph of the changes in tumor volume ($mm^3$) for each of the groups in FIG. 16A.
Figure 16A:
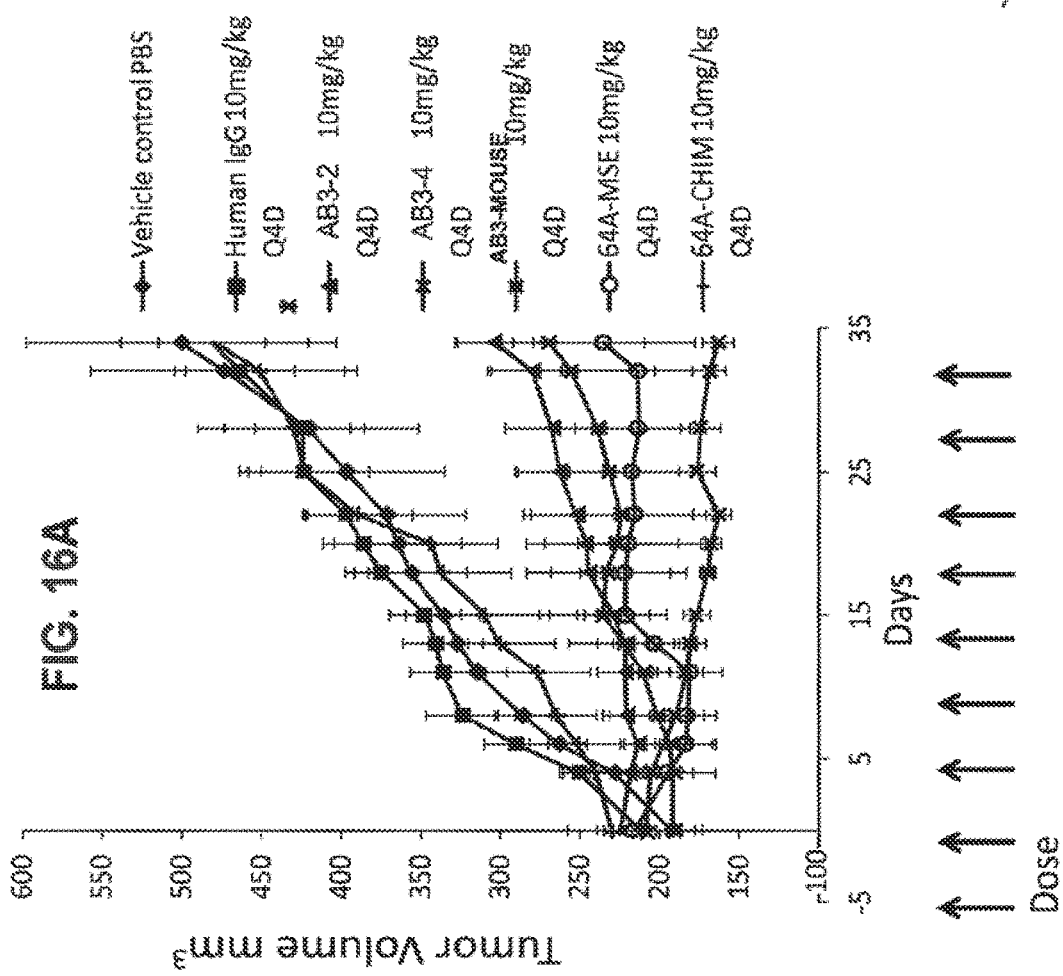
FIG. 16A represents a graph of the mean change in tumor volume ($mm^3$) at Day 35 of tumors in mice bearing bladder tumors treated with vehicle control, control IgG antibody, a mouse form of AB3, a first humanized form of AB3, and a second humanized form of AB3. Two control antibodies (one mouse and one chimeric) are also tested in this experiment.

The results of the xenograft assays are shown in FIG. 15-FIG. 21. FIG. 15 shows the xenograft assay results for two versions of humanized AB3 (AB3-2 and AB3-4), wherein treatment involved 10 mg/kg administered Q4D. Controls included vehicle control (PBS), human IgG (10 mg/kg Q4D), and the murine version of AB3 (10 mg/kg Q4D). As shown in this figure, humanized AB3-4 demonstrated a decrease in tumor volume over the 35 day treatment period. FIG. 16 shows the xenograft assay results for the same treatments as the experiments shown in FIG. 15, except that two additional controls (64A MSE and a chimeric version thereof (64A-CHIM)) were carried out. As in FIG. 15, FIG. 16 shows a marked decrease in tumor volume upon treatment with humanized AB3-4.

FIG. 17 shows the xenograft assay results for humanized AB1-5. Controls included vehicle control (PBS), human IgG (10 mg/kg Q4D), and the murine version of AB1 (10 mg/kg Q4D). As shown in FIG. 17, mice treated with humanized AB1-5 demonstrated a marked decrease in tumor volume.

FIG. 18 shows the xenograft assay results for humanized AB4-3. Controls included vehicle control (PBS), human IgG (10 mg/kg Q4D), and the murine version of AB4 (10 mg/kg Q4D). Mice treated with humanized AB4-3 did not demonstrate a marked decrease in tumor volume.

Figure 21:
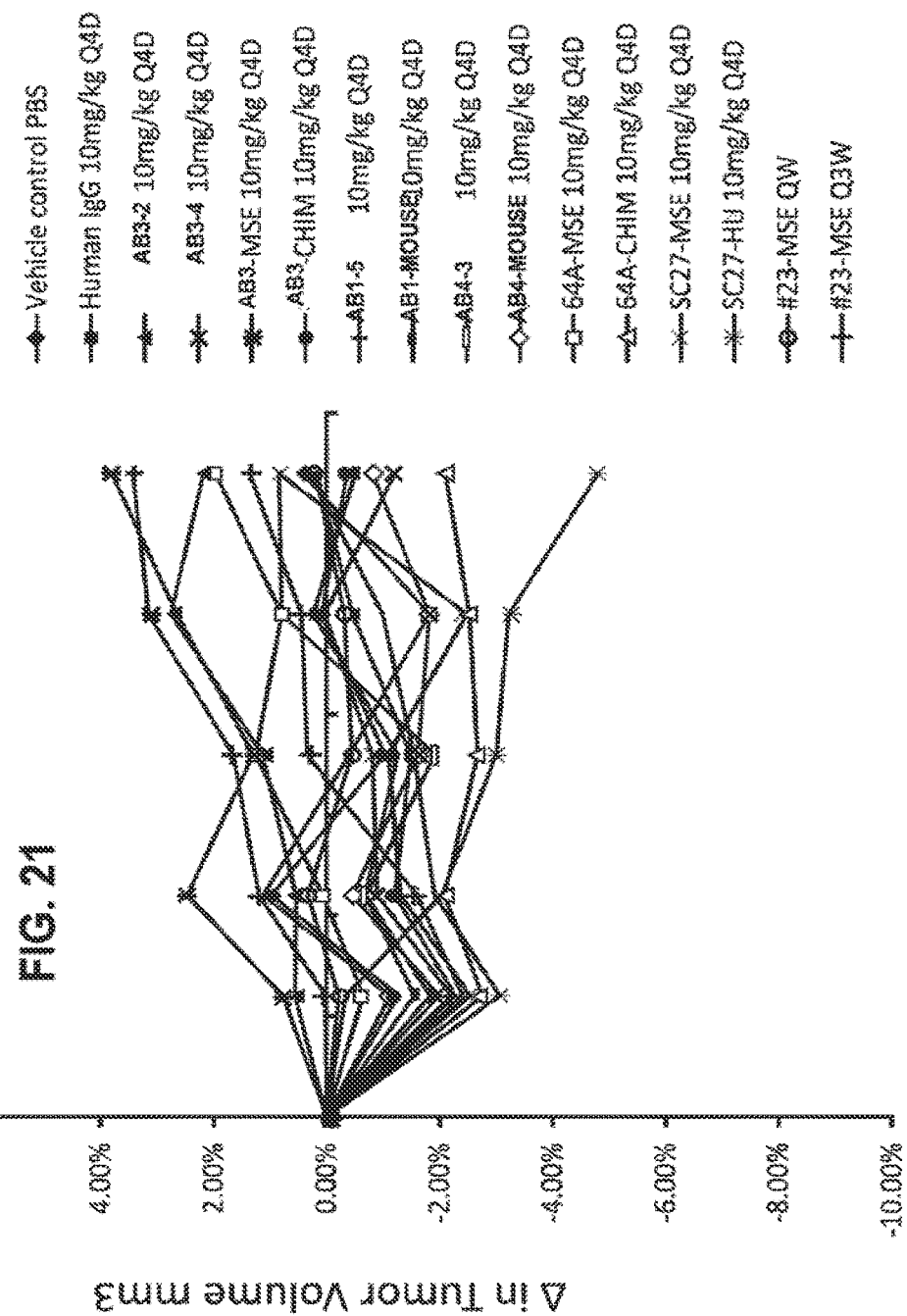
FIG. 21 represents a graph of the % change in body weight of tumor-bearing mice treated at Day 32 treated as described in FIG. 19A.

FIG. 19-FIG. 21 demonstrate the results of a xenograft assay wherein all 4 humanized antibodies of FIG. 15-FIG. 18 were tested. Mouse and Chimeric versions of reference CLDN6 antibodies were used as controls. As shown in FIG. 19, mice treated with humanized AB3-4 and AB1-5 demonstrated decreases in tumor volume. FIG. 20 demonstrates tumor volume over the course of time to Day 55. The body weights of mice in the assay are shown in FIG. 21.

Example 10

An in silico analysis was carried out with different sequences of AB1, AB3, and AB4. In particular, the sequences for (a) the original parental clone, (b) the closest mouse germline sequence, (c) the closest human germline sequence, and (d) the humanized sequence, for each antibody, were aligned. Amino acids believed to have undergone affinity maturation are marked with an asterisk while amino acids that differ from amino acids at that position according to antibody database information are marked with a hashtag. CDRs for each sequence are boxed. Based on this analysis, several humanized antibodies will be made having a sequence listed in TABLE 10.

TABLE 10

| Parent Clone | Consensus Sequence HC | Consensus Sequence LC |
|---|---|---|
| AB1 | 422 | 423 |
| AB3 | 424 | 425 |
| AB4 | 426 | 427 |

Multiples antibodies having a sequence as defined by these consensus sequences are made as essentially described in Example 5 and tested in vitro for antigen binding via FACS (as essentially described in Example 5) and in vivo for the ability to decrease tumor volume in mice (as essentially described in Example 6).

Example 11

This example describes a Next-Generation Sequencing (NGS) analysis of CLDN6 antibodies of the present disclosure.

The sequences of AB1 and AB3 were subjected to NGS analysis to identify somatic hypermutation (SHM) related variants of the heavy chain and light chain for each antibody. The NGS analysis identified points of SHM in both the heavy and light chain sequences for each antibody. The analysis revealed 1452 different heavy chain sequences and 326 different light chain sequences for AB3 and 372 different heavy chain sequences and 3081 different light chain sequences for AB1. Example results are shown in FIG. 23-FIG. 26. FIG. 23 and FIG. 24 show identified changes to heavy and light chains of a variant AB3, respectively, while FIG. 25 and FIG. 26 show identified changes to heavy and light chains of a variant AB1, respectively. Mutations in Chothia numbering are provided at the bottom of each figure.

Antibodies with NGS-identified SHM in the heavy chain were selected based on likelihood for binding involvement. Six antibodies were manufactured based on humanized AB3-7 (AB S1-S6) and six antibodies were made based on humanized AB1-11 (AB S7-S12) and subsequently evaluated for phenotype. FIG. 22 is a listing of the parental and 12 variant heavy chain sequences paired with light chain sequences. FACS binding studies of the 12 antibodies (AB S1-S12) were carried out as essentially described herein and the results are shown in FIG. 27.

FACS binding assays were also carried out with different amounts of AB S1-S12. The antibody concentrations tested in this limiting dilution assay were 0.32 nM, 1.6 nM, 8 nM, 40 nM, 200 nM, and 1000 nM and different cell lines expression CLDN6 were used. The results are shown in FIG. 28.

These data support that the newly identified antibodies (S1-S12) demonstrated increased binding over the corresponding parental humanized antibody.

Example 12

This example demonstrates in vivo analysis of humanized antibodies described herein.

In vivo studies were carried out in xenograft mice injected with human cancer cell lines as essentially described in Example 6. In this study, cells of the UMUC4 cell line, a bladder cancer cell line strongly expressing CLDN6, and of the OV-90 cell line, an ovarian cancer cell line expressing CLDN6, were used. Both cell lines are tumorigenic when administered to mice subcutaneously. Briefly, xenograft models of human cancer cell lines were established in six-week-old CD-1 athymic nude mice (Charles River Laboratories). The following conditions were followed for subcutaneous injection of each cell line: UMUC4 $1.0\times10^7$ and OV90 $1.0\times10^7$ all with 50% matrigel (BD Biosciences). CD-1 nude mice (8 mice per group) were subcutaneously injected in the right flank with the UMUC4 or OV-90 cell line. When tumors reached an average size of 150 to 300 mm$^3$, mice were randomized into treatment groups. For treatment, each therapeutic antibody (humanized AB1-11, humaninzed AB3-7) and a human IgG control antibody were diluted in sterile saline and administered via intravenous tail vein (IV) injection at 10 mg/kg once every 4 days daily (Q4D—FIG. 30) or once weekly (QW—FIG. 31). Tumor xenografts were measured with calipers thrice a week, and tumor volume in mm$^3$ was determined by multiplying height×width×length. Mice were treated for 21-36 days At the end of study, animals were euthanized and tumor tissue was excised and divided to be stored as snap-frozen or formalin fixed paraffin embedded (FFPE) tissue for biomarker analysis. All animal work was carried out under a protocol approved by IACUC and the University of California at Los Angeles Animal Research Committee. Data was analyzed using StudyLog software from StudyDirector (San Francisco, CA). Results are presented as mean volumes for each group. Error bars represent the standard error (SE) of the mean.

Figure 30:
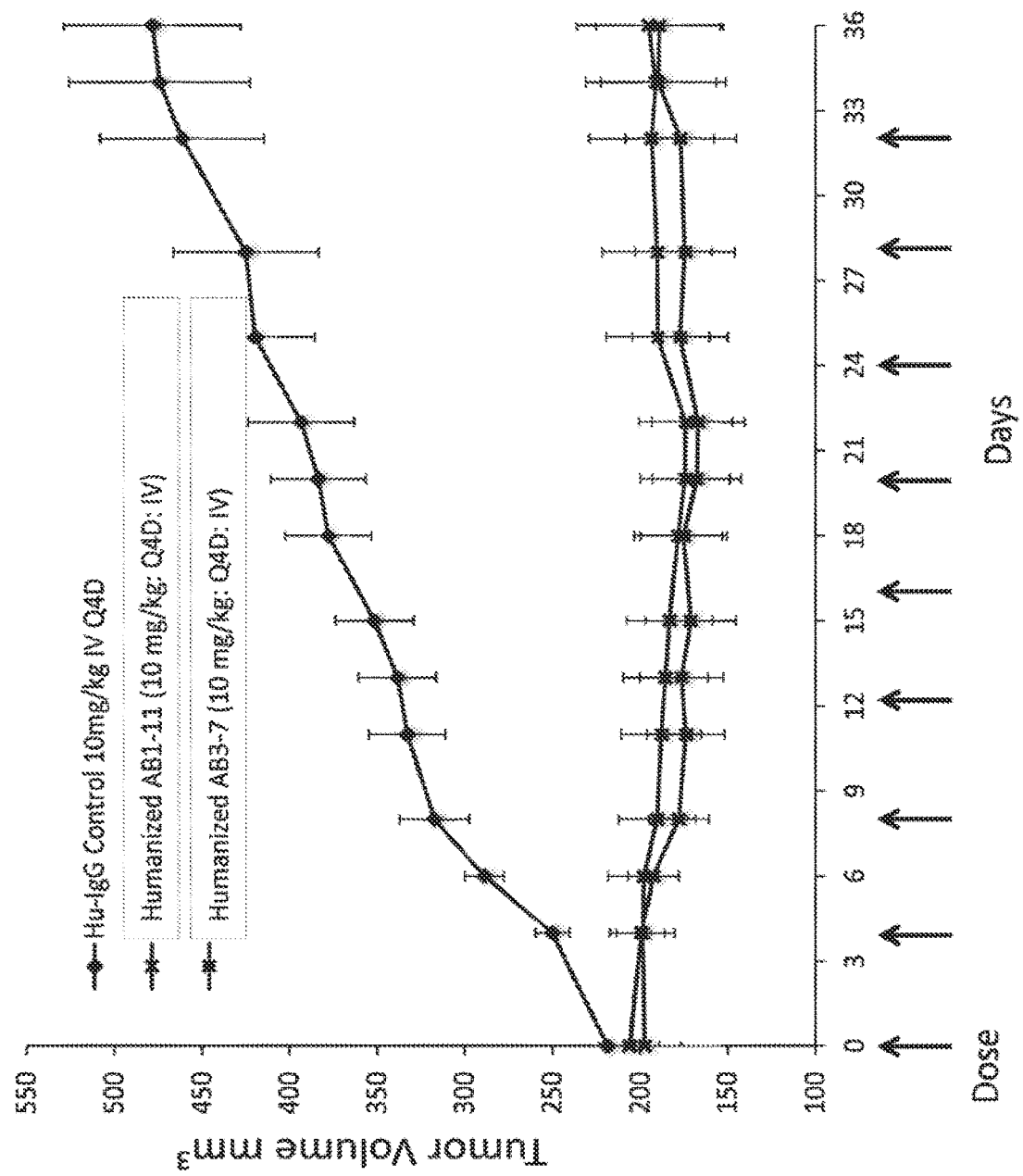
FIG. 30 is a graph of the tumor volume in mice subcutaneously injected with human cancer cells followed by treatment as described herein.
Figure 31:
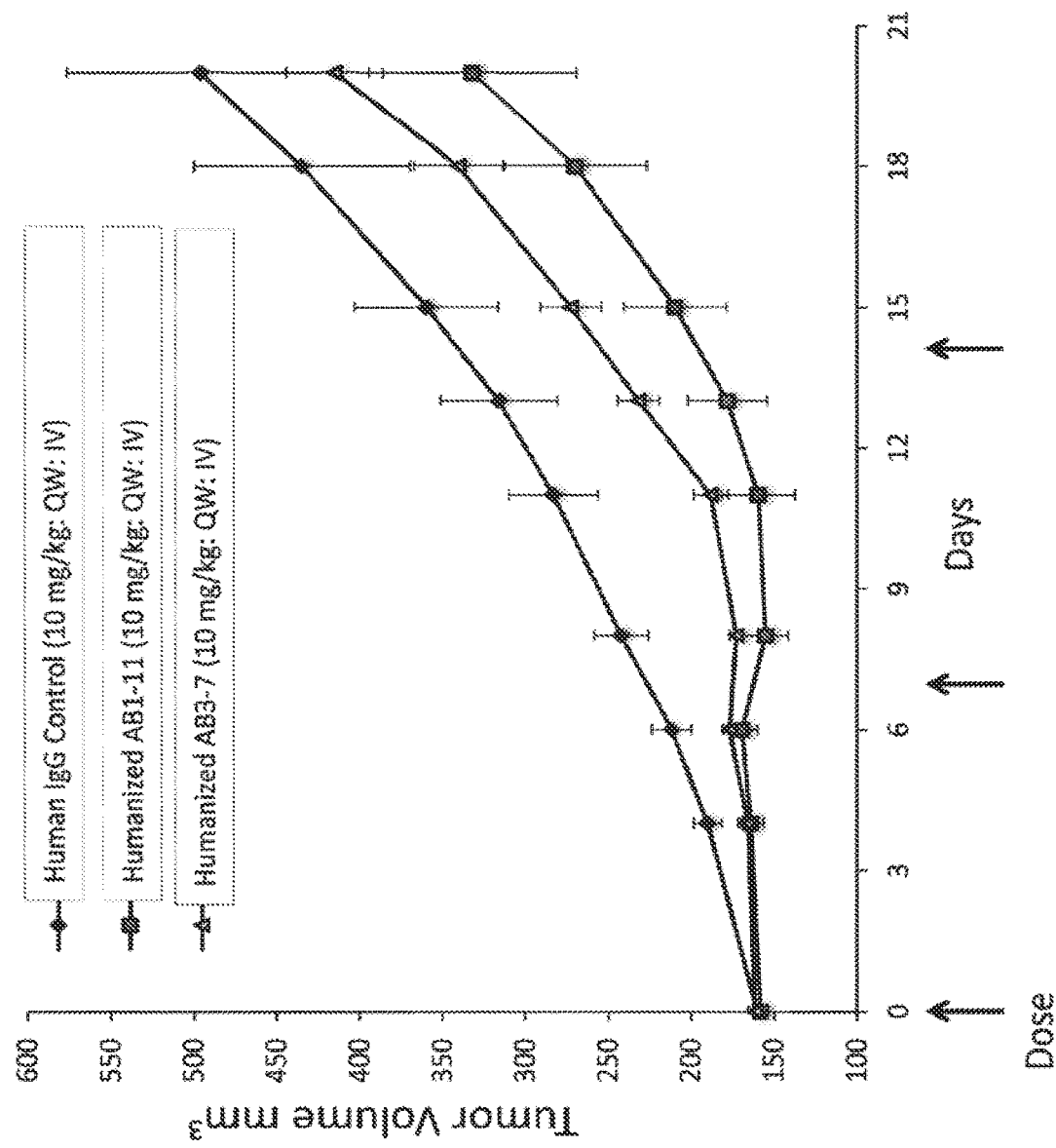
FIG. 31 is a graph of the tumor volume in mice subcutaneously injected with human cancer cells followed by treatment as described herein.

The results of the xenograft assays are shown in FIG. 30 and FIG. 31. As shown in FIG. 30, Q4D treatment with AB1-11 or AB3-7 led to remarkable decreases in tumor volumes or UMUC4 tumors relative to control treated mice. Both humanized antibodies achieved a 60% decrease in tumor volume relative to control mice by the end of the study period.

As shown in FIG. 31, the OV-90 tumor volumes of mice treated with either humanized antibody were less than the tumor volume of control treated mice. By the end of the study, AB1-11 achieved a 33% decrease in tumor volume relative to control mice while AB3-7 achieved a 16% decrease.

These data support that the humanized antibodies maintain the therapeutic efficacy first observed with the corresponding mouse antibodies.

Example 13

This example demonstrates an antibody drug conjugate tested in vivo.

An conjugate comprising MMAE and humanized AB1-11 was made and tested in vivo using xenograft mice injected with OV-90 ovarian cancer cell lines expression CLDN6 as essentially described in Example 6. In this experiment, CD-1 nude mice (8 mice per group) were subcutaneously injected into the right flank with OV-90 cells. When tumors reached an average size of 150 to 300 mm$^3$, mice were randomized into treatment groups. For treatment, mice were administered once weekly by tail vein injection (1) 10 mg/kg humanized AB1-11 antibody, (2) 10 mg/kg a human IgG control antibody, (3) 5 mg/kg untargeted conjugate comprising MMAE without AB1-11, and (4) 10 mg/kg targeted antibody drug conjugate (ADC) comprising MMAE and AB1-11. The untargeted conjugate comprised MMAE conjugated to a non-targeting human IgG control antibody. Tumor xenografts were measured with calipers thrice a week, and tumor volume in mm$^3$ was determined by multiplying height×width×length. Mice were treated for 20-36 days At the end of study, animals were euthanized and tumor tissue was excised and divided to be stored as snap-frozen or formalin fixed paraffin embedded (FFPE) tissue for biomarker analysis. All animal work was carried out under a protocol approved by IACUC and the University of California at Los Angeles Animal Research Committee. Data was analyzed using StudyLog software from StudyDirector (San Francisco, CA). Results are presented as mean volumes for each group. Error bars represent the standard error (SE) of the mean.

Figure 32:
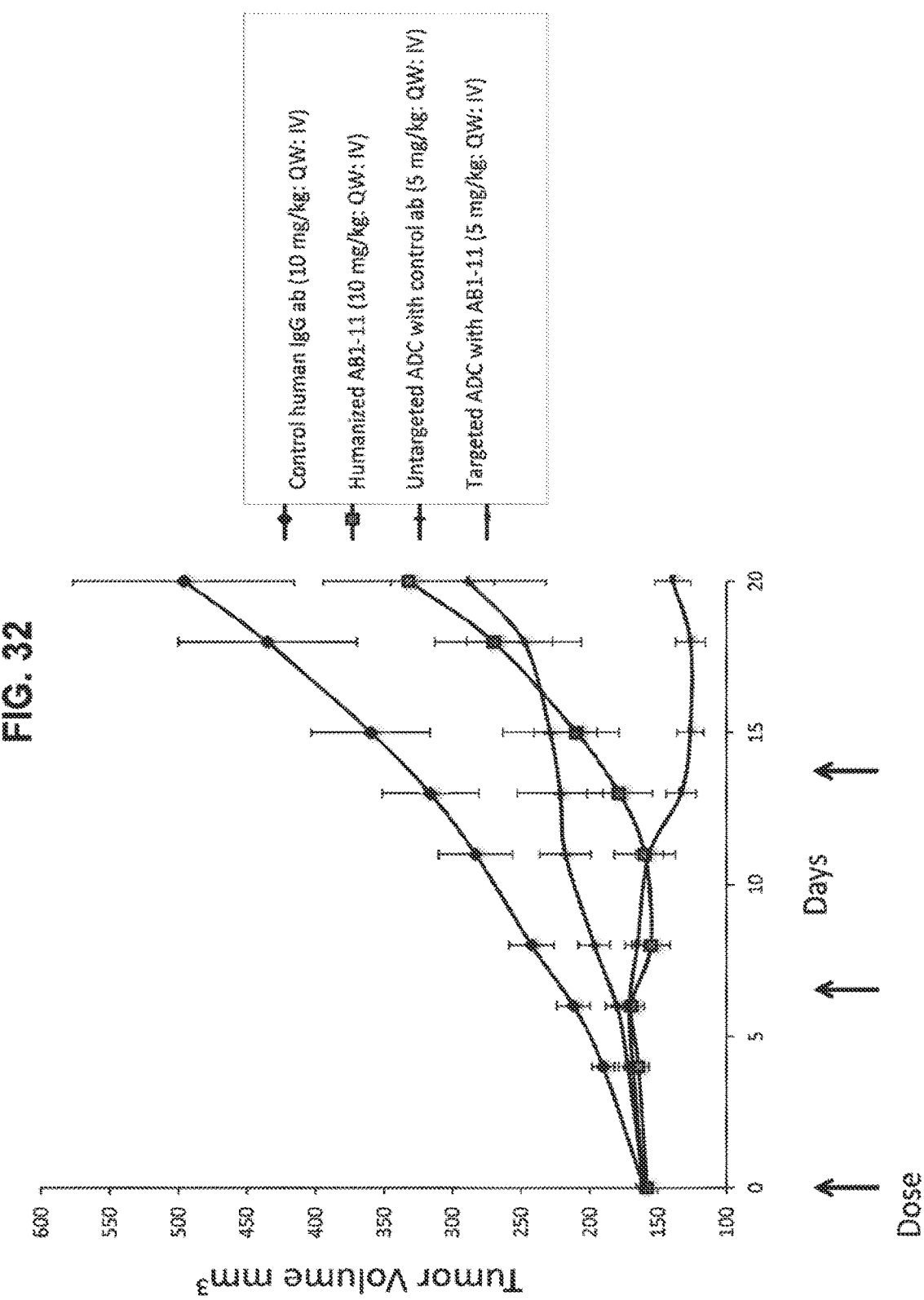
FIG. 32 is a graph of the tumor volume in mice subcutaneously injected with human cancer cells followed by treatment as described herein.

As shown in FIG. 32, the administration of the targeted ADC led to a substantial decrease in tumor volume. By the end of the study, the tumor volume of mice treated with the targeted ADC exhibited a greater than 70% decrease relative to control treated mice.

The same in vivo analysis was carried out with mice subcutaneously injected with UMUC4 bladder cancer cells instead of OV-90 cells and the treatments were administered once weekly by tail vein injection (1) 10 mg/kg humanized AB1-11 antibody, (2) 10 mg/kg a human IgG control antibody, (3) 5 mg/kg untargeted conjugate comprising MMAE without AB1-11, and (4) 10 mg/kg targeted antibody drug conjugate (ADC) comprising MMAE and AB1-11. The untargeted conjugate comprised MMAE conjugated to a non-targeting human IgG control antibody. The targeted conjugate was given a total of 3 times, whereas the other treatments were administered once weekly 5 times in total. Tumor volume measurements were made as described above, though measurements for the targeted ADC treated mice were measured for up to 80 days.

Figure 33:
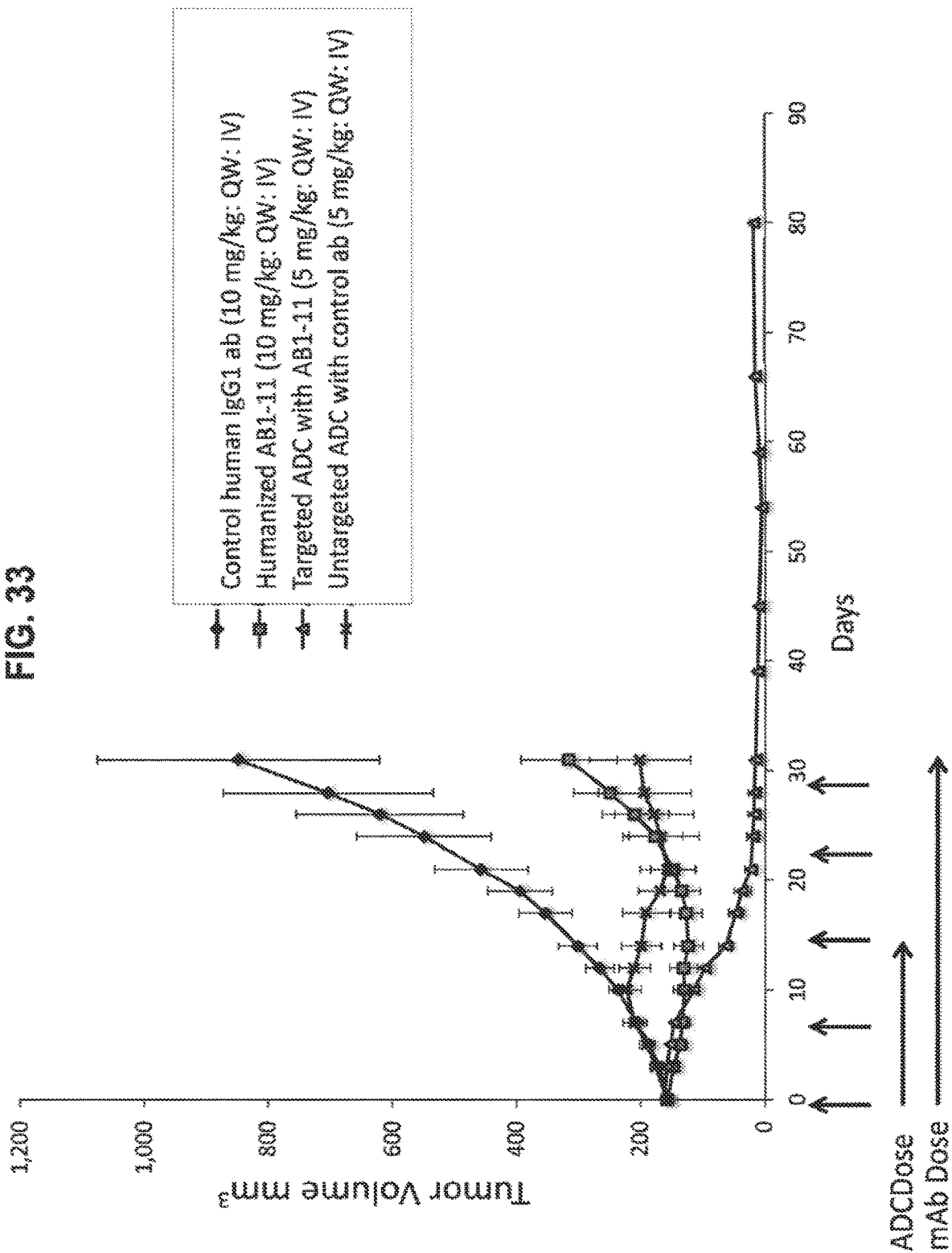
FIG. 33 is a graph of the tumor volume in mice subcutaneously injected with human cancer cells followed by treatment as described herein.

As shown in FIG. 33, the administration of the targeted ADC demonstrates tumor volumes decreasing from almost 200 mm$^3$ to almost 0 mm$^3$. The effect carried on to 80 days of the study or more than about 60 days after the last ADC treatment.

These data support that an antibody drug conjugate comprising an antibody of the present disclosure is effective to reduce tumor size and to treat cancer.

Example 14

This Example demonstrates the in vitro characterization of the CLDN6 ADCs.

ADCs comprising various linker-drug combinations were made with a humanized AB3-7 antibody (also referred to as AB23, see e.g., Table 8): (a) VC-PAB-MMAE, (b) GGFG-MMAE, (c) CL2A-SN38, (d) GGFG-Dxd, and (e) VC-PAB-Dxd. The ADCs were prepared at WuXi Biologics (Shanghai, China).

Figure 34B:
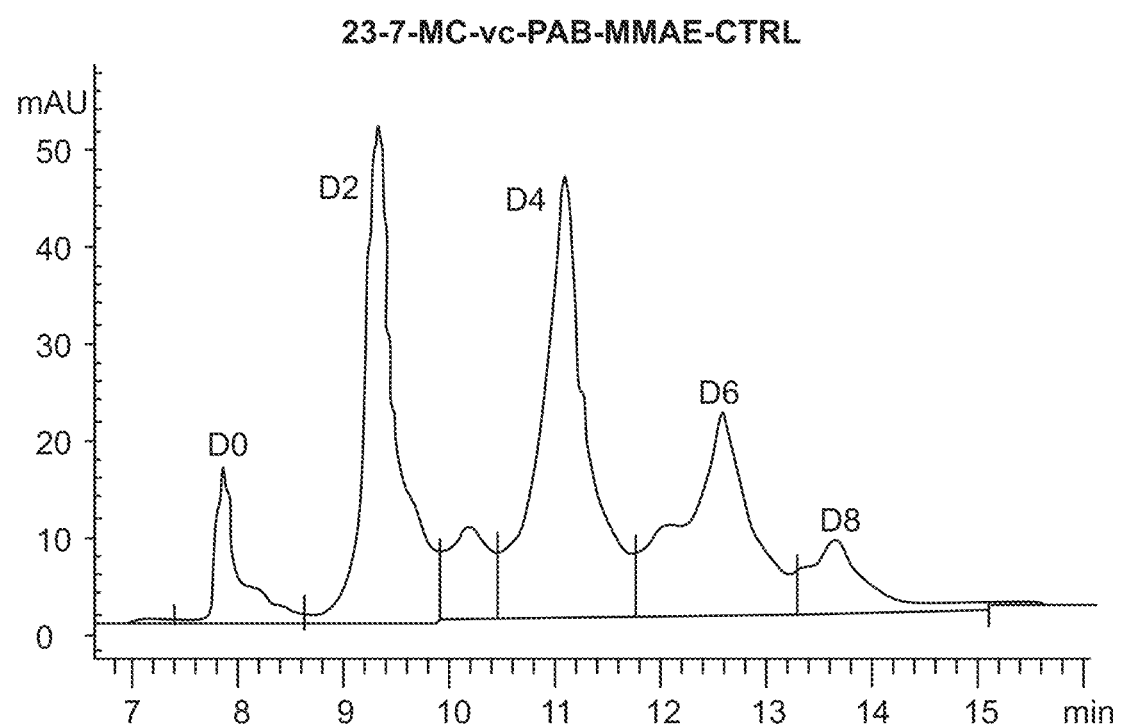
Figure 34C:
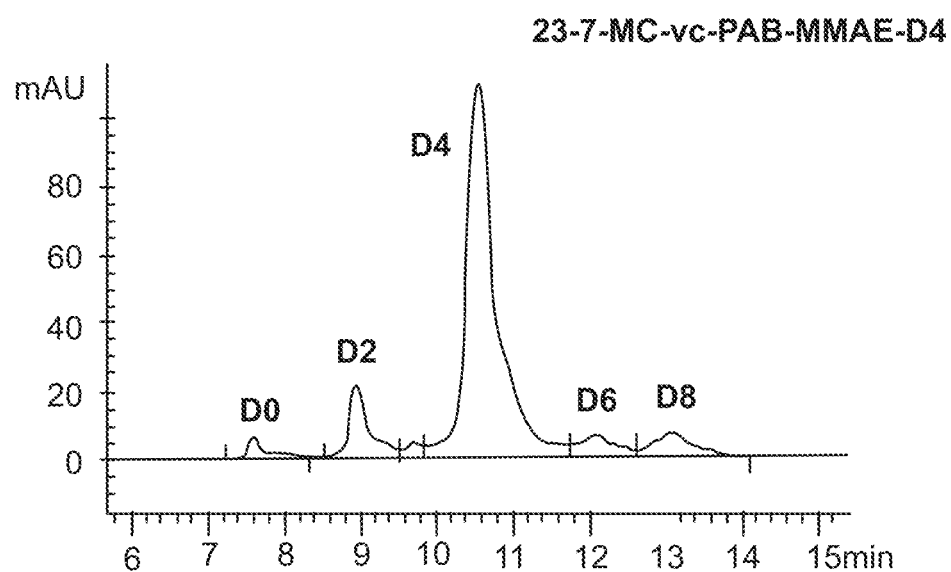
Figure 34D:
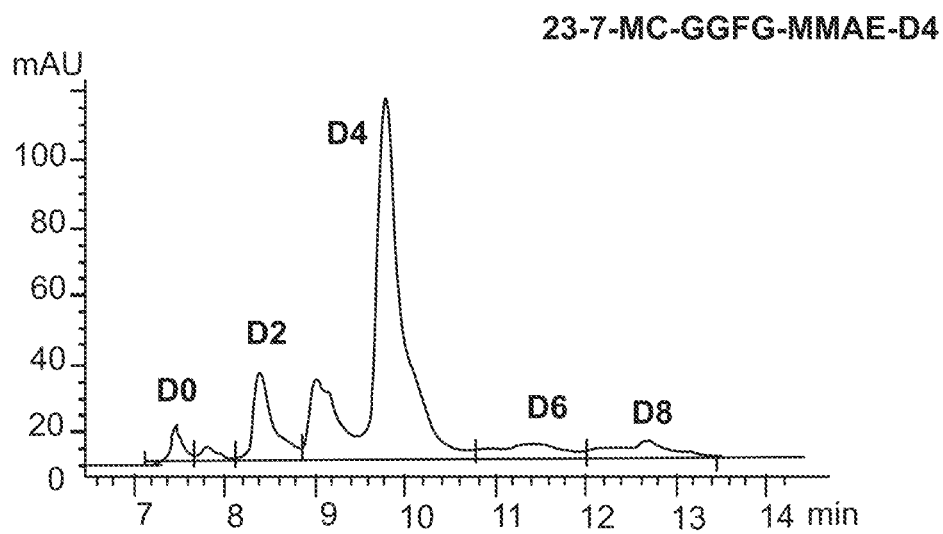
Figure 34E:
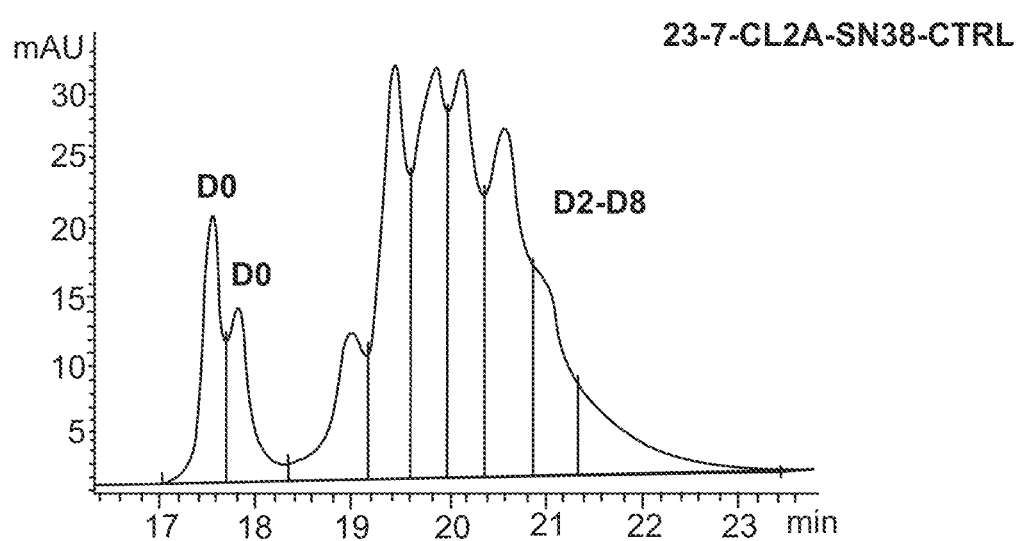
Figure 34F:
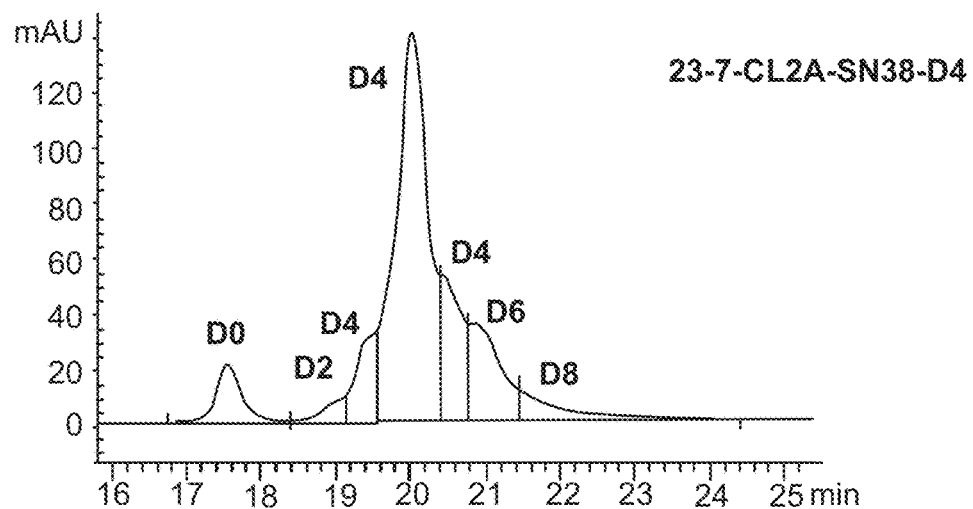
Figure 34G:
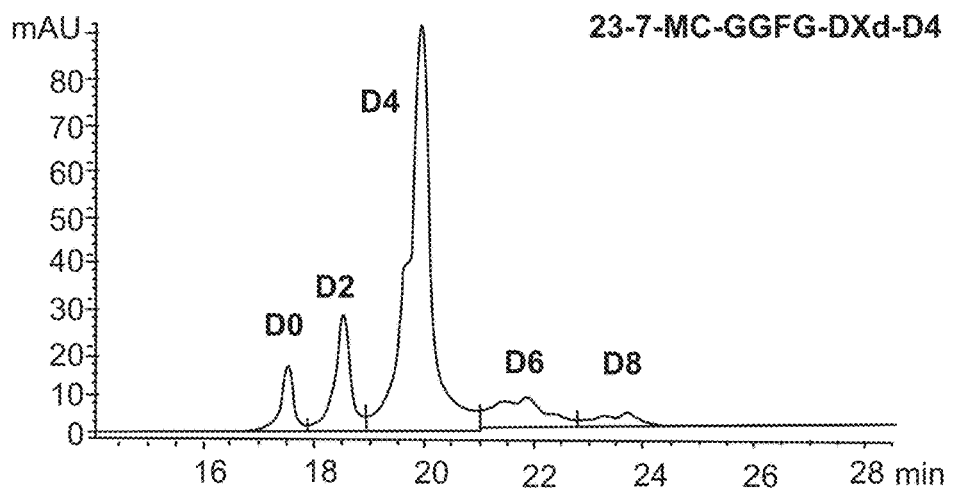
Figure 34H:
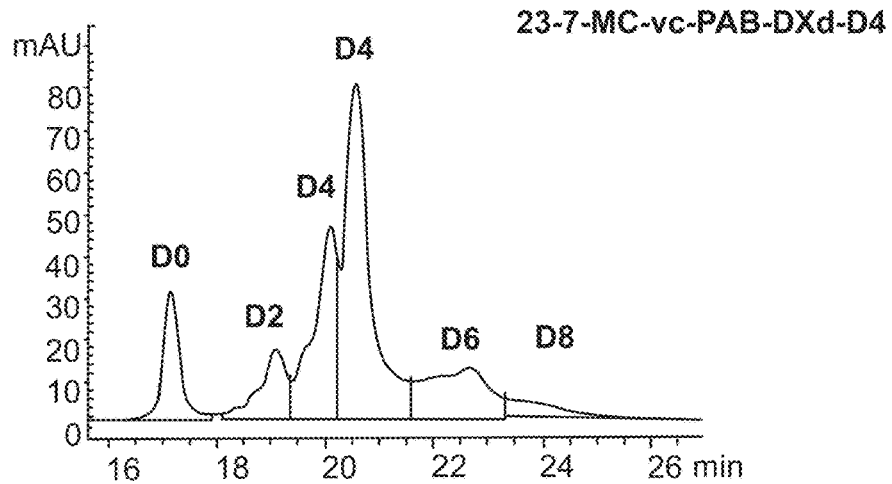

FIG. 34A-FIG. 34H show the biochemical characterization of the CLDN6 ADCs comprising AB3-7. FIG. 34A is a table summarizing the biochemical properties of the seven CLDN6 ADCs comprising AB3-7. The ADCs that are labeled as D4 refers to substantially homogenous conjugates that comprise a significant number of antibodies being conjugated to 4 drugs per antibody (D4 technology, a technology of WuXi Biologics). The ADCs that are labeled as CTRL refers to conventional heterogeneous conjugates (conventional) that comprise the Gaussian distribution of the number of drugs per antibody. The ADCs comprised a low percentage of unconjugated antibody, high-molecular-weight (HMWs) species, and unconjugated free drugs. The ADCs also comprised a low level of endotoxin, rendering them suitable for in vivo studies. FIG. 34B-FIG. 34H represent the HIC-HPLC chromatograms that show the relative abundance of the antibody conjugated to different numbers of drugs for each ADC. For example, the peak area under D0 indicates the relative abundance of the unconjugated AB3-7. Similarly, the peak area under D1, D2, D3 . . . D8 indicates the relative abundance of AB3-7 antibody conjugated to 1, 2, 3 . . . 8 drugs per antibody.

Figure 35:
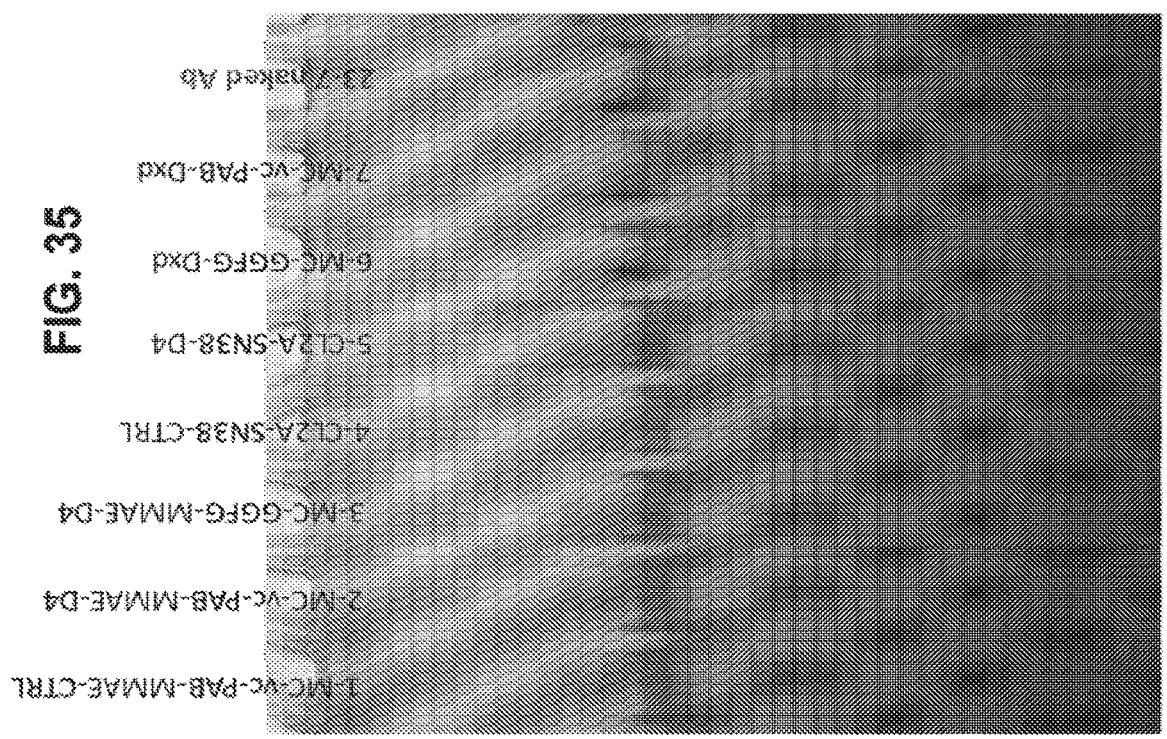
FIG. 35 shows the molecular integrity of the CLDN6 ADCs comprising AB3-7 analyzed by Native PAGE.

FIG. 35 shows that the molecular integrity of the CLDN6 ADCs comprising AB3-7 was not altered by conjugation. The molecular integrity of the CLDN6 ADCs and unconjugated AB3-7 antibody was assessed by NativePAGE (NativePAGE 4-16% Bis-Tris Protein Gels (Cat. #BN1002BOX, ThermoFisher). Native PAGE separates proteins according to the net charge, size, and shape of their native structure. Under the native condition, all seven CLDN6 ADCs remain structurally intact and did exhibit any indication of degradation compared with the unconjugated AB3-7 antibody. Thus, conjugation does not alter the molecular integrity of the AB3-7 antibody.

FIG. 36 shows that conjugation does not affect the binding affinity of the AB3-7 antibody. Flow cytometry shows that the CLDN6 ADCs comprising AB3-7 retained the specific and high binding affinity for CLDN6. The ADC binding activity was analyzed by flow cytometry for three cell lines: (a) UMUC4 bladder cancer cell line (natively expressing CLDN6), (b) HEK293T CLDN6-mGFP A11 (engineered to artificially overexpress (OE) CLDN6), and (c) M202 melanoma cell line (CLDN6-negative cells). Specifically, the ADCs were incubated with ~150,000 cells in 50 μl 2% FBS/PBS at 4° C. for 30 mins followed by washing with 2% FBS/PBS. The ADCs were then incubated with Alexa Fluor® 647 anti-human IgG Fc Antibody from Biolegend (409320) at 4° C. for 30 mins. The binding was measured by BD Accuri™ C6 Flow Cytometer. Seven different CLDN6 ADCs showed similar binding affinity by flow cytometry compared with their unconjugated antibody AB3-7 to CLDN6-positive cell lines (UMUC4 cells and HEK293T CLDN6-mGFP A11), while showing no binding for a CLDN6-negative cell line (M202).

FIG. 37 further shows that conjugation does not affect the binding affinity of the AB3-7 antibody. Measurements of the dissociation constant (KD) demonstrated that the CLDN6 ADCs comprising AB3-7 retained the specific and high binding affinity for CLDN6. The cell-based antibody affinity (KD) of the CLDN6 ADCs was measured by KinExA 4000 (Sapidyne Instrument, Boise, Idaho). Briefly, HEK293T CLDN6-mGFP A11 cells were detached using versene and equilibrated with either 500 pM or 10 nM antibody in 2% FBS/DMEM at 4° C. overnight. The cell concentration started at $5 \times 10^6$ cells/ml and 2-fold serial dilutions were performed up to 10 points. The next day, the cells were centrifuged at 1500 rpm for 10 min and the supernatants were saved. The PMMA beads (Sapidye Instrument, Cat. #440176) were pre-coated with goat-anti-human IgG (Jackson ImmunoResearch Labs (Cat. #109-005-003) at 30 µg/ml. Fluorescent secondary antibody Alexa Fluor® 647 AffiniPure Goat Anti-Human IgG (Jackson ImmunoResearch Labs, Cat. #109-605-088) was diluted in 1% BSA/PBS at 0.5 µg/ml. The antibody solution only (Signal 100%) and nonspecific binding (NSB, buffer only) controls were also included in the measurements. The KD was calculated using two antibody curves analyzed by the n-curve analysis. As demonstrated in FIG. 37, the binding affinity (KD) is similar across all ADCs and unconjugated AB3-7. Thus, conjugation to various linker-drug combinations did not alter the antibody binding affinity for CLDN6 expressed on the HEK293T CLDN6-mGFP A11 cells.

Figure 38:
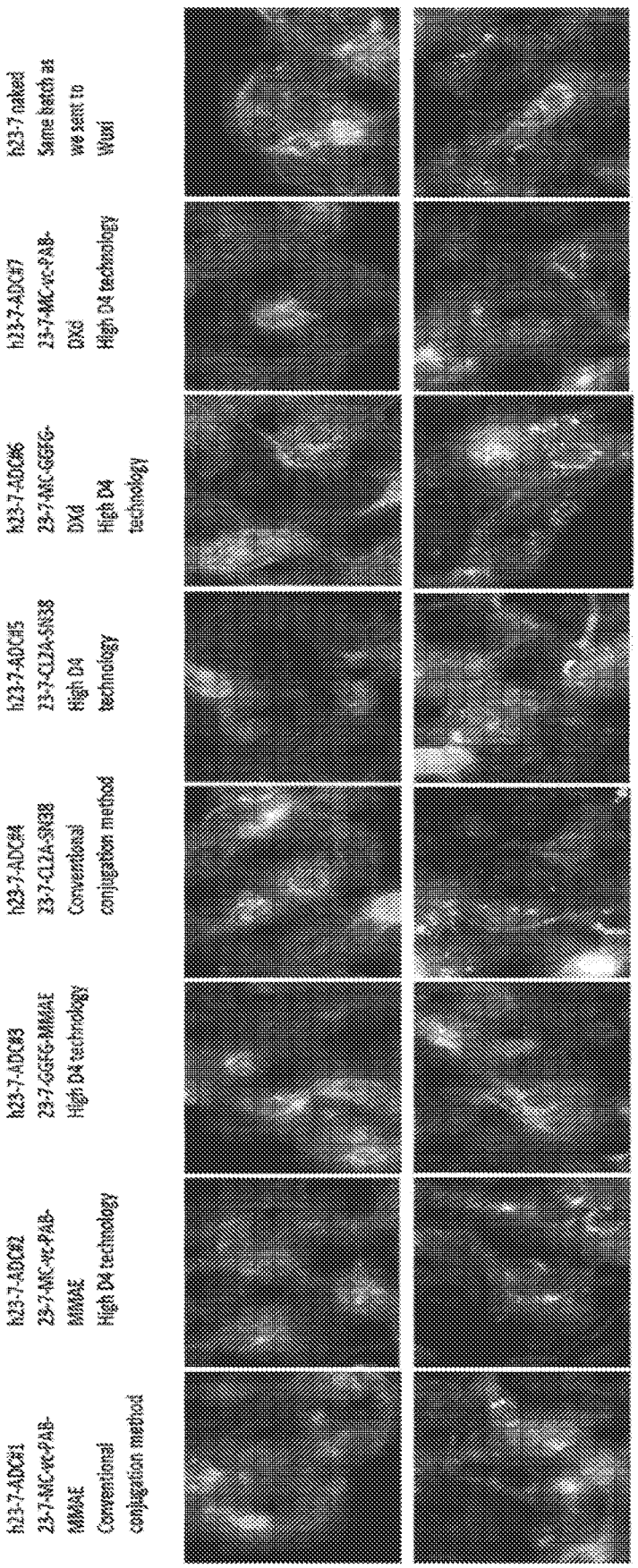
FIG. 38 shows the in vitro characterization of the CLDN6 ADCs comprising AB3-7. The panels demonstrate cell internalization of CLDN6 ADCs. H23-7 refers to AB3-7.
Figure 39D:
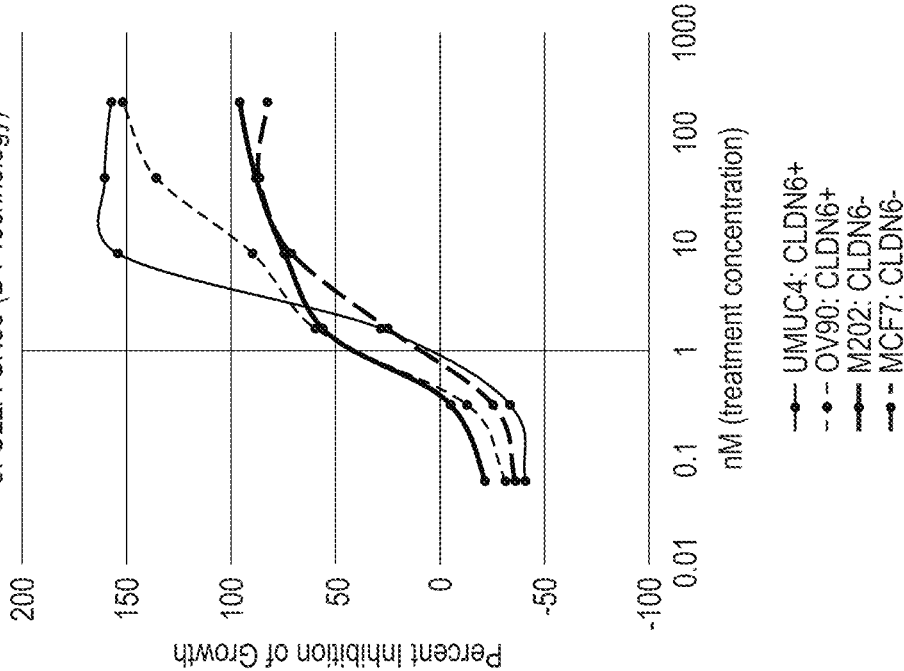
Figure 39E:
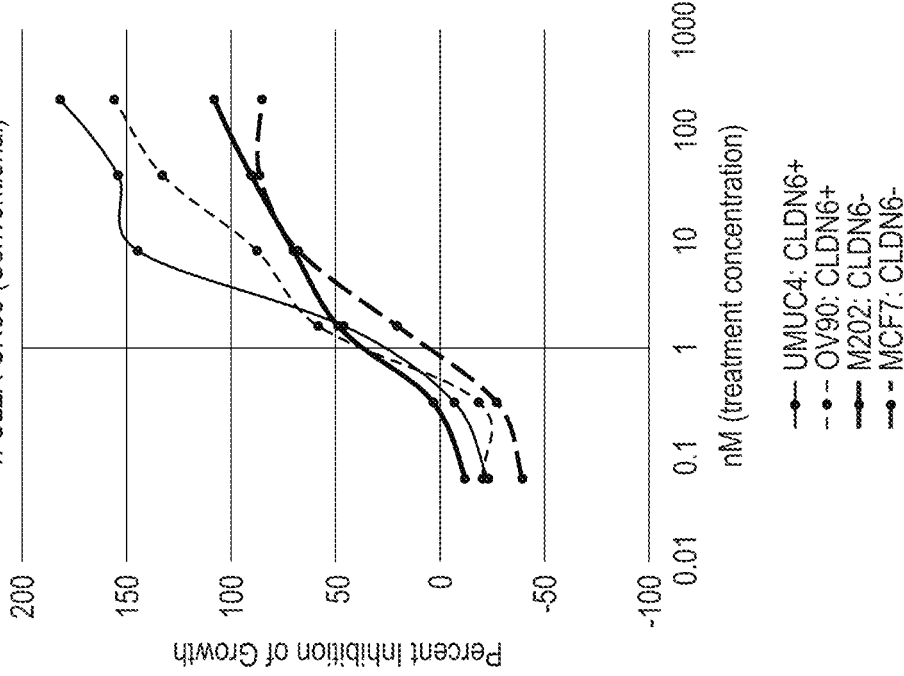
Figure 39F:
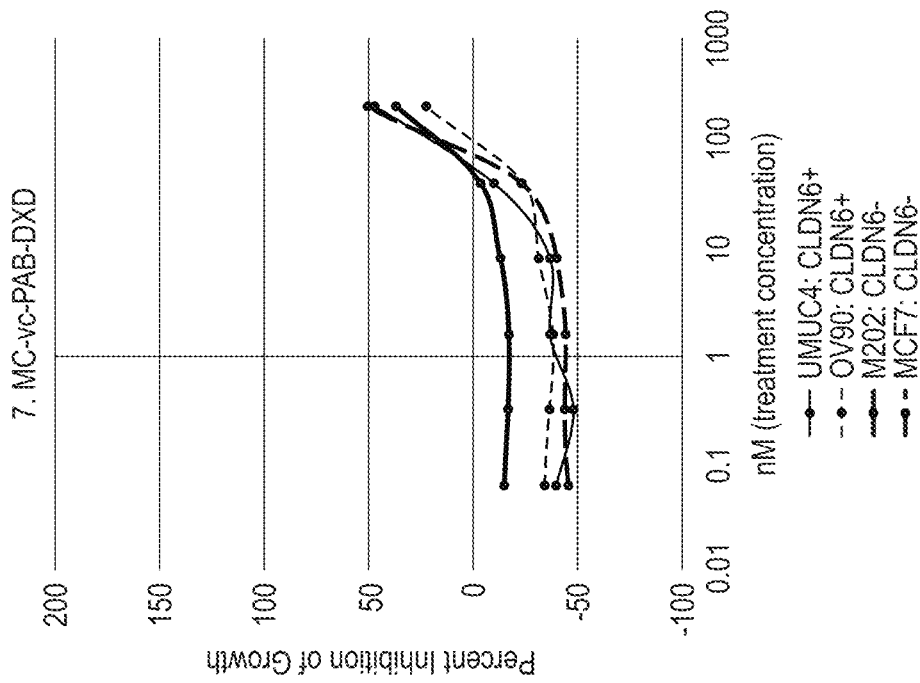
Figure 39G:
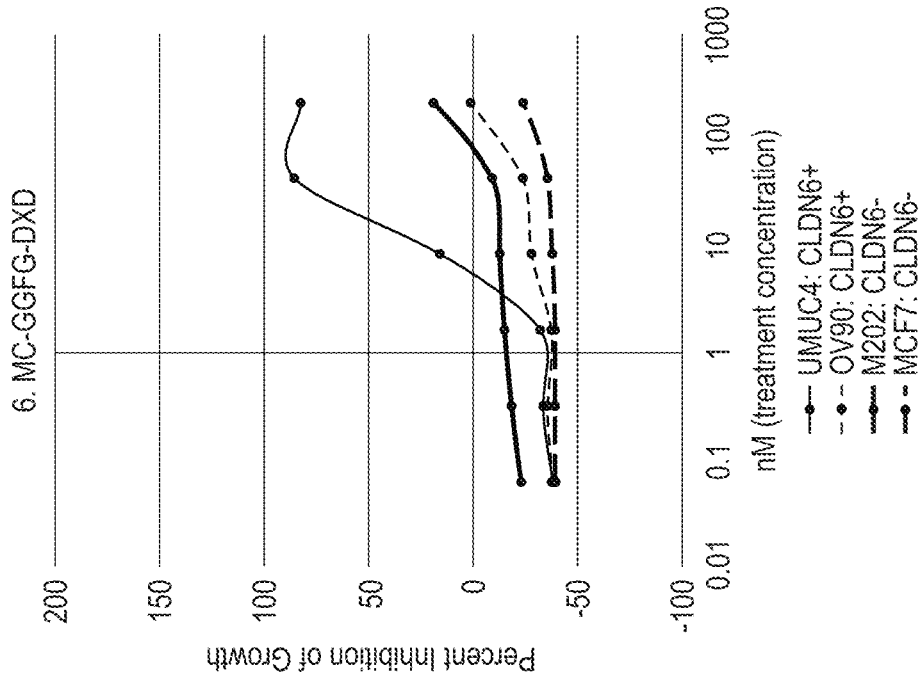
Figure 39H:
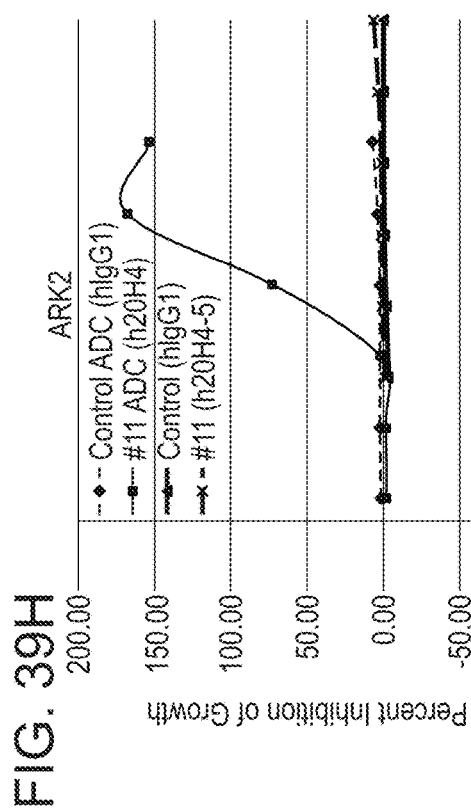
Figure 39I:
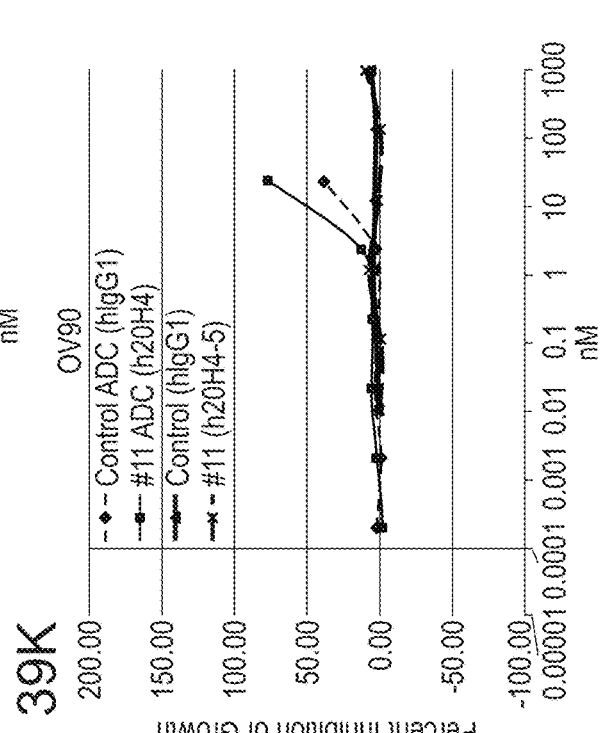
Figure 39J:
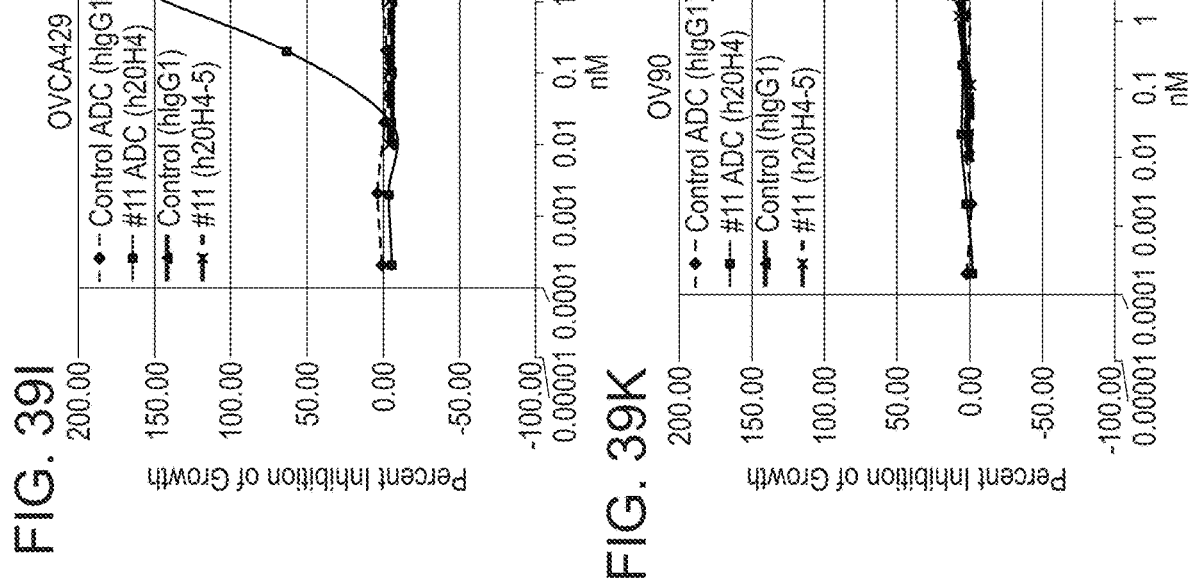
Figure 39K:
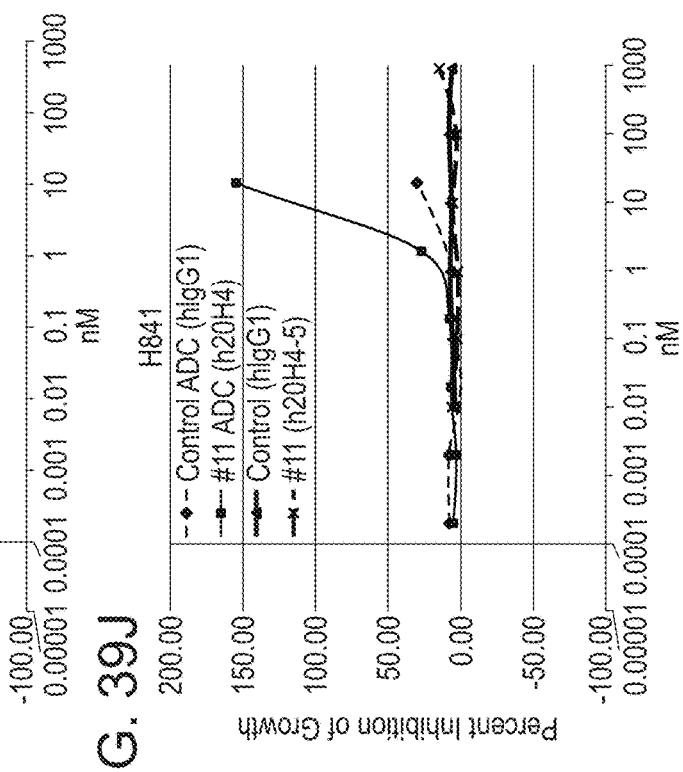
Figure 39M:
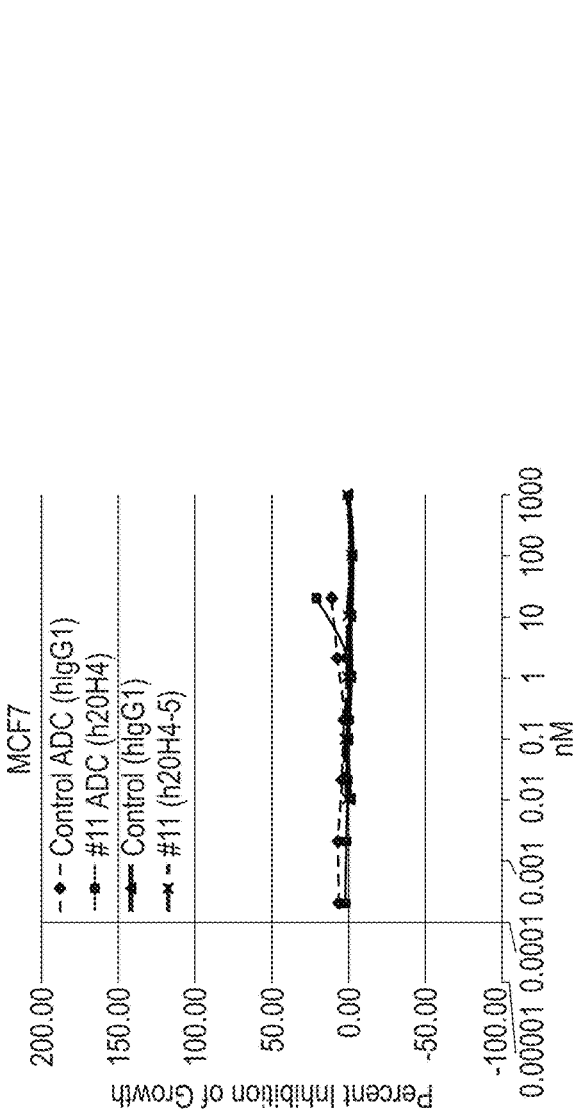
Figure 39L:
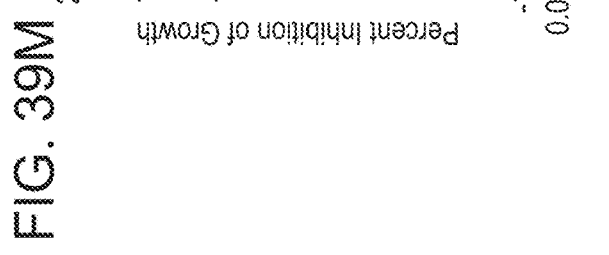
Figure 39N:
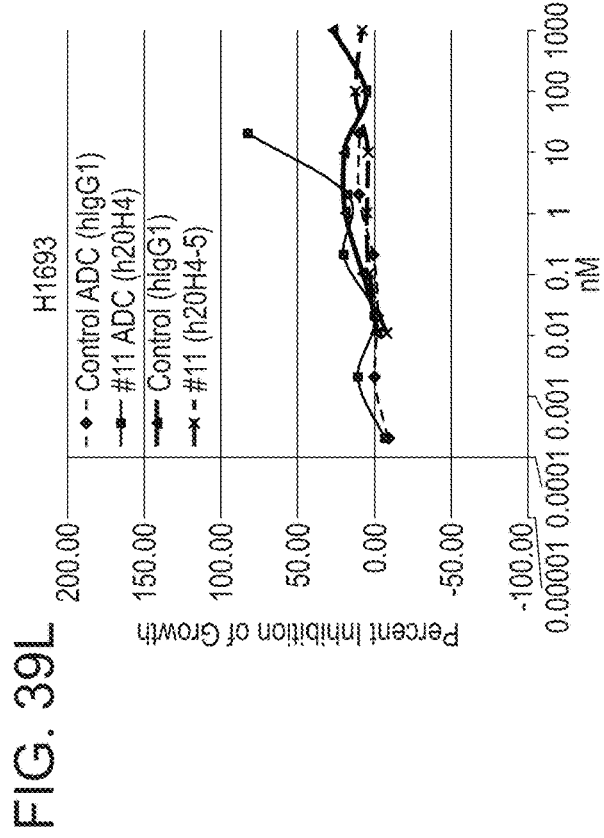

FIG. 38 shows that the CLDN6 ADCs comprising AB3-7 are internalized efficiently by cancer cells, an important step in the activation of ADCs. Specifically, ARK2 cells (uterine carcinosarcoma expressing CLDN6) were stained with nucleus (blue), lysosome (green) and the CLDN6 ADCs (red). Images on the top panels were taken at an early stage (within 30 min after the ADC/antibody staining), and those on the lower panels were taken at a later stage (between 5-6 hours after the ADC/antibody staining) to show the internalization of CLDN6 complexed with ADC or unconjugated antibody. As demonstrated in FIG. 38, conjugation did not change the antibody internalization rates in comparison with those of its unconjugated antibody AB3-7.

Example 15

This Example demonstrates the in vitro anti-cancer activity of CLDN6 ADCs against cancer cells.

FIG. 39A-FIG. 39G show the 2D anti-proliferative effect of different CLDN6 ADCs comprising AB3-7 on cancer cells. The anti-proliferative activity of the CLDN6 ADCs were tested against four cancer cell lines; CLDN6-positive cell lines (UMUC4, OV90) and CLDN6-negative cell lines (MCF7, M202). Each cell line was seeded uniformly into wells of 48-well plates, ranging from 300-1000 cells per well. After 48 hrs, a baseline measurement of the number of cells per well per cell line was measured. The remaining wells of cells were treated with a 1:5 serial dilution of 6 drug concentrations, resulting in a final treatment concentration ranging from 200 nM (30 ng/mL) to 0.064 nm (0.0096 ng/mL). After 7 days, the anti-proliferative activity was assessed by comparing the counts of cells in the treated versus control untreated.

As demonstrated in FIG. 39A-FIG. 39G, the CLDN6 ADCs comprising MC-VC-PAB-MMAE (conventional) and MC-VC-PAB-MMAE (D4 technology) were comparable in exhibiting the greatest anti-proliferative potency and specificity against the CLDN6-positive cells (UMUC4). The CLDN6 ADCs comprising CL2A-SN38 (conventional) and CL2A-SN38 (D4 technology) exhibited equally similar anti-proliferative potency but was nonspecific, killing indiscriminately between the CLDN6-positive cells and CLDN6-negative cells. The CLDN6 ADCs comprising MC-GGFG-MMAE showed low anti-proliferative potency with specificity against the CLDN6-positive cells (UMUC4). The CLDN6 ADCs comprising MC-GGFG-DXD and MC-VC-PAB-DXD show no anti-proliferative effect against any cell line.

FIG. 39H-FIG. 39N show the 2D anti-proliferative effect of the CLDN6 comprising AB1-11 conjugated to VC-PAB-MMAE (ADC-11) against various cell lines. Specifically, four cell lines were tested: CLDN6-positive cell lines (ARK2, OVCA429, H841, OV90, H1693) and CLDN6-negative cell lines (MCF7, M202). Each cell line was seeded uniformly into wells of 48-well plates, ranging from 300-1000 cells per well. After 48 hrs, a baseline measurement of the number of cells per well per cell line was measured. The remaining wells of cells were treated with 1:5 serial dilutions of (a) CLDN6-targeting ADC-11, (b) a control ADC (a non-targeting IgG conjugated to VC-PAB-MMAE), (c) an unconjugated non-targeting IgG, and (d) unconjugated AB1-11, resulting in the final treatment concentration ranging from 1000 nM (150 ng/mL) to 0.32 nM (0.0048 ng/mL). After 7 days, the anti-proliferative activity was assessed by comparing the counts of cells in the treated versus untreated control.

As demonstrated in FIG. 39H-FIG. 39N, ADC-11 exhibited robust anti-proliferative activity against CLDN6-positive cell lines (ARK2, OVCA429, H841, OV90, H1693) with no activity against the CLDN6-negative cell lines (M202 and MCF7).

Example 16

This Example shows the in vivo anti-cancer efficacy of CLDN6 ADCs against cancer cell line xenografts.

For all in vivo experiments, tumor xenografts were measured with calipers 3 times/week, and the tumor volume in $mm^3$ was determined by multiplying height×width×length. All animal work was carried out under a protocol approved by IACUC and the UCLA Animal Research Committee. Data were analyzed using the StudyLog software from StudyDirector (San Francisco, CA).

FIG. 40 shows the anti-cancer efficacy of a CLDN6 ADC against CLDN6-positive ovarian cancer cell line (OV90) xenografts. The CLDN6 ADC tested herein comprises a humanized AB1-11 conjugated to VC-PAB-MMAE (ADC-11; conventional). The OV90 ovarian cancer cell line xenografts were established in six-week-old CD-1 athymic nude mice (Charles River Laboratories) by subcutaneous injection of $1.0 \times 10^7$ cells with 50% matrigel (BD Biosciences) into the right rear flank of the animal. When tumors reached an average size of 100-200 $mm^3$, mice (n=8) were randomized into treatment groups of either 1) non-targeting human IgG1 control antibody at 10 mg/kg QW IV 4 weeks, 2) humanized CLDN6-AB1-11 (HU-11) at 10 mg/kg QW IV (intravenous injection) for 4 weeks, 3) ADC-11 at 5 mg/kg QW IV for 3 weeks, and 4) non-targeting control ADC 5 mg/kg QW IV for 3 weeks. Xenografts were followed post-dosing until tumor progression. Treatment with the CLDN6 ADC resulted in xenograft tumor regression. The activity of the CLDN6 ADC is superior to that observed with the unconjugated CLDN6 mAb or non-targeting control ADC.

Figure 41B:
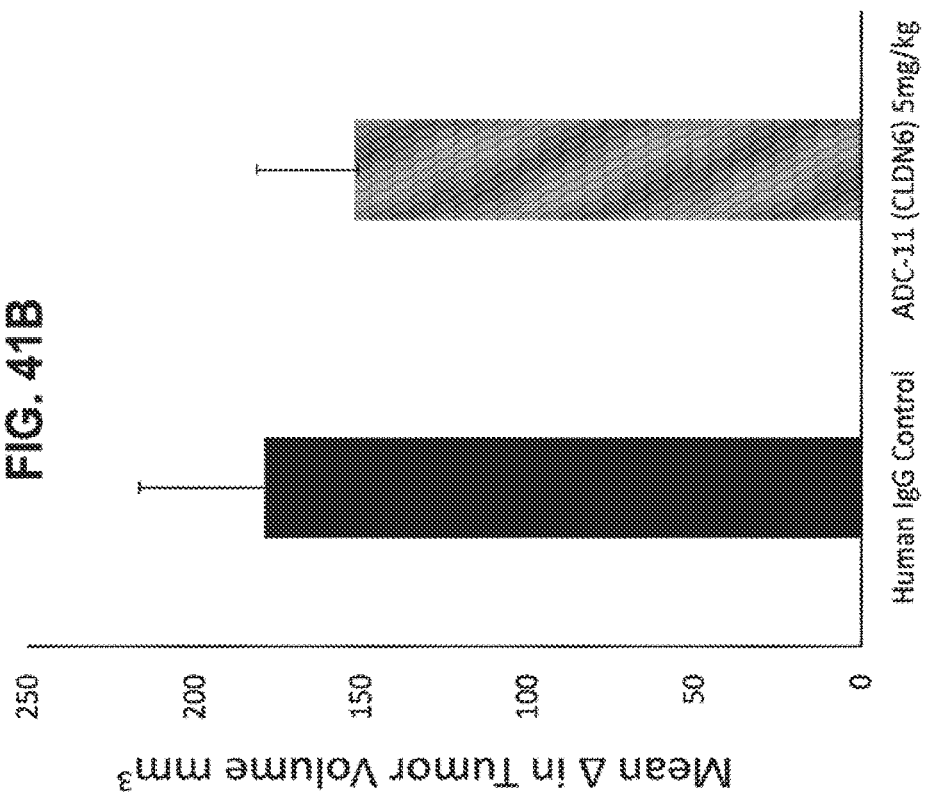
FIG. 41A-FIG. 41B show no anti-cancer activity of CLDN6 ADC-11 against CLDN6-negative melanoma cancer cell line (M202) xenografts.
Figure 41A:
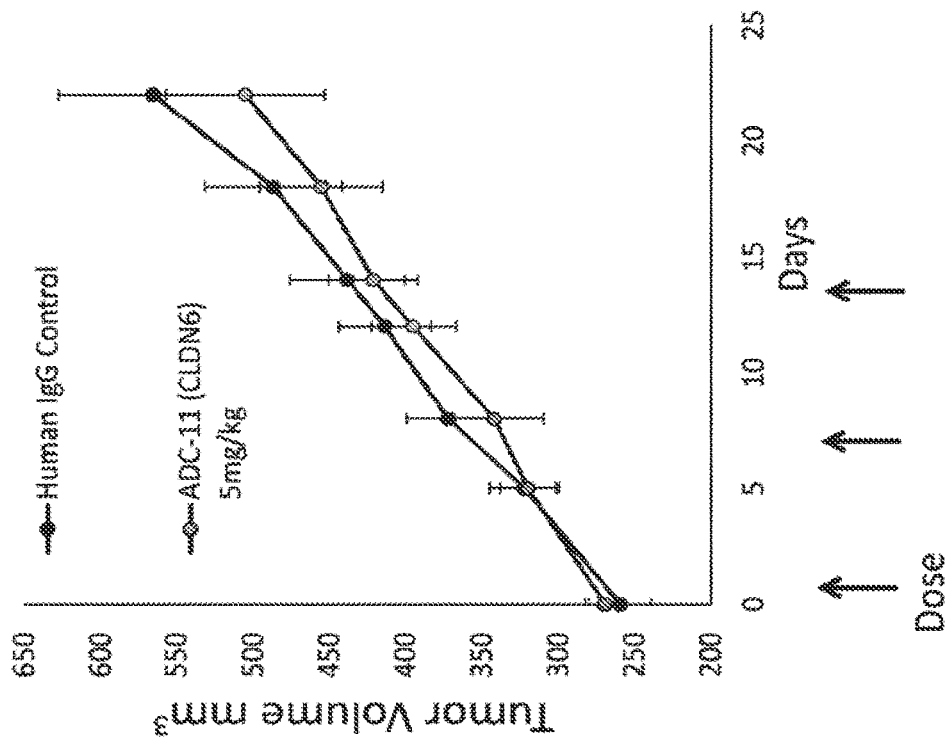

FIG. 41A-FIG. 41B show no anti-cancer activity of CLDN6 ADC-11 (conventional) against CLDN6-negative melanoma cancer cell line (M202) xenografts. ADC-11 did not show any anti-cancer activity in M202 cell line xenografts that do not express CLDN6. The M202 melanoma cancer cell line xenografts were established in six-week-old CD-1 athymic nude mice (Charles River Laboratories) by subcutaneous injection of $1.0 \times 10^7$ cells with 50% matrigel (BD Biosciences) into the right rear flank of the animal. When tumors reached an average size of 100-300 mm$^3$, mice (n=8) were randomized into treatment groups of either 1) non-targeting human IgG1 control antibody at 10 mg/kg QW IV 4 weeks or 2) ADC-11 at 5 mg/kg QW IV for 3 weeks. The lack of anti-cancer activity of the CLDN6 ADC against CLDN6-negative xenografts demonstrates the specificity of the CLDN6 ADC activity.

Figure 42B:
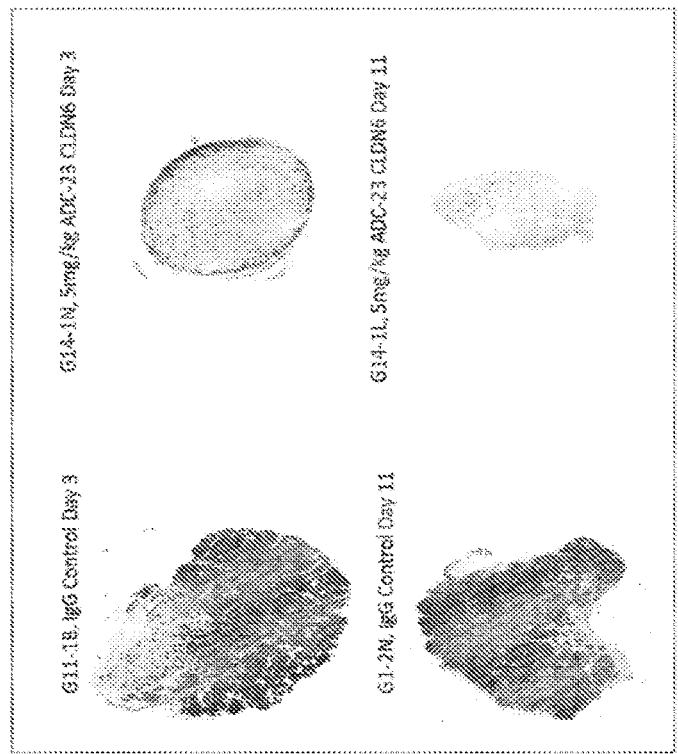
FIG. 42A-FIG. 42B show the in vivo anti-cancer efficacy of the CLDN6 ADC-23 (AB3-7-VC-PAB-MMAE) against cancer cell line xenografts.
Figure 42A:
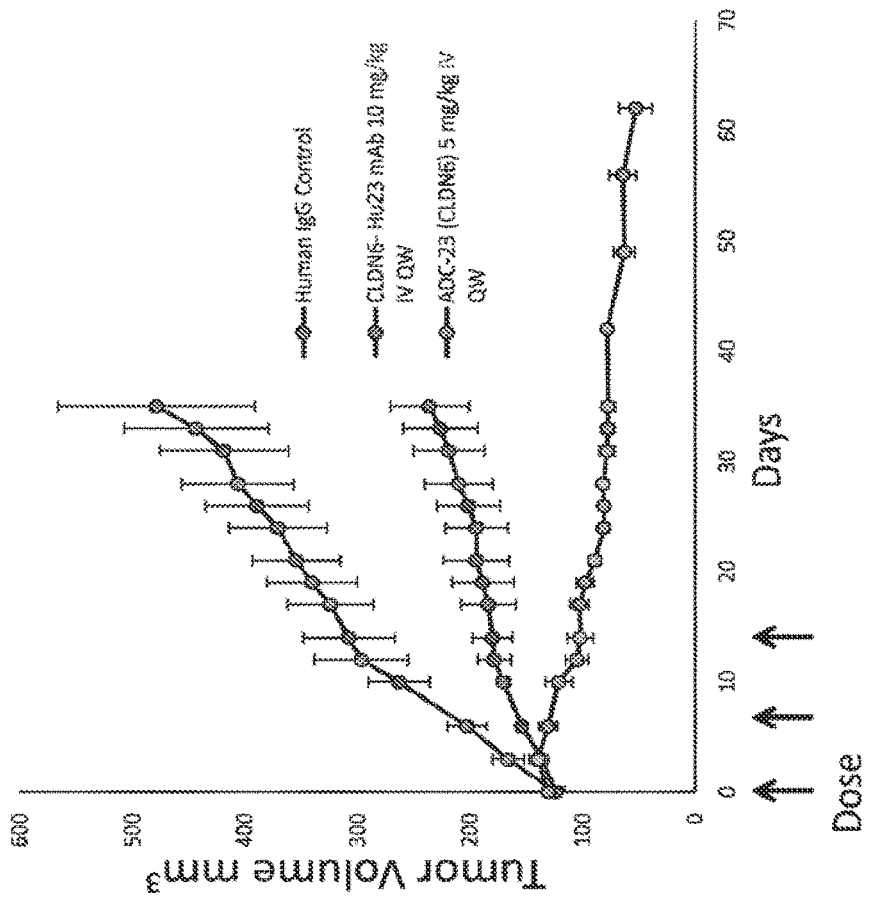

FIG. 42A-FIG. 42B show the in vivo anti-cancer efficacy of CLDN6 ADC-23 against cancer cell line xenografts. The CLDN6 ADC tested herein comprises humanized AB3-7 conjugated to VC-PAB-MMAE (ADC-23; conventional). FIG. 42A shows that CLDN6 ADC-23 is efficacious against CLDN6-positive bladder cell line (UMUC4) xenografts. Specifically, the UMUC4 bladder cancer cell line xenografts were established in six-week-old CD-1 athymic nude mice (Charles River Laboratories) by subcutaneous injection of $1.0 \times 10^7$ cells with 50% matrigel (BD Biosciences) into the right rear flank of the animal. When tumors reached an average size of 100-200 mm$^3$, mice (n=8) were randomized into treatment groups of either 1) non-targeting human IgG1 (Hu-IgG1) control antibody at 10 mg/kg once per week (QW IV) for 4 weeks, 2) humanized CLDN6 AB3-7 antibody (Hu23) at 10 mg/kg QW IV for 4 weeks, 3) ADC-23 at 5 mg/kg QW IV for 3 weeks. Xenografts were followed post-dosing until tumor progression or 60 days post initiation of the treatment. FIG. 42B shows Haemotoxylin and Eosin (H&E) stain of the xenograft tissues collected at the indicated time points post-treatment with either Hu-IgG1 control antibody or 5 mg/kg ADC-23. Histopathological analysis of the xenograft tissue collected during the study showed that epithelial-tumor cell content was lost in ADC-23-treated mice (FIG. 42B).

Treatment with the CLDN6 ADC-23 resulted in xenograft tumor regressions in the UMUC4 CLDN6-positive cell line xenografts. The data presented in FIG. 42A-FIG. 42B and those presented above demonstrate that both CLDN6 ADCs (ADC-11 and ADC-23) are effective in targeting CLDN6-positive cell line xenografts.

Example 17

This Example shows the in vivo anti-cancer activity of CLDN6 ADC-23 against patient-derived xenografts (PDX).

Figure 43A:
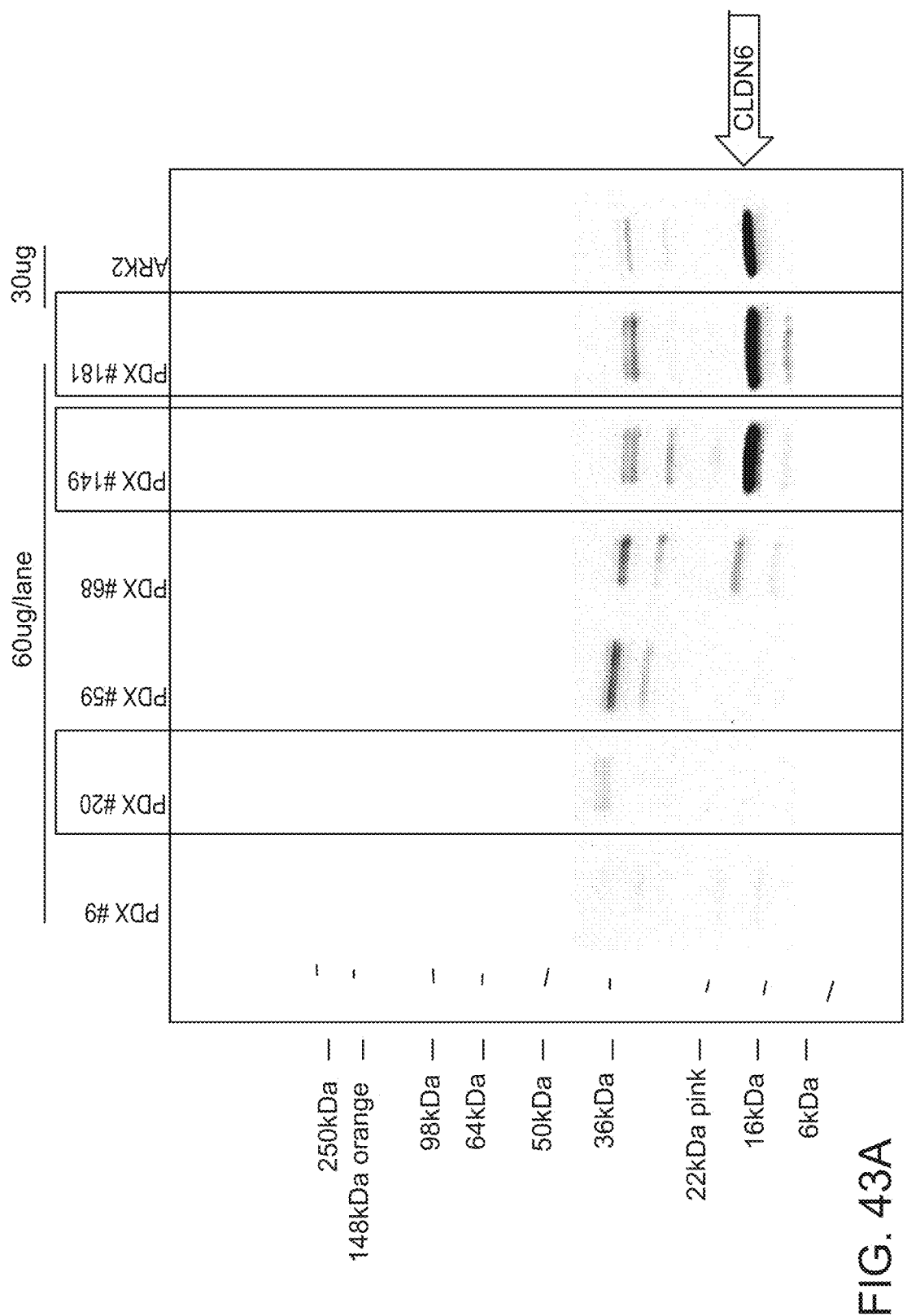
FIG. 43A-FIG. 43E show the in vivo anti-cancer efficacy of the CLDN6 ADC-23 against ovarian cancer patient-derived xenografts (PDX).
Figure 43B:
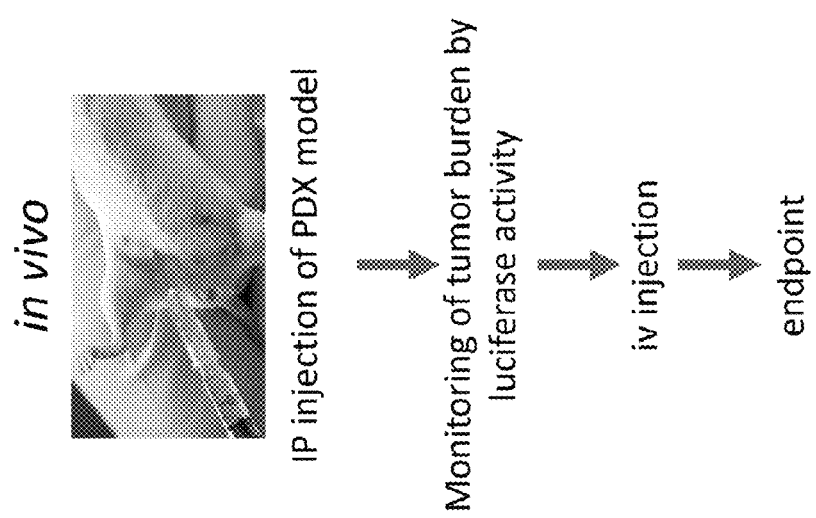
Figure 43C:
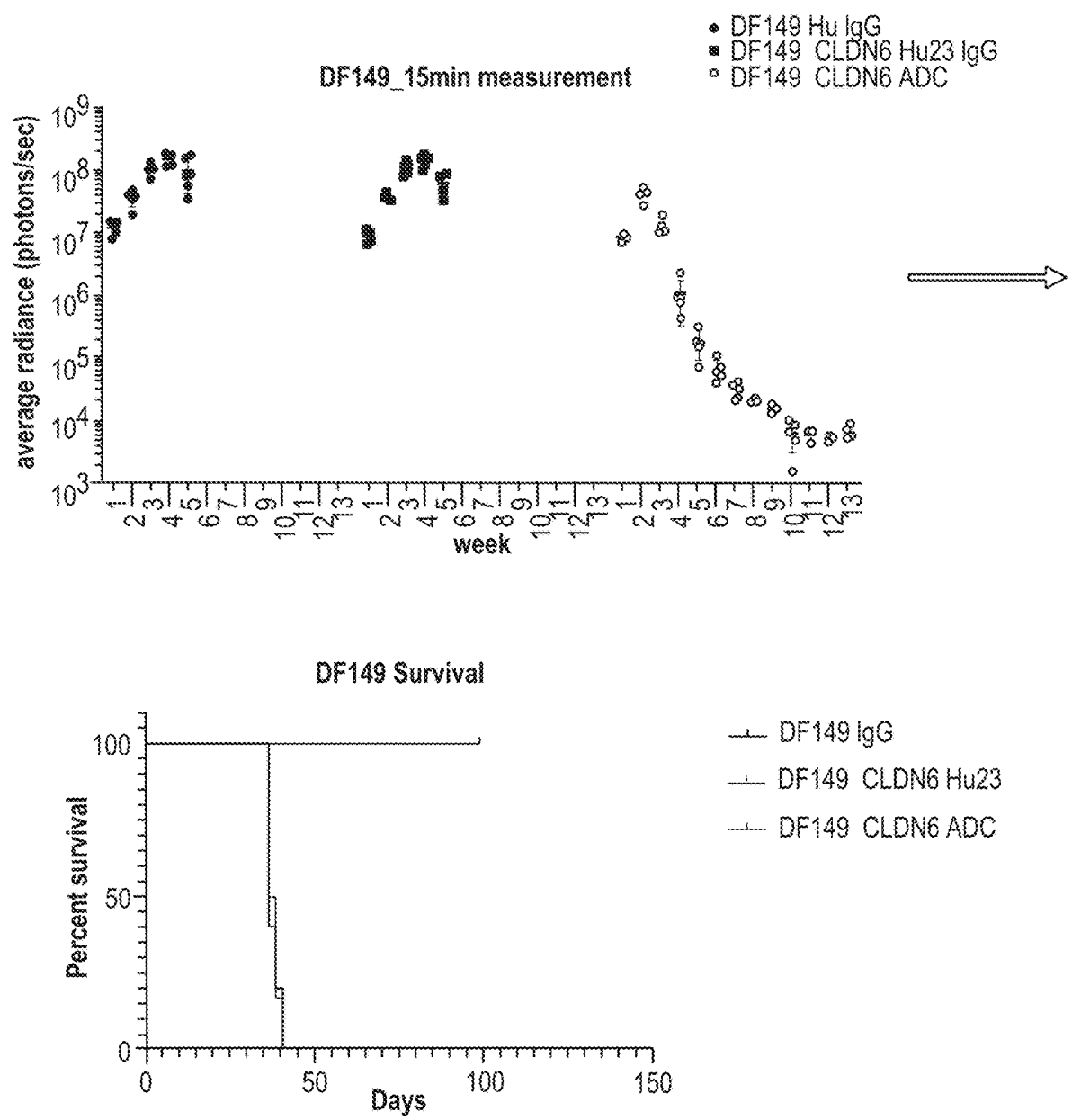
Figure 43D:
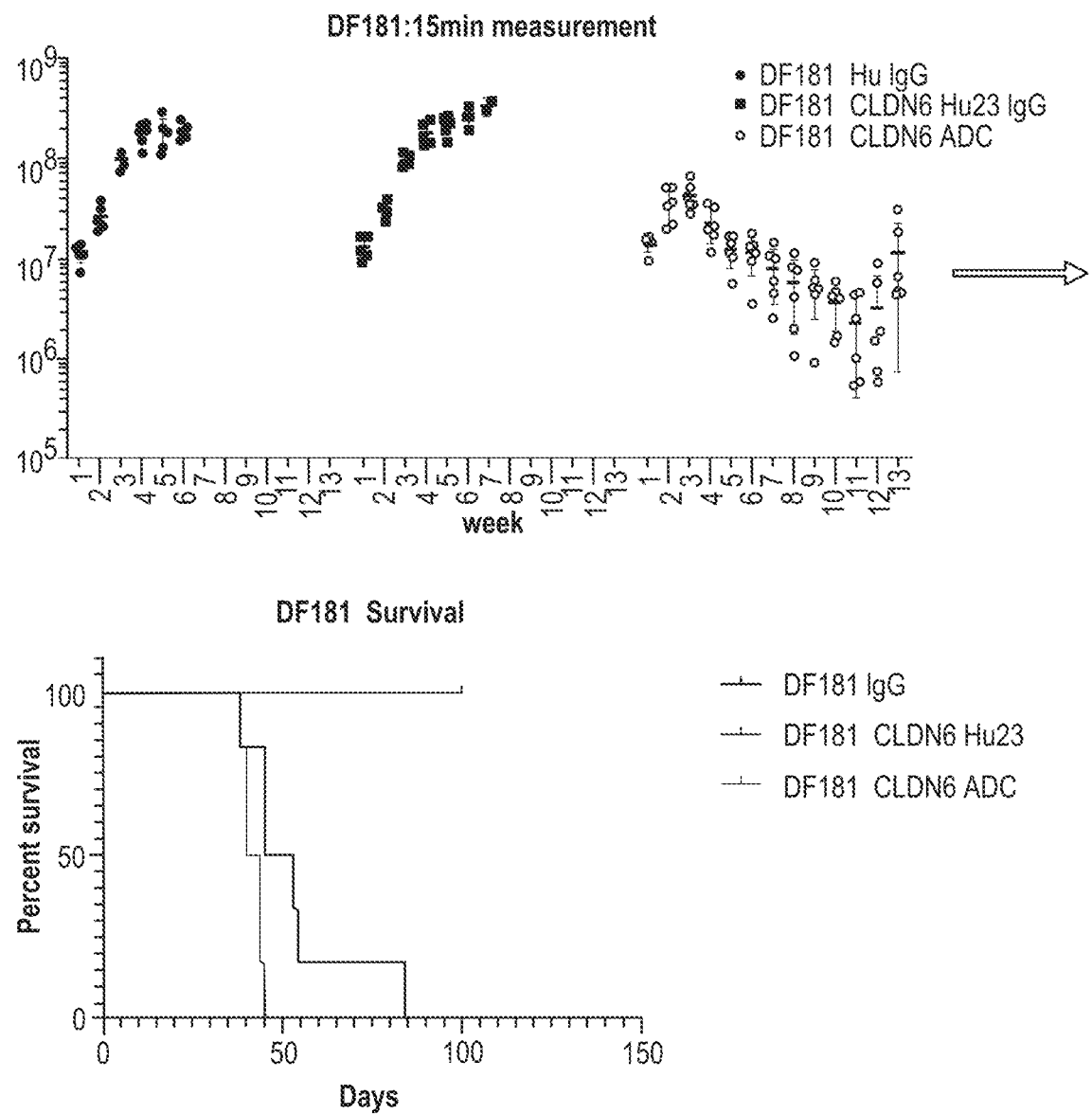
Figure 43E:
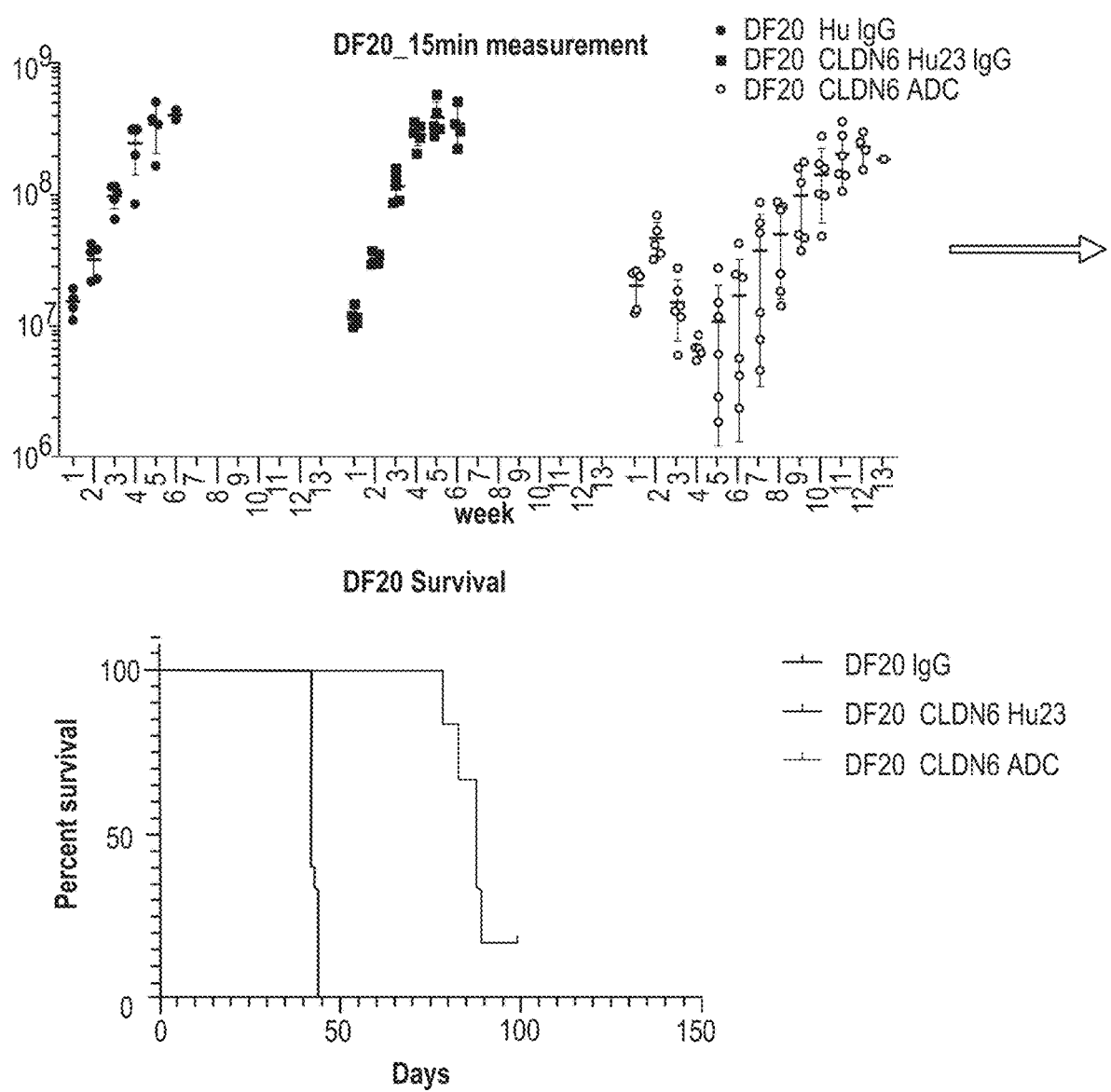

FIG. 43A-FIG. 43E show the in vivo anti-cancer efficacy of CLDN6 ADC-23 (conventional) against ovarian cancer PDX models. Specifically, a panel of ovarian PDX samples was screened for CLDN6 protein expression by the Western blot analysis (FIG. 43A). Two CLDN6-positive (DF189 & DF181) and one CLDN6-negative (DF20) samples were selected for the study. Ovarian cancer cells from each PDX were transfected with the luciferase enzyme before injection into the intraperitoneal space of immunocompromised mice (NSG) (FIG. 43B). FIG. 43C-FIG. 43E show the luciferase activity output that was measured once per week in mice treated with (1) non-targeting Hu-IgG1 control antibody at 10 mg/kg QW IV 4 weeks, (2) humanized CLDN6 AB3-7 at 10 mg/kg QW IV for 4 weeks, or (3) ADC-23 at 5 mg/kg QW IV for 3 weeks. The mice treated with Hu-IgG1 control or CLDN6 AB3-7 mAb showed a continuous increase in tumor burden in the intraperitoneal space until the mice had to be euthanized at approximately 50 days post-implantation of the cancer cells for each of the PDX models tested. However, mice treated with ADC-23 showed a significant reduction in tumor burden and a significant improvement in overall survival. These responses were limited to mice injected with the CLDN6-positive ovarian cancer cells (FIG. 43C and FIG. 43D). The DF20 CLDN6 negative model showed only a limited benefit to treatment with no impact on overall survival (FIG. 43E).

Example 18

This Example shows the dose-dependent activity of CLDN6 ADC-23.

FIG. 44A-FIG. 44C show the dose-dependent anti-cancer activity of CLDN6 ADC-23 (D4 technology) against the CLDN6-positive ovarian cancer cell line (OV90) xenografts. The OV90 ovarian cancer cell line xenografts were established in six-week-old CD-1 athymic nude mice (Charles River Laboratories) by subcutaneous injection of $1.0 \times 10^7$ cells with 50% matrigel (BD Biosciences) into the right rear flank of the animal. When tumors reached an average size of ~200 mm$^3$, mice (n=6) were randomized into treatment groups. Mice with OV90 xenografts were treated with various doses ranging from 0.1 mg/kg to 2.5 mg/kg IV QW for 3 weeks. A reduction in anti-tumor activity was observed as the dosing concentration was decreased. Treatment with 2.5 mg/kg of CLDN6 ADC-23 induced uniform xenograft regressions (FIG. 44A and FIG. 44B). No impact on mouse body weight was observed in response to the treatment with CLDN6 ADC-23 at any dose given (FIG. 44C). Thus, the selective and dose-dependent activity of the novel CLDN6 ADC-23 was confirmed in the CLDN6-positive ovarian cancer cell line xenografts.

FIG. 45A-FIG. 45C show that there is no off-target activity of the CLDN6 ADC-23 (D4 technology) in the CLDN6-negative melanoma cancer cell line (M202) xenografts. The M202 melanoma cancer cell line xenografts were established in six-week-old CD-1 athymic nude mice (Charles River Laboratories) by subcutaneous injection of $1.0 \times 10^7$ cells with 50% matrigel (BD Biosciences) into the right rear flank of the animal. When tumors reached an average size of ~200 mm$^3$, mice (n=6) were randomized into treatment groups. Mice bearing the M202 melanoma xenografts were treated with various doses ranging from 0.1 mg/kg to 2.5 mg/kg IV QW for 3 weeks. No anti-cancer activity of the CLDN6 ADC against CLDN6-negative M202 xenografts was observed at any dose given (FIG. 45A-FIG. 45B). No impact on mouse body weight was observed in response to the treatment with CLDN6 ADC at any dose given (FIG. 45C).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or various language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. An antigen-binding protein that binds to a human Claudin6 (CLDN6) protein (SEQ ID NO: 200) and comprises
    (i) HC CDR1 comprising GFTFSNYW (SEQ ID NO: 23),
    (ii) HC CDR2 comprising IRLKSDNYAT (SEQ ID NO: 24),
    (iii) HC CDR3 comprising NDGPPSGX (SEQ ID NO: 457), wherein X at position 8 is selected from the group consisting of S, T, A, C, and Y;
    (iv) LC CDR1 comprising ENIYSY (SEQ ID NO: 20),
    (v) LC CDR2 comprising NAK (SEQ ID NO: 21), and
    (vi) LC CDR3 comprising QHHYTVPWT (SEQ ID NO: 22).

2. The antigen-binding protein of claim 1, wherein X is S whereby HC CDR3 comprises NDGPPSGS of SEQ ID NO: 457.

3. The antigen-binding protein of claim 1, wherein X is T whereby HC CDR3 comprises NDGPPSGT of SEQ ID NO: 457.

4. The antigen-binding protein of claim 1, wherein X is A whereby HC CDR3 comprises NDGPPSGA of SEQ ID NO: 457.

5. The antigen-binding protein of claim 1, wherein X is C whereby HC CDR3 comprises NDGPPSGC of SEQ ID NO: 457.

6. The antigen-binding protein of claim 1, wherein X is Y whereby HC CDR3 comprises NDGPPSGY of SEQ ID NO: 457.

7. The antigen-binding protein of claim 1, wherein the antigen-binding protein is an antigen-binding antibody fragment.

8. The antigen-binding protein of claim 7, wherein the antigen-binding antibody fragment is selected from the group consisting of scFv, F(ab')2, Fab, Fab', and Fv.

9. The antigen-binding protein of claim 1, wherein the antigen-binding protein is an antibody.

10. The antigen-binding protein of claim 9, wherein the antibody is a monoclonal antibody.

11. The antigen-binding protein of claim 9, wherein the antibody is a human antibody, a humanized antibody, or a chimeric antibody.

12. The antigen-binding protein of any one of claims 9-11, wherein the antibody is an IgG.

13. The antigen-binding protein of claim 12, wherein the IgG is selected from the group consisting of IgG1, IgG2, IgG3, and IgG4.

14. The antigen-binding protein of claim 13, wherein the IgG is IgG1.

15. A pharmaceutical composition comprising an antigen-binding protein that binds to a human Claudin6 (CLDN6) protein (SEQ ID NO: 200) and comprises:
    (i) HC CDR1 comprising GFTFSNYW (SEQ ID NO: 23),
    (ii) HC CDR2 comprising IRLKSDNYAT (SEQ ID NO: 24),
    (iii) HC CDR3 comprising NDGPPSGX (SEQ ID NO: 457), wherein X at position 8 is selected from the group consisting of S, T, A, C, and Y;
    (iv) LC CDR1 comprising ENIYSY (SEQ ID NO: 20),
    (v) LC CDR2 comprising NAK (SEQ ID NO: 21), and
    (vi) LC CDR3 comprising QHHYTVPWT (SEQ ID NO: 22),
and a pharmaceutically acceptable carrier, diluent, and/or excipient.

16. The pharmaceutical composition of claim 15, wherein X is S whereby HC CDR3 comprises NDGPPSGS of SEQ ID NO: 457.

17. The pharmaceutical composition of claim 15, wherein X is T whereby HC CDR3 comprises NDGPPSGT of SEQ ID NO: 457.

18. The pharmaceutical composition of claim 15, wherein X is A whereby HC CDR3 comprises NDGPPSGA of SEQ ID NO: 457.

19. The pharmaceutical composition of claim 15, wherein X is C whereby HC CDR3 comprises NDGPPSGC of SEQ ID NO: 457.

20. The pharmaceutical composition of claim 15, wherein X is Y whereby HC CDR3 comprises NDGPPSGY of SEQ ID NO: 457.

21. The pharmaceutical composition of claim 15, wherein the antigen-binding protein is an antigen-binding antibody fragment.

22. The pharmaceutical composition of claim 21, wherein the antigen-binding antibody fragment is selected from the group consisting of scFv, F(ab')2, Fab, Fab', and Fv.

23. The pharmaceutical composition of claim 15, wherein the antigen-binding protein is an antibody.

24. The pharmaceutical composition of claim 23, wherein the antibody is a monoclonal antibody.

25. The pharmaceutical composition of claim 23, wherein the antibody is a human antibody, a humanized antibody, or a chimeric antibody.

26. The pharmaceutical composition of any one of claims 23-25, wherein the antibody is an IgG.

27. The pharmaceutical composition of claim 26, wherein the IgG is selected from the group consisting of IgG1, IgG2, IgG3, and IgG4.

28. The pharmaceutical composition of claim 27, wherein the IgG is IgG1.

29. The pharmaceutical composition of any one of claims 15 and 16-25, further comprising a cytotoxic agent or a chemotherapeutic agent conjugated to the antigen-binding protein.

30. The pharmaceutical composition of claim 29, further comprising a linker located between the antigen-binding protein and the cytotoxic or chemotherapeutic agent.

31. The conjugate of claim 30, wherein the linker is a cleavable linker.

32. The pharmaceutical composition of claim 31, wherein the cleavable linker comprises VC-PAB.

33. The pharmaceutical composition of claim 32, wherein the cleavable linker comprises MC-VC-PAB.

34. The pharmaceutical composition of claim 29, wherein the cytotoxic or chemotherapeutic agent is an anti-mitotic agent that inhibits cell division by blocking tubulin polymerization.

35. The pharmaceutical composition of claim 34, wherein the anti-mitotic agent is an auristatin.

36. The pharmaceutical composition of claim 35, wherein the auristatin is MMAE.

37. The pharmaceutical composition of claim 29, wherein the antigen-binding protein is conjugated to MMAE via a cleavable linker comprising VC-PAB.

38. A conjugate comprising an antigen-binding protein that binds to a human Claudin6 (CLDN6) protein (SEQ ID NO: 200) and comprises:
(i) HC CDR1 comprising GFTFSNYW (SEQ ID NO: 23),
(ii) HC CDR2 comprising IRLKSDNYAT (SEQ ID NO: 24),
(iii) HC CDR3 comprising NDGPPSGX (SEQ ID NO: 457), wherein X at position 8 is selected from the group consisting of S, T, A, C, and Y;
(iv) LC CDR1 comprising ENIYSY (SEQ ID NO: 20),
(v) LC CDR2 comprising NAK (SEQ ID NO: 21), and
(vi) LC CDR3 comprising QHHYTVPWT (SEQ ID NO: 22),
wherein the antigen-binding protein is conjugated to a cytotoxic or chemotherapeutic agent.

39. The conjugate of claim 38, wherein X is S whereby HC CDR3 comprises NDGPPSGS of SEQ ID NO: 457.

40. The conjugate of claim 39, wherein the antigen-binding protein is conjugated to MMAE via a cleavable linker comprising MC-VC-PAB.

41. The conjugate of claim 38, wherein X is T whereby HC CDR3 comprises NDGPPSGT of SEQ ID NO: 457.

42. The conjugate of claim 38, wherein X is A whereby HC CDR3 comprises NDGPPSGA of SEQ ID NO: 457.

43. The conjugate of claim 38, wherein X is C whereby HC CDR3 comprises NDGPPSGC of SEQ ID NO: 457.

44. The conjugate of claim 38, wherein X is Y whereby HC CDR3 comprises NDGPPSGY of SEQ ID NO: 457.

45. The conjugate of claim 38, wherein the antigen-binding protein is an antigen-binding antibody fragment.

46. The conjugate of claim 45, wherein the antigen-binding antibody fragment is selected from the group consisting of scFv, F(ab')2, Fab, Fab', and Fv.

47. The conjugate of claim 38, wherein the antigen-binding protein is an antibody.

48. The conjugate of claim 47, wherein the antibody is a monoclonal antibody.

49. The conjugate of claim 47, wherein the antibody is a human antibody, a humanized antibody, or a chimeric antibody.

50. The conjugate of any one of claims 47-49, wherein the antibody is an IgG.

51. The conjugate of claim 50, wherein the IgG is selected from the group consisting of IgG1, IgG2, IgG3, and IgG4.

52. The conjugate of claim 51, wherein the IgG is IgG1.

53. The conjugate of claim 38, further comprising a linker located between the antigen-binding protein and the cytotoxic or chemotherapeutic agent.

54. The conjugate of claim 53, wherein the linker is a cleavable linker.

55. The conjugate of claim 54, wherein the cleavable linker comprises an L-Valine-L-Citrulline-p-aminobenzyl group (VC-PAB).

56. The conjugate of claim 55, wherein the cleavable linker comprises a maleimidocaproyl-L-Valine-L-Citrulline-p-aminobenzyl group (MC-VC-PAB).

57. The conjugate of claim 38, wherein the cytotoxic or chemotherapeutic agent is an anti-mitotic agent that inhibits cell division by blocking tubulin polymerization.

58. The conjugate of claim 57, wherein the anti-mitotic agent is an auristatin.

59. The conjugate of claim 58, wherein the auristatin is monomethyl auristatin E (MMAE).

* * * * *

SEQUENCE LISTING

```
<160> NUMBER OF SEQ ID NOS: 513

<210> SEQ ID NO 1
<211> LENGTH: 220
<212> TYPE: PRT
<213> ORGANISM: Homo sapiens
<300> PUBLICATION INFORMATION:
<308> DATABASE ACCESSION NUMBER: NCBI / NP_067018.2
<309> DATABASE ENTRY DATE: 2017-06-04
<313> RELEVANT RESIDUES IN SEQ ID NO: (1)..(220)

<400> SEQUENCE: 1

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220
```

```
<210> SEQ ID NO 2
<211> LENGTH: 23
<212> TYPE: PRT
<213> ORGANISM: Homo sapiens

<400> SEQUENCE: 2

Trp Thr Ala His Ala Ile Ile Arg Asp Phe Tyr Asn Pro Leu Val Ala
1               5                   10                  15

Glu Ala Gln Lys Arg Glu Leu
            20

<210> SEQ ID NO 3
<211> LENGTH: 13
<212> TYPE: PRT
<213> ORGANISM: Homo sapiens

<400> SEQUENCE: 3

Thr Ala His Ala Ile Ile Arg Asp Phe Tyr Asn Pro Leu
1               5                   10

<210> SEQ ID NO 4
<211> LENGTH: 10
<212> TYPE: PRT
<213> ORGANISM: Homo sapiens

<400> SEQUENCE: 4

Leu Val Ala Glu Ala Gln Lys Arg Glu Leu
1               5                   10

<210> SEQ ID NO 5
<211> LENGTH: 220
<212> TYPE: PRT
<213> ORGANISM: Homo sapiens
<300> PUBLICATION INFORMATION:
<308> DATABASE ACCESSION NUMBER: NCBI / NP_001297.1
<309> DATABASE ENTRY DATE: 2017-07-10
<313> RELEVANT RESIDUES IN SEQ ID NO: (1)..(220)

<400> SEQUENCE: 5

Met Ser Met Gly Leu Glu Ile Thr Gly Thr Ala Leu Ala Val Leu Gly
1               5                   10                  15

Trp Leu Gly Thr Ile Val Cys Cys Ala Leu Pro Met Trp Arg Val Ser
            20                  25                  30

Ala Phe Ile Gly Ser Asn Ile Ile Thr Ser Gln Asn Ile Trp Glu Gly
        35                  40                  45

Leu Trp Met Asn Cys Val Val Gln Ser Thr Gly Gln Met Gln Cys Lys
    50                  55                  60

Val Tyr Asp Ser Leu Leu Ala Leu Pro Gln Asp Leu Gln Ala Arg
65                  70                  75                  80

Ala Leu Ile Val Val Ala Ile Leu Leu Ala Ala Phe Gly Leu Leu Val
                85                  90                  95

Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Leu Ala Ala
        115                 120                 125

Leu Leu Thr Leu Val Pro Val Ser Trp Ser Ala Asn Thr Ile Ile Arg
    130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Ala Leu Gln Leu Leu Gly
                165                 170                 175
```

-continued

Gly Ala Leu Leu Cys Cys Ser Cys Pro Pro Arg Glu Lys Lys Tyr Thr
                180                 185                 190

Ala Thr Lys Val Val Tyr Ser Ala Pro Arg Ser Thr Gly Pro Gly Ala
            195                 200                 205

Ser Leu Gly Thr Gly Tyr Asp Arg Lys Asp Tyr Val
        210                 215                 220

<210> SEQ ID NO 6
<211> LENGTH: 209
<212> TYPE: PRT
<213> ORGANISM: Homo sapiens
<300> PUBLICATION INFORMATION:
<308> DATABASE ACCESSION NUMBER: NCBI / NP_001296.1
<309> DATABASE ENTRY DATE: 2017-07-10
<313> RELEVANT RESIDUES IN SEQ ID NO: (1)..(209)

<400> SEQUENCE: 6

Met Ala Ser Met Gly Leu Gln Val Met Gly Ile Ala Leu Ala Val Leu
1               5                   10                  15

Gly Trp Leu Ala Val Met Leu Cys Cys Ala Leu Pro Met Trp Arg Val
                20                  25                  30

Thr Ala Phe Ile Gly Ser Asn Ile Val Thr Ser Gln Thr Ile Trp Glu
            35                  40                  45

Gly Leu Trp Met Asn Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Val Ile Ile Ser Ile Ile Val Ala Ala Leu Gly Val Leu
                85                  90                  95

Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
        115                 120                 125

Gly Leu Met Val Ile Val Pro Val Ser Trp Thr Ala His Asn Ile Ile
    130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Asn Cys Pro Pro Arg Thr Asp Lys Pro
            180                 185                 190

Tyr Ser Ala Lys Tyr Ser Ala Ala Arg Ser Ala Ala Ala Ser Asn Tyr
        195                 200                 205

Val

<210> SEQ ID NO 7
<211> LENGTH: 217
<212> TYPE: PRT
<213> ORGANISM: Homo sapiens
<300> PUBLICATION INFORMATION:
<308> DATABASE ACCESSION NUMBER: NCBI / NP_066192.1
<309> DATABASE ENTRY DATE: 2017-04-15
<313> RELEVANT RESIDUES IN SEQ ID NO: (1)..(217)

<400> SEQUENCE: 7

Met Ala Ser Thr Gly Leu Glu Leu Leu Gly Met Thr Leu Ala Val Leu
1               5                   10                  15

Gly Trp Leu Gly Thr Leu Val Ser Cys Ala Leu Pro Leu Trp Lys Val

```
            20                  25                  30
Thr Ala Phe Ile Gly Asn Ser Ile Val Val Ala Gln Val Val Trp Glu
            35                  40                  45
Gly Leu Trp Met Ser Cys Val Val Gln Ser Thr Gly Gln Met Gln Cys
 50                  55                  60
Lys Val Tyr Asp Ser Leu Leu Ala Leu Pro Gln Asp Leu Gln Ala Ala
 65                  70                  75                  80
Arg Ala Leu Cys Val Ile Ala Leu Leu Ala Leu Leu Gly Leu Leu
                 85                  90                  95
Val Ala Ile Thr Gly Ala Gln Cys Thr Thr Cys Val Glu Asp Glu Gly
                100                 105                 110
Ala Lys Ala Arg Ile Val Leu Thr Ala Gly Val Ile Leu Leu Leu Ala
                115                 120                 125
Gly Ile Leu Val Leu Ile Pro Val Cys Trp Thr Ala His Ala Ile Ile
            130                 135                 140
Gln Asp Phe Tyr Asn Pro Leu Val Ala Glu Ala Leu Lys Arg Glu Leu
145                 150                 155                 160
Gly Ala Ser Leu Tyr Leu Gly Trp Ala Ala Ala Leu Leu Met Leu
                165                 170                 175
Gly Gly Gly Leu Leu Cys Cys Thr Cys Pro Pro Gln Val Glu Arg
                180                 185                 190
Pro Arg Gly Pro Arg Leu Gly Tyr Ser Ile Pro Ser Arg Ser Gly Ala
                195                 200                 205
Ser Gly Leu Asp Lys Arg Asp Tyr Val
            210                 215

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Ser Ser Val Ser Ser Thr Tyr
1               5

<210> SEQ ID NO 9
<211> LENGTH: 3
<212> TYPE: PRT
<213> ORGANISM: Artificial Sequence
<220> FEATURE:
<223> OTHER INFORMATION: Synthetic peptide

<400> SEQUENCE: 9

Ser Thr Ser
1

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

His Gln Tyr His Arg Ser Pro Leu Thr
1               5

<210> SEQ ID NO 11
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Gly Tyr Thr Phe Thr Thr Tyr Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Ile Asn Pro Ser Ser Gly Tyr Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Ala Asn Gly Asp Tyr Tyr Val Ala Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Glu Asn Ile Tyr Ser Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: Synthetic peptide

<400> SEQUENCE: 15

Asn Ala Lys
1

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Gln His His Tyr Thr Val Pro Trp Thr
1               5

<210> SEQ ID NO 17
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 17

Gly Phe Thr Phe Ser Asp Tyr Trp
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Ile Arg Leu Lys Ser Asp Asn Tyr Ala Thr
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Asn Asp Gly Pro Pro Ser Gly Cys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Glu Asn Ile Tyr Ser Tyr
1               5

<210> SEQ ID NO 21
<211> LENGTH: 3
<212> TYPE: PRT
<213> ORGANISM: Artificial Sequence
<220> FEATURE:
<223> OTHER INFORMATION: Synthetic peptide

<400> SEQUENCE: 21

Asn Ala Lys
1

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Gln His His Tyr Thr Val Pro Trp Thr
1               5

<210> SEQ ID NO 23
<211> LENGTH: 8
<212> TYPE: PRT
```

```
<213> ORGANISM: Artificial Sequence
<220> FEATURE:
<223> OTHER INFORMATION: Synthetic peptide

<400> SEQUENCE: 23

Gly Phe Thr Phe Ser Asn Tyr Trp
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Ile Arg Leu Lys Ser Asp Asn Tyr Ala Thr
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Asn Asp Gly Pro Pro Ser Gly Cys
1               5

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Gln Ser Leu Val His Ser Asp Gly Asn Thr Tyr
1               5                   10

<210> SEQ ID NO 27
<211> LENGTH: 3
<212> TYPE: PRT
<213> ORGANISM: Artificial Sequence
<220> FEATURE:
<223> OTHER INFORMATION: Synthetic peptide

<400> SEQUENCE: 27

Lys Val Ser
1

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Ser Gln Ser Thr His Val Pro Tyr Thr
1               5

<210> SEQ ID NO 29
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 29

Gly Tyr Thr Phe Thr Ser Tyr Thr
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Ile Asn Pro Ser Ser Thr Tyr Thr
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31

Ser Arg Gly Glu Leu Gly Gly Phe Ala Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide

<400> SEQUENCE: 32

Gln Ser Ile Val His Ser Asn Gly Asn Thr Tyr
1               5                   10

<210> SEQ ID NO 33
<211> LENGTH: 3
<212> TYPE: PRT
<213> ORGANISM: Artificial Sequence
<220> FEATURE:
<223> OTHER INFORMATION: Synthetic peptide

<400> SEQUENCE: 33

Lys Val Ser
1

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Phe Gln Gly Ser His Val Pro Phe Thr
1               5

<210> SEQ ID NO 35
<211> LENGTH: 8
<212> TYPE: PRT
<213> ORGANISM: Artificial Sequence
<220> FEATURE:
```

```
<223> OTHER INFORMATION: Synthetic peptide

<400> SEQUENCE: 35

Gly Tyr Ile Phe Thr His Tyr Ile
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Ile Asn Pro Tyr Asn Asp Gly Thr
1               5

<210> SEQ ID NO 37
<211> LENGTH: 13
<212> TYPE: PRT
<213> ORGANISM: Artificial Sequence
<220> FEATURE:
<223> OTHER INFORMATION: Synthetic peptide

<400> SEQUENCE: 37

Ala Arg Tyr Tyr Gly Tyr Pro Tyr Tyr Ser Met Asp Tyr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic peptide

<400> SEQUENCE: 38

Gln Ser Leu Leu Asn Ser Arg Thr Arg Lys Asn Tyr
1               5                   10

<210> SEQ ID NO 39
<211> LENGTH: 3
<212> TYPE: PRT
<213> ORGANISM: Artificial Sequence
<220> FEATURE:
<223> OTHER INFORMATION: Synthetic peptide

<400> SEQUENCE: 39

Trp Ala Ser
1

<210> SEQ ID NO 40
<211> LENGTH: 8
<212> TYPE: PRT
<213> ORGANISM: Artificial Sequence
<220> FEATURE:
<223> OTHER INFORMATION: Synthetic peptide

<400> SEQUENCE: 40

Lys Gln Ser Tyr Tyr Leu Tyr Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide
```

<400> SEQUENCE: 41

Gly Tyr Ser Ile Thr Ser Gly Tyr Tyr
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Ile Ser Tyr Asp Gly Gly Ile
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide

<400> SEQUENCE: 43

Ala Arg Phe Gly Lys Gly Ala Met Asp Tyr
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Ser Ser Val Ser Ser Ser Tyr
1               5

<210> SEQ ID NO 45
<211> LENGTH: 3
<212> TYPE: PRT
<213> ORGANISM: Artificial Sequence
<220> FEATURE:
<223> OTHER INFORMATION: Synthetic peptide

<400> SEQUENCE: 45

Ser Thr Ser
1

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

His Gln Tyr His Arg Ser Pro Pro Thr
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 47

Gly Tyr Ser Phe Thr Gly Tyr Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic peptide

<400> SEQUENCE: 48

Ile Asn Pro Tyr Asn Gly Gly Thr
1               5

<210> SEQ ID NO 49
<211> LENGTH: 12
<212> TYPE: PRT
<213> ORGANISM: Artificial Sequence
<220> FEATURE:
<223> OTHER INFORMATION: Synthetic peptide

<400> SEQUENCE: 49

Ala Arg Gly Val Tyr Asp Tyr Asp Gly Phe Thr Tyr
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic peptide

<400> SEQUENCE: 50

Gln Ser Leu Val His Ser Asp Gly Asn Thr Tyr
1               5                   10

<210> SEQ ID NO 51
<211> LENGTH: 3
<212> TYPE: PRT
<213> ORGANISM: Artificial Sequence
<220> FEATURE:
<223> OTHER INFORMATION: Synthetic peptide

<400> SEQUENCE: 51

Lys Val Ser
1

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

Ser Gln Ser Thr His Val Pro Tyr Thr
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic peptide

<400> SEQUENCE: 53
```

```
Gly Tyr Thr Phe Thr Thr Tyr Thr
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic peptide

<400> SEQUENCE: 54

Ile Asn Pro Arg Ser Gly Tyr Ser
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic peptide

<400> SEQUENCE: 55

Ser Arg Gly Glu Leu Gly Gly Phe Ala Tyr
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide

<400> SEQUENCE: 56

Gln Thr Ile Gly Thr Trp
1               5

<210> SEQ ID NO 57
<211> LENGTH: 3
<212> TYPE: PRT
<213> ORGANISM: Artificial Sequence
<220> FEATURE:
<223> OTHER INFORMATION: Synthetic peptide

<400> SEQUENCE: 57

Ala Ala Ala
1

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Gln Gln Leu Tyr Ser Ile Pro Arg Thr
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic peptide

<400> SEQUENCE: 59
```

```
Gly Tyr Arg Phe Thr Asp Tyr Asn
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic peptide

<400> SEQUENCE: 60

Ile Asn Pro Asn Asn Gly Gly Thr
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic peptide

<400> SEQUENCE: 61

Ala Arg Asp Tyr Leu Tyr Phe Phe Asp Cys
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic peptide

<400> SEQUENCE: 62

Gln Ser Leu Val His Ser Asn Gly Asn Thr Tyr
1               5                   10

<210> SEQ ID NO 63
<211> LENGTH: 3
<212> TYPE: PRT
<213> ORGANISM: Artificial Sequence
<220> FEATURE:
<223> OTHER INFORMATION: Synthetic peptide

<400> SEQUENCE: 63

Lys Val Ser
1

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Ser Gln Ile Thr His Val Pro Tyr Thr
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic peptide

<400> SEQUENCE: 65

Gly Tyr Thr Phe Thr Asp Tyr Ser
```

```
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic peptide

<400> SEQUENCE: 66

Ile Ser Thr Glu Thr Gly Glu Pro
1               5

<210> SEQ ID NO 67
<211> LENGTH: 10
<212> TYPE: PRT
<213> ORGANISM: Artificial Sequence
<220> FEATURE:
<223> OTHER INFORMATION: Synthetic peptide

<400> SEQUENCE: 67

Thr Arg Gly Leu Trp Ser Ser Phe Ala Tyr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic peptide

<400> SEQUENCE: 68

Lys Ser Val Ser Thr Ser Gly Tyr Ser Tyr
1               5                   10

<210> SEQ ID NO 69
<211> LENGTH: 3
<212> TYPE: PRT
<213> ORGANISM: Artificial Sequence
<220> FEATURE:
<223> OTHER INFORMATION: Synthetic peptide

<400> SEQUENCE: 69

Leu Ala Ser
1

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide

<400> SEQUENCE: 70

Gln His Ser Arg Glu Leu Pro Leu Thr
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic peptide

<400> SEQUENCE: 71

Gly Phe Thr Phe Ser Ser Phe Gly
1               5
```

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide

<400> SEQUENCE: 72

Ile Ser Ser Asp Ser Arg Thr Ile
1               5

<210> SEQ ID NO 73
<211> LENGTH: 11
<212> TYPE: PRT
<213> ORGANISM: Artificial Sequence
<220> FEATURE:
<223> OTHER INFORMATION: Synthetic peptide

<400> SEQUENCE: 73

Ala Arg Asp Tyr Gly Arg Thr Tyr Glu Ala Tyr
1               5                   10

<210> SEQ ID NO 74
<211> LENGTH: 6
<212> TYPE: PRT
<213> ORGANISM: Artificial Sequence
<220> FEATURE:
<223> OTHER INFORMATION: Synthetic peptide

<400> SEQUENCE: 74

Gln Asp Ile Gly Gly Asn
1               5

<210> SEQ ID NO 75
<211> LENGTH: 3
<212> TYPE: PRT
<213> ORGANISM: Artificial Sequence
<220> FEATURE:
<223> OTHER INFORMATION: Synthetic peptide

<400> SEQUENCE: 75

Ser Thr Ser
1

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

Leu Gln Arg Asn Ala Tyr Pro Leu Thr
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic peptide

<400> SEQUENCE: 77

Gly Phe Thr Phe Ser Ser Tyr Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Ile Arg Ser Gly Gly Thr Thr
1               5

<210> SEQ ID NO 79
<211> LENGTH: 12
<212> TYPE: PRT
<213> ORGANISM: Artificial Sequence
<220> FEATURE:
<223> OTHER INFORMATION: Synthetic peptide

<400> SEQUENCE: 79

Ala Lys Val Gly Gly Asn Pro Tyr Pro Met Asp Tyr
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Ser Ser Ile Ser Ser Asn Tyr
1               5

<210> SEQ ID NO 81
<211> LENGTH: 3
<212> TYPE: PRT
<213> ORGANISM: Artificial Sequence
<220> FEATURE:
<223> OTHER INFORMATION: Synthetic peptide

<400> SEQUENCE: 81

Arg Thr Ser
1

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide

<400> SEQUENCE: 82

Gln Gln Gly Ser Ser Ile Pro Leu Thr
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic peptide

<400> SEQUENCE: 83

Gly Tyr Ala Phe Ser Asn Tyr Leu
1               5

```
<210> SEQ ID NO 84
<211> LENGTH: 8
<212> TYPE: PRT
<213> ORGANISM: Artificial Sequence
<220> FEATURE:
<223> OTHER INFORMATION: Synthetic peptide

<400> SEQUENCE: 84

Ile Asn Pro Gly Ser Gly Gly Thr
1               5

<210> SEQ ID NO 85
<211> LENGTH: 15
<212> TYPE: PRT
<213> ORGANISM: Artificial Sequence
<220> FEATURE:
<223> OTHER INFORMATION: Synthetic peptide

<400> SEQUENCE: 85

Ala Arg Ser Tyr Phe Gly Arg Ser Tyr Pro Tyr Thr Met Asp Tyr
1               5                   10                  15

<210> SEQ ID NO 86
<211> LENGTH: 10
<212> TYPE: PRT
<213> ORGANISM: Artificial Sequence
<220> FEATURE:
<223> OTHER INFORMATION: Synthetic peptide

<400> SEQUENCE: 86

Gln Ser Val Asp Tyr Asp Gly Asp Asn Tyr
1               5                   10

<210> SEQ ID NO 87
<211> LENGTH: 3
<212> TYPE: PRT
<213> ORGANISM: Artificial Sequence
<220> FEATURE:
<223> OTHER INFORMATION: Synthetic peptide

<400> SEQUENCE: 87

Ala Ala Ser
1

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide

<400> SEQUENCE: 88

Gln Gln Ser Asn Glu Asp Pro Phe Thr
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic peptide

<400> SEQUENCE: 89

Gly Tyr Thr Phe Thr Asp Tyr Ala
1               5

<210> SEQ ID NO 90
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 90

Ile Ser Thr Tyr Ser Gly Asn Thr
1               5

<210> SEQ ID NO 91
<211> LENGTH: 13
<212> TYPE: PRT
<213> ORGANISM: Artificial Sequence
<220> FEATURE:
<223> OTHER INFORMATION: Synthetic peptide

<400> SEQUENCE: 91

Ala Arg Arg Gly Asp Tyr Ser Leu Tyr Ala Met Asp Tyr
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic peptide

<400> SEQUENCE: 92

Gln Ser Val Leu Phe Ser Ser Asn Gln Lys Asn Tyr
1               5                   10

<210> SEQ ID NO 93
<211> LENGTH: 3
<212> TYPE: PRT
<213> ORGANISM: Artificial Sequence
<220> FEATURE:
<223> OTHER INFORMATION: Synthetic peptide

<400> SEQUENCE: 93

Trp Ala Ser
1

<210> SEQ ID NO 94
<211> LENGTH: 8
<212> TYPE: PRT
<213> ORGANISM: Artificial Sequence
<220> FEATURE:
<223> OTHER INFORMATION: Synthetic peptide

<400> SEQUENCE: 94

His Gln Tyr Leu Ser Ser Arg Thr
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic peptide

<400> SEQUENCE: 95

Gly Phe Thr Phe Ser Ser Phe Gly
1               5

<210> SEQ ID NO 96
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 96

Ile Ser Ser Asp Ser Arg Thr Ile
1               5

<210> SEQ ID NO 97
<211> LENGTH: 11
<212> TYPE: PRT
<213> ORGANISM: Artificial Sequence
<220> FEATURE:
<223> OTHER INFORMATION: Synthetic peptide

<400> SEQUENCE: 97

Ala Arg Asp Tyr Gly Arg Thr Tyr Glu Ala Tyr
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic peptide

<400> SEQUENCE: 98

Glu Ser Val Asp Asn Tyr Gly Ile Ser Phe
1               5                   10

<210> SEQ ID NO 99
<211> LENGTH: 3
<212> TYPE: PRT
<213> ORGANISM: Artificial Sequence
<220> FEATURE:
<223> OTHER INFORMATION: Synthetic peptide

<400> SEQUENCE: 99

Ala Ala Ser
1

<210> SEQ ID NO 100
<211> LENGTH: 9
<212> TYPE: PRT
<213> ORGANISM: Artificial Sequence
<220> FEATURE:
<223> OTHER INFORMATION: Synthetic peptide

<400> SEQUENCE: 100

Gln Gln Ser Lys Glu Val Pro Leu Thr
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic peptide

<400> SEQUENCE: 101

Gly Phe Pro Phe Ser Ser Ser Ala
1               5

<210> SEQ ID NO 102
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 102

Ile Asn Ser Asp Gly Asn Thr
1               5

<210> SEQ ID NO 103
<211> LENGTH: 13
<212> TYPE: PRT
<213> ORGANISM: Artificial Sequence
<220> FEATURE:
<223> OTHER INFORMATION: Synthetic peptide

<400> SEQUENCE: 103

Thr Arg Asn Gly Asp Tyr Arg Tyr Asp Glu Phe Ala Tyr
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide

<400> SEQUENCE: 104

Ser Ser Val Ser Ser Ser Tyr
1               5

<210> SEQ ID NO 105
<211> LENGTH: 3
<212> TYPE: PRT
<213> ORGANISM: Artificial Sequence
<220> FEATURE:
<223> OTHER INFORMATION: Synthetic peptide

<400> SEQUENCE: 105

Ser Thr Ser
1

<210> SEQ ID NO 106
<211> LENGTH: 9
<212> TYPE: PRT
<213> ORGANISM: Artificial Sequence
<220> FEATURE:
<223> OTHER INFORMATION: Synthetic peptide

<400> SEQUENCE: 106

His Gln Tyr His Arg Ser Pro Pro Thr
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic peptide

<400> SEQUENCE: 107

Gly Tyr Thr Phe Thr Gly Tyr Trp
1               5

<210> SEQ ID NO 108
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 108

Ile Asn Pro Ser Thr Gly Tyr Thr
1               5

<210> SEQ ID NO 109
<211> LENGTH: 12
<212> TYPE: PRT
<213> ORGANISM: Artificial Sequence
<220> FEATURE:
<223> OTHER INFORMATION: Synthetic peptide

<400> SEQUENCE: 109

Ala Arg Glu Gly Ile Thr Thr Val Leu Val Asp Tyr
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic peptide

<400> SEQUENCE: 110

Gln Ser Val Leu Phe Ser Ser Asn Gln Lys Asn Tyr
1               5                   10

<210> SEQ ID NO 111
<211> LENGTH: 3
<212> TYPE: PRT
<213> ORGANISM: Artificial Sequence
<220> FEATURE:
<223> OTHER INFORMATION: Synthetic peptide

<400> SEQUENCE: 111

Trp Ala Ser
1

<210> SEQ ID NO 112
<211> LENGTH: 8
<212> TYPE: PRT
<213> ORGANISM: Artificial Sequence
<220> FEATURE:
<223> OTHER INFORMATION: Synthetic peptide

<400> SEQUENCE: 112

His Gln Tyr Leu Ser Ser Arg Thr
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic peptide

<400> SEQUENCE: 113

Gly Tyr Ser Phe Thr Gly Tyr Asn
1               5

<210> SEQ ID NO 114
<211> LENGTH: 8
<212> TYPE: PRT
<213> ORGANISM: Artificial Sequence
<220> FEATURE:
```

```
<223> OTHER INFORMATION: Synthetic peptide

<400> SEQUENCE: 114

Ile Asp Pro Tyr Tyr Gly Gly Ser
1               5

<210> SEQ ID NO 115
<211> LENGTH: 14
<212> TYPE: PRT
<213> ORGANISM: Artificial Sequence
<220> FEATURE:
<223> OTHER INFORMATION: Synthetic peptide

<400> SEQUENCE: 115

Ala Arg Glu Arg Ser Gly Tyr Val Phe Ser Ala Met Asp Tyr
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic peptide

<400> SEQUENCE: 116

Gln Ser Val Leu Phe Ser Ser Asn Gln Lys Asn Tyr
1               5                   10

<210> SEQ ID NO 117
<211> LENGTH: 3
<212> TYPE: PRT
<213> ORGANISM: Artificial Sequence
<220> FEATURE:
<223> OTHER INFORMATION: Synthetic peptide

<400> SEQUENCE: 117

Trp Ala Ser
1

<210> SEQ ID NO 118
<211> LENGTH: 8
<212> TYPE: PRT
<213> ORGANISM: Artificial Sequence
<220> FEATURE:
<223> OTHER INFORMATION: Synthetic peptide

<400> SEQUENCE: 118

His Gln Tyr Leu Ser Ser Arg Thr
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic peptide

<400> SEQUENCE: 119

Gly Tyr Ser Phe Thr Gly Tyr Thr
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 120

Ile Asn Pro Tyr Asn Gly Val Thr
1               5

<210> SEQ ID NO 121
<211> LENGTH: 16
<212> TYPE: PRT
<213> ORGANISM: Artificial Sequence
<220> FEATURE:
<223> OTHER INFORMATION: Synthetic peptide

<400> SEQUENCE: 121

Thr Arg Asp Pro Leu Tyr Tyr Gly Tyr Arg Asp Ser Thr Met Asp Tyr
1               5                   10                  15

<210> SEQ ID NO 122
<211> LENGTH: 11
<212> TYPE: PRT
<213> ORGANISM: Artificial Sequence
<220> FEATURE:
<223> OTHER INFORMATION: Synthetic peptide

<400> SEQUENCE: 122

Gln Ser Leu Val His Ser Asp Gly Asn Thr Tyr
1               5                   10

<210> SEQ ID NO 123
<211> LENGTH: 3
<212> TYPE: PRT
<213> ORGANISM: Artificial Sequence
<220> FEATURE:
<223> OTHER INFORMATION: Synthetic peptide

<400> SEQUENCE: 123

Lys Val Ser
1

<210> SEQ ID NO 124
<211> LENGTH: 9
<212> TYPE: PRT
<213> ORGANISM: Artificial Sequence
<220> FEATURE:
<223> OTHER INFORMATION: Synthetic peptide

<400> SEQUENCE: 124

Ser Gln Ser Thr His Val Pro Tyr Thr
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic peptide

<400> SEQUENCE: 125

Gly Tyr Thr Phe Thr Ser Tyr Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 126

Ile Asn Pro Ser Ser Thr Tyr Thr
1               5

<210> SEQ ID NO 127
<211> LENGTH: 10
<212> TYPE: PRT
<213> ORGANISM: Artificial Sequence
<220> FEATURE:
<223> OTHER INFORMATION: Synthetic peptide

<400> SEQUENCE: 127

Ser Arg Gly Glu Leu Gly Gly Phe Ala Tyr
1               5                   10

<210> SEQ ID NO 128
<211> LENGTH: 6
<212> TYPE: PRT
<213> ORGANISM: Artificial Sequence
<220> FEATURE:
<223> OTHER INFORMATION: Synthetic peptide

<400> SEQUENCE: 128

Gln Gly Ile Arg Gly Asn
1               5

<210> SEQ ID NO 129
<211> LENGTH: 3
<212> TYPE: PRT
<213> ORGANISM: Artificial Sequence
<220> FEATURE:
<223> OTHER INFORMATION: Synthetic peptide

<400> SEQUENCE: 129

Ser Thr Ser
1

<210> SEQ ID NO 130
<211> LENGTH: 9
<212> TYPE: PRT
<213> ORGANISM: Artificial Sequence
<220> FEATURE:
<223> OTHER INFORMATION: Synthetic peptide

<400> SEQUENCE: 130

Leu Gln Arg Asn Ala Tyr Pro Leu Thr
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic peptide

<400> SEQUENCE: 131

Gly Phe Thr Phe Ser Ser Phe Ala
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic peptide

<400> SEQUENCE: 132
```

```
Ile Arg Ser Gly Gly Ile Thr
1               5

<210> SEQ ID NO 133
<211> LENGTH: 13
<212> TYPE: PRT
<213> ORGANISM: Artificial Sequence
<220> FEATURE:
<223> OTHER INFORMATION: Synthetic peptide

<400> SEQUENCE: 133

Ala Arg Val Ser Thr Ala Thr Tyr Tyr Gly Met Asp Tyr
1               5                   10

<210> SEQ ID NO 134
<211> LENGTH: 108
<212> TYPE: PRT
<213> ORGANISM: Artificial Sequence
<220> FEATURE:
<223> OTHER INFORMATION: Synthetic peptide

<400> SEQUENCE: 134

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Thr
            20                  25                  30

Tyr Phe His Trp Tyr Gln Gln Lys Pro Gly Ser Ser Pro Lys Leu Trp
        35                  40                  45

Ile Tyr Ser Thr Ser Asn Leu Ala Ser Gly Val Pro Arg Arg Phe Ser
    50                  55                  60

Gly Ser Ala Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Leu Thr Phe Gly Ala Gly Thr Lys Leu Glu Leu Lys
            100                 105

<210> SEQ ID NO 135
<211> LENGTH: 116
<212> TYPE: PRT
<213> ORGANISM: Artificial Sequence
<220> FEATURE:
<223> OTHER INFORMATION: Synthetic peptide

<400> SEQUENCE: 135

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Lys Gln Arg Pro Gly Gln Gly Leu Glu Trp Ile
        35                  40                  45

Gly Phe Ile Asn Pro Ser Ser Gly Tyr Thr Asp Tyr Asn Gln Lys Phe
    50                  55                  60

Lys Asp Arg Thr Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ala Asn Gly Asp Tyr Tyr Val Ala Tyr Trp Gly Gln Gly Thr Leu Val
            100                 105                 110
```

Thr Val Ser Ala
        115

<210> SEQ ID NO 136
<211> LENGTH: 107
<212> TYPE: PRT
<213> ORGANISM: Artificial Sequence
<220> FEATURE:
<223> OTHER INFORMATION: Synthetic peptide

<400> SEQUENCE: 136

Asp Ile Gln Met Thr Gln Ser Pro Ala Ser Leu Ser Ala Ser Val Gly
1               5                   10                  15

Glu Thr Val Thr Ile Thr Cys Arg Ile Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Ile Leu Val Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Thr Val Pro Trp
                85                  90                  95

Thr Phe Gly Gly Gly Thr Lys Leu Glu Ile Lys
            100                 105

<210> SEQ ID NO 137
<211> LENGTH: 117
<212> TYPE: PRT
<213> ORGANISM: Artificial Sequence
<220> FEATURE:
<223> OTHER INFORMATION: Synthetic peptide

<400> SEQUENCE: 137

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Arg Ser
65                  70                  75                  80

Val Tyr Leu Gln Met Asn Asn Leu Arg Ala Glu Asp Thr Gly Thr Tyr
                85                  90                  95

Tyr Cys Asn Asp Gly Pro Pro Ser Gly Cys Trp Gly Gln Gly Thr Thr
            100                 105                 110

Leu Ile Val Ser Ser
        115

<210> SEQ ID NO 138
<211> LENGTH: 107
<212> TYPE: PRT
<213> ORGANISM: Artificial Sequence
<220> FEATURE:
<223> OTHER INFORMATION: Synthetic peptide

<400> SEQUENCE: 138

Asp Ile Gln Met Thr Gln Ser Pro Ala Ser Leu Ser Ala Ser Val Gly

-continued

```
                1               5                  10                 15
Glu Thr Val Thr Ile Thr Cys Arg Ile Ser Glu Asn Ile Tyr Ser Tyr
                       20                 25                 30

Leu Ala Trp Tyr Gln Gln Lys Gln Gly Lys Ser Pro Gln Leu Leu Val
               35                  40                 45

Tyr Asn Ala Lys Ile Leu Val Glu Gly Val Pro Ser Arg Phe Ser Gly
 50                 55                  60

Ser Gly Ser Gly Thr Gln Phe Ser Leu Lys Ile Asn Ser Leu Gln Pro
 65                 70                  75                 80

Glu Asp Phe Gly Asn Tyr Tyr Cys Gln His His Tyr Thr Val Pro Trp
                85                  90                 95

Thr Phe Gly Gly Gly Thr Lys Leu Glu Ile Lys
                       100                105
```

<210> SEQ ID NO 139
<211> LENGTH: 117
<212> TYPE: PRT
<213> ORGANISM: Artificial Sequence
<220> FEATURE:
<223> OTHER INFORMATION: Synthetic peptide

<400> SEQUENCE: 139

```
Glu Val Lys Leu Glu Glu Ser Gly Gly Gly Leu Val Gln Pro Gly Gly
 1               5                  10                 15

Ser Met Lys Leu Ser Cys Val Ala Ser Gly Phe Thr Phe Ser Asn Tyr
                20                  25                 30

Trp Met Asn Trp Val Arg Gln Ser Pro Glu Lys Gly Leu Glu Trp Val
               35                  40                 45

Ala Gln Ile Arg Leu Lys Ser Asp Asn Tyr Ala Thr His Tyr Ala Glu
 50                 55                  60

Ser Val Lys Gly Arg Phe Thr Ile Ser Arg Asp Asp Ser Lys Arg Ser
 65                 70                  75                 80

Val Tyr Leu Gln Met Asn Asn Leu Arg Ala Glu Asp Thr Gly Thr Tyr
                85                  90                 95

Tyr Cys Asn Asp Gly Pro Pro Ser Gly Cys Trp Gly Gln Gly Thr Thr
                100                 105                110

Leu Ile Val Ser Ser
        115
```

<210> SEQ ID NO 140
<211> LENGTH: 112
<212> TYPE: PRT
<213> ORGANISM: Artificial Sequence
<220> FEATURE:
<223> OTHER INFORMATION: Synthetic peptide

<400> SEQUENCE: 140

```
Asp Val Val Met Thr Gln Thr Pro Leu Ser Leu Pro Val Ser Leu Gly
 1               5                  10                 15

Asp Gln Ala Ser Ile Ser Cys Arg Ser Ser Gln Ser Leu Val His Ser
                20                  25                 30

Asp Gly Asn Thr Tyr Leu Asn Trp Tyr Leu Gln Lys Pro Gly Gln Ser
               35                  40                 45

Pro Lys Leu Leu Ile Tyr Lys Val Ser Asn Arg Phe Ser Gly Val Pro
 50                 55                  60

Asp Arg Phe Ser Gly Ser Gly Ser Gly Thr Asp Phe Thr Leu Lys Ile
 65                 70                  75                 80
```

```
Arg Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110
```

<210> SEQ ID NO 141
<211> LENGTH: 117
<212> TYPE: PRT
<213> ORGANISM: Artificial Sequence
<220> FEATURE:
<223> OTHER INFORMATION: Synthetic peptide

<400> SEQUENCE: 141

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Ile Lys Gln Arg Pro Gly Gln Gly Gln Glu Trp Ile
            35                  40                  45

Gly Tyr Ile Asn Pro Ser Ser Thr Tyr Thr His Tyr Ile Lys Lys Phe
        50                  55                  60

Lys Asp Lys Ala Thr Leu Thr Ala Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ala
        115
```

<210> SEQ ID NO 142
<211> LENGTH: 112
<212> TYPE: PRT
<213> ORGANISM: Artificial Sequence
<220> FEATURE:
<223> OTHER INFORMATION: Synthetic peptide

<400> SEQUENCE: 142

```
Asp Val Leu Met Thr Gln Thr Pro Leu Ser Leu Pro Val Ser Leu Gly
1               5                   10                  15

Asp Gln Pro Ser Ile Ser Cys Arg Ser Ser Gln Ser Ile Val His Ser
                20                  25                  30

Asn Gly Asn Thr Tyr Leu Asp Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Arg Leu Glu Ile Lys
            100                 105                 110
```

<210> SEQ ID NO 143
<211> LENGTH: 120
<212> TYPE: PRT
<213> ORGANISM: Artificial Sequence
<220> FEATURE:
<223> OTHER INFORMATION: Synthetic peptide

<400> SEQUENCE: 143

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ile Phe Thr His Tyr
            20                  25                  30

Ile Met His Trp Val Lys Gln Lys Pro Gly Gln Gly Leu Glu Trp Ile
        35                  40                  45

Gly Cys Ile Asn Pro Tyr Asn Asp Gly Thr Lys Tyr Asn Glu Lys Phe
50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Tyr Tyr Gly Tyr Pro Tyr Tyr Ser Met Asp Tyr Trp Gly Gln
            100                 105                 110

Gly Thr Ser Val Thr Val Ser Ser
            115                 120

<210> SEQ ID NO 144
<211> LENGTH: 112
<212> TYPE: PRT
<213> ORGANISM: Artificial Sequence
<220> FEATURE:
<223> OTHER INFORMATION: Synthetic peptide

<400> SEQUENCE: 144

Ala Ile Val Met Phe Gln Ser Pro Ser Ser Leu Val Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Tyr Thr Phe Gly Gly Gly Thr Lys Leu Glu Ile Lys
            100                 105                 110

<210> SEQ ID NO 145
<211> LENGTH: 117
<212> TYPE: PRT
<213> ORGANISM: Artificial Sequence
<220> FEATURE:
<223> OTHER INFORMATION: Synthetic peptide

<400> SEQUENCE: 145

Asp Val Gln Leu Gln Glu Ser Gly Pro Gly Leu Val Lys Ser Ser Gln
1               5                   10                  15

Ser Leu Ser Leu Thr Cys Ser Val Thr Gly Tyr Ser Ile Thr Ser Gly
            20                  25                  30

Tyr Tyr Trp Lys Trp Ile Arg Gln Phe Pro Gly Asn Lys Leu Glu Trp
        35                  40                  45

Met Gly Tyr Ile Ser Tyr Asp Gly Gly Ile Asn Tyr Asn Pro Ser Leu
50                  55                  60

```
Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Lys Tyr Tyr Cys
                 85                  90                  95

Ala Arg Phe Gly Lys Gly Ala Met Asp Tyr Trp Gly Gln Gly Thr Ser
            100                 105                 110

Val Thr Val Ser Ser
            115

<210> SEQ ID NO 146
<211> LENGTH: 108
<212> TYPE: PRT
<213> ORGANISM: Artificial Sequence
<220> FEATURE:
<223> OTHER INFORMATION: Synthetic peptide

<400> SEQUENCE: 146

Gln Ile Val Leu Thr Gln Ser Pro Ala Ile Met Ser Ala Ser Leu Gly
  1               5                  10                  15

Asp Arg Val Thr Met Thr Cys Thr Ala Ser Ser Ser Val Ser Ser Ser
                 20                  25                  30

Tyr Leu His Trp Tyr Gln Gln Lys Pro Gly Ser Ser Pro Lys Leu Trp
             35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                 85                  90                  95

Pro Thr Phe Gly Ser Gly Thr Lys Leu Glu Ile Lys
            100                 105

<210> SEQ ID NO 147
<211> LENGTH: 119
<212> TYPE: PRT
<213> ORGANISM: Artificial Sequence
<220> FEATURE:
<223> OTHER INFORMATION: Synthetic peptide

<400> SEQUENCE: 147

Glu Val Gln Leu Gln Gln Ser Gly Pro Glu Leu Val Lys Pro Gly Ala
  1               5                  10                  15

Ser Met Lys Ile Ser Cys Lys Ala Ser Gly Tyr Ser Phe Thr Gly Tyr
                 20                  25                  30

Thr Met Asn Trp Val Lys Gln Ser His Gly Lys Asn Leu Glu Trp Ile
             35                  40                  45

Gly Leu Ile Asn Pro Tyr Asn Gly Gly Thr Asn Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Gly Val Tyr Asp Tyr Asp Gly Phe Thr Tyr Trp Gly Gln Gly
            100                 105                 110

Thr Leu Val Thr Val Ser Ala
            115

<210> SEQ ID NO 148
```

```
<211> LENGTH: 112
<212> TYPE: PRT
<213> ORGANISM: Artificial Sequence
<220> FEATURE:
<223> OTHER INFORMATION: Synthetic peptide

<400> SEQUENCE: 148

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asp Gly Asn Thr Tyr Leu Tyr Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 149
<211> LENGTH: 117
<212> TYPE: PRT
<213> ORGANISM: Artificial Sequence
<220> FEATURE:
<223> OTHER INFORMATION: Synthetic peptide

<400> SEQUENCE: 149

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Met His Trp Leu Lys Gln Arg Pro Gly Gln Gly Leu Glu Trp Ile
        35                  40                  45

Gly Tyr Ile Asn Pro Arg Ser Gly Tyr Ser Asn Tyr Asn Gln Lys Phe
    50                  55                  60

Lys Asp Lys Ala Thr Leu Thr Ala Asp Lys Ser Ser Asn Thr Ala Tyr
65                  70                  75                  80

Met Gln Leu Asn Thr Leu Thr Ser Glu Asp Ser Lys Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ala
        115

<210> SEQ ID NO 150
<211> LENGTH: 107
<212> TYPE: PRT
<213> ORGANISM: Artificial Sequence
<220> FEATURE:
<223> OTHER INFORMATION: Synthetic peptide

<400> SEQUENCE: 150

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30
```

```
Leu Ala Trp Tyr Gln Gln Lys Pro Gly Lys Ser Pro Gln Leu Leu Ile
             35                  40                  45

Tyr Ala Ala Ala Ser Leu Ala Asp Gly Val Pro Ser Arg Phe Ser Gly
 50                      55                  60

Ser Gly Ser Gly Thr Arg Phe Ser Phe Lys Ile Ser Ser Leu Gln Ala
 65                  70                  75                  80

Glu Asp Phe Val Ser Tyr Tyr Cys Gln Gln Leu Tyr Ser Ile Pro Arg
                 85                  90                  95

Thr Phe Gly Gly Gly Thr Lys Leu Glu Ile Lys
            100                 105
```

<210> SEQ ID NO 151
<211> LENGTH: 117
<212> TYPE: PRT
<213> ORGANISM: Artificial Sequence
<220> FEATURE:
<223> OTHER INFORMATION: Synthetic peptide

<400> SEQUENCE: 151

```
Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Arg Phe Thr Asp Tyr
             20                  25                  30

Asn Met His Trp Val Lys Gln Ser His Gly Lys Ser Leu Glu Trp Ile
         35                  40                  45

Gly Tyr Ile Asn Pro Asn Asn Gly Gly Thr Asn Tyr Asn Gln Asn Phe
 50                  55                  60

Lys Gly Lys Ala Thr Leu Thr Val Asn Lys Ser Ser Thr Ala Tyr
 65                  70                  75                  80

Met Glu Leu Arg Ser Leu Thr Ser Glu Asp Ser Ala Ala Tyr Tyr Cys
                 85                  90                  95

Ala Arg Asp Tyr Leu Tyr Phe Phe Asp Cys Trp Gly Gln Gly Thr Thr
            100                 105                 110

Leu Thr Val Ser Ser
        115
```

<210> SEQ ID NO 152
<211> LENGTH: 112
<212> TYPE: PRT
<213> ORGANISM: Artificial Sequence
<220> FEATURE:
<223> OTHER INFORMATION: Synthetic peptide

<400> SEQUENCE: 152

```
Asp Val Val Met Thr Gln Thr Pro Leu Ser Leu Pro Val Ser Leu Gly
 1               5                  10                  15

Asp Gln Ala Ser Ile Ser Cys Arg Ala Ser Gln Ser Leu Val His Ser
             20                  25                  30

Asn Gly Asn Thr Tyr Leu His Trp Phe Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Arg Thr Asp Phe Thr Leu Lys Ile
 65                  70                  75                  80

Ser Arg Val Glu Ala Glu Asp Leu Gly Val Tyr Phe Cys Ser Gln Ile
                 85                  90                  95

Thr His Val Pro Tyr Thr Phe Gly Gly Gly Thr Lys Leu Glu Ile Lys
            100                 105                 110
```

<210> SEQ ID NO 153
<211> LENGTH: 117
<212> TYPE: PRT
<213> ORGANISM: Artificial Sequence
<220> FEATURE:
<223> OTHER INFORMATION: Synthetic peptide

<400> SEQUENCE: 153

Gln Ile Gln Leu Val Gln Ser Gly Pro Ala Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Ile Lys Gln Ala Pro Gly Lys Gly Leu Lys Trp Met
        35                  40                  45

Gly Trp Ile Ser Thr Glu Thr Gly Glu Pro Thr Tyr Ala Asp Gly Phe
    50                  55                  60

Lys Gly Arg Phe Asp Phe Ser Leu Glu Thr Ser Ala Asp Thr Ala Tyr
65                  70                  75                  80

Leu Ser Ile Asn Asn Leu Thr Asn Glu Asp Thr Ala Thr Tyr Phe Cys
                85                  90                  95

Thr Arg Gly Leu Trp Ser Ser Phe Ala Tyr Trp Gly Gln Gly Thr Leu
            100                 105                 110

Val Thr Val Ser Ala
        115

<210> SEQ ID NO 154
<211> LENGTH: 111
<212> TYPE: PRT
<213> ORGANISM: Artificial Sequence
<220> FEATURE:
<223> OTHER INFORMATION: Synthetic peptide

<400> SEQUENCE: 154

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 155
<211> LENGTH: 118
<212> TYPE: PRT
<213> ORGANISM: Artificial Sequence
<220> FEATURE:
<223> OTHER INFORMATION: Synthetic peptide

<400> SEQUENCE: 155

Asp Val Gln Leu Val Glu Ser Gly Gly Gly Leu Val Gln Pro Arg Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Arg Thr Ile Tyr Tyr Ala Asp Thr Val
    50                  55                  60

Lys Gly Arg Phe Thr Ile Ser Arg Asp Asn Pro Thr Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp Tyr Gly Arg Thr Tyr Glu Ala Tyr Trp Gly Gln Gly Thr
            100                 105                 110

Leu Val Thr Val Ser Ala
            115

<210> SEQ ID NO 156
<211> LENGTH: 107
<212> TYPE: PRT
<213> ORGANISM: Artificial Sequence
<220> FEATURE:
<223> OTHER INFORMATION: Synthetic peptide

<400> SEQUENCE: 156

Asp Ile Gln Met Ile Gln Ser Pro Ser Ser Met Phe Ala Ser Leu Gly
1               5                   10                  15

Asp Arg Val Ser Leu Ser Cys Arg Ala Ser Gln Asp Ile Gly Gly Asn
            20                  25                  30

Leu Asp Trp Tyr Gln Gln Lys Pro Gly Gly Thr Ile Lys Leu Leu Ile
        35                  40                  45

Tyr Ser Thr Ser Asn Leu Asn Ser Gly Val Pro Ser Arg Phe Ser Gly
    50                  55                  60

Ser Gly Ser Gly Ser Asp Tyr Ser Leu Thr Ile Thr Ser Leu Glu Ser
65                  70                  75                  80

Glu Asp Phe Ala Asp Tyr Tyr Cys Leu Gln Arg Asn Ala Tyr Pro Leu
                85                  90                  95

Thr Phe Gly Ala Gly Thr Lys Leu Glu Leu Lys
            100                 105

<210> SEQ ID NO 157
<211> LENGTH: 118
<212> TYPE: PRT
<213> ORGANISM: Artificial Sequence
<220> FEATURE:
<223> OTHER INFORMATION: Synthetic peptide

<400> SEQUENCE: 157

Glu Val Lys Leu Met Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Arg Ser Gly Gly Thr Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Arg Met Ser Ser Leu Arg Ser Glu Asp Thr Ala Ile Tyr Tyr Cys Ala
                85                  90                  95

```
Lys Val Gly Gly Asn Pro Tyr Pro Met Asp Tyr Trp Gly Gln Gly Thr
            100                 105                 110

Ser Val Thr Val Ser Ser
        115
```

<210> SEQ ID NO 158
<211> LENGTH: 108
<212> TYPE: PRT
<213> ORGANISM: Artificial Sequence
<220> FEATURE:
<223> OTHER INFORMATION: Synthetic peptide

<400> SEQUENCE: 158

```
Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ile Ser Ser Asn
            20                  25                  30

Tyr Leu His Trp Tyr Gln Gln Lys Pro Gly Phe Ser Pro Lys Leu Leu
            35                  40                  45

Ile Tyr Arg Thr Ser Asn Leu Ala Ser Gly Val Pro Ala Arg Phe Ser
50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ala Gly Thr Lys Leu Glu Leu Lys
            100                 105
```

<210> SEQ ID NO 159
<211> LENGTH: 122
<212> TYPE: PRT
<213> ORGANISM: Artificial Sequence
<220> FEATURE:
<223> OTHER INFORMATION: Synthetic peptide

<400> SEQUENCE: 159

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Arg Pro Gly Gln Gly Leu Glu Trp Ile
            35                  40                  45

Gly Val Ile Asn Pro Gly Ser Gly Gly Thr Asn Tyr Asn Glu Lys Phe
50                  55                  60

Lys Gly Lys Ala Thr Met Thr Ala Asp Lys Ser Ser Ser Thr Ala Tyr
65                  70                  75                  80

Met His Leu Ser Asn Leu Thr Ser Glu Asp Ser Val Val Tyr Phe Cys
                85                  90                  95

Ala Arg Ser Tyr Phe Gly Arg Ser Tyr Pro Tyr Thr Met Asp Tyr Trp
            100                 105                 110

Gly Gln Gly Thr Ser Val Thr Val Ser Ser
            115                 120
```

<210> SEQ ID NO 160
<211> LENGTH: 111
<212> TYPE: PRT
<213> ORGANISM: Artificial Sequence
<220> FEATURE:
<223> OTHER INFORMATION: Synthetic peptide -continued

<400> SEQUENCE: 160

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Asn Tyr Val Asn Trp Tyr Gln Gln Lys Val Gly Gln Pro Pro
        35                  40                  45

Lys Leu Leu Ile Ser Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys
            100                 105                 110

<210> SEQ ID NO 161
<211> LENGTH: 120
<212> TYPE: PRT
<213> ORGANISM: Artificial Sequence
<220> FEATURE:
<223> OTHER INFORMATION: Synthetic peptide

<400> SEQUENCE: 161

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Ser Gly Asn Thr Asn Tyr Asn Gln Lys Phe
    50                  55                  60

Gln Asp Lys Ala Thr Met Thr Val Asp Lys Ser Ser Ser Thr Ala Tyr
65                  70                  75                  80

Met Ala Leu Ala Arg Leu Thr Ser Asp Asp Ser Ala Ile Tyr Tyr Cys
                85                  90                  95

Ala Arg Arg Gly Asp Tyr Ser Leu Tyr Ala Met Asp Tyr Trp Gly Gln
            100                 105                 110

Gly Thr Ser Val Thr Val Ser Ser
        115                 120

<210> SEQ ID NO 162
<211> LENGTH: 112
<212> TYPE: PRT
<213> ORGANISM: Artificial Sequence
<220> FEATURE:
<223> OTHER INFORMATION: Synthetic peptide

<400> SEQUENCE: 162

Asn Ile Met Met Thr Gln Ser Pro Ser Ser Leu Ala Val Ser Ala Gly
1               5                   10                  15

Glu Lys Val Thr Met Ser Cys Ser Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

```
Pro Asp Arg Phe Thr Gly Ser Gly Ser Gly Thr Asp Phe Thr Leu Thr
 65                  70                  75                  80

Ile Ser Asn Val Gln Ala Glu Asp Leu Ala Val Tyr Tyr Cys His Gln
                 85                  90                  95

Tyr Leu Ser Ser Arg Thr Phe Gly Ala Gly Thr Lys Leu Glu Leu Lys
            100                 105                 110

<210> SEQ ID NO 163
<211> LENGTH: 118
<212> TYPE: PRT
<213> ORGANISM: Artificial Sequence
<220> FEATURE:
<223> OTHER INFORMATION: Synthetic peptide

<400> SEQUENCE: 163

Asp Val Gln Leu Val Glu Ser Gly Gly Gly Leu Val Gln Pro Arg Gly
  1               5                  10                  15

Ser Arg Lys Leu Ser Cys Ala Ala Ser Gly Phe Thr Phe Ser Ser Phe
                 20                  25                  30

Gly Met His Trp Val Arg Gln Ala Pro Glu Lys Gly Leu Glu Trp Val
             35                  40                  45

Ala Tyr Ile Ser Ser Asp Ser Arg Thr Ile Tyr Tyr Ala Asp Thr Val
         50                  55                  60

Lys Gly Arg Phe Thr Ile Ser Arg Asp Asn Pro Thr Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Asp Tyr Gly Arg Thr Tyr Glu Ala Tyr Trp Gly Gln Gly Thr
            100                 105                 110

Leu Val Thr Val Ser Ala
            115

<210> SEQ ID NO 164
<211> LENGTH: 111
<212> TYPE: PRT
<213> ORGANISM: Artificial Sequence
<220> FEATURE:
<223> OTHER INFORMATION: Synthetic peptide

<400> SEQUENCE: 164

Asp Ile Val Leu Thr Gln Ser Pro Ala Ser Leu Ala Leu Ser Leu Gly
  1               5                  10                  15

Gln Arg Ala Thr Ile Ser Cys Arg Ala Ser Glu Ser Val Asp Asn Tyr
                 20                  25                  30

Gly Ile Ser Phe Met Asn Trp Phe Gln Gln Lys Pro Gly Gln Pro Pro
             35                  40                  45

Lys Leu Leu Ile Tyr Ala Ala Ser Asn Gln Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Leu Thr Phe Gly Ala Gly Thr Lys Leu Glu Leu Lys
            100                 105                 110

<210> SEQ ID NO 165
<211> LENGTH: 119
<212> TYPE: PRT
```

```
<213> ORGANISM: Artificial Sequence
<220> FEATURE:
<223> OTHER INFORMATION: Synthetic peptide

<400> SEQUENCE: 165

Glu Val Arg Leu Val Glu Ser Gly Gly Gly Leu Met Gln Pro Gly Gly
1               5                   10                  15

Ser Leu Lys Leu Pro Cys Ala Ala Ser Gly Phe Pro Phe Ser Ser Ser
            20                  25                  30

Ala Met Ser Trp Val Arg Gln Thr Pro Glu Lys Arg Leu Glu Trp Val
        35                  40                  45

Ala Ser Ile Asn Ser Asp Gly Asn Thr Tyr Tyr Pro Asp Ser Val Lys
    50                  55                  60

Gly Arg Phe Thr Ile Ser Arg Asp Ser Ala Arg Asn Ile Leu Tyr Leu
65                  70                  75                  80

Gln Met Ser Ser Leu Arg Ser Glu Asp Thr Ala Met Tyr Tyr Cys Thr
                85                  90                  95

Arg Asn Gly Asp Tyr Arg Tyr Asp Glu Phe Ala Tyr Trp Gly Gln Gly
            100                 105                 110

Thr Leu Val Thr Val Ser Ala
        115

<210> SEQ ID NO 166
<211> LENGTH: 108
<212> TYPE: PRT
<213> ORGANISM: Artificial Sequence
<220> FEATURE:
<223> OTHER INFORMATION: Synthetic peptide

<400> SEQUENCE: 166

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Ala Gly Thr Lys Leu Glu Leu Lys
            100                 105

<210> SEQ ID NO 167
<211> LENGTH: 119
<212> TYPE: PRT
<213> ORGANISM: Artificial Sequence
<220> FEATURE:
<223> OTHER INFORMATION: Synthetic peptide

<400> SEQUENCE: 167

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Gly Tyr
            20                  25                  30

Trp Met His Trp Val Lys Gln Arg Pro Gly Gln Gly Leu Glu Trp Leu
        35                  40                  45
```

```
Gly Tyr Ile Asn Pro Ser Thr Gly Tyr Thr Glu Ser Asn Gln Lys Phe
            50                  55                  60

Lys Asp Lys Ala Thr Leu Thr Ala Asp Lys Ser Ser Thr Ala Tyr
 65                  70                  75                  80

Met Gln Leu Arg Ser Leu Thr Pro Glu Asp Ser Ala Val Tyr Tyr Cys
                85                  90                  95

Ala Arg Glu Gly Ile Thr Thr Val Leu Val Asp Tyr Trp Gly Gln Gly
                100                 105                 110

Thr Thr Leu Thr Val Ser Ser
            115

<210> SEQ ID NO 168
<211> LENGTH: 112
<212> TYPE: PRT
<213> ORGANISM: Artificial Sequence
<220> FEATURE:
<223> OTHER INFORMATION: Synthetic peptide

<400> SEQUENCE: 168

Asn Ile Met Met Thr Gln Ser Pro Ser Ser Leu Ala Val Ser Ala Gly
 1               5                  10                  15

Glu Lys Val Thr Met Ser Cys Lys Ser Ser Gln Ser Val Leu Phe Ser
                20                  25                  30

Ser Asn Gln Lys Asn Tyr Leu Ala Trp Tyr Gln Gln Lys Pro Gly Gln
            35                  40                  45

Ser Pro Arg Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65                  70                  75                  80

Ile Ser Asn Val Gln Ala Glu Asp Leu Ala Val Tyr Tyr Cys His Gln
                85                  90                  95

Tyr Leu Ser Ser Arg Thr Phe Gly Ala Gly Thr Lys Leu Glu Leu Lys
                100                 105                 110

<210> SEQ ID NO 169
<211> LENGTH: 121
<212> TYPE: PRT
<213> ORGANISM: Artificial Sequence
<220> FEATURE:
<223> OTHER INFORMATION: Synthetic peptide

<400> SEQUENCE: 169

Gln Val Gln Leu Lys Gln Ser Gly Pro Glu Leu Glu Lys Pro Gly Ala
 1               5                  10                  15

Ser Val Lys Ile Ser Cys Lys Ala Ser Gly Tyr Ser Phe Thr Gly Tyr
                20                  25                  30

Asn Met Asn Trp Val Lys Gln Ser Asn Gly Lys Ser Leu Glu Trp Ile
            35                  40                  45

Gly Asn Ile Asp Pro Tyr Tyr Gly Gly Ser Thr Tyr Asn Gln Lys Phe
        50                  55                  60

Thr Gly Lys Ala Thr Leu Thr Val Asp Lys Ser Ser Ser Thr Ala Tyr
 65                  70                  75                  80

Met Gln Leu Lys Ser Leu Thr Ser Glu Asp Ser Ala Val Tyr Tyr Cys
                85                  90                  95

Ala Arg Glu Arg Ser Gly Tyr Val Phe Ser Ala Met Asp Tyr Trp Gly
                100                 105                 110

Gln Gly Thr Ser Val Thr Val Ser Ser
```

<210> SEQ ID NO 170
<211> LENGTH: 112
<212> TYPE: PRT
<213> ORGANISM: Artificial Sequence
<220> FEATURE:
<223> OTHER INFORMATION: Synthetic peptide

<400> SEQUENCE: 170

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Asn Val Gln Ala Glu Asp Leu Ala Val Tyr Tyr Cys His Gln
                85                  90                  95

Tyr Leu Ser Ser Arg Thr Phe Gly Ala Gly Thr Lys Leu Glu Leu Lys
            100                 105                 110

<210> SEQ ID NO 171
<211> LENGTH: 123
<212> TYPE: PRT
<213> ORGANISM: Artificial Sequence
<220> FEATURE:
<223> OTHER INFORMATION: Synthetic peptide

<400> SEQUENCE: 171

Glu Val Gln Leu Gln Gln Ser Gly Pro Glu Leu Val Lys Pro Gly Gly
1               5                   10                  15

Ser Met Lys Ile Ser Cys Lys Ala Ser Gly Tyr Ser Phe Thr Gly Tyr
            20                  25                  30

Thr Met Asn Trp Val Lys Arg Ser His Gly Lys Asn Leu Glu Trp Ile
        35                  40                  45

Gly Leu Ile Asn Pro Tyr Asn Gly Val Thr Thr Tyr Asn Gln Asn Phe
    50                  55                  60

Lys Gly Lys Ala Thr Leu Ala Val Asp Lys Ser Ser Ser Thr Ala Tyr
65                  70                  75                  80

Met Glu Leu Leu Gly Leu Thr Ser Glu Asp Ser Ala Val Tyr Tyr Cys
                85                  90                  95

Thr Arg Asp Pro Leu Tyr Tyr Gly Tyr Arg Asp Ser Thr Met Asp Tyr
            100                 105                 110

Trp Gly Gln Gly Thr Ser Val Thr Val Ser Ser
        115                 120

<210> SEQ ID NO 172
<211> LENGTH: 112
<212> TYPE: PRT
<213> ORGANISM: Artificial Sequence
<220> FEATURE:
<223> OTHER INFORMATION: Synthetic peptide

<400> SEQUENCE: 172

Asp Val Val Met Thr Gln Thr Pro Leu Ser Leu Pro Val Ser Leu Gly
1               5                   10                  15

```
Asp Gln Ala Ser Ile Ser Cys Arg Ser Ser Gln Ser Leu Val His Ser
            20                  25                  30

Asp Gly Asn Thr Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Arg Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
                100                 105                 110
```

<210> SEQ ID NO 173
<211> LENGTH: 117
<212> TYPE: PRT
<213> ORGANISM: Artificial Sequence
<220> FEATURE:
<223> OTHER INFORMATION: Synthetic peptide

<400> SEQUENCE: 173

```
Glu Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Ile Lys Gln Arg Pro Gly Gln Gly Gln Glu Trp Ile
        35                  40                  45

Gly Tyr Ile Asn Pro Ser Ser Thr Tyr Thr His Tyr Ile Lys Lys Phe
 50                  55                  60

Lys Asp Lys Ala Thr Leu Thr Ala Asp Lys Ser Ser Ser Thr Ala Tyr
 65                  70                  75                  80

Met Gln Leu Arg Ser Leu Thr Ser Glu Asp Ser Ala Val Tyr Tyr Cys
                85                  90                  95

Ser Arg Gly Glu Leu Gly Gly Phe Ala Tyr Trp Gly Gln Gly Thr Leu
                100                 105                 110

Val Thr Val Ser Ala
        115
```

<210> SEQ ID NO 174
<211> LENGTH: 107
<212> TYPE: PRT
<213> ORGANISM: Artificial Sequence
<220> FEATURE:
<223> OTHER INFORMATION: Synthetic peptide

<400> SEQUENCE: 174

```
Asp Ile Gln Met Ile Gln Ser Pro Ser Ser Met Phe Ala Ser Leu Gly
1               5                   10                  15

Asp Arg Val Ser Leu Ser Cys Arg Ala Ser Gln Gly Ile Arg Gly Asn
            20                  25                  30

Leu Asp Trp Tyr Gln Gln Lys Pro Gly Gly Thr Ile Lys Leu Leu Ile
        35                  40                  45

Tyr Ser Thr Ser Ile Leu Asn Ser Gly Val Pro Ser Arg Phe Ser Gly
 50                  55                  60

Ser Gly Ser Gly Ser Asp Tyr Ser Leu Thr Ile Thr Ser Leu Glu Ser
 65                  70                  75                  80

Glu Asp Phe Ala Asp Tyr Tyr Cys Leu Gln Arg Asn Ala Tyr Pro Leu
```

```
                    85                  90                  95

Thr Phe Gly Ser Gly Thr Lys Leu Glu Leu Lys
            100                 105

<210> SEQ ID NO 175
<211> LENGTH: 119
<212> TYPE: PRT
<213> ORGANISM: Artificial Sequence
<220> FEATURE:
<223> OTHER INFORMATION: Synthetic peptide

<400> SEQUENCE: 175

Glu Val Lys Leu Val Glu Ser Gly Gly Gly Leu Met Lys Pro Gly Gly
1               5                   10                  15

Ser Leu Lys Leu Ser Cys Ala Ala Ser Gly Phe Thr Phe Ser Ser Phe
            20                  25                  30

Ala Leu Ser Trp Val Arg Gln Thr Pro Glu Lys Arg Leu Glu Trp Val
        35                  40                  45

Ala Ser Ile Arg Ser Gly Gly Ile Thr Tyr His Ala Asp Ser Val Lys
    50                  55                  60

Gly Arg Phe Thr Ile Ser Arg Asp Asn Ala Gly Asn Ile Leu Tyr Leu
65                  70                  75                  80

Gln Met Asn Ser Leu Arg Ser Glu Asp Thr Ala Met Tyr Phe Cys Ala
                85                  90                  95

Arg Val Ser Thr Ala Thr Tyr Tyr Gly Met Asp Tyr Trp Gly Gln Gly
            100                 105                 110

Thr Ser Val Thr Val Ser Ser
        115

<210> SEQ ID NO 176
<211> LENGTH: 219
<212> TYPE: PRT
<213> ORGANISM: Mus musculus
<300> PUBLICATION INFORMATION:
<308> DATABASE ACCESSION NUMBER: NCBI / NP_061247.1
<309> DATABASE ENTRY DATE: 2017-08-07
<313> RELEVANT RESIDUES IN SEQ ID NO: (1)..(219)

<400> SEQUENCE: 176

Met Ala Ser Thr Gly Leu Gln Ile Leu Gly Ile Val Leu Thr Leu Leu
1               5                   10                  15

Gly Trp Val Asn Ala Leu Val Ser Cys Ala Leu Pro Met Trp Lys Val
            20                  25                  30

Thr Ala Phe Ile Gly Asn Ser Ile Val Val Ala Gln Met Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Val Thr Leu Leu Ile Val Leu Leu Gly Leu Leu
                85                  90                  95

Val Tyr Leu Ala Gly Ala Lys Cys Thr Thr Cys Val Glu Asp Arg Asn
            100                 105                 110

Ser Lys Ser Arg Leu Val Leu Ile Ser Gly Ile Ile Phe Val Ile Ser
        115                 120                 125

Gly Val Leu Thr Leu Ile Pro Val Cys Trp Thr Ala His Ser Ile Ile
    130                 135                 140

Gln Asp Phe Tyr Asn Pro Leu Val Ala Asp Ala Gln Lys Arg Glu Leu
```

```
145                 150                 155                 160
Gly Ala Ser Leu Tyr Leu Gly Trp Ala Ala Ser Gly Leu Leu Leu
            165                 170                 175

Gly Gly Gly Leu Leu Cys Cys Ala Cys Ser Ser Gly Gly Thr Gln Gly
            180                 185                 190

Pro Arg His Tyr Met Ala Cys Tyr Ser Thr Ser Val Pro His Ser Arg
            195                 200                 205

Gly Pro Ser Glu Tyr Pro Thr Lys Asn Tyr Val
            210                 215
```

<210> SEQ ID NO 177
<211> LENGTH: 80
<212> TYPE: PRT
<213> ORGANISM: Artificial Sequence
<220> FEATURE:
<223> OTHER INFORMATION: Synthetic peptide

<400> SEQUENCE: 177

```
Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80
```

<210> SEQ ID NO 178
<211> LENGTH: 220
<212> TYPE: PRT
<213> ORGANISM: Artificial Sequence
<220> FEATURE:
<223> OTHER INFORMATION: Synthetic peptide

<400> SEQUENCE: 178

```
Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu
145                 150                 155                 160
```

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
        180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
210                 215                 220

<210> SEQ ID NO 179
<211> LENGTH: 322
<212> TYPE: PRT
<213> ORGANISM: Artificial Sequence
<220> FEATURE:
<223> OTHER INFORMATION: Synthetic peptide

<400> SEQUENCE: 179

Cys Ala Gly Ala Thr Cys Gly Thr Gly Cys Thr Gly Ala Cys Thr Cys
1               5                   10                  15

Ala Gly Ala Gly Thr Cys Cys Thr Thr Cys Ala Ala Thr Thr Ala Thr
                20                  25                  30

Gly Thr Cys Cys Gly Thr Gly Ala Gly Cys Cys Cys Ala Gly Gly Cys
            35                  40                  45

Gly Ala Gly Ala Ala Gly Gly Thr Cys Ala Cys Ala Thr Cys Thr Ala
        50                  55                  60

Cys Ala Thr Gly Cys Ala Gly Thr Gly Cys Cys Thr Cys Cys Ala Gly
65                  70                  75                  80

Cys Thr Cys Thr Gly Thr Cys Thr Cys Ala Thr Ala Cys Ala Thr Gly
                85                  90                  95

Cys Ala Cys Thr Gly Gly Thr Thr Cys Cys Ala Gly Cys Ala Gly Ala
            100                 105                 110

Ala Gly Cys Cys Ala Gly Gly Ala Cys Cys Ala Gly Thr Cys Cys
        115                 120                 125

Cys Ala Ala Gly Cys Thr Gly Thr Gly Cys Ala Thr Cys Thr Ala Cys
130                 135                 140

Thr Cys Thr Ala Cys Ala Thr Cys Gly Ala Ala Cys Cys Thr Gly Gly
145                 150                 155                 160

Cys Cys Thr Cys Cys Gly Gly Ala Gly Thr Gly Cys Cys Gly Cys
                165                 170                 175

Ala Ala Gly Gly Thr Thr Thr Ala Gly Cys Gly Gly Thr Cys Gly Gly
            180                 185                 190

Gly Gly Cys Thr Cys Thr Gly Gly Ala Ala Cys Thr Thr Cys Ala Thr
        195                 200                 205

Ala Cys Thr Cys Cys Thr Gly Ala Cys Cys Ala Thr Cys Thr Cys
210                 215                 220

Gly Cys Gly Gly Thr Gly Gly Cys Cys Gly Thr Gly Ala Gly
225                 230                 235                 240

Gly Ala Thr Gly Cys Ala Gly Cys Ala Ala Cys Ala Thr Cys Thr
            245                 250                 255

Ala Thr Thr Gly Cys Cys Ala Gly Cys Ala Gly Ala Gly Thr Cys
        260                 265                 270

Cys Ala Ala Thr Thr Ala Thr Cys Cys Cys Cys Thr Thr Gly Gly
        275                 280                 285

Ala Cys Ala Thr Thr Cys Gly Gly Cys Gly Gly Ala Gly Gly Thr Ala
        290                 295                 300

Cys Cys Ala Ala Ala Cys Thr Cys Gly Ala Gly Ala Thr Thr Ala Ala
305                 310                 315                 320

Gly Cys

<210> SEQ ID NO 180
<211> LENGTH: 351
<212> TYPE: PRT
<213> ORGANISM: Artificial Sequence
<220> FEATURE:
<223> OTHER INFORMATION: Synthetic peptide

<400> SEQUENCE: 180

Gly Ala Ala Gly Thr Cys Cys Ala Gly Cys Thr Gly Cys Ala Gly Cys
1               5                   10                  15

Ala Gly Thr Cys Thr Gly Gly Cys Cys Thr Gly Ala Ala Cys Thr
            20                  25                  30

Gly Gly Thr Gly Ala Ala Gly Cys Cys Thr Gly Gly Cys Gly Cys Cys
            35                  40                  45

Ala Gly Cys Ala Thr Gly Ala Ala Gly Ala Thr Cys Thr Cys Cys Thr
        50                  55                  60

Gly Cys Ala Ala Gly Gly Cys Cys Ala Gly Cys Gly Gly Cys Thr Ala
65                  70                  75                  80

Cys Thr Cys Cys Thr Thr Cys Ala Cys Cys Gly Gly Cys Thr Ala Thr
                85                  90                  95

Ala Cys Ala Ala Thr Gly Ala Ala Cys Thr Gly Gly Gly Thr Gly Ala
                100                 105                 110

Ala Gly Cys Ala Gly Thr Cys Cys Cys Ala Cys Gly Gly Cys Ala Ala
            115                 120                 125

Gly Ala Ala Thr Cys Thr Gly Gly Ala Gly Thr Gly Gly Ala Thr Cys
        130                 135                 140

Gly Gly Cys Cys Thr Gly Ala Thr Ala Ala Cys Cys Cys Ala Thr
145                 150                 155                 160

Ala Cys Ala Ala Thr Gly Gly Cys Gly Gly Cys Ala Cys Cys Ala Thr
                165                 170                 175

Cys Thr Ala Cys Ala Ala Cys Cys Ala Gly Ala Ala Gly Thr Thr Thr
                180                 185                 190

Ala Ala Gly Gly Gly Cys Ala Ala Gly Gly Cys Cys Ala Cys Cys Cys
            195                 200                 205

Thr Gly Ala Cys Ala Gly Thr Gly Gly Ala Cys Ala Ala Gly Ala Gly
        210                 215                 220

Cys Thr Cys Cys Thr Cys Thr Ala Cys Cys Gly Cys Cys Thr Ala Cys
225                 230                 235                 240

Ala Thr Gly Gly Ala Gly Cys Thr Gly Cys Thr Gly Thr Cys Thr Cys
                245                 250                 255

Thr Gly Ala Cys Ala Ala Gly Cys Gly Ala Gly Gly Ala Cys Thr Cys
            260                 265                 270

Cys Gly Cys Cys Gly Thr Gly Thr Ala Cys Thr Ala Thr Thr Gly Cys
        275                 280                 285

Gly Cys Cys Cys Gly Gly Gly Ala Cys Thr Ala Cys Gly Gly Cys Thr
        290                 295                 300

Thr Cys Gly Thr Gly Cys Thr Gly Gly Ala Cys Thr Ala Thr Thr Gly
305                 310                 315                 320

Gly Gly Gly Cys Cys Ala Gly Gly Cys Ala Cys Cys Ala Cys Cys Ala
                325                 330                 335

Cys Thr Gly Ala Cys Ala Gly Thr Gly Ala Gly Cys Thr Cys Cys

<210> SEQ ID NO 181
<211> LENGTH: 107
<212> TYPE: PRT
<213> ORGANISM: Artificial Sequence
<220> FEATURE:
<223> OTHER INFORMATION: Synthetic peptide

<400> SEQUENCE: 181

```
Gln Ile Val Leu Thr Gln Ser Pro Ser Ile Met Ser Val Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Cys Ile Tyr
        35                  40                  45

Ser Thr Ser Asn Leu Ala Ser Gly Val Pro Ala Arg Phe Ser Gly Arg
    50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
                85                  90                  95

Thr Phe Gly Gly Gly Thr Lys Leu Glu Ile Lys
            100                 105
```

<210> SEQ ID NO 182
<211> LENGTH: 117
<212> TYPE: PRT
<213> ORGANISM: Artificial Sequence
<220> FEATURE:
<223> OTHER INFORMATION: Synthetic peptide

<400> SEQUENCE: 182

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser
        115
```

<210> SEQ ID NO 183
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 183

```
gaaattgtgc tcacccagtc tccagcactc atggctgcat ctccagggga gaaggtcacc    60
```
atcacctgca gtgtcagctc aagtataagt tccagcaact tgcactggta ccagcagaag    120
tcaggaacct cccccaaact ctggatttat ggcacatcca acctggcttc tggagtccct    180
gttcgcttca gtggcagtgg atctgggacc tcttattctc tcacaatcag caacatggag    240
gctgaagatg ctgccactta ttactgtcaa cagtggagta gttacccaca cacgttcgga    300
ggggggacca agctggaaat aaaa    324

<210> SEQ ID NO 184
<211> LENGTH: 378
<212> TYPE: DNA
<213> ORGANISM: Artificial Sequence
<220> FEATURE:
<223> OTHER INFORMATION: Synthetic polynucleotide

<400> SEQUENCE: 184
caggtccaaa tgcagcagtc tggagctgag ctggtaaggc ctgggacttc agtgaaggtg    60
tcctgcaagg cttctggata cgccttcact aattacttga tagagtgggt aaagcagagg    120
cctggacagg gccttgagtg gattggactg attaatcctg aagtggtgg tactaattac    180 aatgagaagt tcaagggcaa ggcaacactg actgcagaca atcctccac cactgcctac    240 atgcagctca gcagcctgac atctgatgac tctgcggttt atttctgtgc aagacggtcc    300
cctctaggga gttggatcta ctatgcttac gacggtgttg cttactgggg ccaagggact    360
ctggtcactg tctctgca    378

<210> SEQ ID NO 185
<211> LENGTH: 108
<212> TYPE: PRT
<213> ORGANISM: Artificial Sequence
<220> FEATURE:
<223> OTHER INFORMATION: Synthetic peptide

<400> SEQUENCE: 185

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Asn Met Glu
65                  70                  75                  80

Ala Glu Asp Ala Ala Thr Tyr Tyr Cys Gln Gln Trp Ser Ser Tyr Pro
                85                  90                  95

His Thr Phe Gly Gly Gly Thr Lys Leu Glu Ile Lys
            100                 105

<210> SEQ ID NO 186
<211> LENGTH: 126
<212> TYPE: PRT
<213> ORGANISM: Artificial Sequence
<220> FEATURE:
<223> OTHER INFORMATION: Synthetic peptide

<400> SEQUENCE: 186

Gln Val Gln Met Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr

|   |   |   | 20 |   |   |   | 25 |   |   |   | 30 |   |   |
|---|---|---|----|---|---|---|----|---|---|---|----|---|---|

Leu Ile Glu Trp Val Lys Gln Arg Pro Gly Gln Gly Leu Glu Trp Ile
          35                      40                      45

Gly Leu Ile Asn Pro Gly Ser Gly Gly Thr Asn Tyr Asn Glu Lys Phe
     50                      55                     60

Lys Gly Lys Ala Thr Leu Thr Ala Asp Lys Ser Ser Thr Thr Ala Tyr
65                      70                     75                     80

Met Gln Leu Ser Ser Leu Thr Ser Asp Asp Ser Ala Val Tyr Phe Cys
              85                      90                     95

Ala Arg Arg Ser Pro Leu Gly Ser Trp Ile Tyr Tyr Ala Tyr Asp Gly
          100                  105                 110

Val Ala Tyr Trp Gly Gln Gly Thr Leu Val Thr Val Ser Ala
          115                  120                 125

<210> SEQ ID NO 187
<211> LENGTH: 645
<212> TYPE: DNA
<213> ORGANISM: Mus musculus

<400> SEQUENCE: 187

```
gatattgtgc taactcagtc tccagccacc ctgtctgtga ctccaggaaa tagcgtcagt    60
ctttcctgca gggccagcca agtattggc ggtaacctac actggtatca acaaaaatca   120
catgagtctc caaggcttct catcaagtat gcttcccagt ccatctctgg atcccctcc   180
aggttcagtg cagtggatc agggacagat ttcactctca gtatcaacag tgtggagact   240
gaagattttg gaatgtattt ctgtcaacag agtaacagct ggccttacac gttcggaggg   300
gggaccaagc tggaaataaa acgggcagat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gttag                    645
```

<210> SEQ ID NO 188
<211> LENGTH: 1335
<212> TYPE: DNA
<213> ORGANISM: Mus musculus

<400> SEQUENCE: 188

```
gacgtgcagc ttcaggagtc aggacctagc ctcgtgaaac cttctcagac tctgtccctc    60
acctgttctg tcactggcga ctccatcacc agtgattact ggagctggat ccggaaattc   120
ccagggaata gacttgagta catggggtac gtaagctaca gtggtagcac ttactacaat   180
ccatctctca aaagtcgaat ctccatcacc cgagacacat ccaagaacca gtactacctg   240
gatttgaatt ctgtgactac tgaggacaca gccacatatt actgtgcaaa ctgggacggt   300
gattactggg gccaagggac tctggtcact gtctcttcag cagctaaaac aacagcccca   360
tcggtctatc cactggcccc tgtgtgtgga gatacaactg ctcctcggt gactctagga   420
tgcctggtca agggttattt ccctgagcca gtgaccttga cctggaactc tggatccctg   480
tccagtggtg tgcacacctt cccagctgtc ctgcagtctg acctctacac cctcagcagc   540
tcagtgactg taacctcgag cacctggccc agccagtcca tcacctgcaa tgtggcccac   600
ccggcaagca gcaccaaggt ggacaagaaa attgagccca gagggcccac aatcaagccc   660
```

```
tgtcctccat gcaaatgccc agcacctaac ctcttgggtg gaccatccgt cttcatcttc      720
cctccaaaga tcaaggatgt actcatgatc tccctgagcc ccatagtcac atgtgtggtg      780
gtggatgtga gcgaggatga cccagatgtc cagatcagct ggtttgtgaa caacgtggaa      840
gtacacacag ctcagacaca aacccataga gaggattaca acagtactct ccgggtggtc      900
agtgccctcc ccatccagca ccaggactgg atgagtggca aggagttcaa atgcaaggtc      960
aacaacaaag acctcccagc gcccatcgag agaaccatct caaaacccaa agggtcagta     1020
agagctccac aggtatatgt cttgcctcca ccagaagaag agatgactaa gaaacaggtc     1080
actctgacct gcatggtcac agacttcatg cctgaagaca tttacgtgga gtggaccaac     1140
aacgggaaaa cagagctaaa ctacaagaac actgaaccag tcctggactc tgatggttct     1200
tacttcatgt acagcaagct gagagtggaa aagaagaact gggtggaaag aaatagctac     1260
tcctgttcag tggtccacga gggtctgcac aatcaccaca cgactaagag cttctcccgg     1320
actccgggta aatga                                                      1335

<210> SEQ ID NO 189
<211> LENGTH: 8806
<212> TYPE: DNA
<213> ORGANISM: Artificial Sequence
<220> FEATURE:
<223> OTHER INFORMATION: Synthetic peptide

<400> SEQUENCE: 189
aatgtagtct tatgcaatac tcttgtagtc ttgcaacatg gtaacgatga gttagcaaca       60
tgccttacaa ggagagaaaa agcaccgtgc atgccgattg gtggaagtaa ggtggtacga      120
tcgtgcctta ttaggaaggc aacagacggg tctgacatgg attggacgaa ccactgaatt      180
gccgcattgc agagatattg tatttaagtg cctagctcga tacataaacg ggtctctctg      240
gttagaccag atctgagcct gggagctctc tggctaacta gggaacccac tgcttaagcc      300
tcaataaagc ttgccttgag tgcttcaagt agtgtgtgcc cgtctgttgt gtgactctgg      360
taactagaga tccctcagac cctttttagt cagtgtggaa atctctagca gtggcgcccg      420
aacagggact tgaaagcgaa agggaaacca gaggagctct ctcgacgcag gactcggctt      480
gctgaagcgc gcacggcaag aggcgagggg cggcgactgg tgagtacgcc aaaaattttg      540
actagcggag gctagaagga gagagatggg tgcgagagcg tcagtattaa gcgggggaga      600
attagatcgc gatgggaaaa aattcggtta aggccagggg gaagaaaaaa atataaatta      660
aaacatatag tatgggcaag cagggagcta gaacgattcg cagttaatcc tggcctgtta      720
gaaacatcag aaggctgtag acaaatactg ggacagctac aaccatccct tcagacagga      780
tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg gagcagcagg aagcactatg ggcgcagcgt caatgacgct     1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
```

```
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcggtt    1800 aactttttaaa agaaaagggg ggattggggg gtacagtgca ggggaaagaa tagtagacat    1860
aatagcaaca gacatacaaa ctaaagaatt acaaaaacaa attacaaaaa ttcaaaattt    1920
tccgataagc ttgggagttc cgcgttacat aacttacggt aaatggcccg cctggctgac    1980
cgcccaacga cccccgccca ttgacgtcaa taatgacgta tgttcccata gtaacgccaa    2040
tagggacttt ccattgacgt caatgggtgg agtatttacg gtaaactgcc cacttggcag    2100
tacatcaagt gtatcatatg ccaagtacgc cccctattga cgtcaatgac ggtaaatggc    2160
ccgcctggca ttatgcccag tacatgacct tatgggactt tcctacttgg cagtacatct    2220
acgtattagt catcgctatt accatggtga tgcggttttg gcagtacatc aatgggcgtg    2280
gatagcggtt tgactcacgg ggatttccaa gtctccaccc cattgacgtc aatgggagtt    2340
tgttttggca ccaaaatcaa cgggactttc caaaatgtcg taacaactcc gccccattga    2400
cgcaaatggg cggtaggcgt gtacggtggg aggtctatat aagcagagct cgtttagtga    2460
accgtcagat cgcctggaga cgccatccac gctgttttga cctccataga agacaccgac    2520
tctagaacta gtggatcccc cgggctgcag gaattcgtcg actggatccg gtaccgagga    2580
gatctgccgc cgcgatcgcc ggcgcgccag atctcaagct taactagtta gcggaccgac    2640
gcgtacgcgg ccgctcgaga tgagcggggg cgaggagctg ttcgccggca tcgtgcccgt    2700
gctgatcgag ctggacggcg acgtgcacgg ccacaagttc agcgtgcgcg cgagggcga    2760 gggcgacgcc gactacggca agctggagat caagttcatc tgcaccaccg gcaagctgcc    2820
cgtgccctgg cccacccctg tgaccaccct ctgctacggc atccagtgct tcgcccgcta    2880 cccccgagcac atgaagatga acgacttctt caagagcgcc atgcccgagg ctacatcca    2940 ggagcgcacc atccagttcc aggacgacgg caagtacaag acccgcggcg aggtgaagtt    3000
cgagggcgac accctggtga accgcatcga gctgaagggc aaggacttca ggaggacgg    3060 caacatcctg ggccacaagc tggagtacag cttcaacagc cacaacgtgt acatccgccc    3120
cgacaaggcc aacaacggcc tggaggctaa cttcaagacc cgccacaaca tcgagggcgg    3180
cggcgtgcag ctggccgacc actaccagca caacgtgccc ctgggcgacg cccccgtgct    3240
gatccccatc aaccactacc tgagcactca gaccaagatc agcaaggacc gcaacgaggc    3300
ccgcgaccac atggtgctcc tggagtcctt cagcgcctgc tgccacaccc acggcatgga    3360
cgagctgtac aggtccggac tcagataagt ttaaacccga tatcatcatc tagggcggcc    3420
aattccgccc ctctccccc ccctaacgtt actggccgaa gccgcttgga ataaggccgg    3480
tgtgcgtttg tctatatgtt attttccacc atattgccgt cttttggcaa tgtgagggcc    3540
cggaaacctg gccctgtctt cttgacgagc attcctaggg gtctttcccc tctcgccaaa    3600
ggaatgcaag gtctgttgaa tgtcgtgaag gaagcagttc ctctgggaagc ttcttgaaga    3660 caaacaacgt ctgtagcgac cctttgcagg cagcggaacc ccccacctgg cgacaggtgc    3720
```

```
ctctgcggcc aaaagccacg tgtataagat acacctgcaa aggcggcaca accccagtgc    3780
cacgttgtga gttggatagt tgtggaaaga gtcaaatggc tctcctcaag cgtattcaac    3840
aaggggctga aggatgccca gaaggtaccc cattgtatgg gatctgatct ggggcctcgg    3900
tgcacatgct ttacatgtgt ttagtcgagg ttaaaaaaac gtctaggccc cccgaaccac    3960
ggggacgtgg ttttcctttg aaaaacacga tgataagctt gccacaaccc acaaggagac    4020
gaccttccat gaccgagtac aagcccacgg tgcgcctcgc cacccgcgac gacgtccccc    4080
gggccgtacg caccctcgcc gccgcgttcg ccgactaccc cgccacgcgc cacaccgtcg    4140
acccggaccg ccacatcgag cgggtcaccg agctgcaaga actcttcctc acgcgcgtcg    4200
ggctcgacat cggcaaggtg tgggtcgcgg acgacggcgc cgcggtggcg gtctggacca    4260
cgccggagag cgtcgaagcg ggggcggtgt tcgccgagat cggcccgcgc atggccgagt    4320
tgagcggttc ccggctggcc gcgcagcaac agatggaagg cctcctggcg ccgcaccggc    4380
ccaaggagcc cgcgtggttc ctggccaccg tcggcgtctc gcccgaccac cagggcaagg    4440
gtctgggcag cgccgtcgtg ctccccggag tggaggcggc cgagcgcgcc ggggtgcccg    4500
ccttcctgga gacctccgcg ccccgcaacc tcccctccta cgagcggctc ggcttcaccg    4560
tcaccgccga cgtcgaggtg cccgaaggac gcgcacctg tgcatgacc cgcaagcccg    4620
gtgcctgaaa ttagatcgat accgtcgaca atcaacctct ggattacaaa atttgtgaaa    4680
gattgactgg tattcttaac tatgttgctc cttttacgct atgtggatac gctgctttaa    4740
tgcctttgta tcatgctatt gcttcccgta tggctttcat tttctcctcc ttgtataaat    4800
cctggttgct gtctctttat gaggagttgt ggcccgttgt caggcaacgt ggcgtggtgt    4860
gcactgtgtt gctgacgca accccactg gttgggcat tgccaccacc tgtcagctcc    4920
tttccgggac tttcgctttc cccctcccta ttgccacggc ggaactcatc gccgcctgcc    4980
ttgcccgctg ctggacaggg gctcggctgt tgggcactga caattccgtg gtgttgtcgg    5040
ggaagctgac gtccttttcca tggctgctcg cctgtgttgc cacctggatt ctgcgcggga    5100
cgtccttctg ctacgtccct tcggccctca atccagcgga ccttccttcc cgcggcctgc    5160
tgccggctct gcggcctctt ccgcgtcttc gccttcgccc tcagacgagt cggatctccc    5220
tttgggccgc ctccccgcct gaatacgagc tcggtacctt taagaccaat gacttacaag    5280
gcagctgtag atcttagcca ctttttaaaa gaaaagggggg actgaaagg ctaattcac    5340
tcccaacgaa gacaagatct gcttttgct tgtactgggt ctctctggtt agaccagatc    5400
tgagcctggg agctctctgg ctaactaggg aacccactgc ttaagcctca ataaagcttg    5460
ccttgagtgc ttcaagtagt gtgtgcccgt ctgttgtgtg actctggtaa ctagagatcc    5520
ctcagaccct tttagtcagt gtggaaaatc tctagcagta gtagttcatg tcatcttatt    5580
attcagtatt tataacttgc aaagaaatga atatcagaga gtgagaggaa cttgtttatt    5640
gcagcttata atggttacaa ataaagcaat agcatcacaa atttcacaaa taaagcatt    5700
ttttcactgc attctagttg tggtttgtcc aaactcatca atgtatctta tcatgtctgg    5760
ctctagctat cccgccccta actccgccca tcccgcccct aactccgccc agttccgccc    5820
attctccgcc ccatggctga ctaatttttt ttatttatgc agaggccgag gccgcctcgg    5880
cctctgagct attccagaag tagtgaggag ctttttttgg aggcctaggg acgtacccaa    5940
ttcgccctat agtgagtcgt attacgcgcg ctcactggcc gtcgttttac aacgtcgtga    6000
ctgggaaaac cctggcgtta cccaacttaa tcgccttgca gcacatcccc ctttcgccag    6060
```

```
ctggcgtaat agcgaagagg cccgcaccga tcgcccttcc caacagttgc gcagcctgaa    6120
tggcgaatgg gacgcgccct gtagcggcgc attaagcgcg gcgggtgtgg tggttacgcg    6180
cagcgtgacc gctacacttg ccagcgccct agcgcccgct cctttcgctt tcttcccttc    6240
ctttctcgcc acgttcgccg gctttccccg tcaagctcta atcggggggc tccctttagg    6300
gttccgattt agtgctttac ggcacctcga ccccaaaaaa cttgattagg gtgatggttc    6360
acgtagtggg ccatcgccct gatagacggt ttttcgccct ttgacgttgg agtccacgtt    6420
ctttaatagt ggactcttgt tccaaactgg aacaacactc aaccctatct cggtctattc    6480
ttttgattta agggattt tgccgatttc ggcctattgg ttaaaaaatg agctgattta    6540
acaaaatttt aacgcgaatt ttaacaaaat attaacgttt acaatttccc aggtggcact    6600
tttcggggaa atgtgcgcgg aaccctatt tgtttatttt tctaaataca ttcaaatatg    6660
tatccgctca tgagacaata accctgataa atgcttcaat aatattgaaa aaggaagagt    6720
atgagtattc aacatttccg tgtcgccctt attcccttt tgcggcatt ttgccttcct    6780
gttttgctc acccagaaac gctggtgaaa gtaaaagatg ctgaagatca gttgggtgca    6840
cgagtgggtt acatcgaact ggatctcaac agcggtaaga tccttgagag ttttcgcccc    6900
gaagaacgtt ttccaatgat gagcactttt aaagttctgc tatgtggcgc ggtattatcc    6960
cgtattgacg ccgggcaaga gcaactcggt cgccgcatac actattctca gaatgacttg    7020
gttgagtact caccagtcac agaaaagcat cttacgatg gcatgacagt aagagaatta    7080
tgcagtgctg ccataaccat gagtgataac actgcggcca acttacttct gacaacgatc    7140
ggaggaccga aggagctaac cgcttttttg cacaacatgg gggatcatgt aactcgcctt    7200
gatcgttggg aaccggagct gaatgaagcc ataccaaacg acgagcgtga ccaccgatg    7260
cctgtagcaa tggcaacaac gttgcgcaaa ctattaactg gcgaactact tactctagct    7320
tcccggcaac aattaataga ctggatggag gcggataaag ttgcaggacc acttctgcgc    7380
tcggcccttc cggctggctg gtttattgct gataaatctg gagccggtga gcgtgggtct    7440
cgcggtatca ttgcagcact ggggccagat ggtaagccct cccgtatcgt agttatctac    7500
acgacgggga gtcaggcaac tatggatgaa cgaaatagac agatcgctga gataggtgcc    7560
tcactgatta agcattggta actgtcagac caagtttact catatatact ttagattgat    7620
ttaaaacttc attttttaatt taaaaggatc taggtgaaga tcctttttga atctctcatg    7680
accaaaatcc cttaacgtga gttttcgttc cactgagcgt cagaccccgt agaaaagatc    7740
aaaggatctt cttgagatcc tttttttctg cgcgtaatct gctgcttgca acaaaaaaaa    7800
ccaccgctac cagcggtggt ttgtttgccg gatcaagagc taccaactct ttttccgaag    7860
gtaactggct tcagcagagc gcagatacca aatactgtcc ttctagtgta gccgtagtta    7920
ggccaccact tcaagaactc tgtagcaccg cctacatacc tcgctctgct aatcctgtta    7980
ccagtggctg ctgccagtgg cgataagtcg tgtcttaccg ggttggactc aagacgatag    8040
ttaccggata aggcgcagcg gtcgggctga acggggggtt cgtgcacaca gcccagcttg    8100
gagcgaacga cctacaccga actgagatac ctacagcgtg agctatgaga aagcgccacg    8160
cttcccgaag ggagaaaggc ggacaggtat ccggtaagcg gcagggtcgg aacaggagag    8220
cgcacgaggg agcttccagg gggaaacgcc tggtatcttt atagtcctgt cgggtttcgc    8280
cacctctgac ttgagcgtcg atttttgtga tgctcgtcag ggggcggag cctatggaaa    8340
aacgccagca acgcggcctt tttacggttc ctggcctttt gctggccttt tgctcacatg    8400
ttctttcctg cgttatcccc tgattctgtg gataaccgta ttaccgcctt tgagtgagct    8460
```

-continued

```
gataccgctc gccgcagccg aacgaccgag cgcagcgagt cagtgagcga ggaagcggaa    8520
gagcgcccaa tacgcaaacc gcctctcccc gcgcgttggc cgattcatta atgcagctgg    8580
cacgacaggt ttcccgactg gaaagcgggc agtgagcgca acgcaattaa tgtgagttag    8640
ctcactcatt aggcacccca ggctttacac tttatgcttc cggctcgtat gttgtgtgga    8700
attgtgagcg gataacaatt tcacacagga acagctatg  accatgatta cgccaagcgc    8760
gcaattaacc ctcactaaag ggaacaaaag ctggagctgc aagctt                   8806
```

<210> SEQ ID NO 190
<211> LENGTH: 220
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (143)..(143)
<223> OTHER INFORMATION: Xaa can be any naturally occurring amino acid

<400> SEQUENCE: 190

```
Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Xaa Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220
```

<210> SEQ ID NO 191
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 191

```
cagaaactca tctcagaaga ggatctggca gcaaatgata tcctggatta caaggatgac    60
gacgataa                                                             68
```

```
<210> SEQ ID NO 192
<211> LENGTH: 683
<212> TYPE: DNA
<213> ORGANISM: Homo sapiens
<300> PUBLICATION INFORMATION:
<308> DATABASE ACCESSION NUMBER: NCBI / NM_021195.4
<309> DATABASE ENTRY DATE: 2017-06-04
<313> RELEVANT RESIDUES IN SEQ ID NO: (1)..(683)

<400> SEQUENCE: 192
ccgcgatcgc catggcctct gccggaatgc agatcctggg agtcgtcctg acactgctgg    60
gctgggtgaa tggcctggtc tcctgtgccc tgcccatgtg aaggtgacc gctttcatcg    120 gcaacagcat cgtggtggcc caggtggtgt gggagggcct gtggatgtcc tgcgtggtgc    180
agagcaccgg ccagatgcag tgcaaggtgt acgactcact gctggcgctg ccacaggacc    240
tgcaggctgc acgtgccctc tgtgtcatcg ccctccttgt ggccctgttc ggcttgctgg    300
tctaccttgc tggggccaag tgtaccacct gtgtggagga aaggattcc aaggcccgcc    360 tggtgctcac ctctgggatt gtctttgtca tctcaggggt cctgacgcta atccccgtgt    420
gctggacggc gcatgccgtc atccgggact tctataaccc cctggtggct gaggcccaaa    480
agcgggagct gggggcctcc ctctacttgg gctgggcggc ctcaggcctt ttgttgctgg    540
gtggggggtt gctgtgctgc acttgcccct cggggggggtc ccagggcccc agccattaca    600
tggcccgcta ctcaacatct gcccctgcca tctctcgggg gccctctgag taccctacca    660
agaattacgt cacgcgtacg cgg                                            683
```

```
<210> SEQ ID NO 193
<211> LENGTH: 677
<212> TYPE: DNA
<213> ORGANISM: Mus musculas
<300> PUBLICATION INFORMATION:
<308> DATABASE ACCESSION NUMBER: NCBI / NM_018777.4
<309> DATABASE ENTRY DATE: 2017-08-07
<313> RELEVANT RESIDUES IN SEQ ID NO: (1)..(677)

<400> SEQUENCE: 193
gccgcgatcg ccatggcctc tactggtctg caaatcttgg ggatcgtcct gaccctgctt    60
ggctgggtca acgccctggt gtcctgtgcc ctgcccatgt ggaaggtgac cgccttcatc    120
ggcaacagca tcgtcgtggc ccagatggtg tgggaggggc tgtggatgtc ctgtgtggtt    180
cagagcactg ccagatgca gtgcaaggtg tatgactcac tgttggcgct gccccaggac    240
ctgcaggctg ccagagccct ctgtgttgtc accctcctca ttgtcctgct tggcctgctc    300
gtgtacctgg ctggagccaa gtgcactacc tgtgtggaag ataggaactc caagtctcgt    360
ctggtgctca tctctggcat catctttgtc atttctgggg tcctgacgct cattcctgtc    420
tgctggactg cccactctat catccaggac ttctacaacc ccttggtggc tgatgctcaa    480
aagcgggagc tgggggcctc cctctacctg gctgggcag cctcaggcct tttgctgctg    540 ggtgagggc tactatgctg cgcctgctct tctggaggga cccagggacc cagacattac    600
atggcctgct attctacatc tgtcccacat tctcggggac cctccgaata tcccaccaag    660
aattatgtga cgcgtac                                                   677
```

```
<210> SEQ ID NO 194
<211> LENGTH: 683
```

<212> TYPE: DNA
<213> ORGANISM: Artificial Sequence
<220> FEATURE:
<223> OTHER INFORMATION: Synthetic polynucleotide

<400> SEQUENCE: 194

| | | | | | |
|---|---|---|---|---|---|
| cgcgatcgcc | atggcctctg | ccggaatgca | gatcctggga | gtcgtcctga | cactgctggg | 60 |
| ctgggtgaat | ggcctggtct | cctgtgccct | gcccatgtgg | aaggtgaccg | ctttcatcgg | 120 |
| caacagcatc | gtggtggccc | aggtggtgtg | ggagggcctg | tggatgtcct | gcgtggtgca | 180 |
| gagcaccggc | cagatgcagt | gcaaggtgta | cgactcactg | ctggcgctgc | acaggacct | 240 |
| gcaggctgca | cgtgccctct | gtgtcatcgc | cctccttgtg | ccctgttcg | gcttgctggt | 300 |
| ctaccttgct | ggggccaagt | gtaccacctg | tgtggaggag | aaggattcca | aggcccgcct | 360 |
| ggtgctcacc | tctgggattg | tctttgtcat | ctcaggggtc | ctgacgctaa | tcccgtgtg | 420 |
| ctggacggcg | catgccatca | tccgggactt | ctataacccc | ctggtggctg | aggcccaaaa | 480 |
| gcgggagctg | ggggcctccc | tctacttggg | ctgggcggcc | tcaggccttt | tgttgctggg | 540 |
| tgggggttg | ctgtgctgca | cttgcccctc | gggggggtcc | cagggcccca | gccattacat | 600 |
| ggcccgctac | tcaacatctg | ccctgccat | ctctcggggg | ccctctgagt | accctaccaa | 660 |
| gaattacgtc | acgcgtacgc | ggc | | | | 683 |

<210> SEQ ID NO 195
<211> LENGTH: 672
<212> TYPE: DNA
<213> ORGANISM: Homo sapiens
<300> PUBLICATION INFORMATION:
<308> DATABASE ACCESSION NUMBER: NCBI / NM_020982.3
<309> DATABASE ENTRY DATE: 2017-04-15
<313> RELEVANT RESIDUES IN SEQ ID NO: (1)..(672)

<400> SEQUENCE: 195

| | | | | | |
|---|---|---|---|---|---|
| gccgcgatcg | ccatggcttc | gaccggctta | gaactgctgg | gcatgaccct | ggctgtgctg | 60 |
| ggctggctgg | ggaccctggt | gtcctgcgcc | ctgcccctgt | ggaaggtgac | cgccttcatc | 120 |
| ggcaacagca | tcgtggtggc | ccaggtggtg | tgggagggcc | tgtggatgtc | ctgcgtggtg | 180 |
| cagagcacgg | gccagatgca | gtgcaaggtg | tacgactcac | tgctggctct | gccgcaggac | 240 |
| ctgcaggccg | cacgtgccct | ctgtgtcatt | gccctcctgc | tggccctgct | tggcctcctg | 300 |
| gtggccatca | caggtgccca | gtgtaccacg | tgtgtggagg | acgaaggtgc | caaggcccgt | 360 |
| atcgtgctca | ccgcgggggt | catcctcctc | ctcgccggca | tcctggtgct | catccctgtg | 420 |
| tgctggacg | cgcacgccat | catccaggac | ttctacaacc | cctggtggc | tgaggccctc | 480 |
| aagcgggagc | tgggggcctc | cctctacctg | ggctgggcgg | cggctgcact | gcttatgctg | 540 |
| ggcgggggc | tcctctgctg | cacgtgcccc | ccgcccagg | tcgagcggcc | ccgcggacct | 600 |
| cggctgggct | actccatccc | ctcccgctcg | ggtgcatctg | gactggacaa | gagggactac | 660 |
| gtgacgcgta | cg | | | | | 672 |

<210> SEQ ID NO 196
<211> LENGTH: 651
<212> TYPE: DNA
<213> ORGANISM: Homo sapiens
<300> PUBLICATION INFORMATION:
<308> DATABASE ACCESSION NUMBER: NCBI / NM_001305.4
<309> DATABASE ENTRY DATE: 2017-07-10
<313> RELEVANT RESIDUES IN SEQ ID NO: (1)..(651)

<400> SEQUENCE: 196

-continued

```
ccgcgatcgc catggcctcc atggggctac aggtaatggg catcgcgctg gccgtcctgg      60
gctggctggc cgtcatgctg tgctgcgcgc tgcccatgtg gcgcgtgacg gccttcatcg     120
gcagcaacat tgtcacctcg cagaccatct gggagggcct atggatgaac tgcgtggtgc     180
agagcaccgg ccagatgcag tgcaaggtgt acgactcgct gctggcactg ccgcaggacc     240
tgcaggcggc ccgcgccctc gtcatcatca gcatcatcgt ggctgctctg ggcgtgctgc     300
tgtccgtggt ggggggcaag tgtaccaact gcctggagga tgaaagcgcc aaggccaaga     360
ccatgatcgt ggcgggcgtg gtgttcctgt tggccggcct tatggtgata gtgccggtgt     420
cctggacggc ccacaacatc atccaagact tctacaatcc gctggtggcc tccgggcaga     480
agcgggagat gggtgcctcg ctctacgtcg gctgggccgc ctccggcctg ctgctccttg     540
gcggggggct gctttgctgc aactgtccac cccgcacaga caagccttac tccgccaagt     600
attctgctgc ccgctctgct gctgccagca actacgtgac gcgtacgcgg c             651
```

<210> SEQ ID NO 197
<211> LENGTH: 680
<212> TYPE: DNA
<213> ORGANISM: Homo sapiens
<300> PUBLICATION INFORMATION:
<308> DATABASE ACCESSION NUMBER: NCBI / NM_001306.3
<309> DATABASE ENTRY DATE: 2017-07-10
<313> RELEVANT RESIDUES IN SEQ ID NO: (1)..(680)

<400> SEQUENCE: 197

```
gccgcgatcg ccatgtccat gggcctggag atcacgggca ccgcgctggc cgtgctgggc      60
tggctgggca ccatcgtgtg ctgcgcgttg cccatgtggc gcgtgtcggc cttcatcggc     120
agcaacatca tcacgtcgca gaacatctgg gagggcctgt ggatgaactg cgtggtgcag     180
agcaccggcc agatgcagtg caaggtgtac gactcgctgc tggcactgcc acaggacctt     240
caggcggccc gcgccctcat cgtggtggcc atcctgctgg ccgccttcgg gctgctagtg     300
gcgctggtgg gcgcccagtg caccaactgc gtgcaggacg acacggccaa ggccaagatc     360
accatcgtgg caggcgtgct gttccttctc gccgccctgc tcaccctcgt gccggtgtcc     420
tggtcggcca acaccattat ccgggacttc tacaaccccg tggtgcccga ggcgcagaag     480
cgcgagatgg gcgcgggcct gtacgtgggc tgggcggccg cggcgctgca gctgctgggg     540
ggcgcgctgc tctgctgctc gtgtccccca cgcgagaaga agtacacggc caccaaggtc     600
gtctactccg cgccgcgctc caccggcccg ggagccagcc tgggcacagg ctacgaccgc     660
aaggactacg tcacgcgtac                                                 680
```

<210> SEQ ID NO 198
<211> LENGTH: 214
<212> TYPE: PRT
<213> ORGANISM: Artificial Sequence
<220> FEATURE:
<223> OTHER INFORMATION: Synthetic peptide

<400> SEQUENCE: 198

```
Asp Ile Val Leu Thr Gln Ser Pro Ala Thr Leu Ser Val Thr Pro Gly
 1               5                  10                  15

Asn Ser Val Ser Leu Ser Cys Arg Ala Ser Gln Ser Ile Gly Gly Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60
```

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 199
<211> LENGTH: 444
<212> TYPE: PRT
<213> ORGANISM: Artificial Sequence
<220> FEATURE:
<223> OTHER INFORMATION: Synthetic peptide

<400> SEQUENCE: 199

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Asp
            20                  25                  30

Tyr Trp Ser Trp Ile Arg Lys Phe Pro Gly Asn Arg Leu Glu Tyr Met
            35                  40                  45

Gly Tyr Val Ser Tyr Ser Gly Ser Thr Tyr Tyr Asn Pro Ser Leu Lys
50                  55                  60

Ser Arg Ile Ser Ile Thr Arg Asp Thr Ser Lys Asn Gln Tyr Tyr Leu
65                  70                  75                  80

Asp Leu Asn Ser Val Thr Thr Glu Asp Thr Ala Thr Tyr Tyr Cys Ala
                85                  90                  95

Asn Trp Asp Gly Asp Tyr Trp Gly Gln Gly Thr Leu Val Thr Val Ser
            100                 105                 110

Ser Ala Ala Lys Thr Thr Ala Pro Ser Val Tyr Pro Leu Ala Pro Val
            115                 120                 125

Cys Gly Asp Thr Thr Gly Ser Ser Val Thr Leu Gly Cys Leu Val Lys
            130                 135                 140

Gly Tyr Phe Pro Glu Pro Val Thr Leu Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Thr Ser Ser Thr Trp Pro Ser Gln
            180                 185                 190

Ser Ile Thr Cys Asn Val Ala His Pro Ala Ser Ser Thr Lys Val Asp
            195                 200                 205

Lys Lys Ile Glu Pro Arg Gly Pro Thr Ile Lys Pro Cys Pro Pro Cys
210                 215                 220

Lys Cys Pro Ala Pro Asn Leu Leu Gly Gly Pro Ser Val Phe Ile Phe
225                 230                 235                 240

Pro Pro Lys Ile Lys Asp Val Leu Met Ile Ser Leu Ser Pro Ile Val
                245                 250                 255

Thr Cys Val Val Val Asp Val Ser Glu Asp Pro Asp Val Gln Ile
        260                 265                 270

Ser Trp Phe Val Asn Asn Val Glu Val His Thr Ala Gln Thr Gln Thr
            275                 280                 285

His Arg Glu Asp Tyr Asn Ser Thr Leu Arg Val Val Ser Ala Leu Pro
        290                 295                 300

Ile Gln His Gln Asp Trp Met Ser Gly Lys Glu Phe Lys Cys Lys Val
305                 310                 315                 320

Asn Asn Lys Asp Leu Pro Ala Pro Ile Glu Arg Thr Ile Ser Lys Pro
                325                 330                 335

Lys Gly Ser Val Arg Ala Pro Gln Val Tyr Val Leu Pro Pro Pro Glu
            340                 345                 350

Glu Glu Met Thr Lys Lys Gln Val Thr Leu Thr Cys Met Val Thr Asp
        355                 360                 365

Phe Met Pro Glu Asp Ile Tyr Val Glu Trp Thr Asn Asn Gly Lys Thr
370                 375                 380

Glu Leu Asn Tyr Lys Asn Thr Glu Pro Val Leu Asp Ser Asp Gly Ser
385                 390                 395                 400

Tyr Phe Met Tyr Ser Lys Leu Arg Val Glu Lys Lys Asn Trp Val Glu
                405                 410                 415

Arg Asn Ser Tyr Ser Cys Ser Val Val His Glu Gly Leu His Asn His
            420                 425                 430

His Thr Thr Lys Ser Phe Ser Arg Thr Pro Gly Lys
        435                 440

<210> SEQ ID NO 200
<211> LENGTH: 220
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (143)..(143)
<223> OTHER INFORMATION: Xaa can be any naturally occurring amino acid

<400> SEQUENCE: 200

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp

```
                100             105             110
Ser Lys Ala Arg Leu Val Leu Thr Ser Gly Ile Val Phe Val Ile Ser
            115                 120                 125
Gly Val Leu Thr Leu Ile Pro Val Cys Trp Thr Ala His Ala Xaa Ile
        130                 135                 140
Arg Asp Phe Tyr Asn Pro Leu Val Ala Glu Ala Gln Lys Arg Glu Leu
145                 150                 155                 160
Gly Ala Ser Leu Tyr Leu Gly Trp Ala Ala Ser Gly Leu Leu Leu Leu
                165                 170                 175
Gly Gly Gly Leu Leu Cys Cys Thr Cys Pro Ser Gly Ser Gln Gly
            180                 185                 190
Pro Ser His Tyr Met Ala Arg Tyr Ser Thr Ser Ala Pro Ala Ile Ser
        195                 200                 205
Arg Gly Pro Ser Glu Tyr Pro Thr Lys Asn Tyr Val
210                 215                 220

<210> SEQ ID NO 201
<211> LENGTH: 220
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (143)..(143)
<223> OTHER INFORMATION: Xaa can be any naturally occurring amino acid

<400> SEQUENCE: 201

Met Ala Ser Ala Gly Met Gln Ile Leu Gly Val Val Leu Thr Leu Leu
1               5                   10                  15
Gly Trp Val Asn Gly Leu Val Ser Cys Ala Leu Pro Met Trp Lys Val
                20                  25                  30
Thr Ala Phe Ile Gly Asn Ser Ile Val Val Ala Gln Val Val Trp Glu
            35                  40                  45
Gly Leu Trp Met Ser Cys Val Val Gln Ser Thr Gly Gln Met Gln Cys
        50                  55                  60
Lys Val Tyr Asp Ser Leu Leu Ala Leu Pro Gln Asp Leu Gln Ala Ala
65                  70                  75                  80
Arg Ala Leu Cys Val Ile Ala Leu Leu Val Ala Leu Phe Gly Leu Leu
                85                  90                  95
Val Tyr Leu Ala Gly Ala Lys Cys Thr Thr Cys Val Glu Glu Lys Asp
                100                 105                 110
Ser Lys Ala Arg Leu Val Leu Thr Ser Gly Ile Val Phe Val Ile Ser
            115                 120                 125
Gly Val Leu Thr Leu Ile Pro Val Cys Trp Thr Ala His Ala Xaa Ile
        130                 135                 140
Arg Asp Phe Tyr Asn Pro Leu Val Ala Glu Ala Gln Lys Arg Glu Leu
145                 150                 155                 160
Gly Ala Ser Leu Tyr Leu Gly Trp Ala Ala Ser Gly Leu Leu Leu Leu
                165                 170                 175
Gly Gly Gly Leu Leu Cys Cys Thr Cys Pro Ser Gly Ser Gln Gly
            180                 185                 190
Pro Ser His Tyr Met Ala Arg Tyr Ser Thr Ser Ala Pro Ala Ile Ser
        195                 200                 205
Arg Gly Pro Ser Glu Tyr Pro Thr Lys Asn Tyr Val
210                 215                 220
```

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 208
tccagtgtaa gttccactta c                                             21

<210> SEQ ID NO 209
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 209 agcacatcc                                                            9

<210> SEQ ID NO 210
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 210
caccagtatc atcgttcccc gctcacg                                       27

```
<210> SEQ ID NO 211
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 211
ggctacacct ttactaccta cacg                                          24

<210> SEQ ID NO 212
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 212
attaatccta gcagtggata tact                                          24

<210> SEQ ID NO 213
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 213
gcaaacgggg attactacgt cgcttac                                       27

<210> SEQ ID NO 214
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 214
gagaatattt acagttat                                                 18

<210> SEQ ID NO 215
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 215 aatgcaaaa                                                            9

<210> SEQ ID NO 216
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 216
caacatcatt atactgttcc gtggacg                                       27

<210> SEQ ID NO 217
<211> LENGTH: 24
<212> TYPE: DNA
<213> ORGANISM: Artificial Sequence
<220> FEATURE:
<223> OTHER INFORMATION: Synthetic polynucleotide
```

<400> SEQUENCE: 217
ggtttcactt tcagtgatta ctgg                                          24

<210> SEQ ID NO 218
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 218
attagattga aatctgataa ttatgcaaca                                    30

<210> SEQ ID NO 219
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 219
aatgatggcc cccctcggg gtgt                                           24

<210> SEQ ID NO 220
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 220
gagaatattt acagttat                                                 18

<210> SEQ ID NO 221
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 221 aatgcaaaa                                                            9

<210> SEQ ID NO 222
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 222
caacatcatt atactgttcc gtggacg                                       27

<210> SEQ ID NO 223
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 223
ggattcactt tcagtaatta ctgg                                          24

<210> SEQ ID NO 224
<211> LENGTH: 30

```
<212> TYPE: DNA
<213> ORGANISM: Artificial Sequence
<220> FEATURE:
<223> OTHER INFORMATION: Synthetic polynucleotide

<400> SEQUENCE: 224
attagattga aatctgataa ttatgcaaca                                        30

<210> SEQ ID NO 225
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 225
aatgatggcc cccctcggg gtgt                                               24

<210> SEQ ID NO 226
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 226
cagagccttg tacacagtga tggaaacacc tat                                    33

<210> SEQ ID NO 227
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 227 aaagtttcc                                                                9

<210> SEQ ID NO 228
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 228
tctcaaagta cacatgttcc ttacacg                                           27

<210> SEQ ID NO 229
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 229
ggctacacct ttactagcta cacg                                              24

<210> SEQ ID NO 230
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 230
```
attaatccta gcagtactta tact                                              24

<210> SEQ ID NO 231
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 231
tcaagagggg aactgggagg gtttgcttac                                        30

<210> SEQ ID NO 232
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 232
cagagcattg tacatagtaa tggaaacacc tat                                    33

<210> SEQ ID NO 233
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 233 aaagtttcc                                                                9

<210> SEQ ID NO 234
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 234
tttcaaggtt cacatgttcc attcacg                                           27

<210> SEQ ID NO 235
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 235
ggatacatat tcactcacta tatt                                              24

<210> SEQ ID NO 236
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 236
attaatcctt acaatgatgg tact                                              24

<210> SEQ ID NO 237
<211> LENGTH: 39
<212> TYPE: DNA
<213> ORGANISM: Artificial Sequence

```
<220> FEATURE:
<223> OTHER INFORMATION: Synthetic polynucleotide

<400> SEQUENCE: 237
gcaagatact acggctaccc ttactattct atggactac                    39

<210> SEQ ID NO 238
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 238
cagagtctgc tcaacagtag aacccgaaag aactac                       36

<210> SEQ ID NO 239
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 239 tgggcatcc                                                      9

<210> SEQ ID NO 240
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 240
aagcaatctt attatctgta cacg                                    24

<210> SEQ ID NO 241
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 241
ggctactcca tcaccagtgg ttattac                                 27

<210> SEQ ID NO 242
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 242
atcagctacg atggtggcat t                                       21

<210> SEQ ID NO 243
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 243
gcaagatttg gtaaggggc tatggactac                               30
```

<210> SEQ ID NO 244
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 244
tcaagtgtaa gttccagtta c                                     21

<210> SEQ ID NO 245
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 245 agcacatcc                                                    9

<210> SEQ ID NO 246
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 246
caccagtatc atcgttcccc acccacg                               27

<210> SEQ ID NO 247
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 247
ggttactcat tcactggcta cacc                                  24

<210> SEQ ID NO 248
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 248
attaatcctt acaatggtgg tact                                  24

<210> SEQ ID NO 249
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 249
gcaagagggg tctatgatta cgacggattt acttac                     36

<210> SEQ ID NO 250
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 250
cagagccttg tacacagtga tggaaacacc tat                          33

<210> SEQ ID NO 251
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 251 aaagtttcc                                                     9

<210> SEQ ID NO 252
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 252
tctcaaagta cacatgttcc ttacacg                                 27

<210> SEQ ID NO 253
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 253
ggctacacct ttactaccta cacg                                    24

<210> SEQ ID NO 254
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 254
attaatcctc gcagtggtta tagt                                    24

<210> SEQ ID NO 255
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 255
tcaagagggg aactgggagg gtttgcttac                              30

<210> SEQ ID NO 256
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 256
cagaccattg gtacatgg                                           18

<210> SEQ ID NO 257

```
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 257 gctgcagcc                                                              9

<210> SEQ ID NO 258
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 258
caacaacttt acagtattcc tcggacg                                         27

<210> SEQ ID NO 259
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 259
ggatacagat tcactgacta caac                                            24

<210> SEQ ID NO 260
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 260 attaaccota acaatggtgg tact                                            24

<210> SEQ ID NO 261
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 261
gcaagagatt acttgtactt ctttgactgc                                      30

<210> SEQ ID NO 262
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 262
cagagccttg tacacagtaa tggaaacacc tat                                  33

<210> SEQ ID NO 263
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 263
``` aaagtttcc                                                              9

<210> SEQ ID NO 264
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 264
tctcaaatta cacatgttcc gtacacg                                         27

<210> SEQ ID NO 265
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 265
ggttatacct tcacagacta ttca                                            24

<210> SEQ ID NO 266
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 266
ataagcactg agactggtga gcca                                            24

<210> SEQ ID NO 267
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 267
actagaggtc tatggtcctc gtttgcttac                                      30

<210> SEQ ID NO 268
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 268
aaaagtgtca gtacatctgg ctatagttat                                      30

<210> SEQ ID NO 269
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 269 cttgcatcc                                                              9

<210> SEQ ID NO 270
<211> LENGTH: 27
<212> TYPE: DNA

```
<213> ORGANISM: Artificial Sequence
<220> FEATURE:
<223> OTHER INFORMATION: Synthetic polynucleotide

<400> SEQUENCE: 270
cagcacagta gggagcttcc gctcacg                                         27

<210> SEQ ID NO 271
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 271
ggattcactt tcagtagctt tgga                                            24

<210> SEQ ID NO 272
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 272
attagtagtg acagtaggac catc                                            24

<210> SEQ ID NO 273
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 273
gcaagagact acggtagaac ctacgaggct tac                                  33

<210> SEQ ID NO 274
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 274
caggacattg gaggaaat                                                   18

<210> SEQ ID NO 275
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 275 tccacatcc                                                              9

<210> SEQ ID NO 276
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 276
ctacagcgta atgcgtatcc gctcact                                         27
```

<210> SEQ ID NO 277
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 277
ggattcactt tcagtagtta tgcc                                              24

<210> SEQ ID NO 278
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 278
attagaagtg gtggtaccac c                                                 21

<210> SEQ ID NO 279
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 279
gcaaaagtgg gcggtaaccc ctatcctatg gactac                                 36

<210> SEQ ID NO 280
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 280
tcaagtataa gttccaatta c                                                 21

<210> SEQ ID NO 281
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 281 aggacatcc                                                                9

<210> SEQ ID NO 282
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 282
cagcagggta gtagtatacc gctcacg                                           27

<210> SEQ ID NO 283
<211> LENGTH: 24
<212> TYPE: DNA
<213> ORGANISM: Artificial Sequence
<220> FEATURE:

<223> OTHER INFORMATION: Synthetic polynucleotide

<400> SEQUENCE: 283
ggatacgcct tcagtaatta cttg                                                24

<210> SEQ ID NO 284
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 284
attaatcctg gaagtggtgg tact                                                24

<210> SEQ ID NO 285
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 285
gcaagatcat acttcggtag aagctacccc tatactatgg actac                         45

<210> SEQ ID NO 286
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 286
caaagtgttg attatgatgg tgataattat                                          30

<210> SEQ ID NO 287
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 287 gctgcatcc                                                                  9

<210> SEQ ID NO 288
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 288
cagcaaagta atgaggatcc attcacg                                             27

<210> SEQ ID NO 289
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 289
ggctacacat tcactgatta tgct                                                24

```
<210> SEQ ID NO 290
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 290
attagtacat actctggtaa taca                                              24

<210> SEQ ID NO 291
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 291
gcaagaaggg gcgattacag cctctatgct atggactac                              39

<210> SEQ ID NO 292
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 292
caaagtgttt tattcagttc aaatcagaaa aactac                                 36

<210> SEQ ID NO 293
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 293 tgggcatcc                                                                9

<210> SEQ ID NO 294
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 294
catcaatacc tctcctcgcg cacg                                              24

<210> SEQ ID NO 295
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 295
ggattcactt tcagtagctt tgga                                              24

<210> SEQ ID NO 296
<211> LENGTH: 24
<212> TYPE: DNA
<213> ORGANISM: Artificial Sequence
<220> FEATURE:
<223> OTHER INFORMATION: Synthetic polynucleotide
```

```
<400> SEQUENCE: 296
attagtagtg acagtaggac catc                                          24

<210> SEQ ID NO 297
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 297
gcaagagact acggtagaac ctacgaggct tac                                33

<210> SEQ ID NO 298
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 298
gaaagtgttg ataattatgg cattagtttt                                    30

<210> SEQ ID NO 299
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 299 gctgcatcc                                                            9

<210> SEQ ID NO 300
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 300
cagcaaagta aggaggttcc gctcacg                                       27

<210> SEQ ID NO 301
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 301
ggattccctt tcagtagctc tgcc                                          24

<210> SEQ ID NO 302
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 302
attaatagtg atggtaacac c                                             21

<210> SEQ ID NO 303
<211> LENGTH: 39
```

```
<212> TYPE: DNA
<213> ORGANISM: Artificial Sequence
<220> FEATURE:
<223> OTHER INFORMATION: Synthetic polynucleotide

<400> SEQUENCE: 303
acaagaaacg gggactatag gtacgacgag tttgcttac                           39

<210> SEQ ID NO 304
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 304
tcaagtgtaa gttccagtta c                                             21

<210> SEQ ID NO 305
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 305 agcacatcc                                                            9

<210> SEQ ID NO 306
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 306
caccagtatc atcgttcccc acccacg                                       27

<210> SEQ ID NO 307
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 307
ggctacacct ttactggcta ctgg                                          24

<210> SEQ ID NO 308
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 308
attaatccta gcactggtta tact                                          24

<210> SEQ ID NO 309
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 309
```

```
gcaagagagg ggattactac tgtgctggtt gactac                                   36

<210> SEQ ID NO 310
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 310
caaagtgttt tattcagttc aaatcagaaa aactac                                   36

<210> SEQ ID NO 311
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 311 tgggcatcc                                                                  9

<210> SEQ ID NO 312
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 312
catcaatacc tctcctcgcg cacg                                                24

<210> SEQ ID NO 313
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 313
ggttactctt tcactggcta caat                                                24

<210> SEQ ID NO 314
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 314
attgatcctt actatggtgg ttct                                                24

<210> SEQ ID NO 315
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 315
gcaagagaga ggtcgggcta cgttttctct gctatggact ac                            42

<210> SEQ ID NO 316
<211> LENGTH: 36
<212> TYPE: DNA
<213> ORGANISM: Artificial Sequence
```

-continued

<220> FEATURE:
<223> OTHER INFORMATION: Synthetic polynucleotide

<400> SEQUENCE: 316
caaagtgttt tattcagttc aaatcagaaa aactac                              36

<210> SEQ ID NO 317
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 317 tgggcatcc                                                            9

<210> SEQ ID NO 318
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 318
catcaatacc tctcctcgcg cacg                                           24

<210> SEQ ID NO 319
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 319
ggttactcat tcactggcta cacc                                           24

<210> SEQ ID NO 320
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 320
attaatcctt acaatggtgt tact                                           24

<210> SEQ ID NO 321
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 321
acaagagatc ccctttacta cggctacagg gactctacta tggactac                 48

<210> SEQ ID NO 322
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 322
cagagccttg tacacagtga tggaaacacc tat                                 33

```
<210> SEQ ID NO 323
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 323 aaagtttcc                                                                9

<210> SEQ ID NO 324
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 324
tctcaaagta cacatgttcc ttacacg                                           27

<210> SEQ ID NO 325
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 325
ggctacacct ttactagcta cacg                                              24

<210> SEQ ID NO 326
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 326
attaatccta gcagtacgta tact                                              24

<210> SEQ ID NO 327
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 327
tcaagagggg aactgggagg gtttgcttac                                        30

<210> SEQ ID NO 328
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 328
cagggcatta gaggtaat                                                     18

<210> SEQ ID NO 329
<211> LENGTH: 9
<212> TYPE: DNA
<213> ORGANISM: Artificial Sequence
<220> FEATURE:
<223> OTHER INFORMATION: Synthetic polynucleotide
```

<400> SEQUENCE: 329 tccacatcc                                                                  9

<210> SEQ ID NO 330
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 330
ctacagcgta atgcgtatcc tctcacg                                             27

<210> SEQ ID NO 331
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 331
ggattcactt tcagtagttt tgcc                                                24

<210> SEQ ID NO 332
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 332
attagaagtg gtggtattac c                                                   21

<210> SEQ ID NO 333
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 333
gcaagagtta gtacggctac gtactatggt atggactac                                39

<210> SEQ ID NO 334
<211> LENGTH: 325
<212> TYPE: DNA
<213> ORGANISM: Artificial Sequence
<220> FEATURE:
<223> OTHER INFORMATION: Synthetic polynucleotide

<400> SEQUENCE: 334
caaattgttc tcacccagtc tccagcaatc atgtctgcat ctctagggga acgggtcacc         60
atgacctgca ctgccagctc cagtgtaagt tccacttact tcactgtgta ccaacagaag       120
ccaggatcct cccccaaact ctggatttat agcacatcca acctggcttc tggagtccca       180
cgtcgcttca gtggcagtgc gtctgggacc tcttactctc tcacaatcag cagcatggag       240
gctgaagatg ctgccactta ttattgccac cagtatcatc gttccccgct cacgttcggt       300
gctgggacca agctggagct gaaac                                              325

<210> SEQ ID NO 335
<211> LENGTH: 349
<212> TYPE: DNA

<213> ORGANISM: Artificial Sequence
<220> FEATURE:
<223> OTHER INFORMATION: Synthetic polynucleotide

<400> SEQUENCE: 335

```
caggtccagc tgcagcagtc tgcagctgaa ctggcaagac ctggggcctc agtgaagatg    60
tcctgcaagg cttctggcta cacctttact acctacacga tgcactgggt aaaacagagg   120
cctggacagg gtctggaatg gattggattc attaatccta gcagtggata tactgactac   180
aatcagaagt tcaaggacag gaccacattg actgcagaca atcctccag cacagtctac    240
atgcaactga gtagcctgac atctgaggac tctgcggtct attactgtgc aaacggggat   300
tactacgtcg cttactgggg ccaagggact ctggtcactg tctctgcag               349
```

<210> SEQ ID NO 336
<211> LENGTH: 322
<212> TYPE: DNA
<213> ORGANISM: Artificial Sequence
<220> FEATURE:
<223> OTHER INFORMATION: Synthetic polynucleotide

<400> SEQUENCE: 336

```
gacatccaga tgactcagtc tccagcctcc ctatctgcat ctgtgggaga aactgtcacc    60
atcacatgtc gaataagcga gaatatttac agttatttag catggtatca gcagaaacag   120
ggaaaatctc ctcagctcct ggtctataat gcaaaaatct tagtagaagg tgtgccatca   180
aggttcagtg gcagtggatc aggcacacag ttttctctga agatcaacag cctgcagcct   240
gaagattttg ggaattatta ctgtcaacat cattatactg ttccgtggac gttcggtgga   300
ggcaccaaac tggaaatcaa ac                                            322
```

<210> SEQ ID NO 337
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 337

```
gaagtgaagc ttgaggagtc tggaggaggc ttggtgcaac ctggaggatc catgaaactc    60
tcctgtgttg cctctggttt cactttcagt gattactgga tgaactgggt ccgccagtct   120
ccagagaagg ggcttgaatg ggttgctcaa attagattga aatctgataa ttatgcaaca   180
cattatgcgg agtctgtgaa agggaggttc accatctcaa gagatgattc caaaagaagt   240
gtctacctgc aaatgaacaa cttaagggct gaagacactg gaacttatta ctgcaatgat   300
ggccccccct cggggtgttg gggccaaggc accactctca tagtctcctc ag           352
```

<210> SEQ ID NO 338
<211> LENGTH: 322
<212> TYPE: DNA
<213> ORGANISM: Artificial Sequence
<220> FEATURE:
<223> OTHER INFORMATION: Synthetic polynucleotide

<400> SEQUENCE: 338

```
gacatccaga tgactcagtc tccagcctcc ctatctgcat ctgtgggaga aactgtcacc    60
atcacatgtc gaataagtga gaatatttac agttatttag catggtatca gcagaaacag   120
ggaaaatctc ctcagctcct ggtctataat gcaaaaatct tagtagaagg tgtgccatca   180
aggttcagtg gcagtggatc aggcacacag ttttctctga agatcaacag cctgcagcct   240
```

```
gaagattttg ggaattatta ctgtcaacat cattatactg ttccgtggac gttcggtgga    300
ggcaccaaac tggaaatcaa ac                                            322
```

<210> SEQ ID NO 339
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 339

```
gaagtgaagc ttgaggagtc tggaggaggc ttggtgcaac ctggaggatc catgaaactc    60
tcctgtgttg cctctggatt cactttcagt aattactgga tgaactgggt ccgccagtct   120
ccagagaagg ggcttgaatg ggttgctcaa attagattga aatctgataa ttatgcaaca   180
cattatgcgg agtctgtgaa agggaggttc accatctcaa gagatgattc caaaagaagt   240
gtctacctgc aaatgaacaa cttaaggget gaagacactg gaacttatta ctgcaatgat   300
ggccccccct cggggtgttg gggccaaggc accactctca tagtctcctc ag           352
```

<210> SEQ ID NO 340
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 340

```
gatgttgtga tgacccaaac tccactctcc ctgcctgtca gtcttggaga tcaagcctcc    60
atctcttgca gatctagtca gagccttgta cacagtgatg gaaacaccta tttaaattgg   120
tacctgcaga gccaggcca gtctccaaag ctcctgatct acaaagtttc caaccgtttt   180
tctggggtcc cagacaggtt cagtggcagt ggatcaggga cagatttcac actcaagatc   240
aggagagtgg aggctgagga tctgggagtt tatttctgct ctcaaagtac acatgttcct   300
tacacgttcg gagggggac caagctggaa ataaaac                              337
```

<210> SEQ ID NO 341
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 341

```
caggtccagt tgcagcagtc tggggctgaa ctggcaagac ctggggcctc agtgaagatg    60
tcctgcaagg cttctggcta cacctttact agctacacga tgcactggat aaaacagaga   120
cctggacagg gtcaggaatg gattggatac attaatccta gcagtactta tactcattac   180
attaagaaat tcaaggacaa ggccacattg actgcagaca atcctccag cacagcctac    240 atgcaactgc gcagcctgac atctgaggac tctgcagtct attactgttc aagaggggaa   300
ctgggagggt ttgcttactg gggccaaggg actctggtca ctgtctctgc ag            352
```

<210> SEQ ID NO 342
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 342

```
gatgttttga tgacccaaac tccactctcc ctgcctgtca gtcttggaga tcaaccctcc    60
atctcttgca gatctagtca gagcattgta catagtaatg gaaacaccta tttagattgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcca   300
ttcacgttcg gctcggggac aaggttggaa ataaaac                            337
```

<210> SEQ ID NO 343
<211> LENGTH: 361
<212> TYPE: DNA
<213> ORGANISM: Artificial Sequence
<220> FEATURE:
<223> OTHER INFORMATION: Synthetic polynucleotide

<400> SEQUENCE: 343

```
gaagtccagc tgcagcagtc tggacctgag ctggtaaagc ctggggcttc agtgaagatg    60
tcctgcaagg cttctggata catattcact cactatatta tgcactgggt gaagcagaag   120
cctgggcagg gccttgagtg gattggatgt attaatcctt acaatgatgg tactaagtac   180
aatgagaagt tcaaaggcaa ggccacactg acttcagaca atcctccag cacagcctac    240
atggagctca gcagcctgac ctctgaggac tctgcggtct attactgtgc aagatactac   300
ggctacccct actattctat ggactactgg ggtcaaggaa cctcagtcac cgtctcctca   360
g                                                                   361
```

<210> SEQ ID NO 344
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 344

```
gccattgtga tgttccagtc tccatcctcc ctggttgtgt cagcaggaga gaaggtcact    60
atgagctgca atccagtca gtctgctc aacagtagaa cccgaaagaa ctacttggct      120
tggtaccagc agaaaccagg gcagtctcct aaactgctga tctactgggc atccactagg   180
gaatctgggg tccctgatcg cttcacaggc agtggatctg ggacagattt cactctcacc   240
atcagcagtg tgcaggctga agacctggca gtttattact gcaagcaatc ttattatctg   300
tacacgttcg gaggggggac caagctggaa ataaaac                            337
```

<210> SEQ ID NO 345
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 345

```
gatgtgcagc ttcaggagtc aggacctggc ctcgtgaaat cttctcagtc tctgtctctc    60
acctgctctg tcactggcta ctccatcacc agtggttatt actggaaatg gatccggcag   120
tttccaggaa acaaactgga atggatgggc tacatcagct acgatggtgg cattaactac   180
aacccatctc tcaaaaatcg aatctccatc actcgtgaca catctaagaa ccagtttttc   240
ctgaagttga attctgtgac tactgaggac acagccaaat attactgtgc aagatttggt   300
```

```
aaggggggcta tggactactg gggtcaagga acctcagtca ccgtctcctc ag        352
```

<210> SEQ ID NO 346
<211> LENGTH: 325
<212> TYPE: DNA
<213> ORGANISM: Artificial Sequence
<220> FEATURE:
<223> OTHER INFORMATION: Synthetic polynucleotide

<400> SEQUENCE: 346

```
caaattgttc tcacccagtc tccagcaatc atgtctgcat ctctggggga ccgggtcacc    60
atgacctgca ctgccagctc aagtgtaagt tccagttact tgcactggta ccagcagaag   120
ccaggatcct cccccaaact ctggatttat agcacatcca acctggcttc tggagtccca   180
gctcgcttca gtggcagtgg gtctgggacc tcttactctc tcacaatcag cagcatggag   240
gctgaagatg ctgccactta ttactgccac cagtatcatc gttccccacc cacgttcggc   300
tcggggacaa agttggaaat aaaac                                         325
```

<210> SEQ ID NO 347
<211> LENGTH: 358
<212> TYPE: DNA
<213> ORGANISM: Artificial Sequence
<220> FEATURE:
<223> OTHER INFORMATION: Synthetic polynucleotide

<400> SEQUENCE: 347

```
gaggtccagc tgcaacagtc tggacctgag ctggtgaagc ctggagcttc aatgaagata    60
tcctgcaagg cttctggtta ctcattcact ggctacacca tgaactgggt gaagcagagc   120
catggaaaga accttgagtg gattggactt attaatcctt acaatggtgg tactaactac   180
aaccagaagt tcaagggcaa ggccacatta actgtagaca agtcatccag cacagcctac   240
atggagctcc tcagtctgac atctgaggac tctgcagtct attactgtgc aagaggggtc   300
tatgattacg acggatttac ttactggggc caagggactc tggtcactgt ctctgcag    358
```

<210> SEQ ID NO 348
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 348

```
gatgttgtga tgacccaaac tccactctcc ctgcctgtca gtcttggaga tcaagcctcc    60
atctcttgca gatctagtca gagccttgta cacagtgatg gaaacaccta tttatattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttcct   300
tacacgttcg gaggggggac caagctggaa ataaaac                            337
```

<210> SEQ ID NO 349
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 349

```
caggtccagc tgcagcagtc tggggctgaa ctggcaagac ctggggcctc agtgaagatg    60
tcctgcaagg cttctggcta cacctttact acctacacga tgcactggtt aaaacagagg   120
cctggacagg gtctggaatg gattggatac attaatcctc gcagtggtta tagtaattac   180
aatcagaagt tcaaggacaa ggccacattg actgcagaca gtcctccaa cacagcctac    240 atgcaactga acaccctgac atctgaggac tctaaagtct attactgttc aagagggaa    300 ctgggagggt ttgcttactg gggccaaggg actctggtca ctgtctctgc ag           352

<210> SEQ ID NO 350
<211> LENGTH: 322
<212> TYPE: DNA
<213> ORGANISM: Artificial Sequence
<220> FEATURE:
<223> OTHER INFORMATION: Synthetic polynucleotide

<400> SEQUENCE: 350
gacattcaga tgacccagtc tcctgcctcc cagtctgcat ctctgggaga aagtgtcacc    60
atcacatgcc tggcaagtca gaccattggt acatggttag catggtatca gcagaaacca   120
gggaaatctc ctcagctcct gatttatgct gcagccagct ggcagatgg ggtcccatca    180 aggttcagtg gtagtggatc tggcacaaga ttttctttca agatcagcag cctacaggct   240
gaagattttg taagttatta ctgtcaacaa ctttacagta ttcctcggac gttcggtgga   300
ggcaccaagc tggaaatcaa ac                                            322

<210> SEQ ID NO 351
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 351
gaggtccagc tgcaacagtc tggacctgag ctggtgaagc ctggggcttc agtgaagatg    60
tcctgcaagg cttctggata cagattcact gactacaaca tgcactgggt gaagcagagc   120
catggaaaga gccttgagtg gattggatat attaaccctc acaatggtgg tactaactac    180
aaccaaaact tcaagggcaa ggccacattg actgtgaaca gtcctccag cacagcctac     240 atggagctcc gcagcctgac atcggaggat tctgcagcct attactgtgc aagagattac   300
ttgtacttct ttgactgctg gggccaaggc accactctca cagtctcctc ag           352

<210> SEQ ID NO 352
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 352
gatgttgtga tgacccaaac tccactctcc ctgcctgtca gtcttggaga tcaagcctcc    60
atctcttgca gagctagtca gagccttgta cacagtaatg gaaacaccta tttacattgg   120
ttcctgcaga agccaggcca gtctccaaag ctcctgatct acaaagtttc caaccgattt   180
tctggggtcc cagacaggtt cagtggcagt ggatcacgga cagatttcac actcaagatc   240
agcagagtgg aggctgagga tctgggagtt tatttctgct ctcaaattac acatgttccg   300
tacacgttcg gaggggggac caagctggaa ataaaac                            337
```

```
<210> SEQ ID NO 353
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 353
caaatccagt tggtgcagtc tggacctgcg ctgaagaagc ctggagagac agtcaagatc      60
tcctgcaagg cttctggtta taccttcaca gactattcaa tgcactggat aaagcaggct     120
ccaggaaagg gtttaaagtg gatgggctgg ataagcactg agactggtga gccaacatat     180
gcagatggct tcaagggacg gtttgacttc tctttggaaa cctctgccga cactgcctat     240
ttgtccatca acaacctcac aaatgaggac acggctacat atttctgtac tagaggtcta     300
tggtcctcgt ttgcttactg gggccaaggg actctggtca ctgtctctgc ag             352

<210> SEQ ID NO 354
<211> LENGTH: 334
<212> TYPE: DNA
<213> ORGANISM: Artificial Sequence
<220> FEATURE:
<223> OTHER INFORMATION: Synthetic polynucleotide

<400> SEQUENCE: 354
gacattgtgc tgacacagtc tcctgcttcc ttagctgtat ctctggggca gagggccacc      60
atctcatgca gggccagcaa aagtgtcagt acatctggct atagttatat acactggtac     120
caacagaaac caggacagcc acccaaactc ctcatctatc ttgcatccaa cctagaatct     180
ggggtccctg ccaggttcag tggcagtggg tctgggacag acttcaccct caacatccat     240
cctgtggagg aggaggatgc tgcaacctat tactgtcagc acagtaggga gcttccgctc     300
acgttcggtg ctgggaccaa gctggagctg aaac                                  334

<210> SEQ ID NO 355
<211> LENGTH: 355
<212> TYPE: DNA
<213> ORGANISM: Artificial Sequence
<220> FEATURE:
<223> OTHER INFORMATION: Synthetic polynucleotide

<400> SEQUENCE: 355
gatgtgcagc tggtggagtc tgggggaggc ttggtgcagc ctagagggtc ccggaaactc      60
tcctgtgcag cctctggatt cactttcagt agctttggaa tgcactgggt tcgtcaggct     120
ccagagaagg ggctggagtg ggtcgcatac attagtagtg acagtaggac catctattat     180
gcagacacag tgaagggccg attcaccatc tccagagaca atcccacgaa caccctgttc     240
ctgcaaatga ccagtctcag gtctgaggac acggccatgt attactgtgc aagagactac     300 ggtagaaccct acgaggctta ctggggccaa gggactctgg tcactgtctc tgcag         355

<210> SEQ ID NO 356
<211> LENGTH: 322
<212> TYPE: DNA
<213> ORGANISM: Artificial Sequence
<220> FEATURE:
<223> OTHER INFORMATION: Synthetic polynucleotide

<400> SEQUENCE: 356
gacatccaga tgattcagtc tccatcgtcc atgtttgcct ctctgggaga cagagtcagt      60
ctctcttgtc gggctagtca ggacattgga ggaaatttag actggtatca gcagaaacca     120
```

```
ggtggaacta ttaaactcct gatctactcc acatccaatt taaattctgg tgtcccatca    180
aggttcagtg gcagtgggtc tgggtcagat tattctctca ccatcaccag cctggagtct    240
gaagattttg cagactatta ctgtctacag cgtaatgcgt atccgctcac tttcggtgct    300
gggaccaagc tggagctgaa ac                                            322

<210> SEQ ID NO 357
<211> LENGTH: 355
<212> TYPE: DNA
<213> ORGANISM: Artificial Sequence
<220> FEATURE:
<223> OTHER INFORMATION: Synthetic polynucleotide

<400> SEQUENCE: 357
gaagtgaaac tgatggagtc tgggggagac ttagtgaagc ctggagggtc cctgaaactc     60
tcctgtgcag cctctggatt cactttcagt agttatgcca tgtcttgggt tcgccagact    120
ccagagaaga ggctggagtg ggtcgcgtcc attagaagtg gtggtaccac ctactatcca    180
gacagtgtga agggccgatt caccatctcc agagataatg ccaggaacat cctgtacctg    240
cgaatgagta gtctgaggtc tgaggacacg gccatatatt actgtgcaaa agtgggcggt    300 aaccccctatc ctatggacta ctggggtcaa ggaacctcag tcaccgtctc ctcag        355

<210> SEQ ID NO 358
<211> LENGTH: 325
<212> TYPE: DNA
<213> ORGANISM: Artificial Sequence
<220> FEATURE:
<223> OTHER INFORMATION: Synthetic polynucleotide

<400> SEQUENCE: 358
gaaattgtgc tcacccagtc tccaaccacc atggctgcat ctcccgggga gaagatcact     60
atcacctgca gtgccagctc aagtataagt tccaattact tgcattggta tcagcagaag    120
ccaggattct cccctaaaact cttgatttat aggacatcca atctggcttc tggagtccca    180
gctcgcttca gtggcagtgg gtctgggacc tcttactctc tcacaattgg caccatggag    240
gctgaagatg ttgccactta ctactgccag cagggtagta gtataccgct cacgttcggt    300
gctgggacca agctggagct gaaac                                         325

<210> SEQ ID NO 359
<211> LENGTH: 367
<212> TYPE: DNA
<213> ORGANISM: Artificial Sequence
<220> FEATURE:
<223> OTHER INFORMATION: Synthetic polynucleotide

<400> SEQUENCE: 359
caggtccagc tgcagcagtc tggagctgag ctggtaaggc ctgggacttc agtgaaggtg     60
tcctgcaagg cttctggata cgccttcagt aattacttga tagagtgggt taagcagagg    120
cctggacagg gccttgagtg gattggagtg attaatcctg aagtggtgg tactaactac    180 aatgagaagt tcaagggcaa ggcaacaatg actgcagaca atcctccag cactgcctac    240 atgcacctca gcaacctgac atctgaggac tctgtggtct atttctgtgc aagatcatac    300
ttcggtagaa gctaccccta tactatggac tactggggtc aaggaacctc agtcaccgtc    360
tcctcag                                                             367

<210> SEQ ID NO 360
<211> LENGTH: 334
```

```
<212> TYPE: DNA
<213> ORGANISM: Artificial Sequence
<220> FEATURE:
<223> OTHER INFORMATION: Synthetic polynucleotide

<400> SEQUENCE: 360
gatattgtgc tgacccaatc tccagcttct ttggctgtgt ctctagggca gagggccacc      60
atctcctgca aggccagcca agtgttgat tatgatggtg ataattatgt gaactggtac      120
caacagaaag taggacagcc acccaaactc ctcatctctg ctgcatccaa tctagaatct     180
gggatcccag ccaggtttag tggcagtggg tctgggacag acttcaccct caacatccat    240
cctgtggagg aggaggatgc tgcaacctat tactgtcagc aaagtaatga ggatccattc    300
acgttcggct cggggacaaa gttggaaata aaac                                 334

<210> SEQ ID NO 361
<211> LENGTH: 361
<212> TYPE: DNA
<213> ORGANISM: Artificial Sequence
<220> FEATURE:
<223> OTHER INFORMATION: Synthetic polynucleotide

<400> SEQUENCE: 361
caggtccagc tgcagcagtc tggggctgag ctggtgaggc ctggggtctc agtgaagatt     60
tcctgcaagg gttccggcta cacattcact gattatgcta tgcactgggt gaagcagagt   120
catgcaaaga gtctagagtg gattggagtt attagtacat actctggtaa tacaaactac    180
aaccagaagt tcaggacaa ggccaccatg actgtagaca atcctccag cacagcctat     240 atggcacttg ccagattgac atctgacgat tctgccatct attactgtgc aagaaggggc   300
gattacagcc tctatgctat ggactactgg ggtcaaggaa cctcagtcac cgtctcctca   360
g                                                                    361

<210> SEQ ID NO 362
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 362
aacattatga tgacacagtc gccatcatct ctggctgtgt ctgcaggaga aaaggtcact    60
atgagctgta agtccagtca agtgttttta ttcagttcaa atcagaaaaa ctacttggcc  120
tggtaccagc agaaaccagg gcagtctcct agactgctga tctactgggc atccactagg   180
gaatctggtg tccctgatcg cttcacaggc agtggatctg ggacagattt tactcttacc   240
atcagcaatg ttcaagctga agacctggca gtttattact gtcatcaata cctctcctcg   300
cgcacgttcg gtgctgggac caagctggag ctgaaac                             337

<210> SEQ ID NO 363
<211> LENGTH: 355
<212> TYPE: DNA
<213> ORGANISM: Artificial Sequence
<220> FEATURE:
<223> OTHER INFORMATION: Synthetic polynucleotide

<400> SEQUENCE: 363
gatgtgcagc tggtggagtc tggggggaggc ttggtgcagc ctagagggtc ccggaaactc    60
tcctgtgcag cctctggatt cactttcagt agctttggaa tgcactgggt tcgtcaggct   120
```

```
ccagagaagg ggctggagtg ggtcgcatac attagtagtg acagtaggac catctattat    180
gcagacacag tgaagggccg attcaccatc tccagagaca atcccacgaa caccctgttc    240
ctgcaaatga ccagtctcag gtctgaggac acggccatgt attactgtgc aagagactac    300
ggtagaacct acgaggctta ctggggccaa gggactctgg tcactgtctc tgcag         355

<210> SEQ ID NO 364
<211> LENGTH: 334
<212> TYPE: DNA
<213> ORGANISM: Artificial Sequence
<220> FEATURE:
<223> OTHER INFORMATION: Synthetic polynucleotide

<400> SEQUENCE: 364
gacattgtgc tgacccaatc tccagcttct ttggctctgt ctctagggca gagggccacc     60
atctcctgca gagccagcga aagtgttgat aattatggca ttagtttat gaactggttc    120 caacagaaac ccggacagcc acccaaactc ctcatctatg ctgcatccaa ccaaggatcc    180
ggggtccctg ccaggtttag tggcagtggg tctgggacag acttcagcct caacatccat    240
cctatggagg aggatgatac tgcaatgtat ttctgtcagc aaagtaagga ggttccgctc    300
acgttcggtc tgggaccaa gctggagctg aaac                                 334

<210> SEQ ID NO 365
<211> LENGTH: 358
<212> TYPE: DNA
<213> ORGANISM: Artificial Sequence
<220> FEATURE:
<223> OTHER INFORMATION: Synthetic polynucleotide

<400> SEQUENCE: 365
gaagtgaggc tggtggagtc tgggggaggc ttgatgcagc ctggagggtc cctgaaactc     60
ccctgtgcag cctctggatt ccctttcagt agctctgcca tgtcttgggt tcgccagact    120
ccagagaaga ggctggagtg ggtcgcatcc attaatagtg atggtaacac ctactatccc    180
gacagtgtga agggccgatt caccatctcc agagatagtg ccaggaacat cctgtacctc    240
caaatgagca gtctgaggtc tgaggacacg gccatgtatt actgtacaag aaacggggac    300
tataggtacg acgagtttgc ttactggggc caagggactc tggtcactgt ctctgcag     358

<210> SEQ ID NO 366
<211> LENGTH: 325
<212> TYPE: DNA
<213> ORGANISM: Artificial Sequence
<220> FEATURE:
<223> OTHER INFORMATION: Synthetic polynucleotide

<400> SEQUENCE: 366
caaattgttc tcacccagtc tccagcaatc atgtctgcat ctctagggga acgggtcacc     60
atgacctgca ctgccagctc aagtgtaagt tccagttact tgcactggta ccagcagaag    120
ccaggatcct cccccaaact ctggatttat agcacatcca acctggcttc tggagtccca    180
gctcgcttca gtggcagtgg gtctgggacc tcttactctc tcacaatcag cagcatggag    240
gctgaagatg ctgccactta ttactgccac cagtatcatc gttccccacc cacgttcgga    300
gctgggacca agctggagct gaaac                                          325

<210> SEQ ID NO 367
<211> LENGTH: 358
<212> TYPE: DNA
<213> ORGANISM: Artificial Sequence
```

<220> FEATURE:
<223> OTHER INFORMATION: Synthetic polynucleotide

<400> SEQUENCE: 367
caggtccagc ttcagcagtc tggggctgaa ctggcaaaac ctggggcctc agtgaagatg    60
tcctgcaagg cttctggcta cacctttact ggctactgga tgcactgggt aaaacagagg   120
cctggacagg gtctggaatg gcttggatac attaatccta gcactggtta tactgagtcc   180
aatcagaagt tcaaggacaa ggccacattg actgcagaca atcctccac acagcctac    240
atgcaactga aagcctgac acctgaggac tctgcagtct attactgtgc aagagagggg    300
attactactg tgctggttga ctactggggc caaggcacca ctctcacagt ctcctcag    358

<210> SEQ ID NO 368
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 368
aacattatga tgacacagtc gccatcatct ctggctgtgt ctgcaggaga aaaggtcact    60
atgagctgta agtccagtca agtgttttta ttcagttcaa atcagaaaaa ctacttggcc   120
tggtaccagc agaaaccagg gcagtctcct agactgctga tctactgggc atccactagg   180
gaatctggtg tccctgatcg cttcacaggc agtggatctg gacagattt tactcttacc    240
atcagcaatg ttcaagctga agacctggca gtttattact gtcatcaata cctctcctcg   300
cgcacgttcg gtgctgggac caagctggag ctgaaac                            337

<210> SEQ ID NO 369
<211> LENGTH: 364
<212> TYPE: DNA
<213> ORGANISM: Artificial Sequence
<220> FEATURE:
<223> OTHER INFORMATION: Synthetic polynucleotide

<400> SEQUENCE: 369
caggtgcagc tgaagcagtc tggacctgag ctggagaagc ctggcgcttc agtgaagata    60
tcctgcaagg cttctggtta ctctttcact ggctacaata tgaactgggt gaagcagagc   120
aatggaaaga gccttgagtg gattggaaat attgatcctt actatggtgg ttctacctac   180
aaccagaagt tcacgggcaa ggccacattg actgtagaca atcctccag cacagcctac   240
atgcagctca gagcctgac atctgaggac tctgcagtgt attactgtgc aagagagagg    300
tcgggctacg ttttctctgc tatggactac tggggtcaag gaacctcagt caccgtctcc   360
tcag                                                                 364

<210> SEQ ID NO 370
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 370
aacattatga tgacacagtc gccatcatct ctggctgtgt ctgcaggaga aaaggtcact    60
atgagctgta agtccagtca agtgttttta ttcagttcaa atcagaaaaa ctacttggcc   120
tggtaccagc agaaaccagg gcagtctcct agactgctga tctactgggc atccactagg   180

```
gaatctggtg tccctgatcg cttcacaggc agtggatctg ggacagattt tactcttacc      240
atcagcaatg ttcaagctga agacctggca gtttattact gtcatcaata cctctcctcg      300
cgcacgttcg gtgctgggac caagctggag ctgaaac                                337
```

```
<210> SEQ ID NO 371
<211> LENGTH: 370
<212> TYPE: DNA
<213> ORGANISM: Artificial Sequence
<220> FEATURE:
<223> OTHER INFORMATION: Synthetic polynucleotide

<400> SEQUENCE: 371
gaggtccagc tgcaacagtc tggacctgag ctggtgaagc ctggaggttc aatgaagata       60
tcctgcaagg cttctggtta ctcattcact ggctacacca tgaactgggt gaagcggagc      120
catggaaaga accttgagtg gattggactt attaatcctt acaatggtgt tactacctac      180
aaccagaact tcaagggcaa ggccacatta gctgtagaca gtcatccagc acagcctac      240 atggagctcc tcggtctgac atctgaggac tctgcagtct attactgtac aagagatccc      300
ctttactacg gctacaggga ctctactatg gactactggg gtcaaggaac ctcagtcacc      360
gtctcctcag                                                              370
```

```
<210> SEQ ID NO 372
<211> LENGTH: 337
<212> TYPE: DNA
<213> ORGANISM: Artificial Sequence
<220> FEATURE:
<223> OTHER INFORMATION: Synthetic polynucleotide

<400> SEQUENCE: 372
gatgttgtga tgacccaaac tccactctcc ctgcctgtca gtcttggaga tcaagcctcc       60
atctcttgca gatctagtca gagccttgta cacagtgatg gaaacaccta tttaaattgg      120
tacctgcaga agccaggcca gtctccaaag ctcctgatct acaaagtttc caaccgtttt      180
tctggggtcc cagacaggtt cagtggcagt ggatcaggga cagatttcac actcaagatc      240
aggagagtgg aggctgagga tctgggagtt tatttctgct ctcaaagtac acatgttcct      300
tacacgttcg gagggggggac caagctggaa ataaaac                                337
```

```
<210> SEQ ID NO 373
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 373
gaggtccagc tgcagcagtc tggggctgaa ctggcaagac ctggggcctc agtgaagatg       60
tcctgcaagg cttctggcta cacctttact agctacacga tgcactggat aaaacagaga      120
cctggacagg gtcaggaatg gattggatac attaatccta gcagtacgta tactcattac      180
attaagaagt tcaaggacaa ggccacattg actgcagaca atcctccag cacagcctac      240 atgcaactgc gcagcctgac atctgaggac tctgcagtct attactgttc aagagggaa      300 ctgggagggt ttgcttactg gggccaaggg actctggtca ctgtctctgc ag             352
```

```
<210> SEQ ID NO 374
<211> LENGTH: 322
<212> TYPE: DNA
<213> ORGANISM: Artificial Sequence
```

<220> FEATURE:
<223> OTHER INFORMATION: Synthetic polynucleotide

<400> SEQUENCE: 374

```
gacatccaga tgattcagtc tccatcgtcc atgtttgcct ctctgggaga cagagtcagt    60
ctctcttgtc gggctagtca gggcattaga ggtaatttag actggtatca gcagaaacca   120
ggtggaacta ttaaactcct gatctactcc acatccattt aaattctgg tgtcccatca    180
aggttcagtg gcagtgggtc tgggtcagat tattctctca ccatcaccag cctagagtct   240
gaagattttg cagactatta ctgtctacag cgtaatgcgt atcctctcac gttcggttct   300
gggaccaagc tggagctgaa ac                                             322
```

<210> SEQ ID NO 375
<211> LENGTH: 358
<212> TYPE: DNA
<213> ORGANISM: Artificial Sequence
<220> FEATURE:
<223> OTHER INFORMATION: Synthetic polynucleotide

<400> SEQUENCE: 375

```
gaagtgaagt tggtggagtc tgggggaggc ttaatgaagc ctggagggtc cctgaaactc    60
tcctgtgcgg cctctggatt cactttcagt agttttgcct tgtcttgggt tcgccagact   120
ccagagaaga ggctggagtg ggtcgcatcc attagaagtg gtggtattac ctaccatgca   180
gacagtgtga agggccgatt caccatctcc agagataatg ccgggaacat cctgtacctg   240
caaatgaaca gtctgaggtc tgaggacacg gccatgtatt tctgtgcaag agttagtacg   300
gctacgtact atggtatgga ctactggggt caaggaacct cagtcaccgt ctcctcag    358
```

<210> SEQ ID NO 376
<211> LENGTH: 116
<212> TYPE: PRT
<213> ORGANISM: Artificial Sequence
<220> FEATURE:
<223> OTHER INFORMATION: Synthetic peptide

<400> SEQUENCE: 376

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Met His Trp Val Arg Gln Ala Pro Gly Gln Gly Leu Glu Trp Met
        35                  40                  45

Gly Phe Ile Asn Pro Ser Ser Gly Tyr Thr Asp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Tyr Val Ala Tyr Trp Gly Gln Gly Thr Leu Val
            100                 105                 110

Thr Val Ser Ser
        115
```

<210> SEQ ID NO 377
<211> LENGTH: 116
<212> TYPE: PRT
<213> ORGANISM: Artificial Sequence
<220> FEATURE:

<223> OTHER INFORMATION: Synthetic peptide

<400> SEQUENCE: 377

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Thr Met His Trp Val Arg Gln Ala Pro Gly Gln Gly Leu Glu Trp Met
        35                  40                  45

Gly Phe Ile Asn Pro Ser Ser Gly Tyr Thr Asp Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Asn Gly Asp Tyr Tyr Val Ala Tyr Trp Gly Gln Gly Thr Leu Val
            100                 105                 110

Thr Val Ser Ser
        115

<210> SEQ ID NO 378
<211> LENGTH: 116
<212> TYPE: PRT
<213> ORGANISM: Artificial Sequence
<220> FEATURE:
<223> OTHER INFORMATION: Synthetic peptide

<400> SEQUENCE: 378

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Arg Gln Ala Pro Gly Gln Gly Leu Glu Trp Ile
        35                  40                  45

Gly Phe Ile Asn Pro Ser Ser Gly Tyr Thr Asp Tyr Ala Gln Lys Phe
    50                  55                  60

Gln Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Asn Gly Asp Tyr Tyr Val Ala Tyr Trp Gly Gln Gly Thr Leu Val
            100                 105                 110

Thr Val Ser Ser
        115

<210> SEQ ID NO 379
<211> LENGTH: 116
<212> TYPE: PRT
<213> ORGANISM: Artificial Sequence
<220> FEATURE:
<223> OTHER INFORMATION: Synthetic peptide

<400> SEQUENCE: 379

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Arg Gln Ala Pro Gly Gln Gly Leu Glu Trp Ile

```
                35                  40                  45
Gly Phe Ile Asn Pro Ser Ser Gly Tyr Thr Asp Tyr Ala Gln Lys Phe
        50                  55                  60

Gln Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Asn Gly Asp Tyr Tyr Val Ala Tyr Trp Gly Gln Gly Thr Leu Val
            100                 105                 110

Thr Val Ser Ser
        115

<210> SEQ ID NO 380
<211> LENGTH: 108
<212> TYPE: PRT
<213> ORGANISM: Artificial Sequence
<220> FEATURE:
<223> OTHER INFORMATION: Synthetic peptide

<400> SEQUENCE: 380

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Thr
            20                  25                  30

Tyr Phe His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gln Gly Thr Lys Leu Glu Ile Lys
            100                 105

<210> SEQ ID NO 381
<211> LENGTH: 108
<212> TYPE: PRT
<213> ORGANISM: Artificial Sequence
<220> FEATURE:
<223> OTHER INFORMATION: Synthetic peptide

<400> SEQUENCE: 381

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Thr
            20                  25                  30

Tyr Phe His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gln Gly Thr Lys Leu Glu Ile Lys
            100                 105
```

```
<210> SEQ ID NO 382
<211> LENGTH: 108
<212> TYPE: PRT
<213> ORGANISM: Artificial Sequence
<220> FEATURE:
<223> OTHER INFORMATION: Synthetic peptide

<400> SEQUENCE: 382

Asp Ile Gln Leu Thr Gln Ser Pro Ser Leu Ser Ala Ser Val Gly
1               5                   10                  15

Asp Arg Val Thr Met Thr Cys Thr Ala Ser Ser Val Ser Ser Thr
                20                  25                  30

Tyr Phe His Trp Tyr Gln Gln Lys Pro Gly Lys Ala Pro Lys Leu Leu
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Met Gln
65                  70                  75                  80

Pro Glu Asp Ala Ala Thr Tyr Tyr Cys His Gln Tyr His Arg Ser Pro
                85                  90                  95

Leu Thr Phe Gly Gln Gly Thr Lys Leu Glu Ile Lys
            100                 105

<210> SEQ ID NO 383
<211> LENGTH: 108
<212> TYPE: PRT
<213> ORGANISM: Artificial Sequence
<220> FEATURE:
<223> OTHER INFORMATION: Synthetic peptide

<400> SEQUENCE: 383

Asp Ile Gln Leu Thr Gln Ser Pro Ser Leu Ser Ala Ser Val Gly
1               5                   10                  15

Asp Arg Val Thr Met Thr Cys Thr Ala Ser Ser Val Ser Ser Thr
                20                  25                  30

Tyr Phe His Trp Tyr Gln Gln Lys Pro Gly Lys Ala Pro Lys Leu Trp
            35                  40                  45

Ile Tyr Ser Thr Ser Asn Leu Ala Ser Gly Val Pro Ser Arg Phe Ser
        50                  55                  60

Gly Ser Gly Ser Gly Thr Asp Tyr Thr Leu Thr Ile Ser Ser Met Gln
65                  70                  75                  80

Pro Glu Asp Ala Ala Thr Tyr Tyr Cys His Gln Tyr His Arg Ser Pro
                85                  90                  95

Leu Thr Phe Gly Gln Gly Thr Lys Leu Glu Ile Lys
            100                 105

<210> SEQ ID NO 384
<211> LENGTH: 117
<212> TYPE: PRT
<213> ORGANISM: Artificial Sequence
<220> FEATURE:
<223> OTHER INFORMATION: Synthetic peptide

<400> SEQUENCE: 384

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Trp Met Asn Trp Val Arg Gln Ala Pro Gly Lys Gly Leu Glu Trp Val
```

```
                35                  40                  45

Ser Gln Ile Arg Leu Lys Ser Asp Asn Tyr Ala Thr His Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Pro Pro Ser Gly Cys Trp Gly Gln Gly Thr Leu
            100                 105                 110

Val Thr Val Ser Ser
            115

<210> SEQ ID NO 385
<211> LENGTH: 117
<212> TYPE: PRT
<213> ORGANISM: Artificial Sequence
<220> FEATURE:
<223> OTHER INFORMATION: Synthetic peptide

<400> SEQUENCE: 385

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Asp
        50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Gly Val Tyr
                85                  90                  95

Tyr Cys Asn Asp Gly Pro Pro Ser Gly Cys Trp Gly Gln Gly Thr Leu
            100                 105                 110

Leu Thr Val Ser Ser
            115

<210> SEQ ID NO 386
<211> LENGTH: 117
<212> TYPE: PRT
<213> ORGANISM: Artificial Sequence
<220> FEATURE:
<223> OTHER INFORMATION: Synthetic peptide

<400> SEQUENCE: 386

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Asp
        50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Gly Val Tyr
                85                  90                  95
```

```
Tyr Cys Asn Asp Gly Pro Pro Ser Gly Tyr Trp Gly Gln Gly Thr Leu
                100                 105                 110

Leu Thr Val Ser Ser
            115

<210> SEQ ID NO 387
<211> LENGTH: 117
<212> TYPE: PRT
<213> ORGANISM: Artificial Sequence
<220> FEATURE:
<223> OTHER INFORMATION: Synthetic peptide

<400> SEQUENCE: 387

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Asp
50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Gly Val Tyr
                85                  90                  95

Tyr Cys Asn Asp Gly Pro Pro Ser Gly Ser Trp Gly Gln Gly Thr Leu
                100                 105                 110

Leu Thr Val Ser Ser
            115

<210> SEQ ID NO 388
<211> LENGTH: 107
<212> TYPE: PRT
<213> ORGANISM: Artificial Sequence
<220> FEATURE:
<223> OTHER INFORMATION: Synthetic peptide

<400> SEQUENCE: 388

Asp Ile Gln Met Thr Gln Ser Pro Ser Ser Leu Ser Ala Ser Val Gly
1               5                   10                  15

Asp Arg Val Thr Ile Thr Cys Arg Ile Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Ile Leu Val Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Thr Val Pro Trp
                85                  90                  95

Thr Phe Gly Gln Gly Thr Lys Leu Glu Ile Lys
                100                 105

<210> SEQ ID NO 389
<211> LENGTH: 107
<212> TYPE: PRT
<213> ORGANISM: Artificial Sequence
<220> FEATURE:
<223> OTHER INFORMATION: Synthetic peptide
```

```
<400> SEQUENCE: 389

Asp Ile Gln Met Thr Gln Ser Pro Ser Ser Leu Ser Ala Ser Val Gly
1               5                   10                  15

Asp Arg Val Thr Ile Thr Cys Arg Ile Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Ile Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln His His Tyr Thr Val Pro Trp
                85                  90                  95

Thr Phe Gly Gln Gly Thr Lys Leu Glu Ile Lys
            100                 105

<210> SEQ ID NO 390
<211> LENGTH: 107
<212> TYPE: PRT
<213> ORGANISM: Artificial Sequence
<220> FEATURE:
<223> OTHER INFORMATION: Synthetic peptide

<400> SEQUENCE: 390

Asp Ile Gln Met Thr Gln Ser Pro Ser Ser Leu Ser Ala Ser Val Gly
1               5                   10                  15

Asp Arg Val Thr Ile Thr Cys Arg Ile Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Ser Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln His His Tyr Thr Val Pro Trp
                85                  90                  95

Thr Phe Gly Gln Gly Thr Lys Leu Glu Ile Lys
            100                 105

<210> SEQ ID NO 391
<211> LENGTH: 117
<212> TYPE: PRT
<213> ORGANISM: Artificial Sequence
<220> FEATURE:
<223> OTHER INFORMATION: Synthetic peptide

<400> SEQUENCE: 391

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Thr Tyr Thr His Tyr Ala Gln Lys Phe
    50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Gly Glu Leu Gly Gly Phe Ala Tyr Trp Gly Gln Gly Thr Leu
            100                 105                 110

Val Thr Val Ser Ser
        115

<210> SEQ ID NO 392
<211> LENGTH: 117
<212> TYPE: PRT
<213> ORGANISM: Artificial Sequence
<220> FEATURE:
<223> OTHER INFORMATION: Synthetic peptide

<400> SEQUENCE: 392

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Thr Tyr Thr His Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
        115

<210> SEQ ID NO 393
<211> LENGTH: 117
<212> TYPE: PRT
<213> ORGANISM: Artificial Sequence
<220> FEATURE:
<223> OTHER INFORMATION: Synthetic peptide

<400> SEQUENCE: 393

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Thr Met His Trp Ile Arg Gln Ala Pro Gly Gln Gly Leu Glu Trp Ile
        35                  40                  45

Gly Tyr Ile Asn Pro Ser Ser Thr Tyr Thr His Tyr Ala Gln Lys Phe
    50                  55                  60

Gln Gly Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
        115

<210> SEQ ID NO 394
```

```
<211> LENGTH: 117
<212> TYPE: PRT
<213> ORGANISM: Artificial Sequence
<220> FEATURE:
<223> OTHER INFORMATION: Synthetic peptide

<400> SEQUENCE: 394

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Thr Met His Trp Ile Arg Gln Ala Pro Gly Gln Gly Gln Glu Trp Ile
        35                  40                  45

Gly Tyr Ile Asn Pro Ser Ser Thr Tyr Thr His Tyr Ala Gln Lys Phe
    50                  55                  60

Gln Gly Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
            115

<210> SEQ ID NO 395
<211> LENGTH: 117
<212> TYPE: PRT
<213> ORGANISM: Artificial Sequence
<220> FEATURE:
<223> OTHER INFORMATION: Synthetic peptide

<400> SEQUENCE: 395

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Thr Met His Trp Ile Arg Gln Ala Pro Gly Gln Gly Leu Glu Trp Ile
        35                  40                  45

Gly Tyr Ile Asn Pro Ser Ser Thr Tyr Thr His Tyr Ala Gln Lys Phe
    50                  55                  60

Gln Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
            115

<210> SEQ ID NO 396
<211> LENGTH: 117
<212> TYPE: PRT
<213> ORGANISM: Artificial Sequence
<220> FEATURE:
<223> OTHER INFORMATION: Synthetic peptide

<400> SEQUENCE: 396

Gln Val Gln Leu Val Gln Ser Gly Ala Glu Val Lys Lys Pro Gly Ala
1               5                   10                  15
```

Ser Val Lys Met Ser Cys Lys Ala Ser Gly Tyr Thr Phe Thr Ser Tyr
            20                  25                  30

Thr Met His Trp Ile Arg Gln Ala Pro Gly Gln Gly Gln Glu Trp Ile
        35                  40                  45

Gly Tyr Ile Asn Pro Ser Ser Thr Tyr Thr His Tyr Ala Gln Lys Phe
50                  55                  60

Gln Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
                100                 105                 110

Val Thr Val Ser Ser
        115

<210> SEQ ID NO 397
<211> LENGTH: 112
<212> TYPE: PRT
<213> ORGANISM: Artificial Sequence
<220> FEATURE:
<223> OTHER INFORMATION: Synthetic peptide

<400> SEQUENCE: 397

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
                100                 105                 110

<210> SEQ ID NO 398
<211> LENGTH: 112
<212> TYPE: PRT
<213> ORGANISM: Artificial Sequence
<220> FEATURE:
<223> OTHER INFORMATION: Synthetic peptide

<400> SEQUENCE: 398

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Tyr Gln Gln Arg Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 399
<211> LENGTH: 112
<212> TYPE: PRT
<213> ORGANISM: Artificial Sequence
<220> FEATURE:
<223> OTHER INFORMATION: Synthetic peptide

<400> SEQUENCE: 399

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Glu Gly Asn Thr Tyr Leu Asn Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 400
<211> LENGTH: 112
<212> TYPE: PRT
<213> ORGANISM: Artificial Sequence
<220> FEATURE:
<223> OTHER INFORMATION: Synthetic peptide

<400> SEQUENCE: 400

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Ser Gly Asn Thr Tyr Leu Asn Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 401
<211> LENGTH: 112
<212> TYPE: PRT
<213> ORGANISM: Artificial Sequence
<220> FEATURE:
<223> OTHER INFORMATION: Synthetic peptide

<400> SEQUENCE: 401

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Glu Gly Ser Thr Tyr Leu Asn Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 402
<211> LENGTH: 112
<212> TYPE: PRT
<213> ORGANISM: Artificial Sequence
<220> FEATURE:
<223> OTHER INFORMATION: Synthetic peptide

<400> SEQUENCE: 402

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Ser Gly Ser Thr Tyr Leu Asn Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 403
<211> LENGTH: 117
<212> TYPE: PRT
<213> ORGANISM: Artificial Sequence
<220> FEATURE:
<223> OTHER INFORMATION: Synthetic peptide

<400> SEQUENCE: 403

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asp Tyr
            20                  25                  30

Asn Met His Trp Val Arg Gln Ala Pro Gly Gln Gly Leu Glu Trp Met
        35                  40                  45

Gly Tyr Ile Asn Pro Asn Asn Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Leu Tyr Phe Phe Asp Cys Trp Gly Gln Gly Thr Leu
            100                 105                 110

```
Val Thr Val Ser Ser
        115

<210> SEQ ID NO 404
<211> LENGTH: 117
<212> TYPE: PRT
<213> ORGANISM: Artificial Sequence
<220> FEATURE:
<223> OTHER INFORMATION: Synthetic peptide

<400> SEQUENCE: 404

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asp Tyr
                20                  25                  30

Asn Met His Trp Val Arg Gln Ala Pro Gly Gln Gly Leu Glu Trp Met
            35                  40                  45

Gly Tyr Ile Asn Pro Asn Asn Gly Gly Thr Asn Tyr Ala Gln Lys Phe
        50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Leu Tyr Phe Phe Asp Cys Trp Gly Gln Gly Thr Leu
                100                 105                 110

Val Thr Val Ser Ser
        115

<210> SEQ ID NO 405
<211> LENGTH: 117
<212> TYPE: PRT
<213> ORGANISM: Artificial Sequence
<220> FEATURE:
<223> OTHER INFORMATION: Synthetic peptide

<400> SEQUENCE: 405

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Arg Phe Thr Asp Tyr
                20                  25                  30

Asn Met His Trp Val Arg Gln Ala Pro Gly Gln Gly Leu Glu Trp Ile
            35                  40                  45

Gly Tyr Ile Asn Pro Asn Asn Gly Gly Thr Asn Tyr Ala Gln Lys Phe
        50                  55                  60

Gln Gly Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Leu Tyr Phe Phe Asp Cys Trp Gly Gln Gly Thr Leu
                100                 105                 110

Leu Thr Val Ser Ser
        115

<210> SEQ ID NO 406
<211> LENGTH: 117
<212> TYPE: PRT
<213> ORGANISM: Artificial Sequence
<220> FEATURE:
<223> OTHER INFORMATION: Synthetic peptide
```

<400> SEQUENCE: 406

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Arg Phe Thr Asp Tyr
            20                  25                  30

Asn Met His Trp Val Arg Gln Ala Pro Gly Gln Gly Leu Glu Trp Ile
        35                  40                  45

Gly Tyr Ile Asn Pro Asn Asn Gly Gly Thr Asn Tyr Ala Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Leu Tyr Phe Phe Asp Cys Trp Gly Gln Gly Thr Leu
            100                 105                 110

Leu Thr Val Ser Ser
        115

<210> SEQ ID NO 407
<211> LENGTH: 117
<212> TYPE: PRT
<213> ORGANISM: Artificial Sequence
<220> FEATURE:
<223> OTHER INFORMATION: Synthetic peptide

<400> SEQUENCE: 407

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Arg Phe Thr Asp Tyr
            20                  25                  30

Asn Met His Trp Val Arg Gln Ala Pro Gly Gln Gly Leu Glu Trp Ile
        35                  40                  45

Gly Tyr Ile Asn Pro Asn Asn Gly Gly Thr Asn Tyr Ala Gln Lys Phe
    50                  55                  60

Gln Gly Arg Ala Thr Leu Thr Val Asn Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Leu Tyr Phe Phe Asp Cys Trp Gly Gln Gly Thr Leu
            100                 105                 110

Leu Thr Val Ser Ser
        115

<210> SEQ ID NO 408
<211> LENGTH: 117
<212> TYPE: PRT
<213> ORGANISM: Artificial Sequence
<220> FEATURE:
<223> OTHER INFORMATION: Synthetic peptide

<400> SEQUENCE: 408

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Arg Phe Thr Asp Tyr
            20                  25                  30

Asn Met His Trp Val Arg Gln Ala Pro Gly Gln Gly Leu Glu Trp Ile
        35                  40                  45

Gly Tyr Ile Asn Pro Asn Asn Gly Gly Thr Asn Tyr Ala Gln Lys Phe
            50                  55                  60

Gln Gly Arg Ala Thr Leu Thr Val Asn Thr Ser Thr Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Leu Tyr Phe Phe Asp Cys Trp Gly Gln Gly Thr Leu
                100                 105                 110

Leu Thr Val Ser Ser
            115

<210> SEQ ID NO 409
<211> LENGTH: 107
<212> TYPE: PRT
<213> ORGANISM: Artificial Sequence
<220> FEATURE:
<223> OTHER INFORMATION: Synthetic peptide

<400> SEQUENCE: 409

Asp Ile Gln Met Thr Gln Ser Pro Ser Ser Leu Ser Ala Ser Val Gly
 1               5                  10                  15

Asp Arg Val Thr Ile Thr Cys Leu Ala Ser Gln Thr Ile Gly Thr Trp
                 20                  25                  30

Leu Ala Trp Tyr Gln Gln Lys Pro Gly Lys Ala Pro Lys Leu Leu Ile
             35                  40                  45

Tyr Ala Ala Ala Ser Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Leu Tyr Ser Ile Pro Arg
                 85                  90                  95

Thr Phe Gly Gln Gly Thr Lys Leu Glu Ile Lys
            100                 105

<210> SEQ ID NO 410
<211> LENGTH: 107
<212> TYPE: PRT
<213> ORGANISM: Artificial Sequence
<220> FEATURE:
<223> OTHER INFORMATION: Synthetic peptide

<400> SEQUENCE: 410

Asp Ile Gln Met Thr Gln Ser Pro Ser Ser Leu Ser Ala Ser Val Gly
 1               5                  10                  15

Asp Arg Val Thr Ile Thr Cys Leu Ala Ser Gln Thr Ile Gly Thr Trp
                 20                  25                  30

Leu Ala Trp Tyr Gln Gln Lys Pro Gly Lys Ala Pro Lys Leu Leu Ile
             35                  40                  45

Tyr Ala Ala Ala Ser Leu Ala Asp Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Val Thr Tyr Tyr Cys Gln Gln Leu Tyr Ser Ile Pro Arg
                 85                  90                  95

Thr Phe Gly Gln Gly Thr Lys Leu Glu Ile Lys
            100                 105

```
<210> SEQ ID NO 411
<211> LENGTH: 107
<212> TYPE: PRT
<213> ORGANISM: Artificial Sequence
<220> FEATURE:
<223> OTHER INFORMATION: Synthetic peptide

<400> SEQUENCE: 411

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Ala Ser Leu Ala Asp Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Val Thr Tyr Tyr Cys Gln Gln Leu Tyr Ser Ile Pro Arg
                85                  90                  95

Thr Phe Gly Gln Gly Thr Lys Leu Glu Ile Lys
            100                 105

<210> SEQ ID NO 412
<211> LENGTH: 118
<212> TYPE: PRT
<213> ORGANISM: Artificial Sequence
<220> FEATURE:
<223> OTHER INFORMATION: Synthetic peptide

<400> SEQUENCE: 412

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ser Tyr Ile Ser Ser Asp Ser Arg Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Thr Tyr Glu Ala Tyr Trp Gly Gln Gly Thr
            100                 105                 110

Leu Val Thr Val Ser Ser
        115

<210> SEQ ID NO 413
<211> LENGTH: 118
<212> TYPE: PRT
<213> ORGANISM: Artificial Sequence
<220> FEATURE:
<223> OTHER INFORMATION: Synthetic peptide

<400> SEQUENCE: 413

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

```
Gly Met His Trp Val Arg Gln Ala Pro Gly Lys Gly Leu Glu Trp Val
            35                  40                  45

Ala Tyr Ile Ser Ser Asp Ser Arg Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Gly Arg Thr Tyr Glu Ala Tyr Trp Gly Gln Gly Thr
                100                 105                 110

Leu Val Thr Val Ser Ser
            115

<210> SEQ ID NO 414
<211> LENGTH: 111
<212> TYPE: PRT
<213> ORGANISM: Artificial Sequence
<220> FEATURE:
<223> OTHER INFORMATION: Synthetic peptide

<400> SEQUENCE: 414

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
             20                  25                  30

Gly Tyr Ser Tyr Ile His Trp Tyr Gln Gln Lys Pro Gly Gln Pro Pro
         35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Glu Leu Pro Leu Thr Phe Gly Gln Gly Thr Lys Leu Glu Ile Lys
                100                 105                 110

<210> SEQ ID NO 415
<211> LENGTH: 111
<212> TYPE: PRT
<213> ORGANISM: Artificial Sequence
<220> FEATURE:
<223> OTHER INFORMATION: Synthetic peptide

<400> SEQUENCE: 415

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
             20                  25                  30

Gly Tyr Ser Tyr Ile His Trp Tyr Gln Gln Lys Pro Gly Gln Pro Pro
         35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Val Gln Ala Glu Asp Val Ala Val Tyr Tyr Cys Gln His Ser Arg
                 85                  90                  95

Glu Leu Pro Leu Thr Phe Gly Gln Gly Thr Lys Leu Glu Leu Lys
```

<210> SEQ ID NO 416
<211> LENGTH: 121
<212> TYPE: PRT
<213> ORGANISM: Artificial Sequence
<220> FEATURE:
<223> OTHER INFORMATION: Synthetic peptide

<400> SEQUENCE: 416

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Met
        35                  40                  45

Gly Asn Ile Asp Pro Tyr Tyr Gly Gly Ser Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Ser Gly Tyr Val Phe Ser Ala Met Asp Tyr Trp Gly
            100                 105                 110

Gln Gly Thr Leu Val Thr Val Ser Ser
            115                 120

<210> SEQ ID NO 417
<211> LENGTH: 121
<212> TYPE: PRT
<213> ORGANISM: Artificial Sequence
<220> FEATURE:
<223> OTHER INFORMATION: Synthetic peptide

<400> SEQUENCE: 417

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Met
        35                  40                  45

Gly Asn Ile Asp Pro Tyr Tyr Gly Gly Ser Thr Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Ser Gly Tyr Val Phe Ser Ala Met Asp Tyr Trp Gly
            100                 105                 110

Gln Gly Thr Leu Val Thr Val Ser Ser
            115                 120

<210> SEQ ID NO 418
<211> LENGTH: 121
<212> TYPE: PRT
<213> ORGANISM: Artificial Sequence
<220> FEATURE:
<223> OTHER INFORMATION: Synthetic peptide

<400> SEQUENCE: 418

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Ile
        35                  40                  45

Gly Asn Ile Asp Pro Tyr Tyr Gly Gly Ser Thr Tyr Ala Gln Lys Phe
    50                  55                  60

Gln Gly Arg Ala Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ser Gly Tyr Val Phe Ser Ala Met Asp Tyr Trp Gly
            100                 105                 110

Gln Gly Thr Leu Val Thr Val Ser Ser
        115                 120

<210> SEQ ID NO 419
<211> LENGTH: 121
<212> TYPE: PRT
<213> ORGANISM: Artificial Sequence
<220> FEATURE:
<223> OTHER INFORMATION: Synthetic peptide

<400> SEQUENCE: 419

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Ile
        35                  40                  45

Gly Asn Ile Asp Pro Tyr Tyr Gly Gly Ser Thr Tyr Ala Gln Lys Phe
    50                  55                  60

Gln Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ser Gly Tyr Val Phe Ser Ala Met Asp Tyr Trp Gly
            100                 105                 110

Gln Gly Thr Leu Val Thr Val Ser Ser
        115                 120

<210> SEQ ID NO 420
<211> LENGTH: 112
<212> TYPE: PRT
<213> ORGANISM: Artificial Sequence
<220> FEATURE:
<223> OTHER INFORMATION: Synthetic peptide

<400> SEQUENCE: 420

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val

```
              50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                 85                  90                  95

Tyr Leu Ser Ser Arg Thr Phe Gly Gln Gly Thr Lys Leu Glu Ile Lys
            100                 105                 110

<210> SEQ ID NO 421
<211> LENGTH: 112
<212> TYPE: PRT
<213> ORGANISM: Artificial Sequence
<220> FEATURE:
<223> OTHER INFORMATION: Synthetic peptide

<400> SEQUENCE: 421

Asp Ile Val Met Thr Gln Ser Pro Asp Ser Leu Ala Val Ser Leu Gly
  1               5                  10                  15

Glu Arg Val Thr Met Asn Cys Lys Ser Ser Gln Ser Val Leu Phe Ser
                 20                  25                  30

Ser Asn Gln Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys His Gln
                 85                  90                  95

Tyr Leu Ser Ser Arg Thr Phe Gly Gln Gly Thr Lys Leu Glu Ile Lys
            100                 105                 110

<210> SEQ ID NO 422
<211> LENGTH: 117
<212> TYPE: PRT
<213> ORGANISM: Artificial Sequence
<220> FEATURE:
<223> OTHER INFORMATION: Synthetic peptide

<400> SEQUENCE: 422

Glu Val Gln Leu Leu Glu Ser Gly Gly Gly Leu Val Gln Pro Gly Gly
  1               5                  10                  15

Ser Met Arg Leu Ser Cys Ala Ala Ser Gly Phe Thr Phe Ser Asn Tyr
                 20                  25                  30

Trp Met Asn Trp Val Arg Gln Ala Pro Gly Lys Gly Leu Glu Trp Val
             35                  40                  45

Ala Gln Ile Arg Leu Lys Ser Asp Asn Tyr Ala Thr His Tyr Ala Asp
 50                  55                  60

Ser Val Lys Gly Arg Phe Thr Ile Ser Arg Asp Asp Ser Lys Asn Thr
 65                  70                  75                  80

Val Tyr Leu Gln Met Asn Ser Leu Arg Ala Glu Asp Thr Gly Val Tyr
                 85                  90                  95

Tyr Cys Asn Asp Gly Pro Pro Ser Gly Ala Trp Gly Gln Gly Thr Leu
            100                 105                 110

Leu Thr Val Ser Ser
            115

<210> SEQ ID NO 423
<211> LENGTH: 117
```

```
<212> TYPE: PRT
<213> ORGANISM: Artificial Sequence
<220> FEATURE:
<223> OTHER INFORMATION: Synthetic peptide

<400> SEQUENCE: 423

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Thr Tyr Thr His Tyr Ile Lys Lys Phe
    50                  55                  60

Lys Asp Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
            115

<210> SEQ ID NO 424
<211> LENGTH: 117
<212> TYPE: PRT
<213> ORGANISM: Artificial Sequence
<220> FEATURE:
<223> OTHER INFORMATION: Synthetic peptide

<400> SEQUENCE: 424

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Thr Met His Trp Ile Arg Gln Ala Pro Gly Gln Gly Leu Glu Trp Ile
        35                  40                  45

Gly Tyr Ile Asn Pro Ser Ser Thr Tyr Thr His Tyr Ile Lys Lys Phe
    50                  55                  60

Lys Asp Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
            115

<210> SEQ ID NO 425
<211> LENGTH: 117
<212> TYPE: PRT
<213> ORGANISM: Artificial Sequence
<220> FEATURE:
<223> OTHER INFORMATION: Synthetic peptide

<400> SEQUENCE: 425

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
```

```
            20                  25                  30
Thr Met His Trp Ile Arg Gln Ala Pro Gly Gln Gly Gln Glu Trp Ile
        35                  40                  45

Gly Tyr Ile Asn Pro Ser Ser Thr Tyr Thr His Tyr Ile Lys Lys Phe
    50                  55                  60

Lys Asp Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
        115

<210> SEQ ID NO 426
<211> LENGTH: 117
<212> TYPE: PRT
<213> ORGANISM: Artificial Sequence
<220> FEATURE:
<223> OTHER INFORMATION: Synthetic peptide

<400> SEQUENCE: 426

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Thr Met His Trp Ile Arg Gln Ala Pro Gly Gln Gly Leu Glu Trp Ile
        35                  40                  45

Gly Tyr Ile Asn Pro Ser Ser Thr Tyr Thr His Tyr Ile Lys Lys Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
        115

<210> SEQ ID NO 427
<211> LENGTH: 117
<212> TYPE: PRT
<213> ORGANISM: Artificial Sequence
<220> FEATURE:
<223> OTHER INFORMATION: Synthetic peptide

<400> SEQUENCE: 427

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Thr Met His Trp Ile Arg Gln Ala Pro Gly Gln Gly Gln Glu Trp Ile
        35                  40                  45

Gly Tyr Ile Asn Pro Ser Ser Thr Tyr Thr His Tyr Ile Lys Lys Phe
    50                  55                  60

Lys Asp Arg Ala Thr Leu Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ser Arg Gly Glu Leu Gly Gly Phe Ala Tyr Trp Gly Gln Gly Thr Leu
            100                 105                 110

Val Thr Val Ser Ser
        115

<210> SEQ ID NO 428
<211> LENGTH: 116
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (65)..(68)
```

<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(76)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid

<400> SEQUENCE: 428

Gln Val Gln Leu Xaa Gln Ser Xaa Ala Glu Xaa Xaa Xaa Pro Gly Ala
1               5                   10                  15

Ser Val Lys Xaa Ser Cys Lys Ala Ser Gly Tyr Thr Phe Thr Xaa Tyr
            20                  25                  30

Xaa Met Xaa Trp Val Xaa Gln Xaa Pro Gly Gln Gly Leu Glu Trp Xaa
        35                  40                  45

Gly Xaa Ile Asn Pro Ser Xaa Gly Xaa Thr Xaa Tyr Xaa Gln Lys Phe
    50                  55                  60

Xaa Xaa Xaa Xaa Thr Xaa Thr Xaa Asp Xaa Ser Xaa Ser Thr Xaa Xaa
65                  70                  75                  80

Met Xaa Leu Ser Ser Leu Xaa Ser Glu Xaa Xaa Ala Val Tyr Tyr Cys
            85                  90                  95

Ala Xaa Gly Asp Xaa Tyr Val Ala Tyr Trp Gly Gln Gly Thr Leu Val
            100                 105                 110

Thr Val Ser Xaa
        115

<210> SEQ ID NO 429
<211> LENGTH: 116
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(20)
<223> OTHER INFORMATION: Xaa can be any naturally occurring amino acid

```
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 429

Gln Val Gln Leu Val Gln Ser Gly Ala Glu Val Lys Lys Pro Gly Ala
1               5                   10                  15

Ser Val Lys Xaa Ser Cys Lys Ala Ser Gly Tyr Thr Phe Thr Xaa Tyr
            20                  25                  30

Thr Met Xaa Trp Val Arg Gln Ala Pro Gly Gln Gly Leu Glu Trp Xaa
        35                  40                  45

Gly Xaa Ile Asn Pro Ser Ser Gly Tyr Thr Xaa Tyr Ala Gln Lys Phe
    50                  55                  60

Gln Gly Xaa Val Thr Xaa Thr Ala Asp Xaa Ser Thr Ser Thr Xaa Tyr
65                  70                  75                  80

Met Glu Leu Ser Ser Leu Arg Ser Glu Asp Thr Ala Val Tyr Tyr Cys
                85                  90                  95

Ala Xaa Gly Asp Xaa Tyr Val Ala Tyr Trp Gly Gln Gly Thr Leu Val
            100                 105                 110

Thr Val Ser Ser
            115

<210> SEQ ID NO 430
<211> LENGTH: 108
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (71)..(73)
<223> OTHER INFORMATION: Xaa can be any naturally occurring amino acid
<220> FEATURE:
<221> NAME/KEY: misc_feature
<222> LOCATION: (79)..(81)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
```

```
<220> FEATURE:
<221> NAME/KEY: misc_feature
<222> LOCATION: (93)..(96)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 430

Xaa Ile Xaa Xaa Thr Gln Ser Pro Xaa Xaa Xaa Ser Ala Ser Xaa Gly
1               5                   10                  15

Xaa Arg Val Thr Xaa Thr Cys Xaa Ala Ser Xaa Ser Xaa Ser Ser Xaa
            20                  25                  30

Tyr Xaa Xaa Trp Tyr Gln Gln Lys Pro Gly Xaa Xaa Pro Lys Leu Xaa
        35                  40                  45

Ile Tyr Xaa Xaa Xaa Xaa Xaa Xaa Ser Gly Val Pro Xaa Arg Phe Ser
    50                  55                  60

Gly Ser Xaa Ser Gly Thr Xaa Xaa Xaa Leu Thr Ile Ser Ser Xaa Xaa
65                  70                  75                  80

Xaa Glu Asp Xaa Ala Thr Tyr Tyr Cys Xaa Xaa Tyr Xaa Xaa Xaa Xaa
                85                  90                  95

Leu Thr Phe Gly Xaa Gly Thr Lys Leu Glu Xaa Lys
            100                 105

<210> SEQ ID NO 431
<211> LENGTH: 108
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
```

-continued

```
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid

<400> SEQUENCE: 431

Asp Ile Gln Xaa Thr Gln Ser Pro Ser Ser Leu Ser Ala Ser Val Gly
1               5                   10                  15

Asp Arg Val Thr Xaa Thr Cys Thr Ala Ser Ser Ser Val Ser Ser Xaa
            20                  25                  30

Tyr Xaa His Trp Tyr Gln Gln Lys Pro Gly Lys Ala Pro Lys Leu Xaa
        35                  40                  45

Ile Tyr Xaa Thr Xaa Asn Leu Ala Ser Gly Val Pro Xaa Arg Phe Ser
    50                  55                  60

Gly Ser Xaa Ser Gly Thr Asp Tyr Thr Leu Thr Ile Ser Ser Xaa Gln
65                  70                  75                  80

Pro Glu Asp Xaa Ala Thr Tyr Tyr Cys His Xaa Tyr Xaa Arg Ser Pro
                85                  90                  95

Leu Thr Phe Gly Gln Gly Thr Lys Leu Glu Ile Lys
            100                 105

<210> SEQ ID NO 432
<211> LENGTH: 117
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
```

```
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (52)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (79)..(81)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (94)..(95)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid

<400> SEQUENCE: 432

Glu Val Xaa Leu Xaa Glu Ser Gly Gly Gly Leu Val Gln Pro Gly Gly
1               5                   10                  15

Ser Xaa Xaa Leu Ser Cys Xaa Ala Ser Gly Phe Thr Phe Ser Xaa Tyr
            20                  25                  30

Xaa Met Xaa Trp Val Arg Gln Xaa Pro Xaa Lys Gly Leu Glu Trp Val
        35                  40                  45

Xaa Xaa Ile Xaa Xaa Xaa Xaa Xaa Xaa Xaa Thr Xaa Tyr Ala Xaa
    50                  55                  60

Ser Val Lys Gly Arg Phe Thr Ile Ser Arg Asp Xaa Ser Lys Xaa Xaa
65                  70                  75                  80

Xaa Tyr Leu Gln Met Asn Xaa Leu Arg Ala Glu Asp Thr Xaa Xaa Tyr
                85                  90                  95

Tyr Cys Xaa Asp Gly Pro Pro Ser Gly Xaa Trp Gly Gln Gly Thr Xaa
            100                 105                 110

Leu Xaa Val Ser Ser
        115
```

```
<210> SEQ ID NO 433
<211> LENGTH: 117
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid

<400> SEQUENCE: 433

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Xaa Tyr
            20                  25                  30

Trp Met Xaa Trp Val Arg Gln Ala Pro Gly Lys Gly Leu Glu Trp Val
        35                  40                  45

Ala Xaa Ile Arg Leu Lys Xaa Asp Asn Tyr Ala Thr His Tyr Ala Asp
    50                  55                  60

Ser Val Lys Gly Arg Phe Thr Ile Ser Arg Asp Asp Ser Lys Xaa Thr
65                  70                  75                  80

Val Tyr Leu Gln Met Asn Ser Leu Arg Ala Glu Asp Thr Gly Val Tyr
                85                  90                  95

Tyr Cys Xaa Asp Gly Pro Pro Ser Gly Xaa Trp Gly Gln Gly Thr Leu
            100                 105                 110

Leu Thr Val Ser Ser
        115

<210> SEQ ID NO 434
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
```

```
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
```

-continued

<400> SEQUENCE: 434

Asp Ile Gln Met Thr Gln Ser Pro Xaa Ser Leu Ser Ala Ser Val Gly
1               5                   10                  15

Xaa Xaa Val Thr Ile Thr Cys Arg Xaa Ser Xaa Xaa Ile Xaa Ser Tyr
            20                  25                  30

Leu Xaa Trp Tyr Gln Gln Lys Xaa Gly Lys Xaa Pro Xaa Leu Leu Xaa
        35                  40                  45

Tyr Xaa Ala Xaa Xaa Leu Xaa Xaa Gly Val Pro Ser Arg Phe Ser Gly
    50                  55                  60

Ser Gly Ser Gly Thr Xaa Phe Xaa Leu Xaa Ile Xaa Ser Leu Gln Pro
65                  70                  75                  80

Glu Asp Phe Xaa Xaa Tyr Tyr Cys Gln Xaa Xaa Tyr Xaa Xaa Pro Trp
                85                  90                  95

Xaa Phe Gly Xaa Gly Thr Lys Leu Glu Ile Lys
            100                 105

<210> SEQ ID NO 435
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid

<400> SEQUENCE: 435

Asp Ile Gln Met Thr Gln Ser Pro Ser Ser Leu Ser Ala Ser Val Gly
1               5                   10                  15

Asp Arg Val Thr Ile Thr Cys Arg Xaa Ser Glu Asn Ile Tyr Ser Tyr
            20                  25                  30

Leu Xaa Trp Tyr Gln Gln Lys Pro Gly Lys Ala Pro Lys Leu Leu Xaa
        35                  40                  45

Tyr Asn Ala Lys Xaa Leu Xaa Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Xaa Xaa Tyr Tyr Cys Gln Xaa His Tyr Xaa Val Pro Trp
                85                  90                  95

Thr Phe Gly Gln Gly Thr Lys Leu Glu Ile Lys
            100                 105

<210> SEQ ID NO 436
<211> LENGTH: 117
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (55)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (65)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
```

```
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid

<400> SEQUENCE: 436

Gln Val Gln Leu Xaa Gln Ser Gly Ala Glu Xaa Xaa Xaa Pro Gly Ala
1               5                   10                  15

Ser Val Lys Xaa Ser Cys Lys Ala Ser Gly Tyr Thr Xaa Thr Xaa Tyr
            20                  25                  30

Xaa Met His Trp Xaa Xaa Gln Xaa Pro Gly Gln Gly Xaa Glu Trp Xaa
        35                  40                  45

Gly Xaa Ile Asn Pro Ser Xaa Xaa Thr Xaa Tyr Xaa Xaa Lys Phe
    50                  55                  60

Xaa Xaa Xaa Xaa Thr Xaa Thr Xaa Asp Xaa Ser Xaa Ser Thr Xaa Tyr
65                  70                  75                  80

Met Xaa Leu Xaa Ser Leu Xaa Ser Glu Asp Xaa Ala Val Tyr Tyr Cys
            85                  90                  95

Xaa Arg Gly Glu Xaa Gly Gly Phe Ala Tyr Trp Gly Gln Gly Thr Leu
            100                 105                 110

Val Thr Val Ser Xaa
        115

<210> SEQ ID NO 437
<211> LENGTH: 117
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (20)..(20)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (65)..(66)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 437

Gln Val Gln Leu Val Gln Ser Gly Ala Glu Val Lys Lys Pro Gly Ala
1               5                   10                  15

Ser Val Lys Xaa Ser Cys Lys Ala Ser Gly Tyr Thr Xaa Thr Xaa Tyr
            20                  25                  30

Thr Met His Trp Xaa Arg Gln Ala Pro Gly Gln Gly Xaa Glu Trp Xaa
        35                  40                  45

Gly Tyr Ile Asn Pro Ser Ser Xaa Tyr Thr Xaa Tyr Xaa Xaa Lys Phe
```

```
                50                  55                  60
Xaa Xaa Arg Xaa Thr Xaa Thr Ala Asp Xaa Ser Thr Ser Thr Xaa Tyr
 65                  70                  75                  80

Met Glu Leu Xaa Ser Leu Arg Ser Glu Asp Thr Ala Val Tyr Tyr Cys
                 85                  90                  95

Xaa Arg Gly Glu Xaa Gly Gly Phe Ala Tyr Trp Gly Gln Gly Thr Leu
            100                 105                 110

Val Thr Val Ser Ser
            115

<210> SEQ ID NO 438
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
```

```
<222> LOCATION: (94)..(96)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid

<400> SEQUENCE: 438

Asp Val Val Met Thr Gln Xaa Pro Leu Ser Leu Pro Val Xaa Leu Gly
1               5                   10                  15

Xaa Xaa Ala Ser Ile Ser Cys Arg Ser Ser Gln Ser Leu Val Xaa Ser
            20                  25                  30

Xaa Gly Asn Thr Tyr Leu Xaa Trp Xaa Xaa Gln Xaa Pro Gly Gln Ser
        35                  40                  45

Pro Xaa Xaa Asn Pro Ser Xaa Thr Xaa Thr His Tyr Ser Gly Val Pro
    50                  55                  60

Asp Arg Phe Ser Gly Ser Gly Ser Gly Thr Asp Phe Thr Leu Lys Ile
65                  70                  75                  80

Xaa Arg Val Glu Ala Glu Asp Xaa Gly Val Tyr Xaa Cys Xaa Xaa Xaa
                85                  90                  95

Thr His Xaa Xaa Tyr Thr Phe Gly Xaa Gly Thr Lys Leu Glu Ile Lys
            100                 105                 110

<210> SEQ ID NO 439
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid

<400> SEQUENCE: 439

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Xaa Gly Asn Thr Tyr Leu Xaa Trp Tyr Gln Gln Arg Pro Gly Gln Ser
        35                  40                  45

Pro Arg Leu Leu Ile Tyr Xaa Val Xaa Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Xaa Arg Val Glu Ala Glu Asp Val Gly Val Tyr Tyr Cys Ser Xaa Xaa
                85                  90                  95

Thr His Val Pro Tyr Thr Phe Gly Gln Gly Thr Lys Leu Glu Ile Lys
                100                 105                 110

<210> SEQ ID NO 440
<211> LENGTH: 120
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
```

```
<222> LOCATION: (79)..(79)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid

<400> SEQUENCE: 440

Gln Val Gln Leu Xaa Gln Ser Gly Xaa Glu Xaa Xaa Lys Pro Gly Ala
1               5                   10                  15

Ser Val Lys Xaa Ser Cys Lys Ala Ser Gly Tyr Ser Phe Thr Gly Tyr
            20                  25                  30

Asn Met Asn Trp Val Xaa Gln Xaa Xaa Gly Xaa Xaa Leu Glu Trp Xaa
        35                  40                  45

Gly Asn Ile Asp Pro Tyr Tyr Gly Gly Ser Thr Tyr Xaa Gln Lys Phe
    50                  55                  60

Xaa Gly Xaa Xaa Thr Xaa Thr Xaa Asp Xaa Ser Xaa Ser Thr Xaa Tyr
65                  70                  75                  80

Met Xaa Leu Xaa Ser Leu Xaa Ser Glu Asp Xaa Ala Val Tyr Tyr Cys
            85                  90                  95

Ala Arg Glu Arg Ser Gly Tyr Val Phe Ser Ala Met Asp Tyr Trp Gly
            100                 105                 110

Gln Gly Thr Xaa Val Thr Val Ser
        115                 120

<210> SEQ ID NO 441
<211> LENGTH: 120
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 441
```

```
Gln Val Gln Leu Val Gln Ser Gly Ala Glu Val Lys Lys Pro Gly Ala
1               5                   10                  15

Ser Val Lys Xaa Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Xaa
        35                  40                  45

Gly Asn Ile Asp Pro Tyr Tyr Gly Gly Ser Thr Tyr Ala Gln Lys Phe
    50                  55                  60

Gln Gly Arg Xaa Thr Xaa Thr Arg Asp Thr Ser Thr Ser Thr Xaa Tyr
65                  70                  75                  80

Met Glu Leu Ser Ser Leu Arg Ser Glu Asp Thr Ala Val Tyr Tyr Cys
                85                  90                  95

Ala Arg Glu Arg Ser Gly Tyr Val Phe Ser Ala Met Asp Tyr Trp Gly
            100                 105                 110

Gln Gly Thr Leu Val Thr Val Ser
            115                 120

<210> SEQ ID NO 442
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
```

```
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid

<400> SEQUENCE: 442

Xaa Ile Xaa Met Thr Gln Ser Pro Xaa Ser Leu Ala Val Ser Xaa Gly
1               5                   10                  15

Glu Xaa Xaa Thr Xaa Xaa Cys Lys Ser Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Xaa Pro Xaa Leu Leu Ile Tyr Trp Ala Ser Thr Arg Glu Ser Gly Val
50                  55                  60

Pro Asp Arg Phe Xaa Gly Ser Gly Ser Gly Thr Asp Phe Xaa Leu Thr
65                  70                  75                  80

Ile Ser Ser Xaa Gln Ala Glu Asp Val Ala Val Tyr Xaa Cys His Gln
                85                  90                  95

Tyr Leu Ser Ser Arg Thr Phe Gly Xaa Gly Thr Lys Leu Glu Xaa Lys
            100                 105                 110

<210> SEQ ID NO 443
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid

<400> SEQUENCE: 443

Asp Ile Val Met Thr Gln Ser Pro Asp Ser Leu Ala Val Ser Leu Gly
1               5                   10                  15

Glu Arg Xaa Thr Xaa Asn Cys Lys Ser Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Xaa Gln Ala Glu Asp Val Ala Val Tyr Tyr Cys His Gln
                85                  90                  95

Tyr Leu Ser Ser Arg Thr Phe Gly Gln Gly Thr Lys Leu Glu Ile Lys
            100                 105                 110

<210> SEQ ID NO 444
<211> LENGTH: 117
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (72)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
```

```
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid

<400> SEQUENCE: 444

Xaa Val Gln Leu Xaa Gln Ser Gly Xaa Glu Xaa Xaa Lys Pro Gly Ala
1               5                   10                  15

Ser Val Lys Xaa Ser Cys Lys Ala Ser Gly Tyr Arg Phe Thr Asp Tyr
            20                  25                  30

Asn Met His Trp Val Xaa Gln Xaa Gly Xaa Gly Xaa Leu Glu Trp Xaa
        35                  40                  45

Gly Tyr Ile Asn Pro Asn Asn Gly Gly Thr Asn Tyr Xaa Gln Xaa Phe
    50                  55                  60

Xaa Gly Xaa Val Xaa Xaa Thr Xaa Xaa Xaa Ser Xaa Ser Thr Xaa Tyr
65                  70                  75                  80

Met Glu Leu Xaa Ser Leu Xaa Ser Glu Asp Xaa Ala Xaa Tyr Tyr Cys
                85                  90                  95

Ala Arg Asp Tyr Leu Tyr Phe Phe Asp Cys Trp Gly Gln Gly Thr Xaa
                100                 105                 110

Xaa Thr Val Ser Ser
        115

<210> SEQ ID NO 445
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(74)
<223> OTHER INFORMATION: Xaa can be any naturally occurring amino acid
<220> FEATURE:
```

```
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 445

Asp Ile Gln Met Thr Gln Ser Pro Xaa Ser Xaa Ser Ala Ser Xaa Gly
1               5                   10                  15

Xaa Xaa Val Thr Ile Thr Cys Leu Ala Ser Gln Thr Ile Gly Thr Trp
            20                  25                  30

Leu Ala Trp Tyr Gln Gln Lys Pro Gly Lys Xaa Pro Xaa Leu Leu Ile
        35                  40                  45

Tyr Ala Ala Ala Ser Leu Ala Asp Gly Val Pro Ser Arg Phe Ser Gly
50                  55                  60

Ser Gly Ser Gly Thr Xaa Phe Xaa Xaa Xaa Ile Ser Ser Leu Gln Xaa
65                  70                  75                  80

Glu Asp Phe Xaa Xaa Tyr Tyr Cys Gln Gln Leu Tyr Ser Ile Pro Arg
                85                  90                  95

Thr Phe Gly Xaa Gly Thr Lys Leu Glu Ile Lys
            100                 105

<210> SEQ ID NO 446
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
```

```
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid

<400> SEQUENCE: 446

Xaa Val Gln Leu Val Glu Ser Gly Gly Gly Leu Val Gln Pro Xaa Gly
1               5                   10                  15

Ser Xaa Xaa Leu Ser Cys Ala Ala Ser Gly Phe Thr Phe Ser Ser Phe
            20                  25                  30

Gly Met His Trp Val Arg Gln Ala Pro Xaa Lys Gly Leu Glu Trp Val
        35                  40                  45

Xaa Tyr Ile Ser Ser Asp Ser Arg Thr Ile Tyr Tyr Ala Asp Xaa Val
    50                  55                  60

Lys Gly Arg Phe Thr Ile Ser Arg Asp Asn Xaa Xaa Asn Xaa Leu Xaa
65                  70                  75                  80

Leu Gln Met Xaa Ser Leu Arg Xaa Glu Asp Thr Ala Xaa Tyr Tyr Cys
                85                  90                  95

Ala Arg Asp Tyr Gly Arg Thr Tyr Glu Ala Tyr
            100                 105

<210> SEQ ID NO 447
<211> LENGTH: 111
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (80)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
```

```
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid

<400> SEQUENCE: 447

Asp Ile Val Xaa Thr Gln Ser Pro Xaa Ser Leu Ala Val Ser Leu Gly
1               5                   10                  15

Xaa Arg Ala Thr Ile Xaa Cys Arg Ala Ser Lys Ser Val Ser Thr Ser
                20                  25                  30

Gly Tyr Ser Tyr Ile His Trp Tyr Gln Gln Lys Pro Gly Gln Pro Pro
            35                  40                  45

Lys Leu Leu Ile Tyr Leu Ala Ser Asn Leu Glu Ser Gly Val Pro Xaa
    50                  55                  60

Arg Phe Ser Gly Ser Gly Ser Gly Thr Asp Phe Thr Leu Xaa Ile Xaa
65                  70                  75                  80

Xaa Xaa Xaa Xaa Glu Asp Xaa Ala Xaa Tyr Tyr Cys Gln His Ser Arg
                85                  90                  95

Glu Leu Pro Leu Thr Phe Gly Xaa Gly Thr Lys Leu Glu Xaa Lys
            100                 105                 110

<210> SEQ ID NO 448
<211> LENGTH: 111
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid

<400> SEQUENCE: 448

Asp Ile Val Xaa Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
                20                  25                  30

Gly Tyr Ser Tyr Ile His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Xaa Gln Ala Glu Asp Val Ala Val Tyr Tyr Cys Gln His Ser Arg
                85                  90                  95

Glu Leu Pro Leu Thr Phe Gly Gln Gly Thr Lys Leu Glu Xaa Lys
            100                 105                 110

<210> SEQ ID NO 449
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is T, V, F, or D

<400> SEQUENCE: 449

Ser Ser Val Ser Ser Xaa Tyr
1               5

<210> SEQ ID NO 450
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is S, T, Q, or  A
<220> FEATURE:
<221> NAME/KEY: MISC_FEATURE
<222> LOCATION: (3)..(3)
<223> OTHER INFORMATION: Xaa is S, T, D, or Q

<400> SEQUENCE: 450

Xaa Thr Xaa
1

<210> SEQ ID NO 451
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Q, H or S
<220> FEATURE:
<221> NAME/KEY: MISC_FEATURE
<222> LOCATION: (4)..(4)
<223> OTHER INFORMATION: Xaa is H, Y, Q, or S

<400> SEQUENCE: 451

His Xaa Tyr Xaa Arg Ser Pro Leu Thr
1               5

<210> SEQ ID NO 452
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is T, V, D, or S

<400> SEQUENCE: 452

Tyr Thr Phe Thr Xaa Tyr Thr
1               5

<210> SEQ ID NO 453
<211> LENGTH: 9
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (2)..(2)
<223> OTHER INFORMATION: Xaa is N, Q, H, D, S, R, or A

<400> SEQUENCE: 453

Ala Xaa Gly Asp Tyr Tyr Val Ala Tyr
1               5

<210> SEQ ID NO 454
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is H, Q, S, or T
<220> FEATURE:
<221> NAME/KEY: MISC_FEATURE
<222> LOCATION: (5)..(5)
<223> OTHER INFORMATION: Xaa is T, S, N, or G

<400> SEQUENCE: 454

Gln Xaa His Tyr Xaa Val Pro Trp Thr
1               5

<210> SEQ ID NO 455
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is N, S, R, q, s, or a
<220> FEATURE:
<221> NAME/KEY: MISC_FEATURE
<222> LOCATION: (7)..(7)
<223> OTHER INFORMATION: Xaa is w, h, y, or f

<400> SEQUENCE: 455

Phe Thr Phe Ser Xaa Tyr Xaa
1               5

<210> SEQ ID NO 456
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is S, N, A, or T
<220> FEATURE:
<221> NAME/KEY: MISC_FEATURE
<222> LOCATION: (7)..(7)
<223> OTHER INFORMATION: Xaa is Q, S,A, or N

<400> SEQUENCE: 456

Ile Arg Leu Lys Xaa Asp Xaa Tyr Ala Thr
1               5                   10

<210> SEQ ID NO 457
<211> LENGTH: 8
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: Xaa is N, D, A, or T
<220> FEATURE:
<221> NAME/KEY: MISC_FEATURE
<222> LOCATION: (8)..(8)
<223> OTHER INFORMATION: Xaa is S, T, A, C, Y

<400> SEQUENCE: 457

Xaa Asp Gly Pro Pro Ser Gly Xaa
1               5

<210> SEQ ID NO 458
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is D, N, E, Q, S, or A
<220> FEATURE:
<221> NAME/KEY: MISC_FEATURE
<222> LOCATION: (9)..(9)
<223> OTHER INFORMATION: Xaa is Q, S, A, D, or N

<400> SEQUENCE: 458

Gln Ser Leu Val His Ser Xaa Gly Xaa Thr Tyr
1               5                   10

<210> SEQ ID NO 459
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is K, Q, or R
<220> FEATURE:
<221> NAME/KEY: MISC_FEATURE
<222> LOCATION: (3)..(3)
<223> OTHER INFORMATION: Xaa is S, T, or V

<400> SEQUENCE: 459

Xaa Val Xaa
1

<210> SEQ ID NO 460
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Q, H, or T
<220> FEATURE:
<221> NAME/KEY: MISC_FEATURE
<222> LOCATION: (3)..(3)
<223> OTHER INFORMATION: Xaa is S, G, T, or D

<400> SEQUENCE: 460

Ser Xaa Xaa Thr His Val Pro Tyr Thr
1               5

<210> SEQ ID NO 461
```

```
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is F, Y, S, or T
<220> FEATURE:
<221> NAME/KEY: MISC_FEATURE
<222> LOCATION: (5)..(5)
<223> OTHER INFORMATION: Xaa is S, T, Y , or D

<400> SEQUENCE: 461

Tyr Thr Xaa Thr Xaa Tyr Thr Met His
1               5

<210> SEQ ID NO 462
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Q, S, A, or N
<220> FEATURE:
<221> NAME/KEY: MISC_FEATURE
<222> LOCATION: (6)..(6)
<223> OTHER INFORMATION: Xaa is T, S, V, D, or G

<400> SEQUENCE: 462

Ile Xaa Pro Ser Ser Xaa Tyr Thr
1               5

<210> SEQ ID NO 463
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is S, A, T, or V
<220> FEATURE:
<221> NAME/KEY: MISC_FEATURE
<222> LOCATION: (5)..(5)
<223> OTHER INFORMATION: Xaa is L, V, or F

<400> SEQUENCE: 463

Xaa Arg Gly Glu Xaa Gly Gly Phe Ala Tyr
1               5                   10

<210> SEQ ID NO 464
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is W, H, Y, or F

<400> SEQUENCE: 464

Gln Thr Ile Gly Tyr Xaa
1               5
```

```
<210> SEQ ID NO 465
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is R or T
<220> FEATURE:
<221> NAME/KEY: MISC_FEATURE
<222> LOCATION: (8)..(8)
<223> OTHER INFORMATION: Xaa is N, Q, S, or A

<400> SEQUENCE: 465

Gly Tyr Xaa Phe Thr Asp Tyr Xaa
1               5

<210> SEQ ID NO 466
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is N, Q, S, or A
<220> FEATURE:
<221> NAME/KEY: MISC_FEATURE
<222> LOCATION: (4)..(4)
<223> OTHER INFORMATION: Xaa is N, Q, S, or A
<220> FEATURE:
<221> NAME/KEY: MISC_FEATURE
<222> LOCATION: (5)..(5)
<223> OTHER INFORMATION: Xaa is N, Q, S, or A

<400> SEQUENCE: 466

Ile Xaa Pro Xaa Xaa Gly Gly Thr
1               5

<210> SEQ ID NO 467
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is C, Y, S, or A

<400> SEQUENCE: 467

Asp Tyr Leu Tyr Phe Phe Asp Xaa
1               5

<210> SEQ ID NO 468
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is D, E, S, or A

<400> SEQUENCE: 468

Ile Ser Ser Xaa Ser Arg Thr Ile
1               5
```

```
<210> SEQ ID NO 469
<211> LENGTH: 9
<212> TYPE: PRT
<213> ORGANISM: Artificial Sequence
<220> FEATURE:
<223> OTHER INFORMATION: Synthetic peptide

<400> SEQUENCE: 469

Asp Tyr Gly Arg Thr Tyr Glu Ala Tyr
1               5

<210> SEQ ID NO 470
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is Q, S, A, D, or N
<220> FEATURE:
<221> NAME/KEY: MISC_FEATURE
<222> LOCATION: (11)..(11)
<223> OTHER INFORMATION: Xaa is Q, S, A, D, or N

<400> SEQUENCE: 470

Gln Ser Val Leu Phe Ser Ser Xaa Gln Lys Xaa Tyr
1               5                   10

<210> SEQ ID NO 471
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is H, Y, F, or W

<400> SEQUENCE: 471

Xaa Ala Ser
1

<210> SEQ ID NO 472
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is N, Q, S, or A

<400> SEQUENCE: 472

Gly Tyr Ser Phe Thr Phe Tyr Xaa
1               5

<210> SEQ ID NO 473
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is A, S, E, or D
```

-continued

<400> SEQUENCE: 473

Ile Xaa Pro Tyr Tyr Gly Gly Ser
1               5

<210> SEQ ID NO 474
<211> LENGTH: 12
<212> TYPE: PRT
<213> ORGANISM: Artificial Sequence
<220> FEATURE:
<223> OTHER INFORMATION: Synthetic peptide

<400> SEQUENCE: 474

Glu Arg Ser Gly Tyr Val Phe Ser Ala Met Asp Tyr
1               5                   10

<210> SEQ ID NO 475
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Q, S, A, or N

<400> SEQUENCE: 475

Ile Xaa Pro Ser Ser Gly Tyr Thr
1               5

<210> SEQ ID NO 476
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Q, S, A, D, or N

<400> SEQUENCE: 476

Glu Xaa Ile Tyr Ser Tyr
1               5

<210> SEQ ID NO 477
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Q, S, A, D, or N

<400> SEQUENCE: 477

Xaa Ala Lys
1

<210> SEQ ID NO 478
<211> LENGTH: 116
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<222> LOCATION: (20)..(20)
<223> OTHER INFORMATION: Xaa is M or V
<220> FEATURE:
<221> NAME/KEY: MISC_FEATURE
<222> LOCATION: (31)..(31)
<223> OTHER INFORMATION: Xaa is T, V, D, or S
<220> FEATURE:
<221> NAME/KEY: MISC_FEATURE
<222> LOCATION: (48)..(48)
<223> OTHER INFORMATION: Xaa is I or M
<220> FEATURE:
<221> NAME/KEY: MISC_FEATURE
<222> LOCATION: (52)..(52)
<223> OTHER INFORMATION: Xaa is Q, S, A, or N
<220> FEATURE:
<221> NAME/KEY: MISC_FEATURE
<222> LOCATION: (70)..(70)
<223> OTHER INFORMATION: Xaa is L or M
<220> FEATURE:
<221> NAME/KEY: MISC_FEATURE
<222> LOCATION: (74)..(74)
<223> OTHER INFORMATION: Xaa is T or K
<220> FEATURE:
<221> NAME/KEY: MISC_FEATURE
<222> LOCATION: (98)..(98)
<223> OTHER INFORMATION: Xaa is N, Q, H, D, S, R, or A

<400> SEQUENCE: 478

Gln Val Gln Leu Val Gln Ser Gly Ala Glu Val Lys Lys Pro Gly Ala
1               5                   10                  15

Ser Val Lys Xaa Ser Cys Lys Ala Ser Gly Tyr Thr Phe Thr Xaa Tyr
            20                  25                  30

Thr Met His Trp Val Arg Gln Ala Pro Gly Gln Gly Leu Glu Trp Xaa
        35                  40                  45

Gly Phe Ile Xaa Pro Ser Ser Gly Tyr Thr Asp Tyr Ala Gln Lys Phe
    50                  55                  60

Gln Gly Arg Val Thr Xaa Thr Ala Asp Xaa Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Xaa Gly Asp Tyr Tyr Val Ala Tyr Trp Gly Gln Gly Thr Leu Val
            100                 105                 110

Thr Val Ser Ser
            115

<210> SEQ ID NO 479
<211> LENGTH: 108
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is L or M
<220> FEATURE:
<221> NAME/KEY: MISC_FEATURE
<222> LOCATION: (21)..(21)
<223> OTHER INFORMATION: Xaa is M or I
<220> FEATURE:
<221> NAME/KEY: MISC_FEATURE
<222> LOCATION: (32)..(32)
<223> OTHER INFORMATION: Xaa is T, V, F, or D
<220> FEATURE:
<221> NAME/KEY: MISC_FEATURE
<222> LOCATION: (48)..(48)
<223> OTHER INFORMATION: Xaa is W or L
<220> FEATURE:
<221> NAME/KEY: MISC_FEATURE
<222> LOCATION: (51)..(51)
```

```
<223> OTHER INFORMATION: Xaa is S, t, Q or A
<220> FEATURE:
<221> NAME/KEY: MISC_FEATURE
<222> LOCATION: (53)..(53)
<223> OTHER INFORMATION: Xaa is S,T, D or Q
<220> FEATURE:
<221> NAME/KEY: MISC_FEATURE
<222> LOCATION: (79)..(79)
<223> OTHER INFORMATION: Xaa is M or L
<220> FEATURE:
<221> NAME/KEY: MISC_FEATURE
<222> LOCATION: (84)..(84)
<223> OTHER INFORMATION: Xaa is A or F
<220> FEATURE:
<221> NAME/KEY: MISC_FEATURE
<222> LOCATION: (91)..(91)
<223> OTHER INFORMATION: Xaa is Q, H or S
<220> FEATURE:
<221> NAME/KEY: MISC_FEATURE
<222> LOCATION: (93)..(93)
<223> OTHER INFORMATION: Xaa is H, Y, Q, or S

<400> SEQUENCE: 479

Asp Ile Gln Xaa Thr Gln Ser Pro Ser Ser Leu Ser Ala Ser Val Gly
1               5                   10                  15

Asp Arg Val Thr Xaa Thr Cys Thr Ala Ser Ser Ser Val Ser Ser Xaa
            20                  25                  30

Tyr Phe His Trp Tyr Gln Gln Lys Pro Gly Lys Ala Pro Lys Leu Xaa
        35                  40                  45

Ile Tyr Xaa Thr Xaa Asn Leu Ala Ser Gly Val Pro Ser Arg Phe Ser
    50                  55                  60

Gly Ser Gly Ser Gly Thr Asp Tyr Thr Leu Thr Ile Ser Ser Xaa Gln
65              70                  75                  80

Pro Glu Asp Xaa Ala Thr Tyr Tyr Cys His Xaa Tyr Xaa Arg Ser Pro
                85                  90                  95

Leu Thr Phe Gly Gln Gly Thr Lys Leu Glu Ile Lys
            100                 105

<210> SEQ ID NO 480
<211> LENGTH: 117
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (31)..(31)
<223> OTHER INFORMATION: Xaa is N, S, R, Q or A
<220> FEATURE:
<221> NAME/KEY: MISC_FEATURE
<222> LOCATION: (33)..(33)
<223> OTHER INFORMATION: Xaa is W, H, Y or F
<220> FEATURE:
<221> NAME/KEY: MISC_FEATURE
<222> LOCATION: (55)..(55)
<223> OTHER INFORMATION: Xaa is S, N, A, or T
<220> FEATURE:
<221> NAME/KEY: MISC_FEATURE
<222> LOCATION: (57)..(57)
<223> OTHER INFORMATION: Xaa is Q, S, A, or N
<220> FEATURE:
<221> NAME/KEY: MISC_FEATURE
<222> LOCATION: (99)..(99)
<223> OTHER INFORMATION: Xaa is N, D, or T
<220> FEATURE:
<221> NAME/KEY: MISC_FEATURE
<222> LOCATION: (106)..(106)
<223> OTHER INFORMATION: Xaa is S, T, A, C, or Y

<400> SEQUENCE: 480
```

```
Glu Val Gln Leu Leu Glu Ser Gly Gly Gly Leu Val Gln Pro Gly Gly
 1               5                  10                 15

Ser Met Arg Leu Ser Cys Ala Ala Ser Gly Phe Thr Phe Ser Xaa Tyr
            20                  25                  30

Xaa Met Asn Trp Val Arg Gln Ala Pro Gly Lys Gly Leu Glu Trp Val
        35                  40                  45

Ala Gln Ile Arg Leu Lys Xaa Asp Xaa Tyr Ala Thr His Tyr Ala Asp
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Gly Val Tyr
                85                  90                  95

Tyr Cys Xaa Asp Gly Pro Pro Ser Gly Xaa Trp Gly Gln Gly Thr Leu
            100                 105                 110

Leu Thr Val Ser Ser
            115
```

<210> SEQ ID NO 481
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (28)..(28)
<223> OTHER INFORMATION: Xaa is Q, S, A, D, or N
<220> FEATURE:
<221> NAME/KEY: MISC_FEATURE
<222> LOCATION: (48)..(48)
<223> OTHER INFORMATION: Xaa is V or I
<220> FEATURE:
<221> NAME/KEY: MISC_FEATURE
<222> LOCATION: (50)..(50)
<223> OTHER INFORMATION: Xaa is S, T, Q or A
<220> FEATURE:
<221> NAME/KEY: MISC_FEATURE
<222> LOCATION: (84)..(84)
<223> OTHER INFORMATION: Xaa is G or A
<220> FEATURE:
<221> NAME/KEY: MISC_FEATURE
<222> LOCATION: (90)..(90)
<223> OTHER INFORMATION: Xaa is H, Q, S or T
<220> FEATURE:
<221> NAME/KEY: MISC_FEATURE
<222> LOCATION: (93)..(93)
<223> OTHER INFORMATION: Xaa is T, S, N, or G

<400> SEQUENCE: 481

```
Asp Ile Gln Met Thr Gln Ser Pro Ser Ser Leu Ser Ala Ser Val Gly
 1               5                  10                  15

Asp Arg Val Thr Ile Thr Cys Arg Ile Ser Glu Xaa Ile Tyr Ser Tyr
            20                  25                  30

Leu Ala Trp Tyr Gln Gln Lys Pro Gly Lys Ala Pro Lys Leu Leu Xaa
        35                  40                  45

Tyr Xaa Ala Lys Ile Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Xaa Thr Tyr Tyr Cys Gln Xaa His Tyr Xaa Val Pro Trp
                85                  90                  95

Thr Phe Gly Gln Gly Thr Lys Leu Glu Ile Lys
                100                 105
```

```
<210> SEQ ID NO 482
<211> LENGTH: 117
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (20)..(20)
<223> OTHER INFORMATION: Xaa is M or V
<220> FEATURE:
<221> NAME/KEY: MISC_FEATURE
<222> LOCATION: (29)..(29)
<223> OTHER INFORMATION: Xaa is F, Y, S or T
<220> FEATURE:
<221> NAME/KEY: MISC_FEATURE
<222> LOCATION: (31)..(31)
<223> OTHER INFORMATION: Xaa is S, T, Y, or D
<220> FEATURE:
<221> NAME/KEY: MISC_FEATURE
<222> LOCATION: (37)..(37)
<223> OTHER INFORMATION: Xaa is I or V
<220> FEATURE:
<221> NAME/KEY: MISC_FEATURE
<222> LOCATION: (45)..(45)
<223> OTHER INFORMATION: Xaa is Q or L
<220> FEATURE:
<221> NAME/KEY: MISC_FEATURE
<222> LOCATION: (48)..(48)
<223> OTHER INFORMATION: Xaa is I or M
<220> FEATURE:
<221> NAME/KEY: MISC_FEATURE
<222> LOCATION: (52)..(52)
<223> OTHER INFORMATION: Xaa is Q, S, A, or N
<220> FEATURE:
<221> NAME/KEY: MISC_FEATURE
<222> LOCATION: (56)..(56)
<223> OTHER INFORMATION: Xaa is T, S, V, D or G
<220> FEATURE:
<221> NAME/KEY: MISC_FEATURE
<222> LOCATION: (61)..(61)
<223> OTHER INFORMATION: Xaa is I or A
<220> FEATURE:
<221> NAME/KEY: MISC_FEATURE
<222> LOCATION: (62)..(62)
<223> OTHER INFORMATION: Xaa is K or Q
<220> FEATURE:
<221> NAME/KEY: MISC_FEATURE
<222> LOCATION: (65)..(65)
<223> OTHER INFORMATION: Xaa is K or Q
<220> FEATURE:
<221> NAME/KEY: MISC_FEATURE
<222> LOCATION: (66)..(66)
<223> OTHER INFORMATION: Xaa is D or G
<220> FEATURE:
<221> NAME/KEY: MISC_FEATURE
<222> LOCATION: (68)..(68)
<223> OTHER INFORMATION: Xaa is A or V
<220> FEATURE:
<221> NAME/KEY: MISC_FEATURE
<222> LOCATION: (70)..(70)
<223> OTHER INFORMATION: Xaa is L or M
<220> FEATURE:
<221> NAME/KEY: MISC_FEATURE
<222> LOCATION: (74)..(74)
<223> OTHER INFORMATION: Xaa is T or K
<220> FEATURE:
<221> NAME/KEY: MISC_FEATURE
<222> LOCATION: (79)..(79)
<223> OTHER INFORMATION: Xaa is A or V
<220> FEATURE:
<221> NAME/KEY: MISC_FEATURE
<222> LOCATION: (97)..(97)
<223> OTHER INFORMATION: Xaa is S, A, T, or V
<220> FEATURE:
<221> NAME/KEY: MISC_FEATURE
<222> LOCATION: (101)..(97)
<223> OTHER INFORMATION: Xaa is L, V, or F
```

```
<220> FEATURE:
<221> NAME/KEY: misc_feature
<222> LOCATION: (101)..(101)
<223> OTHER INFORMATION: Xaa can be any naturally occurring amino acid

<400> SEQUENCE: 482
```

Gln Val Gln Leu Val Gln Ser Gly Ala Glu Val Lys Lys Pro Gly Ala
1               5                   10                  15

Ser Val Lys Xaa Ser Cys Lys Ala Ser Gly Tyr Thr Xaa Thr Xaa Tyr
            20                  25                  30

Thr Met His Trp Xaa Arg Gln Ala Pro Gly Gln Gly Xaa Glu Trp Xaa
            35                  40                  45

Gly Tyr Ile Xaa Pro Ser Ser Xaa Tyr Thr His Tyr Xaa Xaa Lys Phe
50                  55                  60

Xaa Xaa Arg Xaa Thr Xaa Thr Ala Asp Xaa Ser Thr Ser Thr Xaa Tyr
65                  70                  75                  80

Met Glu Leu Ser Ser Leu Arg Ser Glu Asp Thr Ala Val Tyr Tyr Cys
                85                  90                  95

Xaa Arg Gly Glu Xaa Gly Gly Phe Ala Tyr Trp Gly Gln Gly Thr Leu
            100                 105                 110

Val Thr Val Ser Ser
            115

```
<210> SEQ ID NO 483
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (33)..(33)
<223> OTHER INFORMATION: Xaa is D, N, E, Q, S, or A
<220> FEATURE:
<221> NAME/KEY: MISC_FEATURE
<222> LOCATION: (35)..(35)
<223> OTHER INFORMATION: Xaa is Q, S, A, D, or N
<220> FEATURE:
<221> NAME/KEY: MISC_FEATURE
<222> LOCATION: (55)..(55)
<223> OTHER INFORMATION: Xaa is K, Q, or R
<220> FEATURE:
<221> NAME/KEY: MISC_FEATURE
<222> LOCATION: (57)..(57)
<223> OTHER INFORMATION: Xaa is S, T, or V
<220> FEATURE:
<221> NAME/KEY: MISC_FEATURE
<222> LOCATION: (95)..(95)
<223> OTHER INFORMATION: Xaa is Q, H, or T
<220> FEATURE:
<221> NAME/KEY: MISC_FEATURE
<222> LOCATION: (96)..(96)
<223> OTHER INFORMATION: Xaa is S, G, T, or D

<400> SEQUENCE: 483
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Xaa Thr Tyr Leu Asn Trp Tyr Gln Gln Arg Pro Gly Gln Ser
            35                  40                  45

Pro Arg Leu Leu Ile Tyr Xaa Val Xaa Asn Arg Phe Ser Gly Val Pro
50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Ser Xaa Xaa
            85                  90                  95

Thr His Val Pro Tyr Thr Phe Gly Gln Gly Thr Lys Leu Glu Ile Lys
            100                 105                 110
```

<210> SEQ ID NO 484
<211> LENGTH: 121
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (20)..(20)
<223> OTHER INFORMATION: Xaa is I or V
<220> FEATURE:
<221> NAME/KEY: MISC_FEATURE
<222> LOCATION: (33)..(33)
<223> OTHER INFORMATION: Xaa is N, Q, S, or A
<220> FEATURE:
<221> NAME/KEY: MISC_FEATURE
<222> LOCATION: (48)..(48)
<223> OTHER INFORMATION: Xaa is I or M
<220> FEATURE:
<221> NAME/KEY: MISC_FEATURE
<222> LOCATION: (52)..(52)
<223> OTHER INFORMATION: Xaa is A, S, E or D
<220> FEATURE:
<221> NAME/KEY: MISC_FEATURE
<222> LOCATION: (68)..(68)
<223> OTHER INFORMATION: Xaa is A or V
<220> FEATURE:
<221> NAME/KEY: MISC_FEATURE
<222> LOCATION: (70)..(70)
<223> OTHER INFORMATION: Xaa is L or M
<220> FEATURE:
<221> NAME/KEY: MISC_FEATURE
<222> LOCATION: (79)..(79)
<223> OTHER INFORMATION: Xaa is A or V

<400> SEQUENCE: 484

```
Gln Val Gln Leu Val Gln Ser Gly Ala Glu Val Lys Lys Pro Gly Ala
1               5                   10                  15

Ser Val Lys Xaa Ser Cys Lys Ala Ser Gly Tyr Ser Phe Thr Gly Tyr
            20                  25                  30

Xaa Met Asn Trp Val Arg Gln Ala Pro Gly Gln Gly Leu Glu Trp Xaa
            35                  40                  45

Gly Asn Ile Xaa Pro Tyr Tyr Gly Gly Ser Thr Tyr Ala Gln Lys Phe
        50                  55                  60

Gln Gly Arg Xaa Thr Xaa Thr Val Asp Thr Ser Thr Ser Thr Xaa Tyr
65                  70                  75                  80

Met Glu Leu Ser Ser Leu Arg Ser Glu Asp Thr Ala Val Tyr Tyr Cys
                85                  90                  95

Ala Arg Glu Arg Ser Gly Tyr Val Phe Ser Ala Met Asp Tyr Trp Gly
            100                 105                 110

Gln Gly Thr Leu Val Thr Val Ser Ser
        115                 120
```

<210> SEQ ID NO 485
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (19)..(19)

```
<223> OTHER INFORMATION: Xaa is V or A
<220> FEATURE:
<221> NAME/KEY: MISC_FEATURE
<222> LOCATION: (21)..(21)
<223> OTHER INFORMATION: Xaa is M or I
<220> FEATURE:
<221> NAME/KEY: MISC_FEATURE
<222> LOCATION: (34)..(34)
<223> OTHER INFORMATION: Xaa is Q, S, A, D, or N
<220> FEATURE:
<221> NAME/KEY: MISC_FEATURE
<222> LOCATION: (37)..(37)
<223> OTHER INFORMATION: Xaa is Q, S, A, D, or N
<220> FEATURE:
<221> NAME/KEY: MISC_FEATURE
<222> LOCATION: (56)..(56)
<223> OTHER INFORMATION: Xaa is H, Y, F, or W
<220> FEATURE:
<221> NAME/KEY: MISC_FEATURE
<222> LOCATION: (84)..(84)
<223> OTHER INFORMATION: Xaa is V or L

<400> SEQUENCE: 485

Asp Ile Val Met Thr Gln Ser Pro Asp Ser Leu Ala Val Ser Leu Gly
 1               5                  10                  15

Glu Arg Xaa Thr Xaa Asn Cys Lys Ser Ser Gln Ser Val Leu Phe Ser
            20                  25                  30

Ser Xaa Gln Lys Xaa Tyr Leu Ala Trp Tyr Gln Gln Lys Pro Gly Gln
        35                  40                  45

Pro Pro Lys Leu Leu Ile Tyr Xaa Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Xaa Gln Ala Glu Asp Val Ala Val Tyr Tyr Cys His Gln
                85                  90                  95

Tyr Leu Ser Ser Arg Thr Phe Gly Gln Gly Thr Lys Leu Glu Ile Lys
            100                 105                 110

<210> SEQ ID NO 486
<211> LENGTH: 118
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (54)..(54)
<223> OTHER INFORMATION: Xaa is D, E, S, or A

<400> SEQUENCE: 486

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Xaa Ser Arg Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Tyr Gly Arg Thr Tyr Glu Ala Tyr Trp Gly Gln Gly Thr
            100                 105                 110
```

Leu Val Thr Val Ser Ser
        115

<210> SEQ ID NO 487
<211> LENGTH: 111
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is M or L
<220> FEATURE:
<221> NAME/KEY: MISC_FEATURE
<222> LOCATION: (82)..(82)
<223> OTHER INFORMATION: Xaa is V or L
<220> FEATURE:
<221> NAME/KEY: MISC_FEATURE
<222> LOCATION: (110)..(110)
<223> OTHER INFORMATION: Xaa is I or L

<400> SEQUENCE: 487

Asp Ile Val Xaa Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Xaa Gln Ala Glu Asp Val Ala Val Tyr Tyr Cys Gln His Ser Arg
                85                  90                  95

Glu Leu Pro Leu Thr Phe Gly Gln Gly Thr Lys Leu Glu Ile Lys
            100                 105                 110

<210> SEQ ID NO 488
<211> LENGTH: 117
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (28)..(28)
<223> OTHER INFORMATION: Xaa is R or T
<220> FEATURE:
<221> NAME/KEY: MISC_FEATURE
<222> LOCATION: (33)..(33)
<223> OTHER INFORMATION: Xaa is N, Q, S or A
<220> FEATURE:
<221> NAME/KEY: MISC_FEATURE
<222> LOCATION: (52)..(52)
<223> OTHER INFORMATION: Xaa is N, Q, S or A
<220> FEATURE:
<221> NAME/KEY: MISC_FEATURE
<222> LOCATION: (54)..(54)
<223> OTHER INFORMATION: Xaa is N, Q, S or A
<220> FEATURE:
<221> NAME/KEY: MISC_FEATURE
<222> LOCATION: (55)..(55)
<223> OTHER INFORMATION: Xaa is N, Q, S, or A
<220> FEATURE:
<221> NAME/KEY: MISC_FEATURE
<222> LOCATION: (106)..(106)
<223> OTHER INFORMATION: Xaa is C, Y, S, or A

<400> SEQUENCE: 488

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Xaa Phe Thr Asp Tyr
            20                  25                  30

Xaa Met His Trp Val Arg Gln Ala Pro Gly Gln Gly Leu Glu Trp Ile
        35                  40                  45

Gly Tyr Ile Xaa Pro Xaa Xaa Gly Gly Thr Asn Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Leu Tyr Phe Phe Asp Xaa Trp Gly Gln Gly Thr Leu
            100                 105                 110

Leu Thr Val Ser Ser
            115

<210> SEQ ID NO 489
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (24)..(24)
<223> OTHER INFORMATION: Xaa is L or R
<220> FEATURE:
<221> NAME/KEY: MISC_FEATURE
<222> LOCATION: (32)..(32)
<223> OTHER INFORMATION: Xaa is W, H, Y, or F

<400> SEQUENCE: 489

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Xaa
            20                  25                  30

Leu Ala Trp Tyr Gln Gln Lys Pro Gly Lys Ala Pro Lys Leu Leu Ile
        35                  40                  45

Tyr Ala Ala Ala Ser Leu Ala Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Val Thr Tyr Tyr Cys Gln Gln Leu Tyr Ser Ile Pro Arg
                85                  90                  95

Thr Phe Gly Gln Gly Thr Lys Leu Glu Ile Lys
            100                 105

<210> SEQ ID NO 490
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 490

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Asn Tyr

```
                    20                  25                  30
Trp Met Asn Trp Val Arg Gln Ala Pro Gly Lys Gly Leu Glu Trp Ile
                35                  40                  45
Ala Gln Ile Arg Leu Lys Ser Asp Asn Tyr Ala Thr His Tyr Thr Asp
         50                  55                  60
Ser Val Lys Gly Arg Phe Thr Ile Ser Arg Asp Asp Ser Lys Arg Thr
 65                  70                  75                  80
Val Tyr Leu Gln Met Asn Ser Leu Arg Ala Glu Asp Thr Gly Thr Tyr
                 85                  90                  95
Tyr Cys Ser Asp Gly Pro Pro Ser Gly Ser Trp Gly Gln Gly Thr Leu
                100                 105                 110
Leu Thr Val Ser Ser
        115

<210> SEQ ID NO 491
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 491

Glu Val Gln Leu Leu Glu Ser Gly Gly Gly Leu Val Gln Pro Gly Gly
 1               5                  10                  15
Ser Met Arg Leu Ser Cys Ala Ala Ser Gly Phe Thr Phe Ser Asn Tyr
                20                  25                  30
Trp Met Asn Trp Val Arg Gln Ala Pro Gly Lys Gly Leu Glu Trp Ile
                35                  40                  45
Ala Gln Ile Arg Leu Lys Ser Asp Asn Tyr Ala Thr His Tyr Ala Asp
         50                  55                  60
Ser Val Lys Gly Arg Phe Thr Ile Ser Arg Asp Asp Ser Lys Arg Thr
 65                  70                  75                  80
Val Tyr Leu Gln Met Asn Ser Leu Arg Ala Glu Asp Thr Gly Thr Tyr
                 85                  90                  95
Tyr Cys Ser Asp Gly Pro Pro Ser Gly Ser Trp Gly Gln Gly Thr Leu
                100                 105                 110
Leu Thr Val Ser Ser
        115

<210> SEQ ID NO 492
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 492

Glu Val Gln Leu Leu Glu Ser Gly Gly Gly Leu Val Gln Pro Gly Gly
 1               5                  10                  15
Ser Met Arg Leu Ser Cys Ala Ala Ser Gly Phe Thr Phe Ser Asn Tyr
                20                  25                  30
Trp Met Asn Trp Val Arg Gln Ala Pro Gly Lys Gly Leu Glu Trp Ile
                35                  40                  45
Ala Gln Ile Arg Leu Lys Ser Asp Asn Tyr Val Thr His Tyr Thr Asp
         50                  55                  60
Ser Val Lys Gly Arg Phe Thr Ile Ser Arg Asp Asp Ser Lys Arg Thr
 65                  70                  75                  80
```

```
Val Tyr Leu Gln Met Asn Ser Leu Arg Ala Glu Asp Thr Gly Ile Tyr
                85                  90                  95

Tyr Cys Ser Asp Gly Pro Pro Ser Gly Ser Trp Gly Gln Gly Thr Leu
            100                 105                 110

Leu Thr Val Ser Ser
        115

<210> SEQ ID NO 493
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 493

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Ile
        35                  40                  45

Ala Gln Ile Arg Leu Lys Ser Asp Asn Tyr Ala Thr His Tyr Thr Asp
    50                  55                  60

Ser Val Lys Gly Arg Phe Thr Ile Ser Arg Asp Asp Ser Lys Ser Thr
65                  70                  75                  80

Val Tyr Leu Gln Met Asn Ser Leu Arg Ala Glu Asp Thr Gly Thr Tyr
                85                  90                  95

Tyr Cys Asn Asp Gly Pro Pro Ser Gly Ser Trp Gly Gln Gly Thr Leu
            100                 105                 110

Leu Thr Val Ser Ser
        115

<210> SEQ ID NO 494
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 494

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Leu
        35                  40                  45

Ala Gln Ile Arg Leu Lys Ser Asp Asn Tyr Ala Thr His Tyr Thr Asp
    50                  55                  60

Ser Val Lys Gly Arg Phe Thr Ile Ser Arg Asp Asp Ser Lys Arg Thr
65                  70                  75                  80

Val Tyr Leu Gln Met Asn Ser Leu Arg Ala Glu Asp Thr Gly Ile Tyr
                85                  90                  95

Tyr Cys Ser Asp Gly Pro Pro Ser Gly Ser Trp Gly Gln Gly Thr Leu
            100                 105                 110

Leu Thr Val Ser Ser
        115

<210> SEQ ID NO 495
```

```
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 495

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Leu
        35                  40                  45

Ala Gln Ile Arg Leu Lys Ser Asp Asn Tyr Val Thr His Tyr Ala Asp
    50                  55                  60

Ser Val Lys Gly Arg Phe Thr Ile Ser Arg Asp Asp Ser Lys Arg Thr
65                  70                  75                  80

Val Tyr Leu Gln Met Asn Ser Leu Arg Ala Glu Asp Thr Gly Thr Tyr
                85                  90                  95

Tyr Cys Asn Asp Gly Pro Pro Ser Gly Ser Trp Gly Gln Gly Thr Leu
            100                 105                 110

Leu Thr Val Ser Ser
            115

<210> SEQ ID NO 496
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 496

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Ile
        35                  40                  45

Gly Phe Ile Asn Pro Ser Ser Gly Tyr Thr Glu Tyr Ala Gln Lys Phe
    50                  55                  60

Gln Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Asn Gly Asp Tyr Tyr Val Ala Tyr Trp Gly Gln Gly Thr Leu Val
            100                 105                 110

Thr Val Ser Ser
            115

<210> SEQ ID NO 497
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 497

Gln Val Gln Leu Val Gln Ser Gly Ala Glu Val Lys Lys Pro Gly Ala
1               5                   10                  15
```

Ser Val Lys Met Ser Cys Lys Ala Ser Gly Tyr Thr Phe Thr Thr Tyr
            20                  25                  30

Thr Met His Trp Val Arg Gln Ala Pro Gly Gln Gly Leu Glu Trp Ile
            35                  40                  45

Gly Val Ile Asn Pro Ser Ser Gly Tyr Thr Glu Tyr Ala Gln Lys Phe
    50                  55                  60

Gln Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Asn Gly Asp Tyr Tyr Val Gly Tyr Trp Gly Gln Gly Thr Leu Val
            100                 105                 110

Thr Val Ser Ser
        115

<210> SEQ ID NO 498
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 498

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Ile
            35                  40                  45

Gly Val Ile Asn Pro Ser Ser Gly Tyr Thr Asp Tyr Ala Gln Lys Phe
    50                  55                  60

Gln Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Asn Gly Asp Tyr Tyr Val Gly Tyr Trp Gly Gln Gly Thr Leu Val
            100                 105                 110

Thr Val Ser Ser
        115

<210> SEQ ID NO 499
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 499

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Arg Gln Ala Pro Gly Gln Gly Leu Glu Trp Ile
            35                  40                  45

Gly Phe Ile Asn Pro Ser Ser Gly Tyr Thr Glu Tyr Ala Gln Lys Phe
    50                  55                  60

Gln Gly Arg Val Thr Leu Thr Ala Asp Lys Ser Thr Ser Thr Val Tyr
65                  70                  75                  80

```
Met Glu Leu Ser Ser Leu Arg Ser Glu Asp Thr Ala Val Tyr Tyr Cys
                85                  90                  95

Ala Asn Gly Asp Tyr Tyr Val Gly Tyr Trp Gly Gln Gly Thr Leu Val
            100                 105                 110

Thr Val Ser Ser
        115

<210> SEQ ID NO 500
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 500

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Thr Tyr
            20                  25                  30

Thr Ile His Trp Val Arg Gln Ala Pro Gly Gln Gly Leu Glu Trp Ile
        35                  40                  45

Gly Val Ile Asn Pro Ser Ser Gly Tyr Thr Glu Tyr Ala Gln Lys Phe
    50                  55                  60

Gln Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Asn Gly Asp Tyr Tyr Val Ala Tyr Trp Gly Gln Gly Thr Leu Val
            100                 105                 110

Thr Val Ser Ser
        115

<210> SEQ ID NO 501
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 501

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Arg Gln Ala Pro Gly Gln Gly Leu Glu Trp Ile
        35                  40                  45

Gly Phe Ile Asn Pro Ser Ser Gly Tyr Thr Glu Tyr Ala Gln Lys Phe
    50                  55                  60

Gln Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Asn Gly Asp Tyr Tyr Val Gly Tyr Trp Gly Gln Gly Thr Leu Val
            100                 105                 110

Thr Val Ser Ser
        115
```

```
<210> SEQ ID NO 502
<211> LENGTH: 117
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (48)..(48)
<223> OTHER INFORMATION: Xaa is any aliphatic amino acid, optionally Ile
      or Leu
<220> FEATURE:
<221> NAME/KEY: MISC_FEATURE
<222> LOCATION: (59)..(59)
<223> OTHER INFORMATION: Xaa is any aliphatic amino acid, optionally,
      Ala or Val
<220> FEATURE:
<221> NAME/KEY: MISC_FEATURE
<222> LOCATION: (63)..(63)
<223> OTHER INFORMATION: Xaa is any aliphatic or any amino acid with a
      polar side chain, optionally, Ala or Thr
<220> FEATURE:
<221> NAME/KEY: MISC_FEATURE
<222> LOCATION: (79)..(79)
<223> OTHER INFORMATION: Xaa is any basic amino acid or any amino acid
      with a polar side chain, optionally Arg or Ser
<220> FEATURE:
<221> NAME/KEY: MISC_FEATURE
<222> LOCATION: (95)..(95)
<223> OTHER INFORMATION: Xaa is any aliphatic amino acid or any amino
      acid with a polar side chain, optionally, Thr or Ile
<220> FEATURE:
<221> NAME/KEY: MISC_FEATURE
<222> LOCATION: (99)..(99)
<223> OTHER INFORMATION: Xaa is any acidic amino acid or any amino acid
      with a polar side chain, optionally, Ser or Asn

<400> SEQUENCE: 502

Glu Val Gln Leu Leu Glu Ser Gly Gly Gly Leu Val Gln Pro Gly Gly
1               5                   10                  15

Ser Met Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Xaa
        35                  40                  45

Ala Gln Ile Arg Leu Lys Ser Asp Asn Tyr Xaa Thr His Tyr Xaa Asp
    50                  55                  60

Ser Val Lys Gly Arg Phe Thr Ile Ser Arg Asp Asp Ser Lys Xaa Thr
65                  70                  75                  80

Val Tyr Leu Gln Met Asn Ser Leu Arg Ala Glu Asp Thr Gly Xaa Tyr
                85                  90                  95

Tyr Cys Xaa Asp Gly Pro Pro Ser Gly Ser Trp Gly Gln Gly Thr Leu
            100                 105                 110

Leu Thr Val Ser Ser
        115

<210> SEQ ID NO 503
<211> LENGTH: 116
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (34)..(34)
<223> OTHER INFORMATION: Xaa is any aliphatic amino acid or any amino
      acid comprising a sulfur containing side chain; optionally, Ile or
      Met
<220> FEATURE:
<221> NAME/KEY: MISC_FEATURE
<222> LOCATION: (50)..(50)
```

```
<223> OTHER INFORMATION: Xaa is any aliphatic amino acid or any aromatic
      amino acid, optionally, Phe or Val
<220> FEATURE:
<221> NAME/KEY: MISC_FEATURE
<222> LOCATION: (59)..(59)
<223> OTHER INFORMATION: Xaa is any acidic amino acid, optionally, Glu
      or Asp
<220> FEATURE:
<221> NAME/KEY: MISC_FEATURE
<222> LOCATION: (95)..(95)
<223> OTHER INFORMATION: Xaa is any aromatic amino acid, optionally, Phe
      or Tyr
<220> FEATURE:
<221> NAME/KEY: MISC_FEATURE
<222> LOCATION: (104)..(104)
<223> OTHER INFORMATION: Xaa is any aliphatic amino acid, optionally,
      Gly or Ala

<400> SEQUENCE: 503

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Thr Tyr
            20                  25                  30

Thr Xaa His Trp Val Arg Gln Ala Pro Gly Gln Gly Leu Glu Trp Ile
        35                  40                  45

Gly Xaa Ile Asn Pro Ser Ser Gly Tyr Thr Xaa Tyr Ala Gln Lys Phe
    50                  55                  60

Gln Gly Arg Val Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Xaa Cys
                85                  90                  95

Ala Asn Gly Asp Tyr Tyr Val Xaa Tyr Trp Gly Gln Gly Thr Leu Val
            100                 105                 110

Thr Val Ser Ser
        115

<210> SEQ ID NO 504
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 504

Gly Tyr Thr Phe Thr Thr Tyr Thr
1               5

<210> SEQ ID NO 505
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 505

Ile Asn Pro Ser Ser Gly Tyr Thr
1               5

<210> SEQ ID NO 506
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

-continued

```
<222> LOCATION: (8)..(8)
<223> OTHER INFORMATION: Xaa is any aliphatic amino acid, optionally,
      Gly or Ala

<400> SEQUENCE: 506

Ala Asn Gly Asp Tyr Tyr Val Xaa Tyr
1               5

<210> SEQ ID NO 507
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 507

Gly Phe Thr Phe Ser Asn Tyr Trp
1               5

<210> SEQ ID NO 508
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Xaa is any aliphatic amino acid, optionally,
      Ala or Val

<400> SEQUENCE: 508

Ile Arg Leu Lys Ser Asp Asn Tyr Xaa Thr
1               5                   10

<210> SEQ ID NO 509
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is any acidic amino acid or any amino acid
      with a polar side chain, optionally, Ser or Asn

<400> SEQUENCE: 509

Xaa Asp Gly Pro Pro Ser Gly Ser
1               5

<210> SEQ ID NO 510
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 510

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60
```

```
Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Asn Asp Gly Pro Pro Ser Gly Cys Trp Gly Gln Gly Thr Thr
            100                 105                 110

Leu Thr Val Ser Ser
        115

<210> SEQ ID NO 511
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 511

Asp Ile Gln Met Thr Gln Ser Pro Ala Ser Leu Ser Ala Ser Val Gly
  1               5                  10                  15

Glu Thr Val Thr Ile Thr Cys Arg Ala Ser Glu Asn Ile Tyr Ser Tyr
                 20                  25                  30

Leu Ala Trp Tyr Gln Gln Lys Gln Gly Lys Ser Pro Gln Leu Leu Val
             35                  40                  45

Tyr Asn Ala Lys Ile Leu Val Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Asn Tyr Tyr Cys Gln His His Tyr Thr Val Pro Trp
                 85                  90                  95

Thr Phe Gly Gly Gly Thr Lys Leu Glu Ile Lys
            100                 105

<210> SEQ ID NO 512
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 512

Gln Ile Val Leu Thr Gln Ser Pro Ala Ile Met Ser Ala Ser Leu Gly
  1               5                  10                  15

Glu Arg Val Thr Met Thr Cys Thr Ala Ser Ser Ser Val Ser Ser Ser
                 20                  25                  30

Tyr Leu His Trp Tyr Gln Gln Lys Pro Gly Ser Ser Pro Lys Leu Trp
             35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                 85                  90                  95

Leu Thr Phe Gly Ala Gly Thr Lys Leu Glu Leu Lys
            100                 105

<210> SEQ ID NO 513
<211> LENGTH: 116
<212> TYPE: PRT
```

```
<213> ORGANISM: Artificial Sequence
<220> FEATURE:
<223> OTHER INFORMATION: Synthetic Polypeptide

<400> SEQUENCE: 513

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Phe Ile Asn Pro Ser Ser Gly Tyr Thr Asp Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Asn Gly Asp Tyr Tyr Val Ala Tyr Trp Gly Gln Gly Thr Leu Val
            100                 105                 110

Thr Val Ser Ala
            115
```